(12) United States Patent
Baryza et al.

(10) Patent No.: US 10,227,588 B2
(45) Date of Patent: *Mar. 12, 2019

(54) 3'END CAPS FOR RNAI AGENTS FOR USE IN RNA INTERFERENCE

(71) Applicant: Novartis AG, Basel (CH)

(72) Inventors: Jeremy Lee Baryza, Cambridge, MA (US); Marcel Blommers, Basel (CH); Cesar Fernandez, Basel (CH); Erin Geno, Cambridge, MA (US); Alvar Gossert, Basel (CH); Paulette Greenidge, Basel (CH); Dieter Huesken, Basel (CH); Juerg Hunziker, Basel (CH); Francois Jean-Charles Natt, Basel (CH); Anup Patnaik, Cambridge, MA (US); Andrew Patterson, Cambridge, MA (US); Jean-Michel Rene Rondeau, Basel (CH); Jan Weiler, Cambridge, MA (US); Meicheng Zhu, Cambridge, MA (US)

(73) Assignee: NOVARTIS AG, Basel (CH)

( * ) Notice: Subject to any disclaimer, the term of this patent is extended or adjusted under 35 U.S.C. 154(b) by 0 days.

This patent is subject to a terminal disclaimer.

(21) Appl. No.: 15/025,779

(22) PCT Filed: Oct. 1, 2014

(86) PCT No.: PCT/US2014/058705
§ 371 (c)(1),
(2) Date: Mar. 29, 2016

(87) PCT Pub. No.: WO2015/051045
PCT Pub. Date: Apr. 9, 2015

(65) Prior Publication Data
US 2016/0304863 A1    Oct. 20, 2016

Related U.S. Application Data

(60) Provisional application No. 61/886,739, filed on Oct. 4, 2013.

(51) Int. Cl.
| | |
|---|---|
| C07H 21/04 | (2006.01) |
| C12N 15/11 | (2006.01) |
| C07D 215/12 | (2006.01) |
| C07D 215/14 | (2006.01) |
| C07D 311/80 | (2006.01) |
| C07C 69/40 | (2006.01) |
| C07D 217/14 | (2006.01) |
| C07D 401/04 | (2006.01) |
| C07D 213/30 | (2006.01) |
| C07C 43/23 | (2006.01) |
| C07C 233/01 | (2006.01) |
| C07D 217/16 | (2006.01) |
| C07D 217/18 | (2006.01) |

(52) U.S. Cl.
CPC .......... *C12N 15/111* (2013.01); *C07C 43/23* (2013.01); *C07C 69/40* (2013.01); *C07C 233/01* (2013.01); *C07D 213/30* (2013.01); *C07D 215/12* (2013.01); *C07D 215/14* (2013.01); *C07D 217/14* (2013.01); *C07D 217/16* (2013.01); *C07D 217/18* (2013.01); *C07D 311/80* (2013.01); *C07D 401/04* (2013.01); *C12N 2310/14* (2013.01); *C12N 2310/344* (2013.01); *C12N 2310/351* (2013.01); *C12N 2320/51* (2013.01)

(58) Field of Classification Search
None
See application file for complete search history.

(56) References Cited

U.S. PATENT DOCUMENTS

| | | |
|---|---|---|
| 3,687,808 A | 8/1972 | Merigan, Jr. et al. |
| 4,065,489 A | 12/1977 | Steinstrasser et al. |
| 4,469,863 A | 9/1984 | Ts'o et al. |
| 5,023,243 A | 6/1991 | Tullis |
| 5,034,506 A | 7/1991 | Summerton et al. |
| 5,134,066 A | 7/1992 | Rogers et al. |
| 5,212,295 A | 5/1993 | Cook |
| 5,214,134 A | 5/1993 | Weis et al. |
| 5,216,141 A | 6/1993 | Benner |
| 5,218,105 A | 6/1993 | Cook et al. |
| 5,264,423 A | 11/1993 | Cohen et al. |
| 5,264,562 A | 11/1993 | Matteucci |
| 5,321,131 A | 6/1994 | Agrawal et al. |
| 5,359,044 A | 10/1994 | Cook et al. |
| 5,399,676 A | 3/1995 | Froehler |
| 5,405,939 A | 4/1995 | Suhadolnik et al. |
| 5,453,496 A | 9/1995 | Caruthers et al. |
| 5,455,233 A | 10/1995 | Spielvogel et al. |
| 5,459,255 A | 10/1995 | Cook et al. |
| 5,466,677 A | 11/1995 | Baxter et al. |
| 5,466,786 A | 11/1995 | Buhr et al. |
| 5,470,967 A | 11/1995 | Huie et al. |

(Continued)

FOREIGN PATENT DOCUMENTS

| | | |
|---|---|---|
| CN | 1120838 A | 4/1996 |
| CN | 1430602 A | 7/2003 |

(Continued)

OTHER PUBLICATIONS

Ashayev, A.V., "A New Universal Solid Support for Oligonucleotide Synthesis," *Tetrahedron*, 55, (1999) pp. 787-800.

(Continued)

*Primary Examiner* — Kimberly Chong
(74) *Attorney, Agent, or Firm* — Brinks Gilson & Lione

(57) ABSTRACT

The disclosure relates to novel compounds and compositions comprising a RNAi agent comprising a novel compound as a 3' end cap. The disclosure also relates to processes for making such compositions, and methods and uses of such compositions, e.g., to mediate RNA interference.

18 Claims, 47 Drawing Sheets

Specification includes a Sequence Listing.

(56) References Cited

U.S. PATENT DOCUMENTS

| | | | |
|---|---|---|---|
| 5,489,677 A | 2/1996 | Sanghvi et al. | |
| 5,506,351 A | 4/1996 | McGee | |
| 5,519,134 A | 5/1996 | Acevedo et al. | |
| 5,521,302 A | 5/1996 | Cook | |
| 5,539,082 A | 7/1996 | Nielsen et al. | |
| 5,541,307 A | 7/1996 | Cook et al. | |
| 5,552,540 A | 9/1996 | Haralambidis | |
| 5,554,746 A | 9/1996 | Ravikumar et al. | |
| 5,571,902 A | 11/1996 | Ravikumar et al. | |
| 5,578,718 A | 11/1996 | Cook et al. | |
| 5,581,469 A | 12/1996 | Kim | |
| 5,587,361 A | 12/1996 | Cook et al. | |
| 5,587,469 A | 12/1996 | Cook et al. | |
| 5,587,470 A | 12/1996 | Cook et al. | |
| 5,591,722 A | 1/1997 | Montgomery et al. | |
| 5,594,121 A | 1/1997 | Froehler et al. | |
| 5,596,091 A | 1/1997 | Switzer | |
| 5,597,909 A | 1/1997 | Urdea et al. | |
| 5,602,240 A | 2/1997 | De Mesmaeker et al. | |
| 5,608,046 A | 3/1997 | Cook et al. | |
| 5,610,289 A | 3/1997 | Cook et al. | |
| 5,646,265 A | 7/1997 | McGee | |
| 5,663,312 A | 9/1997 | Chaturvedula | |
| 5,670,633 A | 9/1997 | Cook et al. | |
| 5,700,920 A | 12/1997 | Altmann et al. | |
| 5,998,203 A | 12/1999 | Matulic-Adamic et al. | |
| 6,127,533 A | 10/2000 | Cook et al. | |
| 6,166,197 A | 12/2000 | Cook et al. | |
| 6,172,209 B1 | 1/2001 | Manoharan et al. | |
| 6,262,241 B1 | 7/2001 | Cook et al. | |
| 6,271,358 B1 | 8/2001 | Manoharan et al. | |
| 7,056,704 B2 | 6/2006 | Tuschl et al. | |
| 7,078,196 B2 | 7/2006 | Tuschl et al. | |
| 8,058,255 B2 | 11/2011 | Ford et al. | |
| 8,084,600 B2 | 12/2011 | Natt et al. | |
| 8,097,716 B2 | 1/2012 | Weiler et al. | |
| 8,344,128 B2 | 1/2013 | Natt et al. | |
| 8,404,831 B2 | 3/2013 | Natt et al. | |
| 8,404,832 B2 | 3/2013 | Natt et al. | |
| 8,809,293 B2 | 8/2014 | Chin et al. | |
| 2003/0124651 A1 | 7/2003 | Pasupuleti et al. | |
| 2003/0143732 A1 | 7/2003 | Fosnaugh et al. | |
| 2003/0206887 A1 | 11/2003 | Morissey et al. | |
| 2003/0232802 A1 | 12/2003 | Heil et al. | |
| 2004/0053875 A1 | 3/2004 | Kreutzer et al. | |
| 2005/0032733 A1 | 2/2005 | McSwiggen et al. | |
| 2008/0145436 A1 | 6/2008 | Ng et al. | |
| 2009/0209626 A1 | 8/2009 | Khvorova et al. | |
| 2010/0127212 A1 | 5/2010 | Lietzau et al. | |
| 2011/0135600 A1 | 6/2011 | Stieber et al. | |
| 2011/0178157 A1* | 7/2011 | Jin | A61K 31/713 514/44 A |
| 2012/0252027 A1* | 10/2012 | Butora | C12N 15/111 435/6.12 |
| 2014/0303232 A1 | 10/2014 | Baryza et al. | |
| 2016/0150787 A1 | 6/2016 | Azuma et al. | |

FOREIGN PATENT DOCUMENTS

| | | |
|---|---|---|
| CN | 102123710 A | 7/2011 |
| EP | 1752536 | 2/2007 |
| EP | 1 407 044 B1 | 9/2007 |
| JP | 2004/526422 | 9/2004 |
| WO | 1991/006309 | 5/1991 |
| WO | 1993/007883 | 4/1993 |
| WO | WO 1994/024116 A1 | 10/1994 |
| WO | WO 1998/038156 A1 | 9/1998 |
| WO | WO 1999/032619 A1 | 7/1999 |
| WO | 2000/022113 | 4/2000 |
| WO | 2000/031105 | 6/2000 |
| WO | WO 2000/044895 A1 | 8/2000 |
| WO | WO 2001/029058 A1 | 4/2001 |
| WO | WO 2001/074763 A1 | 10/2001 |
| WO | WO 2002/044321 A2 | 6/2002 |
| WO | 2003/020931 | 3/2003 |
| WO | WO 2003/070918 A2 | 8/2003 |
| WO | WO2003/10059 A3 | 12/2003 |
| WO | 2005/065719 | 7/2005 |
| WO | WO 2005/060697 A2 | 7/2005 |
| WO | 2005/116204 | 12/2005 |
| WO | 2006/017932 | 2/2006 |
| WO | WO 2007/107162 A2 | 9/2007 |
| WO | WO 2007/128477 A2 | 11/2007 |
| WO | WO 2008/128622 A2 | 10/2008 |
| WO | WO 2008/147824 A2 | 12/2008 |
| WO | WO 2010/017870 A1 | 2/2010 |
| WO | WO2010/032147 A2 | 3/2010 |
| WO | WO 2010/032147 A2 | 3/2010 |
| WO | WO 2010/083384 A2 | 7/2010 |
| WO | 2010/135322 | 11/2010 |
| WO | 2011/003780 | 1/2011 |
| WO | WO2011/034828 A1 | 3/2011 |
| WO | WO 2011/034828 A1 | 3/2011 |
| WO | WO 2011/076807 A2 | 6/2011 |
| WO | WO2012/027206 A1 | 3/2012 |
| WO | WO 2014/136086 A1 | 9/2014 |
| WO | WO 2015/005499 A1 | 1/2015 |
| WO | WO 2015/050871 A2 | 4/2015 |
| WO | WO 2015/051044 A2 | 4/2015 |
| WO | WO2015/051045 | 4/2015 |
| WO | WO 2015/051135 A2 | 4/2015 |
| WO | WO 2015/051366 A2 | 4/2015 |
| WO | WO 2015/095340 A1 | 6/2015 |
| WO | WO 2015/095346 A1 | 6/2015 |
| WO | WO 2016/010840 A1 | 1/2016 |
| WO | WO 2016/037053 A1 | 3/2016 |

OTHER PUBLICATIONS

Ashayev, A.V. et al., "Amide Group Assisted 3'-Dephosphorylation of Oligonucleotides Synthesized on Universal A-Supports," *Tetrahedron*, 57, (2001) pp. 4977-4986.

Bartel, D. P., "MicroRNAs: Target Recognition and Regulatory Functions," *Cell*, 136, (2009), pp. 215-233.

Bentwich, I. et al., "Identification of Hundreds of Conserved and Nonconserved Human MicroRNAs," *Nature Genetics*, vol. 37, No. 7 (2005) pp. 766-770.

Bernstein, E. et al., "Role for a Bidentate Ribonuclease in the Initiation Step of RNA Interference," *Nature*, vol. 409, (2001) pp. 363-366.

Bradsher, C.K. et al., "Synthesis and Fungistatic Activity of Some 3-Hydroxybiphenyl Derivatives," *Journal of the American Chemical Society*, vol. 76, (1954) pp. 2357-2362.

Brodersen, P. et al., "Widespread Translational Inhibition by Plant miRNAs and siRNAs," *Science*, 320, 1185 (2008) pp. 1185-1190.

Choung, S. et al., "Chemical Modification of siRNAs to Improve Serum Stability without Loss of Efficacy," *Biochemical and Biophysical Research Communications*, 342 (2006) pp. 919-927.

Chu, Chia-Ying, et al., "Potent RNAi by Short RNA Triggers," *RNA*, vol. 14, No. 9 (2008) pp. 1714-1719.

Clerici, A. et al., "Facile Reduction of Aromatic Aldehydes, Ketones, Diketones and Oxo Aldehydes to Alcohols by an Aqueous TiCl$_3$/NH$_3$ System: Selectivity and Scope," *Eur. J. Chem.*, 19, (2002) pp. 3326-3335.

Czauderna, F. et al., "Structural Variations and Stabilising Modifications of Synthetic siRNAs in Mammalian Cells," *Nucleic Acids Research*, vol. 31, No. 11, (2003), pp. 2705-2716.

Database Registry (Online), Database Accession No. 2012:1445296 (2012), Chemical Abstracts Service, "Preparation of pyrazole compounds as inhibitors of phosphodiesterase 10A," WO2012133607; XP002736566, pp. 1-3.

Database Registry (Online), Database Accession No. 1349719-03-4 (Dec. 6, 2011), Chemical Catalog; Supplier: Oakwood Products, Inc. XP002736567, 1 pp.

Database Registry (Online), Database Accession No. 1267961-49-8, Abstract, (Mar. 10, 2011), Chemical Catalog; Supplier: Otava Chemicals, XP002736568, 1 pp.

(56) References Cited

OTHER PUBLICATIONS

Database Registry (Online), Database Accession No. 773872-41-6 (Nov. 2, 2004), Chemical Library: Supplier: Rare Chemicals GmbH, XP002736569, 1 pp.

Deleavey, G.F. et al., "Chemical Modification of siRNA," *Current Protocols in Nucleic Acid Chemistry*, Supplement 39 (2009) pp. 16.3.1-16.3.22.

Elbashir, S.M. et al., "Duplexes of 21-Nucleotide RNAs Mediate RNA Interference in Cultured Mammalian Cells," *Nature*, vol. 411, (2001) pp. 494-498.

Elbashir, S.M. et al., "Functional Anatomy of SiRNAs for Mediating Efficient RNAi in *Drosophila melanogaster* Embryo Lysate," *The EMBO Journal*, vol. 20, No. 23, (2001) pp. 6877-6888.

Elbashir, S.M. et al., "RNA Interference is Mediated by 21-and 22-Nucleotide RNAs," *Genes Dev.*, 15, (2001) pp. 188-200.

Frank, F. et al., "Structural Basis for 5'-Nucleotide Base-Specific Recognition of Guide RNA by Human AGO2," *Nature*, vol. 465 (2010) pp. 818-822.

Friedman, R.C. et al., "Most Mammalian mRNAs Are Conserved Targets of MicroRNAs," *Genome Research*, 19, (2009) pp. 92-105.

Guzaev, A. P. et al., "A Conformationally Preorganized Universal Solid Support for Efficient Oligonucleotide Synthesis," *J. Am. Chem. Soc.*, 125, (2003) pp. 2380-2381.

Hadwiger, P. et al., "Chemical Modifications to Achieve Increased Stability and Sensitive Detection of siRNA," *RNA Interference Technology*, Edited by Krishnarao Appasani, Cambridge University Press (2005) pp. 194-206.

Harborth, J. et al., "Sequence, Chemical, and Structural Variation of Small Interfering RNAs and Short Hairpin RNAs and the Effect on Mamalian Gene Silencing," *Antisense and Nucleic Acid Drug Develoopment*, 13:83, (2003) pp. 83-105.

He, L. et al., "MicroRNAs: Small RNAs with a Big Role in Gene Regulation," *Nature Reviews/Genetics*, vol. 5, (2004) pp. 522-531.

Hutvágner, G. et al., "A Cellular Function for the RNA-Interference Enzyme Dicer in the Maturation of the let-7 Small Temporal RNA," *Science*, vol. 293, (2001) pp. 834-838.

International Search Report and Written Opinion for International Patent Application No. PCT/US2014/058705 dated Jun. 12, 2015, 28 pp.

Jackson, A.L. et al., "Expression Profiling Reveals Off-Target Gene Regulation by RNAi," *Nature Biotechnology*, vol. 21, No. 6, (2003) pp. 635-637.

Jia, X. et al., "Iridium Complexes of New NCP Pincer Ligands: Catalytic Alkane Dehydrogenation and Alkene Isomerization," *Chem. Commun.* 50 (2014) pp. 11056-11059.

Kraynack, B. et al., "Small Interfering RNAs Containing Full 2'-O-Methylribonucleotide-Modified Sense Strands Display Argonaute2/eIF2C2-Dependent Activity," *RNA*, 12, (2006) pp. 163-176.

Kumar, R. et al., "Efficient Synthesis of Antisense Phosphorothioate Oligonucleotides Using a Universal Solid Support," *Tetrahedron*, 62, (2006) pp. 4528-4534.

Kusenda, B. et al., "MicroRNA Biogenesis, Functionality and Cancer Relevance," *Biomed Pap Med Fac Univ Palacky Olomouc Czech Repub.*, 150(2), (2006) pp. 205-215.

Layzer, J.M. et al., "In Vivo Activity of Nuclease-Resistant siRNAs," *RNA*, 10, (2004) pp. 766-771.

Lewis, B.P. et al., "Prediction of Mammalian MicroRNA Targets," *Cell Press*, vol. 115 (2003) pp. 787-798.

Lewis, B.P. et al., "Conserved Seed Pairing, Often Flanked by Adenosines, Indicates that Thousands of Human Genes are MicroRNA Targets," *Cell*, vol. 120, (2005) pp. 15-20.

Lim, L.P. et al., "The microRNAs of Caenorhabditis Elegans," *Genes & Development*, 17, (2003) pp. 991-1008.

Lingel, A. et al., "Structure and Nucleic-Acid Binding of the *Drosophila* Argonaute 2 PAZ Domain," *Nature*, vol. 426, (2003) pp. 465-469.

Lingel, A. et al., "Nucleic Acid 3'-end Recognition by the Argonaute2 PAZ Domain," *Nature Structural & Molecular Biology*, vol. 11, No. 6, (2004) pp. 576-577.

Lipardi, C. et al., "RNAi as Random Degradative PCR: siRNA Primers Convert mRNA into dsRNAs that Are Degraded to Generate New siRNAs," *Cell Press*, vol. 107 (2001) pp. 297-307.

Lombardo, A. et al., "Gene Editing in Human Stem Cells Using Zinc Finger Nucleases and Integrase-Defective Lentiviral Vector Delivery," *Nature Biotechnology*, vol. 25, No. 11, (2007) pp. 1298-1306.

Ma, J-B. et al., "Structural Basis for Overhang-Specific Small Interfering RNA Recognition by the PAZ Domain," *Nature*, 429: 318-322 (2004) pp. 1-12.

Macrae, I.J. et al., "Structural Basis for Double-Stranded RNA Processing by Dicer," *Science*, 13 (2006) pp. 195-198. Reproduced in RNA: Collection, a booklet from *Science*, at pp. 16-22.

Martin, V.P. "38. Ein neuer Zugang zu 2'-0-Alkylribonucleosiden und Eigenschaften deren Oligonucleotide," *Helvetica Chimica Acta*, vol. 78 (1995) pp. 486-504. (Abstract in English).

Mor, M. et al., "Cyclohexylcarbamic Acid 3'- or 4'-Substituted Biphenyl-3-yl Esters as Fatty Acid Amide Hydrolase Inhibitors: Synthesis, Quantitative Structure-Activity Relationships, and Molecular Modeling Studies," *J. Med. Chem.*, 47, (2004) pp. 4998-5008.

Morrissey, D.V. et al., "Potent and Persistent in vivo anti-HBV Activity of Chemically Modified siRNAs," *Nature Biotechnology*, vol. 23, No. 8, (2005) pp. 1002-1007.

Myers, J.W. et al., "Dicer in RNAi: Its Roles in vivo and utility in vitro," *RNA Interference Technology*, Edited by: Krishnarao Appasani, Cambridge University Press, pp. 29-54.

Nykanen, A. et al., "ATP Requirements and Small Interfering RNA Structure in the RNA Interference Pathway," *Cell*, vol. 107, (2001) pp. 309-321.

Parker, J.S. et al., "Structural Insights into mRNA Recognition from a PIWI Domain-siRNA Guide Complex," *Nature*, 434(7033) (2005) pp. 663-666. Reproduced in Europe PMC Founders Group pp. 1-8.

Pon, R. T. et al., "Hydroquinone-O,O'-diacetic Acid ('Q-linker') as a Replacement for Succinyl and Oxalyl Linker Arms in Solid Phase Oligonucleotide Synthesis," *Nucleic Acids Research*, vol. 25, No. 18, (1997) pp. 3629-3635.

Sato, A. et al., "Polymer Brush-Stabilized Polyplex for a siRNA Carrier with Long Circulatory Half-Life," *Journal of Controlled Release*, 122, (2007) pp. 209-216.

Schwarz, D.S. et al., "Evidence that siRNAs Function as Guides, Not Primers, in the *Drosophila* and Human RNAi Pathways," *Molecular Cell*, vol. 10, (2002) pp. 537-548.

Senzer, N. et al., "Phase I Trial of "bi-shRNAi$^{furin}$/GMCSF DNA/Autologous Tumor Cell" Vaccine (FANG) in Advanced Cancer," *Molecular Therapy*, vol. 20, No. 3., (2012) pp. 679-686.

Schauer, S.E. et al., DICER-LIKE1: Blind Men and Elephants in *Arabidopsis* Development, *TRENDS in Plant Science*, vol. 7, No. 11, (2002) pp. 487-491.

Scott, S. et al., "Innovation and Perspectives in Solid Phase Synthesis," *Ed Roger Epton, Mayflower Worldwide* (1994) pp. 115-124.

Seung-H.K. et al., "2-Pyridyl and 3-Pyridylzinc Bromides: Direct Preparation and Coupling Reaction," *Tetrahedron*, 66 (2010) pp. 3135-3146.

Sharp, P.A., "RNA Interference—2001," *Genes & Development*, 15, (2001) pp. 485-490.

Song, Ji-Joon, et al., "The Crystal Structure of the Argonaute2 PAZ Domain Reveals an Rna Binding Motif in RNAi Effector Complexes," *Nature Structural Biology*, vol. 10, No. 12, (2003) pp. 1026-1032.

Song, E. et al., "RNA Interference Targeting Fas Protects Mice from Fulminant Hepatitis," *Nature Medicine*, vol. 9, No. 3. (2003) pp. 347-351.

Sun, X. et al., "Asymmetric RNA Duplexes Mediate RNA Interference in Mammalian Cells," *Nature Biotechnology*, vol. 26, No. 12, (2008) pp. 1379-1382.

Terrazas, M. et al., "RNA Major Groove Modifications Improve siRNA Stability and Biological Activity," *Nucleic Acids Research*, vol. 37, No. 2. (2009) pp. 346-353.

Wang, Z. et al., "RNA Interference and Cancer Therapy," *Pharm. Res.*, 28, (2011) pp. 2983-2995.

Xiang, S. et al., "Short Hairpin RNA-Expressing Bacteria Elicit RNA Interference in Mammals," *Nature Biotechnology*, vol. 24, No. 6, (2006) pp. 697-702.

(56) References Cited

OTHER PUBLICATIONS

Yamato, K. et al., "Enhanced Specificity of HPV16 E6E7 siRNA by RNA-DNA Chimera Modification," *Cancer Gene Therapy*, 18, (2011) pp. 587-597.
Yan, K. S. et al., "Structure and Conserved RNA Binding of the PAZ Domain," *Nature*, vol. 426, (2003) pp. 469-474.
Zamore, P.D. et al., "Ribo-gnome: The Big World of Small RNAs," *Science*, 309 (2005) pp. 1519-1524.
Zamore, P.D. et al., "RNAi: Double-Stranded RNA Directs the ATP-Dependent Cleavage of mRNA at 21 to 23 Nucleotide Intervals," *Cell*, vol. 101, (2000) pp. 25-33.
Zendegui, J.G. et al., "In Vivo Stability and Kinetics of Absorption and Disposition of 3' Phosphopropyl Amine Oligonucleotides," *Nucleic Acids Research*, vol. 20, No. 2, (1992) pp. 307-314.
Zhang, H. et al., "Single Processing Center Models for Human Dicer and Bacterial RNase III," *Cell*, vol. 118, (2004) pp. 57-68.
Zhang, R. et al., "Small But Influential: The Role of MicroRNAs on Gene Regulatory Network and 3'UTR Evolution," *J. Genet. Genomics*, 36 (2009) pp. 1-6.
Chinese Office Action dated Jun. 16, 2017 and English Translation.
RN 773872-85-8, ACS, STN Registry Database, Nov. 2, 2004; RN 19172410-4, ACS, STN Registry Database, Jul. 25, 1997.
Kayo Yoshikawa, et al., "Incorporation of Biaryl Units into 5' and 3' Ends of Sense and Antisense Strands of si RNA Duplexes Improves Strand Selectivity and Nuclease Resistance," Bioconjugate Chemistry, vol. 22, No. 1, pp. 42-49, published on Dec. 9, 2010.
Dande, Prasad, et al., "Improving RNA Interference in Mammalian Cells by 4'-Thio-Modified Small Interfering RNA (siRNA): Effect on siRNA Activity and Nuclease Stability When Used in Combination with 2'-O-Alkyl Modifications," J. Med. Chem., 2006, 49, pp. 1624-1634.
Al-Anouti, Fatme, et al., "Comparative Analysis of Antisense RNA, Double-Stranded RNA, and Delta Ribozyme-Mediated Gene Regulation in *Toxoplasma gondii*," Antisense and Nucleic Acid Drug Development, 12, 2002, pp. 275-281.
Bass, Brenda L., "The Short Answer," News and Views, Macmillan Magazines Ltd, 2001, Nature, vol. 411, pp. 428-429.
Beigelman, Leonid, et al., "Chemical Modification of Hammerhead Ribozymes," Catalytic Activity and Nuclease Resistance, the Journal of Biological Chemistry, The American Society for Biochemistry and Molecular Biology, Inc., 1995, vol. 270, No. 43, Issue of Oct. 27, pp. 25702-2708.
Braasch, Dwaine A., et al., "Novel Antisense and Peptide Nucleic Acid Strategies for Controlling Gene Expression," Biochemistry, The American Chemical Society, 2002, vol. 41, No. 14, pp. 4503-4510.
Braasch, Dwain A., et al., "RNA Interference in Mammalian Cells by Chemically-Modified RNA," Biochemistry, 2003, 42, pp. 7967-7975.
Bramsen, Jesper B., et al., "A large-scale chemical modification screen identifies design rules to generate siRNAs with high activity, high stability and low toxicity," Nucleic Acids Research, 2009, vol. 37, No. 9, pp. 2867-2881 and supplementary Figures.
Chiu, Ya-Lin, et al., "Visualizing a Correlation between siRNA Localization, Cellular Uptake, and RNAi in Living Cells," Chemistry & Biology, vol. 11, 2004, pp. 1165-1175.
Chiu, Ya-Lin, et al., "siRNA function in RNAi: A chemical modification analysis," RNA Society, 2003, 9, pp. 1034-1048.
Corey, David R., "Chemical modification: the key to clinical application of RNA interference?," The Journal of Clinical Investigation, vol. 117, No. 12, 2007, pp. 3615-3622.
Crooke, Rosanne M., "Metabolism of Antisense Oligonucleotides in Rat Liver Homogenates," The Journal of Pharmacology and Experimental Therapeutics, 2000, vol. 292, No. 1, pp. 140-149.
"Pre-Synthesis Labeling of Aminomodifier C3 or C7 CPG," Glen Research (Sterling VA).
Dorsett, Yair, "siRNAs: Applications in Functional Genomics and Potential as Therapeutics," 2004, vol. 3, pp. 318-329.
Hoerter et al. "siRNA-Like Double-Stranded RNAs are Specifically Protected Against Degradation in Human Cell Extract," PLoS One, vol. 6, Issue 5, May 27, 2011, pp. 1-9.
International Search Report of PCT/US2014/058314.
International Search Report of PCT/US2014/059301.
Kawasaki, Hiroaki, et al., "World of small RNAs: from ribozymes to siRNA and miRNA," International Society of Differentiation, 2004, 72, pp. 58-64.
Khan, Alim, et al., "Sustained Polymeric Delivery of Gene Silencing Antisense ODNs, siRNA, DNAzymes an dRibozymes: In Vitro and In Vivo Studies," Journal of Drug Targeting, Jul. 2004, vol. 12, 6, pp. 393-404.
Kim, Sun Hwa, et al., "Local and systemic delivery of VEGF siRNA using polyelectrolyte complex micelles for effective treatment of cancer," Journal of Controlled Release, 129, 2008, pp. 107-116.
Miyagishi, Makoto, et al., "Comparison of the Suppressive Effects of Antisense Oligonucleotides and siRNAs Directed Against the Same Targets in Mammalian Cells," Antisense and Nucleic Acid Drug Development, 13, 2003, pp. 1-7.
Parrish, Susan, et al., "Functional anatomy of a dsRNA Trigger: Differential Requirement for the Two Trigger Strands in RNA Interference," Molecular Cell, vol. 6, 2000, pp. 1077-1087.
Prakash, Thazha, P., "Positional Effect of Chemical Modifications on Short Interference RNA Activity in Mammalian Cells," J. Med. Chem., 2005, 48, pp. 4247-4253.
Shah, Samit, et al., "An ESI-MS method for characterization of native and modified oligonucleotides used for RNA interference and other biological applications," Nature Protocol, Division of Pharmaceutical Sciences, vol. 3, No. 3, 2008, pp. 351-356.
Sioud, M., Ribozymes and siRNAs: From Structure to Preclinical Applications, HEP, 2006, 173: pp. 223-242.
Takahashi, Mayumi, et al., "Synthesis and characterization of 2'-modified-4'-thioRNA: a comprehensive comparison of nuclease stability," Nucleic Acids Research, 2009, vol. 37, No. 4, pp. 1353-1362.
Tavernarakis, Nektarios, et al., "Heritable and inducible genetic interference by double-stranded RNA encoded by transgenes," Nature America Inc., 2000, vol. 24, pp. 180-183.
Zhang, Y-L, et al., "RNA Interference inhibits hepatitis B virus of different genotypes in vitro and in vivo," BMC Microbiol. 2010, vol. 10:214, p. 1-10.
Akhtar S., et al., "Nonviral delivery of synthetic siRNAs in vivo," Journal of Clinical Investigation (2007) 117: 3623-3632.
Atherton E., et al., "The Fluorenylmethoxycarbonyl Amino Protecting Group," The Peptides, S. Udenfriend, J. Meienhofer, Eds., Academic Press, Inc. (1987) 9: 138.
Berkner KL et al., "Development of adenovirus vectors for the expression of heterologous genes," BioTechniques (1988) 6: 616-629.
Bucchini D et al., "Pancreatic expression of human insulin gene in transgenic mice," Proc. Natl. Acad. Sci. USA (1986) 83: 2511-2515.
Cook PD, "Medicinal Chemistry of Antisense Oligonucleotides-Future Opportunities," Anti-Cancer Drug Design (1991) 6: 585-607.
Chen S-H et al., "Gene therapy for brain turners: Regression of experimental gliomas by adenovirus-mediated gene transfer in vivo," Proc. Natl. Acad. Sci. USA (1994) 91: 3054-3057.
Cone RD et al., "High-efficiency gene transfer into mammalian cells: Generation of helper-free recombinant retrovirus with broad mammalian host range," Proc. Natl. Acad. Sci. USA (1984) 81: 6349-6353.
Cornetta K et al., "Safety tissues related to retroviral-mediated gene transfer in humans," Human Gene Therapy (1991) 2: 5-14.
Crooke et al., "Pharmacokinetic Properties of Several Novel Oligonucleotide Analogs in Mice," J. Pharmacal. Exp. Ther. (1996), 277: 923-927.
Danos O et al., "Safe and efficient generation of recombinant retroviruses with amphotropic and ecotropic host ranges," Proc. Natl. Acad. Sci. USA (1988) 85: 6460-6464.
Delgado C et al., "The Uses and Properties of PEG-Linked Proteins," Critical Reviews in Therapeutic Drug Carrier Systems (1992) 9(3,4): 249-304.

(56) References Cited

OTHER PUBLICATIONS

Docherty K et al., "Nutrient regulation of insulin gene expression," FASEB J. (1994) 8: 20-24.

Englisch U et al., "Chemically Modified Oligonucleotides as Probes and Inhibitors," Angewandte Chemie, International Edition (1991) 30(6): 613-629.

Gassmann M et al., "Maintenance of an extrachromosomal plasmid vector in mouse embryonic stem cells," Proc. Natl. Acad. Sci. USA (1995) 92: 1292-1296.

Kroschwitz JL, "Monomers," Encyclopedia of Polymer Science and Engineering, John Wiley & Sons, New York, pp. 715-727, 2007.

Greene et al., Protective Groups in Organic Synthesis, Chapter 2, 2d ed., John Wiley & Sons, New York, 1991, and Oligonucleotides and Analogues A Practical Approach, Ekstein, F. Ed., IRL Press, N.Y., 1991.

Hamm ML et al., "Incorporation of 2'-Deoxy-2'-mercaptocytidine into Oligonucleotides via Phosphoramidite Chemistry," J.Org. Chem. (1997) 62: 3415-3420.

Hsu K-HL et al., "Immunogenicity of Recombinant Adenovirus-Respiratory Syncytial Virus Vaccines with Adenovirus Types 4, 5, and 7 Vectors in Dogs and a Chimpanzee," J. Infectious Disease, (1992) 166: 769-775.

Kabanov, et al., "A new class of antivirals; antisense oligonucleotides combined with a hydrophobic substituent effectively inhibit influenza virus reproduction and synthesis of virus-specific proteins in MDCK cells," FEBS Lett. (1990) 259: 327-330.

Letsinger RL et al., "Cholesteryl-conjugated oligonucleotides: Synthesis, properties, and activity as inhibitors of replication of human immunodeficiency virus in cell culture," Proc. Natl. Acad. Sci. USA (1989) 85: 5553-5556.

Li S et al., "Folate-Mediated Targeting of Antisense Oligodeoxynucleotides to Ovarian Cancer Cells," Pharmaceutical Research (1998) 15(10): 1540-4545.

Manoharan M et al., "Chemical Modifications to Improve Uptake and Bioavailability of Antisense Oligonucleotides," Ann. N.Y. Acad. Sci. (1992) 660: 306-309.

Manoharan M et al., "Introduction of a Lipophilic Thioether Tether in the Minor Groove of Nucleic Acids for Antisense Applications," Bioorg. & Med. Chem. Letters (1993) 3: 2765-2770.

Manoharan M et al., "Cholic Acid-Oligonucleotide Conjugates for Antisense Applications," Bioorg. Med. & Chem. Lett. (1994) 4: 1053-1060.

Manoharan M et al., "Oligonucleotide Conjugates: Alteration of the Pharmacokinetic Properties of Antisense Agents," Nucleosides & Nucleotides (1995) 14: 969-973.

Manoharan M et al., "Lipidic Nucleic Acids," Tetrahedron Letters (1995) 36: 3651-3654.

Manoharan M., "Oligonucleotide Conjugates as Potential Antisense Drugs with Improved Uptake, Biodistribution, Targeted Delivery, and Mechanism of Action," Antisense & Nucleic Acid Drug Devel. (2002) 12: 103-128.

Mishra RK et al., "Improved leishmanicidal effect of phosphorothioate antisense oligonucleotides by LDL-mediated delivery," Biohim. et Biophysica Acta (1995) 1264: 229-237.

Nawrot B et al., "Chemical and Structural Diversity of siRNA Molecules," Current Topics in Medicinal Chemistry (2006) 6: 913-925.

Nguyen T et al., "RNAi therapeutics: an update on delivery," Current Opinion in Molecular Therapeutics (2008) 10(2): 158-167.

Oberhauser et al., "Effective incorporation of 2'-O-methyl-oligoribonucleotides Into Liposomes an dEnhanced Cell Association Through Modification with Tiocholesterol," Nucl. Acids Research (1992) 20: 533-538.

Polisuin NN et al., "Synthesis of Oligonucleotides Containing 2'-Azido-and2'-amino-2'deoxyuridine Using Phosphotriester Chemistry," Tetrahedron Letters (1996) 37(19): 3227-3230.

Rosenfeld MA et al., "Adenovirus-mediated transfer of a recombinant alpha 1-antitrypsin gene to the lung epithelium in vivo," Science (1991) 252: 431-434.

Saison-Behmoaras et al., "Short Modified Antisense Oligonucleotides Directed Against Ha-ras Point Mutation Induce Selective Cleavage of the mRNA and Inhibit T24 Cells Proliferation," The EMBO Journal (1991) 10: 1111-1118.

Samukov VV et al., "2-(4-Nitrophenyl)sulfonylethoxycarbonyl (Nsc) Group as a Base-Labile α-Amino Protection for Solid Phase Peptide Synthesis," Tetrahedron Letters (1994) 35(42): 7821-7824.

Shea et al., "Synthesis, Hybridzation Properties and Antiviral Activity of Lipid-oligodeoxynucleotide Conjugates," Nucl. Acids Research (1990) 18: 3777-3783.

Svinarchuk et al., "Inhibition of HIV proliferation in MT-4 cells by antisense oligonucleotide conjugated to lipophilic groups," Biochimie (1993) 75: 49-54.

Thomson JB et al., "Synthesis and Properties of Diuridine Phosphate Analogues Containing Thio and Amino Modifications," J. Org. Chem. (1996) 61: 6273-6281.

Wagner RW, "The state of the art in antisense research," Nature Medicine (1995) 1(11): 1116-1118.

Williams DJ et al., "Thermodynamic Comparison of the Salt Dependence of Natural RNA Hairpins and RNA Hairpins with Non-Nucleotide Spacers," Biochemistry (1996) 35: 14665-14670.

Zamboni, "Liposomal, Nanoparticle, and Conjugated Formulations of Anticancer Agents," Clin. Cancer Res. (2005) 11: 8230-8234.

Ikeda et al, "Ligand-Targeting Delivery of Therapeutic siRNA," Pharmaceutical Research (2006) 23: 1631-1640.

Rosenfeld MA et al., "In vivo transfer of the human cystic fibrosis transmembrane conductance regulator gene to the airway epithelium," Cell (1992) 68(1): 143-155.

Sanghvi, Antisense Research and Applications, (1993) Chapter 15, p. 289-302, Crook ST and Lebleu B ed., CRC Press.

Genbank Accession Nos. AP007263 AB 602818, AB644286, and 2010 AB554024.

Japanese Office Action with translation dated Jul. 10, 2018.

Brizzi, Antonella, et al., "Synthesis of new anandamide related compounds," Bollettino Chimico Farmaceutico, 2005, 144(4), e1/1-e1/19.

Berst, F., et al., "A latent aryl hydrazine 'safety-catch' linker compatible with N-alkylation," Tetrahedron Letters, 2000, 41(34), 6649-6653.

Database Registry, Apr. 23, 2008, RN 1016749-67-9, Retrieved from STN international [online]; retrieved on Apr. 27, 2018.

Database Registry, Apr. 23, 2008, RN 1016512-00-7, Retrieved from STN international [online]; retrieved on Apr. 27, 2018.

Chinese Office Action with translation dated Dec. 5, 2017.

* cited by examiner

FIG. 1

```
   5'-NNNNNNNNNNNNNNNNNNNN-X-3'
3'-X-NNNNNNNNNNNNNNNNNNNN-5'
```

A12S17 modification scheme

```
   5'-UUuAAUUGAAACcAAGACA-X-3' antisense mF7-3
3'-X-AAAuuAAcuuuGGuucuGu-5' sense
```

X = C3, C6, C12, glycol, cyclohex, phenyl, biphenyl, lithochol (lithocholic acid), C7 amino, C3 amino A = 2'-MOE A; u = 2'-OMe
C = 2'-MOE (5-Me)C; c = 2'-Ome

FIG. 6A

Lead-Optimization 18mers hs_HAMP_400 +_402
Guide

| | Format | Pos | P1 | P2 | P3 | P4 | P5 | P6 | P7 | P8 | P9 | P10 | P11 | P12 | P13 | P14 | P15 | P16 | P17 | P18 | P19 | OV20 | OV21 |
|---|---|---|---|---|---|---|---|---|---|---|---|---|---|---|---|---|---|---|---|---|---|---|---|
| 400 18mer | A106S42 | 400 | T | A | t | t | C | C | A | A | G | A | C | C | t | A | t | G | | | ribp | C6 | |
| | A107S42 | 400 | | A | t | t | C | C | A | A | G | A | C | C | t | A | t | G | | | ribp | C6 | |
| | A107*S42 | 400 | | A | t | t | C | c | A | A | G | A | c | C | t | A | t | G | | | ribp | C6 | |
| | A107*3'X058_pos4_DNA_S42 | 400 | | A | t | | C | c | A | A | G | A | c | C | t | A | t | G | | | ribp | X058 | |
| | A107*3'X058_pos7_DNA_S42 | 400 | | A | t | t | C | c | | A | G | A | c | C | t | A | t | G | | | ribp | X058 | |
| | A107*3'X058_pos8_DNA_S42 | 400 | | A | t | t | C | c | A | | G | A | c | C | t | A | t | G | | | ribp | X058 | |
| 402 18mer | A106S42 | 402 | T | T | t | A | t | t | C | C | A | A | G | A | C | C | t | A | | | ribp | C6 | |
| | A107S42 | 402 | | T | t | A | t | t | C | C | A | A | G | A | C | C | t | A | | | ribp | C6 | |
| | A107*S42 | 402 | | T | t | A | t | t | C | c | A | A | G | A | c | C | t | A | | | ribp | C6 | |
| | A107*_3'X058_pos2_DNA_S42 | 402 | | | t | A | t | t | C | c | A | A | G | A | c | C | t | A | | | ribp | X058 | |
| | A107*_3'X058_pos4_DNA_S42 | 402 | | T | t | | t | t | C | c | A | A | G | A | c | C | t | A | | | ribp | X058 | |
| | A107*_3'X058_pos2,4_DNA_S42 | 402 | | | t | | t | t | C | c | A | A | G | A | c | C | t | A | | | ribp | X058 | |
| 400 21mer endo-light | 21mer A22S26 | 400 | T | A | T | T | C | c | A | A | G | A | C | C | t | A | T | G | T | T | C | u | u |

FIG. 6B

Sense

| S1 | S2 | S3 | S4 | S5 | S6 | S7 | S8 | S9 | S10 | S11 | S12 | S13 | S14 | S15 | S16 | S17 | S18 | S19 | OV20 | OV21 |
|----|----|----|----|----|----|----|----|----|-----|-----|-----|-----|-----|-----|-----|-----|-----|-----|------|------|
|    | A  | A  | c  | A  | t  | A  | G  | G  | t   | c   | t   | t   | G   | G   | A   | A   |     |     | ribp | c6   |
|    | A  | A  | c  | A  | t  | A  | G  | G  | t   | c   | t   | t   | G   | G   | A   | A   |     |     | ribp | c6   |
|    | A  | A  | c  | A  | t  | A  | G  | G  | t   | c   | t   | t   | G   | G   | A   | A   |     |     | ribp | c6   |
|    | A  | A  | c  | A  | t  | A  | G  | G  | t   | c   | t   | t   | G   | G   | A   | A   |     |     | ribp | c6   |
|    | A  | A  | c  | A  | t  | A  | G  | G  | t   | c   | t   | t   | G   | G   | A   | A   |     |     | ribp | c6   |
|    | A  | A  | c  | A  | t  | A  | G  | G  | t   | c   | t   | t   | G   | G   | A   | A   |     |     | ribp | c6   |
|    |    |    |    |    |    |    |    |    |     |     |     |     |     |     |     |     |     |     |      |      |
|    | c  | A  | t  | A  | G  | G  | t  | c  | t   | t   | G   | G   | A   | A   | t   | A   |     |     | ribp | c6   |
|    | c  | A  | t  | A  | G  | G  | t  | c  | t   | t   | G   | G   | A   | A   | t   | A   |     |     | ribp | c6   |
|    | c  | A  | t  | A  | G  | G  | t  | c  | t   | t   | G   | G   | A   | A   | t   | A   |     |     | ribp | c6   |
|    | c  | A  | t  | A  | G  | G  | t  | c  | t   | t   | G   | G   | A   | A   | t   | A   |     |     | ribp | c6   |
|    | c  | A  | t  | A  | G  | G  | t  | c  | t   | t   | G   | G   | A   | A   | t   | A   |     |     | ribp | c6   |
|    | c  | A  | t  | A  | G  | G  | t  | c  | t   | t   | G   | G   | A   | A   | t   | A   |     |     | ribp | c6   |
|    |    |    |    |    |    |    |    |    |     |     |     |     |     |     |     |     |     |     |      |      |
| G  | A  | A  | c  | A  | t  | A  | G  | G  | t   | c   | t   | t   | G   | G   | A   | A   | t   | A   | u    | u    |

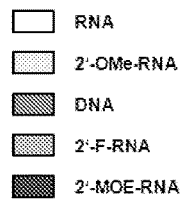

☐ RNA
▨ 2'-OMe-RNA
▨ DNA
▨ 2'-F-RNA
▨ 2'-MOE-RNA

**Hepcidin *in vivo* knockdown – 48 hours post dose**

<u>*Hamp1* specific Taqman Assay*</u>

X058 and C6 Ago2 Pulldown
Hepcidin 18-mer oligonucleotides

*In vivo* comparison of A160 & A161 format

FIG. 11
5'-N NN NNNN NNNNNNN-spacer-L-3'
3'-L-spacer-NN NN N NNNN-5'
| (siRNA 400) | | | 1 | 2 | 3 | 4 | 5 | 6 | 7 | 8 | 9 | 10 | 11 | 12 | 13 | 14 | 15 | 16 | 17 | 18 | | |
|---|---|---|---|---|---|---|---|---|---|---|---|---|---|---|---|---|---|---|---|---|---|---|
| Guide strand | | | | A | u | | C | c | A | A | G | A | c | C | u | A | u | G | | | nbp | X058 |
| Sense strand | C6 | nbp | | | A | A | G | G | u | u | c | u | G | G | A | u | A | c | A | A | | |
| (siRNA 402) | | | 1 | 2 | 3 | 4 | 5 | 6 | 7 | 8 | 9 | 10 | 11 | 12 | 13 | 14 | 15 | 16 | 17 | 18 | | |
|---|---|---|---|---|---|---|---|---|---|---|---|---|---|---|---|---|---|---|---|---|---|---|
| Guide strand | | | | | u | | u | u | C | c | A | A | G | A | c | C | u | A | | | nbp | X058 |
| Sense strand | C6 | nbp | | | A | u | A | A | G | G | u | u | c | u | G | G | A | u | A | c | | |
☐ RNA
▨ 2'-OMe-RNA
▨ DNA
▨ 2'-MOE-RNA
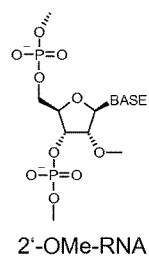
2'-OMe-RNA
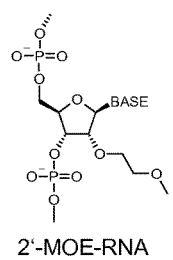
2'-MOE-RNA

FIG. 15B.

‚wt' siRNA:

5`-UCGAAGUACUCAGCGUAAGdTdT-3`
  3`-dTdTAGCUUCAUGAGUCGCAUUC-5`

Modified siRNA:

5`-UCGAAG ACU AGCG AAGdT dT-3`
  3`-dT dTAG    A GAG  G A   -5`

N = RNA    N = 2`-OMe-U/C
dN = DNA    s = phosphorothioate

FIG. 15C.

Canonical 21-mer siRNA:

```
                                    19bp stem
                              ┌─────────────┴─────────────┐
guide strand       5'-N NN NNNN NNNNN NNNN-3'
passenger strand   3'-NN N NN      N    NNN  -5'
```

N: 2'-OMe
N: 2'-MOE
L: 3' end cap 19-mer or 18-mer format:

```
guide strand       5'-N NN NNNN NNNNN NNL-3'
passenger strand   3'-LNN NN    N    NNN  -5'
                       └─────────┬─────────┘
                          18 or 19bp stem
```

FIG. 16B.

| Duplex ID | PAZ ligand | NB ref. label or Nickname |
|---|---|---|
| 20 | X109 | hs_ELAVL1_1186_MAN_S42 |
| 21 | X110 | hs_ELAVL1_1186_MAN_S42 |
| 22 | X111 | hs_ELAVL1_1186_MAN_S42 |
| 23 | X112 | hs_ELAVL1_1186_MAN_S42 |
| 24 | X113 | hs_ELAVL1_1186_MAN_S42 |
| 25 | X058 | hs_ELAVL1_1186_MAN_S42 |
| 26 | 21-mer | hs_ELAVL1_1186_A22_S26 |
| 27 | C6 | hs_ELAVL1_1186_A106_S42 |
| 28 | mHamp | mm_HAMP_254_A106*_3'X058_S42 |

PAZ oligos have a DNA modification on the 5' end of AS strand which is different than X058. This could make a big difference in duration of effect.

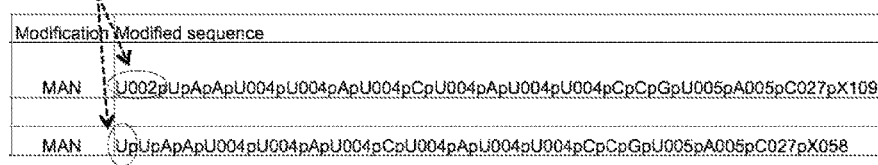

| Modification | Modified sequence |
|---|---|
| MAN | U002pUpApApU004pU004pApU004pCpU004pApU004pU004pCpCpGpU005pA005pC027pX109 |
| MAN | UpUpApApU004pU004pApU004pCpU004pApU004pU004pCpCpGpU005pA005pC027pX058 |

Sequences of guide strands:

| | | |
|---|---|---|
| 10 | UUG AAG UUC ACC UUG AUG CdCdG | |
| 11 | dUUG AAG UUC ACC UUG AUG CdCdG | |
| 12 | dTUG AAG UUC ACC UUG AUG CdCdG | |
| 13 | ddTUG AAG UUC ACC UUG AUG CdCdG | |
| 14 | UCG AAG UAC UCA GCG UAA GdTdT | (neg. control siRNA) |
| 15 | ddTCG AAG UAC UCA GCG UAA GdTdT | (neg. control siRNA) |

I	II	III	IV

FIG. 18A.
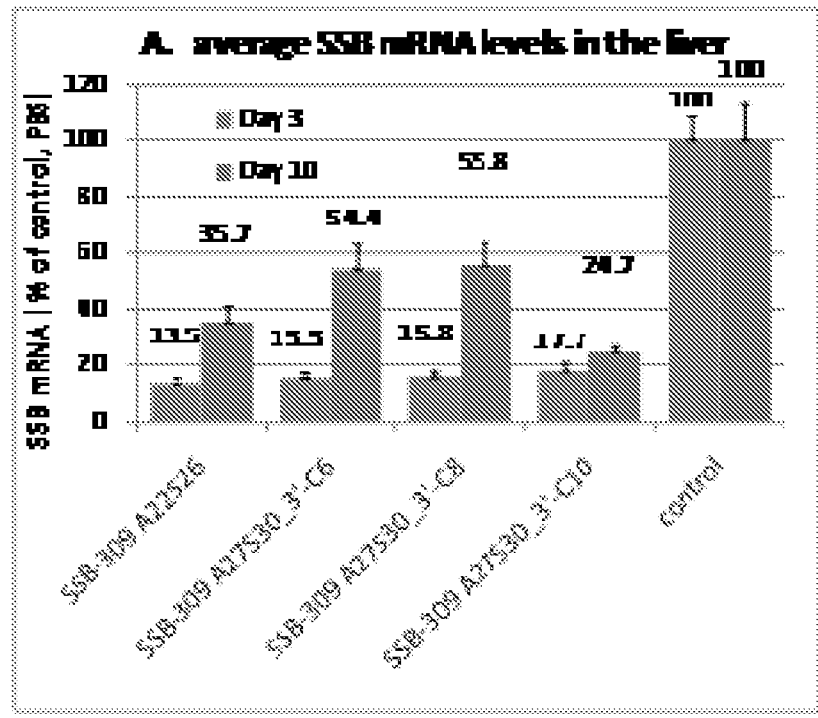
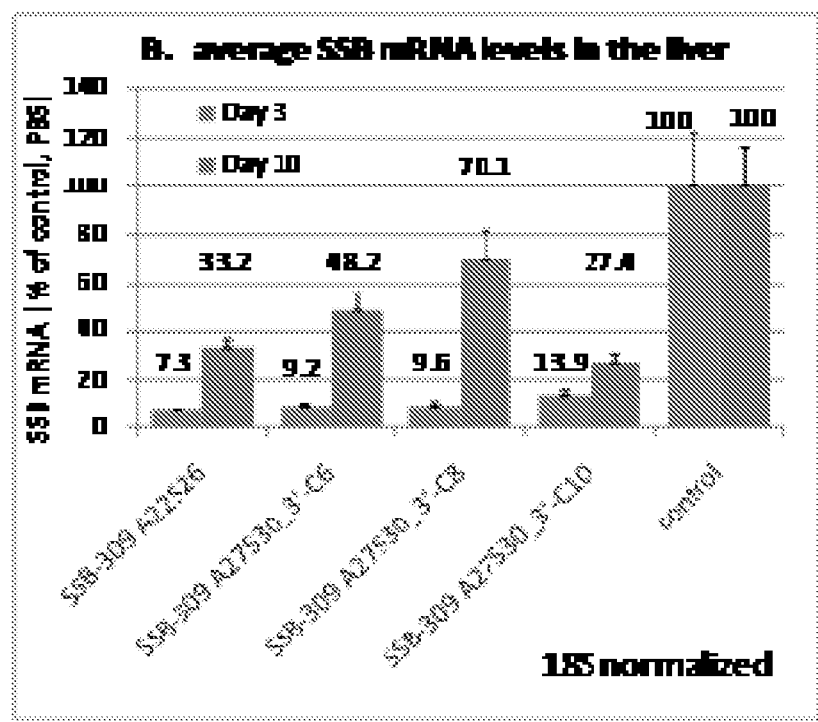

FIG. 18B.
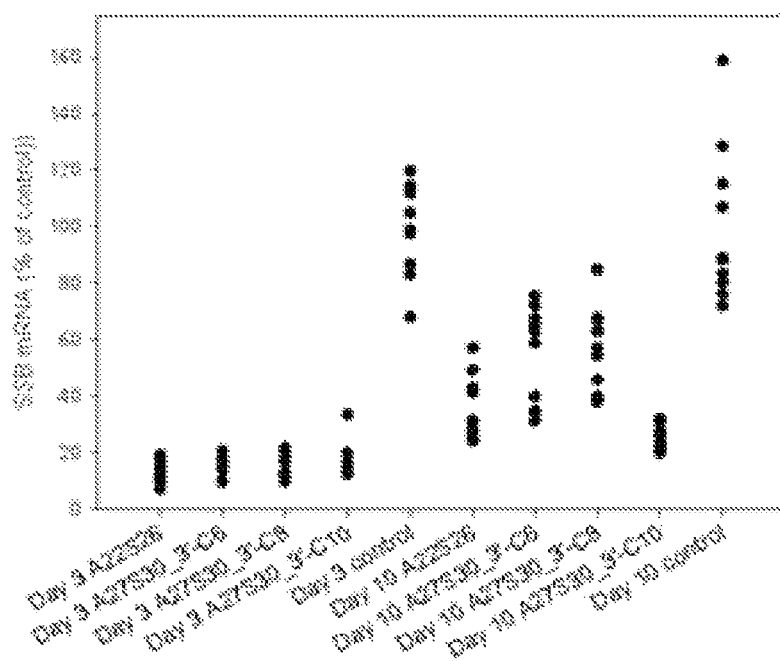
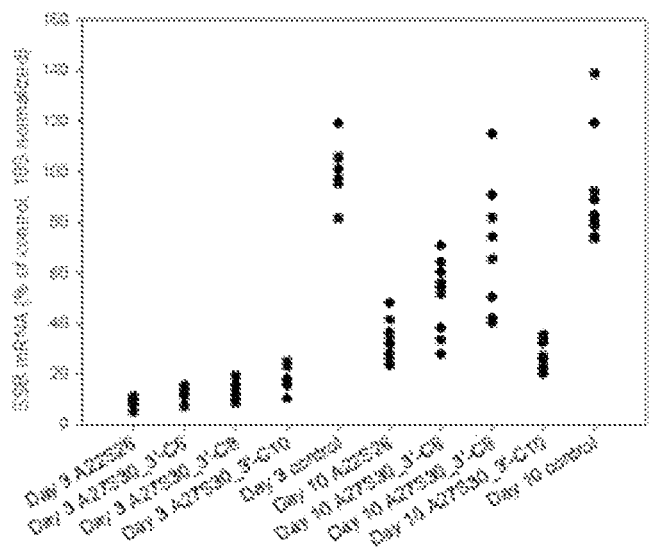

FIG. 18C.
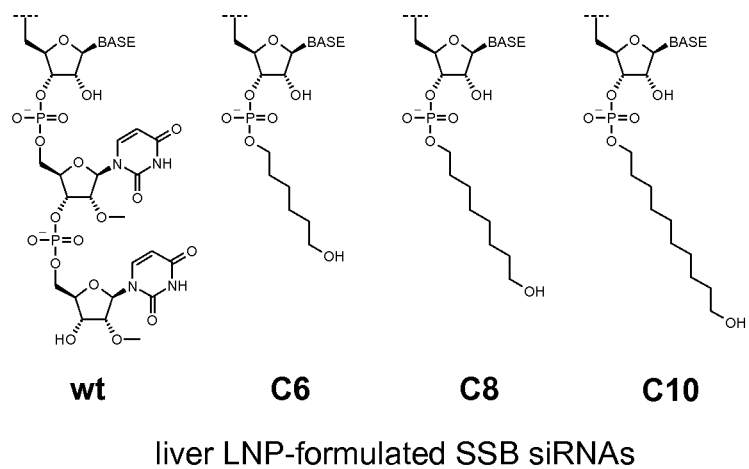
liver LNP-formulated SSB siRNAs
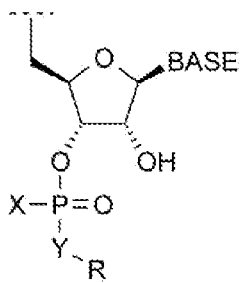
$X = O^-, S^-, NH_2, BH_3, CH_3$, alkyl, aryl, O-alkyl, O-aryl
$Y = O, S, NH, CH_2$
$R =$ alkyl, aryl, alkyl-aryl, aryl-alkyl, ... (PAZ ligand)

FIG. 19.
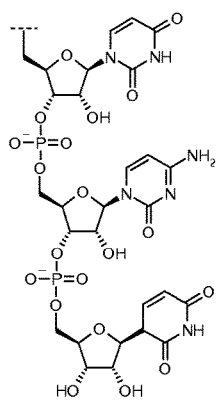
CU overhang
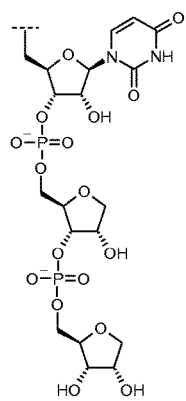
diribitol
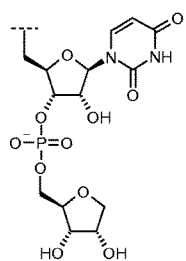
ribitol
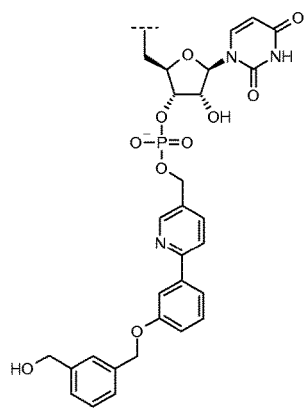
X027
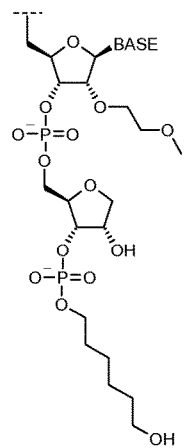
ribitol with C6 cap
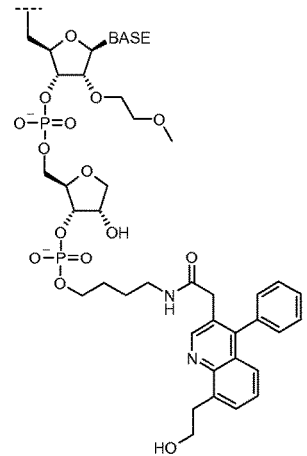
ribitol with X058 cap

FIG. 20A

Four mm_F7 siRNAs with PO or PS linkage to C3 overhang:

```
5'-GUUGG ACGCCUUGCC  C3-3'         mm_F7_154   antisense
3'-C3  A  G G GGAAA GGA    -5'                 sense 5'-AU ACUG AAA AAUC   C3-3'        mm_F7_286   antisense
3'-C3  G A  G  AGG    -5'                      sense 5'-UU AUUGAAAC AAGAC C3-3'         mm_F7_1841  antisense
3'-C3  A AAA       GG  G  -5'                  sense 5'-UUC A AA AGG AUU  C3-3'         mm_F7_574   antisense
3'-C3  GA G G  A AAG G-5'                      sense
```

Control 21-mer siRNAs with dT_PO_dT or dT_PS_dT overhangs:

```
5'-UU AUUUGAAAC AAGACAdTpdT-3'     mm_F7_1841  antisense
3'-dTpdTAAA AAA        GG     -5'              sense 5'-UU AUUUGAAAC AAGACAdT dT-3'     mm_F7_1841  antisense
3'-dT dTAAA AAA        GG     -5'              sense
```

N = RNA    n = 2'-OMe-U/C    W = 2'-MOE    p = PO    p = PS

FIG. 20C

A12S17 blunt-end siRNA format:

5'-UU*AUUGAAAC*AAGA*C*C3-3'   antisense
3'-C3*A*A*AAA*GG*G-5'   sense

N = RNA    n = 2'-OMe-U/C    N = RNA/DNA/2'-OMe/2'-MOE/2'-F/LNA    p = PO/PS

FIG. 21
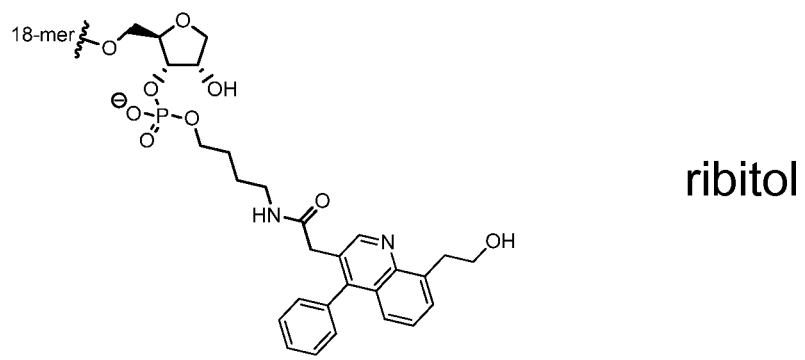
ribitol
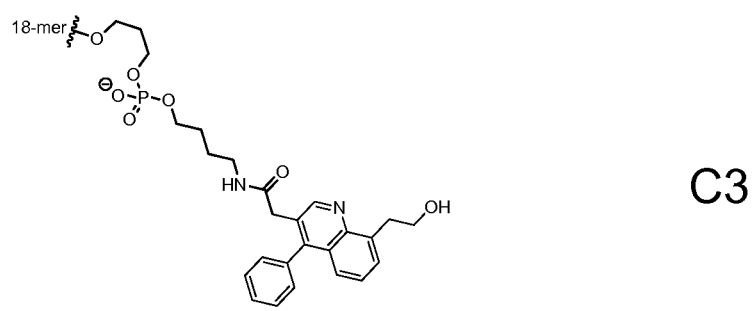
C3
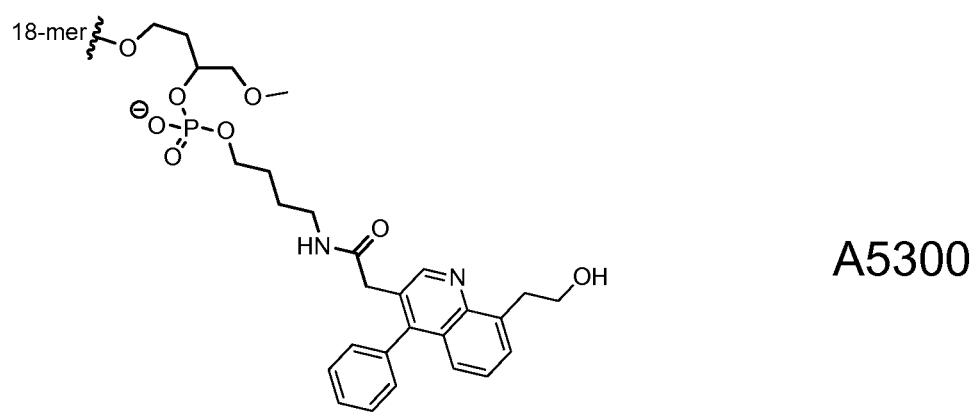
A5300

| Duplex ID | HuR description | IC50 |
|---|---|---|
| 1 | ribitol and X058 (control) | 2.92 pM |
| 2 | ribitol and C6 (control) | 1.48 pM |
| 3 | C3 in place of ribitol and X058 | 11.83 pM |
| 4 | C3 in place of ribitol and C6 | 2.41 pM |
| 5 | C5300 in place of ribitol and X058 | 3.72 pM |
| 6 | C5300 in place of ribitol and C6 | 1.83 pM |

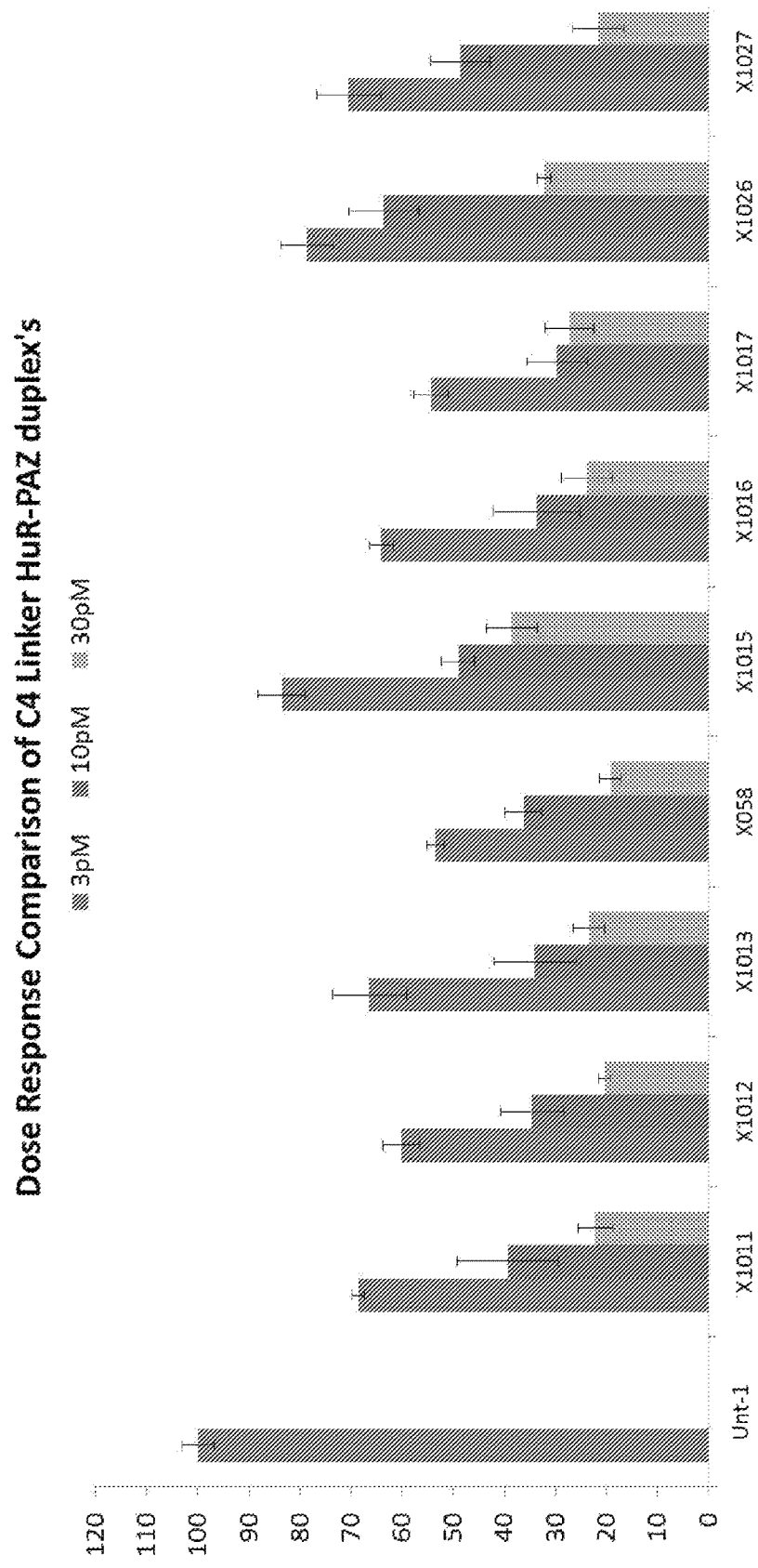

SEQUENCE LISTING

<160> NUMBER OF SEQ ID NOS: 139

<210> SEQ ID NO 1
<211> LENGTH: 19
<212> TYPE: RNA
<213> ORGANISM: Artificial Sequence

```
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(19)
<223> OTHER INFORMATION: a, c, u, g, unknown or other

<400> SEQUENCE: 1
nnnnnnnnnn nnnnnnnnn                                                19

<210> SEQ ID NO 2
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(19)
<223> OTHER INFORMATION: a, c, u, g, unknown or other

<400> SEQUENCE: 2
nnnnnnnnnn nnnnnnnnn                                                19

<210> SEQ ID NO 3
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 3
uuuaauugaa accaagaca                                                19

<210> SEQ ID NO 4
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 4
ugucuugguu ucaauuaaa                                                19

<210> SEQ ID NO 5
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 5
tattccaaga cctatgtt                                                 18
```

-continued

```
<210> SEQ ID NO 6
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 6
tattccaaga cctatgtt                                                   18

<210> SEQ ID NO 7
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 7
tattccaaga cctatgtt                                                   18

<210> SEQ ID NO 8
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 8
tattccaaga cctatgtt                                                   18

<210> SEQ ID NO 9
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 9
tattccaaga cctatgtt                                                   18

<210> SEQ ID NO 10
<211> LENGTH: 18
<212> TYPE: DNA
<213> ORGANISM: Artificial Sequence
```

```
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 10
tattccaaga cctatgtt                                                 18

<210> SEQ ID NO 11
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 11
tttattccaa gacctatg                                                 18

<210> SEQ ID NO 12
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 12
tttattccaa gacctatg                                                 18

<210> SEQ ID NO 13
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 13
tttattccaa gacctatg                                                 18

<210> SEQ ID NO 14
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

<220> FEATURE:
<221> NAME/KEY: source
<223> OTHER INFORMATION: /note="Description of Combined DNA/RNA
      Molecule: Synthetic oligonucleotide"

<400> SEQUENCE: 14
tttattccaa gacctatg                                                    18

<210> SEQ ID NO 15
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 15
tttattccaa gacctatg                                                    18

<210> SEQ ID NO 16
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 16
tttattccaa gacctatg                                                    18

<210> SEQ ID NO 17
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 17
tattccaaga cctatgttcu u                                                21

<210> SEQ ID NO 18
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

```
<400> SEQUENCE: 18
aacataggtc ttggaata                                              18

<210> SEQ ID NO 19
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 19
aacataggtc ttggaata                                              18

<210> SEQ ID NO 20
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 20
aacataggtc ttggaata                                              18

<210> SEQ ID NO 21
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 21
aacataggtc ttggaata                                              18

<210> SEQ ID NO 22
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 22
aacataggtc ttggaata                                              18
```

```
<210> SEQ ID NO 23
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 23
aacataggtc ttggaata                                                  18

<210> SEQ ID NO 24
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 24
cataggtctt ggaataaa                                                  18

<210> SEQ ID NO 25
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 25
cataggtctt ggaataaa                                                  18

<210> SEQ ID NO 26
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 26
cataggtctt ggaataaa                                                  18

<210> SEQ ID NO 27
<211> LENGTH: 18
<212> TYPE: DNA
<213> ORGANISM: Artificial Sequence
```

```
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 27
cataggtctt ggaataaa                                                 18

<210> SEQ ID NO 28
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 28
cataggtctt ggaataaa                                                 18

<210> SEQ ID NO 29
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 29
cataggtctt ggaataaa                                                 18

<210> SEQ ID NO 30
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 30
gaacataggt cttggaatau u                                             21

<210> SEQ ID NO 31
<211> LENGTH: 17
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (1)..(17)
<223> OTHER INFORMATION: a, c, t, u, g, unknown or other

<400> SEQUENCE: 31
nnnnnnnnnn nnnnnnn                                                      17

<210> SEQ ID NO 32
<211> LENGTH: 17
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (1)..(17)
<223> OTHER INFORMATION: a, c, t, u, g, unknown or other

<400> SEQUENCE: 32
nnnnnnnnnn nnnnnnn                                                      17

<210> SEQ ID NO 33
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 33
tautccaaga ccuaugtt                                                     18

<210> SEQ ID NO 34
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 34
aacauagguc uuggaata                                                     18

<210> SEQ ID NO 35
<211> LENGTH: 18
<212> TYPE: DNA
<213> ORGANISM: Artificial Sequence
```

```
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 35
ttuauuccaa gaccuatg                                                  18

<210> SEQ ID NO 36
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 36
cauaggucuu ggaauaaa                                                  18

<210> SEQ ID NO 37
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 37
uuacauuaaa gucuguuguu u                                              21

<210> SEQ ID NO 38
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 38
acaacagacu uuaauguaau u                                              21

<210> SEQ ID NO 39
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 39
uuacauuaaa gucuguugu                                                 19

<210> SEQ ID NO 40
<211> LENGTH: 19
<212> TYPE: RNA
<213> ORGANISM: Artificial Sequence
```

-continued

```
<220> FEATURE:
<221> NAME/KEY: source
<223> OTHER INFORMATION: /note="Description of Artificial Sequence:
      Synthetic oligonucleotide"

<400> SEQUENCE: 40
acaacagacu uuaauguaa                                                    19

<210> SEQ ID NO 41
<211> LENGTH: 18
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 41
uuacauuaaa gucuguug                                                     18

<210> SEQ ID NO 42
<211> LENGTH: 18
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 42
caacagacuu uaauguaa                                                     18

<210> SEQ ID NO 43
<211> LENGTH: 18
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 43
uuacauuaaa gucuguug                                                     18

<210> SEQ ID NO 44
<211> LENGTH: 18
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 44
caacagacuu uaauguaa                                                     18

<210> SEQ ID NO 45
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
```

-continued

```
<220> FEATURE:
<221> NAME/KEY: modified_base
<222> LOCATION: (1)..(19)
<223> OTHER INFORMATION: a, c, t, u, g, unknown or other

<400> SEQUENCE: 45
nnnnnnnnnn nnnnnnnnn                                              19

<210> SEQ ID NO 46
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (1)..(19)
<223> OTHER INFORMATION: a, c, t, u, g, unknown or other

<400> SEQUENCE: 46
nnnnnnnnnn nnnnnnnnn                                              19

<210> SEQ ID NO 47
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (1)..(19)
<223> OTHER INFORMATION: a, c, t, u, g, unknown or other

<400> SEQUENCE: 47
nnnnnnnnnn nnnnnnnnn                                              19

<210> SEQ ID NO 48
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (1)..(19)
<223> OTHER INFORMATION: a, c, t, u, g, unknown or other

<400> SEQUENCE: 48
nnnnnnnnnn nnnnnnnnn                                              19
```

```
<210> SEQ ID NO 49
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 49
ucgaaguacu cagcguaagt t                                              21

<210> SEQ ID NO 50
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 50
cuuacgcuga guacuucgat t                                              21

<210> SEQ ID NO 51
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 51
ucgaaguacu cagcguaagt t                                              21

<210> SEQ ID NO 52
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 52
cuuacgcuga guacuucgat t                                              21

<210> SEQ ID NO 53
<211> LENGTH: 20
<212> TYPE: RNA
<213> ORGANISM: Artificial Sequence
```

<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(20)
<223> OTHER INFORMATION: a, c, u, g, unknown or other

<400> SEQUENCE: 53
nnnnnnnnnn nnnnnnnnnn                                              20

<210> SEQ ID NO 54
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(20)
<223> OTHER INFORMATION: a, c, u, g, unknown or other

<400> SEQUENCE: 54
nnnnnnnnnn nnnnnnnnnn                                              20

<210> SEQ ID NO 55
<211> LENGTH: 18
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(18)
<223> OTHER INFORMATION: a, c, u, g, unknown or other

<400> SEQUENCE: 55
nnnnnnnnnn nnnnnnnn                                                18

<210> SEQ ID NO 56
<211> LENGTH: 18
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(18)
<223> OTHER INFORMATION: a, c, u, g, unknown or other

<400> SEQUENCE: 56
nnnnnnnnnn nnnnnnnn                                                18

<210> SEQ ID NO 57
<211> LENGTH: 18
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

```
<400> SEQUENCE: 57
uuaauuaucu auuccgua                                                18

<210> SEQ ID NO 58
<211> LENGTH: 18
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 58
uuaauuaucu auuccgua                                                18

<210> SEQ ID NO 59
<211> LENGTH: 17
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 59
tauuccaaga ccuautt                                                 17

<210> SEQ ID NO 60
<211> LENGTH: 17
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 60
tauuccaaga ccuautt                                                 17

<210> SEQ ID NO 61
<211> LENGTH: 17
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 61
tauuccaaga ccuautt                                                 17

<210> SEQ ID NO 62
<211> LENGTH: 17
<212> TYPE: DNA
<213> ORGANISM: Artificial Sequence
```

```
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 62
tauuccaaga ccuauutt                                                  17

<210> SEQ ID NO 63
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 63
aacauagguc uuggaata                                                  18

<210> SEQ ID NO 64
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 64
aacauagguc uuggaata                                                  18

<210> SEQ ID NO 65
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 65
aacauagguc uuggaata                                                  18

<210> SEQ ID NO 66
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<220> FEATURE:
<221> NAME/KEY: source
<223> OTHER INFORMATION: /note="Description of Combined DNA/RNA
      Molecule: Synthetic oligonucleotide"

<400> SEQUENCE: 66
aacauagguc uuggaata                                                      18

<210> SEQ ID NO 67
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 67
uugaaguuca ccuugaugcc g                                                  21

<210> SEQ ID NO 68
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 68
uugagguuca ccuugaugcc g                                                  21

<210> SEQ ID NO 69
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 69
tugaaguuca ccuugaugcc g                                                  21

<210> SEQ ID NO 70
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
```

```
<400> SEQUENCE: 70
tugaaguuca ccuugaugcc g                                              21

<210> SEQ ID NO 71
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 71
ucgaaguacu cagcguaagt t                                              21

<210> SEQ ID NO 72
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 72
tcgaaguacu cagcguaagt t                                              21

<210> SEQ ID NO 73
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 73
guuggcacgc cuuugccug                                                 19

<210> SEQ ID NO 74
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 74
caggcaaagg cgugccaac                                                 19

<210> SEQ ID NO 75
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 75
aucacuguaa acaauccag                                                    19

<210> SEQ ID NO 76
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 76
cuggauuguu uacagugau                                                    19

<210> SEQ ID NO 77
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 77
uuuauuugaa accaagaca                                                    19

<210> SEQ ID NO 78
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 78
ugucuugguu ucaaauaaa                                                    19

<210> SEQ ID NO 79
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 79
uucuacaaca gguauucac                                                    19

<210> SEQ ID NO 80
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 80
gugaauaccu guuguagaa                                                    19

<210> SEQ ID NO 81
<211> LENGTH: 21
<212> TYPE: DNA
<213> ORGANISM: Artificial Sequence
```

<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 81
uuuauuugaa accaagacat t                                              21

<210> SEQ ID NO 82
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 82
ugucuugguu ucaaauaaat t                                              21

<210> SEQ ID NO 83
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 83
uuuauuugaa accaagacat t                                              21

<210> SEQ ID NO 84
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 84
ugucuugguu ucaaauaaat t                                              21

<210> SEQ ID NO 85
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

```
<220> FEATURE:
<221> NAME/KEY: source
<223> OTHER INFORMATION: /note="Description of Combined DNA/RNA
      Molecule: Synthetic oligonucleotide"

<400> SEQUENCE: 85
uuuauuugaa accaagaca                                                19

<210> SEQ ID NO 86
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 86
ugucuugguu ucaaauaaa                                                19

<210> SEQ ID NO 87
<211> LENGTH: 18
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 87
uuaauuaucu auuccgua                                                 18

<210> SEQ ID NO 88
<211> LENGTH: 18
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 88
uacggaauag auaauuaa                                                 18

<210> SEQ ID NO 89
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 89
uuaauuaucu auuccgua                                                 18

<210> SEQ ID NO 90
<211> LENGTH: 18
<212> TYPE: DNA
<213> ORGANISM: Artificial Sequence
```

```
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 90
uuacauuaaa gucugutg                                                 18

<210> SEQ ID NO 91
<211> LENGTH: 18
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 91
caacagacuu uaauguaa                                                 18

<210> SEQ ID NO 92
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 92
ugucuugguu ucaauuaaa                                                19

<210> SEQ ID NO 93
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 93
ugucuugguu ucaauuaaa                                                19

<210> SEQ ID NO 94
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 94
ugucuugguu ucaauuaaa                                                19

<210> SEQ ID NO 95
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

<400> SEQUENCE: 95
ugucuugguu ucaauuaaa                                                    19

<210> SEQ ID NO 96
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 96
ugucuugguu ucaauuaaa                                                    19

<210> SEQ ID NO 97
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 97
ugucuugguu ucaauuaaa                                                    19

<210> SEQ ID NO 98
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 98
ugucuugguu ucaauuaaa                                                    19

<210> SEQ ID NO 99
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 99
ugucuugguu ucaauuaaa                                                    19

<210> SEQ ID NO 100
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 100
ugucuugguu ucaauuaaa                                                    19

<210> SEQ ID NO 101
<211> LENGTH: 19
<212> TYPE: RNA
<213> ORGANISM: Artificial Sequence

```
<220> FEATURE:
<221> NAME/KEY: source
<223> OTHER INFORMATION: /note="Description of Artificial Sequence:
      Synthetic oligonucleotide"

<400> SEQUENCE: 101
ugucuugguu ucaauuaaa                                                    19

<210> SEQ ID NO 102
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 102
tcgaagtact cagcgtaagt t                                                 21

<210> SEQ ID NO 103
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 103
ugucuugguu ucaauuaaat t                                                 21

<210> SEQ ID NO 104
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 104
ugucuugguu ucaauuaaa                                                    19

<210> SEQ ID NO 105
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 105
ugucuugguu ucaauuaaa                                                    19

<210> SEQ ID NO 106
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 106
ugucuugguu ucaauuaaa                                              19

<210> SEQ ID NO 107
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 107
ugucuugguu ucaauuaaa                                              19

<210> SEQ ID NO 108
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 108
ugucuugguu ucaauuaaa                                              19

<210> SEQ ID NO 109
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 109
ugucuugguu ucaauuaaa                                              19

<210> SEQ ID NO 110
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 110
ugucuugguu ucaauuaaa                                              19

<210> SEQ ID NO 111
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 111
ugucuugguu ucaauuaaa                                              19

<210> SEQ ID NO 112
<211> LENGTH: 19
<212> TYPE: RNA
<213> ORGANISM: Artificial Sequence
```

```
<220> FEATURE:
<221> NAME/KEY: source
<223> OTHER INFORMATION: /note="Description of Artificial Sequence:
      Synthetic oligonucleotide"

<400> SEQUENCE: 112
ugucuugguu ucaauuaaa                                                    19

<210> SEQ ID NO 113
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 113
ugucuugguu ucaauuaaa                                                    19

<210> SEQ ID NO 114
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 114
ugucuugguu ucaauuaaat t                                                 21

<210> SEQ ID NO 115
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 115
uuuaauugaa accaagaca                                                    19

<210> SEQ ID NO 116
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 116
uuuaauugaa accaagaca                                                    19

<210> SEQ ID NO 117
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 117
uuuaauugaa accaagaca                                                    19

<210> SEQ ID NO 118
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 118
uuuaauugaa accaagaca                                                    19

<210> SEQ ID NO 119
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 119
uuuaauugaa accaagaca                                                    19

<210> SEQ ID NO 120
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 120
uuuaauugaa accaagaca                                                    19

<210> SEQ ID NO 121
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 121
uuuaauugaa accaagaca                                                    19

<210> SEQ ID NO 122
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 122
uuuaauugaa accaagaca                                                    19

<210> SEQ ID NO 123
<211> LENGTH: 19
<212> TYPE: RNA
<213> ORGANISM: Artificial Sequence
```

```
<220> FEATURE:
<221> NAME/KEY: source
<223> OTHER INFORMATION: /note="Description of Artificial Sequence:
      Synthetic oligonucleotide"

<400> SEQUENCE: 123
uuuaauugaa accaagaca                                                    19

<210> SEQ ID NO 124
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 124
uuuaauugaa accaagaca                                                    19

<210> SEQ ID NO 125
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 125
cttacgctga gtacttcgat t                                                 21

<210> SEQ ID NO 126
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 126
uuuaauugaa accaagacat t                                                 21

<210> SEQ ID NO 127
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 127
uuuaauugaa accaagaca                                                    19

<210> SEQ ID NO 128
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 128
uuuaauugaa accaagaca                                                19

<210> SEQ ID NO 129
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 129
uuuaauugaa accaagaca                                                19

<210> SEQ ID NO 130
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 130
uuuaauugaa accaagaca                                                19

<210> SEQ ID NO 131
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 131
uuuaauugaa accaagaca                                                19

<210> SEQ ID NO 132
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 132
uuuaauugaa accaagaca                                                19

<210> SEQ ID NO 133
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 133
uuuaauugaa accaagaca                                                19

<210> SEQ ID NO 134
<211> LENGTH: 19
<212> TYPE: RNA
<213> ORGANISM: Artificial Sequence
```

```
<220> FEATURE:
<221> NAME/KEY: source
<223> OTHER INFORMATION: /note="Description of Artificial Sequence:
      Synthetic oligonucleotide"

<400> SEQUENCE: 134
uuuaauugaa accaagaca                                                    19

<210> SEQ ID NO 135
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 135
uuuaauugaa accaagaca                                                    19

<210> SEQ ID NO 136
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 136
uuuaauugaa accaagaca                                                    19

<210> SEQ ID NO 137
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 137
uuuaauugaa accaagacat t                                                 21

<210> SEQ ID NO 138
<211> LENGTH: 18
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 138
uuaauuaucu auuccgua                                                     18

<210> SEQ ID NO 139
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<220> FEATURE:
<221> NAME/KEY: source
<223> OTHER INFORMATION: /note="Description of Combined DNA/RNA
      Molecule: Synthetic oligonucleotide"

<400> SEQUENCE: 139
tgttacagca tttacagc                                              18
```

3'END CAPS FOR RNAI AGENTS FOR USE IN RNA INTERFERENCE

RELATED APPLICATIONS

This application is the U.S. National Phase under 35 U.S.C. § 371 of International Patent Application No. PCT/US2014/058705, filed Oct. 1, 2014, which claims priority to and the benefit of U.S. Provisional Application Serial No. 61/886,739, filed Oct. 4, 2013.

SEQUENCE LISTING

The instant application contains a Sequence Listing which has been submitted electronically in ASCII format. Said ASCII copy, created on Jan. 21, 2015, is named PAT055438-WO-PCT_SL.txt and is 44,683 bytes in size.

FIELD OF THE INVENTION

The disclosure relates to novel compounds and compositions comprising a RNAi agent comprising a novel compound as a 3' end cap. The disclosure also relates to processes for making such compositions, and methods of making and uses for such compositions, e.g., to mediate RNA interference.

BACKGROUND OF THE INVENTION

RNA interference (RNAi) is a sequence-specific gene silencing mechanism. This process can be induced artificially by introducing into the cell a RNAi agent targeting a particular sequence. Many structures are suitable for RNAi agents, including but not limited to short interfering RNAs (siRNAs). RNAi agents can have any of a variety of structures, including double-stranded RNA, which can be modified.

RNAi agents are desirable for therapeutic use. However, this use is limited by a short duration of activity, sometimes mediated by the degradation of these molecules in blood serum. Naked RNAi agents often have a half-life of minutes. Layzer et al. 2004 RNA 10: 766-771; Choung et al. 2006 Biochem. Biophys. Res. Comm. 342: 919-927; Sato et al. 2007 J. Control. Rel. 122: 209-216.

There thus exists the need for novel modifications for RNAi agents which do not interfere with RNA interference activity, but which increase the activity, biological half-life in blood serum, and/or duration of activity.

RNAi agents with these modifications would be useful in methods of target-specific silencing via the RNA interference mechanism.

BRIEF SUMMARY OF THE INVENTION

In one embodiment, the present disclosure encompasses a compound of formula Ia:

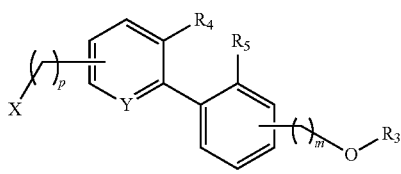

Ia in which:
X is H; OH, wherein the hydroxyl group can optionally be functionalized as succinate or attached to a solid support; ODMT; carboxylic acid; the 3' end of a strand of a RNAi agent; or the 3' end of a molecule comprising a strand of a RNAi agent, wherein the 3' end of the strand terminates in a phosphate or modified internucleoside linker and further comprises in 5' to 3' order: a spacer, and a second phosphate or modified internucleoside linker;
Y is CH or N;
m is 0 or 1;
p is 1, 2 or 3;
$R_3$ is hydrogen, 2-(hydroxy-methyl)-benzyl, 3-(hydroxy-methyl)-benzyl, succinate, or a solid support (e.g., beads or resin);
wherein the $(CH_2)_m$—O—$R_3$ moiety is attached to the phenyl ring at position 3 or 4;
$R_4$ is hydrogen;
$R_5$ is hydrogen; or $R_4$ and $R_5$, together with the phenyl rings to which $R_4$ and $R_5$ are attached, form 6H-benzo[c]chromene.
ODMT is DMT (4,4'-dimethoxytrityl) linked via an oxygen atom.

In various embodiments described herein, a solid support includes, without limitation, bead, resins, or a carrier. A number of suitable solid supports may be employed for immobilization of the compounds. Examples of suitable solid supports include agarose, cellulose, dextran (commercially available as, i.e., Sephadex, Sepharose) carboxymethyl cellulose, polystyrene, polyethylene glycol (PEG), filter paper, nitrocellulose, ion exchange resins, plastic films, polyaminemethylvinylether maleic acid copolymer, glass beads, amino acid copolymer, ethylene-maleic acid copolymer, nylon, silk, etc.

In various embodiment, the compound of formula Ia is selected from Table 1A:

TABLE 1A

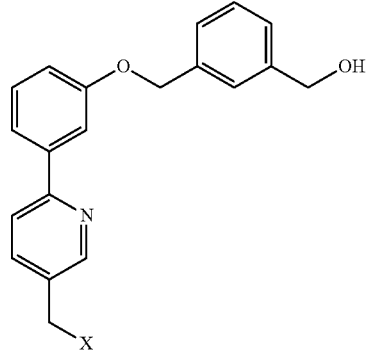

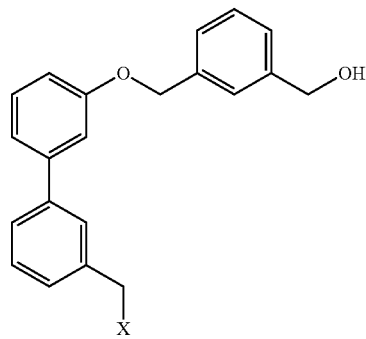

TABLE 1A-continued
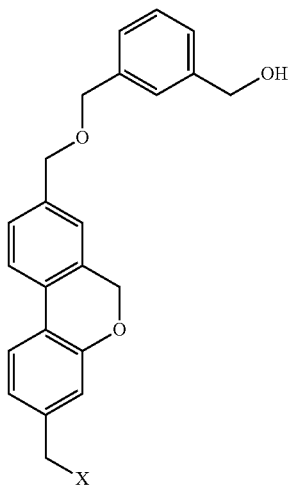
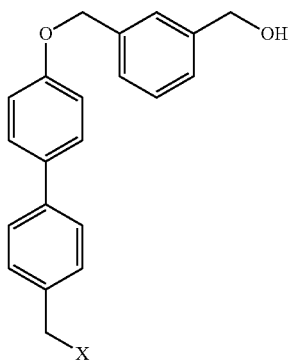
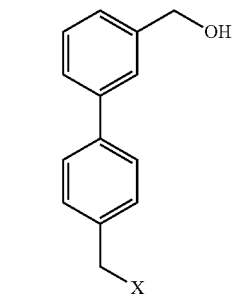
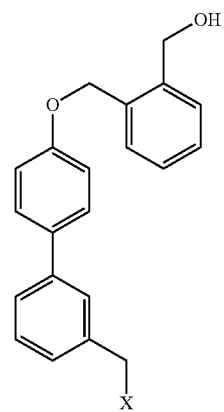
TABLE 1A-continued
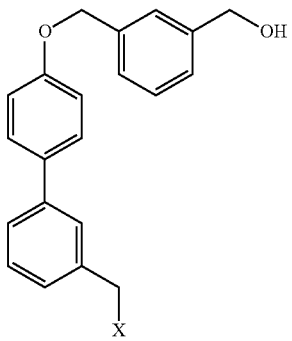
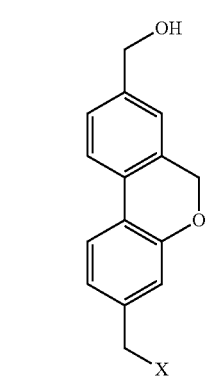
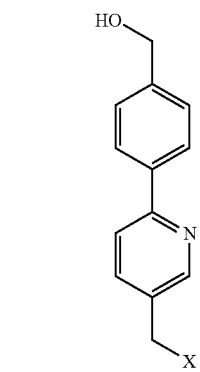
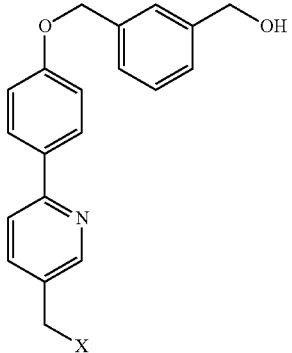

TABLE 1A-continued

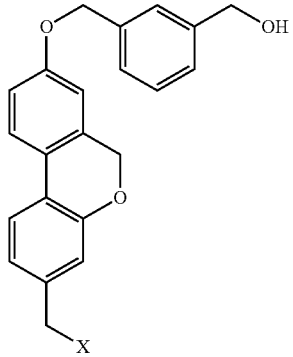

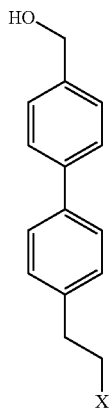

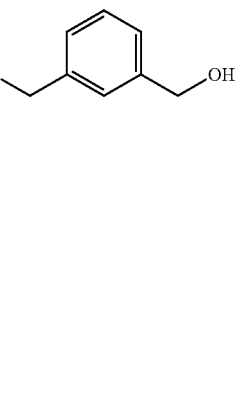

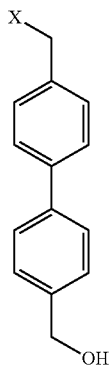

In one embodiment, the present disclosure encompasses a compound of formula Ib:

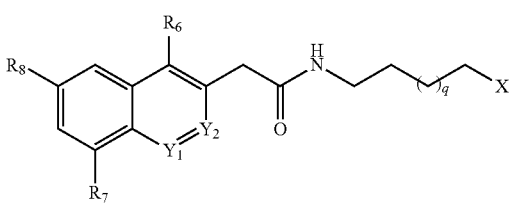

in which:
X is H; OH, wherein the hydroxyl group can optionally be functionalized as succinate or attached to a solid support; ODMT; carboxylic acid; the 3' end of a strand of a RNAi agent; or the 3' end of a molecule comprising a strand of a RNAi agent, wherein the 3' end of the strand terminates in a phosphate or modified internucleoside linker and further comprises in 5' to 3' order: a spacer, and a second phosphate or modified internucleoside linker;
q is 0, 1 or 2;
$R_6$ is phenyl which is unsubstituted or substituted with a group selected from benzoxy and 3,4-dihydroxybutyl;
$R_7$ is hydrogen or hydroxy-ethyl, wherein if $R_7$ is hydroxy-ethyl, the hydroxyl can be optionally functionalized as succinate or attached to a solid support;
$R_8$ is hydrogen or methoxy;
$Y_1$ is CH or N; and
$Y_2$ is N or $CR_9$; wherein $R_9$ is selected from hydrogen and methyl.

In various embodiments, the compound of Ib is selected from Table 1B:

TABLE 1B

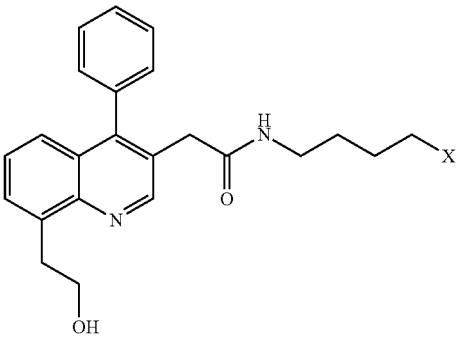

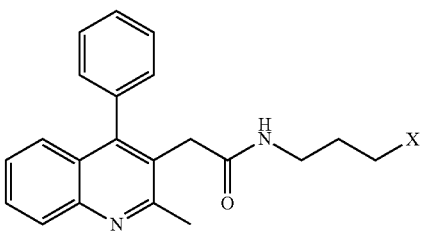

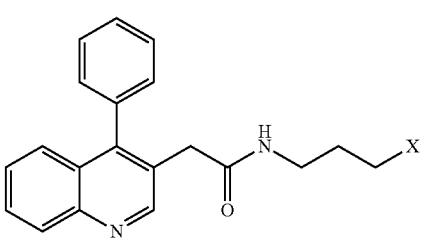

TABLE 1B-continued
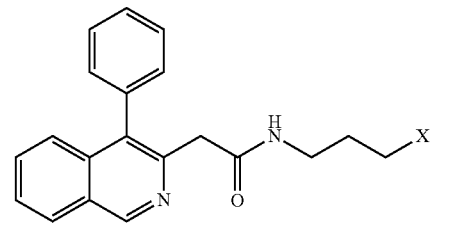
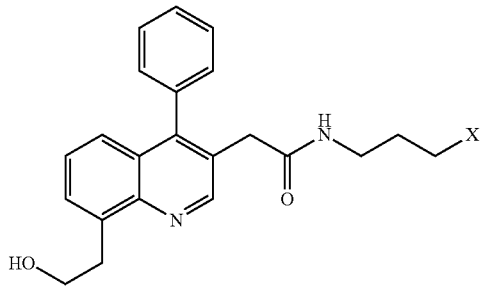
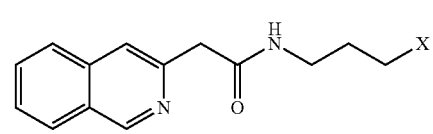
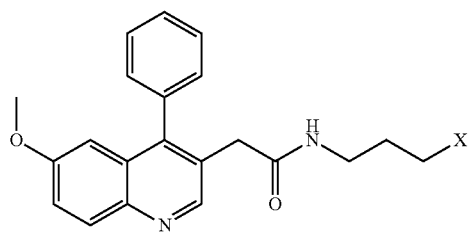
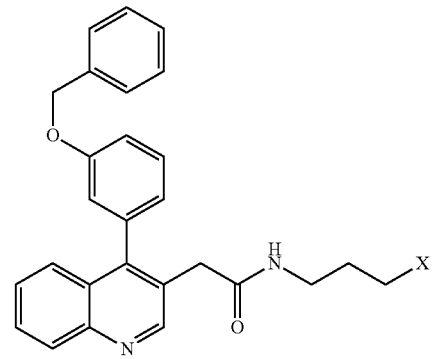
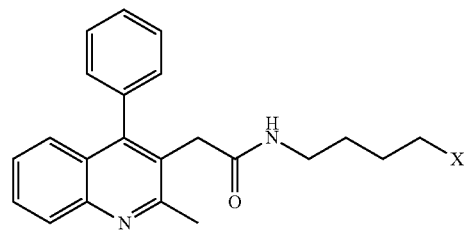
TABLE 1B-continued
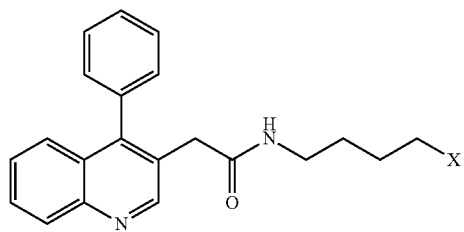
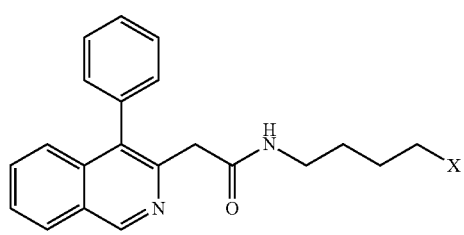
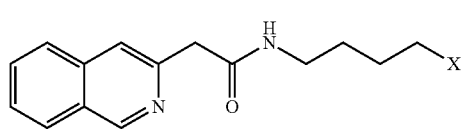
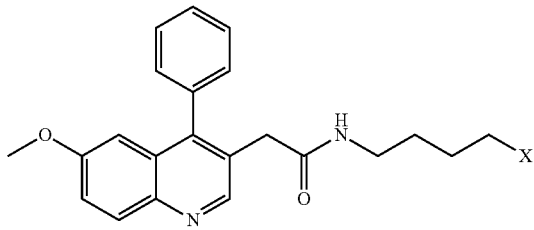
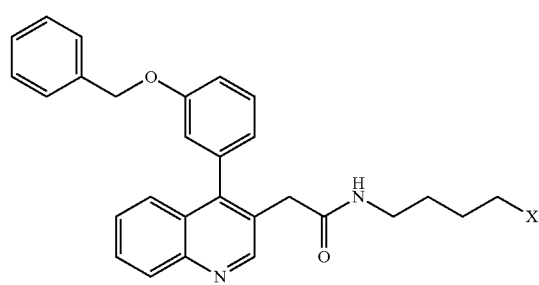
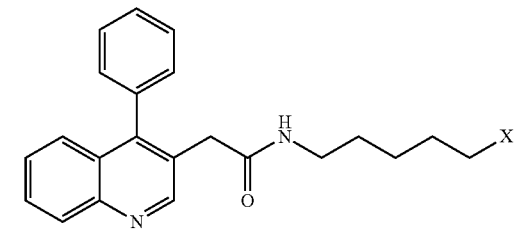

TABLE 1B-continued
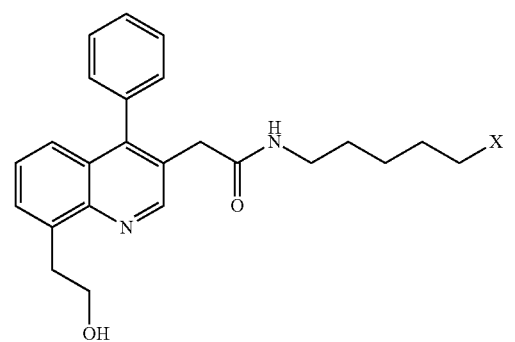
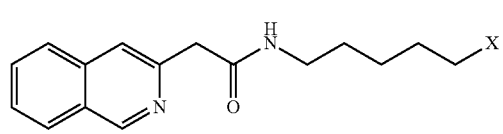
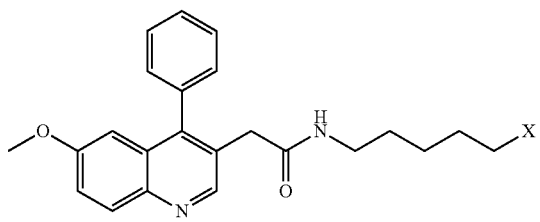
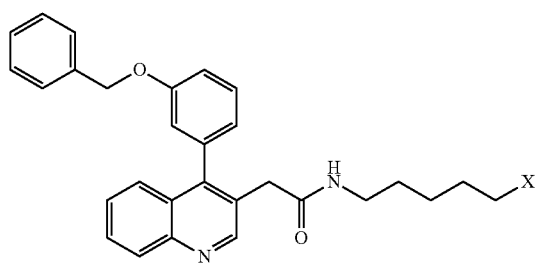
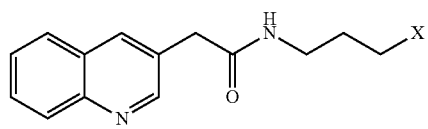
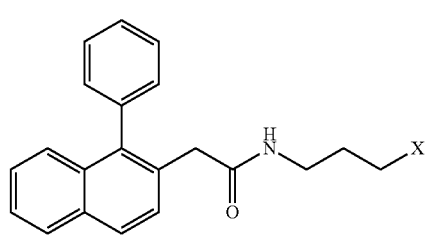
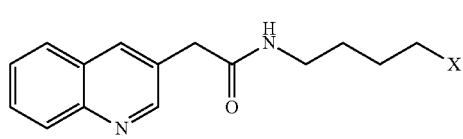
TABLE 1B-continued
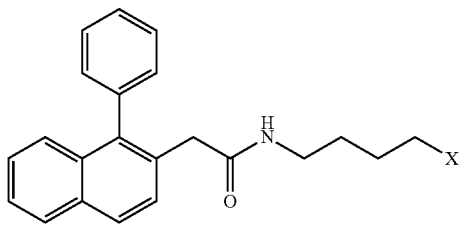
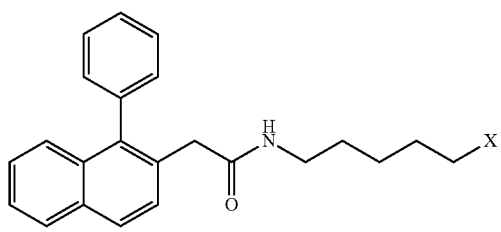
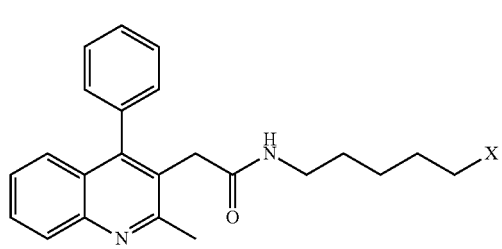
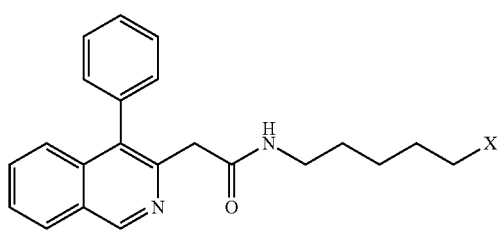
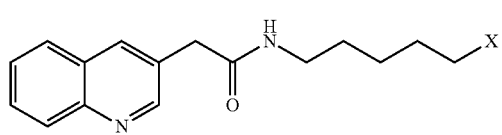
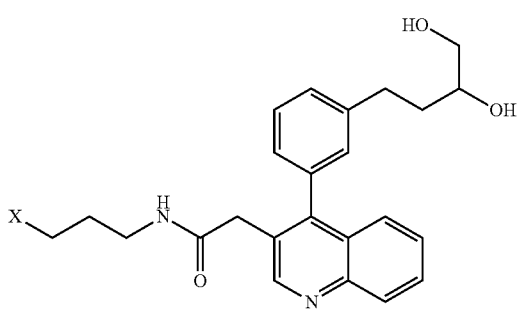

TABLE 1B-continued

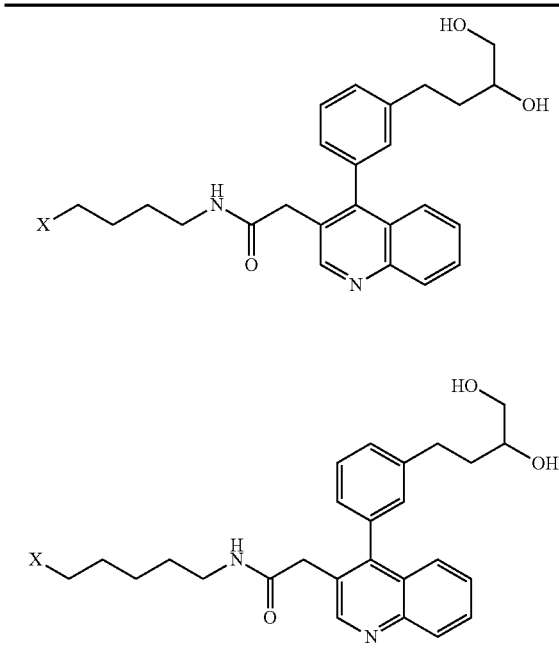

In various embodiments, the disclosure pertains to a compound selected from Table 1C:

TABLE 1C

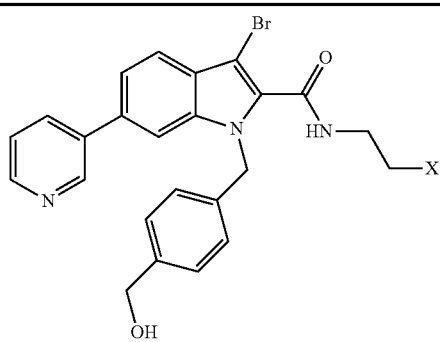

TABLE 1C-continued

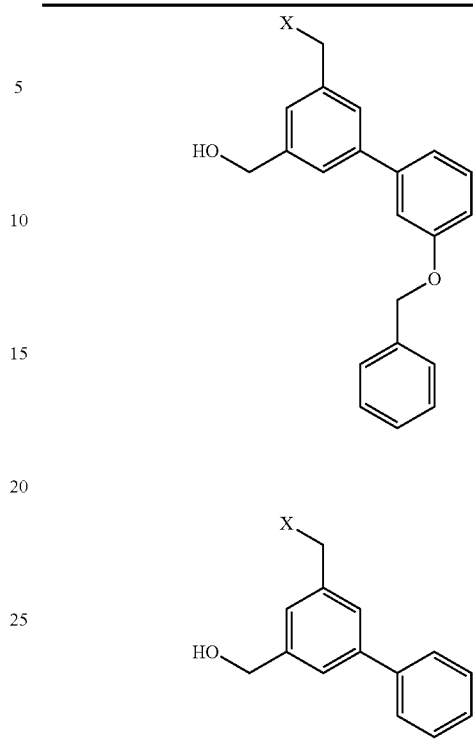

in which:

X is H; OH, wherein the hydroxyl group can optionally be functionalized as succinate or attached to a solid support; ODMT; carboxylic acid; the 3' end of a strand of a RNAi agent; or the 3' end of a molecule comprising a strand of a RNAi agent, wherein the 3' end of the strand terminates in a phosphate or modified internucleoside linker and further comprises in 5' to 3' order: a spacer, and a second phosphate or modified internucleoside linker, and q is selected from 1 and 2.

In one embodiment, the present disclosure encompasses a method for capping the 3' end of a strand of an RNAi agent comprising reacting the RNAi agent with a compound selected from Table 1 D:

TABLE 1D

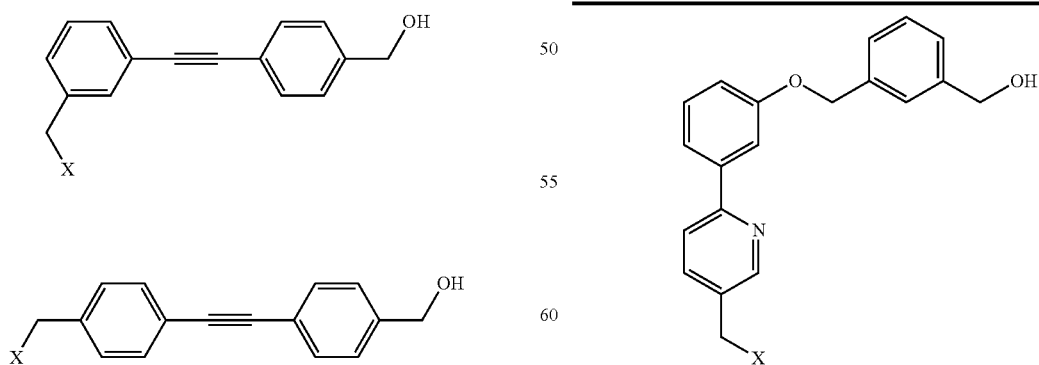

TABLE 1D-continued
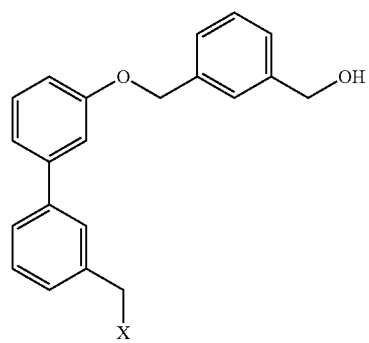
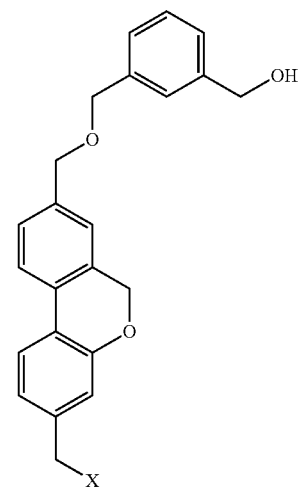
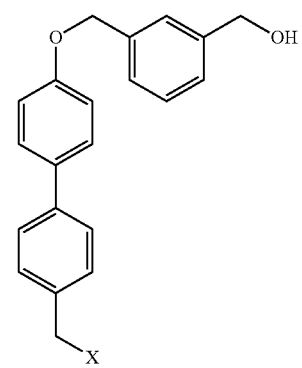
TABLE 1D-continued
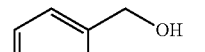
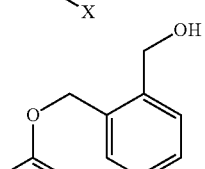
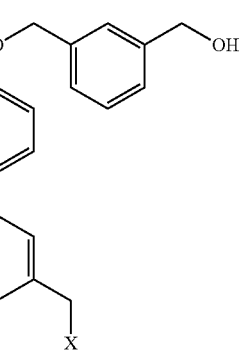
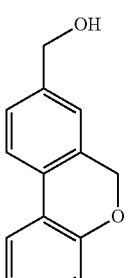
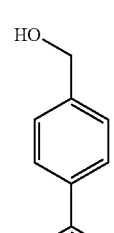

TABLE 1D-continued
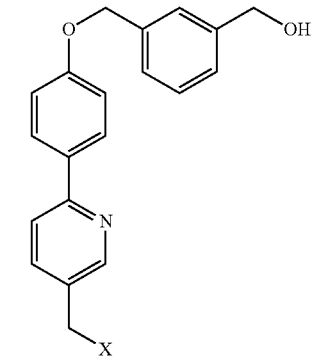
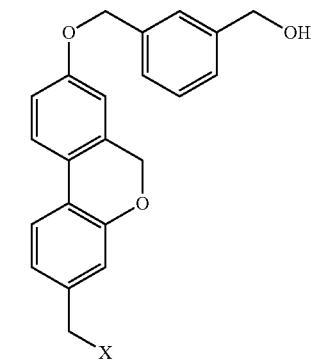
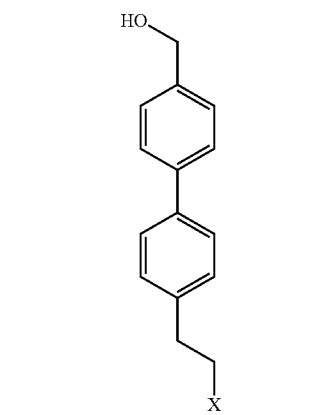
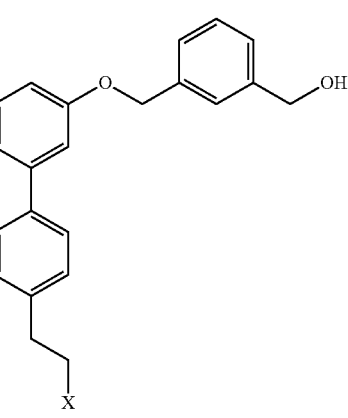
TABLE 1D-continued
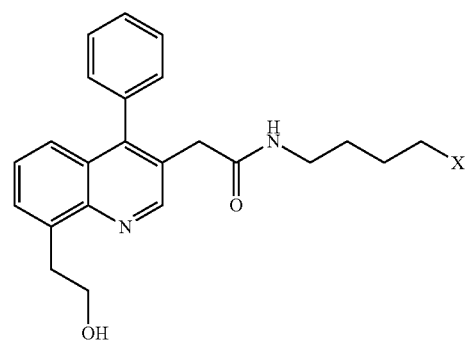
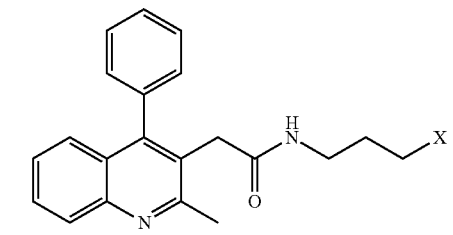
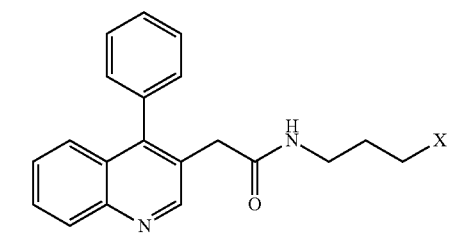
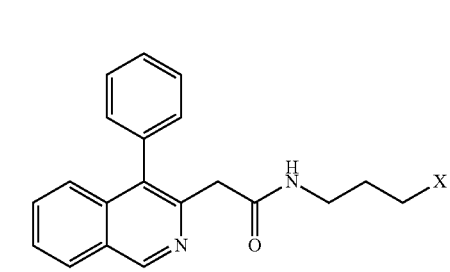

TABLE 1D-continued
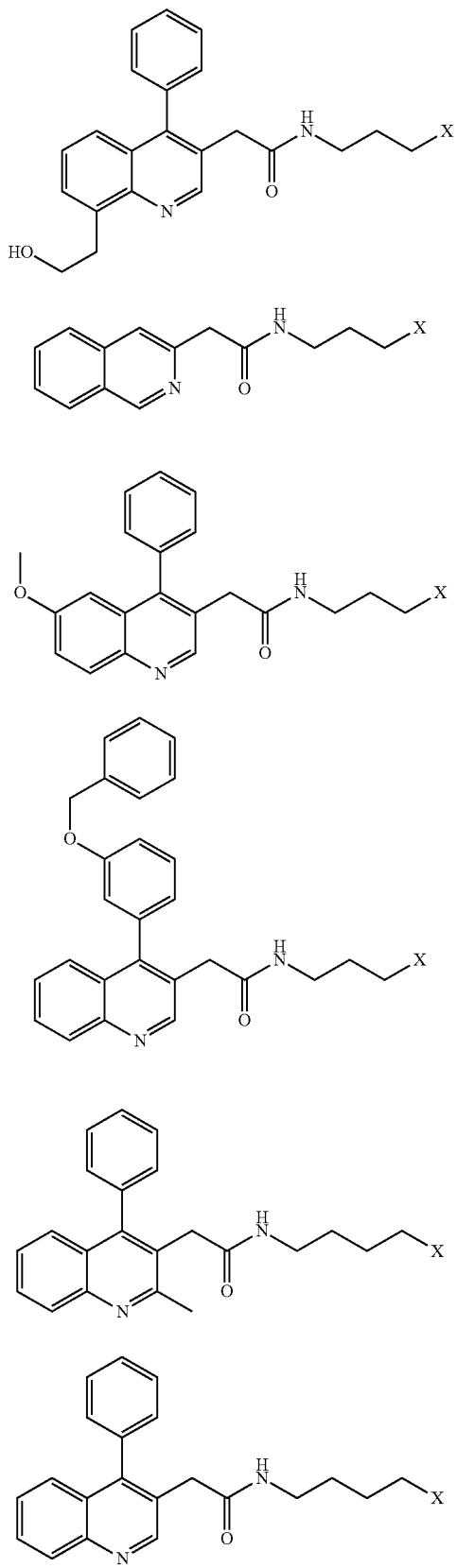
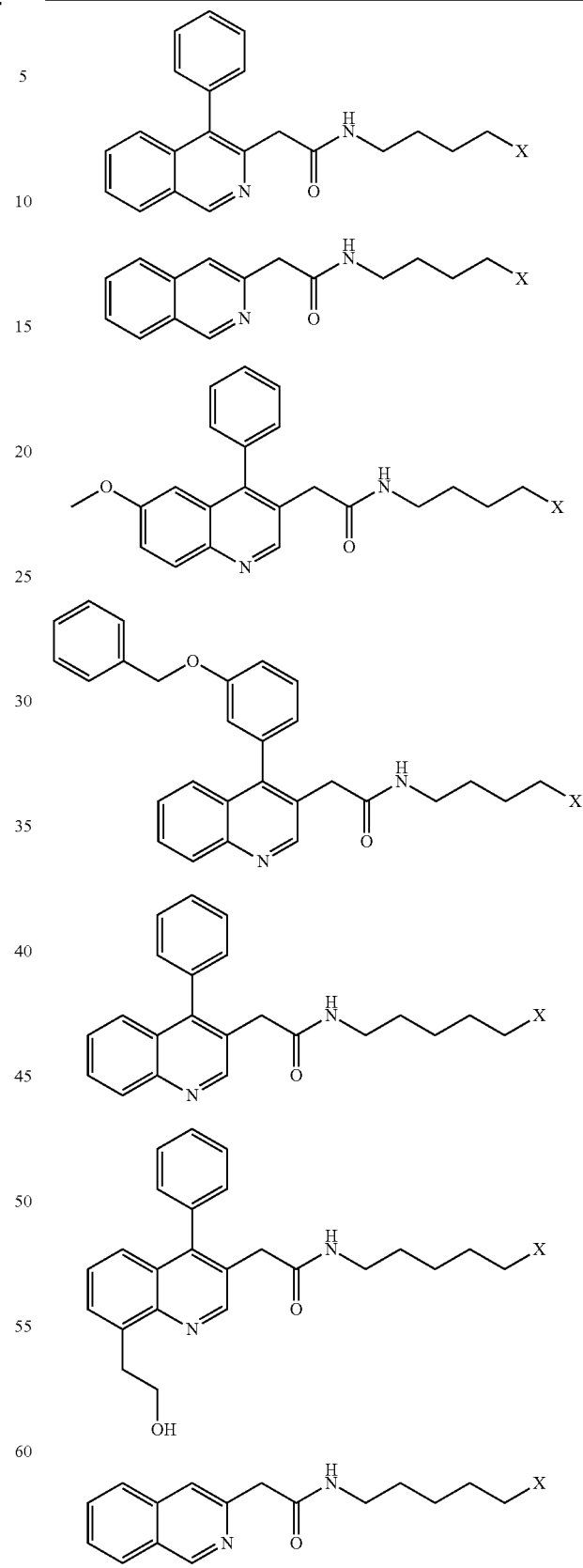

TABLE 1D-continued
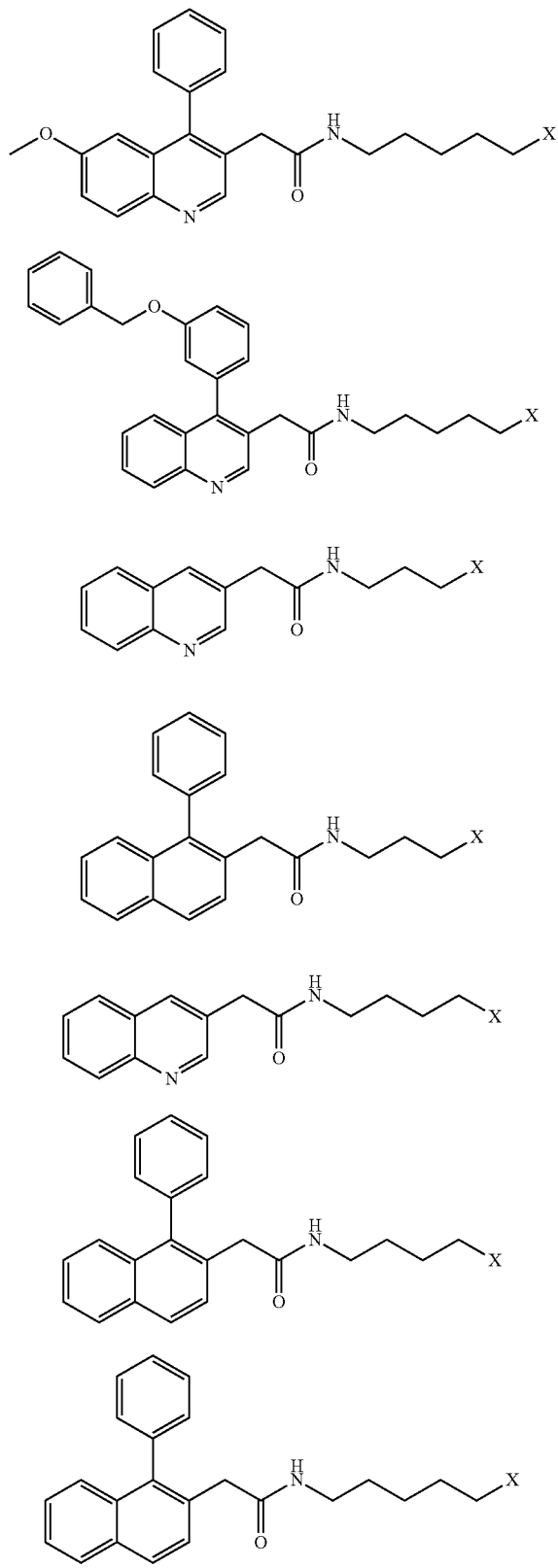
TABLE 1D-continued
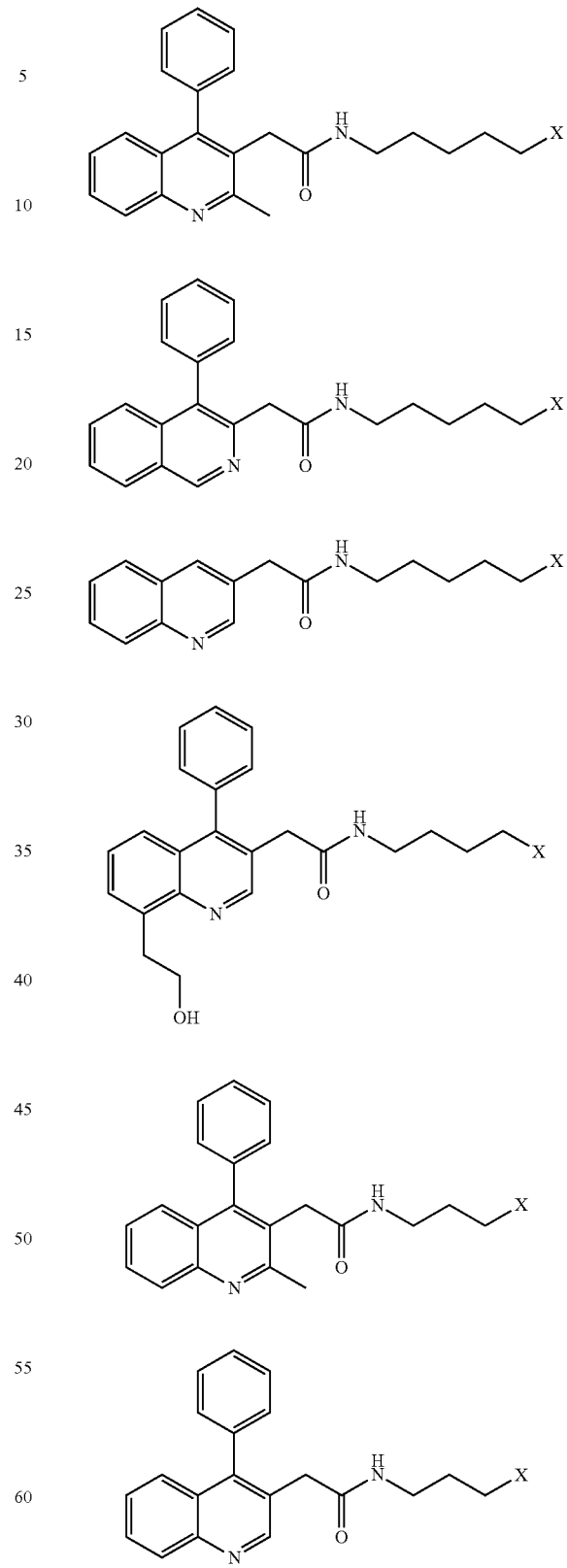

TABLE 1D-continued
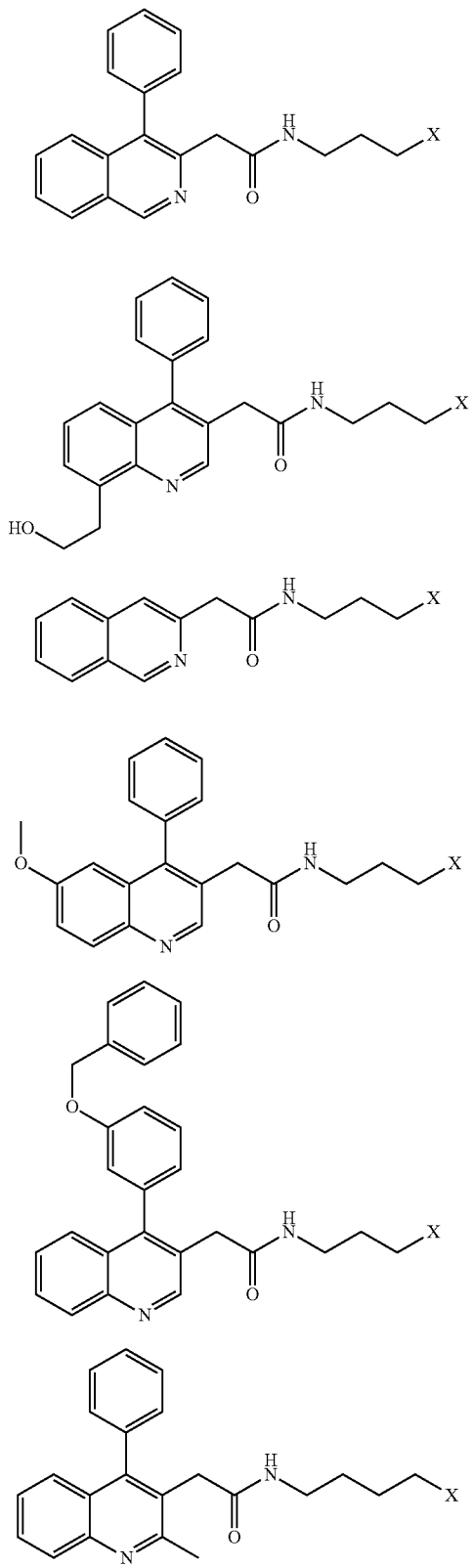
TABLE 1D-continued
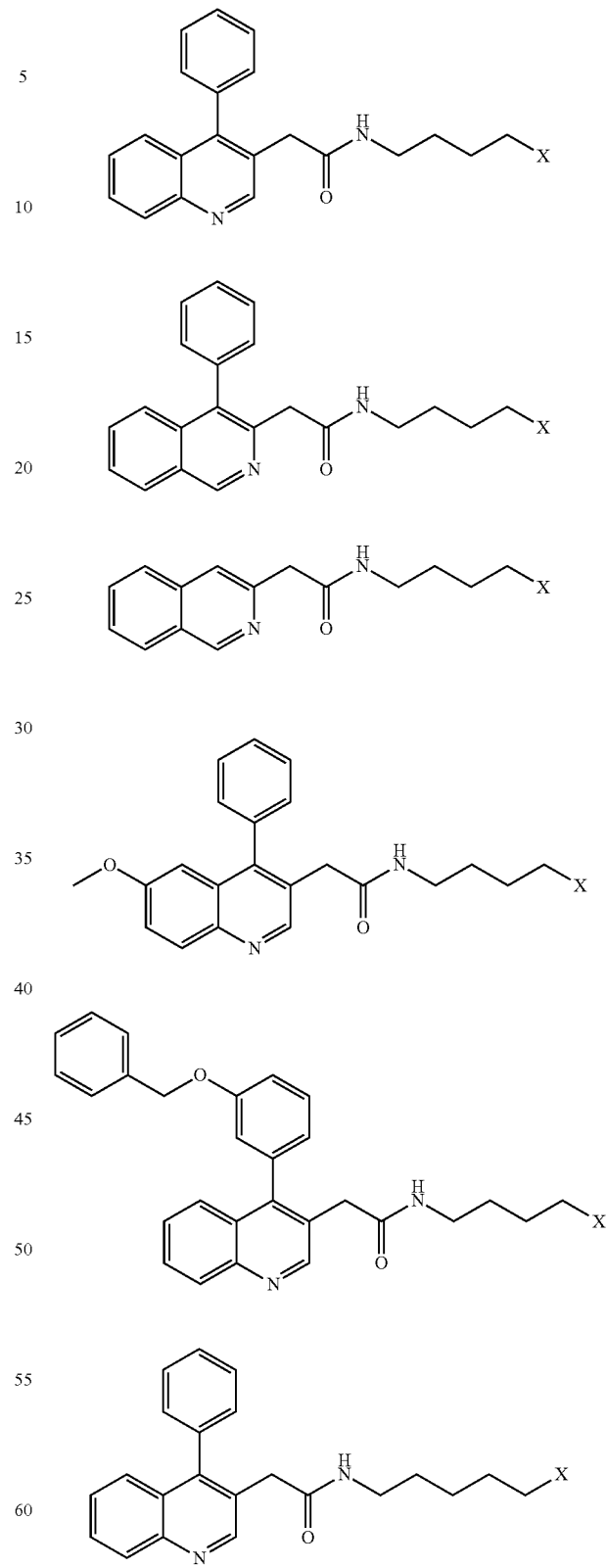

TABLE 1D-continued
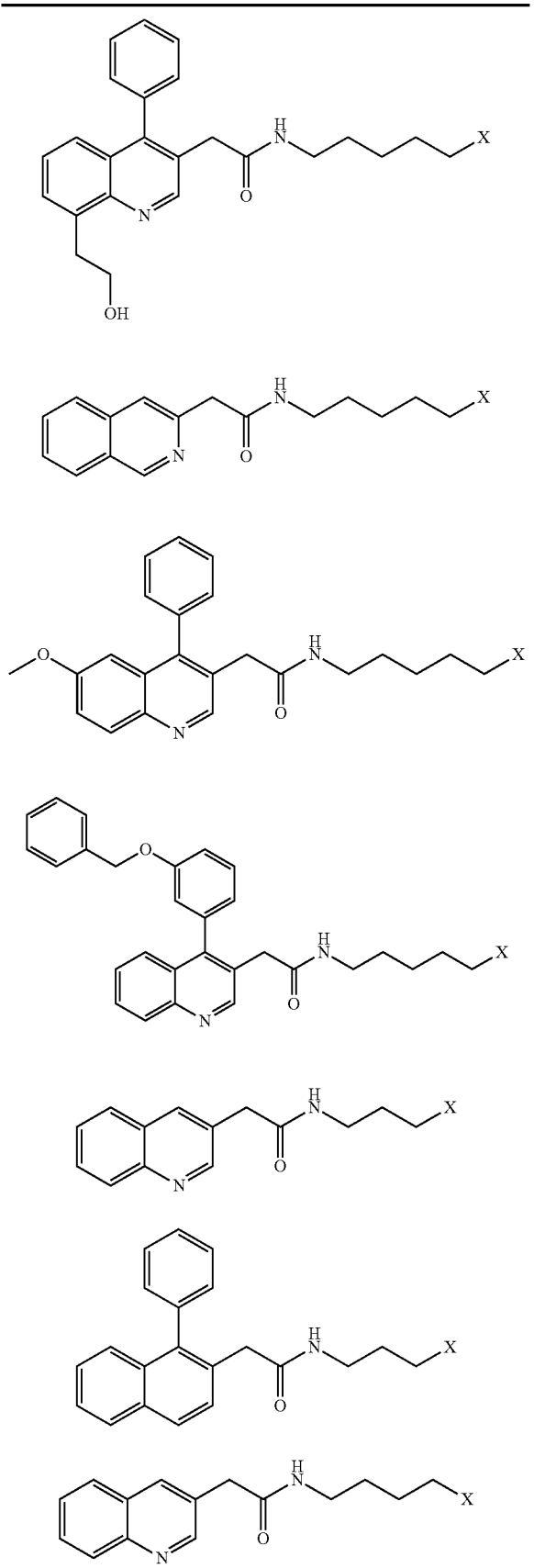
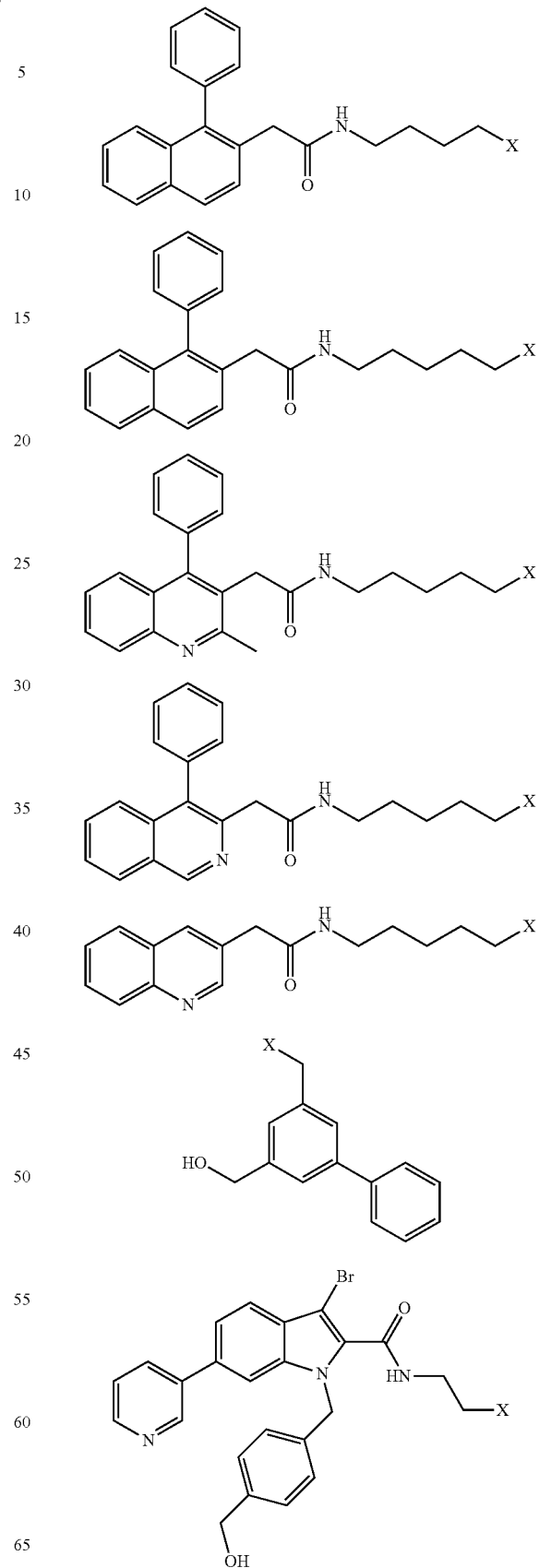

TABLE 1D-continued

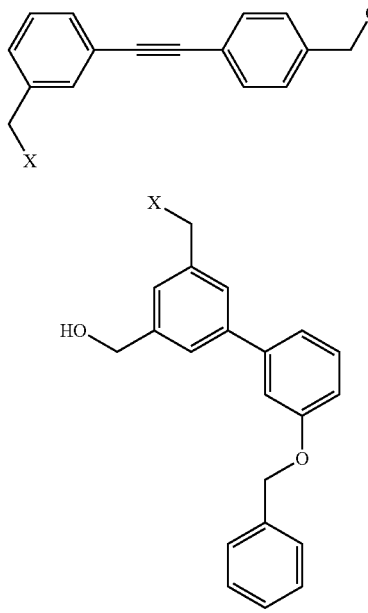

in which:

X is H; OH, wherein the hydroxyl group can optionally be functionalized as succinate or attached to a solid support; ODMT; carboxylic acid; the 3' end of a strand of a RNAi agent; or the 3' end of a molecule comprising a strand of a RNAi agent, wherein the 3' end of the strand terminates in a phosphate or modified internucleoside linker and further comprises in 5' to 3' order: a spacer, and a second phosphate or modified internucleoside linker, and q is selected from 1 and 2.

In various embodiments, the disclosure pertains to a DMT-ligand, succinate-ligand and/or carboxylate ligand, such as those listed in Table 4. These are useful in producing an RNAi agent comprising a 3' end cap comprising a compound of formula Ia or Ib, a compound from any Table herein, or any 3' end cap disclosed herein.

In various embodiments, the disclosure pertains to a compound of formula Ia, wherein X is selected from H; OH, wherein the hydroxyl group can optionally be functionalized as succinate or attached to a solid support; ODMT; carboxylic acid; the 3' end of a strand of a RNAi agent; and the 3' end of a molecule comprising a strand of a RNAi agent, wherein the 3' end of the strand terminates in a phosphate or modified internucleoside linker and further comprises in 5' to 3' order: a spacer, and a second phosphate or modified internucleoside linker; and $R_3$ is selected from hydrogen, 2-(hydroxy-methyl)-benzyl, 3-(hydroxy-methyl)-benzyl and succinate, or is attached to a solid support (e.g., beads or resin).

In various embodiments, the disclosure pertains to a compound of formula Ia, wherein X is the 3' end of a molecule comprising a strand of a RNAi agent, wherein the 3' end of the strand terminates in a phosphate or modified internucleoside linker and further comprises in 5' to 3' order: a spacer, and a second phosphate or modified internucleoside linker.

In one embodiment, the disclosure encompasses a RNAi agent comprising a first strand and a second strand, wherein the 3'-terminus of at least one strand comprises a 3' end cap, wherein the 3' end cap is selected from a compound of formula Ia or Ib (wherein X is 3' end of a strand of a RNAi agent), a compound from any Table herein, or any 3' end cap disclosed herein.

In one embodiment, the first and/or second strands of the RNAi agent are no more than about 49 nucleotides long.

In one embodiment, the first and/or second strands of the RNAi agent are no more than about 30 nucleotides long.

In one embodiment, the first and/or second strand are 19 nucleotides long.

In one embodiment, the first strand is the anti-sense strand and is 19 nucleotides long.

In one embodiment, the RNAi agent has 1 or 2 blunt-ends.

In another embodiment, the RNAi agent comprises an overhang on at least one 5' end or 3' end.

In another embodiment, the RNAi agent comprises a 1 to 6 nucleotide overhang on at least one 5' end or 3' end.

In one embodiment, the RNAi agent comprises a spacer.

In one embodiment, the spacer is a ribitol or other type of abasic nucleotide.

In one embodiment, the spacer is a ribitol or other type of abasic nucleotide, 2'-deoxy-ribitol, diribitol, 2'-methoxy-ethoxy-ribitol (ribitol with 2'-MOE), C3, C4, C5, C6, or 4-methoxybutane-1,3-diol.

In one embodiment, at least one nucleotide of the RNAi agent is modified.

In one embodiment, said at least one modified nucleotide is selected from among 2' alkoxyribonucleotide, 2' alkoxy-alkoxy ribonucleotide, or 2'-fluoro ribonucleotide. In another embodiment, said at least one modified nucleotide is selected from 2'-OMe, 2'-MOE and 2'-H. In various aspects, the nucleotide subunit is chemically modified at the 2' position of the sugar. In one aspect, the 2' chemical modification is selected from a halo, a $C_{1-10}$ alkyl, a $C_{1-10}$ alkoxy, a halo, and the like. In specific aspects, the 2' chemical modification is a $C_{1-10}$ alkoxy selected from —OCH$_3$ (i.e., "OMe"), —OCH$_2$CH$_3$ (i.e., "OEt") or —CH$_2$OCH$_2$CH$_3$ (i.e., methoxyethyl or "MOE"); or is a halo selected from F.

In various embodiments, one or more nucleotides is modified or is DNA or is replaced by a peptide nucleic acid (PNA), locked nucleic acid (LNA), morpholino nucleotide, threose nucleic acid (TNA), glycol nucleic acid (GNA), arabinose nucleic acid (ANA), 2'-fluoroarabinose nucleic acid (FANA), cyclohexene nucleic acid (CeNA), anhydrohexitol nucleic acid (HNA), and/or unlocked nucleic acid (UNA); and/or at least one nucleotide comprises a modified internucleoside linker (e.g., wherein at least one phosphate of a nucleotide is replaced by a modified internucleoside linker), wherein the modified internucleoside linker is selected from phosphorothioate, phosphorodithioate, phosphoramidate, boranophosphonate, an amide linker, and a compound of formula (I) (as described elsewhere herein).

In one embodiment, the first two base-pairing nucleotides on the 3' end of the first and/or second strand are modified.

In one embodiment, the first two base-pairing nucleotides on the 3' end of the first and/or second strand are 2'-MOE.

In one embodiment, the 3' terminal phosphate of the first and/or second strands is replaced by a modified internucleoside linker.

In another embodiment, the first or second strand is a sense strand comprising an 5' end cap which reduces the amount of the RNA interference mediated by the sense strand.

In various embodiments, the sense strand comprises a 5' end cap selected: a nucleotide lacking a 5' phosphate or 5'-OH; a nucleotide lacking a 5' phosphate or a 5'-OH and also comprising a 2-OMe or 2'-MOE modification; 5'-deoxy-2'-O-methyl modification; 5'-OME-dT; ddT; and 5'-OTr-dT.

In various embodiments, the disclosure encompasses a RNAi agent comprising a first strand and a second strand, wherein the 3'-terminus of at least one strand comprises a 3' end cap, wherein the 3' end cap is selected from a compound of formula Ia or Ib, a compound from any Table herein, or any 3' end cap disclosed herein; wherein optionally each strand is a 49-mer or shorter, optionally the first and/or second strand is about 30 nucleotides long or shorter, and/or optionally the first and/or second strand is 19 nucleotides long; wherein optionally the RNAi agent has 1 or 2 blunt-ends or the RNAi agent comprises an overhang, optionally a 1 to 6 nucleotide overhang on at least one 5' end or 3' end; wherein the RNAi agent optionally comprises a spacer, wherein optionally the spacer is a ribitol or other type of abasic nucleotide, 2'-deoxy-ribitol, diribitol, 2'-methoxy-ethoxy-ribitol (ribitol with 2'-MOE), C3, C4, C5, C6, or 4-methoxybutane-1,3-diol; wherein optionally one or both strands are RNA or optionally at least one nucleotide of the RNAi agent is modified, wherein optionally said at least one modified nucleotide is selected from among 2' alkoxyribo-nucleotide, 2' alkoxyalkoxy ribonucleotide, or 2'-fluoro ribo-nucleotide, and optionally said at least one modified nucleo-tide is selected from 2'-OMe, 2'-MOE and 2'-H; wherein optionally one or more nucleotides is modified or is DNA or is replaced by a peptide nucleic acid (PNA), locked nucleic acid (LNA), morpholino nucleotide, threose nucleic acid (TNA), glycol nucleic acid (GNA), arabinose nucleic acid (ANA), 2'-fl uoroarabinose nucleic acid (FANA), cyclohex-ene nucleic acid (CeNA), anhydrohexitol nucleic acid (HNA), and/or unlocked nucleic acid (UNA) (a non-nucleo-tide, acyclic analog wherein the C2'-C3' bond is not present); and/or at least one nucleotide comprises a modified inter-nucleoside linker, wherein the modified internucleoside linker is selected from phosphorothioate, phosphorodithio-ate, phosphoramidate, boranophosphonoate, an amide linker, and a compound of formula (I); and wherein option-ally the first two base-pairing nucleotides on the 3' end of the first and/or second strand are modified, and optionally the first two base-pairing nucleotides on the 3' end of the first and/or second strand are 2'-MOE; and wherein optionally the 3' terminal phosphate of the first and/or second strands is replaced by a modified internucleoside linker; and wherein optionally the first or the second strand is a sense strand comprising an 5' end cap which reduces the amount of the RNA interference mediated by the sense strand, wherein optionally the 5' end cap selected a nucleotide lacking a 5' phosphate or 5'-OH; a nucleotide lacking a 5' phosphate or a 5'-OH and also comprising a 2-OMe or 2'-MOE modification; 5'-deoxy-2'-O-methyl modification; 5'-OME-dT; ddT; and 5'-OTr-dT.

Various elements of various embodiments disclosed herein [e.g., compositions and methods; and selection of 3' end caps, nucleotide modifications or replacements (such as with DNA), patterns of modifications, strand length, presence or absence of overhangs, and/or 5' end caps and delivery vehicles] which are not mutually exclusive can be combined.

In one embodiment, the invention provides a pharmaceu-tical composition comprising an RNAi agent with any one or more of the above properties.

In another embodiment, the invention provides an RNAi agent with any one or more of the above properties for use as a medicament.

In another embodiment, the disclosure pertains to a method for the inhibition or a method for inhibiting or reducing the level and/or activity of a target gene in a cell comprising the step of introducing into the cell one or more of any RNAi agent as described above.

Multiple RNAi agents (which can comprise the same or different types of RNAi agents, and/or combinations of 3' end caps, sequences, lengths, overhangs, 5' end caps, nucleotide replacements and/or modifications and/or patterns of modification, etc.) can be administered separately or co-administered. The multiple RNAi agents can be administered in the same delivery vehicle, the same type of delivery vehicle, or in different delivery vehicles.

Various additional embodiments are described below.

The details of one or more aspects of the present disclo-sure are set forth in the accompanying drawings and the description below. Elements of the various aspects (e.g., sequences, modifications, substitutions, spacers, modified internucleoside linkers, endcaps, combinations of RNAi agents, delivery vehicles, combination therapy involving a RNAi agent and another agent, etc.) disclosed herein or known in the art which are not mutually exclusive can be combined with each other, provided that the agent or agents are still capable of mediating RNA interference. For example, any RNAi agent sequence disclosed herein can be combined with any set of modifications or endcaps disclosed herein. Similarly, any combination of modifications, 5' end caps, and/or 3' end caps can be used with any RNAi agent sequence disclosed herein. Any RNAi agent disclosed herein (with any combination of modifications or endcaps or without either modifications or endcaps) can be combined with any other RNAi agent or other treatment composition or method disclosed herein.

Other features, objects, and advantages of the present disclosure will be apparent from this description, the drawings, and from the claims.

BRIEF DESCRIPTION OF THE FIGURES

FIG. 1 illustrates the structures and sequence of the RNAi agents comprising a 3' end cap used in Example 1. The sequences in FIG. 1 are represented, from top to bottom, by SEQ ID NO: 1 and 2 (generic sequence); and 3 and 4 (antisense and sense F7). The structures of the 3' end caps ("X") are provided herein and/or in U.S. Pat. No. 8,084,600.

FIGS. 6A and 6B detail some of the RNAi agents used in the data shown in FIGS. 5A and 5B and Example 3A and others. The sequences in FIG. 6A are represented by, from top to bottom, by SEQ ID NOs: 5 to 10 (400), 11 to 16 (402) and 17 (400 21-mer). The sequences in FIG. 6B are represented, from top to bottom, by SEQ ID NOs: 18 to 23 (400); 24 to 29 (402) and 30 (400 21-mer). These are RNAi agents to Hepcidin.

FIG. 7 discloses SEQ ID NO: 139.

FIG. 11 (TOP) shows a non-limiting example of the 18-mer RNAi agent format. "L" indicates a non-nucleotidic "ligand", e.g., any of various 3' end caps which can be used (e.g., PAZ Ligands). This generic sequence is represented by SEQ ID NOs: 31 and 32. FIG. 11 (MIDDLE) also shows specific examples of an 18-mer RNAi agent, comprising at the 3' termini of various strands, in 5' to 3' order, and bound to the 3' terminal phosphate: a ribitol spacer (rib), a phosphate (p) and a 3' end cap (X058 or C6). These sequences are represented by SEQ ID NOs: 33 and 34 (400) and 35 and 36 (402). Various modifications are also shown (BOTTOM).

FIGS. 15A and 15B shows several different modification schemes for RNAi agents. These RNAi agents comprise a 3' end cap (C3). FIG. 15B shows a modification scheme in the context of a "wt" (wild-type) and a modified RNAi agent, wherein the RNAi agents comprise nucleotidic dTdT or dTsdT overhangs, which can be replaced by a 3' end cap. FIG. 15C also shows example modification schemes in the context of a 19 bp or 18 bp stem (double-stranded region), which can further comprise 3' dinucleotide overhangs or 3' end caps (L, or non-nucleotidic Ligands). The various modification schemes shown can be used with various RNAi agents comprising a 3' end cap as disclosed herein. In FIG. 15A, the generic sequences are represented, from top to bottom, by SEQ ID NOs: 45 to 48. In FIG. 15B, these sequences are represented, from top to bottom, by SEQ ID NOs: 49 to 52. In FIG. 15C, the generic sequences are represented, from top to bottom, by SEQ ID NOs: 53 to 56. In FIG. 15C, an example 19-mer can be converted into a 18-mer by, in one example, deleting the terminal 3' nucleotide on the antisense strand and the 5' terminal nucleotide on the sense strand to retain a double-stranded molecule.

FIG. 16B shows the structure of the molecules used in this experiment and others. The RNAi agents comprising X109, X110, X111, X112, or X113 comprise a DNA modification at the 5' end of the anti-sense strand. The duplexes are numbered 20 to 28. The sequences in FIG. 16B are represented by SEQ ID NOs: 57 (first sequence) and 58 (second). These are RNAi agents to HuR (ELAVL1). The sequence is designated hs (human) 1186, but is cross-reactive between human, mouse and rat.

FIG. 17A shows two 5' ends. FIG. 17B shows the effect of 5' end capping on HAMP RNAi agents. FIG. 17C diagrams various 5' end caps. FIG. 17D illustrates various 5' end caps and sequences. The sequences in FIG. 17A are represented, from top to bottom and left to right by SEQ ID NOs: 59 to 66. The sequences in FIG. 17C are represented, from top to bottom, by SEQ ID NOs: 67 to 72. The duplexes in FIGS. 17D and 17F are numbered 10 to 15.

FIGS. 18A, B and C show the structure and efficacy of various SSB RNAi agents comprising a C6, C8 or C10 3' end cap, as described in Example 5. FIG. 18C shows example structures of the 3' end of an RNAi agent strand. The strand terminates in a nucleotide (with BASE) and 3' phosphate which is bound to: a dinucleotide (wt or wild-type); or a 3' end cap (C6, C8 or C10). These structures were used in, for example, LNP-formulated SSB siRNAs, but can be used for any RNAi agent of any length, any sequence or target. The RNAi agents are to SSB (Sjogren's Syndrome antigen B) and comprise a 19-mer with a 3' end cap (C6, C8 or C10). The compound designated SSB-309 A22S26 is a 21-mer control. The experiment was done in vivo in mouse. FIG. 18B shows data points used to generate the bar graph shown in FIG. 18A. FIG. 18C also shows that a 3' terminal phosphate can be replaced by the depicted compound. Any of the phosphates of either or both strands of the RNAi agent can be replaced by the depicted compound.

FIG. 19 diagrams the structure of the 3' terminal nucleotide of an RNAi agent bound to: a dinucleotide (e.g., CU overhang), or a 3' end cap which is a diribitol, ribitol and X027. Also shown are the structures of a 3' terminal nucleotide (a 2'-MOE) and phosphate bound to, in 5' to 3' order: a spacer (ribitol), a second phosphate, and a 3' end cap (C6 or X058).

FIGS. 20A and B show the efficacy of RNAi agents comprising a 3' end cap of phosphorothioate-C3 (PS-C3).

FIG. 21 shows the structures of example RNAi agents comprising a spacer [which is a ribitol (rib), C3 or 4-methoxybutane-1,3-diol (A5300)]; a phosphate; and a 3' end cap which is X058. The Figure depicts the spacers in the context of an 18-mer RNAi agent and a specific 3' end cap, but the spacers can be used with any RNAi agent strand of any length, sequence or target, and with any 3' end cap.

FIG. 23A-C shows efficacy of RNAi agents comprising a 3' end cap which is: X109, X110, X111, X112, X113, X1009, X1010, X1024 or X1025 (FIG. 23A); X1011, X1012, X1013, X058, X1015, X1016, X1017, X1026, X1027 (FIG. 23B): or X1018; X1019, X1020, X1021, X1022 or X1028 (FIG. 23C). The terms C3 linker, C4 linker, and C5 linker indicate portions of the 3' end cap.

DETAILED DESCRIPTION OF THE INVENTION

Figure 2:
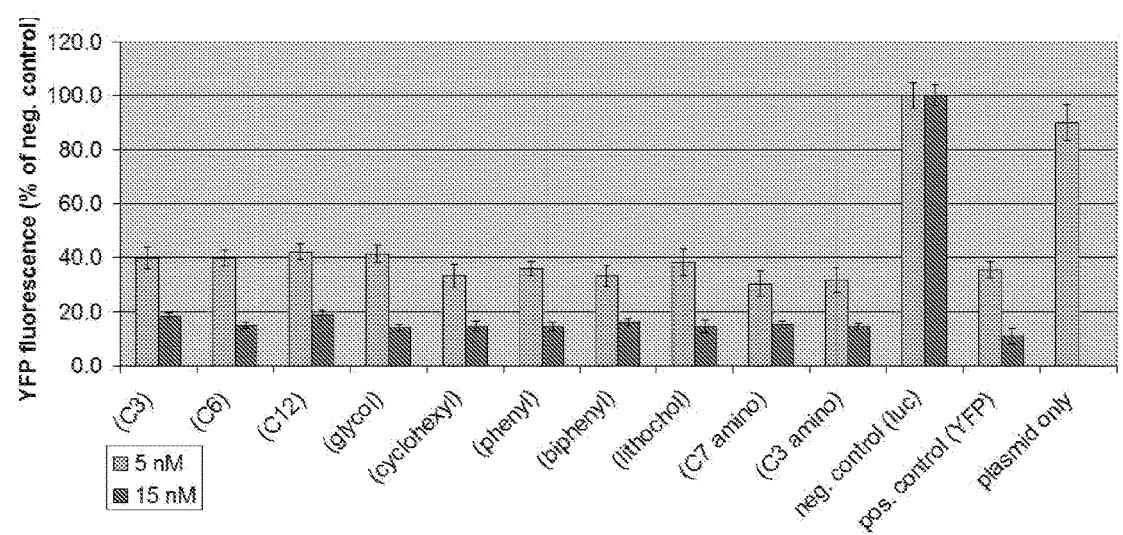
FIG. 2 shows the efficacy of RNAi agent comprising a 3' end cap (C3, C6, C12, glycol, cyclohexyl, phenyl, biphenyl, lithochol, C7 amino or C3 amino) as described in Example 1. in allowing the RNAi agent to mediate RNA interference. The structures of the 3' end caps ("X") are provided herein and/or in U.S. Pat. No. 8,084,600.

The present disclosure pertains to novel compounds, including: a compound of formula Ia or Ib, a compound from any Table herein, or any 3' end cap disclosed herein.

In various embodiment, the disclosure pertains to a DMT-ligand, succinate-ligand and/or carboxylate ligand, such as those listed in Table 4, which are useful in producing an RNAi agent comprising a 3' end cap comprising a compound of formula Ia or Ib (e.g., wherein X is H or OH), a compound from any Table herein, or any 3' end cap disclosed herein.

In various embodiments, the disclosure pertains to a compound of formula Ia, wherein X is selected from H, OH, ODMT, carboxylic acid, and the 3' end of a strand of a RNAi agent; and $R_3$ is selected from hydrogen, 2-(hydroxy-methyl)-benzyl, 3-(hydroxy-methyl)-benzyl and succinate, or is attached to a solid support (e.g, beads or resin).

In various embodiments, the disclosure pertains to a compound designated herein as X058, wherein X is selected from H, OH, ODMT, carboxylic acid, and the 3' end of a strand of a RNAi agent; and $R_3$ is selected from hydrogen, 2-(hydroxy-methyl)-benzyl, 3-(hydroxy-methyl)-benzyl and succinate, or is attached to a solid support (e.g, beads or resin).

In various embodiments, the disclosure pertains to a RNAi agent comprising a first strand and a second strand, wherein the 3' end of the first and/or second strand terminates in a phosphate or modified internucleoside linker and further comprises a 3' end cap which is X058. In this case, X represents the first or second strand.

In one embodiment, the compounds of formula Ia and Ib and those of Table 1A, 1B or 1C can be used as 3' end cap on a RNAi agent; in these embodiments X is the 3' end of a RNAi agent strand.

In one embodiment, the present disclosure encompasses a RNAi agent comprising a first strand and a second strand, wherein each strand is a 49-mer or shorter, and wherein the 3'-terminus of at least one strand comprises a 3' end cap (e.g., a modification at the 3' end), wherein the 3' end cap is selected from the 3' end caps listed in Tables 1 or 2 or those otherwise disclosed herein.

In various embodiments, the present disclosure encompasses a RNAi agent comprising a sense strand and an antisense strand, wherein each strand is a 49-mer or shorter, and wherein the 3'-terminus of the antisense strand comprises a 3' end cap (e.g., a modification at the 3' end), wherein the 3' end cap is selected from the 3' end caps listed in Tables 1 or 2 or those otherwise disclosed herein.

In various embodiments, the RNAi agent can be a double-stranded RNA. In various embodiments, one or more RNA nucleotides can be replaced by DNA, PNA, LNA, morpholino, TNA, GNA, ANA, HNA, CeNA, FANA, and/or UNA. In some embodiments, the replacement or substitution of RNA with DNA, or a nucleotide of a different backbone, or PNA, LNA, Morpholino, TNA, GNA, ANA, HNA, CeNA, FANA can be considered a "modification". In various embodiments, one or more phosphates can be replaced by phosphorothioate, phosphorodithioate, phosphoramidate, boranophosphonoate, an amide linker or a compound of formula (I) (as described elsewhere herein).

In various embodiments, the disclosure pertains to an RNAi agent comprising a first strand and a second strand, wherein each strand is a 49-mer or shorter, and wherein the 3' end of at least one strand terminates in a phosphate (designated herein as "p" or "PO") or modified internucleoside linker and further comprises, in 5' to 3' order: a spacer, a second phosphate or a modified internucleoside linker, and a 3' end cap, wherein the spacer is ribitol, 2'-deoxy-ribitol, diribitol, 2'-methoxyethoxy-ribitol (ribitol with 2'-MOE), or a C3, C4, C5 or C6 or 4-methoxybutane-1,3-diol; wherein the 3' end cap is selected from the 3' end caps listed in Tables 1 or 2 or otherwise disclosed herein; wherein optionally one or more nucleotides is modified or is DNA or is replaced by a peptide nucleic acid (PNA), locked nucleic acid (LNA), morpholino nucleotide, threose nucleic acid (TNA), glycol nucleic acid (TNA), and/or unlocked nucleic acid (UNA); and wherein optionally one or more nucleotides comprise a modified internucleoside linker a modified internucleoside linker (e.g., wherein at least one phosphate of a nucleotide is replaced by a modified internucleoside linker).

The 3' end caps and spacers disclosed herein can be used with one or both strands of any RNAi agent, regardless of length, sequence or target.

Naked siRNAs (e.g., those lacking a 3' end cap as disclosed) are known to have a very short biological half-life in blood serum in intestinal fluid, often only minutes. This short half-life may be due to degradation, e.g., by nucleases. Many 3' end caps have been tested for use in RNAi agents, though most do not both (1) allow RNA interference activity and (2) increase duration of activity (e.g., reduce degradation). In contrast, 3' end caps of the present invention are able to both allow RNA interference and increase time of duration of RNAi agents (e.g., reduce degradation). Preferred 3' end caps have improved knockdown (RNA interference activity), and/or further improved duration of activity. Without wishing to be bound by any particular scientific theory, this disclosure suggests that one or both of these effects may result from specific interactions with the PAZ domain of Dicer and/or through improvements in stability via reduced exonuclease activity.

In addition, because an RNAi agent is double-stranded, either strand can be loaded into RISC (the RNA induced silencing complex). The problem is thus that the sense strand can be loaded, but only the antisense strand targets the correct sequence. The novel 3' end caps disclosed herein, including those designated "PAZ ligands", help load the antisense strand, which increases efficiency, stability and duration of effect. Thus, in some embodiments, the 3' end of the antisense strand comprises a 3' end cap as disclosed herein.

The present disclosure also encompasses methods of decreasing the expression of a target gene or inhibiting or reducing the level and/or activity of its gene product, or of treating a disease associated with over-expression of a target gene, in vitro, or in an organism, such as a mammal, such as a human being, wherein the method comprises the step of administering to the human being a physiologically active amount of a composition comprising a RNAi agent comprising a first strand and a second strand, wherein each strand is a 49-mer or shorter, and wherein the 3'-terminus of at least one strand comprises a 3' end cap (e.g., a modification at the 3' carbon), wherein the 3' end cap is selected from the 3' end caps listed in Tables 1 or 2 or otherwise disclosed herein.

The structures of various 3' end caps (including those designated "PAZ ligands") are shown below in Table 1, below. It is noted that, although some 3' end caps are designated "PAZ ligands", this disclosure is not bound by any particular theory.

TABLE 1

STRUCTURES OF 3' END CAPS (INCLUDING "PAZ LIGANDS") FOR RNAi AGENTS FOR RNA INTERFERENCE

| Nickname | PAZ ligand |
|---|---|
| C3 Amino | X~~~NH₂ |
| C7 Amino | X~~~~~NH₂ with OH branch |
| C3 | X~~~OH |

TABLE 1-continued

STRUCTURES OF 3' END CAPS (INCLUDING "PAZ LIGANDS") FOR RNAi AGENTS FOR RNA INTERFERENCE

| Nickname | PAZ ligand |
|---|---|
| C6 | X~~~~~OH |
| C8 | X~~~~~~~OH |
| C10 | X~~~~~~~~~OH |
| C12 | X~~~~~~~~~~~OH |
| BP | biphenyl structure with X and OH |
| X027 | aryl-ether-pyridine structure with X and OH |
| X038 | bromoindole carboxamide structure with pyridyl and benzyl-OH groups, X |
| X050 | biphenyl-ether-benzyl structure with X and OH |

TABLE 1-continued

STRUCTURES OF 3' END CAPS (INCLUDING "PAZ LIGANDS") FOR RNAi AGENTS FOR RNA INTERFERENCE

| Nickname | PAZ ligand |
|---|---|
| X051 | |
| X052 | |
| X058 | |
| X059 | |
| X060 | |
| X061 | |
| X062 | |
| X063 | |

TABLE 1-continued

STRUCTURES OF 3' END CAPS (INCLUDING "PAZ LIGANDS") FOR RNAi AGENTS FOR RNA INTERFERENCE

| Nickname | PAZ ligand |
|---|---|
| X064 | (structure) |
| X065 | (structure) |
| X066 | (structure) |
| X067 | (structure) |
| X068 | (structure) |
| X069 | (structure) |
| X097 | (structure) |
| X098 | (structure) |
| X109 | (structure) |

TABLE 1-continued

STRUCTURES OF 3' END CAPS (INCLUDING "PAZ LIGANDS") FOR RNAi AGENTS FOR RNA INTERFERENCE

| Nickname | PAZ ligand |
|---|---|
| X110 | (structure) |
| X111 | (structure) |
| X112 | (structure) |
| X113 | (structure) |
| X1009 | (structure) |
| X1010 | (structure) |
| X1011 | (structure) |
| X1012 | (structure) |
| X1013 | (structure) |
| X1015 | (structure) |
| X1016 | (structure) |
| X1017 | (structure) |
| X1018 | (structure) |

TABLE 1-continued
STRUCTURES OF 3' END CAPS (INCLUDING "PAZ LIGANDS") FOR RNAi AGENTS FOR RNA INTERFERENCE
| Nickname | PAZ ligand |
|---|---|
| X1019 | 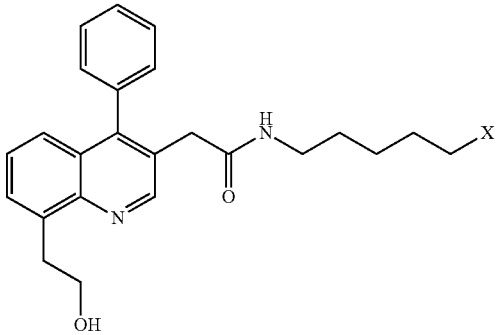 |
| X1020 | 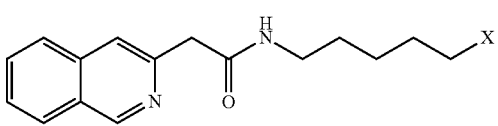 |
| X1021 | 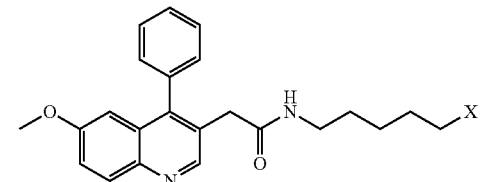 |
| X1022 | 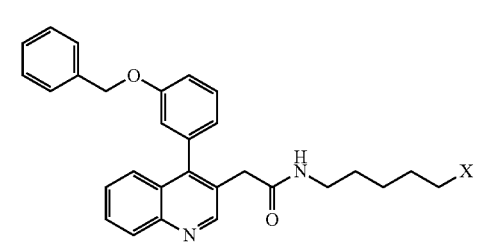 |
| X1024 | 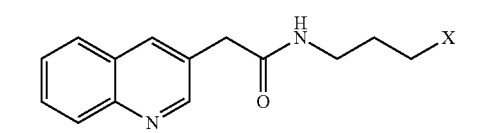 |
| X1025 | 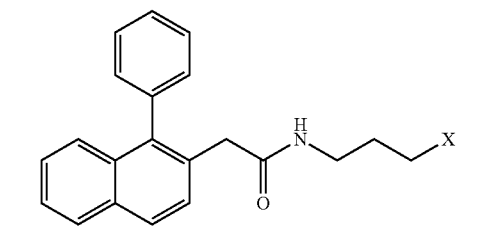 |
| X1026 | 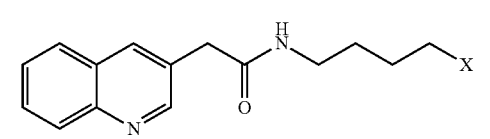 |
| X1027 | 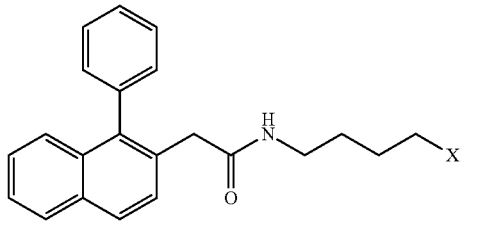 |
| X1028 | 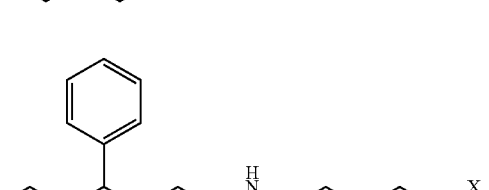 |
| X1047 | 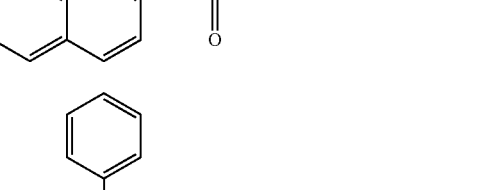 |
| X1048 | 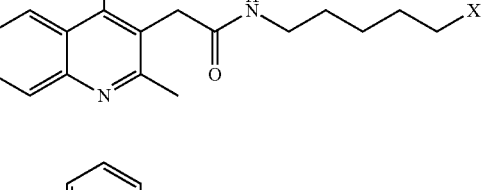 |
| X1049 | 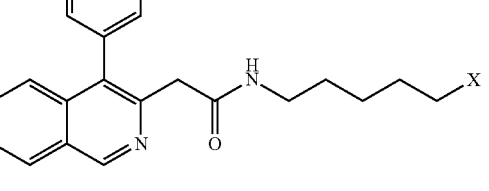 |
| X1062 | 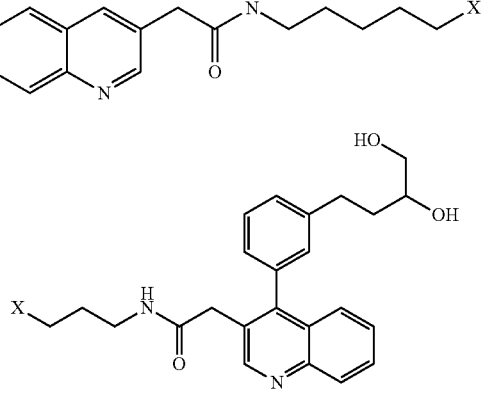 |

TABLE 1-continued

STRUCTURES OF 3' END CAPS (INCLUDING "PAZ LIGANDS") FOR RNAi AGENTS FOR RNA INTERFERENCE

| Nickname | PAZ ligand |
|---|---|
| X1063 | 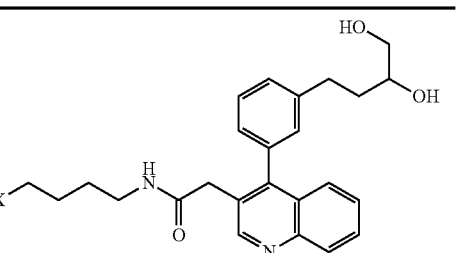 |
| X1064 | 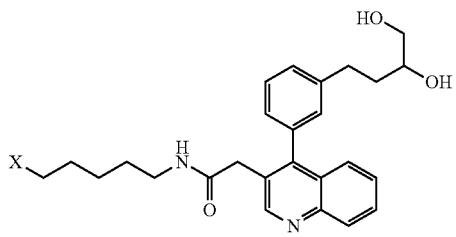 |

The structures of Table 1 represent 3' end caps that can be at the 3' end of one or both strands of an RNAi agent (represented by X). In some embodiments, the 3' end cap is on the 3' end of the antisense strand.

Specific embodiments of the structures of Table 1 are diagrammed in Table 2.

In the structures of Tables 1 and 2:

In some embodiments, hydroxyl groups are present and X represents the 3' end of a strand of an RNAi agent. For example, the 3' end of a strand of a RNAi can terminate at a phosphate group, to which the 3' end cap is bound. Non-limiting examples of such a structure are shown in, for example, FIG. 15A (C3), FIG. 18C (C6, C8, and C10); and FIG. 19 (X027, C6 and X058). Among others, X027 and X058 are active on 19-mers in vitro. Table 2 shows the structures of various 3' end caps bound to the phosphate at the 3' end of a strand of an RNAi agent. As a non-limiting example: X058 has been shown (data shown herein and data not shown) to be a functional 3' end cap on a variety of different RNAi agents of different lengths, sequences and targets, both in vitro and in vivo. X058 was an effective 3' end cap, for example, on 21-mer blunt-ended HuR RNAi agents, wherein each strand is a 21-mer, and the two strands together form a blunt-ended duplex, and the 3' end of each strand terminates in a phosphate and further comprises a 3' end cap which was X058. X058 was also effective with several different targets and sequences in the 18-mer format. For example, several effective RNAi agents were constructed comprising a first and a second strand, wherein the first and second strands both were 18-mers, and the two strands together formed a blunt-ended duplex, wherein the 3' end of the guide strand terminates in a phosphate or modified internucleoside linker and further comprises, in 5' to 3' order: a spacer, a phosphate or modified internucleoside linker, and a 3' end cap which is X058. Several effective RNAi agents were constructed comprising a first and a second strand, wherein the first and second strands both were 18-mers, and the two strands together formed a blunt-ended duplex, wherein the 3' end of the guide strand terminates in a phosphate and further comprises, in 5' to 3' order: a spacer, a phosphate, and a 3' end cap which is X058.

Several effective RNAi agents were constructed comprising a first and a second strand, wherein the first and second strands both were 18-mers, and the two strands together formed a blunt-ended duplex, wherein the 3' end of the guide strand terminates in a phosphate and further comprises, in 5' to 3' order: a spacer which is ribitol, a phosphate, and a 3' end cap which is X058. X058 was also effective on other RNAi agents. X058 is thus an effective 3' end cap on a variety of RNAi agents of different lengths, targets, and sequences, both in vivo and in vitro.

In some embodiments, where hydroxyl groups are present, the hydroxyl can exist in a protected form. Suitable protecting groups for OH are known in the art. Protected forms of OH include, but are not limited to, ethers, phosphate esters, methyl tetraacetyl glucuronates, peracetyl glycosides and amino acid polypeptide esters.

Embodiments Comprising a Spacer, a Phosphate or Modified Internucleoside Linker, and a 3' End Cap In some embodiments, one or both strands of the RNAi agent further comprise, at the 3' end and in 5' to 3' order: a spacer, a phosphate or modified internucleoside linker, and a 3' end cap (e.g., a 3' end cap as disclosed herein).

Thus:

In one embodiment, X is the 3' end of a molecule comprising a strand of a RNAi agent, wherein the 3' end of the strand terminates in a phosphate or modified internucleoside linker and further comprises in 5' to 3' order: a spacer, and a second phosphate or modified internucleoside linker. In various embodiments, the spacer is a ribitol, 2'-deoxyribitol, or 2'-methoxyethoxy ribitol (ribitol with 2'-MOE), a C3, C4, C5 or C6, or 4-methoxybutane-1,3-diol. Various embodiments are described in more detail below.

SPACERS: Ribitol, Diribitol, 2'-deoxyribitol, 2'-methoxyethoxy Ribitol, C3, C4, C5, C6, or 4-methoxybutane-1,3-Diol (5300)

In some embodiments, the 3' end of one or both strands of the RNAi agent terminates in a phosphate or modified internucleoside linker and further comprises, in 5' to 3' order: a spacer, a phosphate or modified internucleoside linker, and a 3' end cap (e.g., a 3' end cap as disclosed herein). A spacer is a chemical moiety intended or used to create or maintain a space (e.g., a proper or functional spacing) between two other chemical moieties; e.g., between two phosphates or modified internucleoside linkers. The spacer can be selected from, for example, ribitol, diribitol, 2'-deoxyribitol, or 2'-methoxyethoxy ribitol (ribitol with 2'-MOE) or an equivalent abasic nucleotide known to one skilled in the art, or a lower alkyl or alkoxy group such as a C3, C4, C5 or C6, or 4-methoxybutane-1,3-diol, as described below.

Ribitol Spacer.

In some embodiments, the spacer is ribitol or other type of abasic nucleotide.

In one embodiment, the RNAi agent comprises a strand, wherein the 3' end of the strand terminates in a phosphate or modified internucleoside linker and further comprises, in 5' to 3' order: a spacer which is ribitol, a second phosphate or modified internucleoside linker, and a 3' end (e.g., any 3' end cap described herein or known in the art). In other words: In one embodiment, the RNAi agent comprises, in 5' to 3' order: a strand comprising a 3' terminal phosphate or a modified internucleoside linker; a spacer which is ribitol; a phosphate or a modified internucleoside linker; and a 3' end cap (e.g., any 3' end cap described herein or known in the art). Thus: In one embodiment, the RNAi agent comprises, in 5' to 3' order: a strand comprising a 3' terminal phosphate;

a spacer which is ribitol; a phosphate or a modified internucleoside linker; and a 3' end cap.

The structure of the 3' terminal phosphate and ribitol spacer is shown here:

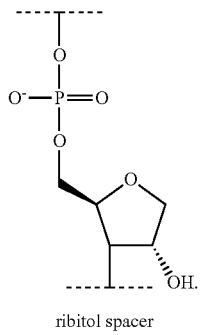

ribitol spacer

In some documents, the ribitol spacer is designated as N027 (C0027, etc.).

One embodiment is shown in FIG. 18, wherein the RNAi agent comprises, in 5' to 3' order: an 18-mer strand, wherein the 3' end of the 18-mer strand terminates in a phosphate and further comprises, in 5' to 3' order: a spacer which is ribitol, a phosphate, and a 3' end cap which is X058. This structure can be on any RNAi strand of any sequence or target. In addition, any 3' end cap disclosed herein can be used in place of X058.

A related structure is shown in FIG. 19 ("ribitol with X058"), wherein the last nucleotide of the 18-mer strand is shown (and is a 2'-MOE), and the 3' end of the 18-mer strand terminates in a phosphate and further comprises, in 5' to 3' order: a spacer which is ribitol, a second phosphate, and a 3' end cap which is X058.

Another embodiment is shown in FIG. 19 ("ribitol with C6 cap"), wherein the last nucleotide of the 18-mer strand is shown (and is a 2'-MOE), and the 3' end of the 18-mer strand terminates in a phosphate and further comprises, in 5' to 3' order: a spacer which is ribitol, a phosphate, and a 3' end cap which is C6.

In one embodiment, the RNAi agent comprises, in 5' to 3' order: an 18-mer strand terminating in a 3' phosphate, a ribitol spacer, a phosphate, and a C6 3' end cap. This is diagrammed as ribpC6 (or ribC6) in Table 2.

In one embodiment, the RNAi agent comprises, in 5' to 3' order: an 18-mer strand terminating in a 3' phosphate, a ribitol spacer, a phosphate, and a BP 3' end cap. This is diagrammed as ribpBP (or ribBP) in Table 2.

In one embodiment, the RNAi agent comprises, in 5' to 3' order: an 18-mer strand terminating in a 3' phosphate, a ribitol spacer, a phosphate, and a C10 3' end cap. This is diagrammed as ribpC10 (or ribC10) in Table 2.

One embodiment is shown in FIG. 21, wherein the RNAi agent comprises a strand, wherein the 3' end of the strand terminates in a phosphate and further comprises, in 5' to 3' order: a spacer which is ribitol, a phosphate, and a 3' end cap which is X058. While the structure illustrated in FIG. 21 is an 18-mer RNAi agent, this structure can be on any RNAi strand of any length, sequence or target. In addition, any 3' end cap disclosed herein can be used in place of X058.

In some embodiments, the 3' end cap is a ribitol. Thus, the RNAi agent comprises an 18-mer strand, wherein the 3' end of the 18-mer strand terminates in a phosphate or modified internucleoside linker and further comprises, in 5' to 3' order: a spacer which is ribitol, a second phosphate or modified internucleoside linker, and a 3' end cap which is a second ribitol. In one embodiment, the 3' end of the 18-mer strand terminates in a phosphate and further comprises, in 5' to 3' order: a spacer which is ribitol, a second phosphate, and a 3' end cap which is a second ribitol. Such as structure is illustrated in FIG. 19 (including the 3' terminal nucleotide and phosphate) and designated "diribitol".

In various embodiments, the 3' end cap is triethylene glycol, cyclohexyl, phenyl, BP (biphenyl), lithochol (lithocholic acid), adamantane, C3 amino, C7 amino, C3, C6, C8, C10, C12, X027, X038, X050, X051, X052, X058, X059, X060, X061, X062, X063, X064, X065, X066, X067, X068, X069, X097, X098, X109, X110, X111, X112, X113, X1009, X1010, X1011, X1012, X1013, X1015, X1016, X1017, X1018, X1019, X1020, X1021, X1022, X1024, X1025, X1026, X1027, X1028, X1047, X1048, X1049, X1062, X1063, X1064, or ribitol, or any 3' end cap disclosed herein or known in the art. The structure comprising an RNAi agent comprising, in 5' to 3' order, a strand terminating in a 3' terminal phosphate or a modified internucleoside linker, a ribitol spacer, a phosphate or a modified internucleoside linker, and a 3' end cap (e.g., any 3' end cap disclosed herein including but not limited to those listed in the previous sentence) can be used on any RNAi agent of any length, sequence or target, including but not limited to a double-stranded RNA, wherein optionally one or more phosphates are replaced by a modified internucleoside linker, optionally one or more nucleotides are modified, and optionally one or more RNA nucleotides are replaced by DNA, PNA, LNA, morpholino, TNA, GNA, ANA, HNA, CeNA, FANA, and/or UNA.

Diribitol Spacer.

In some embodiments, the spacer is Diribitol.

In one embodiment, the RNAi agent comprises a strand, wherein the 3' end of the strand terminates in a phosphate or a modified internucleoside linker and further comprises, in 5' to 3' order: a spacer (wherein the spacer comprises in 5' to 3' order: a first ribitol; a phosphate or a modified internucleoside linker; a second ribitol; a phosphate or a modified internucleoside linker); and a 3' end cap.

In one embodiment, the RNAi agent comprises, in 5' to 3' order: a strand comprising a 3' terminal phosphate; a first ribitol spacer; a phosphate; a second ribitol spacer; a phosphate or a modified internucleoside linker; and a 3' end cap. This structure of the 3' terminal phosphate, the first ribitol, a phosphate, and the second ribitol is shown here:

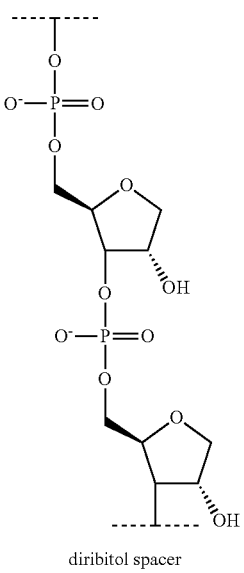

diribitol spacer

In one embodiment, the RNAi agent comprises, in 5' to 3' order: a strand terminating in a 3' terminal phosphate or a modified internucleoside linker, a first ribitol spacer, a phosphate or a modified internucleoside linker, a second ribitol spacer, a phosphate or a modified internucleoside linker, and a 3' end cap which is a ribitol; this structure is designated a triribitol.

In one embodiment, the RNAi agent comprises, in 5' to 3' order: a strand terminating in a 3' phosphate, a ribitol spacer, a phosphate, and a C6 3' end cap. This is diagrammed as ribpC6 (or ribC6) in Table 2.

In one embodiment, the RNAi agent comprises, in 5' to 3' order: a strand terminating in a 3' phosphate, a ribitol spacer, a phosphate, and a BP 3' end cap. This is diagrammed as ribpBP (or ribBP) in Table 2.

In one embodiment, the RNAi agent comprises, in 5' to 3' order: a strand terminating in a 3' phosphate, a ribitol spacer, a phosphate, and a C10 3' end cap. This is diagrammed as ribpC10 (or ribC10) in Table 2. In various embodiments, the 3' end cap is triethylene glycol, cyclohexyl, phenyl, BP (biphenyl), lithochol (lithocholic acid), adamantane, C3 amino, C7 amino, C3, C6, C8, C10, C12, X027, X038, X050, X051, X052, X058, X059, X060, X061, X062, X063, X064, X065, X066, X067, X068, X069, X097, X098, X109, X110, X111, X112, X113, X1009, X1010, X1011, X1012, X1013, X1015, X1016, X1017, X1018, X1019, X1020, X1021, X1022, X1024, X1025, X1026, X1027, X1028, X1047, X1048, X1049, X1062, X1063, X1064, or any 3' end cap disclosed herein or known in the art.

The structure comprising an RNAi agent comprising, in 5' to 3' order, a strand terminating in a 3' terminal phosphate or a modified internucleoside linker, a first ribitol spacer, a phosphate or a modified internucleoside linker, a second ribitol spacer, a phosphate or a modified internucleoside linker, and a 3' end cap (e.g., any 3' end cap disclosed herein) can be used on any RNAi agent of any length, sequence or target, including but not limited to a double-stranded RNA, wherein optionally one or more phosphates are replaced by a modified internucleoside linker, optionally one or more nucleotides are modified, and optionally one or more RNA nucleotides are replaced by DNA, PNA, LNA, morpholino, TNA, GNA, ANA, HNA, CeNA, FANA, and/or UNA.

2'-methoxyethoxy Ribitol Spacer.

In some embodiments, the spacer is 2'-methoxyethoxy ribitol or other type of abasic nucleotide.

In one embodiment, the RNAi agent comprises a strand, wherein the 3' end of the strand terminates in a phosphate or modified internucleoside linker and further comprises, in 5' to 3' order: a spacer which is 2'-methoxyethoxy ribitol, a second phosphate or modified internucleoside linker, and a 3' end (e.g., any 3' end cap described herein or known in the art). In other words: In one embodiment, the RNAi agent comprises, in 5' to 3' order: a strand comprising a 3' terminal phosphate or a modified internucleoside linker; a spacer which is 2'-methoxyethoxy ribitol; a phosphate or a modified internucleoside linker; and a 3' end cap (e.g., any 3' end cap described herein or known in the art). Thus: In one embodiment, the RNAi agent comprises, in 5' to 3' order: a strand comprising a 3' terminal phosphate; a spacer which is 2'-methoxyethoxy ribitol; a phosphate or a modified internucleoside linker; and a 3' end cap.

The structure of the 3' terminal phosphate and 2'-methoxyethoxy ribitol spacer is shown here:

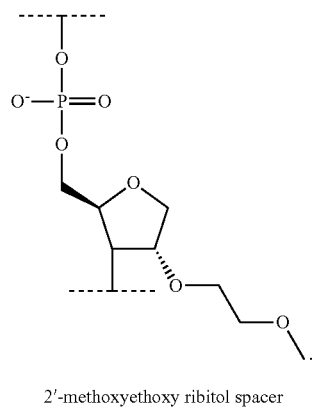

2'-methoxyethoxy ribitol spacer

In one embodiment, the RNAi agent comprises, in 5' to 3' order: an 18-mer strand, wherein the 3' end of the 18-mer strand terminates in a phosphate and further comprises, in 5' to 3' order: a spacer which is 2'-methoxyethoxy ribitol, a phosphate, and a 3' end cap which is X058. This structure can be on any RNAi strand of any sequence or target. In addition, any 3' end cap disclosed herein can be used in place of X058.

A related structure is 2'-methoxyethoxy ribitol with X058, wherein the last nucleotide of the 18-mer strand is a 2'-MOE), and the 3' end of the 18-mer strand terminates in a phosphate and further comprises, in 5' to 3' order: a spacer which is 2'-methoxyethoxy ribitol, a second phosphate, and a 3' end cap which is X058.

Another embodiment is 2'-methoxyethoxy ribitol with C6 cap, wherein the last nucleotide of the 18-mer strand is a 2'-MOE), and the 3' end of the 18-mer strand terminates in a phosphate and further comprises, in 5' to 3' order: a spacer which is 2'-methoxyethoxy ribitol, a phosphate, and a 3' end cap which is C6.

In one embodiment, the RNAi agent comprises, in 5' to 3' order: an 18-mer strand terminating in a 3' phosphate, a 2'-methoxyethoxy ribitol spacer, a phosphate, and a C6 3' end cap.

In one embodiment, the RNAi agent comprises, in 5' to 3' order: an 18-mer strand terminating in a 3' phosphate, a 2'-methoxyethoxy ribitol spacer, a phosphate, and a BP 3' end cap.

In one embodiment, the RNAi agent comprises, in 5' to 3' order: an 18-mer strand terminating in a 3' phosphate, a 2'-methoxyethoxy ribitol spacer, a phosphate, and a C10 3' end cap.

In another embodiment, the RNAi agent comprises a strand, wherein the 3' end of the strand terminates in a phosphate and further comprises, in 5' to 3' order: a spacer which is 2'-methoxyethoxy ribitol, a phosphate, and a 3' end cap which is X058.

In some embodiments, the 3' end cap is a 2'-methoxyethoxy ribitol. Thus, the RNAi agent comprises an 18-mer strand, wherein the 3' end of the 18-mer strand terminates in a phosphate or modified internucleoside linker and further comprises, in 5' to 3' order: a spacer which is 2'-methoxyethoxy ribitol, a second phosphate or modified internucleoside linker, and a 3' end cap which is a second 2'-methoxyethoxy ribitol. In one embodiment, the 3' end of the 18-mer strand terminates in a phosphate and further comprises, in 5' to 3' order: a spacer which is 2'-methoxyethoxy ribitol, a second phosphate, and a 3' end cap which is a second 2'-methoxyethoxy ribitol.

In various embodiments, the 3' end cap is triethylene glycol, cyclohexyl, phenyl, BP (biphenyl), lithochol (lithocholic acid), adamantane, C3 amino, C7 amino, C3, C6, C8, C10, C12, X027, X038, X050, X051, X052, X058, X059, X060, X061, X062, X063, X064, X065, X066, X067, X068, X069, X097, X098, X109, X110, X111, X112, X113, X1009, X1010, X1011, X1012, X1013, X1015, X1016, X1017, X1018, X1019, X1020, X1021, X1022, X1024, X1025, X1026, X1027, X1028, X1047, X1048, X1049, X1062, X1063, X1064, or 2'-methoxyethoxy ribitol, or any 3' end cap disclosed herein or known in the art. The structure comprising an RNAi agent comprising, in 5' to 3' order, a strand terminating in a 3' terminal phosphate or a modified internucleoside linker, a 2'-methoxyethoxy ribitol spacer, a phosphate or a modified internucleoside linker, and a 3' end cap (e.g., any 3' end cap disclosed herein including but not limited to those listed in the previous sentence) can be used on any RNAi agent of any length, sequence or target, including but not limited to a double-stranded RNA, wherein optionally one or more phosphates are replaced by a modified internucleoside linker, optionally one or more nucleotides are modified, and optionally one or more RNA nucleotides are replaced by DNA, PNA, LNA, morpholino, TNA, GNA, ANA, HNA, CeNA, FANA, and/or UNA.

2'-deoxyribitol Spacer.

In some embodiments the spacer is 2'-deoxyribitol.

In one embodiment, the RNAi agent comprises, in 5' to 3' order: a strand terminating in a 3' phosphate or a modified internucleoside linker, a spacer which is 2'-deoxyribitol (2'-deoxyrib), a phosphate or a modified internucleoside linker, and a 3' end cap.

In one embodiment, the RNAi agent comprises, in 5' to 3' order: a strand terminating in a 3' phosphate, a spacer which is 2'-deoxyribitol (2'-deoxyrib), a phosphate or a modified internucleoside linker, and a 3' end cap. The structure of the 3' terminal phosphate and 2'-deoxyribitol is shown here:

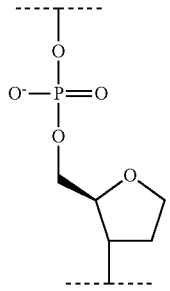

2'-deoxyribitol (2'-deoxyrib).

In one embodiment, the RNAi agent comprises, in 5' to 3' order: a strand comprising a 3' terminal phosphate; a first ribitol spacer; a phosphate; a second ribitol spacer; a phosphate or a modified internucleoside linker; and a 3' end cap.

In one embodiment, the RNAi agent comprises, in 5' to 3' order: a strand terminating in a 3' phosphate, a 2'-deoxyribitol spacer, a phosphate, and a C12 3' end cap. This is diagrammed as ribpC12 (or ribC12) in Table 2. This embodiment is designated "2'DeoxyribC12" and illustrated in Table 2.

In various embodiments, the 3' end cap is In various embodiments, the 3' end cap is triethylene glycol, cyclohexyl, phenyl, BP (biphenyl), lithochol (lithocholic acid), adamantane, C3 amino, C7 amino, C3, C6, C8, C10, C12, X027, X038, X050, X051, X052, X058, X059, X060, X061, X062, X063, X064, X065, X066, X067, X068, X069, X097, X098, X109, X110, X111, X112, X113, X1009, X1010, X1011, X1012, X1013, X1015, X1016, X1017, X1018, X1019, X1020, X1021, X1022, X1024, X1025, X1026, X1027, X1028, X1047, X1048, X1049, X1062, X1063, X1064, or any 3' end cap disclosed herein or known in the art.

The structure comprising an RNAi agent comprising, in 5' to 3' order, a strand terminating in a 3' terminal phosphate or a modified internucleoside linker, a 2'-deoxyribitol spacer, a phosphate or a modified internucleoside linker, and a 3' end cap (e.g., any 3' end cap disclosed herein) can be used on any RNAi agent of any length, sequence or target, including but not limited to a double-stranded RNA, wherein optionally one or more phosphates are replaced by a modified internucleoside linker, optionally one or more nucleotides are modified, and optionally one or more RNA nucleotides are replaced by DNA, PNA, LNA, morpholino, TNA, GNA, ANA, HNA, CeNA, FANA, and/or UNA.

C3 Spacer.

In some embodiments the spacer is C3.

In one embodiment, the RNAi agent comprises, in 5' to 3' order: a strand terminating in a 3' phosphate or a modified internucleoside linker, a spacer which is C3, a phosphate or a modified internucleoside linker, and a 3' end cap.

In one embodiment, the RNAi agent comprises, in 5' to 3' order: a strand terminating in a 3' phosphate, a spacer which is C3, a phosphate or a modified internucleoside linker, and a 3' end cap.

The C3 spacer has the chemical formula $-(CH_2)_3-$. The structure of a 3' terminal phosphate and the C3 spacer is shown here:

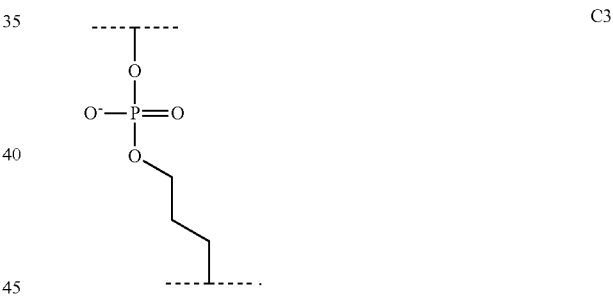

One embodiment is shown in FIG. 21, wherein the RNAi agent comprises, in 5' to 3' order: a strand terminating in a 3' phosphate, a C3 spacer, a phosphate, and a 3' end cap which is X058. While the structure illustrated in FIG. 21 is an 18-mer RNAi agent, this structure can be on any RNAi strand of any length, sequence or target. In addition, any 3' end cap disclosed herein can be used in place of X058.

Figure 14:
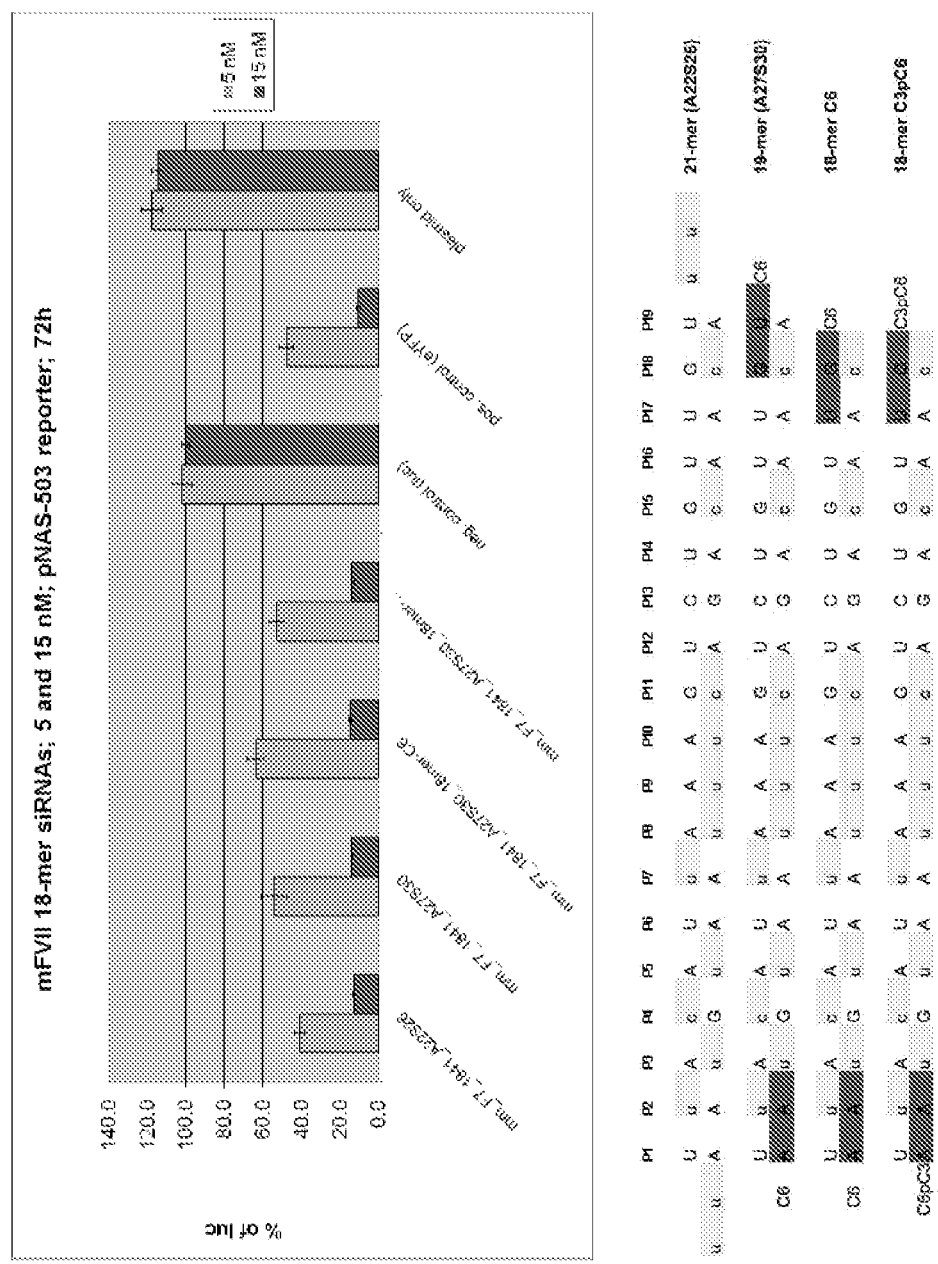
FIG. 14 shows the in vitro efficacy of various RNAi agents comprising a 3' end cap (C6); or, in 5' to 3' order, a spacer (C3), a phosphate (p) and a 3' end cap (C6), or C3pC6. These sequences are represented, from top to bottom, by SEQ ID NOs: 37 to 44. The RNAi agents tested are to mouse Factor VII.

Another embodiment is shown in FIG. 14, which illustrates a portion of a RNAi agent to Factor VII comprising a strand, wherein the strand terminates in a phosphate and further comprises in 5' to 3' order: a C3 spacer, a phosphate and a 3' end cap which is C6. This is designated "C3pC6 overhang". This structure can be on any RNAi strand of any sequence or target. In addition, any 3' end cap disclosed herein or known in the art can be used in place of C6, and any modified internucleoside linker can be used in place of phosphate.

Figure 22:
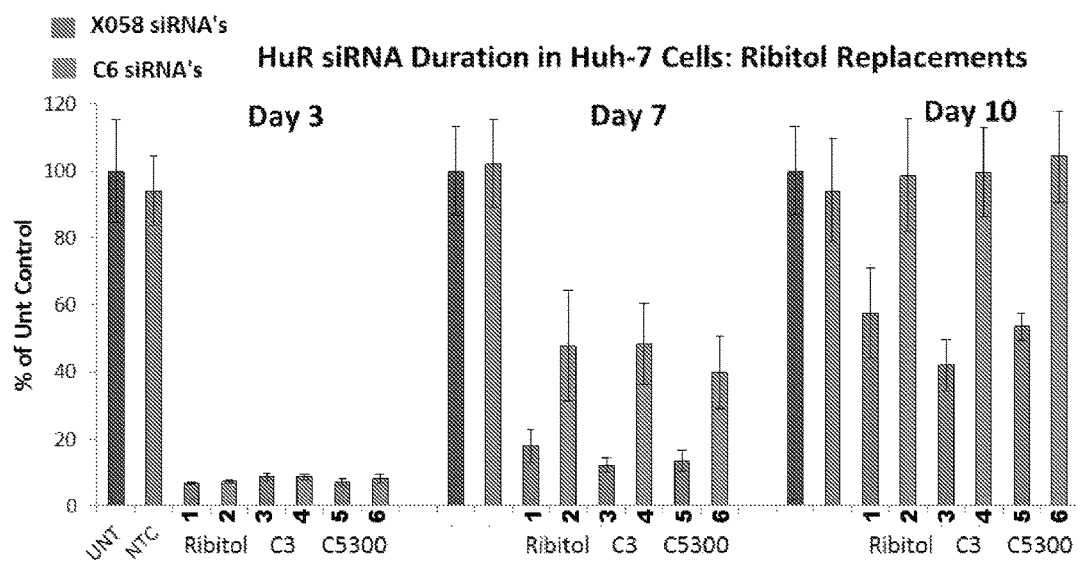
FIG. 22 shows the efficacy and duration of RNAi agent activity of example RNAi agents comprising a strand, wherein the 3' end of the strand terminates in a phosphate and further comprises, in 5' to 3' order: a spacer which is a ribitol (rib), C3 or 4-methoxybutane-1,3-diol (A5300); a phosphate; and a 3' end cap which is X058 or C6. The duplexes are numbered 1 to 6. These are RNAi agents to HuR (ELAVL1). UNT: Untreated (negative control). NTC: Non-target control (negative control using an unrelated RNAi that targets a different target).

The efficacy of a RNAi agent comprising a C3 spacer is shown in FIG. 22. Two different HuR constructs were prepared comprising a strand, wherein the 3' end of the strand terminates in a phosphate and further comprises in 5' to 3' order: a C3 spacer, a phosphate and a 3' end cap (which is C6 or X058). Both of these were able to mediate RNA interference.

In various embodiments, the 3' end cap is triethylene glycol, cyclohexyl, phenyl, BP (biphenyl), lithochol (lithocholic acid), adamantane, C3 amino, C7 amino, C3, C6, C8, C10, C12, X027, X038, X050, X051, X052, X058, X059, X060, X061, X062, X063, X064, X065, X066, X067, X068, X069, X097, X098, X109, X110, X111, X112, X113, X1009, X1010, X1011, X1012, X1013, X1015, X1016, X1017, X1018, X1019, X1020, X1021, X1022, X1024, X1025, X1026, X1027, X1028, X1047, X1048, X1049, X1062, X1063, X1064, or any 3' end cap disclosed herein or known in the art.

The structure comprising an RNAi agent comprising, in 5' to 3' order, a strand terminating in a 3' terminal phosphate or a modified internucleoside linker, a C3 spacer, a phosphate or a modified internucleoside linker, and a 3' end cap (e.g., any 3' end cap disclosed herein) can be used on any RNAi agent of any length, sequence or target, including but not limited to a double-stranded RNA, wherein optionally one or more phosphates are replaced by a modified internucleoside linker, optionally one or more nucleotides are modified, and optionally one or more RNA nucleotides are replaced by DNA, PNA, LNA, morpholino, TNA, GNA, ANA, HNA, CeNA, FANA, and/or UNA.

C4 Spacer, C5 Spacer and C6 Spacer.

In various embodiments, the spacer is C4 or C5 or C6.

In one embodiment, the RNAi agent comprises a strand, wherein the 3' end of the strand terminates in a 3' phosphate or a modified internucleoside linker, and further comprises a spacer which is C4 or C5 or C6, a phosphate or a modified internucleoside linker, and a 3' end cap.

In one embodiment, the RNAi agent comprises two strands, wherein the 3' end of each strand terminates in a 3' phosphate or a modified internucleoside linker, and further comprises a spacer, a second phosphate or a modified internucleoside linker, and a 3' end cap, wherein the spacer in one or both strands is C4 or C5 or C6.

The C3 to C6 spacers can be defined as:
C3=1,3-propane-diol
C4=1,4-butane-diol
C5=1,5-pentane-diol
C6=1,6-hexane-diol In some contexts:
The C4 spacer has the chemical formula $-(CH_2)_4-$.
The C5 spacer has the chemical formula $-(CH_2)_5-$.
The C6 spacer has the chemical formula $-(CH_2)_6-$.

In various embodiments, the 3' end cap is triethylene glycol, cyclohexyl, phenyl, BP (biphenyl), lithochol (lithocholic acid), adamantane, C3 amino, C7 amino, C3, C6, C8, C10, C12, X027, X038, X050, X051, X052, X058, X059, X060, X061, X062, X063, X064, X065, X066, X067, X068, X069, X097, X098, X109, X110, X111, X112, X113, X1009, X1010, X1011, X1012, X1013, X1015, X1016, X1017, X1018, X1019, X1020, X1021, X1022, X1024, X1025, X1026, X1027, X1028, X1047, X1048, X1049, X1062, X1063, X1064, or any 3' end cap disclosed herein or known in the art.

The structure comprising an RNAi agent comprising, in 5' to 3' order, a strand terminating in a 3' terminal phosphate or a modified internucleoside linker, a C4 or C5 or C6 spacer, a phosphate or a modified internucleoside linker, and a 3' end cap (e.g., any 3' end cap disclosed herein) can be used on any RNAi agent of any sequence or target, including but not limited to a double-stranded RNA, wherein optionally one or more phosphates are replaced by a modified internucleoside linker, optionally one or more nucleotides are modified, and optionally one or more RNA nucleotides are replaced by DNA, PNA, LNA, morpholino, TNA, GNA and/or UNA.

Figure 13:
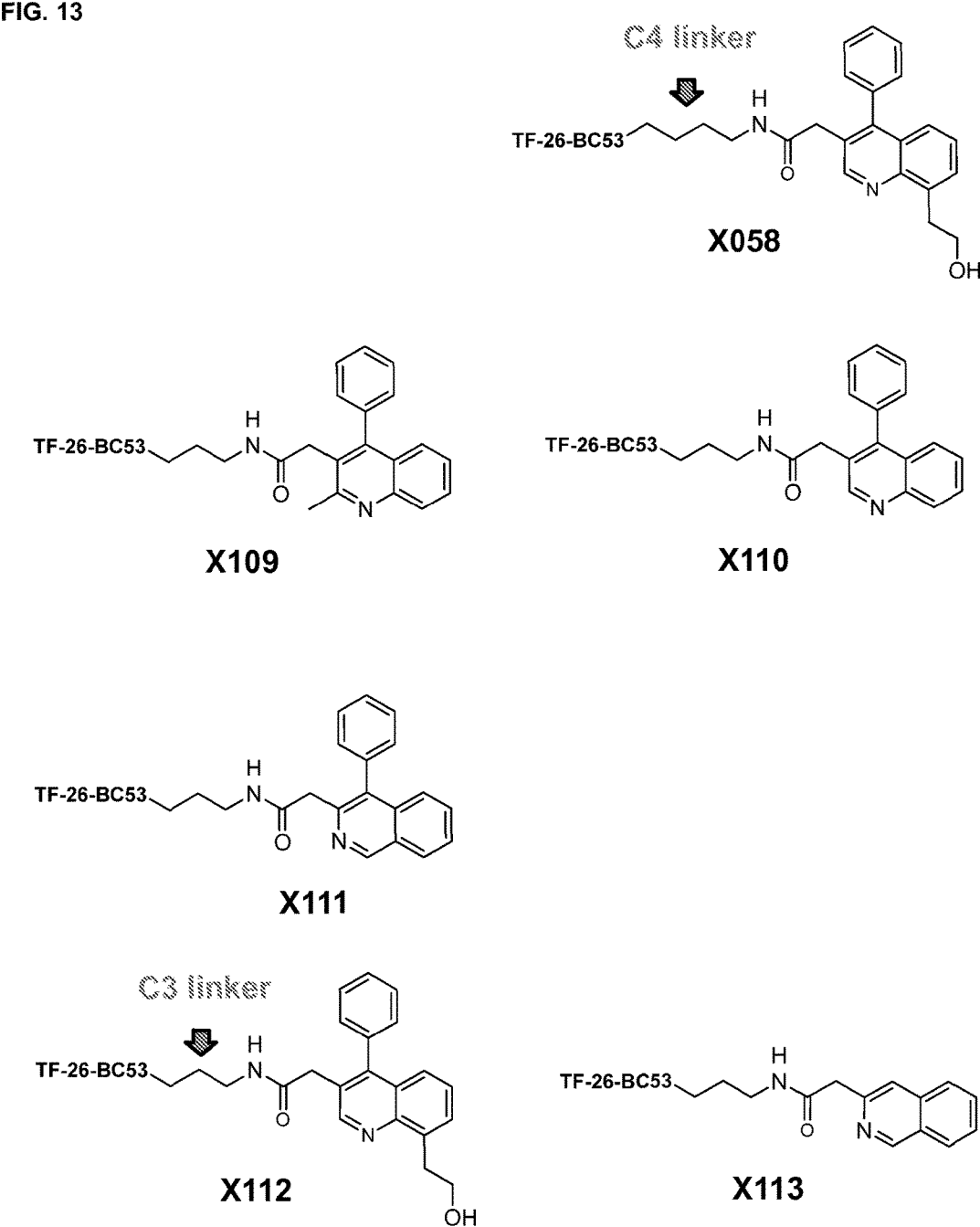
FIG. 13 shows the structure of the X058, X109, X110, X111, X112 and X113 3' end caps. TF-26-BC53 indicates a RNAi agent, and these 3' end caps can be used with either or both strands of any RNAi agent of any sequence or target.

As a note of clarification, this disclosure notes that the terms "C3" $[-(CH_2)_3-]$, "C4" $[-(CH_2)_4-]$, and "C5" $[-(CH_2)_5-]$ are generally used herein to designate spacers, similar terms (C3, C4, C5 "linkers") are also used to designate a portion of a 3' end cap. In these figures, the different linkers are used to differentiate portions of various 3' end caps. It is also noted that the term "C3" is used to designate a C3 3' end cap (e.g., FIG. 15A), a C3 spacer (FIG. 21), and a C3 linker (FIG. 13). The C6 spacer should also be differentiated from the C6 end cap.

4-methoxybutane-1,3-diol (5300) Spacer.

In various embodiments, the spacer is 4-methoxybutane-1,3-diol. 4-methoxybutane-1,3-diol is also designated 5300, A5300, C5300, G5300, and UG5300.

In one embodiment, the RNAi agent comprises, in 5' to 3' order: a strand terminating in a 3' phosphate (a 3' terminal phosphate) or a modified internucleoside linker, a spacer which is 4-methoxybutane-1,3-diol, a phosphate or a modified internucleoside linker, and a 3' end cap.

The structure of a 3' terminal phosphate and the 4-methoxybutane-1,3-diol spacer is shown here:

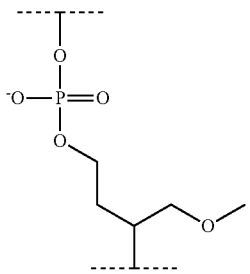

4-methoxybutane-1,3-diol is also designated 5300, A5300, C5300, G5300, and UG5300. In one embodiment, the RNAi agent comprises, in 5' to 3' order: a strand terminating in a 3' phosphate, a spacer which is 4-methoxybutane-1,3-diol, a phosphate or a modified internucleoside linker, and a 3' end cap.

One embodiment is shown in FIG. 21, wherein the RNAi agent comprises, in 5' to 3' order: a strand terminating in a 3' phosphate, a 4-methoxybutane-1,3-diol spacer, a phosphate, and a 3' end cap which is X058. While the structure illustrated in FIG. 21 is an 18-mer RNAi agent, this structure can be on any RNAi strand of any length, sequence or target. In addition, any 3' end cap disclosed herein can be used in place of X058.

The efficacy of a RNAi agent comprising a C5300 spacer is shown in FIG. 22. Two different HuR constructs were prepared comprising an 18-mer, wherein the 3' end of the 18-mer terminates in a phosphate and further comprises a C5300 spacer, a phosphate and a 3' end cap (which is C6 or X058). Both of these were able to mediate RNA interference.

In various embodiments, the 3' end cap is triethylene glycol, cyclohexyl, phenyl, BP (biphenyl), lithochol (lithocholic acid), adamantane, C3 amino, C7 amino, C3, C6, C8, C10, C12, X027, X038, X050, X051, X052, X058, X059, X060, X061, X062, X063, X064, X065, X066, X067, X068, X069, X097, X098, X109, X110, X111, X112, X113, X1009, X1010, X1011, X1012, X1013, X1015, X1016, X1017, X1018, X1019, X1020, X1021, X1022, X1024, X1025, X1026, X1027, X1028, X1047, X1048, X1049, X1062, X1063, X1064, or any 3' end cap disclosed herein or known in the art.

The structure comprising an RNAi agent comprising, in 5' to 3' order, a strand terminating in a 3' terminal phosphate or a modified internucleoside linker, a 4-methoxybutane-1,3-diol spacer, a phosphate or a modified internucleoside linker, and a 3' end cap (e.g., any 3' end cap disclosed herein) can be used on any RNAi agent of any length, sequence or target, including but not limited to a double-stranded RNA, wherein optionally one or more phosphates are replaced by a modified internucleoside linker, optionally one or more nucleotides are modified, and optionally one or more RNA nucleotides are replaced by DNA, PNA, LNA, morpholino, TNA, GNA, ANA, HNA, CeNA, FANA, and/or UNA.

Phosphate or Modified Internucleoside Linker

In various embodiments, the modified internucleoside linker is: phosphorothioate, phosphorodithioate, phosphoramidate, boranophosphonoate, an amide linker, or a compound of formula (I), as detailed below.

In some embodiments, one or both strands of the RNAi agent comprise, at the 3' end, a spacer, a phosphate or modified internucleoside linker, and a 3' end cap (e.g., a 3' end cap as disclosed herein).

In various embodiments, one or more of the phosphates of one or both strands of the RNAi agent are replaced. Thus: In various embodiments, one or more nucleotide of one or both strands has a modified internucleoside linker. In some embodiments, the 3' terminal phosphate is replaced. In some embodiments, one or more nucleotide of one or both strands has a modified internucleoside linker, and/or a modified internucleoside linker is interposed between the spacer and the 3' end cap.

In one embodiment, the present disclosure encompasses a RNAi agent comprising a first strand and a second strand, wherein each strand is a 49-mer or shorter, and wherein the 3'-terminus of at least one strand comprises a 3' end cap, wherein the 3' end cap is selected from the 3' end caps listed in Tables 1 or 2 or otherwise disclosed herein, and wherein at least one nucleotide has a modified internucleoside linker a modified internucleoside linker (e.g., wherein at least one phosphate of a nucleotide is replaced by a modified internucleoside linker), where the modified internucleoside linker is:

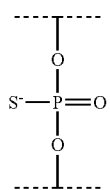

phosphorothioate (PS),

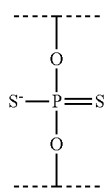

phosphorodithioate, phosphoramidate, boranophosphonoate, an amide linker, or a compound of formula (I):

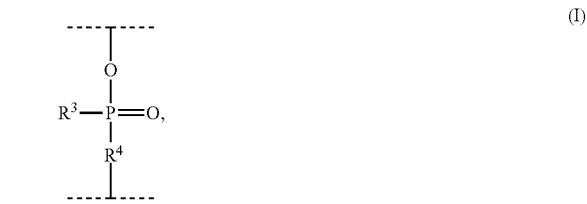

where $R^3$ is selected from $O^-$, $S^-$, $NH_2$, $BH_3$, $CH_3$, $C_{1-6}$ alkyl, $C_{6-10}$ aryl, $C_{1-6}$ alkoxy and $C_{6-10}$ aryl-oxy, wherein $C_{1-6}$ alkyl and $C_{6-10}$ aryl are unsubstituted or optionally independently substituted with 1 to 3 groups independently selected from halo, hydroxyl and $NH_2$; and $R^4$ is selected from O, S, NH, or $CH_2$.

Figure 20B:
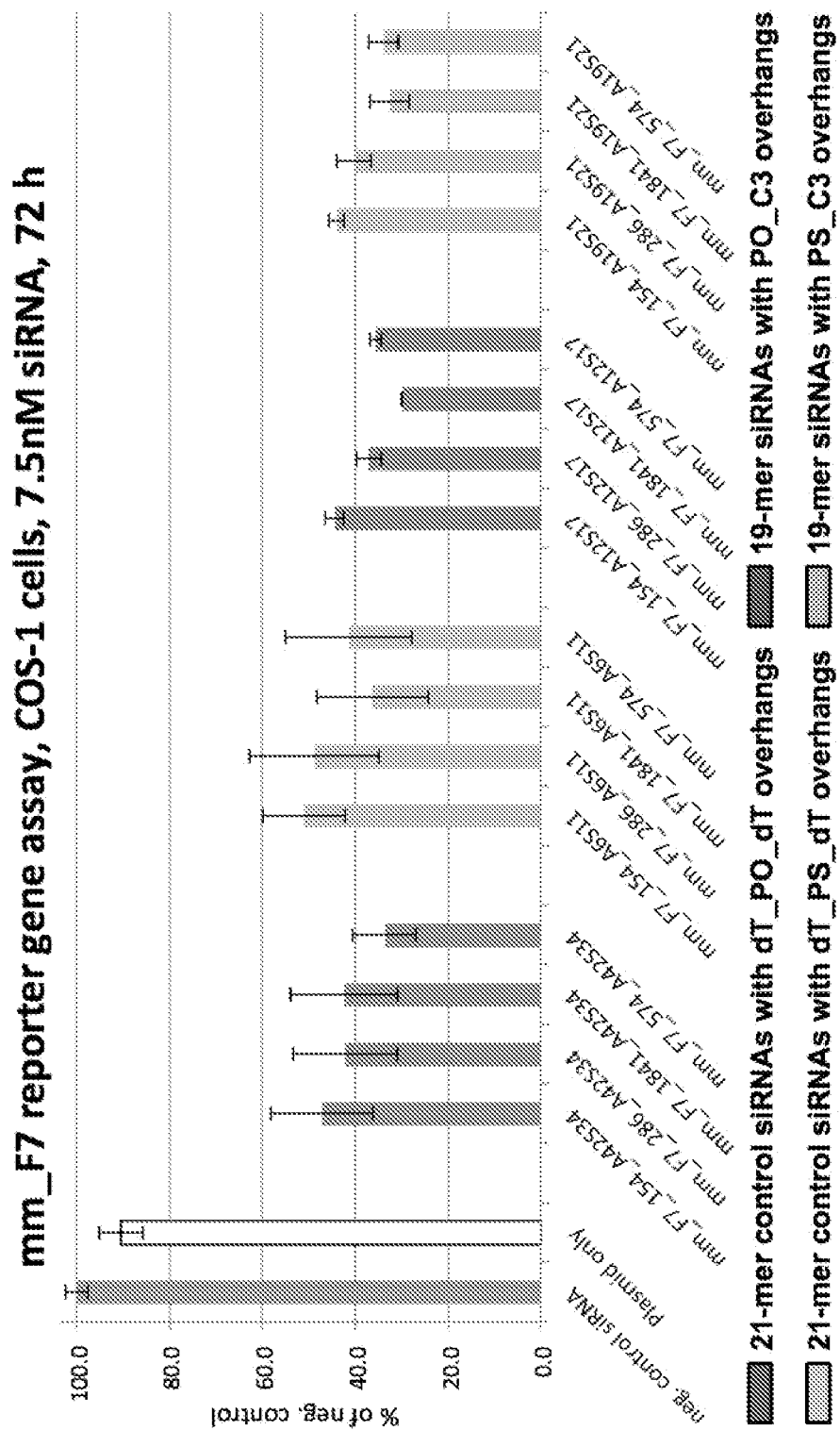
FIGS. 20A and B show the efficacy of 3' end caps and 2'-MOE clamps comprising various modifications. In various RNAi agents, the 3' terminal phosphate (P or PO) of both strands is replaced by a phosphorothioate (P or PS), and the 3' end cap is a C3. Control RNAi agents lack a 3' end cap and comprise a 3' terminal dinucleotide which (dTpdT, where "p" is a phosphate or phosphorothioate).
FIGS. 20 C, D and E show the efficacy of RNAi agents comprising a 2'-MOE clamp, wherein the last two base-pairing nt counting from 5' to 3' are RNA, DNA, 2'-MOE, 2'-F, or LNA. Thus, in various RNAi agents, one or more nucleotides is replaced by LNA. For the RNAi agents in FIGS. 20D and 20E, all the tested RNAi agents were efficacious. It is noted that the percentages do not represent knockdown, but knockdown relative to other RNAi agents. 100%, for example, represents the average knockdown of all antisense strands of these efficacious RNAi agents. The sequences in FIG. 20A are represented from top to bottom by SEQ ID NOs: 73 to 84. The sequences in FIG. 20C are represented from top to bottom by SEQ ID NOs: 85 and 86.
Figure 20D:
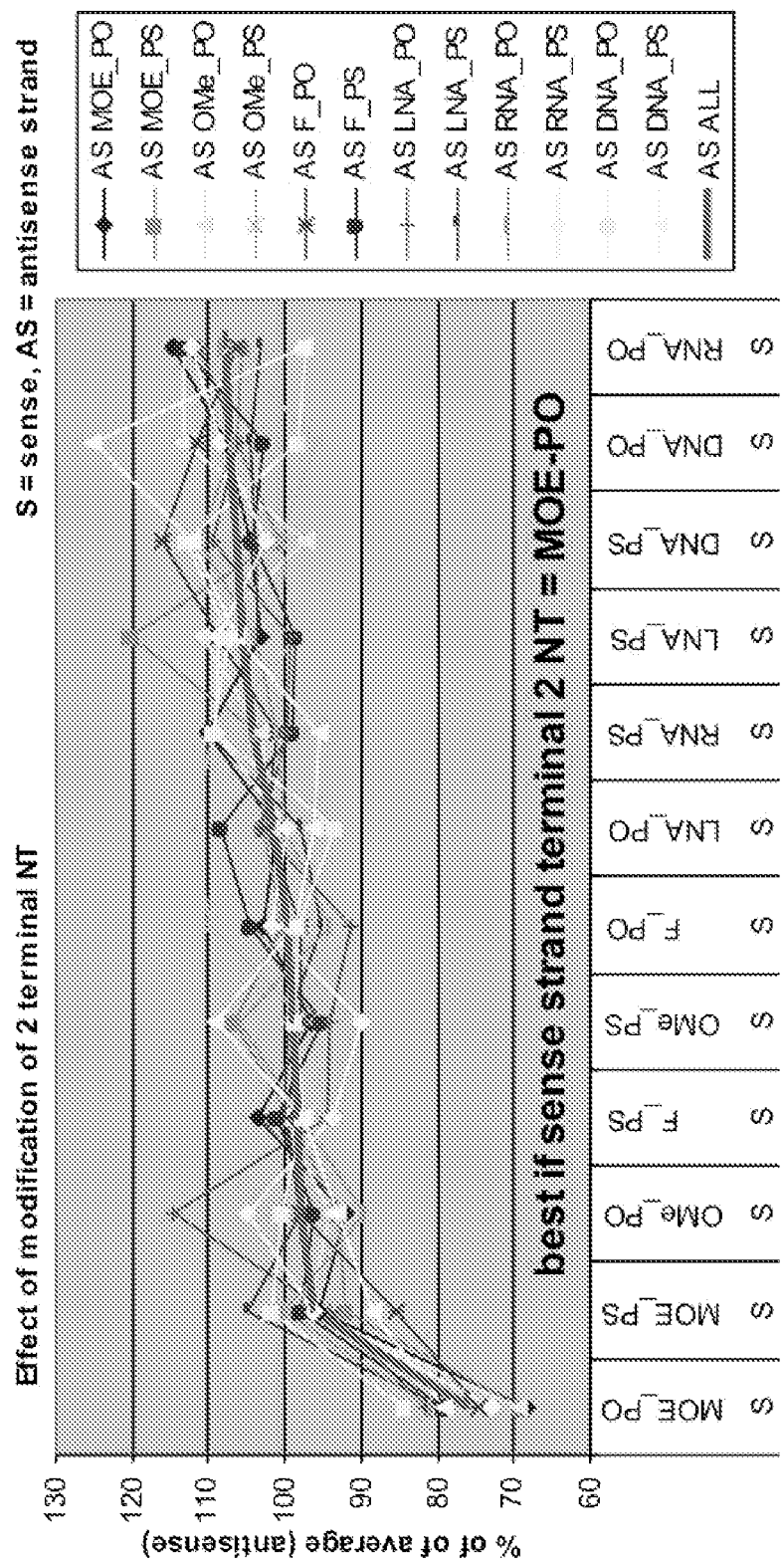

FIGS. 20D and E show the efficacy of various RNAi agents wherein the 2 3' terminal NT (nucleotides) of the sense (S) or antisense (AS) strand are 2' MOE phosphate (MOE_PO), 2'OMe phosphate (OMe-PO), RNA (RNA_PO), DNA (DNA_PO), 2'F PS (F_PS), RNA PS (RNA_PS), LNA phosphate (LNA_PO), 2'F phosphate (F_PO), 2'OMe PS (OMe_PS), 2'MOE PS (MOE_PS), DNA PS (DNA_PS), or LNA PS (LNA_PS). For the RNAi agents in FIGS. 20D and 20E, all the tested RNAi agents were efficacious. It is noted that the percentages do not represent knockdown, but knockdown relative to other RNAi agents. 100%, for example, represents the average knockdown of all antisense strands of these efficacious RNAi agents.

In one embodiment, the present disclosure encompasses a RNAi agent comprising a first strand and a second strand, wherein each strand is a 49-mer or shorter, and wherein the 3'-terminus of at least one strand comprises a 3' end cap, wherein the 3' end cap is selected from the 3' end caps listed in Tables 1 or 2 or otherwise disclosed herein, and wherein at least the 3' terminal nucleotide on one or both strands has a modified internucleoside linker (e.g., wherein the phosphate of the 3' nucleotide on one or both strands is replaced by a modified internucleoside linker), wherein the modified internucleoside linker is phosphorothioate, phosphorodithioate, phosphoramidate, boranophosphonoate, an amide linker, or a compound of formula (I).

In one embodiment, compounds of table 1 are linked via a terminal phosphate group, which is bound to the 3' carbon at the 3' end of at least one RNAi agent strand. Such compounds are shown in, for example, Table 2.

In one embodiment, compounds of table 2 have a terminal phosphorothioate group bound to the 3' carbon at the 3' end of at least one RNAi agent strand. Thus, in various embodiments, in the 3' end caps listed in Table 2, the phosphate group is replaced by a phosphorothioate. In additional embodiments, the phosphate group of various 3' end caps listed herein as C3, C6, C12, Triethylene glycol, Cyclohexyl, Phenyl, Biphenyl, Adamantane, Lithocholic acid can be replaced by phosphorothioate. In one particular embodiment, the phosphate group in the C3 3' end cap is replaced by phosphorothioate (and designated "PS—C3", as illustrated in Table 2 and described in Example 6 and FIGS. 20 A-E). In one particular embodiment, the phosphate group in the C6 3' end cap is replaced by phosphorothioate (and designated "PS-C6", as illustrated in Table 2). In one particular embodiment, the phosphate group in the C10 3' end cap is replaced by phosphorothioate (and designated "PS- C10", as illustrated in Table 2). In one particular embodiment, the phosphate group in the biphenyl (BP) 3' end cap is replaced by phosphorothioate (and designated "PS-BP", as illustrated in Table 2).

In various embodiments, $R_1$=OH; and $R_2$=a compound of formula (I). This structure is also shown in FIG. 18C.

3' End Caps

In some embodiments, one or both strands of the RNAi agent comprise, at the 3' end, a spacer, a phosphate or modified internucleoside linker, and a 3' end cap (e.g., a 3' end cap as disclosed herein).

A 3' end cap is a non-nucleotidic chemical moiety bound to the 3' end of a molecule comprising a RNAi agent, e.g., the 3' terminus (or 3' end) of (a) a molecule comprising a strand, wherein the 3' end of the strand terminates in a phosphate or modified internucleoside linker; or (b) a molecule comprising, in 5' to 3' order: a strand (wherein the 3' end of the strand terminates in a phosphate or modified internucleoside linker), a spacer, and a second phosphate or modified internucleoside linker. The 3' end cap performs at least one of the following functions: allowing RNA interference mediated by the molecule, protecting the molecule from degradation or reducing the amount or rate of degradation of the molecule (e.g., by nucleases), reducing the off-target effects of the sense strand, or increasing the activity, duration or efficacy of RNA interference mediated by the molecule. By describing a 3' end cap as "non-nucleotidic", it is meant that a nucleotide comprises three components: a phosphate, a pentose (e.g., a ribose or deoxyribose) and a nucleobase, and a 3' end cap does not comprise all three of the components.

Table 2, below, presents some structures of various 3' end caps, including some of those shown in Table 1. In several of the structures, the terminal 3' phosphate of a RNAi agent strand is also shown for context, although this phosphate is not part of the 3' end cap.

Additional information can be found in U.S. patent applications 61/886,753; 61/930,681; 61/886,748; 61/886,739; and 61/886,760, which are all incorporated by reference in their entirety.

TABLE 2

3' END CAPS FOR RNAi AGENTS FOR USE IN RNA INTERFERENCE

2.A. 3' end caps for use in RNAi agents.

| Structure (shown bond to phosphate) | Nickname (Alternative nickname) |
|---|---|

In some embodiments, the 3' end of a strand of a RNAi agent terminates in a phosphate or modifief internucleoside linker and optionally further comprises in 5' to 3' order, a spacer and a phosphate or modified internucleosider linker. As non-limiting examples, the phosphate is shown here bound to the 3' end cap.

| | |
|---|---|
| [Structure: phosphate group O⁻—P(=O)(O)—O—CH₂CH₂CH₂—NH₂] | C3 amino |
| [Structure: phosphate group O⁻—P(=O)(O)—O—CH₂—CH(CH₂OH)—(CH₂)₃—NH₂] | C7 amino |
| [Structure: phosphate group O⁻—P(=O)(O)—O—(CH₂)₈—OH] | C8 amino |

TABLE 2-continued
3' END CAPS FOR RNAi AGENTS FOR USE IN RNA INTERFERENCE
2.A. 3' end caps for use in RNAi agents.
| Structure (shown bond to phosphate) | Nickname (Alternative nickname) |
|---|---|
| 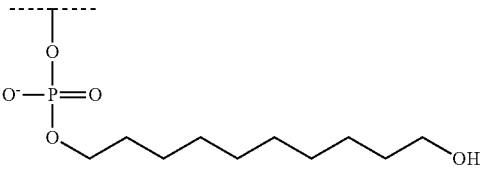 | C10 |
| 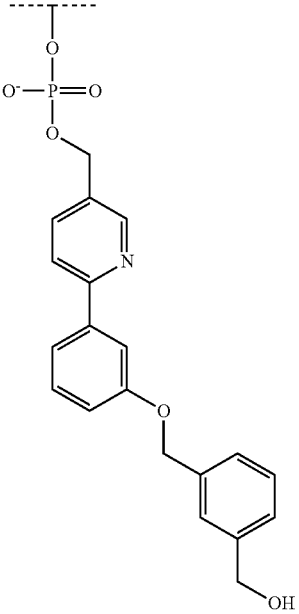 | X027 |
| 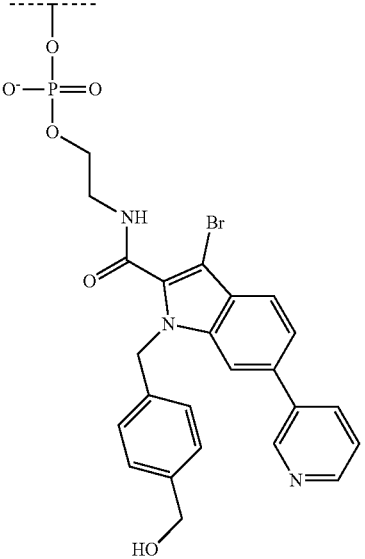 | X038 |

TABLE 2-continued
3' END CAPS FOR RNAi AGENTS FOR USE IN RNA INTERFERENCE
2.A. 3' end caps for use in RNAi agents.
| Structure (shown bond to phosphate) | Nickname (Alternative nickname) |
|---|---|
| 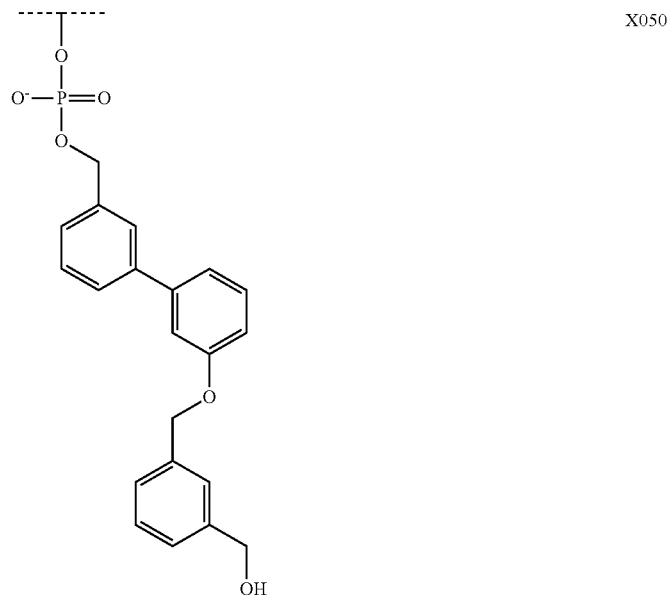 | X050 |
| 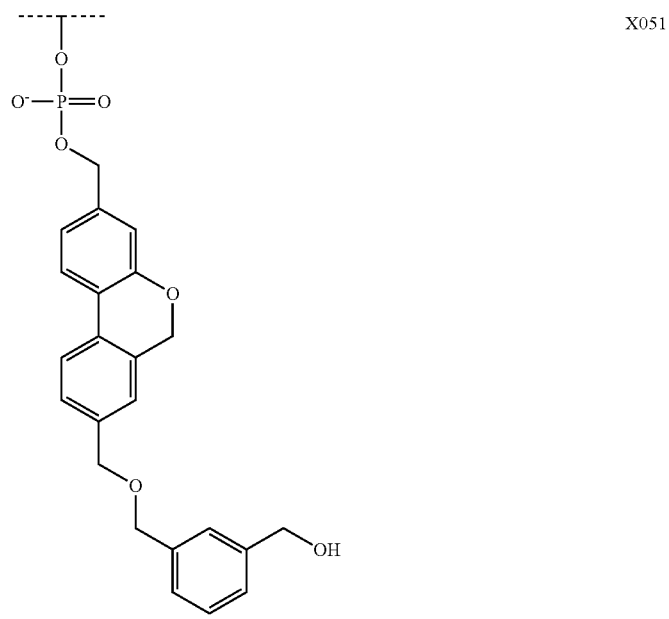 | X051 |

TABLE 2-continued
3' END CAPS FOR RNAi AGENTS FOR USE IN RNA INTERFERENCE
2.A. 3' end caps for use in RNAi agents.
| Structure (shown bond to phosphate) | Nickname (Alternative nickname) |
|---|---|
| 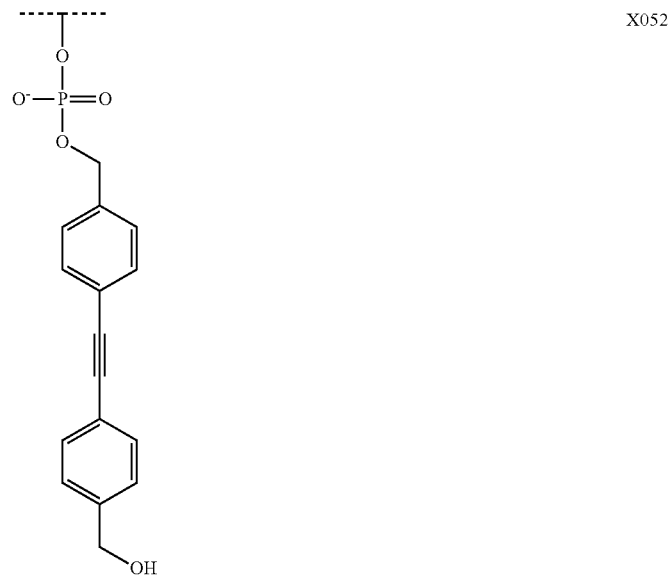 | X052 |
| 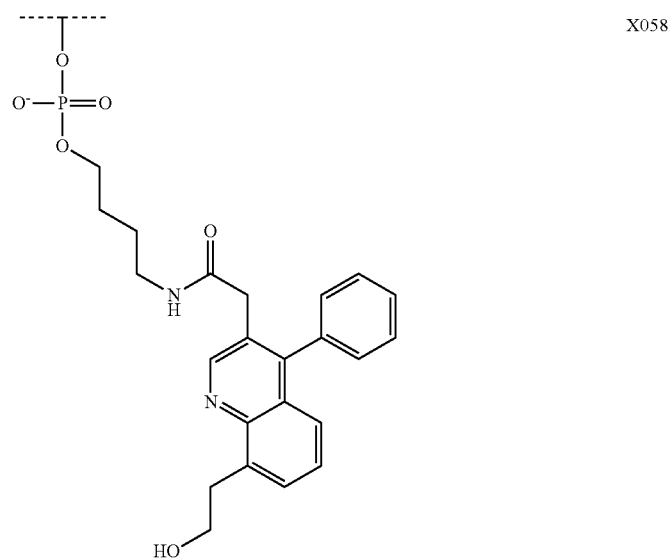 | X058 |

TABLE 2-continued
3' END CAPS FOR RNAi AGENTS FOR USE IN RNA INTERFERENCE
2.A. 3' end caps for use in RNAi agents.
| Structure (shown bond to phosphate) | Nickname (Alternative nickname) |
|---|---|
| 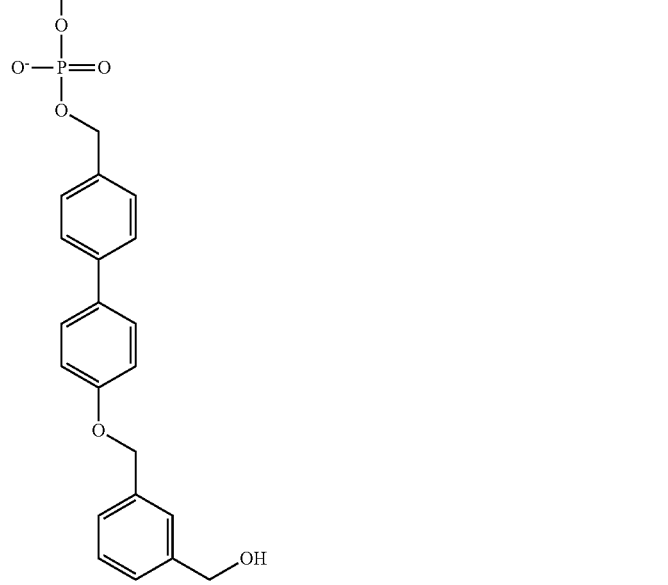 | X059 |
| 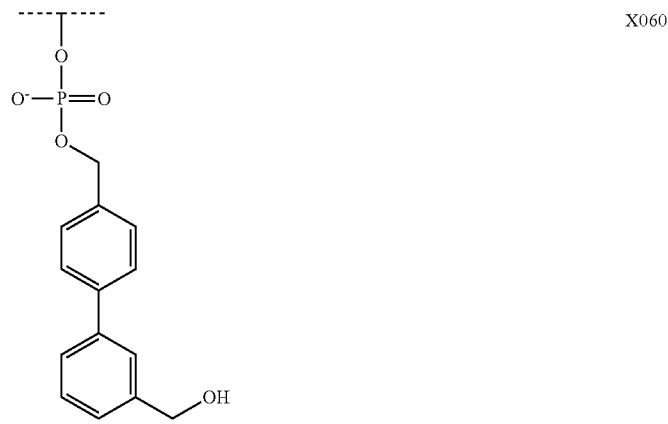 | X060 |
| 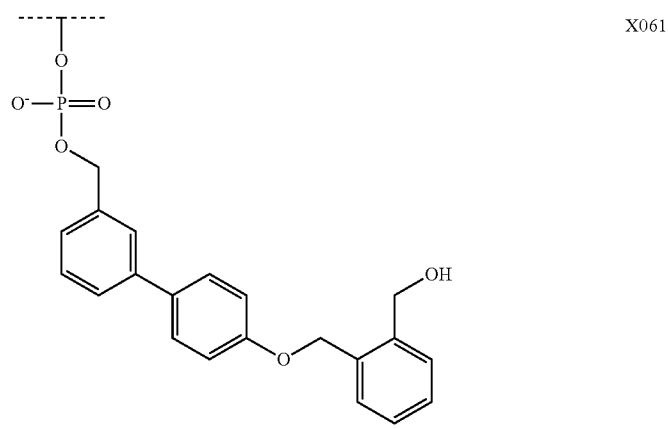 | X061 |

TABLE 2-continued
3' END CAPS FOR RNAi AGENTS FOR USE IN RNA INTERFERENCE
2.A. 3' end caps for use in RNAi agents.
| Structure (shown bond to phosphate) | Nickname (Alternative nickname) |
|---|---|
| 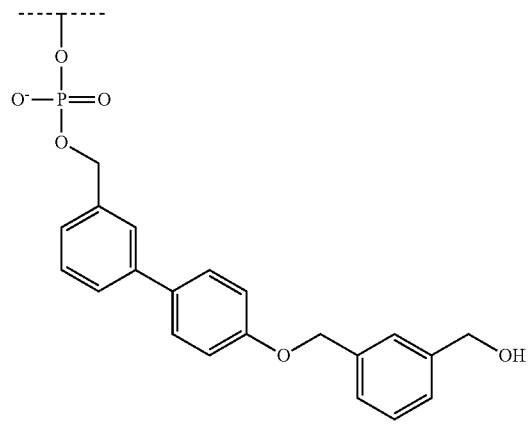 | X062 |
| 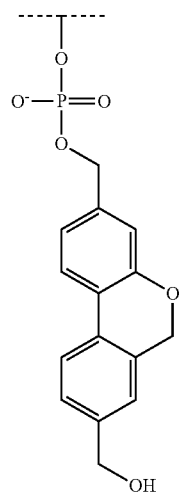 | X063 |
| 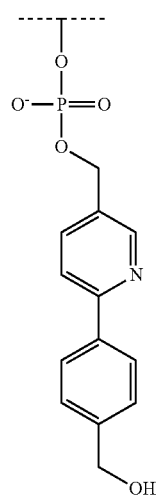 | X064 |

TABLE 2-continued
3' END CAPS FOR RNAi AGENTS FOR USE IN RNA INTERFERENCE
2.A. 3' end caps for use in RNAi agents.
| Structure (shown bond to phosphate) | Nickname (Alternative nickname) |
|---|---|
| 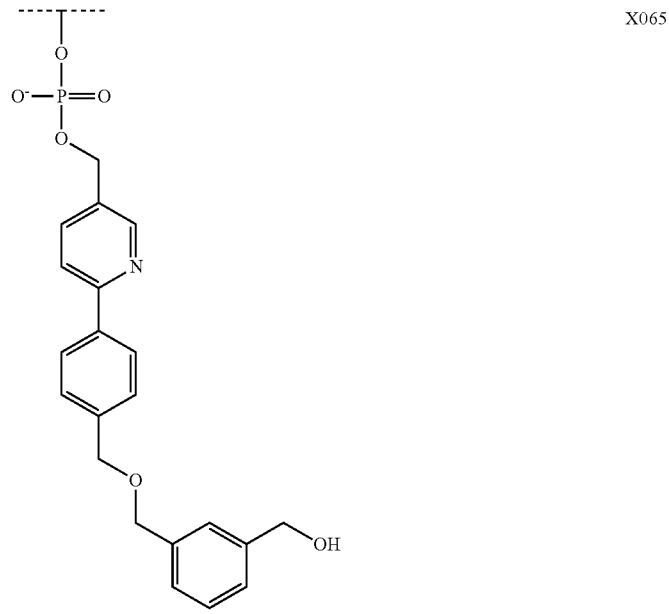 | X065 |
| 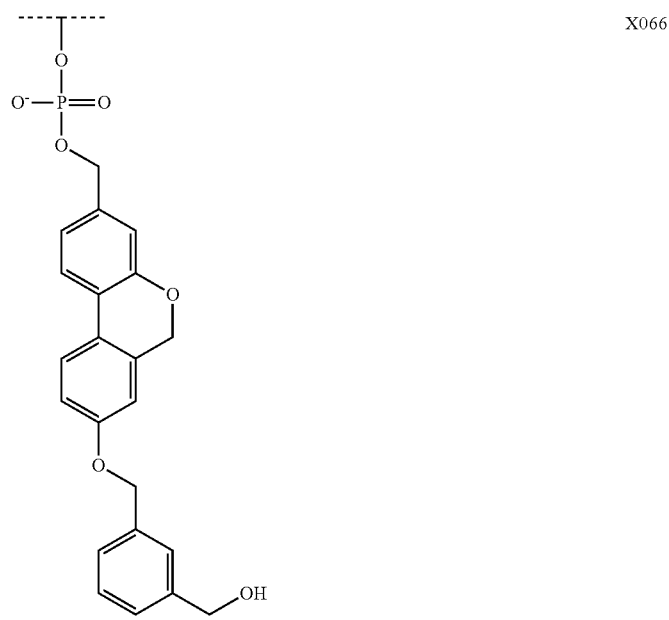 | X066 |

TABLE 2-continued
3' END CAPS FOR RNAi AGENTS FOR USE IN RNA INTERFERENCE
2.A. 3' end caps for use in RNAi agents.
| Structure (shown bond to phosphate) | Nickname (Alternative nickname) |
|---|---|
| 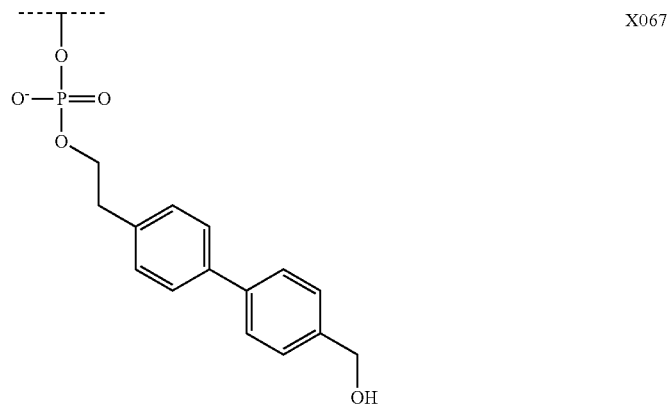 | X067 |
| 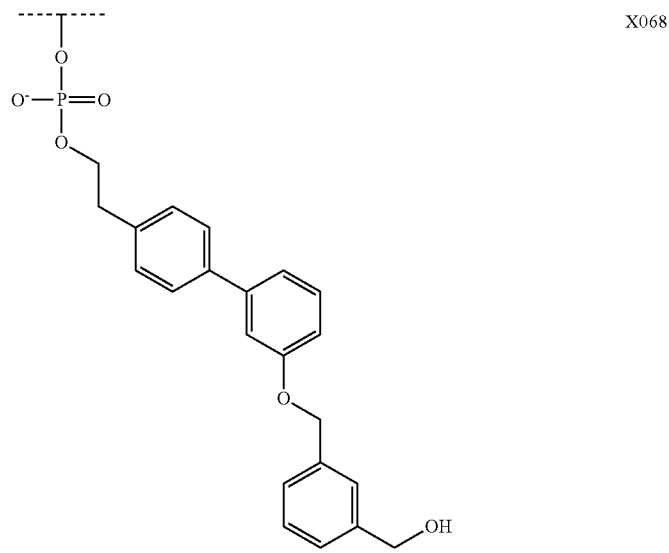 | X068 |
| 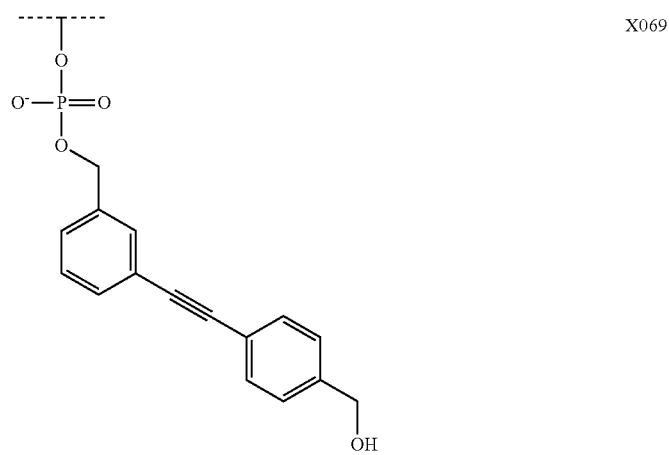 | X069 |

TABLE 2-continued

3' END CAPS FOR RNAi AGENTS FOR USE IN RNA INTERFERENCE
2.A. 3' end caps for use in RNAi agents.

| Structure (shown bond to phosphate) | Nickname (Alternative nickname) |
|---|---|
| [Structure] | X097 |
| [Structure] | X098 |
| [Structure] | X109 |
| [Structure] | X110 |

TABLE 2-continued

3' END CAPS FOR RNAi AGENTS FOR USE IN RNA INTERFERENCE
2.A. 3' end caps for use in RNAi agents.

| Structure (shown bond to phosphate) | Nickname (Alternative nickname) |
|---|---|
| [structure] | X111 |
| [structure] | X112 |
| [structure] | X113 |
| [structure] | X1009 |
| [structure] | X1011 |
| [structure] | X1012 |

TABLE 2-continued

3' END CAPS FOR RNAi AGENTS FOR USE IN RNA INTERFERENCE
2.A. 3' end caps for use in RNAi agents.

| Structure (shown bond to phosphate) | Nickname (Alternative nickname) |
| --- | --- |
| [structure] | X1013 |
| [structure] | X1015 |
| [structure] | X1016 |
| [structure] | X1017 |
| [structure] | X1018 |

TABLE 2-continued

3' END CAPS FOR RNAi AGENTS FOR USE IN RNA INTERFERENCE
2.A. 3' end caps for use in RNAi agents.

| Structure (shown bond to phosphate) | Nickname (Alternative nickname) |
|---|---|
| | X1019 |
| | X1020 |
| | X1021 |
| | X1022 |
| | X1024 |

TABLE 2-continued

3' END CAPS FOR RNAi AGENTS FOR USE IN RNA INTERFERENCE
2.A. 3' end caps for use in RNAi agents.

| Structure (shown bond to phosphate) | Nickname (Alternative nickname) |
|---|---|
| | X1025 |
| | X1026 |
| | X1027 |
| | X1028 |
| | X1047 |
| | X1048 |

TABLE 2-continued

3' END CAPS FOR RNAi AGENTS FOR USE IN RNA INTERFERENCE

2.A. 3' end caps for use in RNAi agents.

| Structure (shown bond to phosphate) | Nickname (Alternative nickname) |
|---|---|
| 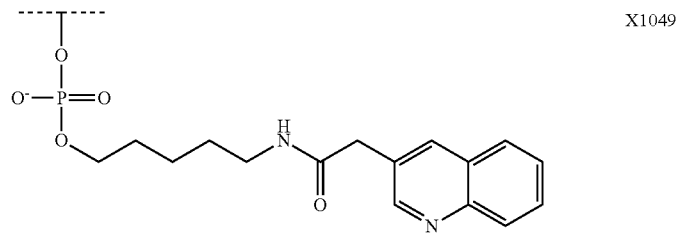 | X1049 |
|  | Ribitol (rib or ribp) |

2.B. RNAi agents comprising a strand, wherein the 3' end of the strand terminates in a phosphate or modified internucleoside linker and further comprises in 5' to 3' order a spacer, a phosphate or modified internucleoside linker, and a 3' end cap. Non-limiting examples below show, for example, RNAi agents wherein the spacer is a C3, ribitol or 2'-deoxyribitol. Specific 3' end caps (C3, C6, C8, C10, C12, BP, C058, etc.) are shown but any 3' end cap can be used in combination with any spacer or phosphate or modified internucleoside linker.

| | |
|---|---|
| 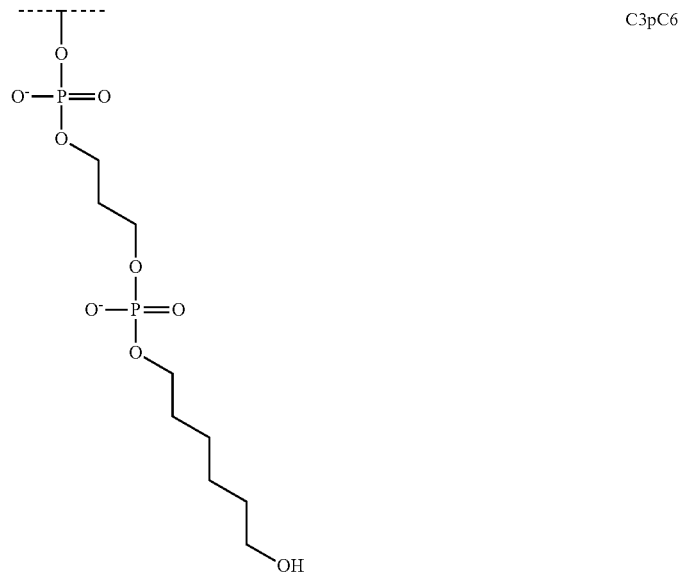 | C3pC6 |

TABLE 2-continued

3' END CAPS FOR RNAi AGENTS FOR USE IN RNA INTERFERENCE
2.A. 3' end caps for use in RNAi agents.

| Structure (shown bond to phosphate) | Nickname (Alternative nickname) |
| --- | --- |
| | ribpC3 (ribC3) |
| | ribpC6 (ribC6) |
| | ribpC8 (ribC8) |

TABLE 2-continued

3' END CAPS FOR RNAi AGENTS FOR USE IN RNA INTERFERENCE
2.A. 3' end caps for use in RNAi agents.

| Structure (shown bond to phosphate) | Nickname (Alternative nickname) |
|---|---|
| | ribpC10 (ribC10) |
| | ribpC12 (ribC12) |
| | ribpBP (ribBP) |

TABLE 2-continued
3' END CAPS FOR RNAi AGENTS FOR USE IN RNA INTERFERENCE
2.A. 3' end caps for use in RNAi agents.
| Structure (shown bond to phosphate) | Nickname (Alternative nickname) |
|---|---|
| 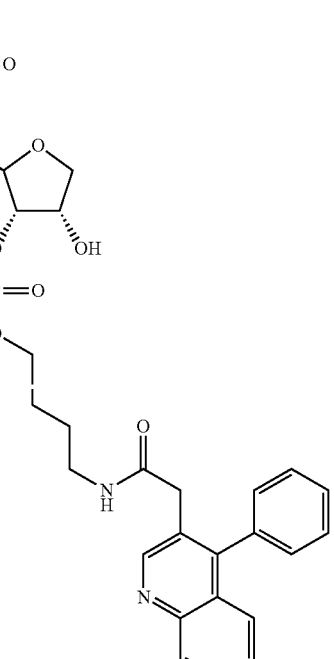 | ribpX058 (ribX058) |
| 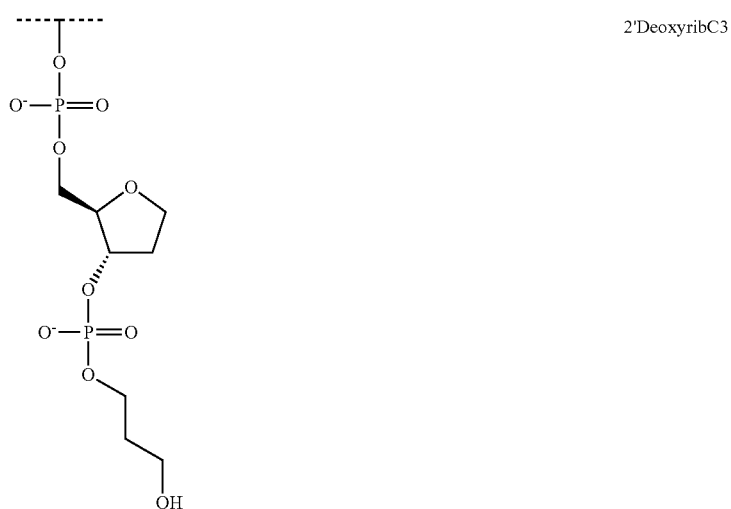 | 2'DeoxyribC3 |

TABLE 2-continued

3' END CAPS FOR RNAi AGENTS FOR USE IN RNA INTERFERENCE
2.A. 3' end caps for use in RNAi agents.

| Structure (shown bond to phosphate) | Nickname (Alternative nickname) |
|---|---|
| [structure] | 2'DeoxyribC6 |
| [structure] | 2'DeoxyribC8 |
| [structure] | 2'DeoxyribC10 |

TABLE 2-continued
3' END CAPS FOR RNAi AGENTS FOR USE IN RNA INTERFERENCE
2.A. 3' end caps for use in RNAi agents.
| Structure (shown bond to phosphate) | Nickname (Alternative nickname) |
|---|---|
| 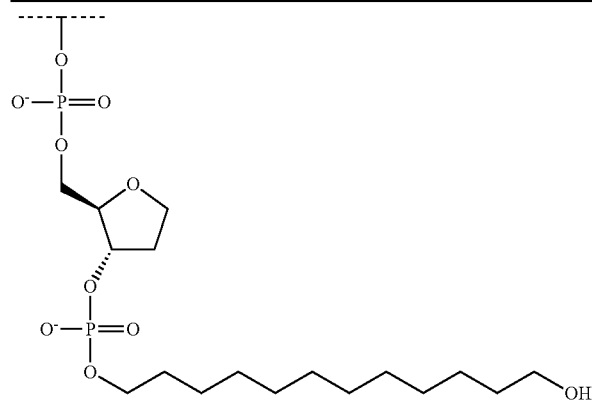 | 2'DeoxyribC12 |
| 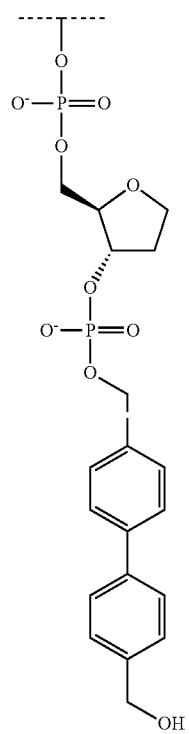 | 2'-DeoxyribBP |

TABLE 2-continued

3' END CAPS FOR RNAi AGENTS FOR USE IN RNA INTERFERENCE
2.A. 3' end caps for use in RNAi agents.

| Structure (shown bond to phosphate) | Nickname (Alternative nickname) |
|---|---|
| | Diribitol (dirib or diribp) |

Additional structures include, inter alia: ribptriethylene glycol, ribpcyclohexyl, ribpphenyl, ribpBP (biphenyl), ribplithochol (lithocholic acid), ribpadamantane, ribpC3 amino, ribpC7 amino, ribpC3, ribpC6, ribpC8, ribpC10, ribpC12, ribpX027, ribpX027, ribpX038, ribpX050, ribpX051, ribpX052, ribpX059, ribpX060, ribpX061, ribpX062, ribpX063, ribpX064, ribpX065, ribpX066, ribpX067, ribpX068, ribpX069, ribpX097, ribpX098, ribpX109, ribpX110, ribpX111, ribpX112, ribpX113, ribpX1009, ribpX1011, ribpX1012, ribpX1013, ribpX1015, ribpX1016, ribpX1017, ribpX1018, ribpX1019, ribpX1020, ribpX1021, ribpX1022, ribpX1024, ribpX1025, ribpX1026, ribpX1027, ribpX1028, ribpX1047, ribpX1048, ribpX1049, ribpX1062, ribpX1063, ribpX1064, ribpribitol, etc. These represent a spacer which is ribitol, a phosphate, and a 3' end cap which is triethylene glycol, cyclohexyl, phenyl, BP (biphenyl), lithochol (lithocholic acid), adamantane, C3 amino, C7 amino, C3, C6, C8, C10, C12, X027, X038, X050, etc.

Additional structures include, inter alia: diribptriethylene glycol, diribpcyclohexyl, diribpphenyl, diribpBP (biphenyl), diribplithochol (lithocholic acid), diribpadamantane, diribpC3 amino, diribpC7 amino, diribpC3, diribpC6, diribpC8, diribpC10, diribpC12, diribpX027, diribpX027, diribpX038, diribpX050, diribpX051, diribpX052, diribpX059, diribpX060, diribpX061, diribpX062, diribpX063, diribpX064, diribpX065, diribpX066, diribpX067, diribpX068, diribpX069, diribpX097, diribpX098, diribpX109, diribpX110, diribpX111, diribpX112, diribpX113, diribpX1009, diribpX1011, diribpX1012, diribpX1013, diribpX1015, diribpX1016, diribpX1017, diribpX1018, diribpX1019, diribpX1020, diribpX1021, diribpX1022, diribpX1024, diribpX1025, diribpX1026, diribpX1027, diribpX1028, diribpX1047, diribpX1048, diribpX1049, diribp1062, diribp1063, diribp1064, diribpribitol, etc. These represent a spacer which is diribitol, a phosphate, and a 3' end cap which is triethylene glycol, cyclohexyl, phenyl, BP (biphenyl), lithochol (lithocholic acid), adamantane, C3 amino, C7 amino, C3, C6, C8, C10, C12, X027, X038, X050, etc.

Additional structures include, inter alia: 2'-deoxyribptriethylene glycol, 2'-deoxyribpcyclohexyl, 2'-deoxyribpphenyl, 2'-deoxyribpBP (biphenyl), 2'-deoxyribplithochol (lithocholic acid), 2'-deoxyribpadamantane, 2'-deoxyribpC3 amino, 2'-deoxyribpC7 amino, 2'-deoxyribpC3, 2'-deoxyribpC6, 2'-deoxyribpC8, 2'-deoxyribpC10, 2'-deoxyribpC12, 2'-deoxyribpX027, 2'-deoxyribpX027, 2'-deoxyribpX038, 2'-deoxyribpX050, 2'-deoxyribpX051, 2'-deoxyribpX052, 2'-deoxyribpX059, 2'-deoxyribpX060, 2'-deoxyribpX061, 2'-deoxyribpX062, 2'-deoxyribpX063, 2'-deoxyribpX064, 2'-deoxyribpX065, 2'-deoxyribpX066, 2'-deoxyribpX067, 2'-deoxyribpX068, 2'-deoxyribpX069, 2'-deoxyribpX097, 2'-deoxyribpX098, 2'-deoxyribpX109, 2'-deoxyribpX110, 2'-deoxyribpX111, 2'-deoxyribpX112, 2'-deoxyribpX113, 2'-deoxyribpX1009, 2'-deoxyribpX1011, 2'-deoxyribpX1012, 2'-deoxyribpX1013, 2'-deoxyribpX1015, 2'-deoxyribpX1016, 2'-deoxyribpX1017, 2'-deoxyribpX1018, 2'-deoxyribpX1019, 2'-deoxyribpX1020, 2'-deoxyribpX1021, 2'-deoxyribpX1022, 2'-deoxyribpX1024, 2'-deoxyribpX1025, 2'-deoxyribpX1026, 2'-deoxyribpX1027, 2'-deoxyribpX1028, 2'-deoxyribpX1047, 2'-deoxyribpX1048, 2'-deoxyribpX1049, 2'-deoxyribp 1062, 2'-deoxyribp 1063, 2'-deoxyribp 1064, 2'-deoxyribpribitol, etc. These represent a spacer which is 2'-deoxyribitol, a phosphate, and a 3' end cap which is triethylene glycol, cyclohexyl, phenyl, BP (biphenyl), lithochol (lithocholic acid), adamantane, C3 amino, C7 amino, C3, C6, C8, C10, C12, X027, X038, X050, etc.

Additional structures include, inter alia: C3ptriethylene glycol, C3pcyclohexyl, C3pphenyl, C3pBP (biphenyl), C3plithochol (lithocholic acid), C3padamantane, C3pC3 amino, C3pC7 amino, C3pC3, C3pC6, C3pC8, C3pC10, C3pC12, C3pX027, C3pX027, C3pX038, C3pX050, C3pX051, C3pX052, C3pX059, C3pX060, C3pX061, C3pX062, C3pX063, C3pX064, C3pX065, C3pX066, C3pX067, C3pX068, C3pX069, C3pX097, C3pX098, C3pX109, C3pX110, C3pX111, C3pX112, C3pX113, C3pX1009, C3pX1011, C3pX1012, C3pX1013, C3pX1015, C3pX1016, C3pX1017, C3pX1018, C3pX1019, C3pX1020, C3pX1021, C3pX1022, C3pX1024, C3pX1025, C3pX1026, C3pX1027, C3pX1028, C3pX1047, C3pX1048, C3pX1049, C3pX1062, C3pX1063, C3pX1064, C3pribitol, etc. These represent a spacer which is C3, a phosphate, and a 3' end cap which is triethylene glycol, cyclohexyl, phenyl, BP (biphenyl), lithochol (lithocholic acid),

TABLE 2-continued

3' END CAPS FOR RNAi AGENTS FOR USE IN RNA INTERFERENCE
2.A. 3' end caps for use in RNAi agents.

| Structure (shown bond to phosphate) | Nickname (Alternative nickname) |
|---|---| adamantane, C3 amino, C7 amino, C3, C6, C8, C10, C12, X027, X038, X050, etc.
Additional structures include, inter alia: C4ptriethylene glycol, C4pcyclohexyl, C4pphenyl,
C4pBP (biphenyl), C4plithochol (lithocholic acid), C4padamantane, C4pC4 amino, C4pC7
amino, C4pC4, C4pC6, C4pC8, C4pC10, C4pC12, C4pX027, C4pX027, C4pX038, C4pX050,
C4pX051, C4pX052, C4pX059, C4pX060, C4pX061, C4pX062, C4pX063, C4pX064, C4pX065,
C4pX066, C4pX067, C4pX068, C4pX069, C4pX097, C4pX098, C4pX109, C4pX110, C4pX111,
C4pX112, C4pX113, C4pX1009, C4pX1011, C4pX1012, C4pX1013, C4pX1015, C4pX1016,
C4pX1017, C4pX1018, C4pX1019, C4pX1020, C4pX1021, C4pX1022, C4pX1024, C4pX1025,
C4pX1026, C4pX1027, C4pX1028, C4pX1047, C4pX1048, C4pX1049, C4pX1062, C4p1063,
C4p1064, C4pribitol, etc. These represent a spacer which is C4, a phosphate, and a 3' end cap
which is triethylene glycol, cyclohexyl, phenyl, BP (biphenyl), lithochol (lithocholic acid),
adamantane, C4 amino, C7 amino, C4, C6, C8, C10, C12, X027, X038, X050, etc.
Additional structures include, inter alia: C5ptriethylene glycol, C5pcyclohexyl, C5pphenyl,
C5pBP (biphenyl), C5plithochol (lithocholic acid), C5padamantane, C5pC5 amino, C5pC7
amino, C5pC5, C5pC6, C5pC8, C5pC10, C5pC12, C5pX027, C5pX027, C5pX038, C5pX050,
C5pX051, C5pX052, C5pX059, C5pX060, C5pX061, C5pX062, C5pX063, C5pX064, C5pX065,
C5pX066, C5pX067, C5pX068, C5pX069, C5pX097, C5pX098, C5pX109, C5pX110, C5pX111,
C5pX112, C5pX113, C5pX1009, C5pX1011, C5pX1012, C5pX1013, C5pX1015, C5pX1016,
C5pX1017, C5pX1018, C5pX1019, C5pX1020, C5pX1021, C5pX1022, C5pX1024, C5pX1025,
C5pX1026, C5pX1027, C5pX1028, C5pX1047, C5pX1048, C5pX1049, C5pX1062, C5pX1063,
C5pX1064, C5pribitol, etc. These represent a spacer which is C5, a phosphate, and a 3' end
cap which is triethylene glycol, cyclohexyl, phenyl, BP (biphenyl), lithochol (lithocholic acid),
adamantane, C5 amino, C7 amino, C5, C6, C8, C10, C12, X027, X038, X050, etc.

2.C. RNAi agents wherein a strand terminates in a 3' terminal phosphorothioate, and a 3' end cap.
In some RNAi agents of the present disclosure, the 3' end of a strand terminates in a modified
internucleoside linker (e.g., a PS) and further comprises a 3' end cap (C3, C6, etc.). Non-
limiting examples of such structures are shown here, including the 3' end cap, the terminal
modified internucleoside linker, and, in the first case, sugar and base. In other words, the 3'-
terminus of at least one strand comprises a modification at the 3' carbon, wherein the
modification is selected from PS-C3, PS-C6, PS-C8, PS-C10, PS-C12, PS-BP, PS-X058, etc.,
or any modified internucleoside linker described herein, and any 3' end cap described herein.

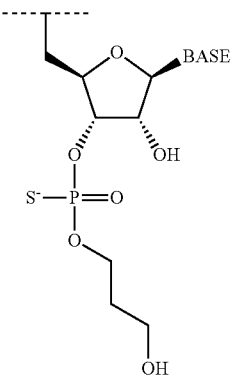

PS-C3

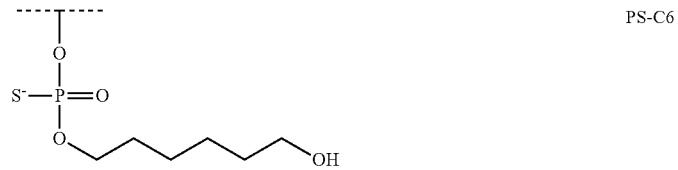

PS-C6

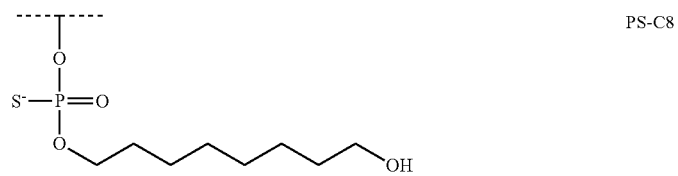

PS-C8

TABLE 2-continued
3' END CAPS FOR RNAi AGENTS FOR USE IN RNA INTERFERENCE
2.A. 3' end caps for use in RNAi agents.
| Structure (shown bond to phosphate) | Nickname (Alternative nickname) |
|---|---|
| 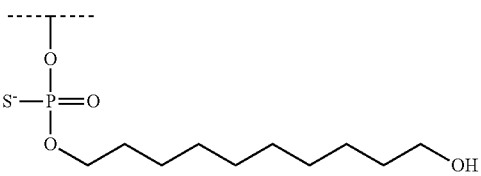 | PS-C10 |
| 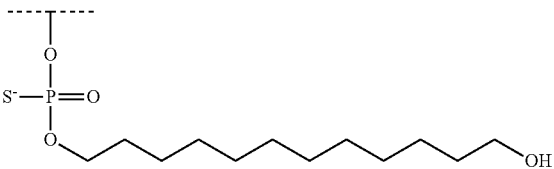 | PS-C12 |
| 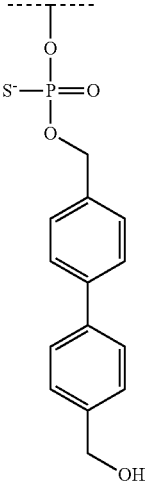 | PS-BP |
| 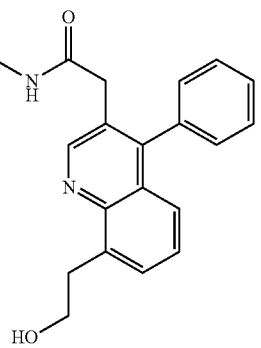 | PS-X058 |

TABLE 2-continued

3' END CAPS FOR RNAi AGENTS FOR USE IN RNA INTERFERENCE
2.A. 3' end caps for use in RNAi agents.

| Structure (shown bond to phosphate) | Nickname (Alternative nickname) |
|---|---|
| [chemical structure] | PS-X097 |
| [chemical structure] | PS-X098 |
| [chemical structure] | PS-X109 |
| [chemical structure] | PS-X110 |

TABLE 2-continued

3' END CAPS FOR RNAi AGENTS FOR USE IN RNA INTERFERENCE
2.A. 3' end caps for use in RNAi agents.

| Structure (shown bond to phosphate) | Nickname (Alternative nickname) |
|---|---|
| [Chemical structure: S⁻—P(=O)(O)—O—CH₂CH₂CH₂—NH—C(=O)—CH₂— attached to a 4-phenylisoquinoline] | PS-X111 |

Additional structures include, inter alia: PS-triethylene glycol, PS-cyclohexyl, PS-phenyl, PS-BP (biphenyl), PS-lithochol (lithocholic acid), PS-adamantane, PS-C3 amino, PS-C7 amino, PS-C3, PS-C6, PS-C8, PS-C10, PS-C12, PS-X027, PS-X027, PS-X038, PS-X050, PS-X051, PS-X052, PS-X059, PS-X060, PS-X061, PS-X062, PS-X063, PS-X064, PS-X065, PS-X066, PS-X067, PS-X068, PS-X069, PS-X097, PS-X098, PS-X109, PS-X110, PS-X111, PS-X112, PS-X113, PS-X1009, PS-X1011, PS-X1012, PS-X1013, PS-X1015, PS-X1016, PS-X1017, PS-X1018, PS-X1019, PS-X1020, PS-X1021, PS-X1022, PS-X1024, PS-X1025, PS-X1026, PS-X1027, PS-X1028, PS-X1047, PS-X1048, PS-X1049, PS-X1062, PS-X1063, PS-X1064, PS-ribitol, etc. These represent phosphorothioate (PS) and a 3' end cap which is triethylene glycol, cyclohexyl, phenyl, BP (biphenyl), lithochol (lithocholic acid), adamantane, C3 amino, C7 amino, C3, C6, C8, C10, C12, X027, X038, X050, etc.

Regarding Table 2 (including 2.A, 2.B and 2.C):

Synthesis schemes for C7 amino and C3 amino (also designated amino C7 or amino C3, respectively) are not provided, as these molecules are commercially available from and synthesis schemes were previously published by Glen Research (Sterling, Va.).

C7 amino: Catalog Number: 20-2957-xx; Description: 3'-Amino-Modifier C7 CPG 500; 2-Dimethoxytrityloxymethyl-6-fluorenylmethoxycarbonylamino-hexane-1-succinoyl-long chain alkylamino-CPG; Technical Bulletin: Pre-Synthesis Labeling of Aminomodifier C3 or C7 CPG, Glen Research (Sterling, Va.).

C3 amino: Catalog Number: 20-2913-xx; Description: 3'-Spacer C3 CPG; (1-Dimethoxytrityloxy-propanediol-3-succinoyl)-long chain alkylamino-CPG, Glen Research (Sterling, Va.). Glen Research also notes that Glen Research has no definitive data on the propyl CPG to support the assertion that it protects oligos from exonuclease digestion and does not permit polymerase extension. Glen Research's conclusion is based by analogy to the propylamino-modifier CPG [Zendegui et al. Nucleic Acids Research, 1992, 20, 307-314] (Cat. No. 20-2950-41). This modification protects oligos from exonuclease digestion but permits polymerase extension to a small extent since the modifier is eliminated to a level of about 10% from the 3' end, leaving the 3'-hydroxyl group available. HPLC experiments have shown that there is no detectable elimination of the propyl group from oligos made from the spacer C3-CPG.

Example 3' end caps C8 and C10 are also illustrated in FIG. 18C, and ribitol and diribitol in FIG. 19, in the context of a RNAi agent strand.

It is noted that Table 2 lists various 3' end caps that comprise both a spacer (e.g., C3p, ribitol, or 2'-deoxyribitol) and a 3' end cap. Thus, for example, "C3pC6" can be, depending on context, considered as a "3' endcap", or as "a spacer and a phosphate and a 3' end cap" (C3+p+C6) or a spacer, a phosphate and a 3' end cap. The efficacy of RNAi agents comprising a spacer and a 3' end cap is shown in, for example, 5A, 5B, 10 and 14.

The present disclosure encompasses any RNAi agent comprising a 3' end cap as shown in Tables 1 or 2 or otherwise disclosed herein.

Use of 3' End Caps for Different Sequences and Targets

Various experiments that have shown the 3' end caps disclosed herein can be used at the 3' end of various strands of effective RNAi agents that can mediate RNA interference against a variety of different mRNA targets, including Hepcidin, HuR (ELAVL1), PLK1, SSB and FVII (Factor 7 of F7). The 3' end caps can also be used on RNAi agents for a variety of species, including a variety of mammalian species, as RNAi agents comprising different 3' end caps were efficacious in both mouse and human cells. Successful RNAi agents comprising various 3' end caps disclosed herein were also constructed for several additional gene targets (not described herein). The 3' end caps described herein have been found to be useful in RNAi agents in vivo and in vitro. Furthermore, a variety of successful RNAi agents were constructed and tested wherein one or both strands comprised at the 3' end, in 5' to 3' order, a spacer as disclosed herein, a phosphate or internucleoside linker as disclosed herein, and a 3' end cap as disclosed herein.

Clearly, as would be known to one of ordinary skill in the art, not every tested sequence will yield a successful RNAi agent, and certainly not in combination with any 3' end cap, or with any spacer, phosphate or internucleoside linker, and 3' end cap. However, the 3' end caps described herein can be used to devise and test various RNAi agents, some of which can have activity approximately equal to that of other formats (e.g., the canonical structure); and some can produce improved qualities (e.g., increased activity, duration or activity, decreased off-target effects, etc.).

The novel 3' end caps disclosed herein, therefore, can be used with a variety of different sequences and gene targets.

Hepcidin RNAi Agents Comprising a 3' End Cap.

As detailed herein e.g., FIGS. 5A to 9, effective RNAi agents comprising various 3' end caps disclosed herein were constructed targeting Hepcidin.

These constructs are detailed in the Figures and FIGURE legends. These constructs successfully targeted both mouse and human Hepcidin.

Successful 3' end caps used in these RNAi agents include BP, C6, X027, X038, X050, X051, X052, X058, X059, X060, X061, X062, X063, X064, X065, X066, X067, X068, X069, etc. Some of these RNAi agents comprise a strand wherein the 3' end of the strand terminates in a phosphate and further comprises a 3' end cap. Other RNAi agents comprise a strand wherein the 3' end of the strand terminates in a phosphate and further comprises in 5' to 3' order: a spacer (e.g., ribitol), a phosphate, and a 3' end cap.

HuR (ELAV1) RNAi Agents Comprising a 3' End Cap.

Effective RNAi agents to HuR were constructed comprising various 3' end caps. See FIGS. 16A and B, and 22-24, FIGURE legends, etc.

For example: An effective 18-mer RNAi agent to another target, HuR, is shown below:

```
AS:  u U a A u U a U c U a U u C c G u A rib C6

S:   C6 rib A a U u A a U a G a U a A g G c A u
``` n (a, u, c, g): 2'Ome-n (a, u, c, g)

The sequence of the AS (anti-sense) strand, shown above 5' to 3', is SEQ ID NO: 87; the sequence of the S (sense) strand, shown above, 3' to 5', is SEQ ID NO: 88. This RNAi agent comprises two strands, each comprising, in 5' to 3' order, a RNAi agent strand, a spacer (ribitol or rib), a phosphate (not shown), and a 3' end cap (C6). Other spacers and 3' end caps can be used, and this and other phosphates can be replaced by a modified internucleoside linker.

Other effective HuR RNAi agents were produced wherein the sequence used was:

```
                                        (SEQ ID NO: 89)
U002pUpApApU004pU004pApU004pCpU004pApU004pU004pCpC
pGpU005pA005pC027pXnnnn
```

Where C0027 is ribitol (or other spacer such as C3 or C5300 as needed).
002=DNA
004=2'Ome
005=2'MOE
All other positions are RNA
027=ribitol
p=phosphate
Xnnn=3' end cap (X058, X109, etc.)
In this and various other sequences disclosed herein, U004 indicates a nucleotide with a U base with a 2'Ome modification; U002 indicates a nucleotide with a U base which is DNA; U005 indicates a nt with a U base with a 2'MOE modification. Similarly, other nucleotides are modified, e.g., U004 indicates a nucleotide with a U base and a 2'Ome modification.

With this HuR sequence, effective RNAi agents were produced which comprise an RNAi agent strand, further comprising at the 3' end, in 5' to 3' order: a spacer (ribitol), a phosphate and a 3' end cap (X058, X109, X110, X111, X112, X113, X1009, X1010, X1011, X1012, X1013, X1015, X1016, X1017, X1018, X1019, X1020, X1021, X1022, X1024, X1025, X1026, X1027, or X1028). These were tested in vitro in Huh-7 cells and all demonstrated at least about 60% to 80% gene knockdown at 30 pM.

Several of these HuR constructs were further tested, including those comprising the RNAi agent strand, further comprising at the 3' end, in 5' to 3' order: a spacer (ribitol), a phosphate and a 3' end cap (X058, X110, X111, X112, X1012, X1013, X1018, X1019, X1025, X1027, X1028).

These were tested in vitro in Huh-7 cells and all demonstrated at least about 80% to 90% gene knockdown at Day 3 at 1 nM.

Additional HuR constructs comprising a 3' end cap were constructed, which comprised a strand with the 18-mer sequence above, further comprising at the 3' end, in 5' to 3' order: (a) a ribitol spacer, a phosphate and X058 3' end cap; (b) a ribitol spacer, a phosphate and C6 3' end cap; (c) a C3 spacer, a phosphate and a X058 3' end cap; (d) a C3 spacer, a phosphate and a C6 3' end cap; (e) a C5300 spacer, a phosphate and a X058 3' end cap; and (f) a C5300 spacer, a phosphate and a C6 3' end cap. Each of these constructs was tested in vitro in Huh-7 cells and all demonstrated about 90% gene knockdown at Day 3 at 1 nM.

Additional RNAi agents to HuR were constructed comprising two strands, each an 18-mer, the two strands together forming a blunt-ended duplex, wherein at least one strand terminates at a 3' phosphorothioate (PS), the strand further comprising at the 3' end, in 5' to 3' order, a spacer (ribitol), a modified internucleoside linker (another phosphorothioate), and a 3' end cap (C6).

SSB RNAi Agents Comprising a 3' End Cap.

Effective RNAi agents were also constructed targeting SSB and comprising a 3' end cap, or spacer, phosphate or modified internucleoside linker and 3' end cap, as disclosed herein. For example, in some RNAi agents to these targets, one or both strand further comprises at the 3' end, in 5' to 3' order, a spacer (e.g., C3), a phosphate and a 3' end cap (C6).

For example, the human SSB RNAi agent designated hs_SSB_309_AS_18mer-C3-C6 was effective at mediating RNA interference in vitro, and is shown below:

```
AS:   UuAcAUuAAAGUCUGU87-C3pC6
8 = 2' methoxy ethyl T; 7 = 2' methoxy ethyl G S:    cAAcAGAcuuuAAuGu55-C3pC6
5 = 2' methoxy ethyl A
``` n: 2'Ome-n

The sequence of the AS (anti-sense) strand, shown above 5' to 3', is SEQ ID NO: 90. The sequence of the S (sense) strand, shown above 5' to 3', is SEQ ID NO: 91.8, 7, 5 and 5 are 2'-MOE nucleosides, as defined as above.

A variety of RNAi agents targeting SSB and comprising a 3' end cap or spacer, phosphate or modified internucleoside linker and 3' end cap, as disclosed herein, were constructed. These have a variety of target sequences. For example, in various SSB RNAi agents that were constructed, one or both 18-mer strand further comprises, at the 3' end, in 5' to 3' order: a spacer (C3 or ribitol), a phosphate, and a 3' end cap (C6, BP, a second ribitol, or a diribitol). Other RNAi agents can be constructed targeting SSB.

Factor VII RNAi Agents Comprising a 3' End Cap.

Figure 3:
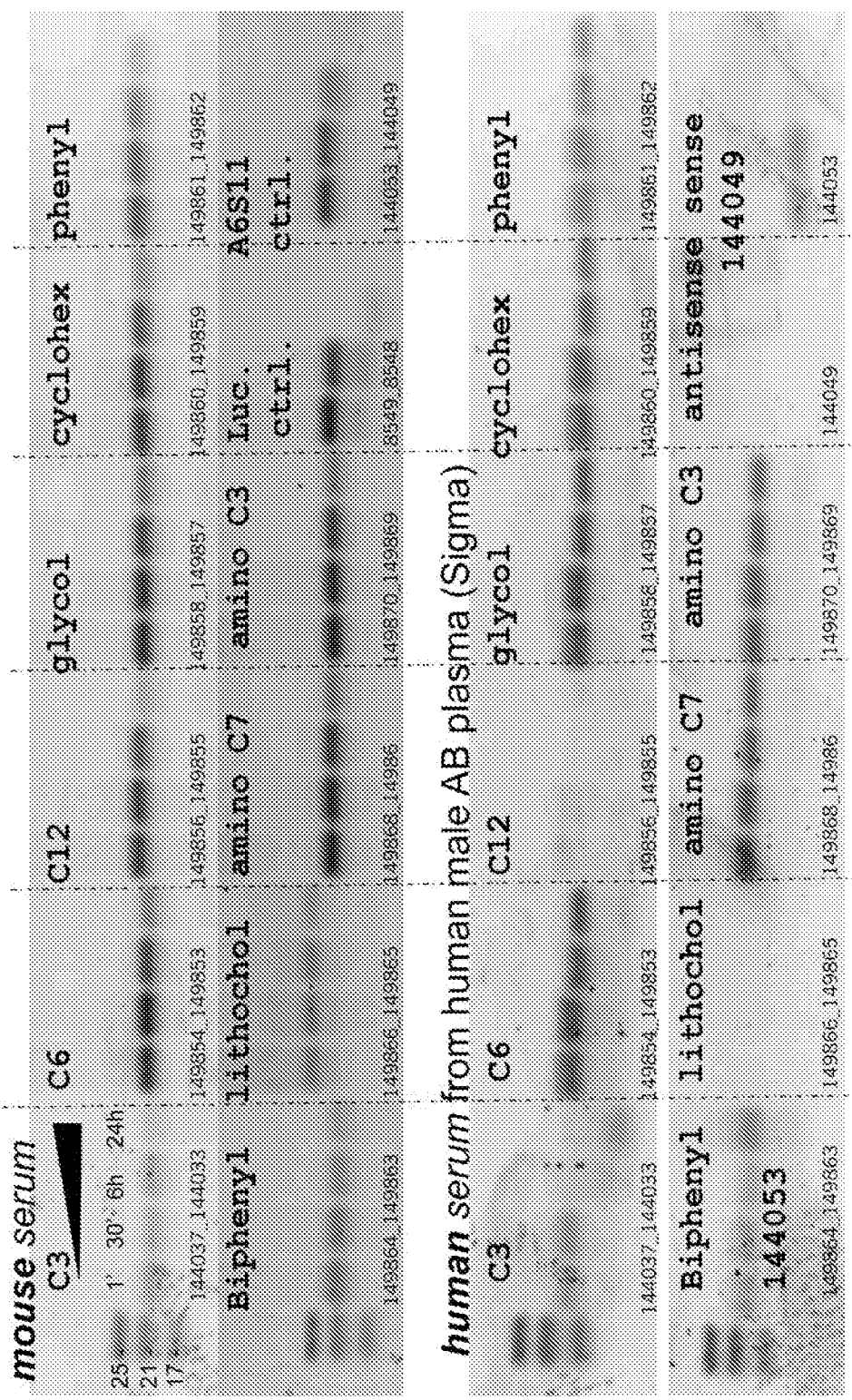
FIG. 3 shows the efficacy of the 3' end caps described in Example 1 in reducing and/or preventing nuclease degrada-tion in serum.

A variety of RNAi agents targeting Factor VII (F7) and comprising a 3' end cap (C3, C6, C12, glycol, cyclohex, phenyl, biphenyl, lithochol, C7 amino and C3 amino) were constructed; the efficacy of these constructs is shown in FIGS. 1 to 3.

A variety of RNAi agents targeting Factor VII (F7) and comprising a 3' end cap or spacer, phosphate or modified internucleoside linker and 3' end cap, as disclosed herein, were also constructed. This includes, as a non-limiting example, a RNAi comprising a strand further comprising at the 3' end, in 5' to 3' order, a spacer (C3), a phosphate, and a 3' end cap (C6). Other RNAi agents can be constructed targeting F7.

PLK1 RNAi Agents Comprising a 3' End Cap.

A variety of PLK1 RNAi agents comprising a 3' end cap were constructed and tested.

An RNAi agent was constructed to the target PLK1 and comprising a 3' end cap or spacer, phosphate or modified internucleoside linker and 3' end cap, as disclosed herein, e.g., comprising a strand further comprising at the 3' end, in 5' to 3' order, a spacer (C3), a phosphate, and a 3' end cap (C6).

Improved Activity of 3' End Caps.

As noted above, in several cases, the RNAi agent comprising a 3' end cap or spacer, phosphate or modified internucleoside linker and 3' end cap, as disclosed herein, has been shown to have increased activity relative to a corresponding siRNA lacking such a 3' end cap. Various siRNAs comprising a 3' end cap or spacer, phosphate or modified internucleoside linker and 3' end cap, as disclosed herein, have shown, in different experiments, in vitro and in vivo, to have increased RNA interference activity, increased duration of activity, increased resistance to nuclease degradation, and/or increased specificity. See, for example, FIGS. 1 to 3.

For example, several test siRNAs were constructed against the target F7, including a 21-mer (of the canonical structure, with two dinucleotide overhangs) and a blunt-ended 18-mer, comprising a C3pC6. In the C3pC6 molecule, the 3' end of the anti-sense strand further comprises, in 5' to 3' order: a spacer which is C3, a phosphate, and a 3' end cap which is C6. Both the 21-mer and 18-mer target the same sequence; both have the same 5' start. The RNAi agent comprising the C3pC6, however, showed a lower ED50 (0.44 (±0.022) mg/kg) than the 21-mer (0.61 (±0.017) mg/kg).

In addition, when a Hepcidin RNAi agent (with a X058 3' end cap) was tested in vivo, it was found, after 2 days, to be more potent than a corresponding 21-mer RNAi agents (which has a dinucleotide overhang). For hepcidin, some RNAi agents with a 3' end cap as disclosed herein more potent than corresponding 21-mers (with a dinucleotide overhang) have been developed.

It was also found that a hepcidin 21-mer siRNA was more prone to sense strand incorporation into RISC than the corresponding 18-mer with a 3' end comprising a spacer, a phosphate or internucleoside linker and a 3' end cap. Thus, in this case, the 21-mer is less specific.

Thus, in various experiments, the RNAi agent comprising a 3' end comprising a spacer, a phosphate or internucleoside linker and a 3' end cap can demonstrate improved activity compared to a corresponding 21-mer siRNA.

The present disclosure also encompasses methods of decreasing the expression of a target gene or inhibiting or reducing the level and/or activity of its gene product, or of treating a disease associated with over-expression of a target gene, in vitro, or in an organism, such as a mammal, such as a human being, wherein the method comprises the step of administering to the human being a physiologically active amount of a composition comprising a RNAi agent with a 3' end comprising a spacer, a phosphate or internucleoside linker and a 3' end cap, as disclosed herein.

RNAi Agents Comprising a 3' End Cap

In various embodiments, the disclosure encompasses:

A RNAi agent comprising a first strand and a second strand, wherein each strand is a 49-mer or shorter, and wherein the 3' end of at least one strand comprises a 3' end cap, and wherein the 3' end cap is C7 amino.

A RNAi agent comprising a first strand and a second strand, wherein each strand is a 49-mer or shorter, and wherein the 3' end of at least one strand comprises a 3' end cap, and wherein the 3' end cap is C3 amino.

A RNAi agent comprising a first strand and a second strand, wherein each strand is 18 nucleotides, and wherein the 3' end of at least one strand comprises a 3' end cap, and wherein the 3' end cap is C6. The C6 has been demonstrated to be active in vitro and in vivo with the 18-mer format.

A RNAi agent comprising a first strand and a second strand, wherein each strand is a 49-mer or shorter, and wherein the 3' end of at least one strand comprises a 3' end cap, and wherein the 3' end cap is C8.

A RNAi agent comprising a first strand and a second strand, wherein each strand is a 49-mer or shorter, and wherein the 3' end of at least one strand comprises a 3' end cap, and wherein the 3' end cap is C10. The C10 has demonstrated beneficial duration of siRNAs with the 18-mer and 19-mer format.

A RNAi agent comprising a first strand and a second strand, wherein each strand is a 49-mer or shorter, and wherein the 3' end of at least one strand comprises a 3' end cap, and wherein the 3' end cap is C12. The C12 has been shown to be active on siRNAs in vitro.

A RNAi agent comprising a first strand and a second strand, wherein each strand is a 49-mer or shorter, and wherein the 3' end of at least one strand comprises a 3' end cap, and wherein the 3' end cap is X027.

A RNAi agent comprising a first strand and a second strand, wherein each strand is a 49-mer or shorter, and wherein the 3' end of at least one strand comprises a 3' end cap, and wherein the 3' end cap is X038.

A RNAi agent comprising a first strand and a second strand, wherein each strand is a 49-mer or shorter, and wherein the 3' end of at least one strand comprises a 3' end cap, and wherein the 3' end cap is X050.

A RNAi agent comprising a first strand and a second strand, wherein each strand is a 49-mer or shorter, and wherein the 3' end of at least one strand comprises a 3' end cap, and wherein the 3' end cap is X051.

A RNAi agent comprising a first strand and a second strand, wherein each strand is a 49-mer or shorter, and wherein the 3' end of at least one strand comprises a 3' end cap, and wherein the 3' end cap is X052.

A RNAi agent comprising a first strand and a second strand, wherein each strand is a 49-mer or shorter, and wherein the 3' end of at least one strand comprises a 3' end cap, and wherein the 3' end cap is X058.

A RNAi agent comprising a first strand and a second strand, wherein each strand is a 49-mer or shorter, and wherein the 3' end of at least one strand comprises a 3' end cap, and wherein the 3' end cap is X059.

A RNAi agent comprising a first strand and a second strand, wherein each strand is a 49-mer or shorter, and wherein the 3' end of at least one strand comprises a 3' end cap, and wherein the 3' end cap is X060.

A RNAi agent comprising a first strand and a second strand, wherein each strand is a 49-mer or shorter, and wherein the 3' end of at least one strand comprises a 3' end cap, and wherein the 3' end cap is X061.

A RNAi agent comprising a first strand and a second strand, wherein each strand is a 49-mer or shorter, and wherein the 3' end of at least one strand comprises a 3' end cap, and wherein the 3' end cap is X062.

A RNAi agent comprising a first strand and a second strand, wherein each strand is a 49-mer or shorter, and wherein the 3' end of at least one strand comprises a 3' end cap, and wherein the 3' end cap is X063.

A RNAi agent comprising a first strand and a second strand, wherein each strand is a 49-mer or shorter, and wherein the 3' end of at least one strand comprises a 3' end cap, and wherein the 3' end cap is X064.

A RNAi agent comprising a first strand and a second strand, wherein each strand is a 49-mer or shorter, and wherein the 3' end of at least one strand comprises a 3' end cap, and wherein the 3' end cap is X065.

A RNAi agent comprising a first strand and a second strand, wherein each strand is a 49-mer or shorter, and wherein the 3' end of at least one strand comprises a 3' end cap, and wherein the 3' end cap is X066.

A RNAi agent comprising a first strand and a second strand, wherein each strand is a 49-mer or shorter, and wherein the 3' end of at least one strand comprises a 3' end cap, and wherein the 3' end cap is X067.

A RNAi agent comprising a first strand and a second strand, wherein each strand is a 49-mer or shorter, and wherein the 3' end of at least one strand comprises a 3' end cap, and wherein the 3' end cap is X068.

A RNAi agent comprising a first strand and a second strand, wherein each strand is a 49-mer or shorter, and wherein the 3' end of at least one strand comprises a 3' end cap, and wherein the 3' end cap is X069.

A RNAi agent comprising a first strand and a second strand, wherein each strand is a 49-mer or shorter, and wherein the 3' end of at least one strand comprises a 3' end cap, and wherein the 3' end cap is X097.

A RNAi agent comprising a first strand and a second strand, wherein each strand is a 49-mer or shorter, and wherein the 3' end of at least one strand comprises a 3' end cap, and wherein the 3' end cap is X098.

A RNAi agent comprising a first strand and a second strand, wherein each strand is a 49-mer or shorter, and wherein the 3' end of at least one strand comprises a 3' end cap, and wherein the 3' end cap is X109.

A RNAi agent comprising a first strand and a second strand, wherein each strand is a 49-mer or shorter, and wherein the 3' end of at least one strand comprises a 3' end cap, and wherein the 3' end cap is X110.

A RNAi agent comprising a first strand and a second strand, wherein each strand is a 49-mer or shorter, and wherein the 3' end of at least one strand comprises a 3' end cap, and wherein the 3' end cap is X111.

A RNAi agent comprising a first strand and a second strand, wherein each strand is a 49-mer or shorter, and wherein the 3' end of at least one strand comprises a 3' end cap, and wherein the 3' end cap is X112.

A RNAi agent comprising a first strand and a second strand, wherein each strand is a 49-mer or shorter, and wherein the 3' end of at least one strand comprises a 3' end cap, and wherein the 3' end cap is X113.

A RNAi agent comprising a first strand and a second strand, wherein each strand is a 49-mer or shorter, and wherein the 3' end of at least one strand comprises a 3' end cap, and wherein the 3' end cap is X1009.

A RNAi agent comprising a first strand and a second strand, wherein each strand is a 49-mer or shorter, and wherein the 3' end of at least one strand comprises a 3' end cap, and wherein the 3' end cap is X1010.

A RNAi agent comprising a first strand and a second strand, wherein each strand is a 49-mer or shorter, and wherein the 3' end of at least one strand comprises a 3' end cap, and wherein the 3' end cap is X1011.

A RNAi agent comprising a first strand and a second strand, wherein each strand is a 49-mer or shorter, and wherein the 3' end of at least one strand comprises a 3' end cap, and wherein the 3' end cap is X1012.

A RNAi agent comprising a first strand and a second strand, wherein each strand is a 49-mer or shorter, and wherein the 3' end of at least one strand comprises a 3' end cap, and wherein the 3' end cap is X1013.

A RNAi agent comprising a first strand and a second strand, wherein each strand is a 49-mer or shorter, and wherein the 3' end of at least one strand comprises a 3' end cap, and wherein the 3' end cap is X1015.

A RNAi agent comprising a first strand and a second strand, wherein each strand is a 49-mer or shorter, and wherein the 3' end of at least one strand comprises a 3' end cap, and wherein the 3' end cap is X1016.

A RNAi agent comprising a first strand and a second strand, wherein each strand is a 49-mer or shorter, and wherein the 3' end of at least one strand comprises a 3' end cap, and wherein the 3' end cap is X1017.

A RNAi agent comprising a first strand and a second strand, wherein each strand is a 49-mer or shorter, and wherein the 3' end of at least one strand comprises a 3' end cap, and wherein the 3' end cap is X1018.

A RNAi agent comprising a first strand and a second strand, wherein each strand is a 49-mer or shorter, and wherein the 3' end of at least one strand comprises a 3' end cap, and wherein the 3' end cap is X1019.

A RNAi agent comprising a first strand and a second strand, wherein each strand is a 49-mer or shorter, and wherein the 3' end of at least one strand comprises a 3' end cap, and wherein the 3' end cap is X1020.

A RNAi agent comprising a first strand and a second strand, wherein each strand is a 49-mer or shorter, and wherein the 3' end of at least one strand comprises a 3' end cap, and wherein the 3' end cap is X1021.

A RNAi agent comprising a first strand and a second strand, wherein each strand is a 49-mer or shorter, and wherein the 3' end of at least one strand comprises a 3' end cap, and wherein the 3' end cap is X1022.

A RNAi agent comprising a first strand and a second strand, wherein each strand is a 49-mer or shorter, and wherein the 3' end of at least one strand comprises a 3' end cap, and wherein the 3' end cap is X1024.

A RNAi agent comprising a first strand and a second strand, wherein each strand is a 49-mer or shorter, and wherein the 3' end of at least one strand comprises a 3' end cap, and wherein the 3' end cap is X1025.

A RNAi agent comprising a first strand and a second strand, wherein each strand is a 49-mer or shorter, and wherein the 3' end of at least one strand comprises a 3' end cap, and wherein the 3' end cap is X1026.

A RNAi agent comprising a first strand and a second strand, wherein each strand is a 49-mer or shorter, and wherein the 3' end of at least one strand comprises a 3' end cap, and wherein the 3' end cap is X1027.

A RNAi agent comprising a first strand and a second strand, wherein each strand is a 49-mer or shorter, and wherein the 3' end of at least one strand comprises a 3' end cap, and wherein the 3' end cap is X1028.

A RNAi agent comprising a first strand and a second strand, wherein each strand is a 49-mer or shorter, and wherein the 3' end of at least one strand comprises a 3' end cap, and wherein the 3' end cap is X1047.

A RNAi agent comprising a first strand and a second strand, wherein each strand is a 49-mer or shorter, and wherein the 3' end of at least one strand comprises a 3' end cap, and wherein the 3' end cap is X1048.

A RNAi agent comprising a first strand and a second strand, wherein each strand is a 49-mer or shorter, and wherein the 3' end of at least one strand comprises a 3' end cap, and wherein the 3' end cap is X1049.

A RNAi agent comprising a first strand and a second strand, wherein each strand is a 49-mer or shorter, and wherein the 3' end of at least one strand comprises a 3' end cap, and wherein the 3' end cap is X1062.

A RNAi agent comprising a first strand and a second strand, wherein each strand is a 49-mer or shorter, and wherein the 3' end of at least one strand comprises a 3' end cap, and wherein the 3' end cap is X1063.

A RNAi agent comprising a first strand and a second strand, wherein each strand is a 49-mer or shorter, and wherein the 3' end of at least one strand comprises a 3' end cap, and wherein the 3' end cap is X1064.

A RNAi agent comprising a first strand and a second strand, wherein each strand is a 49-mer or shorter, and wherein the 3' end of at least one strand comprises a 3' end cap, and wherein the 3' end cap is ribitol.

For each and every of the RNAi agents listed in this section, the RNAi agent can be of any length, sequence or target, and can be, as a non-limiting example, a double-stranded RNA, wherein optionally one or more phosphates are replaced by a modified internucleoside linker, optionally one or more nucleotides are modified, and optionally one or more RNA nucleotides are replaced by DNA, PNA, LNA, morpholino, TNA, GNA, ANA, HNA, CeNA, FANA, and/or UNA.

RNAi Agents Terminating in a Phosphate or Modified Internucleoside Linker and Further Comprising in 5' to 3' Order: A Spacer, a Phosphate or Modified Internucleoside Linker, and a 3' End Cap In various embodiments, the disclosure pertains to an RNAi agent comprising, in 5' to 3' order, a strand terminating in a 3' terminal phosphate or a modified internucleoside linker, a spacer, a phosphate or a modified internucleoside linker, and a 3' end cap (e.g., any 3' end cap listed in Tables 1 or 2 or otherwise disclosed herein).

In various embodiments, the disclosure encompasses:

An RNAi agent comprising a first and a second strand, wherein the 3' end of the first and/or second strand terminates in a phosphate or a modified internucleoside linker and further comprises, in 5' to 3' order: a spacer, a phosphate or a modified internucleoside linker, and a 3' end cap.

An RNAi agent comprising a first and a second strand, wherein the 3' end of the first and/or second strand terminates in a phosphate or a modified internucleoside linker and further comprises, in 5' to 3' order: a spacer, a phosphate or a modified internucleoside linker, and a 3' end cap, and wherein the spacer is a ribitol.

An RNAi agent comprising a first and a second strand, wherein the 3' end of the first and/or second strand terminates in a phosphate or a modified internucleoside linker and further comprises, in 5' to 3' order: a spacer, a phosphate or a modified internucleoside linker, and a 3' end cap, and wherein the spacer is a 2'-deoxy-ribitol.

An RNAi agent comprising a first and a second strand, wherein the 3' end of the first and/or second strand terminates in a phosphate or a modified internucleoside linker and further comprises, in 5' to 3' order: a spacer, a phosphate or a modified internucleoside linker, and a 3' end cap, and wherein the spacer is a diribitol.

An RNAi agent comprising a first and a second strand, wherein the 3' end of the first and/or second strand terminates in a phosphate or a modified internucleoside linker and further comprises, in 5' to 3' order: a spacer, a phosphate or a modified internucleoside linker, and a 3' end cap, and wherein the spacer is a 2'-methoxyethoxy-ribitol.

An RNAi agent comprising a first and a second strand, wherein the 3' end of the first and/or second strand terminates in a phosphate or a modified internucleoside linker and further comprises, in 5' to 3' order: a spacer, a phosphate or a modified internucleoside linker, and a 3' end cap, and wherein the spacer is a C3.

An RNAi agent comprising a first and a second strand, wherein the 3' end of the first and/or second strand terminates in a phosphate or a modified internucleoside linker and further comprises, in 5' to 3' order: a spacer, a phosphate or a modified internucleoside linker, and a 3' end cap, and wherein the spacer is a C4.

An RNAi agent comprising a first and a second strand, wherein the 3' end of the first and/or second strand terminates in a phosphate or a modified internucleoside linker and further comprises, in 5' to 3' order: a spacer, a phosphate or a modified internucleoside linker, and a 3' end cap, and wherein the spacer is a C5.

An RNAi agent comprising a first and a second strand, wherein the 3' end of the first and/or second strand terminates in a phosphate or a modified internucleoside linker and further comprises, in 5' to 3' order: a spacer, a phosphate or a modified internucleoside linker, and a 3' end cap, and wherein the spacer is a C6.

An RNAi agent comprising a first and a second strand, wherein the 3' end of the first and/or second strand terminates in a phosphate or a modified internucleoside linker and further comprises, in 5' to 3' order: a spacer, a phosphate or a modified internucleoside linker, and a 3' end cap, and wherein the spacer is 4-methoxybutane-1,3-diol.

In each and every RNAi agent in this second strand, the 3' end cap is selected from: is triethylene glycol, cyclohexyl, phenyl, BP (biphenyl), lithochol (lithocholic acid), adamantane, C3 amino, C7 amino, C3, C6, C8, C10, C12, X027, X038, X050, X051, X052, X058, X059, X060, X061, X062, X063, X064, X065, X066, X067, X068, X069, X097, X098, X109, X110, X111, X112, X113, X1009, X1010, X1011, X1012, X1013, X1015, X1016, X1017, X1018, X1019, X1020, X1021, X1022, X1024, X1025, X1026, X1027, X1028, X1047, X1048, X1049, X1062, X1063, X1064, or ribitol. In addition, for each and every of the RNAi agents listed in this section, the RNAi agent can be of any length, sequence or target, and can be, as a non-limiting example, a double-stranded RNA, wherein optionally one or more phosphates are replaced by a modified internucleoside linker, optionally one or more nucleotides are modified, and optionally one or more RNA nucleotides are replaced by DNA, PNA, LNA, morpholino, TNA, GNA, ANA, HNA, CeNA, FANA, and/or UNA.

Additional Embodiments Comprising a Spacer, a Phosphate or Modified Internucleoside Linker, and a 3' End Cap This disclosure encompasses, inter alia:

An RNAi agent comprising a first and a second strand, wherein the first and/or second strand terminates in a 3' terminal phosphate and further comprises, in 5' to 3' order: a spacer, a phosphate, and a 3' end cap, and wherein the spacer is C3 and the 3' end cap is C6. This structure is designated C3pC6.

An RNAi agent comprising a first and a second strand, wherein the first and/or second strand terminates in a 3' terminal phosphate and further comprises, in 5' to 3' order: a spacer, a phosphate, and a 3' end cap, and wherein the spacer is ribitol and the 3' end cap is C3. This structure is designated ribC3 or ribpC3.

Figure 5A:
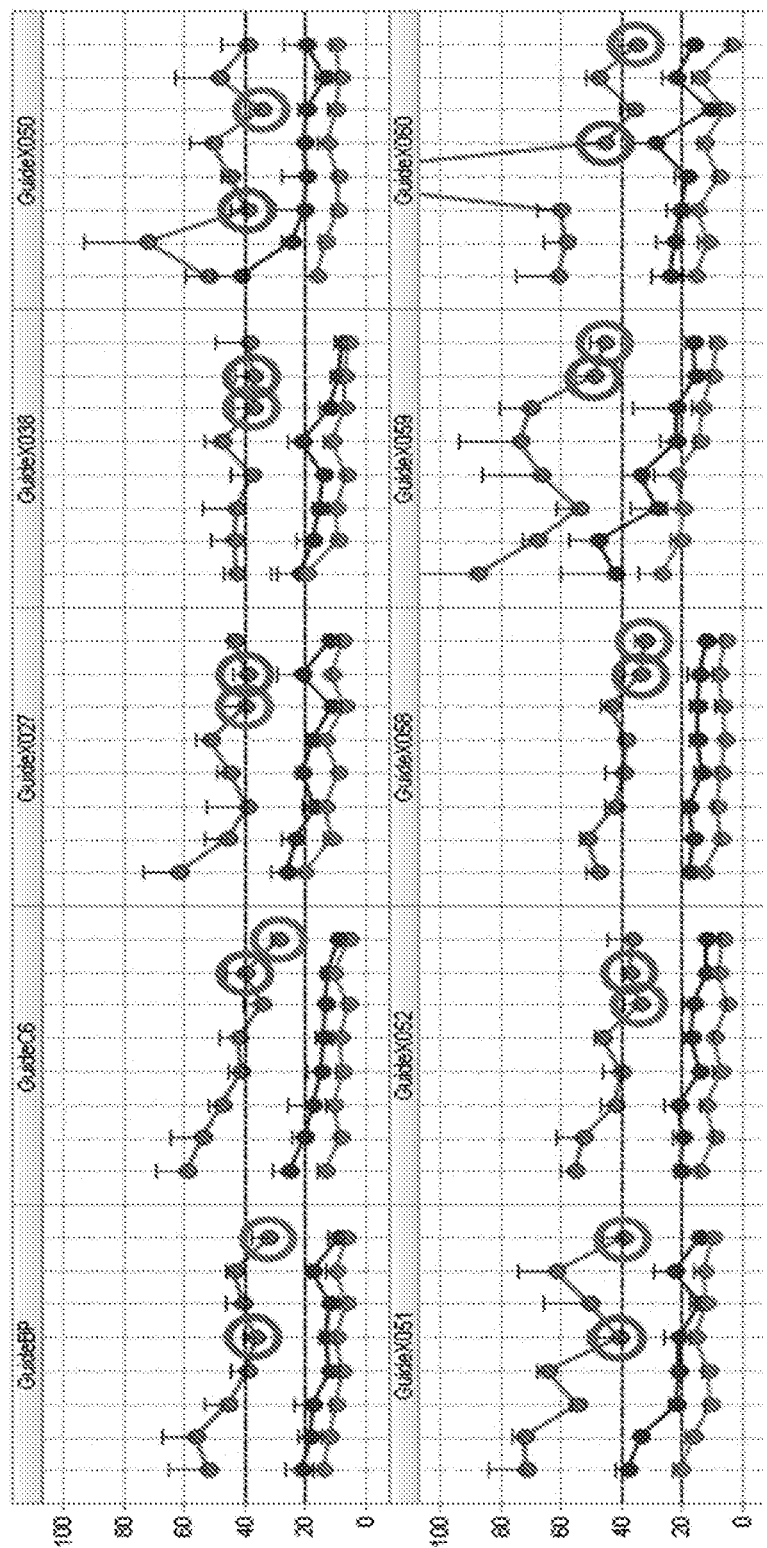
FIGS. 5A and 5B show residual expression level, indi-cating in vitro RNA interference or KD (knockdown) medi-ated by various RNAi agents comprising a 3' end cap: BP (biphenyl), C6, X027, X038, X050, X051, X052, X058, X059, X060, X061, X062, X063, X064, X065, X066, X067, X068, and X069 on the guide strand, as described in Example 3A. These RNAi agents are without a 2'-MOE clamp (−) or with a 2'-MOE clamp (MOE); or without a ribitol spacer (−) or with a ribitol spacer (rib). Descriptions for FIG. 5A are provided at the bottom of FIG. 5B, and this data pertains to Example 3A. These are RNAi agents to Hepcidin.

An RNAi agent comprising a first and a second strand, wherein the first and/or second strand terminates in a 3' terminal phosphate and further comprises, in 5' to 3' order: a spacer, a phosphate, and a 3' end cap, and wherein the spacer is ribitol and the 3' end cap is C6. This structure is designated ribpC6. The efficacy of a RNAi agent comprising a ribpC6 is shown in FIG. 5A. An efficacious RNAi agent comprising this 3' end cap is shown in FIG. 11. RibpC6 is also active in vivo on the 18-mer format.

An RNAi agent comprising a first and a second strand, wherein the first and/or second strand terminates in a 3' terminal phosphate and further comprises, in 5' to 3' order: a spacer, a phosphate, and a 3' end cap, and wherein the spacer is ribitol and the 3' end cap is C6. This structure is designated ribC6 or ribpC6.

An RNAi agent comprising a first and a second strand, wherein the first and/or second strand terminates in a 3' terminal phosphate and further comprises, in 5' to 3' order: a spacer, a phosphate, and a 3' end cap, and wherein the spacer is ribitol and the 3' end cap is C8. This structure is designated ribC8 or ribpC8.

An RNAi agent comprising a first and a second strand, wherein the first and/or second strand terminates in a 3' terminal phosphate and further comprises, in 5' to 3' order: a spacer, a phosphate, and a 3' end cap, and wherein the spacer is ribitol and the 3' end cap is C10. This structure is designated ribC10 or ribpC10.

An RNAi agent comprising a first and a second strand, wherein the first and/or second strand terminates in a 3' terminal phosphate and further comprises, in 5' to 3' order: a spacer, a phosphate, and a 3' end cap, and wherein the spacer is ribitol and the 3' end cap is C12. This structure is designated ribC12 or ribpC12.

An RNAi agent comprising a first and a second strand, wherein the first and/or second strand terminates in a 3' terminal phosphate and further comprises, in 5' to 3' order: a spacer, a phosphate, and a 3' end cap, and wherein the spacer is ribitol and the 3' end cap is BP. This structure is designated ribpBP. The efficacy of a RNAi agent comprising this 3' end cap is shown in FIG. 5A. This 3' end cap is active in vitro in the 18-mer format.

An RNAi agent comprising a first and a second strand, wherein the first and/or second strand terminates in a 3' terminal phosphate and further comprises, in 5' to 3' order: a spacer, a phosphate, and a 3' end cap, and wherein the spacer is ribitol and the 3' end cap is X027. This structure is designated ribX027. The efficacy of a RNAi agent comprising this 3' end cap is shown in FIG. 5A.

An RNAi agent comprising a first and a second strand, wherein the first and/or second strand terminates in a 3' terminal phosphate and further comprises, in 5' to 3' order: a spacer, a phosphate, and a 3' end cap, and wherein the spacer is ribitol and the 3' end cap is X038. This structure is designated ribX038. The efficacy of a RNAi agent comprising this 3' end cap is shown in FIG. 5A.

An RNAi agent comprising a first and a second strand, wherein the first and/or second strand terminates in a 3' terminal phosphate and further comprises, in 5' to 3' order: a spacer, a phosphate, and a 3' end cap, and wherein the spacer is ribitol and the 3' end cap is X050. This structure is designated ribX050. The efficacy of a RNAi agent comprising this 3' end cap is shown in FIG. 5A.

An RNAi agent comprising a first and a second strand, wherein the first and/or second strand terminates in a 3' terminal phosphate and further comprises, in 5' to 3' order: a spacer, a phosphate, and a 3' end cap, and wherein the spacer is ribitol and the 3' end cap is X051. This structure is designated ribX051. The efficacy of a RNAi agent comprising this 3' end cap is shown in FIG. 5A.

An RNAi agent comprising a first and a second strand, wherein the first and/or second strand terminates in a 3' terminal phosphate and further comprises, in 5' to 3' order: a spacer, a phosphate, and a 3' end cap, and wherein the spacer is ribitol and the 3' end cap is X052. This structure is designated ribX052. The efficacy of a RNAi agent comprising this 3' end cap is shown in FIG. 5A.

An RNAi agent comprising a first and a second strand, wherein the first and/or second strand terminates in a 3' terminal phosphate and further comprises, in 5' to 3' order: a spacer, a phosphate, and a 3' end cap, and wherein the spacer is ribitol and the 3' end cap is X058. This structure is designated ribX058. The efficacy of a RNAi agent comprising this 3' end cap is shown in FIG. 5A. An efficacious RNAi agent comprising this 3' end cap is shown in FIG. 11.

An RNAi agent comprising a first and a second strand, wherein the first and/or second strand terminates in a 3' terminal phosphate and further comprises, in 5' to 3' order: a spacer, a phosphate, and a 3' end cap, and wherein the spacer is ribitol and the 3' end cap is X059. This structure is designated ribX059. The efficacy of a RNAi agent comprising this 3' end cap is shown in FIG. 5A.

An RNAi agent comprising a first and a second strand, wherein the first and/or second strand terminates in a 3' terminal phosphate and further comprises, in 5' to 3' order: a spacer, a phosphate, and a 3' end cap, and wherein the spacer is ribitol and the 3' end cap is X060. This structure is designated ribX060. The efficacy of a RNAi agent comprising this 3' end cap is shown in FIG. 5A.

Figure 5B:
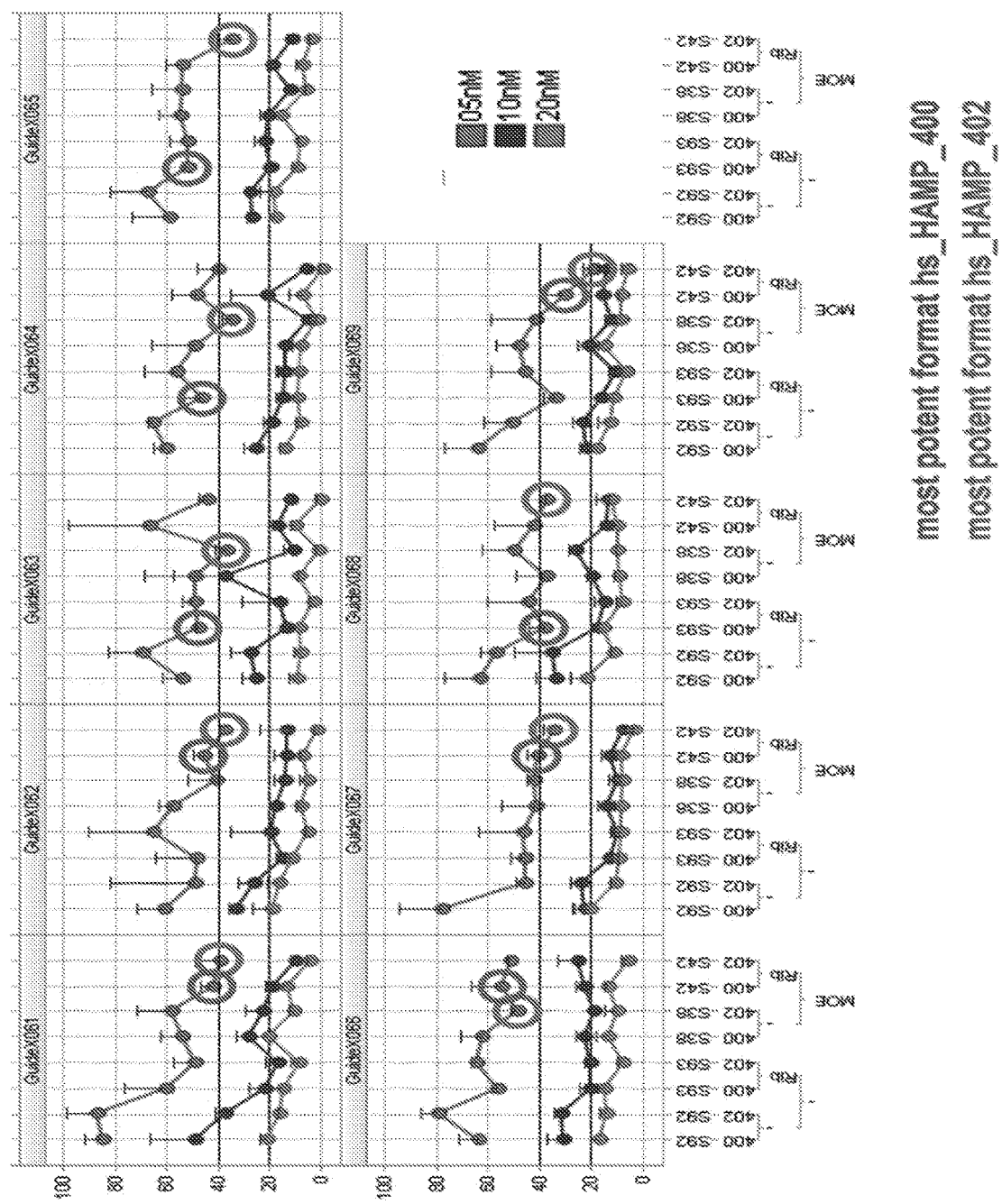

An RNAi agent comprising a first and a second strand, wherein the first and/or second strand terminates in a 3' terminal phosphate and further comprises, in 5' to 3' order: a spacer, a phosphate, and a 3' end cap, and wherein the spacer is ribitol and the 3' end cap is X061. This structure is designated ribX061. The efficacy of a RNAi agent comprising this 3' end cap is shown in FIG. 5B.

An RNAi agent comprising a first and a second strand, wherein the first and/or second strand terminates in a 3' terminal phosphate and further comprises, in 5' to 3' order: a spacer, a phosphate, and a 3' end cap, and wherein the spacer is ribitol and the 3' end cap is X062. This is designated ribX062. The efficacy of a RNAi agent comprising this 3' end cap is shown in FIG. 5B.

An RNAi agent comprising a first and a second strand, wherein the first and/or second strand terminates in a 3' terminal phosphate and further comprises, in 5' to 3' order: a spacer, a phosphate, and a 3' end cap, and wherein the spacer is ribitol and the 3' end cap is X063. This structure is designated ribX063. The efficacy of a RNAi agent comprising this 3' end cap is shown in FIG. 5B.

An RNAi agent comprising a first and a second strand, wherein the first and/or second strand terminates in a 3' terminal phosphate and further comprises, in 5' to 3' order: a spacer, a phosphate, and a 3' end cap, and wherein the spacer is ribitol and the 3' end cap is X064. ribX064. The efficacy of a RNAi agent comprising this 3' end cap is shown in FIG. 5B.

An RNAi agent comprising a first and a second strand, wherein the first and/or second strand terminates in a 3' terminal phosphate and further comprises, in 5' to 3' order: a spacer, a phosphate, and a 3' end cap, and wherein the spacer is ribitol and the 3' end cap is X065. This structure is designated ribX065. The efficacy of a RNAi agent comprising this 3' end cap is shown in FIG. 5B.

An RNAi agent comprising a first and a second strand, wherein the first and/or second strand terminates in a 3' terminal phosphate and further comprises, in 5' to 3' order: a spacer, a phosphate, and a 3' end cap, and wherein the spacer is ribitol and the 3' end cap is X066. This structure is designated ribX066. The efficacy of a RNAi agent comprising this 3' end cap is shown in FIG. 5B.

An RNAi agent comprising a first and a second strand, wherein the first and/or second strand terminates in a 3' terminal phosphate and further comprises, in 5' to 3' order: a spacer, a phosphate, and a 3' end cap, and wherein the spacer is ribitol and the 3' end cap is X067. This structure is designated ribX067. The efficacy of a RNAi agent comprising this 3' end cap is shown in FIG. 5B.

An RNAi agent comprising a first and a second strand, wherein the first and/or second strand terminates in a 3' terminal phosphate and further comprises, in 5' to 3' order: a spacer, a phosphate, and a 3' end cap, and wherein the spacer is ribitol and the 3' end cap is X068. This structure is designated ribX068. The efficacy of a RNAi agent comprising this 3' end cap is shown in FIG. 5B.

An RNAi agent comprising a first and a second strand, wherein the first and/or second strand terminates in a 3' terminal phosphate and further comprises, in 5' to 3' order: a spacer, a phosphate, and a 3' end cap, and wherein the spacer is ribitol and the 3' end cap is X069. This structure is designated ribX069. The efficacy of a RNAi agent comprising this 3' end cap is shown in FIG. 5B.

An RNAi agent comprising a first and a second strand, wherein the first and/or second strand terminates in a 3' terminal phosphate and further comprises, in 5' to 3' order: a spacer, a phosphate, and a 3' end cap, and wherein the spacer is ribitol and the 3' end cap is X097.

An RNAi agent comprising a first and a second strand, wherein the first and/or second strand terminates in a 3' terminal phosphate and further comprises, in 5' to 3' order: a spacer, a phosphate, and a 3' end cap, and wherein the spacer is ribitol and the 3' end cap is X098.

An RNAi agent comprising a first and a second strand, wherein the first and/or second strand terminates in a 3' terminal phosphate and further comprises, in 5' to 3' order: a spacer, a phosphate, and a 3' end cap, and wherein the spacer is ribitol and the 3' end cap is X109.

An RNAi agent comprising a first and a second strand, wherein the first and/or second strand terminates in a 3' terminal phosphate and further comprises, in 5' to 3' order: a spacer, a phosphate, and a 3' end cap, and wherein the spacer is ribitol and the 3' end cap is X110.

An RNAi agent comprising a first and a second strand, wherein the first and/or second strand terminates in a 3' terminal phosphate and further comprises, in 5' to 3' order: a spacer, a phosphate, and a 3' end cap, and wherein the spacer is ribitol and the 3' end cap is X111.

An RNAi agent comprising a first and a second strand, wherein the first and/or second strand terminates in a 3' terminal phosphate and further comprises, in 5' to 3' order: a spacer, a phosphate, and a 3' end cap, and wherein the spacer is ribitol and the 3' end cap is X112.

An RNAi agent comprising a first and a second strand, wherein the first and/or second strand terminates in a 3' terminal phosphate and further comprises, in 5' to 3' order: a spacer, a phosphate, and a 3' end cap, and wherein the spacer is ribitol and the 3' end cap is X113.

An RNAi agent comprising a first and a second strand, wherein the first and/or second strand terminates in a 3' terminal phosphate and further comprises, in 5' to 3' order: a spacer, a phosphate, and a 3' end cap, and wherein the spacer is ribitol and the 3' end cap is X1009.

An RNAi agent comprising a first and a second strand, wherein the first and/or second strand terminates in a 3' terminal phosphate and further comprises, in 5' to 3' order: a spacer, a phosphate, and a 3' end cap, and wherein the spacer is ribitol and the 3' end cap is X1010.

An RNAi agent comprising a first and a second strand, wherein the first and/or second strand terminates in a 3' terminal phosphate and further comprises, in 5' to 3' order: a spacer, a phosphate, and a 3' end cap, and wherein the spacer is ribitol and the 3' end cap is X1011.

An RNAi agent comprising a first and a second strand, wherein the first and/or second strand terminates in a 3' terminal phosphate and further comprises, in 5' to 3' order: a spacer, a phosphate, and a 3' end cap, and wherein the spacer is ribitol and the 3' end cap is X1012.

An RNAi agent comprising a first and a second strand, wherein the first and/or second strand terminates in a 3' terminal phosphate and further comprises, in 5' to 3' order: a spacer, a phosphate, and a 3' end cap, and wherein the spacer is ribitol and the 3' end cap is X1013.

An RNAi agent comprising a first and a second strand, wherein the first and/or second strand terminates in a 3' terminal phosphate and further comprises, in 5' to 3' order: a spacer, a phosphate, and a 3' end cap, and wherein the spacer is ribitol and the 3' end cap is X1015.

An RNAi agent comprising a first and a second strand, wherein the first and/or second strand terminates in a 3' terminal phosphate and further comprises, in 5' to 3' order: a spacer, a phosphate, and a 3' end cap, and wherein the spacer is ribitol and the 3' end cap is X1016.

An RNAi agent comprising a first and a second strand, wherein the first and/or second strand terminates in a 3' terminal phosphate and further comprises, in 5' to 3' order: a spacer, a phosphate, and a 3' end cap, and wherein the spacer is ribitol and the 3' end cap is X1017.

An RNAi agent comprising a first and a second strand, wherein the first and/or second strand terminates in a 3' terminal phosphate and further comprises, in 5' to 3' order: a spacer, a phosphate, and a 3' end cap, and wherein the spacer is ribitol and the 3' end cap is X1018.

An RNAi agent comprising a first and a second strand, wherein the first and/or second strand terminates in a 3' terminal phosphate and further comprises, in 5' to 3' order: a spacer, a phosphate, and a 3' end cap, and wherein the spacer is ribitol and the 3' end cap is X1019.

An RNAi agent comprising a first and a second strand, wherein the first and/or second strand terminates in a 3' terminal phosphate and further comprises, in 5' to 3' order: a spacer, a phosphate, and a 3' end cap, and wherein the spacer is ribitol and the 3' end cap is X1020.

An RNAi agent comprising a first and a second strand, wherein the first and/or second strand terminates in a 3' terminal phosphate and further comprises, in 5' to 3' order: a spacer, a phosphate, and a 3' end cap, and wherein the spacer is ribitol and the 3' end cap is X1021.

An RNAi agent comprising a first and a second strand, wherein the first and/or second strand terminates in a 3' terminal phosphate and further comprises, in 5' to 3' order: a spacer, a phosphate, and a 3' end cap, and wherein the spacer is ribitol and the 3' end cap is X1022.

An RNAi agent comprising a first and a second strand, wherein the first and/or second strand terminates in a 3' terminal phosphate and further comprises, in 5' to 3' order: a spacer, a phosphate, and a 3' end cap, and wherein the spacer is ribitol and the 3' end cap is X1024.

An RNAi agent comprising a first and a second strand, wherein the first and/or second strand terminates in a 3' terminal phosphate and further comprises, in 5' to 3' order: a spacer, a phosphate, and a 3' end cap, and wherein the spacer is ribitol and the 3' end cap is X1025.

An RNAi agent comprising a first and a second strand, wherein the first and/or second strand terminates in a 3' terminal phosphate and further comprises, in 5' to 3' order: a spacer, a phosphate, and a 3' end cap, and wherein the spacer is ribitol and the 3' end cap is X1026.

An RNAi agent comprising a first and a second strand, wherein the first and/or second strand terminates in a 3' terminal phosphate and further comprises, in 5' to 3' order: a spacer, a phosphate, and a 3' end cap, and wherein the spacer is ribitol and the 3' end cap is X1027.

An RNAi agent comprising a first and a second strand, wherein the first and/or second strand terminates in a 3' terminal phosphate and further comprises, in 5' to 3' order: a spacer, a phosphate, and a 3' end cap, and wherein the spacer is ribitol and the 3' end cap is X1028.

An RNAi agent comprising a first and a second strand, wherein the first and/or second strand terminates in a 3' terminal phosphate and further comprises, in 5' to 3' order: a spacer, a phosphate, and a 3' end cap, and wherein the spacer is ribitol and the 3' end cap is X1047.

An RNAi agent comprising a first and a second strand, wherein the first and/or second strand terminates in a 3' terminal phosphate and further comprises, in 5' to 3' order: a spacer, a phosphate, and a 3' end cap, and wherein the spacer is ribitol and the 3' end cap is X1048.

An RNAi agent comprising a first and a second strand, wherein the first and/or second strand terminates in a 3' terminal phosphate and further comprises, in 5' to 3' order: a spacer, a phosphate, and a 3' end cap, and wherein the spacer is ribitol and the 3' end cap is X1049.

An RNAi agent comprising a first and a second strand, wherein the first and/or second strand terminates in a 3' terminal phosphate and further comprises, in 5' to 3' order: a spacer, a phosphate, and a 3' end cap, and wherein the spacer is ribitol and the 3' end cap is X1062.

An RNAi agent comprising a first and a second strand, wherein the first and/or second strand terminates in a 3' terminal phosphate and further comprises, in 5' to 3' order: a spacer, a phosphate, and a 3' end cap, and wherein the spacer is ribitol and the 3' end cap is X1063.

An RNAi agent comprising a first and a second strand, wherein the first and/or second strand terminates in a 3' terminal phosphate and further comprises, in 5' to 3' order: a spacer, a phosphate, and a 3' end cap, and wherein the spacer is ribitol and the 3' end cap is X1064.

An RNAi agent comprising a first and a second strand, wherein the first and/or second strand terminates in a 3' terminal phosphate and further comprises, in 5' to 3' order: a spacer, a phosphate, and a 3' end cap, and wherein the spacer is ribitol and the 3' end cap is ribitol.

For each and every of structure listed in this section, the RNAi agent can be of any length, sequence or target, and can be, as a non-limiting example, a double-stranded RNA, wherein optionally one or more phosphates are replaced by a modified internucleoside linker, optionally one or more nucleotides are modified, and optionally one or more RNA nucleotides are replaced by DNA, PNA, LNA, morpholino, TNA, GNA, ANA, HNA, CeNA, FANA, and/or UNA.

Additional Embodiments Comprising a Spacer, a Phosphate or Modified Internucleoside Linker, and a 3' End Cap This disclosure encompasses, inter alia:

An RNAi agent comprising a first and a second strand, wherein the 3' end of the first and/or second strand terminates in a phosphate or modified internucleoside linker and further comprises, in 5' to 3' order: a spacer, a phosphate or modified internucleoside linker, and a 3' end cap, and wherein and the 3' end cap is C3.

An RNAi agent comprising a first and a second strand, wherein the 3' end of the first and/or second strand terminates in a phosphate or modified internucleoside linker and further comprises, in 5' to 3' order: a spacer, a phosphate or modified internucleoside linker, and a 3' end cap, and wherein and the 3' end cap is C6.

An RNAi agent comprising a first and a second strand, wherein the 3' end of the first and/or second strand terminates in a phosphate or modified internucleoside linker and further comprises, in 5' to 3' order: a spacer, a phosphate or modified internucleoside linker, and a 3' end cap, and wherein and the 3' end cap is C8.

An RNAi agent comprising a first and a second strand, wherein the 3' end of the first and/or second strand terminates in a phosphate or modified internucleoside linker and further comprises, in 5' to 3' order: a spacer, a phosphate or modified internucleoside linker, and a 3' end cap, and wherein and the 3' end cap is C10.

An RNAi agent comprising a first and a second strand, wherein the 3' end of the first and/or second strand terminates in a phosphate or modified internucleoside linker and further comprises, in 5' to 3' order: a spacer, a phosphate or modified internucleoside linker, and a 3' end cap, and wherein and the 3' end cap is C12.

An RNAi agent comprising a first and a second strand, wherein the 3' end of the first and/or second strand terminates in a phosphate or modified internucleoside linker and further comprises, in 5' to 3' order: a spacer, a phosphate or modified internucleoside linker, and a 3' end cap, and wherein and the 3' end cap is BP.

An RNAi agent comprising a first and a second strand, wherein the 3' end of the first and/or second strand terminates in a phosphate or modified internucleoside linker and further comprises, in 5' to 3' order: a spacer, a phosphate or modified internucleoside linker, and a 3' end cap, and wherein and the 3' end cap is X027.

An RNAi agent comprising a first and a second strand, wherein the 3' end of the first and/or second strand terminates in a phosphate or modified internucleoside linker and further comprises, in 5' to 3' order: a spacer, a phosphate or modified internucleoside linker, and a 3' end cap, and wherein and the 3' end cap is X038.

An RNAi agent comprising a first and a second strand, wherein the 3' end of the first and/or second strand terminates in a phosphate or modified internucleoside linker and further comprises, in 5' to 3' order: a spacer, a phosphate or modified internucleoside linker, and a 3' end cap, and wherein and the 3' end cap is X050.

An RNAi agent comprising a first and a second strand, wherein the 3' end of the first and/or second strand terminates in a phosphate or modified internucleoside linker and further comprises, in 5' to 3' order: a spacer, a phosphate or modified internucleoside linker, and a 3' end cap, and wherein and the 3' end cap is X051.

An RNAi agent comprising a first and a second strand, wherein the 3' end of the first and/or second strand terminates in a phosphate or modified internucleoside linker and further comprises, in 5' to 3' order: a spacer, a phosphate or modified internucleoside linker, and a 3' end cap, and wherein and the 3' end cap is X052.

An RNAi agent comprising a first and a second strand, wherein the 3' end of the first and/or second strand terminates in a phosphate or modified internucleoside linker and further comprises, in 5' to 3' order: a spacer, a phosphate or modified internucleoside linker, and a 3' end cap, and wherein and the 3' end cap is X058.

An RNAi agent comprising a first and a second strand, wherein the 3' end of the first and/or second strand terminates in a phosphate or modified internucleoside linker and further comprises, in 5' to 3' order: a spacer, a phosphate or modified internucleoside linker, and a 3' end cap, and wherein and the 3' end cap is X059.

An RNAi agent comprising a first and a second strand, wherein the 3' end of the first and/or second strand terminates in a phosphate or modified internucleoside linker and further comprises, in 5' to 3' order: a spacer, a phosphate or modified internucleoside linker, and a 3' end cap, and wherein and the 3' end cap is X060.

An RNAi agent comprising a first and a second strand, wherein the 3' end of the first and/or second strand terminates in a phosphate or modified internucleoside linker and further comprises, in 5' to 3' order: a spacer, a phosphate or modified internucleoside linker, and a 3' end cap, and wherein and the 3' end cap is X061.

An RNAi agent comprising a first and a second strand, wherein the 3' end of the first and/or second strand terminates in a phosphate or modified internucleoside linker and further comprises, in 5' to 3' order: a spacer, a phosphate or modified internucleoside linker, and a 3' end cap, and wherein and the 3' end cap is X062. This is designated ribX062. The efficacy of a RNAi agent comprising this 3' end cap is shown in FIG. 5B.

An RNAi agent comprising a first and a second strand, wherein the 3' end of the first and/or second strand terminates in a phosphate or modified internucleoside linker and further comprises, in 5' to 3' order: a spacer, a phosphate or modified internucleoside linker, and a 3' end cap, and wherein and the 3' end cap is X063.

An RNAi agent comprising a first and a second strand, wherein the 3' end of the first and/or second strand terminates in a phosphate or modified internucleoside linker and further comprises, in 5' to 3' order: a spacer, a phosphate or modified internucleoside linker, and a 3' end cap, and wherein and the 3' end cap is X064. ribX064. The efficacy of a RNAi agent comprising this 3' end cap is shown in FIG. 5B.

An RNAi agent comprising a first and a second strand, wherein the 3' end of the first and/or second strand terminates in a phosphate or modified internucleoside linker and further comprises, in 5' to 3' order: a spacer, a phosphate or modified internucleoside linker, and a 3' end cap, and wherein and the 3' end cap is X065.

An RNAi agent comprising a first and a second strand, wherein the 3' end of the first and/or second strand terminates in a phosphate or modified internucleoside linker and further comprises, in 5' to 3' order: a spacer, a phosphate or modified internucleoside linker, and a 3' end cap, and wherein and the 3' end cap is X066.

An RNAi agent comprising a first and a second strand, wherein the 3' end of the first and/or second strand terminates in a phosphate or modified internucleoside linker and further comprises, in 5' to 3' order: a spacer, a phosphate or modified internucleoside linker, and a 3' end cap, and wherein and the 3' end cap is X067.

An RNAi agent comprising a first and a second strand, wherein the 3' end of the first and/or second strand terminates in a phosphate or modified internucleoside linker and further comprises, in 5' to 3' order: a spacer, a phosphate or modified internucleoside linker, and a 3' end cap, and wherein and the 3' end cap is X068.

An RNAi agent comprising a first and a second strand, wherein the 3' end of the first and/or second strand terminates in a phosphate or modified internucleoside linker and further comprises, in 5' to 3' order: a spacer, a phosphate or modified internucleoside linker, and a 3' end cap, and wherein and the 3' end cap is X069.

An RNAi agent comprising a first and a second strand, wherein the 3' end of the first and/or second strand terminates in a phosphate or modified internucleoside linker and further comprises, in 5' to 3' order: a spacer, a phosphate or modified internucleoside linker, and a 3' end cap, and wherein and the 3' end cap is X097.

An RNAi agent comprising a first and a second strand, wherein the 3' end of the first and/or second strand terminates in a phosphate or modified internucleoside linker and further comprises, in 5' to 3' order: a spacer, a phosphate or modified internucleoside linker, and a 3' end cap, and wherein and the 3' end cap is X098.

An RNAi agent comprising a first and a second strand, wherein the 3' end of the first and/or second strand terminates in a phosphate or modified internucleoside linker and further comprises, in 5' to 3' order: a spacer, a phosphate or modified internucleoside linker, and a 3' end cap, and wherein and the 3' end cap is X109.

An RNAi agent comprising a first and a second strand, wherein the 3' end of the first and/or second strand terminates in a phosphate or modified internucleoside linker and further comprises, in 5' to 3' order: a spacer, a phosphate or modified internucleoside linker, and a 3' end cap, and wherein and the 3' end cap is X110.

An RNAi agent comprising a first and a second strand, wherein the 3' end of the first and/or second strand terminates in a phosphate or modified internucleoside linker and further comprises, in 5' to 3' order: a spacer, a phosphate or modified internucleoside linker, and a 3' end cap, and wherein and the 3' end cap is X111.

An RNAi agent comprising a first and a second strand, wherein the 3' end of the first and/or second strand terminates in a phosphate or modified internucleoside linker and further comprises, in 5' to 3' order: a spacer, a phosphate or modified internucleoside linker, and a 3' end cap, and wherein and the 3' end cap is X112.

An RNAi agent comprising a first and a second strand, wherein the 3' end of the first and/or second strand terminates in a phosphate or modified internucleoside linker and further comprises, in 5' to 3' order: a spacer, a phosphate or modified internucleoside linker, and a 3' end cap, and wherein and the 3' end cap is X113.

An RNAi agent comprising a first and a second strand, wherein the 3' end of the first and/or second strand terminates in a phosphate or modified internucleoside linker and further comprises, in 5' to 3' order: a spacer, a phosphate or modified internucleoside linker, and a 3' end cap, and wherein and the 3' end cap is X1009.

An RNAi agent comprising a first and a second strand, wherein the 3' end of the first and/or second strand terminates in a phosphate or modified internucleoside linker and further comprises, in 5' to 3' order: a spacer, a phosphate or modified internucleoside linker, and a 3' end cap, and wherein and the 3' end cap is X1010.

An RNAi agent comprising a first and a second strand, wherein the 3' end of the first and/or second strand terminates in a phosphate or modified internucleoside linker and further comprises, in 5' to 3' order: a spacer, a phosphate or modified internucleoside linker, and a 3' end cap, and wherein and the 3' end cap is X1011.

An RNAi agent comprising a first and a second strand, wherein the 3' end of the first and/or second strand terminates in a phosphate or modified internucleoside linker and further comprises, in 5' to 3' order: a spacer, a phosphate or modified internucleoside linker, and a 3' end cap, and wherein and the 3' end cap is X1012.

An RNAi agent comprising a first and a second strand, wherein the 3' end of the first and/or second strand terminates in a phosphate or modified internucleoside linker and further comprises, in 5' to 3' order: a spacer, a phosphate or modified internucleoside linker, and a 3' end cap, and wherein and the 3' end cap is X1013.

An RNAi agent comprising a first and a second strand, wherein the 3' end of the first and/or second strand terminates in a phosphate or modified internucleoside linker and further comprises, in 5' to 3' order: a spacer, a phosphate or modified internucleoside linker, and a 3' end cap, and wherein and the 3' end cap is X1015.

An RNAi agent comprising a first and a second strand, wherein the 3' end of the first and/or second strand terminates in a phosphate or modified internucleoside linker and further comprises, in 5' to 3' order: a spacer, a phosphate or modified internucleoside linker, and a 3' end cap, and wherein and the 3' end cap is X1016.

An RNAi agent comprising a first and a second strand, wherein the 3' end of the first and/or second strand terminates in a phosphate or modified internucleoside linker and further comprises, in 5' to 3' order: a spacer, a phosphate or modified internucleoside linker, and a 3' end cap, and wherein and the 3' end cap is X1017.

An RNAi agent comprising a first and a second strand, wherein the 3' end of the first and/or second strand terminates in a phosphate or modified internucleoside linker and further comprises, in 5' to 3' order: a spacer, a phosphate or modified internucleoside linker, and a 3' end cap, and wherein and the 3' end cap is X1018.

An RNAi agent comprising a first and a second strand, wherein the 3' end of the first and/or second strand terminates in a phosphate or modified internucleoside linker and further comprises, in 5' to 3' order: a spacer, a phosphate or modified internucleoside linker, and a 3' end cap, and wherein and the 3' end cap is X1019.

An RNAi agent comprising a first and a second strand, wherein the 3' end of the first and/or second strand terminates in a phosphate or modified internucleoside linker and further comprises, in 5' to 3' order: a spacer, a phosphate or modified internucleoside linker, and a 3' end cap, and wherein and the 3' end cap is X1020.

An RNAi agent comprising a first and a second strand, wherein the 3' end of the first and/or second strand terminates in a phosphate or modified internucleoside linker and further comprises, in 5' to 3' order: a spacer, a phosphate or modified internucleoside linker, and a 3' end cap, and wherein and the 3' end cap is X1021.

An RNAi agent comprising a first and a second strand, wherein the 3' end of the first and/or second strand terminates in a phosphate or modified internucleoside linker and further comprises, in 5' to 3' order: a spacer, a phosphate or modified internucleoside linker, and a 3' end cap, and wherein and the 3' end cap is X1022.

An RNAi agent comprising a first and a second strand, wherein the 3' end of the first and/or second strand terminates in a phosphate or modified internucleoside linker and further comprises, in 5' to 3' order: a spacer, a phosphate or modified internucleoside linker, and a 3' end cap, and wherein and the 3' end cap is X1024.

An RNAi agent comprising a first and a second strand, wherein the 3' end of the first and/or second strand terminates in a phosphate or modified internucleoside linker and further comprises, in 5' to 3' order: a spacer, a phosphate or modified internucleoside linker, and a 3' end cap, and wherein and the 3' end cap is X1025.

An RNAi agent comprising a first and a second strand, wherein the 3' end of the first and/or second strand terminates in a phosphate or modified internucleoside linker and further comprises, in 5' to 3' order: a spacer, a phosphate or modified internucleoside linker, and a 3' end cap, and wherein and the 3' end cap is X1026.

An RNAi agent comprising a first and a second strand, wherein the 3' end of the first and/or second strand terminates in a phosphate or modified internucleoside linker and further comprises, in 5' to 3' order: a spacer, a phosphate or modified internucleoside linker, and a 3' end cap, and wherein and the 3' end cap is X1027.

An RNAi agent comprising a first and a second strand, wherein the 3' end of the first and/or second strand terminates in a phosphate or modified internucleoside linker and further comprises, in 5' to 3' order: a spacer, a phosphate or modified internucleoside linker, and a 3' end cap, and wherein and the 3' end cap is X1028.

An RNAi agent comprising a first and a second strand, wherein the 3' end of the first and/or second strand terminates in a phosphate or modified internucleoside linker and further comprises, in 5' to 3' order: a spacer, a phosphate or modified internucleoside linker, and a 3' end cap, and wherein and the 3' end cap is X1047.

An RNAi agent comprising a first and a second strand, wherein the 3' end of the first and/or second strand terminates in a phosphate or modified internucleoside linker and further comprises, in 5' to 3' order: a spacer, a phosphate or modified internucleoside linker, and a 3' end cap, and wherein and the 3' end cap is X1048.

An RNAi agent comprising a first and a second strand, wherein the 3' end of the first and/or second strand terminates in a phosphate or modified internucleoside linker and further comprises, in 5' to 3' order: a spacer, a phosphate or modified internucleoside linker, and a 3' end cap, and wherein and the 3' end cap is X1049.

An RNAi agent comprising a first and a second strand, wherein the 3' end of the first and/or second strand terminates in a phosphate or modified internucleoside linker and further comprises, in 5' to 3' order: a spacer, a phosphate or modified internucleoside linker, and a 3' end cap, and wherein and the 3' end cap is X1062.

An RNAi agent comprising a first and a second strand, wherein the 3' end of the first and/or second strand terminates in a phosphate or modified internucleoside linker and further comprises, in 5' to 3' order: a spacer, a phosphate or modified internucleoside linker, and a 3' end cap, and wherein and the 3' end cap is X1063.

An RNAi agent comprising a first and a second strand, wherein the 3' end of the first and/or second strand terminates in a phosphate or modified internucleoside linker and further comprises, in 5' to 3' order: a spacer, a phosphate or modified internucleoside linker, and a 3' end cap, and wherein and the 3' end cap is X1064.

An RNAi agent comprising a first and a second strand, wherein the 3' end of the first and/or second strand terminates in a phosphate or modified internucleoside linker and further comprises, in 5' to 3' order: a spacer, a phosphate or modified internucleoside linker, and a 3' end cap, and wherein and the 3' end cap is ribitol.

An RNAi agent comprising a first and a second strand, wherein the 3' end of the first and/or second strand terminates in a phosphate or modified internucleoside linker and further comprises, in 5' to 3' order: a spacer, a phosphate or modified internucleoside linker, and a 3' end cap, and wherein and the 3' end cap is triethylene glycol, cyclohexyl, phenyl, BP (biphenyl), lithochol (lithocholic acid), adamantane, C3 amino, C7 amino, C3, C6, C8, C10, C12, X027, X038, X050, X051, X052, X058, X059, X060, X061, X062, X063, X064, X065, X066, X067, X068, X069, X097, X098, X109, X110, X111, X112, X113, X1009, X1010, X1011, X1012, X1013, X1015, X1016, X1017, X1018, X1019, X1020, X1021, X1022, X1024, X1025, X1026, X1027, X1028, X1047, X1048, X1049, X1062, X1063, X1064, or ribitol.

For each and every of structure listed in this section, the RNAi agent can be of any length, sequence or target, and can be, as a non-limiting example, a double-stranded RNA, wherein optionally one or more phosphate or modified internucleoside linkers are replaced by a modified internucleoside linker, optionally one or more nucleotides are modified, and optionally one or more RNA nucleotides are replaced by DNA, PNA, LNA, morpholino, TNA, GNA, ANA, HNA, CeNA, FANA, and/or UNA.

The disclosure also encompasses a RNAi agent comprising a first strand and a second strand, wherein the first and/or second strand terminates in a PS (phosphorothioate), and further comprises a 3' end cap. The disclosure also a RNAi agent comprising a first strand and a second strand, wherein the first and/or second strand terminates in a PS (phosphorothioate), and further comprises, in 5' to 3' order: a spacer, phosphate or a modified internucleoside linker, and a 3' end cap.

Thus, the disclosure encompasses:

A RNAi agent comprising a first strand and a second strand, wherein each strand is a 49-mer or shorter, and wherein the first and/or second strand terminates in a PS and further comprises a 3' end cap, wherein the 3' end cap is C3. This structure is designated PS-C3. This efficacy of a RNAi agent comprising this 3' end cap is described in Example 6 and FIGS. 20 A-E).

A RNAi agent comprising a first strand and a second strand, wherein each strand is a 49-mer or shorter, and wherein the first and/or second strand terminates in a PS and further comprises a 3' end cap, wherein the 3' end cap is C6. This structure is designated PS-C6.

A RNAi agent comprising a first strand and a second strand, wherein each strand is a 49-mer or shorter, and wherein the first and/or second strand terminates in a PS and further comprises a 3' end cap, wherein the 3' end cap is C8. This structure is designated PS-C8.

A RNAi agent comprising a first strand and a second strand, wherein each strand is a 49-mer or shorter, and wherein the first and/or second strand terminates in a PS and further comprises a 3' end cap, wherein the 3' end cap is C10. This structure is designated PS-C10.

A RNAi agent comprising a first strand and a second strand, wherein each strand is a 49-mer or shorter, and wherein the first and/or second strand terminates in a PS and further comprises a 3' end cap, wherein the 3' end cap is C12. This structure is designated PS-C12.

A RNAi agent comprising a first strand and a second strand, wherein each strand is a 49-mer or shorter, and wherein the first and/or second strand terminates in a PS and further comprises a 3' end cap, wherein the 3' end cap is BP. This structure is designated PS-BP.

Alternative Names and DMT, Succinate and Carboxylate Variants of 3' End Caps

In various embodiments, the disclosure encompasses DMT, succinate and carboxylate forms of the various 3' end caps, which can be used to construct RNAi agents comprising a 3' end cap (or a spacer and a 3' end cap). In the compounds shown in Table 1, for example, independently, R1=OH, succinate or protected forms of OH; and R2=ODMT (where ODMT is DMT (4,4'-dimethoxytrityl) linked via an oxygen atom), or carboxylate. Protected forms of OH include, but are not limited to, ethers, phosphate esters, methyl tetraacetyl glucuronates, peracetyl glycosides and amino acid polypeptide esters.

Alternative nicknames have been devised for various DMT, Succinate and Carboxylate forms of various 3' end caps (also called "ligands").

Figure 12:
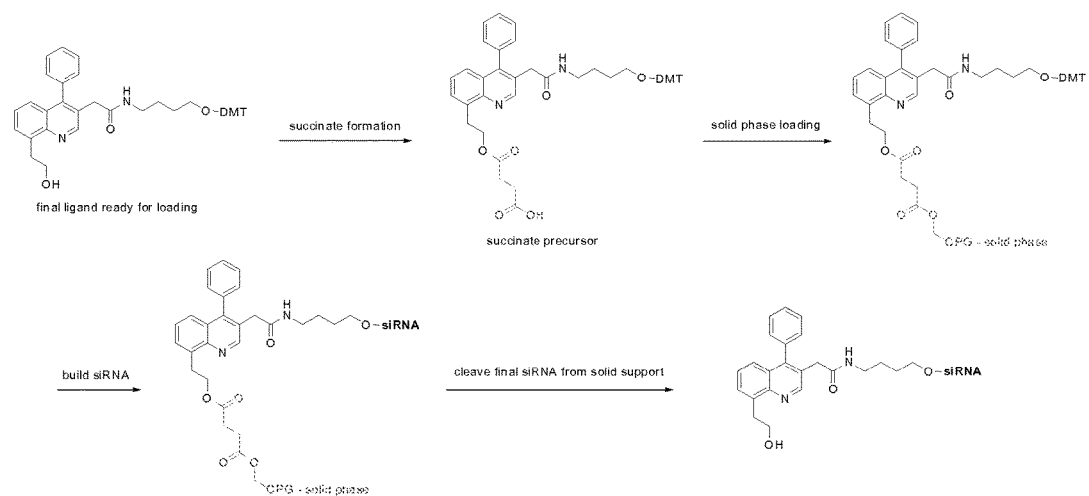
FIG. 12 shows a non-limiting example of synthesis of an RNAi agent comprising a 3' end cap (X058), using a succinate form.

The succinate form can optionally be used to load these molecules onto solid support for RNAi agent synthesis. One such synthesis is shown in FIG. 12, although other routes are also possible.

In addition to the succinyl (CO2H—(CH2)n-CO2H; n=2) linker used for solid-phase φG loading and oligonuceotide synthesis, other diacids of varying length [CO2H—(CH2)n-CO2H] can be used, as well as other "universal support" strategies known in the art, (for example, Glen UnySupport™ from Glen Research, Sterling, Va.), including hydroquinone-O,O'-diacyl (Pon et al. Nucl. Acids Res. 1997, 18, 3629-3635), N-Methyl-succinimido[3,4-b]-7-oxabicyclo[2.2.1]heptane-6-(4,4'-dimethoxytrityloxy)-5-succinoyl (Guzaev et al. J. Am. Chem. Soc. 2003, 125, 2380-2381; Kumar et al. Tetrahedron 2006, 62, 4528-4534), (2S,3S,4R,5R)-4-(bis(4-methoxyphenyl)(phenyl)methoxy)-2,5-dimethoxytetrahydrofuran-3-succinoyl (Scott et al. "Innovations and Perspectives in Solid Phase Synthesis, 3rd International Symposium," 1994, Ed. Roger Epton, Mayflower Worldwide, 115-124), and 1-Dimethoxytrityloxy-2-O-dichloroacetyl-propyl-3-N-succinyl (Azhayev. Tetrahedron, 1999, 55, 787-800; Azhayev et al. Tetrahedron 2001, 57, 4977-4986).

The succinate is traceless as it is only a synthetic handle not present in the final form of the siRNA.

It is noted, though, that the PAZ binding assay using the carboxylate variant was not predictive of efficacy, since several of the disclosed PAZ ligands below did not bind the PAZ ligand in this assay, but were later found to be effective as 3' caps when conjugated to an siRNA.

The structures of DMT-ligand, Succinate-ligand and carboxylate forms of the 3' end caps are shown in Table 4, below.

TABLE 4

DMT-LIGAND, SUCCINATE-LIGAND, AND CARBOXYLATE FORMS OF 3' END CAPS

| Ligand | DMT-ligand | Succinate-ligand | Carboxylate |
|---|---|---|---|
| X027 | | | |
| X038 | | | |

TABLE 4-continued

DMT-LIGAND, SUCCINATE-LIGAND, AND CARBOXYLATE FORMS OF 3' END CAPS

| Ligand | DMT-ligand | Succinate-ligand | Carboxylate |
|---|---|---|---|
| X050 | | | |
| X051 | | | |

TABLE 4-continued
DMT-LIGAND, SUCCINATE-LIGAND, AND CARBOXYLATE FORMS OF 3' END CAPS
| Ligand | DMT-ligand | Succinate-ligand | Carboxylate |
|---|---|---|---|
| X052 | 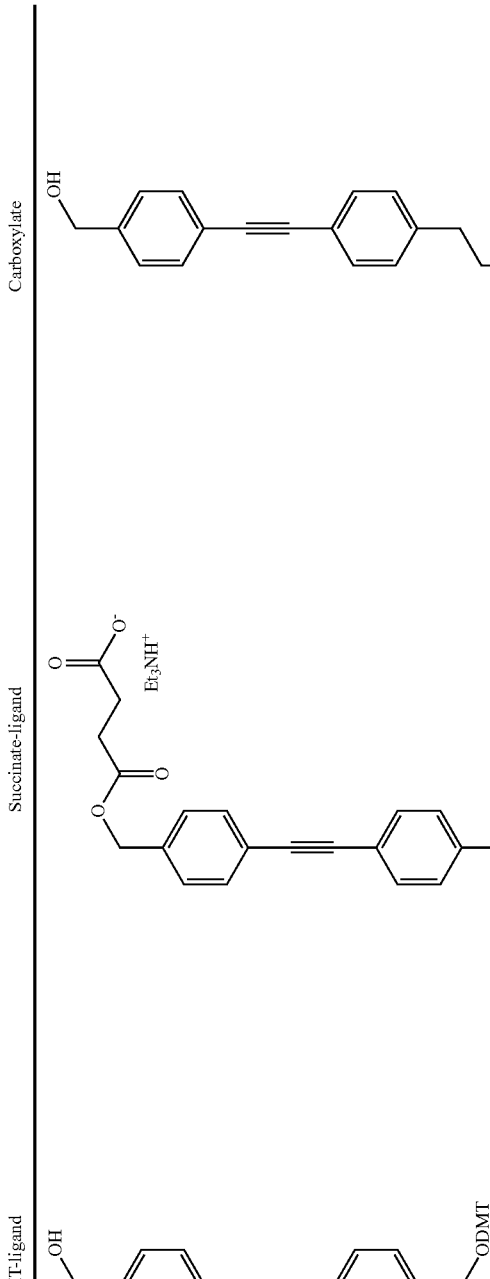 | 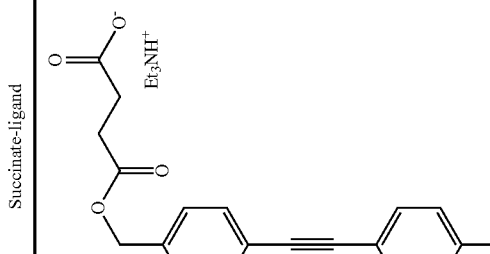 | 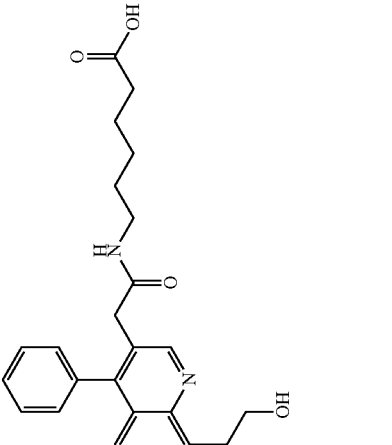 |
| X058 | 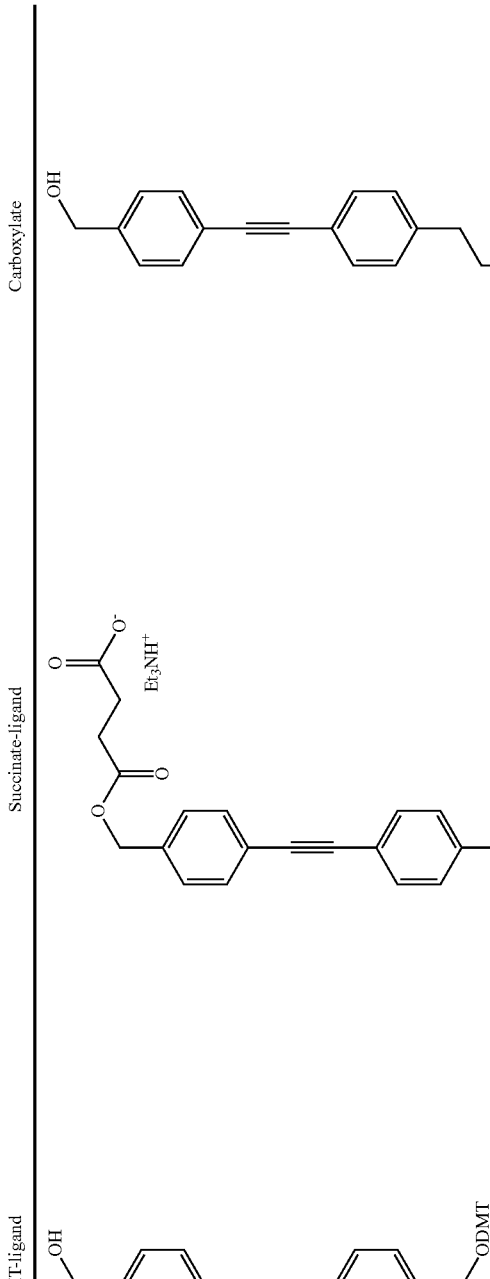 | 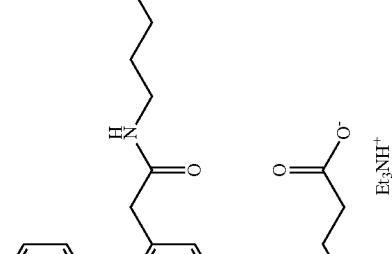 | 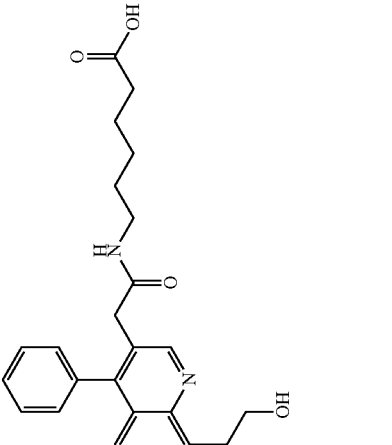 |

TABLE 4-continued

DMT-LIGAND, SUCCINATE-LIGAND, AND CARBOXYLATE FORMS OF 3' END CAPS

| Ligand | DMT-ligand | Succinate-ligand | Carboxylate |
|---|---|---|---|
| X059 | | | |
| X060 | | | |

TABLE 4-continued

DMT-LIGAND, SUCCINATE-LIGAND, AND CARBOXYLATE FORMS OF 3' END CAPS

| Ligand | DMT-ligand | Succinate-ligand | Carboxylate |
|---|---|---|---|
| X061 | | | |
| X062 | | | |

TABLE 4-continued

DMT-LIGAND, SUCCINATE-LIGAND, AND CARBOXYLATE FORMS OF 3' END CAPS

| Ligand | DMT-ligand | Succinate-ligand | Carboxylate |
|---|---|---|---|
| X063 | | | |
| X064 | | | |

TABLE 4-continued

DMT-LIGAND, SUCCINATE-LIGAND, AND CARBOXYLATE FORMS OF 3' END CAPS

| Ligand | DMT-ligand | Succinate-ligand | Carboxylate |
|---|---|---|---|
| X065 | (structure) | (structure) | (structure) |
| X066 | (structure) | (structure) | (structure) |

TABLE 4-continued
DMT-LIGAND, SUCCINATE-LIGAND, AND CARBOXYLATE FORMS OF 3' END CAPS
| Ligand | DMT-ligand | Succinate-ligand | Carboxylate |
|---|---|---|---|
| X067 | 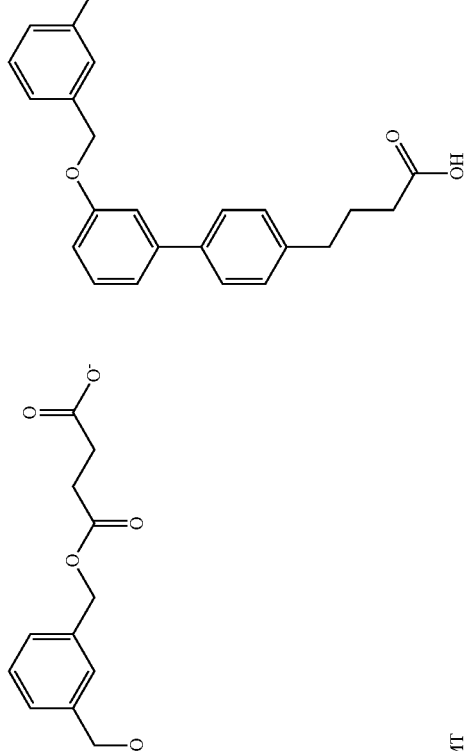 | 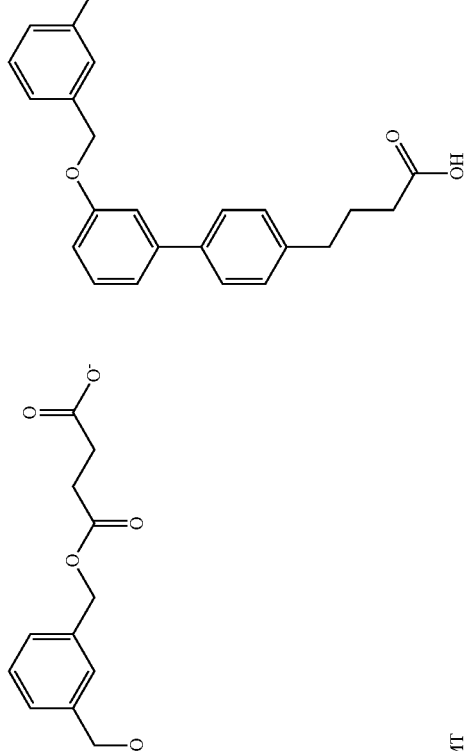 | 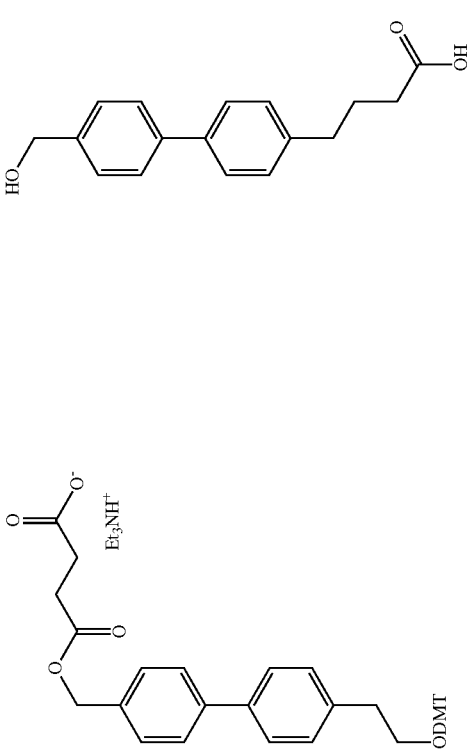 |
| X068 | 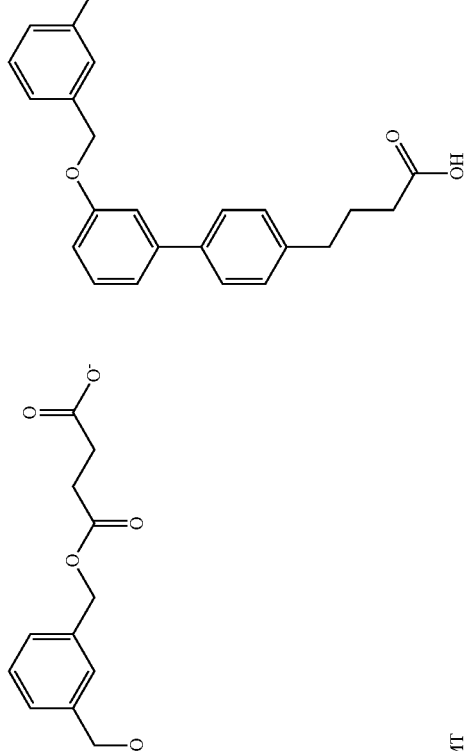 | 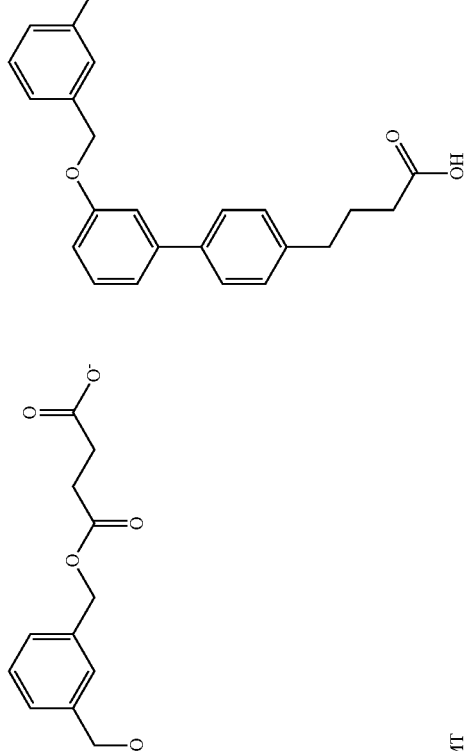 | 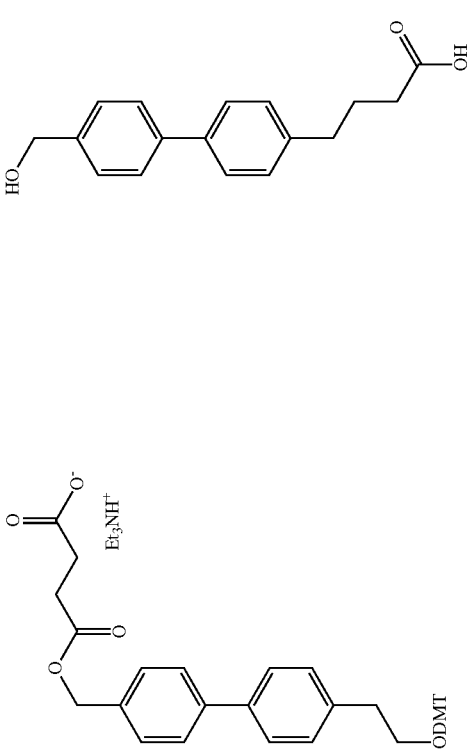 |

TABLE 4-continued
DMT-LIGAND, SUCCINATE-LIGAND, AND CARBOXYLATE FORMS OF 3' END CAPS
| Ligand | DMT-ligand | Succinate-ligand | Carboxylate |
|---|---|---|---|
| X069 | 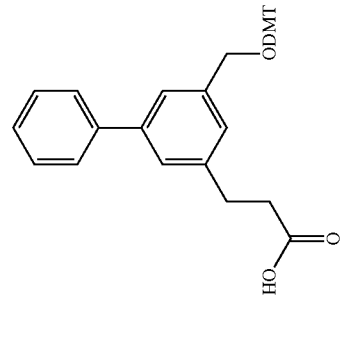 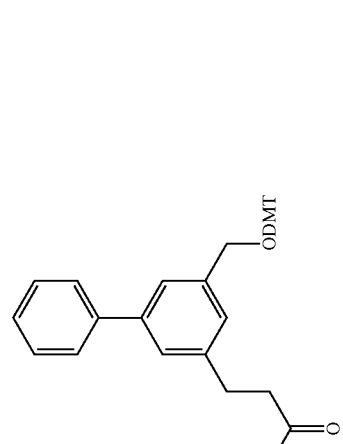 | 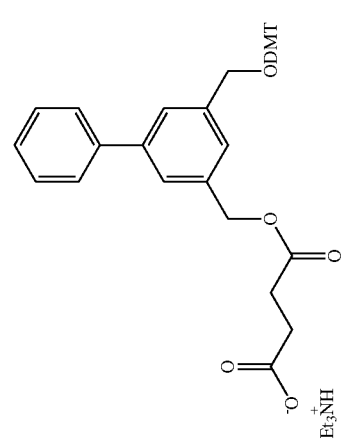 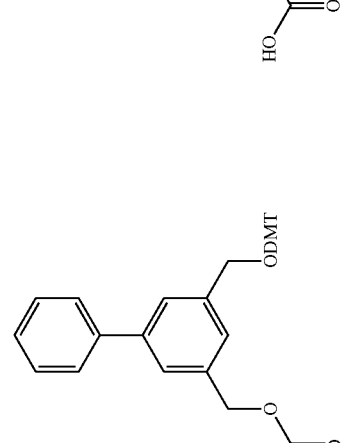 | 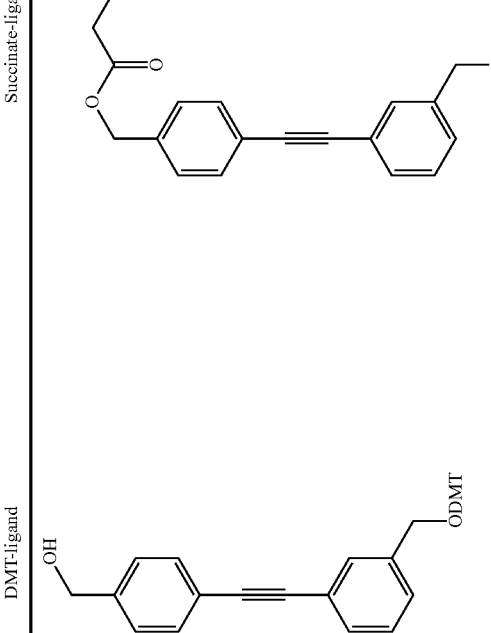 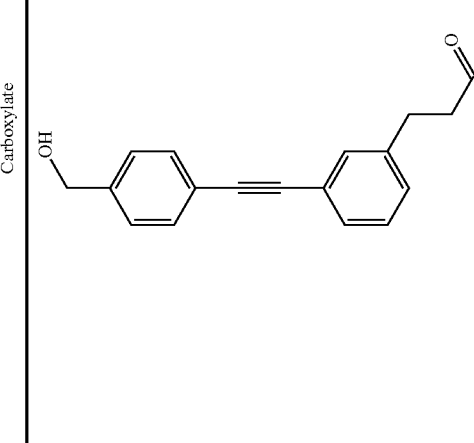 |

TABLE 4-continued

DMT-LIGAND, SUCCINATE-LIGAND, AND CARBOXYLATE FORMS OF 3' END CAPS

| Ligand | DMT-ligand | Succinate-ligand | Carboxylate |
|---|---|---|---|

RNAi Agents Comprising a 3' End Cap

The present disclosure thus provides a double-stranded RNAi agent (a double-stranded molecule capable of mediating RNA interference, including but not limited to a siRNA) comprising a first and a second strand, wherein the first and/or second strand comprise at least 15 to at least 19 or more contiguous nucleotides of target gene, wherein the RNAi agent comprises a 3' end cap on one or both strands. The first and second strand can be, depending on context, an antisense and a sense strand, or a sense and an antisense strand. The sense and anti-sense strand can be non-contiguous, contiguous, or covalently bound, e.g., via a loop or linker. In particular, the 3' end cap is selected from those listed in Tables 1 or 2 or otherwise disclosed herein. If both strands comprise a 3' end cap, the 3' end cap on each strand can be the same or different. The RNAi agent particularly can in one embodiment comprise less than 30 nucleotides per strand, e.g., such as 17-23 nucleotides, 15-19, 18-22 nucleotides, and/or 19-21 nucleotides, and be modified and unmodified (e.g., at the 2' carbon) at one or more nucleotides.

The double-stranded RNAi agents can have 0, 1 or 2 blunt ends, and/or overhangs [e.g., of 1, 2, 3 or 4 nucleotides (i.e., 1 to 4 nt)] from one or both 3' and/or 5' ends.

The RNAi agent can either contain only naturally-occurring nucleotide subunits (e.g., ribonucleotides), or one or more modifications to the sugar, phosphate or base of one or more of the replacement nucleotide subunits, whether they comprise ribonucleotide subunits or deoxyribonucleotide subunits or other related modified variants. RNAi agents thus include those that contain substitutions of a naturally-occurring nucleotide by an alternative backbone nucleotide (e.g., a PNA, morpholino, LNA, TNA, GNA, ANA, HNA, CeNA, FANA, and/or UNA, etc.) and/or a modified nucleotide.

In one embodiment, modified variants of the disclosed RNAi agents have a thymidine (as RNA, or, preferably, DNA) replacing a uridine, or have an inosine base. In some embodiments, the modified variants of the disclosed RNAi agents can have a nick in the "passenger" (aka "sense") strand, mismatches between the guide and passenger strand, DNA replacing the RNA of a portion of both the guide and passenger strand (e.g., the seed region), and/or a shortened passenger strand (e.g., 15, 16, 17 or 18 nt). Once a functional 3' end cap suitable for use with a guide strand is identified, modifications and variants of the RNAi agent can be readily made. The disclosed 3' end caps can be used in any RNAi agent comprising any combination of embodiments or features which are not mutually exclusive (e.g., the combination of base modifications with shortened passenger strand; or nicked passenger strand and base modifications; or DNA replacing part or all of the seed region and base modifications in the remaining RNA; or the combination of modifications with any delivery vehicle; etc.).

In one embodiment, the modifications improve efficacy, stability (e.g., against nucleases in, for example, blood serum or intestinal fluid), and/or reduce immunogenicity of the RNAi agent. One embodiment of the present disclosure relates to a double-stranded oligonucleotide comprising at least one non-natural nucleobase. In certain embodiments, the non-natural nucleobase is difluorotolyl, nitroindolyl, nitropyrrolyl, or nitroimidazolyl. In a particular embodiment, the non-natural nucleobase is difluorotolyl. In certain embodiments, only one of the two oligonucleotide strands contains a non-natural nucleobase. In certain embodiments, both of the oligonucleotide strands contain a non-natural nucleobase.

The RNAi agent(s) can optionally be attached to a ligand selected to improve one or more characteristic, such as, e.g., stability, distribution and/or cellular uptake of the agent, e.g., cholesterol or a derivative thereof. The RNAi agent(s) can be isolated or be part of a pharmaceutical composition used for the methods described herein. Particularly, the pharmaceutical composition can be formulated for delivery to specific tissues (e.g., those afflicted with a target gene-related disease) or formulated for parenteral administration. The pharmaceutical composition can optionally comprise two or more types or sequences of RNAi agents, each one directed to the same or a different segment of the target gene mRNA. Optionally, the pharmaceutical composition can further comprise or be used in conjunction with any known treatment for any target gene-related disease. The pharmaceutical composition can comprise a RNAi agent comprising a 3' end cap and any suitable delivery vehicle disclosed herein or known in the art.

The present disclosure further provides methods for inhibiting or reducing the level and/or activity of target gene mRNA in a cell, particularly in the case of a disease characterized by over-expression or hyper-activity of the target gene. Cells comprising an alteration such as a mutation, over-expression and/or hyperactivity of target gene are termed "target gene-defective" cells. Such methods comprise the step of administering one or more of the RNAi agents of the present disclosure to a cell, as further described below. The present methods utilize the cellular mechanisms involved in RNA interference to selectively degrade the target RNA in a cell and are comprised of the step of contacting a cell with one or more of the RNAi agents of the present disclosure.

The present disclosure also encompasses a method of treating a human subject having a pathological state mediated at least in part by target gene expression, the method comprising the step of administering to the subject a therapeutically effective amount of a RNAi agent targeting the target gene.

The methods and compositions of the present disclosure, e.g., the methods and target gene RNAi agent compositions, can be used in any appropriate dosage and/or formulation described herein or known in the art, as well as with any suitable route of administration described herein or known in the art.

The method also optionally further comprises the step of administering a second agent. In some embodiments, this second agent is another RNAi agent to target gene. In other embodiments, the second agent is another treatment, such as one directed to another target, which is also hyper-active, mutated and/or over-expressed in the pathological state.

The details of one or more embodiments of the present disclosure are set forth in the accompanying drawings and the description below. Elements of the various embodiments (e.g., 3' end caps, sequences, modifications, patterns of modifications, 5' end caps, combinations of RNAi agents, combination therapy involving a target gene RNAi agent and another agent, etc.) which are not mutually-exclusive can be combined with each other as described herein and as known or developed in the art. For example, any 3' end cap disclosed herein can be combined with any set of modifications or sequence disclosed herein. Any combination of modifications, 5' end caps, and/or sequence can be used with any 3' end cap disclosed herein. Any RNAi agent disclosed herein (with any combination of modifications or endcaps or without either modifications or endcaps) can be combined with any other RNAi agent or other treatment composition or method disclosed herein.

Thus, the present disclosure encompasses any RNAi agent disclosed herein, or any method involving any RNAi agent disclosed herein, wherein the RNAi agent comprises at least one 3' end cap as disclosed herein.

Definitions

For convenience, the meaning of certain terms and phrases used in the specification, examples, and appended claims, are provided below. If there is an apparent discrepancy between the usage of a term in other parts of this specification and its definition provided in this section, the definition in this section shall prevail.

"Alkyl" is a monovalent saturated hydrocarbon chain having the specified number of carbon atoms. For example, $C_{1-6}$ alkyl refers to an alkyl group having from 1 to 6 carbon atoms. Alkyl groups may be straight or branched. Representative branched alkyl groups have one, two, or three branches. Examples of alkyl groups include, but are not limited to, methyl, ethyl, propyl (n-propyl and isopropyl), butyl (n-butyl, isobutyl, sec-butyl, and t-butyl), pentyl (n-pentyl, isopentyl, and neopentyl), and hexyl.

"Aryl" is a hydrocarbon ring system having an aromatic ring. Aryl groups are monocyclic ring systems or bicyclic ring systems. Monocyclic aryl ring refers to phenyl. Bicyclic aryl rings refer to naphthyl and to rings wherein phenyl is fused to a $C_{5-7}$ cycloalkyl or $C_{5-7}$ cycloalkenyl ring as defined herein.

RNA Interference

As used herein, "RNA interference" (RNAi) is a post-transcriptional, targeted gene-silencing technique that uses a RNAi agent to degrade messenger RNA (mRNA) containing a sequence which is the same as or very similar to the RNAi agent. See: Zamore and Haley, 2005, Science, 309, 1519-1524; Zamore et al., 2000, Cell, 101, 25-33; Elbashir et al., 2001, Nature, 411, 494-498; and Kreutzer et al., PCT Publication WO 00/44895; Fire, PCT Publication WO 99/32619; Mello and Fire, PCT Publication WO 01/29058; and the like. The process of RNAi occurs naturally when long dsRNA is introduced into a cell and cleaved by ribonuclease III (Dicer) into shorter fragments called siRNAs. Naturally produced siRNAs are typically about 21 nucleotides long and comprise about 19 base pair duplexes with two 2-nt overhangs (the "canonical" structure). One strand of the siRNA is incorporated into the RNA-induced silencing complex (RISC). This strand (known as the anti-sense or guide strand strand) guides RISC to a complementary mRNA. One or more nucleases in the RISC then mediates cleavage of the target mRNA to induce silencing. Cleavage of the target RNA takes place in the middle of the region complementary to the anti-sense strand. See: Nykanen, et al. 2001 Cell 107:309; Sharp et al. 2001 Genes Dev. 15:485; Bernstein, et al. 2001 Nature 409:363; Elbashir, et al. 2001 Genes Dev. 15:188.

As used herein, the term "RNAi agent" encompasses siRNAs (including but not limited to those of the "canonical" structure), in addition to various natural and artificial structures capable of mediating RNA interference. As detailed below, these structures can be longer or shorter than the canonical, and/or blunt-ended, and/or comprise one or more modification, mismatch, gap, and/or nucleotide replacement. The 3' end caps of the present disclosure can be used with any RNAi agent and can allow two functions: (1) allowing RNA interference; and (2) increasing duration of activity and/or biological half-life, which may be accomplished, for example, by increased binding to the PAZ domain of Dicer and/or reducing or preventing degradation of the RNAi agent (e.g., by nucleases such as those in the serum or intestinal fluid).

The RNAi agent(s) of the present disclosure target (e.g., bind to, anneal to, etc.) the target mRNA. The use of the RNAi agent to the target results in a decrease of target activity, level and/or expression, e.g., a "knock-down" or "knock-out" of the target gene or target sequence. Particularly, in one embodiment, in the case of a disease state characterized by over-expression or hyper-activity of target gene, administration of a RNAi agent to target gene knocks down the target gene target enough to restore a normal level of target gene activity.

A suitable RNAi agent can be selected by any process known in the art or conceivable by one of ordinary skill in the art. For example, the selection criteria can include one or more of the following steps: initial analysis of the target gene sequence and design of RNAi agents; this design can take into consideration sequence similarity across species (human, cynomolgus, mouse, etc.) and dissimilarity to other (non-target gene) genes; screening of RNAi agents in vitro (e.g., at 10 nM in cells); determination of EC50 in cells; determination of viability of cells treated with RNAi agents, including insensitive cells which do not require target gene for survival, or sensitive cells, which do require target gene for survival; testing with human PBMC (peripheral blood mononuclear cells), e.g., to test levels of TNF-alpha to estimate immunogenicity, wherein immunostimulatory sequences are less desired; testing in human whole blood assay, wherein fresh human blood is treated with an RNAi agent and cytokine/chemokine levels are determined [e.g., TNF-alpha (tumor necrosis factor-alpha) and/or MCP1 (monocyte chemotactic protein 1)], wherein Immunostimulatory sequences are less desired; determination of gene knockdown in vivo using subcutaneous tumors in test animals; target gene target gene modulation analysis, e.g., using a pharmacodynamic (PD) marker, for example, other factors whose expression is affected by target gene, wherein target gene knockdown leads to a dose-dependent reduction of abundance of those components; and optimization of specific modifications of the RNAi agents.

RNAi agents comprising a 3' end cap described herein are thus useful in RNA interference of target gene.

It is known in the art that naked siRNA (lacking a suitable 3' end cap, such as those disclosed herein) has a short duration of activity in vivo; it is rapidly degraded by nucleases in serum, often with a half-life of minutes. Layzer et al. 2004 RNA 10: 766-771; Choung et al. 2006 Biochem. Biophys. Res. Comm. 342: 919-927; and Sato et al. 2007 J. Control. Rel. 122: 209-216. Many 3' end caps previously described do not both allow RNA interference and either protect the molecules from nucleases or extend time of duration.

RNAi agents comprising 3' end caps disclosed herein mediate these activities.

Non-limiting examples of RNAi agent structures suitable for use with the disclosed 3' end caps are described below.

Structure of a RNAi Agent: Antisense Strand and Sense Strand of Various Lengths, (Optional) Overhangs, (Optional) 5' End Caps, (Optional) Modifications; (Optional) Patterns of Modification.

RNAi agents mediate RNA interference and comprise a first strand and a second strand, e.g., a sense strand and an antisense strand (or an antisense and a sense strand), wherein the strands are optionally primarily RNA (optionally wherein one or more nucleotides are replaced and/or modified), (optionally) further comprising one or two overhangs, and (optionally) one or two 5' end caps, wherein the optional modifications can optionally be in various patterns of modification, and the strands can optionally be of varyious lengths. RNAi agents of the present disclosure comprise a 3' end cap on either the sense and/or anti-sense strand.

Anti-sense and Sense Strands

The term "antisense strand" (AS), as used herein, refers to the strand of a RNAi agent which includes a region that is fully or substantially complementary to a target sequence. The "antisense strand" is sometimes termed the "guide" strand. As used herein, the term "region of complementarity" refers to the region on the antisense strand that is fully or substantially complementary to a target mRNA sequence. Where the region of complementarity is not fully complementary to the target sequence, the mismatches may be in the internal or terminal regions of the molecule. Generally, the most tolerated mismatches are in the terminal regions, e.g., within 5, 4, 3, or 2 nucleotides of the 5' and/or 3' end. The portion of antisense strand most sensitive to mismatches is termed the "seed region". In a RNAi agent comprising strands of exactly 19 nt, the 19$^{th}$ position (counting from 5' to 3') can tolerate some mismatches.

The term "sense strand" (S), as used herein, refers to the strand of a RNAi agent that includes a region that is substantially complementary to a region of the antisense strand as that term is defined herein. The "sense" strand is sometimes termed the "passenger" or "anti-guide" strand. By their sequences, the antisense strand targets the desired mRNA, while the sense strands targets a different target. Thus, if the antisense strand is incorporated into RISC, the correct target is targeted. Incorporation of the sense strand can lead to off-target effects. These off-target effects can be limited by use of modifications, or use of 5' end caps on the sense strand, as described below.

The sequence of a gene may vary from individual to individual, especially at wobble positions within the coding segment, or in the untranslated region; individuals may also differ from each other in coding sequence, resulting in additional differences in mRNA. The sequence of the sense and antisense strands of the RNAi agent can thus be tailored to correspond to that of an individual patient, if and where needed. RNAi agents can also be modified in sequence to reduce immunogenicity, binding to undesired mRNAs (e.g., "off-target effects") or to increase stability in the blood. These sequence variants are independent of chemical modification of the bases or 5' or 3' or other end-caps of the RNAi agents.

Lengths of Antisense and Sense Strands

The antisense and sense strands of RNAi agents can be of various lengths, as described herein and as known in the art.

In one embodiment, each strand is a 49-mer or shorter.

Shorter lengths of siRNAs have been found to yield effective siRNAs. For example, each of the two RNA strands can be 19 to 25 nucleotides (nt), with a double-stranded region of 14-24 base pairs (bp), and at least one 3' end overhang of 1-5 nt. See, for example: U.S. Pat. Nos. 7,056,704 and 7,078,196; Japanese JP 2002/546670; and European EP 1407044. Alternatively, the strand can each be 21 nt long, forming a 19 bp region with two 2 nt overhangs. Such a structure is defined herein as the "canonical" structure.

Alternatively, the strands can each be an 19-mer and together the two strands can form a blunt-ended duplex.

Alternatively, the strands can each be an 18-mer and together the two strands can form a blunt-ended duplex.

Alternatively, the sense strand can be significantly shorter than the antisense strand. In some embodiments, the antisense strand is about 21 nt long, while the sense strand is only 15 or 16 nt long. Shortening the sense strand decreases the off-target effects mediated by the sense strand being incorporated into RISC. Sun et al. 2008 Nature Biotech. 26: 1379-1382; Chu and Rana. 2008 RNA 14: 1714-1719. The sense strand can be, in various combinations, shortened, modified and/or 5' end capped to decrease its RNAi activity.

Any length of either the antisense or sense strand can be combined with any other embodiment of a RNAi agent as described herein (e.g., any 3' end cap, modification, nucleotide replacement, 5' end cap, overhang, delivery vehicle, etc.) as long as such combinations are not mutually exclusive (e.g., the presence or absence of an overhang may be dictated by particular lengths of antisense and sense strands).

The 3' end caps described herein thus can be used with any functional RNAi agent with strand(s) of any length.

(Optional) Overhang(s)

The RNAi agents can also have overhangs of 0, 1, or 2 overhangs; in the case of a 0 nt overhang, they are blunt-ended. A RNAi agent can thus have 0, 1 or 2 blunt ends. In a "blunt-ended RNAi agent" both strands terminate in a base-pair; thus a blunt-ended molecule lacks either 3' or 5' single-stranded nucleotide overhangs.

A 3' end cap of the present disclosure can replace the functionality of an overhang, or can be used in addition to an overhang on one or both strands.

As used herein, the term "overhang" or "nucleotide overhang" refer to at least one unpaired nucleotide that protrudes from the end of at least one of the two strands of the duplex structure of a RNAi agent. The overhang(s) may be on the 5' and/or 3' end of the sense and/or the antisense strand.

While both strands of the siRNA are generally RNA (although one or more of the nucleotides can be replaced and/or modified), the overhang can be RNA or a variant thereof. Suitable overhangs include: RNA of any sequence or length (e.g., 1-5 nt), TT (a dithymidine dinucleotide) or UU or a variant thereof, such as dTdT, sdT, dTsdT, sdTsdT, or sdTdT, or the like, which may be in either the inverted/reverse orientation or in the same 5' to 3' orientation as the target gene specific sequence in the duplex.

Nucleotidic overhangs such as TT or UU do not recognize the target mRNA and are not considered part of the target sequence. Nonetheless, the overhangs can be functional, as many canonical siRNAs do not function as well without them. In addition, the overhangs provide some protection of the RNAi agent from degradation by nucleases, such as those in blood serum or intestinal fluid. See: Elbashir et al. 2001 EMBO J. 23: 6877-6888, especially FIG. 1F; Elbashir et al. 2001 Nature 411: 494-498; and Kraynack et al. 2006 RNA 12:163-176

As shown herein and as is known in the art, many attempts have been made to replace overhangs with 3' end caps to yield superior RNAi agents. These attempts, however, as detailed below, often yielded RNAi agents which were unable to both (1) mediate RNA interference and to (2) have increased resistance to nucleases and/or prolonged duration in blood serum. In contrast, the 3' end caps disclosed herein allow RNA interference and increased duration of RNA interference activity in the serum.

Because they sometimes replace a dinucleotide overhang, a 3' end cap (particularly a PAZ ligand) is in some documents referred to as a "dinucleotide surrogate". However, it is noted that a 3' end cap as disclosed herein can also be used in addition to an overhang.

This document thus encompasses 3' end caps, e.g., as shown in Tables 1 and 2 and/or otherwise described herein, for use in RNAi agents.

(Optional) 5' End Cap(s)

A "5' cap" can be optionally attached at the 5' end of the sense or antisense strand. The functions of the antisense and strands differ, as do the structural requirements of the 5' ends of these strands. A 5' end cap on the antisense strand should not interfere with RNAi activity mediated by this strand; however, in some embodiments, the 5' end cap on the sense strand can interfere with RNAi activity mediated by the sense strand. Either strand can be loaded into RISC, but only the antisense strand targets the desired target. Loading of the sense strand can lead to off-target effects, e.g., RNA interference of an undesired target. Jackson et al. 2003 Nat. Biotech. 21: 635-637

In the case of the antisense strand: the 5' end cap should not interfere with RNAi activity of this strand, but can provide at least some protection (e.g., from nucleases such as those in serum or intestinal fluid). A 5'-phosphate on the guide strand is generally required for optimal RNAi activity. A 5' dT modification provides antisense strand stability and increases potency. Blocking of phosphorylation leads to decreased activity. In contrast, 1 to 3 ribonucleotides added to the 5' end improved inhibition. Morrissey et al. 2005 Nat. Biotech. 23: 1002-1007. Some of the molecular interactions of the antisense strand 5' end with the Argonaute-2 (Ago2) component of RISC have been elucidated. Parker et al. 2005. Nature 434: 663-666; and Frank et al. 2010 Nature 465: 818-822.

In contrast, in the case of the sense strand: a 5' end cap that inhibits RNA interference can be useful on this strand. As noted above, a 5'-phosphate is generally required for optimal RNAi activity. Removal of the 5'-OH group is the simplest approach to prevent phosphorylation of the sense strand In addition to 5' end caps, other modifications or sets of modifications can be used to reduce activity of the sense strand.

The 3' end caps of the present disclosure can be used with any RNAi agent comprising a 5' end cap on the sense strand and/or any modification or set of modifications which reduces activity of the sense strand.

(Optional) Additional Nucleotide Replacements and/or Modifications

The strands of a siRNA can generally comprise RNA molecules as expressed or found in nature (i.e., are naturally occurring), but also non-naturally occurring analogs and derivatives of nucleotides comprising one or more ribonucleotide/ribonucleoside analogs or derivatives as described herein or as known in the art.

In some of the positions, the RNA nucleotides can be replaced by DNA, or a nucleotide of a different backbone, or PNA, LNA, Morpholino, TNA, GNA, ANA, HNA, CeNA, FANA, and/or UNA; and/or modified (including, but not limited to, 2'-MOE, 2'-OMe, 2'-F, and 2'-H). In various embodiments, the RNAi agent can comprise one or more LNA which are at 5' end and/or at 3' end (e.g., positions 18 and 19 in a 19-mer or positions 17 and 18 in an 18-mer), and/or in the middle of a strand.

In some embodiments, the nucleotide replacements are in the last two base-pairing nt (counting from 5' to 3'), forming a clamp. A clamp includes without limitation a 2'-MOE clamp [wherein the last two base-pairing nt (counting from 5' to 3') each have a 2'-MOE modification]. Other variants of the clamp are possible, wherein, for example, wherein the last two base-pairing nt (counting from 5' to 3') each are DNA, 2'-OMe, 2'-F or LNA, as shown in FIG. 20 C-E. It is noted that the last two nt (counting from 5' to 3') can also be considered to be the first two base-pairing nucleotides at the 3' end of each strand (counting from 3' to 5'). As shown herein and in U.S. Pat. No. 8,084,600, the clamp can be on the antisense and/or sense strands.

Figure 17A:
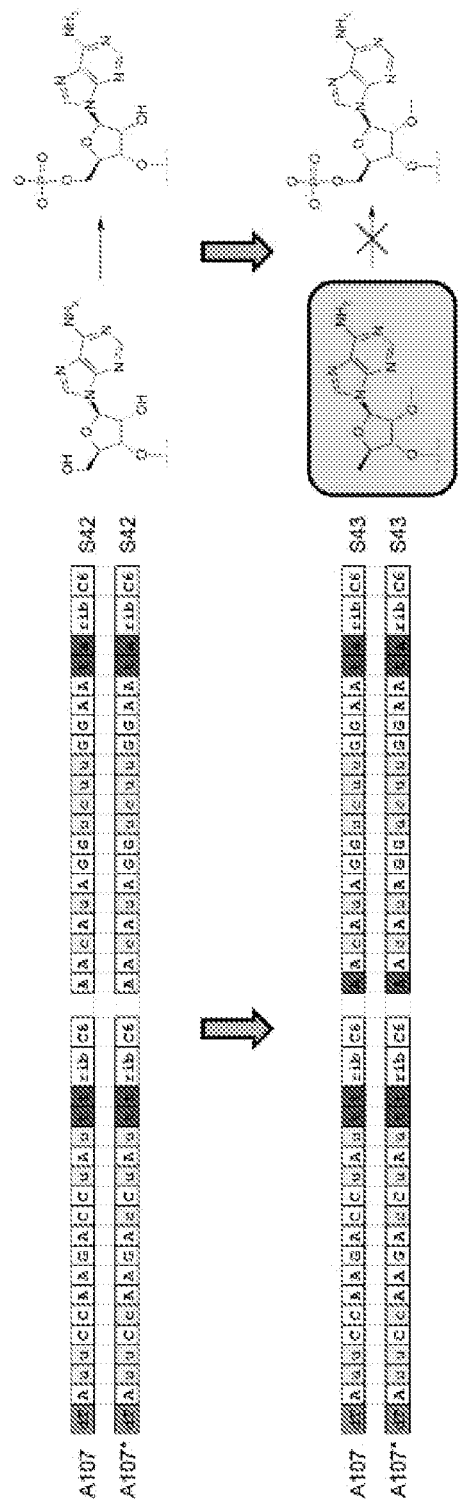
FIGS. 17A to 17I show data related to 5' end capping of RNAi agents.
Figure 17B:
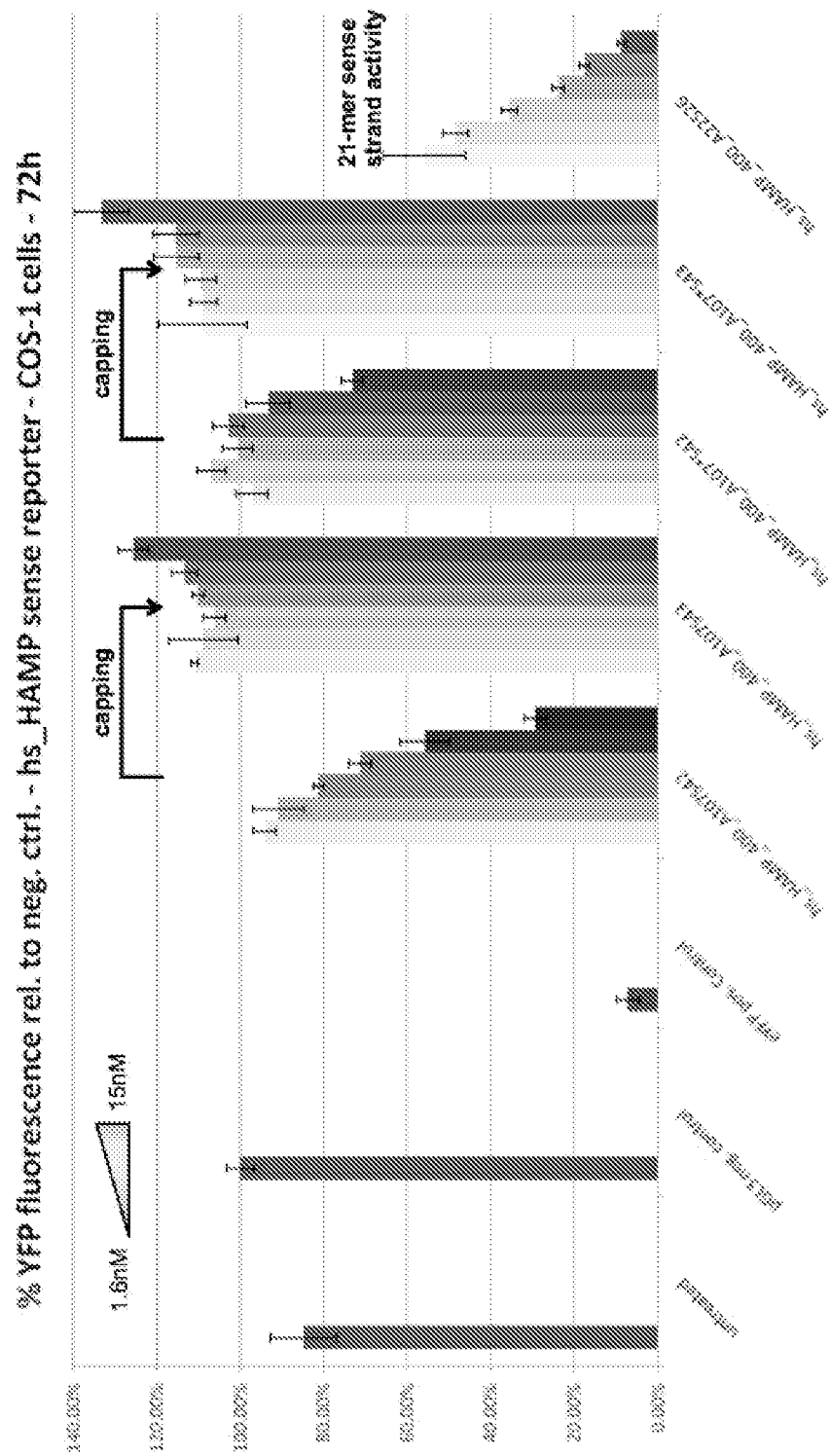

Thus, while the nucleotides in each strand are generally RNA (meaning that most of the nucleotides are RNA), some may be replaced by DNA or nucleotides of an alternative backbone such as peptide nucleic acids (PNA), locked nucleic acid (LNA), Morpholino, threose nucleic acid (TNA), and/or glycol nucleic acid (GNA). In some embodiments, only 1 or 2 or 3 nt in one or both strands are replaced. In some embodiments, only about 1-3 nt in one or both strands are replaced by DNA. Non-limiting examples of this are shown in FIGS. 15B and 17A.

The RNA nucleotides in either strand can thus be replaced and/or modified.

The RNA can be modified in the nucleobase structure or in the ribose-phosphate backbone structure. However, in most embodiments, the molecules comprising ribonucleoside analogs or derivatives retains the ability to form a duplex. As non-limiting examples, an RNA molecule can also include at least one modified ribonucleoside, including but not limited to a 2'-O-methyl modified nucleotide, a nucleoside comprising a 5' phosphorothioate group, a terminal nucleoside linked to a cholesteryl derivative or dodecanoic acid bisdecylamide group, a locked nucleoside, an abasic nucleoside, a 2'-deoxy-2'-fluoro modified nucleoside, a 2'-amino-modified nucleoside, 2'-alkyl-modified nucleoside, morpholino nucleoside, an unlocked ribonucleotide (e.g., an acyclic nucleotide monomer, as described in WO 2008/147824), a phosphoramidate or a non-natural base comprising nucleoside, or any combination thereof. Alternatively, an RNA molecule can comprise at least two modified ribonucleosides, at least 3, at least 4, at least 5, at least 6, at least 7, at least 8, at least 9, at least 10, at least 15, at least 20 or more, up to the entire length of the dsRNA molecule. The modifications need not be the same for each of such a plurality of modified ribonucleosides in an RNA molecule. In one embodiment, modified RNAs contemplated for use in methods and compositions described herein comprise a 3' end cap as disclosed herein and have the ability to form the required duplex structure and that permit or mediate the specific degradation of a target RNA via a RISC pathway.

Examples of modified nucleotides which can be used to generate the RNAi agent include 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine.

A "modified variant" of a sequence disclosed herein includes any variant comprising the same sequence, but with a modification in the base, sugar, phosphate or backbone (but not a base substitution, e.g., A for G, or C for U). Thus, a modified variant can comprise any modified nucleotide described above (e.g., 5-fluorouracil, 5-bromouracil, 5-chlorouracil, 5-iodouracil, hypoxanthine, xantine, 4-acetylcytosine, 5-(carboxyhydroxylmethyl) uracil, etc.). When a base is replaced by a corresponding modified base (e.g., A for modified A), these modified nucleotides do not constitute a mismatch or base difference. Thus a given sequence with a U at a particular position and a modified variant comprising a 5-fluorouracil, 5-bromouracil, 5-chlorouracil, or 5-iodouracil at the same sequence would differ by 0 nt (or have no mismatches); however, a given sequence with a C at a particular position and a different sequence with a 5-fluorouracil (wherein the two sequences are otherwise identical) would differ by 1 nt (1 mismatch).

In some embodiments, the RNAi agent according to the present invention confers a high in vivo stability by including a 3' end cap and at least one modified nucleotide in at least one of the strands. Thus the RNAi agent according to the present invention preferably contains at least one modified or non-natural ribonucleotide. A lengthy description of many known chemical modifications are set out in published PCT patent application WO 200370918 and will not be repeated here. Suitable modifications for oral delivery are more specifically set out in the Examples and description herein. Suitable modifications include, but are not limited to, modifications to the sugar moiety (i.e. the 2' position of the sugar moiety, such as for instance 2'-O-(2-methoxyethyl) or 2'-MOE) (Martin et al., Helv. Chim. Acta, 1995, 78, 486-504) i.e., an alkoxyalkoxy group) or the base moiety (i.e. a non-natural or modified base which maintains ability to pair with another specific base in an alternate nucleotide chain).

Other modifications include so-called 'backbone' modifications including, but not limited to, replacing the phosphoester group (connecting adjacent ribonucleotides with for instance phosphorothioates, chiral phosphorothioates or phosphorodithioates). In various embodiments, one or more phosphate group is replaced with:

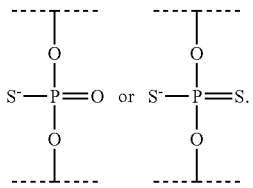

In various additional embodiments, one or more phosphate group is replaced by:

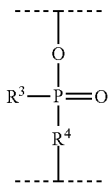

where $R^3$ is selected from $O^-$, $S^-$, $NH_2$, $BH_3$, $CH_3$, $C_{1-6}$ alkyl, $C_{6-10}$ aryl, $C_{1-6}$ alkoxy and $C_{6-10}$ aryl-oxy, wherein $C_{1-6}$ alkyl and $C_{6-10}$ aryl are unsubstituted or optionally independently substituted with 1 to 3 groups independently selected from halo, hydroxyl and $NH_2$; and $R^4$ is selected from O, S, NH, or $CH_2$. Some of these replacement phosphate groups are also shown in FIG. 18C.

In various embodiments, the phosphate of the phosphate group is replaced by arsenic (As), selenium (Se), or antimony (Sb). In one embodiment, the spacer is ribitol and no phosphate groups are replaced. In various embodiments, the phosphate group is replaced by a sulfonamide group or a cyano group or carboxamide. In various embodiments, the phosphate group of the 3' end cap is replaced by an arsenic, selenium, antimony or sulfonamide group or a cyano group or carboxamide. In various embodiments, the phosphate group of the linker (e.g., C3, C4, or C6 or ribitol, Diribitol, 2'-deoxyribitol, or 2'-methoxyethoxyribitol) is replaced by an arsenic, selenium, antimony or sulfonamide group or a cyano group or carboxamide.

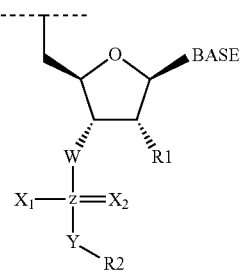

$W=O, S, NH, CH_2, \ldots$
$X_1, X_2=O^-, S^-, NH_2, BH_3^-, CH_3$, alkyl, aryl, O-alkyl, O-aryl, $\ldots$
$Y=O, S, NH, CH_2, \ldots$
$Z=C, Si, P, S, As, Se, Sb, Te, \ldots$
$R1=H, OH, F, NH_2$, O-alkyl, O-aryl, O-alkyl-aryl, O-aryl-alkyl, NH-alkyl, N-dialkyl, $\ldots$
$R2$=alkyl, aryl, alkyl-aryl, aryl-alkyl, $\ldots$ (PAZ ligand)
BASE=H, adenine, cytosine, guanine, uracil, thymine, $\ldots$ Thus, the nucleotides of either or both strands of a RNAi agent useful with 3' end caps disclosed herein can be replaced and/or modified.

(Optional) Patterns of Modifications

In some cases of modifying the nucleotides of a RNAi agent, the modifications are not random, but are arrayed in patterns. These patterns (or schemes) increase the efficacy (RNAi activity), decrease activity of the sense strand or otherwise decrease off-target effects, reduce degradation or immunogenicity, and/or increase the biological half-life (e.g., time of duration of activity) of the RNAi agent.

In one pattern of modification, multiple positions of the sense strand are 2'-MOE. As a non-limiting example, most or all of the pyrimidines are 2'MOE in the sense strand. Modifying more than half of the positions in a sense strand with 2'-MOE can decrease activity. When all the positions of the sense strand are 2'-MOE often abolishes activity.

Various patterns of modifications are shown in FIGS. 7, 11, 14, 15A, 15B, and 17A.

Figure 15A:
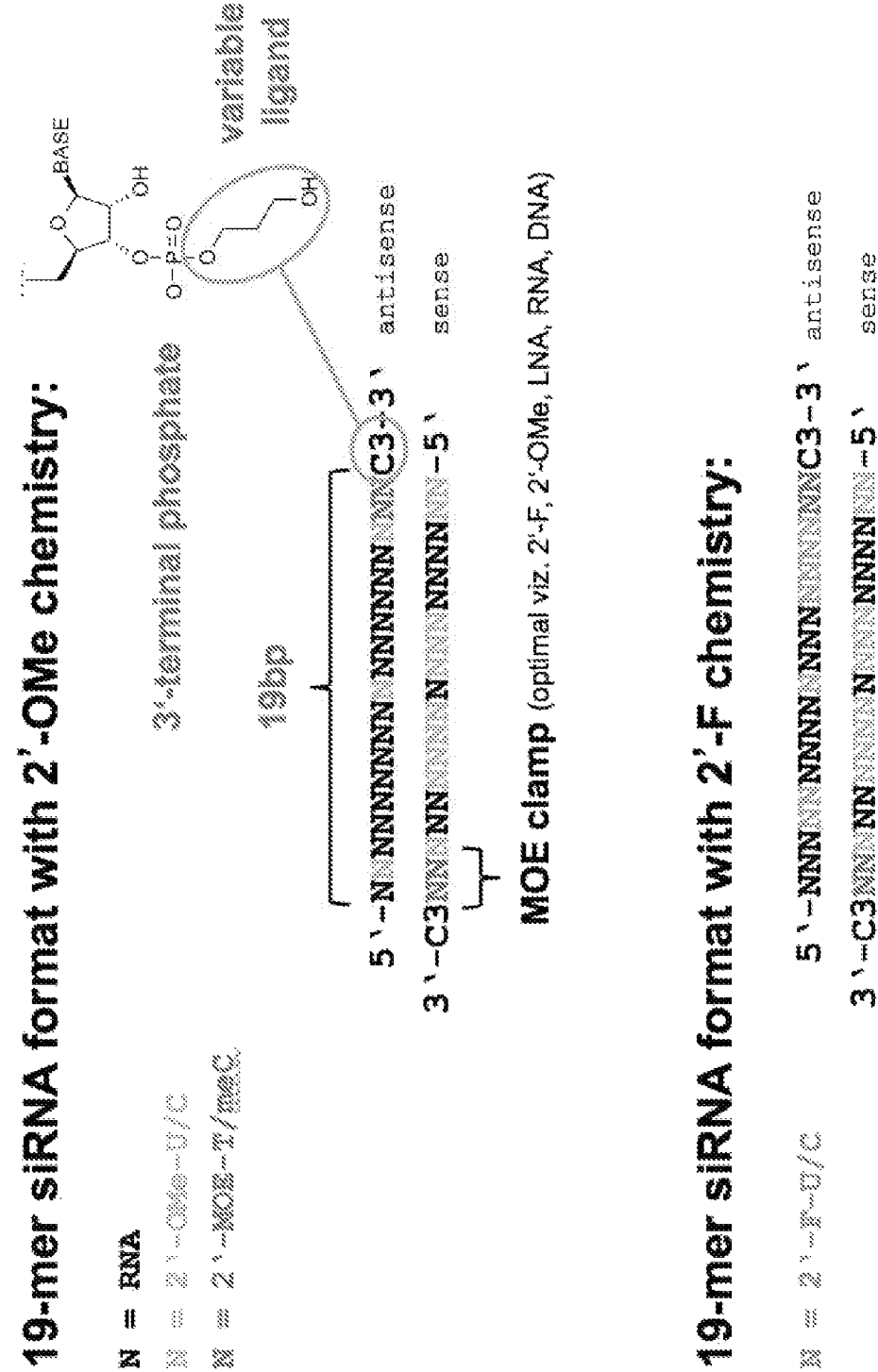

FIG. 15A (top) shows a non-limiting example of the arrangement of a pattern of 2'-OMe and 2'-MOE modifications in a 19-mer blunt-ended RNAi agent. In the example, the 3' end cap shown is C3, but other 3' end caps can be used with this modification pattern (e.g., those disclosed herein). This modification pattern also includes a MOE clamp (wherein the last two base-pairing nucleotides counting from 5' to 3' have 2'-MOE modifications). The last two nt counting from 5' to 3' can also be considered to be the first two base-pairing nucleotides at the 3' end of each strand (counting from 3' to 5').

FIG. 15A (bottom) shows a non-limiting example of a modification pattern using 2'F modifications. Again, in this example, the 3' end cap shown is C3, but other 3' end caps can be used with this modification scheme (e.g., those disclosed herein).

FIG. 15B (top) shows a "wt" ("wild-type") siRNA and a corresponding non-limiting example modification scheme of this siRNA. The example modified siRNA has 2'-OMe and phosphorothioate (s).

FIG. 15B (bottom) shows non-limiting examples of modification schemes for the canonical 21-mer siRNA, and for the 18- or 19-mer formats. In these schemes, "L" indicates the 3' end cap (e.g., a PAZ Ligand).

In various other modification patterns, the RNAi agent comprises at least one 5'-uridine-adenine-3' (5'-ua-3') dinucleotide, wherein the uridine is a 2'-modified nucleotide; at least one 5'-uridine-guanine-3' (5'-ug-3') dinucleotide, wherein the 5'-uridine is a 2'-modified nucleotide; at least one 5'-cytidine-adenine-3' (5'-ca-3') dinucleotide, wherein the 5'-cytidine is a 2'-modified nucleotide; and/or at least one 5'-uridine-uridine-3' (5'-uu-3') dinucleotide, wherein the 5'-uridine is a 2'-modified nucleotide.

Other patterns of modifications can be used with any RNAi agent comprising a 3' end cap as disclosed herein.

Particularly preferred modification patterns include but are not limited to:

All 3' overhangs as 2'-OMe-U 2'-OMe-U
A85: All U as 2'-OMe-U, except pos. 1, 2 and 14
S26: All U as 2'-OMe-U and all C as 2'-OMe-C
A51: All U as 2'-OMe-U and all C as 2'-OMe-C, except pos. 1, 2 and 14
S26: All U as 2'-OMe-U and all C as 2'-OMe-C
A48: UA as 2'-OMe-U A and all CA as 2'-OMe-C A, first 5'-N is DNA
S26: All U as 2'-OMe-U and all C as 2'-OMe-C The 3' end caps disclosed herein can thus be used with any RNAi agent, wherein at least one nucleotide of at least one strand of the RNAi agent has been replaced and/or modified, and wherein the modification(s) of the nucleotide(s) can be arrayed in a pattern(s) of modification.

In various patterns of modification, the pattern comprises a 2'-MOE clamp [wherein the last two base-pairing nt (counting from 5' to 3') each have a 2'-MOE modification]. Other variants of the clamp are possible, wherein, for example, wherein the last two base-pairing nt (counting from 5' to 3') each are DNA, 2'-OMe, 2'-F or LNA, as shown in FIG. 20 C-E. It is noted that the last two nt (counting from 5' to 3') can also be considered to be the first two base-pairing nucleotides at the 3' end of each strand (counting from 3' to 5'). As shown herein and in U.S. Pat. No. 8,084,600, the clamp can be on the antisense and/or sense strands.

Any embodiments of any RNAi agent described herein can be combined with any other embodiment, provided that the embodiments are not mutually exclusive (e.g., a single RNAi agent cannot simultaneously have both exactly 0 and exactly 2 overhangs).

Thus, the 3' end caps disclosed herein can be used with any RNAi agent as described herein or as known in the art, wherein the strands of the RNAi agent are of any length, the RNAi agent can comprise 0, 1, or 2 overhangs or 0, 1 or 2 blunt ends, one or more nucleotides of one or both stands can be replaced or modified, and the modification(s) can be arrayed in a pattern(s) or scheme(s) of modification, and the antisense and/or sense strand can comprise a 5' end cap, wherein the 5' end cap of the sense strand (if present) reduces RNA interference activity mediated by the sense strand.

The 3' end caps disclosed herein can also be used with any additional RNAi agent format or structure disclosed herein or known in the art.

Additional RNAi Agents

In additional to the structures listed above, additional types of molecules have been devised which are also capable of mediating RNA interference. In these structures, the strands are not necessarily RNA, and the strands can be can be longer or shorter than the canonical, and/or blunt-ended, and/or comprise one or more modification, mismatch, gap, and/or nucleotide replacement.

The term "RNAi agent" is intended to encompass any molecule described herein or known in the art capable of mediating RNA interference, including, without limitation, siRNA (whether of canonical or other structure), or any other molecule capable of mediating RNA interference. The 3' end caps described herein can be used with any RNAi agent.

Thus, the 3' end caps disclosed herein can be used on any RNAi agent (including siRNA) or on any other RNAi agent, including, inter alia, and without limitation:

shRNA (small hairpin RNA or short hairpin RNA), which comprises a sequence of RNA that makes a tight hairpin turn and, like siRNAs, silences targets via RISC. The antisense and sense strand are thus connected by a hairpin. shRNAs can be expressed, for example, via delivery of plasmids or through viral or bacterial vectors. Various varieties of shRNAs are known in the art. See, for example: Xiang et al. 2006. Nature Biotech. 24: 697-702; Macrae et al. 2006 Science 311: 195-8. Lombardo et al. 2007. Nature Biotech. 25: 1298-1306; Wang et al. 2011. Pharm. Res. 28: 2983-2995; Senzer et al. 2011. Mol. Ther. 20: 679-686.

miRNA (microRNA), which is a small RNA molecule (ca. 22 nt) that, like siRNAs, also silences targets via RISC. Naturally-occurring miRNAs are encoded by eukaryotic nuclear DNA; miRNAs are generated by post-transcriptional RNA processing, and function via base-pairing with complementary sequences within mRNA molecules, usually resulting in translational repression or target degradation and gene silencing. The human genome can encode over 1000 miRNAs, which may target about 60% of mammalian genes and are abundant in many human cell types. Various varieties of naturally-occurring and artificial derivatives of miRNAs are known in the art. See, for example: Lewis et al. 2003. Cell 115: 787-798; Lim et al. 2003. Genes Dev. 17: 991-1008; He et al. 2004. Nat. Rev. Genet. 5: 522-31; Bentwich et al. 2005. Nat. Genet. 37: 766-70; Lewis et al. 2005. Cell 120: 15-20; Kusenda et al. 2006. Biomed Pap Med Fac Univ Palacky Olomouc Czech Repub 150: 205-15; Zhang et al. 2006. J. Gen. Gen. 36: 1-6; Brodersen et al. 2008. Science 320: 1185-90; Friedman et al. 2009. Genome Res. 19 (1): 92-105; Bartel 2009. Cell 136 (2): 215-33.

sisiRNA (small internally segmented interfering RNA), wherein the sense strand comprises at least one single-stranded nick. This nick decreases the incorporation of the sense strand into the RISC complex and thus reduces off-target effects. See: WO 2007/107162.

DNA-RNA chimera, wherein the seed portion of each strand is DNA, while the remainder of each strand is RNA. See: Yamato et al. 2011. Cancer Gene Ther. 18: 587-597.

siRNA comprising two mismatches, wherein that the molecule comprises three short double-stranded regions. In one embodiment of this RNAi agent, the guide (antisense) strand is a 22-mer, while the sense strand is a 20-mer (producing only a single 2-nt overhang on the 3' end of the anti-sense strand; and two mismatches produce double-stranded regions of 6, 8 and 4 bp. See: U.S. Pat. App. 2009/0209626 aiRNA (assymetrical interfering RNA), wherein the sense strand is shorter than 19-nt long, so that the anti-sense strand is preferentially loaded into RISC, and thus off-target effects are reduced. In various embodiments of this RNAi agent, the anti-sense strand is 21-nt long, but the sense strand is only 15 or 16 nt long. See: Sun et al. 2008 Nature Biotech. 26: 1379-1382; and Chu and Rana. 2008 RNA 14: 1714-1719.

Thus, any 3' end cap disclosed herein can be used with any of the various formats of RNAi agents described above or otherwise known in the art, including siRNAs (including but not limited to those of the canonical structure), shRNAs, miRNAs, sisiRNAs, DNA-RNA chimeras, siRNAs comprising two mismatches (or more mismatches), or aiRNAs.

3' End Caps

The RNAi agent of the present disclosure comprises a 3' end cap. The terms "3' end cap", "3' end cap modification", "end cap", "Cap", "3' end modification" and the like include a chemical moiety attached to the end of a double-stranded nucleotide duplex, but is used herein to exclude a chemical moiety that is a nucleotide or nucleoside. A "3' end cap" is attached at the 3' end of a nucleotide or oligonucleotide (e.g., is a modification at the 3' carbon of the 3' nucleotide at the 3' terminus of at least one strand) and protects the molecule from degradation, e.g., from nucleases, such as those in blood serum or intestinal fluid. "3' end caps" include but are not limited to "PAZ ligands," which term includes 3' end caps which interact with the PAZ domain of the enzyme Dicer. 3' end caps are sometimes referred to as "non-nucleotide overhang mimics" or "LMW mimics of dinucleotide overhangs" or the like.

This disclosure notes that some documents refer to a 3' end cap as described herein (e.g., X109 or X110 or X111, etc.) as an "overhang" or a "3' overhang"; however, this document differentiates a 3' end cap from an "overhang" and uses the term "overhang" only to refer to a nucleotidic overhang (e.g., one comprising only nucleotides such as A, C, G, U or T, such as UU or TT). Thus, as defined herein, a "3' end cap" is not an overhang.

As defined herein, a 3' end cap can be used in place of or in addition to an overhang (i.e., a nucleotidic overhang). Earlier work with canonical siRNA structures suggested that the 2-nt overhang was useful for RNA interference activity, while blunt-ended dsRNAs (lacking the overhangs) were generally not effective. See, for example, Elbashir et al. 2001 EMBO J. 23: 6877-6888, especially FIG. 1F. However, dsRNA, even with the overhangs, were subject to enzymatic degradation. As noted elsewhere by the Applicants, "unmodified siRNAs are subject to enzymatic digestion, mainly by nucleases." (WO 2007/128477, page 1). 3' end caps were thus designed to perform several functions, including (1) allowing the molecule to mediate RNA interference activity, and (2) protecting the molecule from degradation.

It is noted, though, that the 3' end caps disclosed herein can be used in addition to as well as in place of 3' overhangs.

Because a 3' end cap can be used instead of an overhang such as UU or TT, the 3' end caps described herein are sometimes referred to as "3'-Dinucleotide surrogates".

A few 3' end caps have been disclosed for use with siRNAs. It is noted that of the 3' end caps which have been described chemically, many of these have been shown not to be functional. A functional 3' end cap can be able to perform these functions: (1) allow the double-stranded RNA to function in RNA interference; and (2) increase the stability of the molecule, e.g., by protecting it from nucleases, such as those found in blood serum or intestinal fluid.

Non-functional 3' End Caps

Many 3' end caps described in the literature are unable to perform both of these functions. In some cases, the placement of the end caps is important; some end caps may be functional when placed on only one strand, but not functional if placed on both strands and/or on both 5' and 3' ends of both strands.

It is impossible to predict which 3' end caps will perform both functions without experimentation. In fact, while many endcaps were predicted to be suitable for RNA interference (e.g., in US 2003/0143732), many later were discovered not to perform both functions.

Other scientists have empirically found that, despite predictions, some endcaps or overhangs (1) stabilized the siRNA but (2) did NOT allow RNAi activity. For example, the TT (dithymidine) in combination with 2'-OMe modifications at all positions, Czauderna et al. 2003 Nucl. Acids Res. 31:2705-2716, FIG. 4B. Hadwiger et al. also note that complete 2'-O-methylation rendered the siRNA serum nuclease-resistant, although gene silencing activity was almost completely abolished. Hadwiger et al. 2005, pages 194-206, in RNA Interference Technology, ed. K. Appasani, Cambridge University Press, Cambridge, UK.

Other endcaps or overhangs (1) did NOT stabilize the siRNA, though (2) they did allow RNAi activity. For example, the TT at both 3' ends or both 5' ends of a siRNA. Czauderna et al. 2003, FIG. 4B.

Still other endcaps (1) did NOT stabilize the siRNA AND (2) did NOT allow RNAi activity such examples include: the amino-C6 linker or inverted abasic nucleotide. Czauderna et al. 2003, FIG. 4B.

Additional examples of 3' end caps which are non-functional under at least some conditions include:

Inverted (deoxy) a basics, which were neither stabilize siRNA nor allow siRNA activity when present on both 5' and both 3' ends. See: Czauderna et al. 2003 Nucl. Acids Res. 31:2705-2716, FIG. 4B.

Modified base nucleotides such as 5-propynyl-U, which do not both stabilize the siRNA and allow RNAi activity. Deleavey et al. 2009 Curr. Prot. Nucl. Acid Chem. 16.3.1-16.3.22; Terrazas et al. 2009 Nucleic Acids Res. 37: 346-353.

At least some amino-substituted lower alkyls, including aminohexyl phosphate, which was not able to stabilize the siRNA. When present on both 5' ends and both 3' ends, it prevented RNAi activity. See: Czauderna et al. 2003, FIG. 4B.

Fluorescein (e.g., a fluorescent chromophore), which was found to inhibit RNA interference activity when conjugated to the 3' end of the antisense strand. The sense strand can tolerate, for example, a conjugation of fluorescein at the 3'-end, but the antisense strand cannot. Harboth et al. 2003 Antisense Nucl. Acid Drug Dev. 13: 83-105. See: Harboth et al. 2003 Antisense Nucl. Acid Drug Dev 13: 83-105.

Cyanine (e.g., Cy5), which is non-functional. See: Song et al. 2003 Nature Med. 9: 347-351. See page 347, second col.

3' phosphate as a 3' end cap, suggested by U.S. Pat. No. 5,998,203 (paragraph [017]), but later shown not to both stabilize the 3' end of a siRNA and allow RNAi activity, Schwarz et al. 2002 Mol. Cell 10: 537-548; and Lipardi et al. 2001 Cell 107: 299-307.

3'-aminopropylphosphoester, which reduced RNA interference activity. See: Schwarz et al. 2002 Mol. Cell 10: 537-548, FIG. 2.

Thus, not all moieties tested as 3' end caps are capable of both allowing RNA interference and protecting the molecule from degradation.

Functional 3' End Caps

In contrast to the non-functional 3' end caps and overhangs described above, functional 3' end caps are described in, for example, U.S. Pat. Nos. 8,097,716; 8,084,600; 8,344,128; 8,404,831; and 8,404,832. These disclose functional 3' end caps comprising a phosphate and nicknamed as C3, C6, C12, Triethylene glycol, Cyclohexyl (or Cyclohex), Phenyl, Biphenyl, Adamantane and Lithocholic acid (or Lithochol).

These functional 3' end caps are diagrammed below, wherein they are shown bonded to a phosphate:

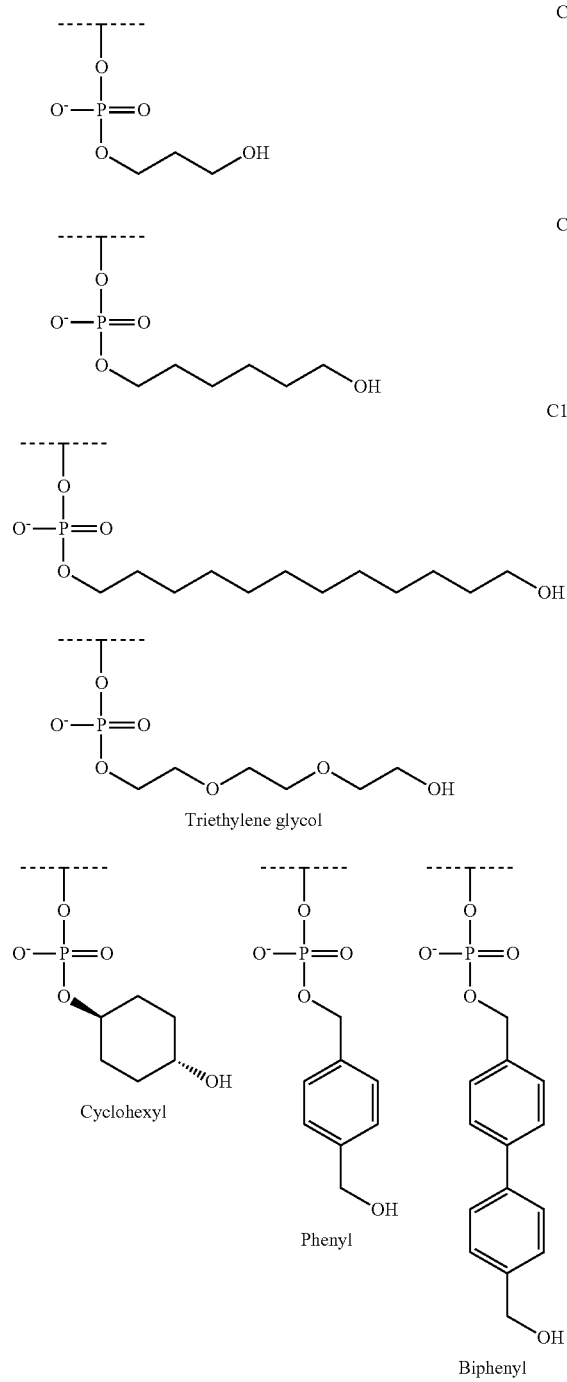

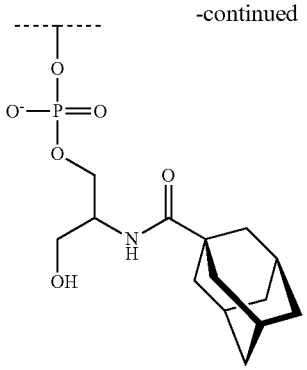

Adamantane

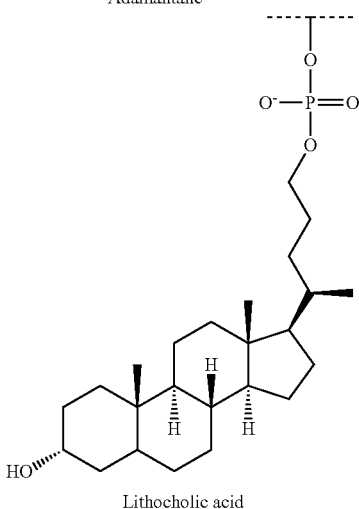

Lithocholic acid

It is noted that the terminology used in the present disclosure differs slightly from that used in U.S. Pat. Nos. 8,097,716; 8,084,600; 8,344,128; 8,404,831; and 8,404,832. In various embodiments, the present disclosure pertains to RNAi agents comprising a first strand and a second strand, wherein, in some embodiments, the 3' end of the first and/or second strand terminates in a phosphate (or modified internucleoside linker) and further comprises a 3' end cap. In the diagrams directly above, the phosphate and the 3' end cap are shown.

The 3' end caps disclosed in U.S. Pat. Nos. 8,097,716; 8,084,600; 8,344,128; 8,404,831; and 8,404,832 were superior to those which were devised before them. For example, unlike other possible endcaps, these were able to both protect the siRNAs from degradation (e.g., from nucleases, such as in blood or intestinal fluid), and also allow RNA interference.

However, many of the novel 3' end caps of the present disclosure (e.g., those listed in Tables 1 and 2) are even further improved. For example, siRNAs with X058 (as disclosed herein) show a higher duration of activity than a siRNA with C6 (FIG. 22). HuR siRNAs with X058 showed greater efficacy at Day 7 and at Day 10 in Huh-7 cells.

Various novel 3' end caps disclosed herein include those designated as PAZ ligands, as they interact with the PAZ domain of Dicer.

PAZ Ligands

As noted above, when a long dsRNA molecule is introduced into a cell, Dicer chops the dsRNA is shorter segments called siRNAs. A homologue of Dicer is common to all organisms in which dsRNA-mediated gene silencing has been observed. Myers et al. 2005. In RNA Interference Technology, ed. Appasani, Cambridge University Press, Cambridge UK, p. 29-54; Bernstein et al. 2001 Nature 409: 363-366; and Schauer et al. 2002 Trends Plant Sci. 7: 487-491. Dicer is an RNase III enzyme and is composed of six recognizable domains. At or near the N-terminus is an approx. 550 aa DExH-box RNA helicase domain, which is immediately followed by a conserved approx. 100 aa domain called DUF283. Just C-terminal to DUF283 domain is the PAZ (for Piwi/Argonaute/Zwille) domain. The domain recognizes single stranded dinucleotide overhangs. Lingel et al. 2003 Nature 426: 465-469; Song et al. 2003 Nature Struct. Biol. 10: 1026-1032; Yan et al. 2003 Nature 426: 468-474; Lingel et al. 2004 Nature Struct. Mol. Biol. 11: 576-577; Ma et al. 2004 Nature 429: 318-322. Presumably, the PAZ domain in Dicer could also bind RNA to position the catalytic domains for cleavage. Zhang et al. 2004 Cell 118: 57-68. The C-terminus of the Dicer protein is composed of two RNAse III catalytic domains and a putative dsRNA-binding domain.

Table 2 lists various 3' end caps, including many PAZ ligands.

Arrangement and Non-identical Nature of 3' End Caps

The anti-sense and sense strands are biochemically distinct. As noted above, the antisense strand is preferably loaded into RISC, as this strand targets the desired target. Incorporation of the sense strand can lead to off-target effects.

It is known that some 3' end caps can be more useful on one strand than on the other. For example, as noted above, The sense strand can tolerate, for example, a conjugation of fluorescein at the 3'-end, but the antisense strand cannot. Harboth et al. 2003 Antisense Nucl. Acid Drug Dev. 13: 83-105.

An RNAi Agent Comprising a 3' End Cap Described Herein

In one particular specific embodiment, the present disclosure relates to a composition comprising a RNAi agent comprising a first strand and a second strand, wherein the first or second strand comprise a 3' end cap selected from the 3' end caps listed in Table 2. In one embodiment, the composition comprises a RNAi agent comprising a first and an second strand, wherein the first and second strand comprise a 3' end cap selected from the 3' end caps listed in Table 2. Thus, in short: In one embodiment, the composition comprises a RNAi agent comprising a first and an second strand, wherein the first and/or second strand comprise a 3' end cap selected from the 3' end caps listed in Table 2. In some embodiments, the first and second strand are the anti-sense and sense strands, respectively. In some embodiments, the first and second strands are the sense and anti-sense strands, respectively.

A RNAi agent is a double-stranded molecule capable of mediating RNA interference, including but not limited to siRNAs.

Various specific embodiments of this embodiment are described below.

In one embodiment, the composition further comprises a second RNAi agent. In various embodiments, the second RNAi agent is physically separate from the first; or the two RNAi agents are physically connected (e.g., covalently linked or otherwise conjugated) or combined in the same pharmaceutical composition, or are both elements in the same treatment regimen.

In one embodiment, the antisense strand is about 30 or fewer nt in length.

In one embodiment, the sense strand and the antisense strand form a duplex region of about 15 to about 30 nucleotide pairs in length.

In one embodiment, the antisense strand is about 15 to about 36 nt in length, including about 18 to about 30 nt in length, and further including about 19 to about 21 nt in length and about 19 to about 23 nt in length. In one embodiment, the antisense strand has at least the length selected from about 15 nt, about 16 nt, about 17 nt, about 18 nt, about 19 nt, about 20 nt, about 21 nt, about 22 nt, about 23 nt, about 24 nt, about 25 nt, about 26 nt, about 27 nt, about 28 nt, about 29 nt and about 30 nt.

In one embodiment, the 3' end cap causes the RNAi agent to have increased stability in a biological sample or environment, e.g., cytoplasm, interstitial fluids, blood serum, lung or intestinal lavage fluid.

In one embodiment, the RNAi agent further comprises at least one sugar backbone modification (e.g., phosphorothioate linker) and/or at least one 2'-modified nucleotide. In one embodiment, all the pyrimidines are 2' O-methyl-modified nucleotides.

In one embodiment, the RNAi agent comprises: at least one 5'-uridine-adenine-3' (5'-ua-3') dinucleotide, wherein the uridine is a 2'-modified nucleotide; and/or at least one 5'-uridine-guanine-3' (5'-ug-3') dinucleotide, wherein the 5'-uridine is a 2'-modified nucleotide; and/or at least one 5'-cytidine-adenine-3' (5'-ca-3') dinucleotide, wherein the 5'-cytidine is a 2'-modified nucleotide; and/or at least one 5'-uridine-uridine-3' (5'-uu-3') dinucleotide, wherein the 5'-uridine is a 2'-modified nucleotide.

In one embodiment, the RNAi agent comprises a 2'-modification selected from the group consisting of: 2'-deoxy, 2'-deoxy-2'-fluoro, 2'-O-methyl, 2'-O-methoxyethyl (2'-O-MOE), 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), and 2'-O—N-methylacetamido (2'-O-NMA). In one embodiment, all the pyrimidines are 2' O-methyl-modified nucleotides.

In one embodiment, the RNAi agent comprises a blunt end.

In one embodiment, the RNAi agent comprises an overhang having 1 to 4 unpaired nucleotides.

In one embodiment, the RNAi agent comprises an overhang at the 3'-end of the antisense strand of the RNAi agent.

In one embodiment, the RNAi agent is ligated to one or more diagnostic compound, reporter group, cross-linking agent, nuclease-resistance conferring moiety, natural or unusual nucleobase, lipophilic molecule, cholesterol, lipid, lectin, steroid, uvaol, hecigenin, diosgenin, terpene, triterpene, sarsasapogenin, Friedelin, epifriedelanol-derivatized lithocholic acid, vitamin, carbohydrate, dextran, pullulan, chitin, chitosan, synthetic carbohydrate, oligo lactate 15-mer, natural polymer, low- or medium-molecular weight polymer, inulin, cyclodextrin, hyaluronic acid, protein, protein-binding agent, integrin-targeting molecule, polycationic, peptide, polyamine, peptide mimic, and/or transferrin.

In one embodiment, the RNAi agent is capable of inhibiting expression of target gene by at least about 60% at a concentration of 10 nM in cells in vitro.

In one embodiment, the RNAi agent is capable of inhibiting expression of target gene by at least about 70% at a concentration of 10 nM in cells in vitro.

In one embodiment, the RNAi agent is capable of inhibiting expression of target gene by at least about 80% at a concentration of 10 nM in cells in vitro.

In one embodiment, the RNAi agent is capable of inhibiting expression of target gene by at least about 90% at a concentration of 10 nM in cells in vitro.

In one embodiment, the RNAi agent has an EC50 of no more than about 0.1 nM in cells in vitro.

In one embodiment, the RNAi agent has an EC50 of no more than about 0.01 nM in cells in vitro.

In one embodiment, the RNAi agent has an EC50 of no more than about 0.001 nM in cells in vitro.

Pharmaceutical Compositions of a RNAi Agent to Target Gene

In one particular specific embodiment, the present disclosure relates to a composition comprising a RNAi agent comprising a first and an second strand, wherein the first and/or second strand comprise a 3' end cap selected from the 3' end caps listed in Table 2, wherein the composition is in a pharmaceutically effective formulation.

In one embodiment, the present disclosure pertains to the use of a RNAi agent in the manufacture of a medicament for treatment of a target gene-related disease, wherein the RNAi agent comprises a sense strand and an antisense strand, wherein the antisense strand comprises at least 15 contiguous nucleotides differing by 0, 1, 2, or 3 nucleotides from the antisense strand of a RNAi agent to target gene selected from those specific duplex provided herein and as listed, e.g., in Table 2.

In one embodiment, the pharmaceutical composition comprises a delivery vehicle and a RNAi agent comprising a 3' end cap.

Other modifications known to one skilled in the art are contemplated as being encompassed within the invention. Exemplary modifications include, but are not limited to, the presence of gaps or mismatches between the base pairs in the sense and antisense strands, the presence of nicks or breaks in the internucleoside linkages in the sense strand, and the like.

Pharmaceutical Compositions

Compositions intended for oral use can be prepared according to any method known to the art for the manufacture of pharmaceutical compositions and such compositions can contain one or more such sweetening agents, flavoring agents, coloring agents or preservative agents in order to provide pharmaceutically elegant and palatable preparations. Tablets contain the active ingredient in admixture with non-toxic pharmaceutically acceptable excipients that are suitable for the manufacture of tablets. These excipients can be, for example, inert diluents; such as calcium carbonate, sodium carbonate, lactose, calcium phosphate or sodium phosphate; granulating and disintegrating agents, for example, corn starch, or alginic acid; binding agents, for example starch, gelatin or acacia; and lubricating agents, for example magnesium stearate, stearic acid or talc. The tablets can be uncoated or they can be coated by known techniques. Formulations for oral use can also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions contain the active materials in a mixture with excipients suitable for the manufacture of aqueous suspensions.

Oral administration of the compositions of the invention include all standard techniques for administering substances directly to the stomach or gut, most importantly by patient controlled swallowing of the dosage form, but also by other mechanical and assisted means of such delivery.

Dosage levels of the order of from about 0.1 mg to about 140 mg per kilogram of body weight per day are useful in the treatment of the above-indicated conditions (about 0.5 mg to about 7 g per subject per day). The amount of active ingredient that can be combined with the carrier materials to produce a single dosage form varies depending upon the host treated and the particular mode of administration. Dosage unit forms generally contain between from about 1 mg to about 500 mg of an active ingredient. It is understood that the specific dose level for any particular subject depends upon a variety of factors including the activity of the specific compound employed, the age, body weight, general health, sex, diet, time of administration, route of administration, and rate of excretion, drug combination and the severity of the particular disease undergoing therapy.

Therapeutic effect of the therapeutic agents of the invention may be enhanced by combination with other agents. Typically such other agents will include agents known for use in treating similar diseases, such as angiogenic disorders.

The RNAi agents of the invention and formulations thereof can be administered orally, topically, parenterally, by inhalation or spray, or rectally in dosage unit formulations containing conventional non-toxic pharmaceutically acceptable carriers, adjuvants and/or vehicles. The term parenteral as used herein includes percutaneous, subcutaneous, intravascular (e.g., intravenous), intramuscular, intraperitoneal, or intrathecal injection, or infusion techniques and the like. Where two or more different RNAi agents are administered, each may be administered separately or co-administered. Where each is administered separately, the method and/or site of administration may be the same or different, e.g., both RNAi agents may be administered intravenously or subcutaneously, or a first RNAi agent may be administered intravenously with a second Rai agent administered subcutaneously, etc.

In various embodiments, the disclosure encompasses a composition or pharmaceutical composition comprising a RNAi agent, wherein one or both strands comprises a 3' end cap, the composition further comprising a helper lipid, a neutral lipid, and/or a stealth lipid.

In various embodiments, the composition further comprises a helper lipid.

In various embodiments, the composition further comprises a neutral lipid.

In various embodiments, the composition further comprises a stealth lipid.

In various embodiments, the helper lipid, neutral lipid and stealth lipid are selected from those disclosed in: published patent app. US 2011-0200582. Additional compositions that can be used for delivery of the various RNAi agents are known in the art, e.g., are provided in U.S. Applications No. 61/774,759; 61/918,175, filed Dec. 19, 2013; 61/918,927;

61/918,182; 61/918941; 62/025224; 62/046487; and International Applications No. PCT/US04/042911; PCT/EP2010/070412; PCT/IB2014/059503.

In various embodiments, the composition further comprises an additional biologically active agent.

In various embodiments, the helper lipid is cholesterol and the biologically active agent is a siRNA.

In various embodiments, the composition is in the form of a lipid nanoparticle.

A Method of Treatment Using a RNAi Agent Described Herein

In one particular specific embodiment, the present disclosure relates to a method of treating a target gene-related disease in an individual, comprising the step of administering to the individual a therapeutically effective amount of a composition comprising a RNAi agent comprising a first strand and a second strand, wherein the first and/or second strand comprise a 3' end cap selected from the 3' end caps listed in Table 2. In one particular specific embodiment, the present disclosure relates to a method of inhibiting the expression of target gene in an individual, comprising the step of administering to the individual a therapeutically effective amount of a composition comprising a RNAi agent of the present disclosure.

In one embodiment of the method, the composition further comprises a pharmaceutically effective formulation.

Various particular specific embodiments of these embodiments are described below.

In one embodiment, the method further comprises the administration of an additional treatment. In one embodiment, the additional treatment is a therapeutically effective amount of a composition.

In one embodiment, the additional treatment is a method (or procedure).

In one embodiment, the additional treatment and the RNAi agent can be administered in any order, or can be administered simultaneously.

In one embodiment, the method further comprises the step of administering an additional treatment for the disease.

In one embodiment, the method further comprises the step of administering an additional treatment or therapy selected from the list of an additional antagonist to a target gene-related disease.

In one embodiment, the composition comprises a second RNAi agent to target gene. In various embodiments, the second RNAi agent is physically separate from the first, or the two are physically connected (e.g., covalently linked or otherwise conjugated).

Other Embodiments

Various particular specific embodiments of this disclosure are described below.

In one embodiment, the disclosure pertains to a composition according to any of the embodiments described herein, for use in a method of treating a target gene-related disease in an individual, the method comprising the step of administering to the individual a therapeutically effective amount of a composition according to any of the claims.

One embodiment of the disclosure is the use of a composition according to any of these embodiments, in the manufacture of a medicament for treatment of an target gene-related disease.

In one embodiment, the disclosure pertains to the composition of any of the above embodiments, for use in the treatment of an target gene-related disease.

Additional Definitions

Unless defined otherwise, the technical and scientific terms used herein have the same meaning as that usually understood by a specialist familiar with the field to which the present disclosure belongs.

Unless indicated otherwise, all methods, steps, techniques and manipulations that are not specifically described in detail can be performed and have been performed in a manner known per se, as will be clear to the skilled person. Reference is for example again made to the standard handbooks and the general background art mentioned herein and to the further references cited therein.

Claims to the present disclosure are non-limiting and are provided below.

Although particular embodiments and claims have been disclosed herein in detail, this has been done by way of example for purposes of illustration only, and is not intended to be limiting with respect to the scope of the appended claims, or the scope of subject matter of claims of any corresponding future application. In particular, it is contemplated by the inventors that various substitutions, alterations, and modifications may be made to the present disclosure without departing from the spirit and scope of the present disclosure as defined by the claims. The choice of nucleic acid starting material, clone of interest, or library type is believed to be a matter of routine for a person of ordinary skill in the art with knowledge of the embodiments described herein. Other aspects, advantages, and modifications considered to be within the scope of the following claims. Redrafting of claim scope in later-filed corresponding applications may be due to limitations by the patent laws of various countries and should not be interpreted as giving up subject matter of the claims.

Various additional formulations and obvious variants of the described 3' end caps can be devised by those of ordinary skill in the art. Non-limiting example RNAi agents wherein one or both strands comprises a 3' end cap are described in the Examples below, which do not limit the scope of the present disclosure as described in the claims.

EXAMPLES

Example 1

Serum Stability of siRNAs with 3' End Caps

The efficacy of a variety of different 3' end caps (3'-terminal overhangs) was tested.

10 siRNAs were prepared with an identical sequence (mF7-III target gene, 19-mer blunt-ended, A12S17 modification scheme)

10 different non-nucleotidic 3'-terminal caps were used.

These were tested in mouse and human sera at 4 time points

Parent mF7-III in A6S11 format and wt (wild-type) luc (luciferase) siRNAs were used as controls The molecules used are diagrammed in FIG. 1.

Table 5 below provides the sequences for these molecules.

TABLE 5

| siRNA ID | Project | Serum | Format sense | siRNA passenger sequence | Format anti | siRNA guide sequence |
|---|---|---|---|---|---|---|
| 144033 | mFVII 3'-caps | Mouse | S17 | uGu cuu GGu uuc AAu uA5 5 C3 | A12 | UUu AAU UGA AAC cAA GA6 5 C3 |
| 149853 | mFVII 3'-caps | Mouse | S17 | uGu cuu GGu uuc AAu uA5 5 C6 | A12 | UUu AAU UGA AAC cAA GA6 5 C6 |
| 149855 | mFVII 3'-caps | Mouse | S17 | uGu cuu GGu uuc AAu uA5 5 C12 | A12 | UUu AAU UGA AAC cAA GA6 5 C12 |
| 149857 | mFVII 3'-caps | Mouse | S17 | uGu cuu GGu uuc AAu uA5 5 glycol | A12 | UUu AAU UGA AAC cAA GA6 5 glycol |
| 149859 | mFVII 3'-caps | Mouse | S17 | uGu cuu GGu uuc AAu uA5 5 cyclohex | A12 | UUu AAU UGA AAC cAA GA6 5 cyclohex |
| 149861 | mFVII 3'-caps | Mouse | S17 | uGu cuu GGu uuc AAu uA5 5 phenyl | A12 | UUu AAU UGA AAC cAA GA6 5 phenyl |
| 149863 | mFVII 3'-caps | Mouse | S17 | uGu cuu GGu uuc AAu uA5 5 biphenyl | A12 | UUu AAU UGA AAC cAA GA6 5 biphenyl |
| 149865 | mFVII 3'-caps | Mouse | S17 | uGu cuu GGu uuc AAu uA5 5 lithochol | A12 | UUu AAU UGA AAC cAA GA6 5 lithochol |
| 149867 | mFVII 3'-caps | Mouse | S17 | uGu cuu GGu uuc AAu uA5 5 amino C7 | A12 | UUu AAU UGA AAC cAA GA6 5 amino C7 |
| 149869 | mFVII 3'-caps | Mouse | S17 | uGu cuu GGu uuc AAu uA5 5 amino C3 | A12 | UUu AAU UGA AAC cAA GA6 5 amino C3 |
| 8548 | Luc stability ctrl. | Mouse | S0 | TCGAAGTACTCAGCGTAAGTT | A0 | CTTACGCTGAGTACTTCGATT |
| 144049 | mFVII w/o cap | Mouse | S1 | uGu cuu GGu uuc AAu uAA AdTsdT | A1 | UUu AAU UGA AAC cAA GAc AdTsdT |
| 144033 | mFVII 3'-caps | Human | S17 | uGu cuu GGu uuc AAu uA5 5 C3 | A12 | UUu AAU UGA AAC cAA GA6 5 C3 |
| 149853 | mFVII 3'-caps | Human | S17 | uGu cuu GGu uuc AAu uA5 5 C6 | A12 | UUu AAU UGA AAC cAA GA6 5 C6 |
| 149855 | mFVII 3'-caps | Human | S17 | uGu cuu GGu uuc AAu uA5 5 C12 | A12 | UUu AAU UGA AAC cAA GA6 5 C12 |
| 149857 | mFVII 3'-caps | Human | S17 | uGu cuu GGu uuc AAu uA5 5 glycol | A12 | UUu AAU UGA AAC cAA GA6 5 glycol |
| 149859 | mFVII 3'-caps | Human | S17 | uGu cuu GGu uuc AAu uA5 5 cyclohex | A12 | UUu AAU UGA AAC cAA GA6 5 cyclohex |
| 149861 | mFVII 3'-caps | Human | S17 | uGu cuu GGu uuc AAu uA5 5 phenyl | A12 | UUu AAU UGA AAC cAA GA6 5 phenyl |
| 149863 | mFVII 3'-caps | Human | S17 | uGu cuu GGu uuc AAu uA5 5 biphenyl | A12 | UUu AAU UGA AAC cAA GA6 5 biphenyl |
| 149865 | mFVII 3'-caps | Human | S17 | uGu cuu GGu uuc AAu uA5 5 lithochol | A12 | UUu AAU UGA AAC cAA GA6 5 lithochol |
| 149867 | mFVII 3'-caps | Human | S17 | uGu cuu GGu uuc AAu uA5 5 amino C7 | A12 | UUu AAU UGA AAC cAA GA6 5 amino C7 |
| 149869 | mFVII 3'-caps | Human | S17 | uGu cuu GGu uuc AAu uA5 5 amino C3 | A12 | UUu AAU UGA AAC cAA GA6 5 amino C3 |
| 144049 | mFVII w/o cap anti | Human | NA | NA | A12 | UUu AAU UGA AAC cAA GAc AdTsdT |
| 144053 | mFVII w/o cap sense | Human | S17 | uGu cuu GGu uuc AAu uAA AdTsdT | NA | NA |

The sense sequences are represented from top to bottom by SEQ ID NOs: 92 to 114; the guide (anti-sense) sequences are represented from top to bottom by SEQ ID NOs: 115 ro 137. The 3' end caps used in this example are diagrammed below, in the context of the RNAi agent strand.
C3
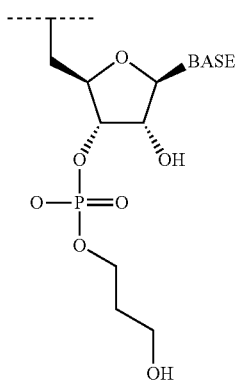
C6
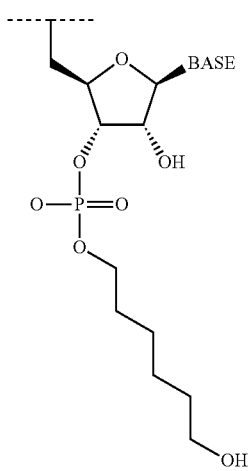
C12
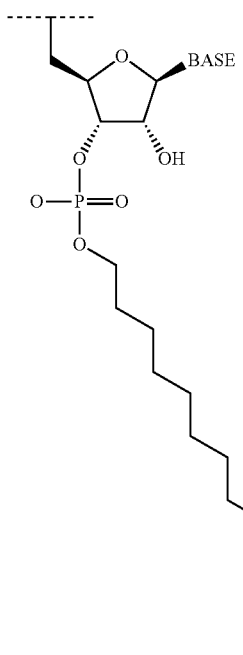
-continued
glycol
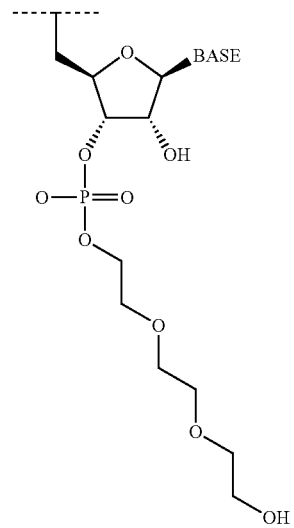
cyclohex
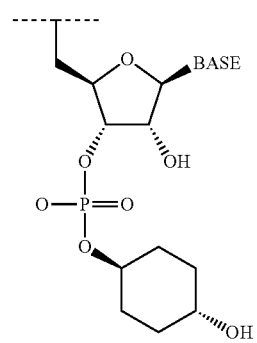
phenyl
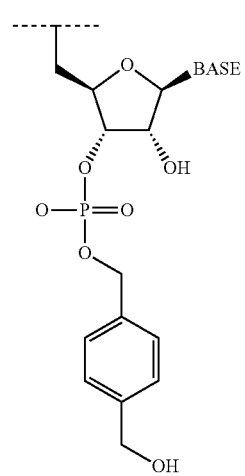

biphenyl

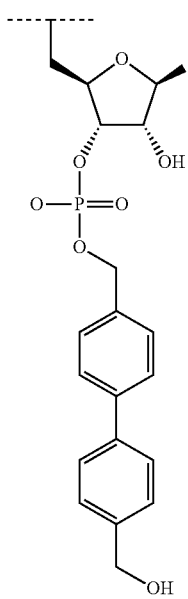

lithochol

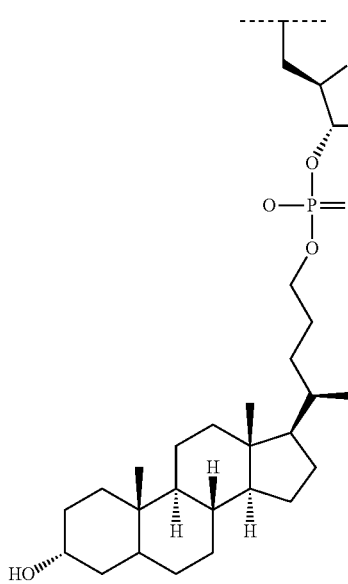

amino C7

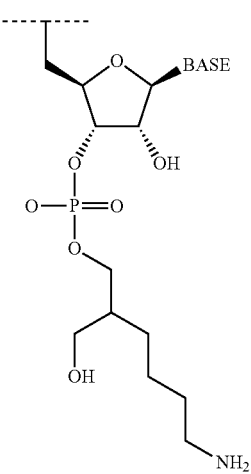

amino C3

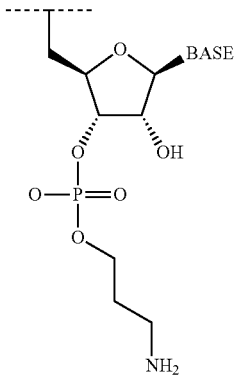

Materials and Methods:

RNA samples were incubated in 100% mouse serum and human serum at 37° C., withdrawn at 0, 5', 6 h and 24 h time points and snap-frozen. Oligos were separated by precast hydrogels (Elchrom Scientific) and visualized with SYBR gold (Biorad, Chemidoc XRS).

FIG. 2 shows the efficacy of various 3' end caps described in Example 1 in allowing the RNAi agent to mediate RNA interference. All of the 3' end caps—C3, C6, C12, Triethylene glycol, Cyclohexyl, Phenyl, Biphenyl, Adamantane and Lithocholic acid—allow the RNAi agent to perform RNA interference.

FIG. 3 shows the efficacy of various 3' end caps described in Example 1 in reducing and/or preventing nuclease degradation in serum.

In mouse serum all 3'-capped A12S17 siRNAs display high resistance up to 24 h.

In human serum C3, C12 and lithochol appear to be less stable as compared to the other derivatives. However, in both experiments, C3, biphenyl and litochol display significantly weaker bands as compared to the other derivatives. However, there is a need to clarify whether this is due to lower synthesis/dsRNA quality (as indicated by gel-based QC) or due to a technical gel-based artifact (lithocholic acid may stick to human serum and thus gets protected from SYBR GOLD intercalation).

Single-strand antisense A12 is degraded rapidly in human serum whereas the parent sense S17 strand (with more chemical modifications) resists a bit longer but not as long as the dsRNA. Enzymatic stability correlates with thermal dsRNA stability.

Thus, this Example shows that siRNAs with these various 3' end caps were able to mediate RNA interference against FVII (Factor VII). The 3' end cap modifications designated as C3, C6, C12, glycol, cyclohex, phenyl, biphenyl, lithochol, C7 amino and C3 amino showed increased stability in mouse serum at 1',30', 6 h and 24 hrs compared to luciferase and dTsdT controls. Those 3'-end modifications designated C3, C6, glycol, cyclohex, phenyl and biphenyl, C7 amino and C3 amino also showed increased stability in human serum compared to controls.

Example 2

The Synthesis of Various 3' End Cap Succinate Esters and Alcohols are Presented Below

| | |
|---|---|
| Example 2.A | X027 succinate ester |
| Example 2.B | X038 succinate ester |
| Example 2.C | X052 succinate ester |
| Example 2.D | X058 succinate ester |
| Example 2.E | X067 succinate ester |
| Example 2.F | X069 succinate ester |
| Example 2.G | General procedure for the high density loading of controlled pore glass supports with PAZ ligand succinates |
| Example 2.H | Synthesis of X050, X059, X061, X062, X065, X068 alcohols and succinate esters |
| Example 2.I | X060 and X064 alcohols and succinate esters |
| Example 2.J | X063 succinate ester |
| Example 2.K | X066 succinate ester |
| Example 2.L | X051 succinate ester |
| Example 2.M | Synthesis of X097 succinate ester |
| Example 2.N | Synthesis of X098 succinate ester |
| Example 2.O | Synthesis of siRNA conjugated with X109 |
| Example 2.P | Synthesis of siRNA conjugated with X110 |
| Example 2.Q | Synthesis of siRNA conjugated with X111 |
| Example 2.R | Synthesis of siRNA conjugated with X112 |
| Example 2.S | Synthesis of siRNA conjugated with X113 |
| Example 2.T | General procedure for the high density loading of controlled pore glass supports with PAZ ligand succinates |

Example 2

The Synthesis of Various 3' End Cap Succinate Esters and Alcohols are Presented Below

| | |
|---|---|
| Example 2.A | X027 succinate ester |
| Example 2.B | X038 succinate ester |
| Example 2.C | X052 succinate ester |
| Example 2.D | X058 succinate ester |
| Example 2.E | X067 succinate ester |
| Example 2.F | X069 succinate ester |
| Example 2.G | General procedure for the high density loading of controlled pore glass supports with PAZ ligand succinates |
| Example 2.H | Synthesis of X050, X059, X061, X062, X065, X068 alcohols and succinate esters |
| Example 2.I | X060 and X064 alcohols and succinate esters |
| Example 2.J | X063 succinate ester |
| Example 2.K | X066 succinate ester |
| Example 2.L | X051 succinate ester |
| Example 2.M | Synthesis of X097 succinate ester |
| Example 2.N | Synthesis of X098 succinate ester |
| Example 2.O | Synthesis of siRNA conjugated with X109 |
| Example 2.P | Synthesis of siRNA conjugated with X110 |
| Example 2.Q | Synthesis of siRNA conjugated with X111 |
| Example 2.R | Synthesis of siRNA conjugated with X112 |
| Example 2.S | Synthesis of siRNA conjugated with X113 |
| Example 2.T | General procedure for the high density loading of controlled pore glass supports with PAZ ligand succinates |

2.A. Synthesis of X027 Succinate Ester

Scheme 1: Overview of the synthesis of succinate 9.

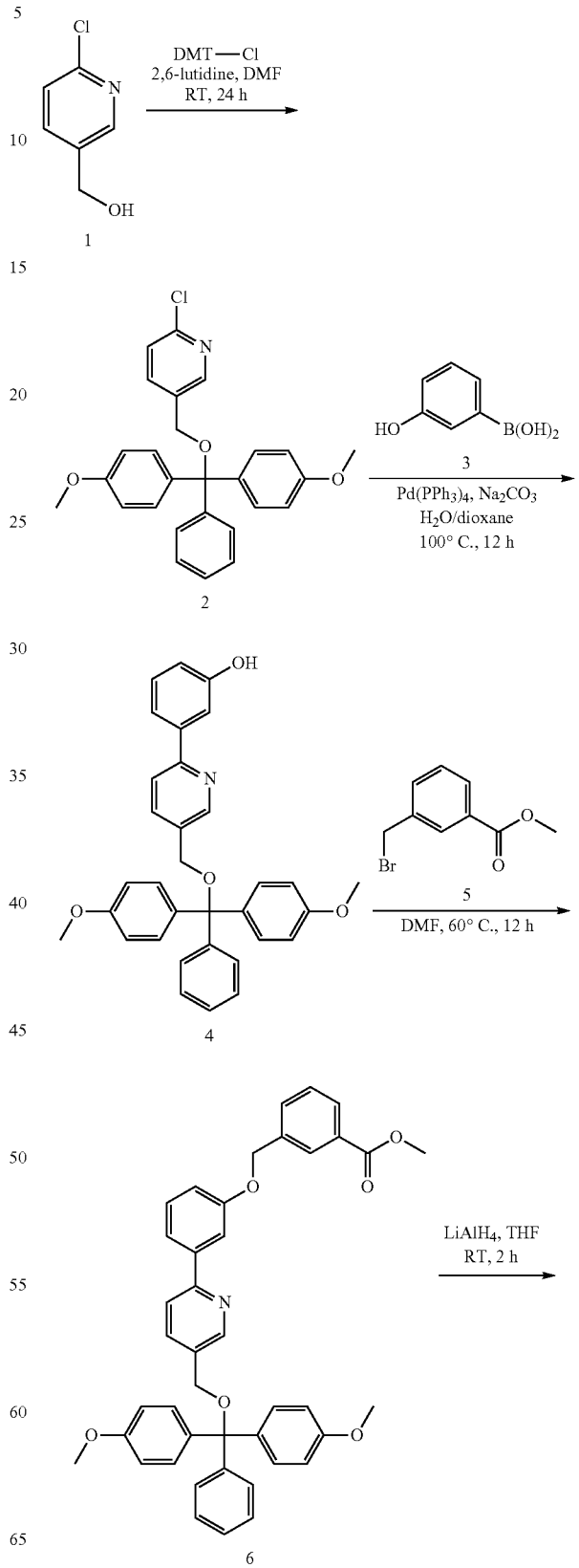

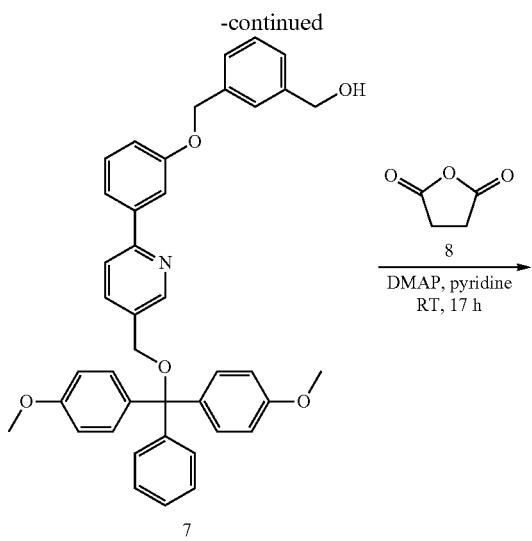

7

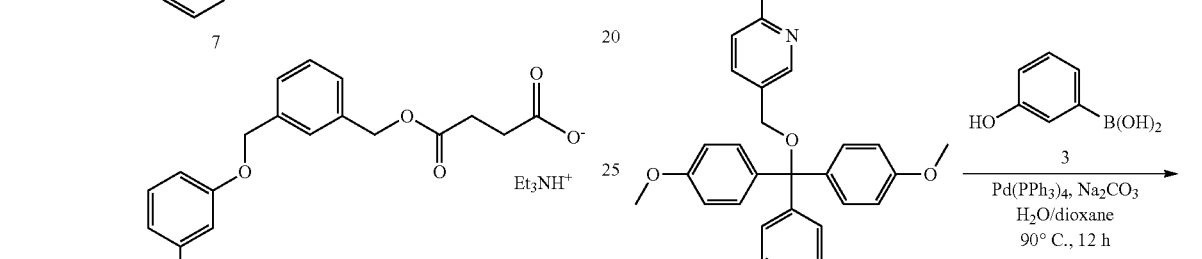

9

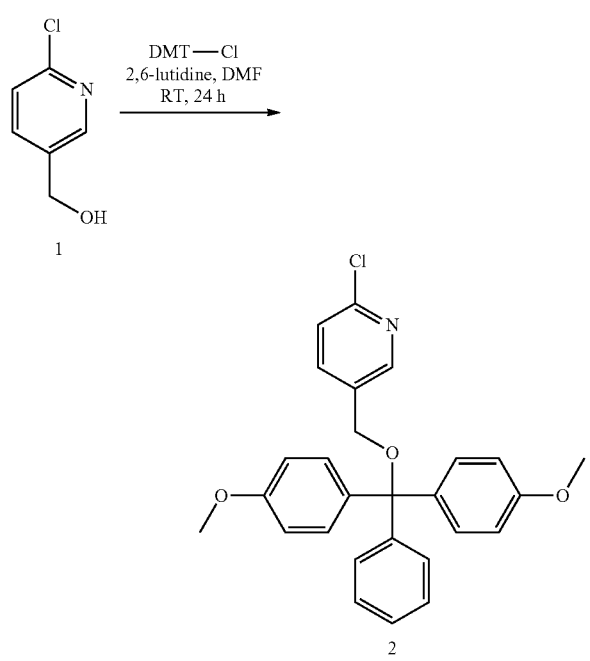

To a solution of compound 1 (10.0 g, 70.0 mmol) in DMF (200 mL) were added DMT-Cl 2 (28.4 g, 84.0 mmol) and 2,6-lutidine (15.0 g, 140 mmol). The reaction mixture was stirred at rt overnight. The reaction mixture was poured into ice water and extracted with EtOAc (3×500 mL). The organic extracts was dried over sodium sulfate and concentrated in vacuum to give the crude product, which was purified by silica gel chromatography (heptane/ethyl acetate/ NEt$_3$) to give the desired product as white solid (16 g, 36%). $^1$H NMR (DMSO-d$_6$, 400 MHz): 3.73 (s, 6H), 4.17 (s, 2H), 6.91 (d, J=8.8 Hz, 4H), 7.35-7.22 (m, 7H), 7.42 (d, J=7.6 Hz, 2H), 7.48 (d, J=8.4 Hz, 1H), 7.83-7.80 (m, 1H), 8.33 (d, J=1.6 Hz, 1H).

To a solution of compound 2 (8.0 g, 18 mmol) in dioxane (160 mL)/H$_2$O (40 mL) were added 3-hydroxyphenylboronic acid 4 (3.5 g, 25 mmol), Pd(PPh$_3$)$_4$ (1.1 g, 1.0 mmol), and Na$_2$CO$_3$ (4.0 g, 38 mmol). The reaction mixture was bubbled with nitrogen gas and stirred at 90° C. overnight. Then reaction mixture was poured into water and extracted with EtOAc (3×800 mL). The organic extracts was dried over sodium sulfate, concentrated in vacuum, and purified by silica gel chromatography (heptane/ethyl acetate/NEt$_3$) to give 4 as an impure light yellow oil (6 g).

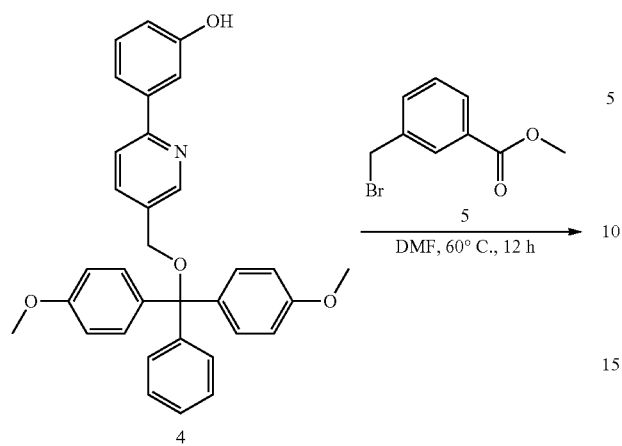

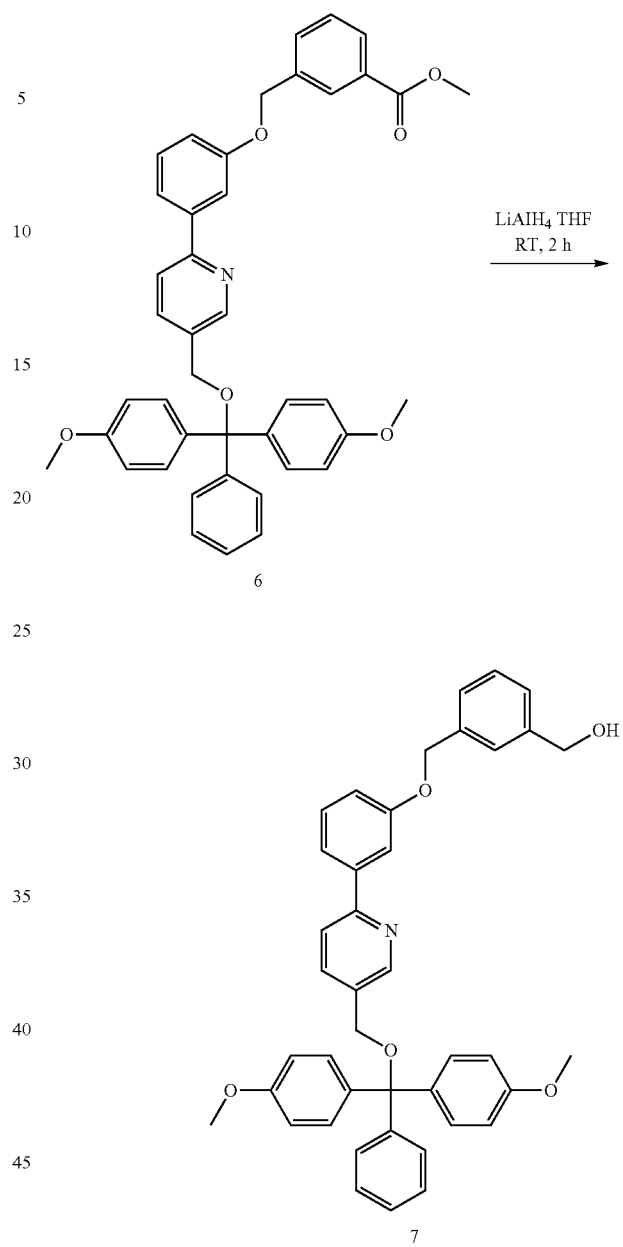

To a solution of compound 4 (10 g crude, 20 mmol) in acetone (600 mL) were added compound 5 (4.0 g, 17.6 mmol), $K_2CO_3$ (4.0 g, 28 mmol), and KI (316 mg, 1.9 mmol). The reaction mixture was stirred at reflux overnight. After the reaction mixture was cooled, the solvent was concentrated in vacuum. The reside was diluted with water and extracted with EtOAc (3×800 mL). The organic phase was dried over sodium sulfate and concentrated in vacuum to give the crude product, which was purified by silica gel chromatography (heptane/ethyl acetate/$NEt_3$) to give 6 as light yellow oil (9 g, 69%). $^1$H NMR (DMSO-$d_6$, 400 MHz): 3.74 (s, 6H), 3.84 (s, 3H), 4.19 (s, 2H), 6.93 (d, J=8.8 Hz, 4H), 7.11-7.08 (m, 1H), 7.27-7.23 (t, J=7.2 Hz, 1H), 7.46-7.31 (m, 9H), 7.59-7.55 (t, J=7.6 Hz, 1H), 7.68 (d, J=8.0 Hz, 1H), 7.79-7.75 (m, 2H), 7.84-7.80 (m, 1H), 7.97-7.92 (m, 2H), 8.10 (s, 1H), 8.61 (d, J=1.6 Hz, 1H).

Lithium aluminum hydride (30.7 mL of 1.0 M suspension in THF, 30.7 mmol) was added to a solution of compound 6 (8.0 g, 12 mmol) in THF (150 mL) at 0° C. After 2 hours at 0° C., the reaction mixture was quenched with water (200 mL), and then the reaction mixture was extracted with dichloromethane (3×200 mL), The combined organic phase was dried over sodium sulfate, filtered, and concentrated in vacuum to give the desired product 7 as white solid (6.1 g, 80%). $^1$H NMR (DMSO-$d_6$, 400 MHz): 3.74 (s, 6H), 4.19 (s, 2H), 5.54 (d, J=5.6 Hz, 2H), 5.18 (s, 2H), 5.27-5.24 (t, J=6.0 Hz, 1H), 6.93 (d, J=8.8 Hz, 4H), 7.10-7.07 (m, 1H), 7.47-7.23 (m, 14H), 7.67 (d, J=8.0 Hz, 1H), 7.75 (s, 1H), 7.83-7.81 (m, 1H), 7.95 (d, J=8.0 Hz, 1H), 8.61 (d, J=1.2 Hz, 1H).

2. B Synthesis of X038 Succinate Ester

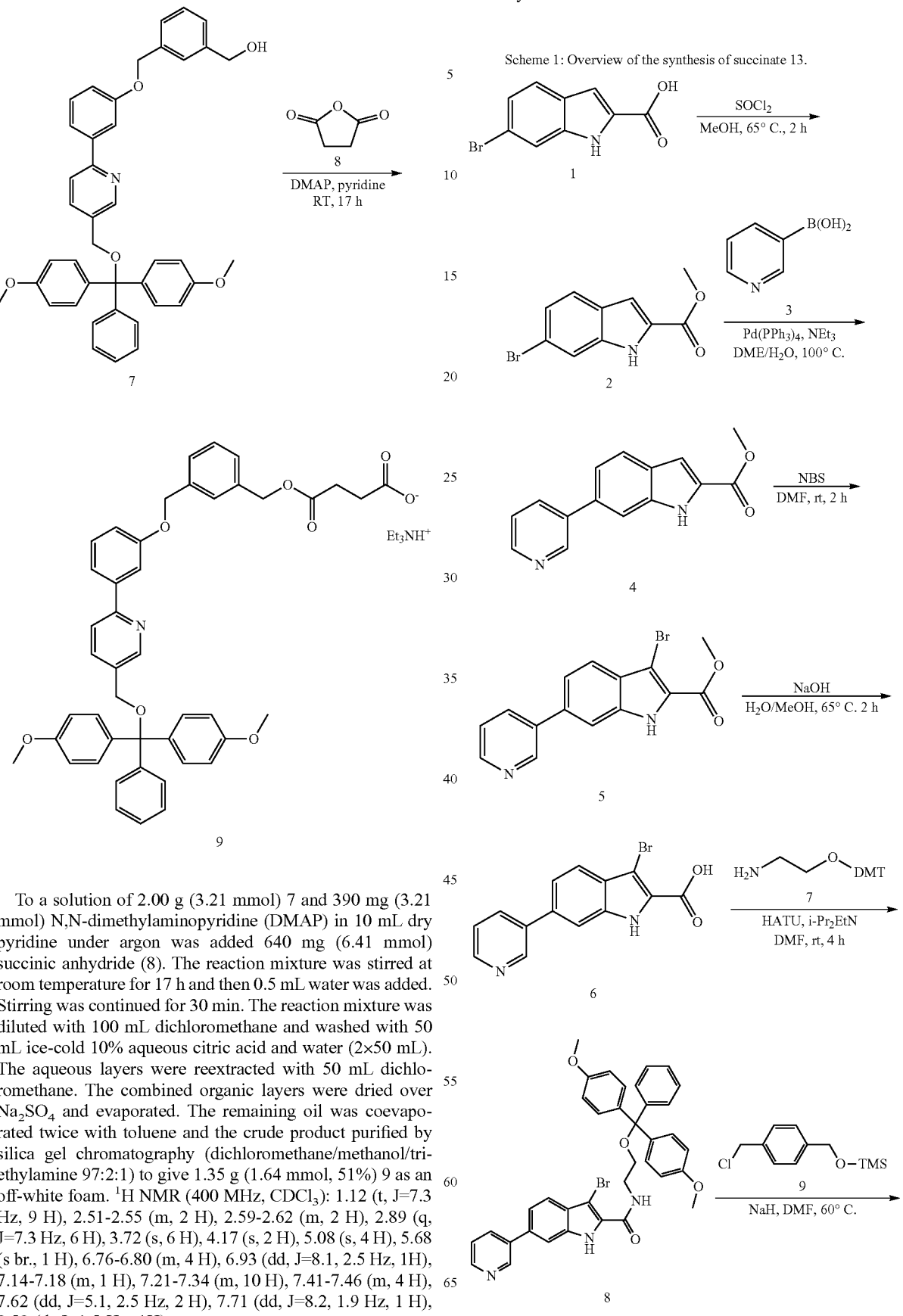

Scheme 1: Overview of the synthesis of succinate 13.

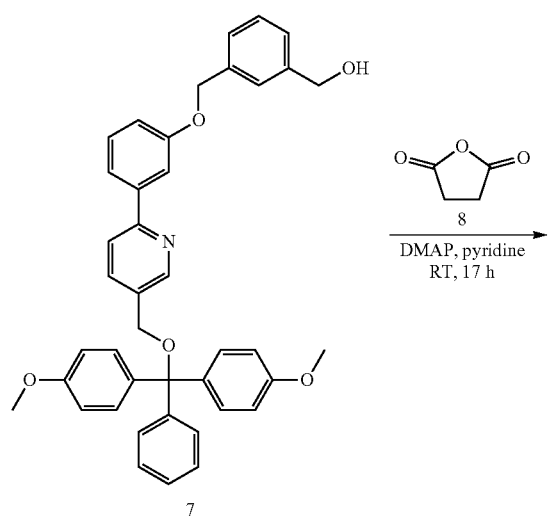

To a solution of 2.00 g (3.21 mmol) 7 and 390 mg (3.21 mmol) N,N-dimethylaminopyridine (DMAP) in 10 mL dry pyridine under argon was added 640 mg (6.41 mmol) succinic anhydride (8). The reaction mixture was stirred at room temperature for 17 h and then 0.5 mL water was added. Stirring was continued for 30 min. The reaction mixture was diluted with 100 mL dichloromethane and washed with 50 mL ice-cold 10% aqueous citric acid and water (2×50 mL). The aqueous layers were reextracted with 50 mL dichloromethane. The combined organic layers were dried over $Na_2SO_4$ and evaporated. The remaining oil was coevaporated twice with toluene and the crude product purified by silica gel chromatography (dichloromethane/methanol/triethylamine 97:2:1) to give 1.35 g (1.64 mmol, 51%) 9 as an off-white foam. $^1$H NMR (400 MHz, $CDCl_3$): 1.12 (t, J=7.3 Hz, 9 H), 2.51-2.55 (m, 2 H), 2.59-2.62 (m, 2 H), 2.89 (q, J=7.3 Hz, 6 H), 3.72 (s, 6 H), 4.17 (s, 2 H), 5.08 (s, 4 H), 5.68 (s br., 1 H), 6.76-6.80 (m, 4 H), 6.93 (dd, J=8.1, 2.5 Hz, 1H), 7.14-7.18 (m, 1 H), 7.21-7.34 (m, 10 H), 7.41-7.46 (m, 4 H), 7.62 (dd, J=5.1, 2.5 Hz, 2 H), 7.71 (dd, J=8.2, 1.9 Hz, 1 H), 8.59 (d, J=1.5 Hz, 1H).

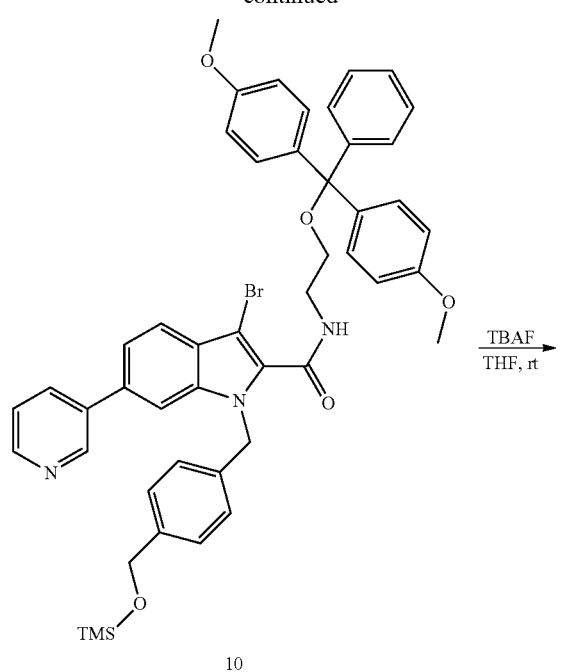
10
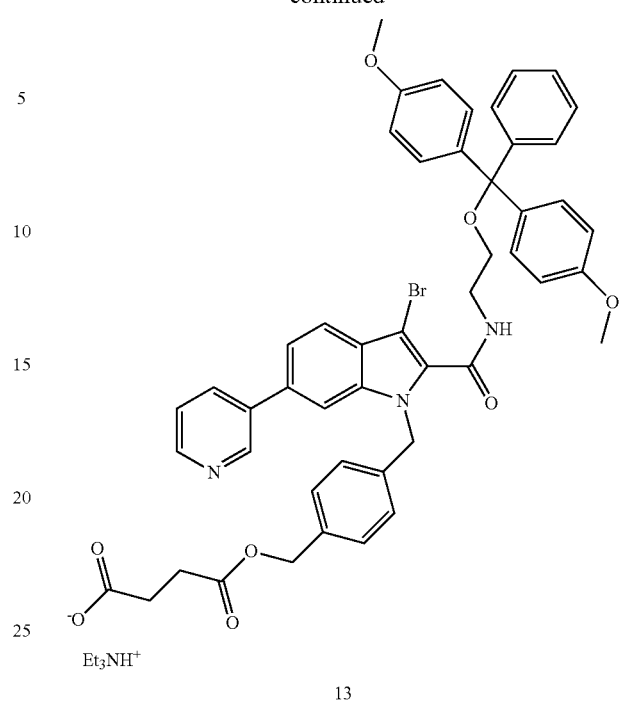
13
Scheme 2: Overview of the synthesis of 7.
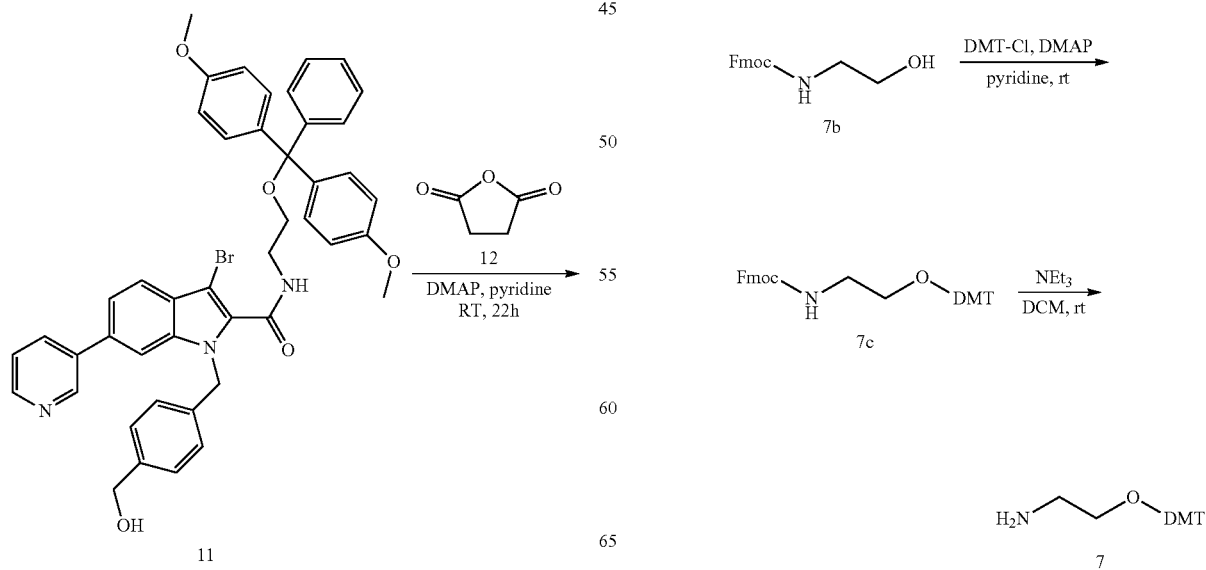

Scheme 3: Overview of the synthesis of 9.

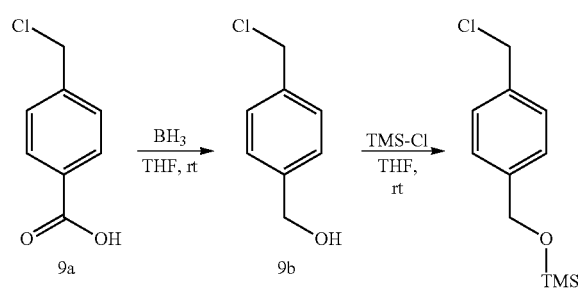

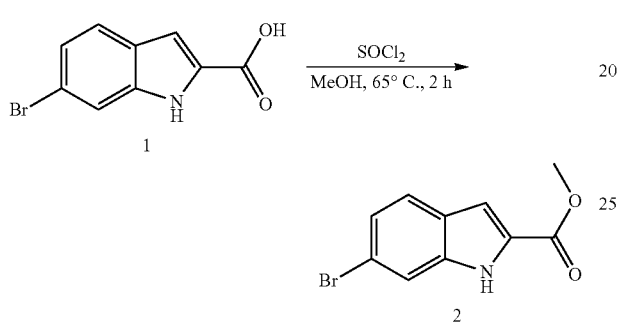

Into a 2000-mL 3-necked round-bottom flask was placed a solution of 6-bromo-1H-indole-2-carboxylic acid 1 (100 g, 417 mmol) in methanol (1000 mL). This was followed by the addition of thionyl chloride (100 g, 840 mmol) dropwise with stirring. The resulting solution was heated to reflux for 2 h. The reaction mixture was cooled to rt and a precipitate was formed. The solids were collected by filtration, washing with methanol, and dried in an oven under reduced pressure, giving 2 (95 g, 90%) as a white solid.

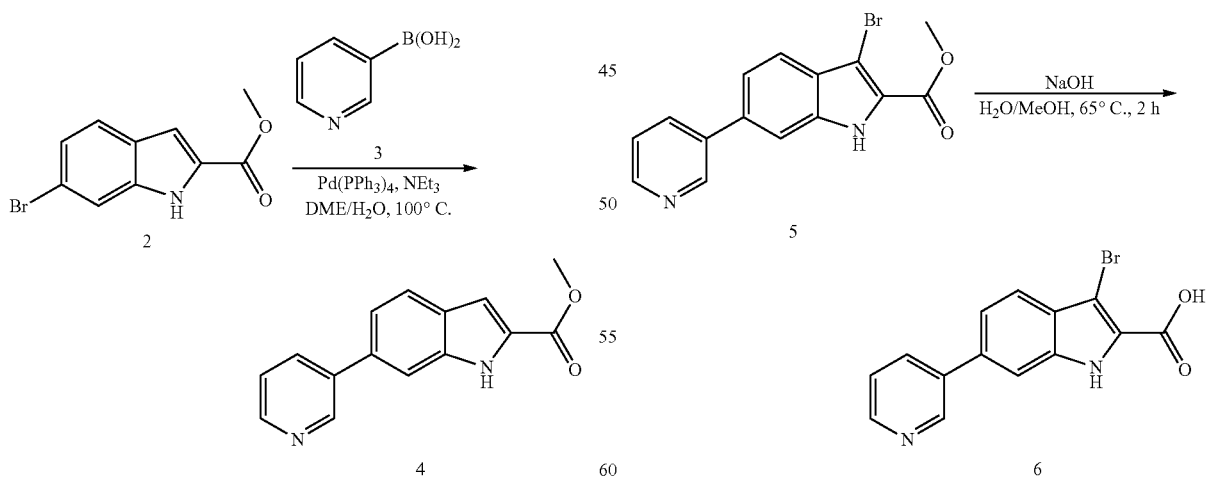

Into a 2000-mL 3-necked round-bottom flask, purged and maintained with an inert atmosphere of nitrogen, was placed a solution of 2 (90 g, 354 mmol) in ethylene glycol dimethyl ether (500 mL), water (500 mL), (pyridin-3-yl)boronic acid 3 (43.6 g, 355 mmol), NEt$_3$ (107 g, 1.06 mol), and Pd(PPh$_3$)$_4$ (9 g, 7.79 mmol). The resulting solution was heated to reflux overnight. The reaction mixture was cooled to room temperature and was quenched by the addition of 800 mL of water, forming a precipitate. The solids were collected by filtration, washing with water, and dried in an oven under reduced pressure, giving 4 (78 g, 87%) as a brown solid.

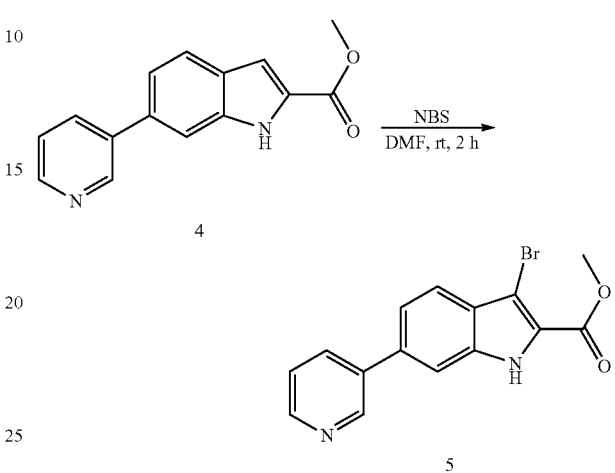

Into a 2000-mL round-bottom flask was placed a solution of 4 (75 g, 297 mmol) in DMF (500 mL). This was followed by the addition of NBS (53.5 g, 301 mmol), portionwise. The resulting solution was stirred for 2 h at rt. The reaction was then quenched by the addition of 1000 mL of water, forming a precipitate. The solids were collected by filtration, washing with water and dried in an oven under reduced pressure, giving 5 (70 g, 71%) as a brown solid. $^1$H NMR (400 MHz, CDCl$_3$): 3.94 (s, 3 H), 7.51-7.58 (m, 2 H), 7.67-7.76 (m, 2 H), 8.11 (d, J=7.6 Hz, 1 H), 8.60 (d, J=4.4 Hz, 1 H), 8.91 (s, 1 H), 12.48 (s, 1 H).

Into a 2000-mL round-bottom flask was placed a solution of 5 (68 g, 205) in methanol (500 mL), water (100 mL), and sodium hydroxide (25 g, 625 mmol). The resulting solution was heated to reflux for 2 hr. The resulting solution was cooled to room temperature and diluted with 500 mL of water. The pH value of the solution was adjusted to 5-6 with 2N HCl (aq), forming a precipitate. The solids were collected by filtration, washing with water, and dried in an oven under reduced pressure, giving 6 (50 g, 77%) as a light yellow solid. $^1$H NMR (400 MHz, CDCl$_3$): 7.50-7.53 (m, 2H), 7.65-7.71 (m, 2H), 8.09 (d, J=7.6 Hz, 1H), 8.59 (d, J=4 Hz, 1H), 8.91 (s, 1H), 12.30 (s, 1H), 13.55 (s, 1H).

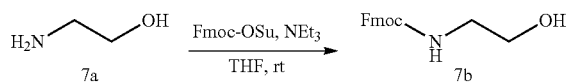

Into a 2000-mL round-bottom flask was placed a solution of 2-aminoethan-1-ol 7a (30 g, 491 mmol) in THF (600 mL), Fmoc-OSu (166 g, 491 mmol), and NEt$_3$ (199 g, 1.97 mol). The resulting solution was stirred overnight at rt. The mixture was concentrated under vacuum and purified by silica gel chromatography (ethyl acetate/petroleum ether), giving 7b (130 g, 93%) as a white solid.

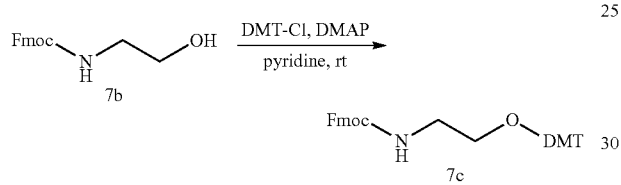

Into a 2000-mL round-bottom flask was placed a solution of 7b (130 g, 459 mmol) in pyridine (500 mL), 1-[chloro(4-methoxyphenyl)benzyl]-4-methoxybenzene (DMT-Cl) (233 g, 688 mmol), and 4-dimethylaminopyridine (2.8 g, 22.9 mmol). The resulting solution was stirred overnight at rt. The reaction was then quenched by the addition of water, and the resulting solution was extracted with ethyl acetate (3×500 mL). The combined organic layers were dried over sodium sulfate and concentrated in vacuum. The residue was purified by silica gel chromatography (ethyl acetate/petroleum ether), giving 7c (210 g, 78%) as a brown solid.

Into a 2000-mL round-bottom flask was placed a solution of 7c (210 g, 359 mmol) in dichloromethane (500 mL) and NEt$_3$ (500 mL). The resulting solution was stirred overnight at rt. The resulting mixture was concentrated under vacuum. The residue was purified by silica gel chromatography (ethyl acetate/petroleum ether), giving 7 (95 g, 73%) a brown solid. $^1$H NMR (400 MHz, CDCl$_3$) 2.42 (br. s, 2 H), 3.70-3.82 (m, 2 H), 3.80 (s, 6 H), 6.79-6.87 (m, 4 H), 7.19-7.25 (m, 2 H), 7.29 (d, J=9.2 Hz, 2 H), 7.33-7.40 (m, 3 H), 7.49 (d, J=7.6 Hz, 2 H).

Into a 2000-mL round-bottom flask was placed a solution of 6 (40 g, 126 mmol) in DMF (800 mL), 7 (69 g, 190 mmol), HATU (96 g, 252 mmol), and i-Pr$_2$EtN (65 g, 503 mmol). The resulting solution was stirred for 4 h at rt and then quenched by the addition of 1000 mL of water. The resulting solution was extracted with ethyl acetate (3×800 mL). The combined organic layers were dried over sodium sulfate and concentrated under vacuum. The residue was purified by silica gel chromatography (ethyl acetate/petroleum ether), giving 8 (30 g, 36%) of as a light yellow solid.

Into a 2000-mL round-bottom flask was placed a solution of 4-(chloromethyl)benzoic acid 9a (50 g, 293 mmol) in THF (200 mL). This was followed by the addition of 1 M BH$_3$/THF (586 mL, 586 mmol) dropwise with stirring at 0° C. over 1 hr. The resulting solution was stirred for 4 h at rt. The reaction was then quenched by the addition of 600 mL of 1 N HCl. The solution was extracted with 500 ml of ethyl acetate. The organic layer was washed with 300 ml of sodium carbonate (aq.), and 300 ml of brine. The organic layer was dried over sodium sulfate and concentrated under vacuum giving 9b (35 g, 76%) as a white solid. $^1$H NMR (400 MHz, CDCl$_3$) 4.50 (d, J=4.8 Hz, 2 H), 4.75 (s, 2 H), 5.21 (t, J=4.8 Hz, 1 H), 7.32 (d, J=7.6 Hz, 2 H), 7.39 (d, J=7.6 Hz, 2 H).

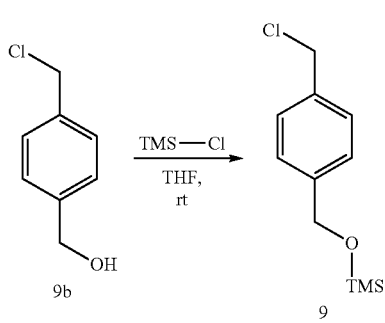 [SMILES: OCc1ccc(CCl)cc1 ; C[Si](C)(C)Cl ; C[Si](C)(C)OCc1ccc(CCl)cc1]

Into a 1000-mL 3-necked round-bottom flask was placed a solution 9b (35 g, 223 mmol) in THF (300 mL) and TEA (68 g, 672 mmol). This was followed by the addition of TMS-Cl (36.4 g, 335 mmol) dropwise with stirring. The resulting solution was stirred overnight at rt. The reaction was then quenched by the addition of 500 mL of water and extracted with 500 ml of ethyl acetate. The organic layer was washed with 500 ml of NaHCO₃ (aq.), 500 ml of brine, and dried over sodium sulfate. The residue was concentrated under vacuum giving 9 (35 g, 68%) as colorless oil.

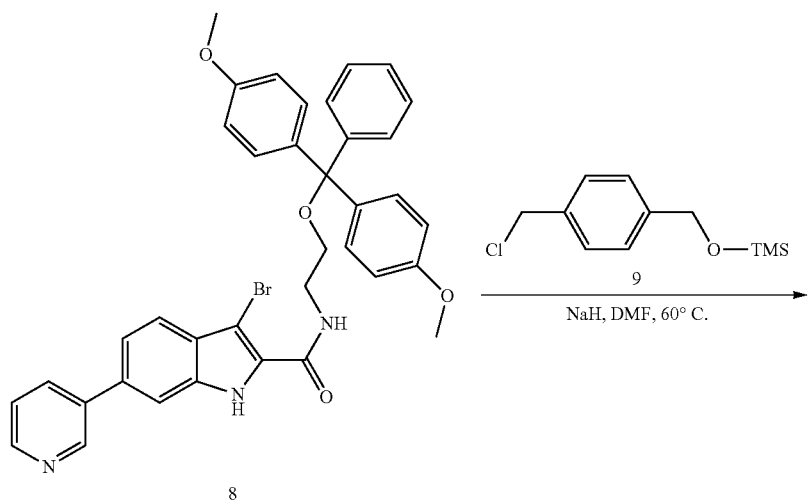

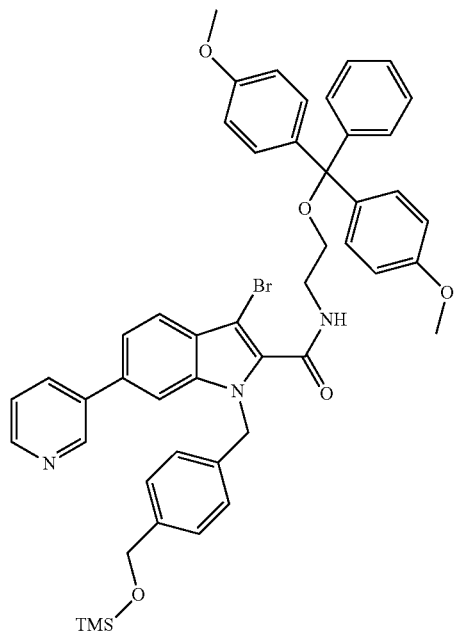

Into a 1000-mL 3-necked round-bottom flask was placed a solution of 8 (30 g, 45.3 mmol) in DMF (300 mL), and sodium hydride (1.1 g, 45.8 mmol). The mixture was stirred at rt for 0.5 h. A solution of 9 (15.5 g, 67.8 mmol) in THF (100 ml) was then added, and the resulting solution was stirred overnight at 60° C. The reaction mixture was cooled to rt and quenched by the addition of 500 mL of water. The resulting solution was extracted with dichloromethane (3×500 mL), and the combined organic layers were concentrated under vacuum. The residue was purified by silica gel chromatography (ethyl acetate/petroleum ether), giving 10 (15 g, 39%) as a white solid.

brine, and dried over sodium sulfate. The resulting mixture was concentrated under vacuum and the crude product was re-crystallized from hexane, giving 11 (5.5 g, 40%) as a yellow solid. $^1$H NMR (400 MHz, CDCl$_3$): 3.30 (m, 2 H), 3.66-3.65 (m, 2 H), 3.78 (s, 6 H), 4.51 (s, 2 H), 5.68 (s, 2 H), 6.84 (d, J=8.8 Hz, 4 H), 7.09 (d, J=8 Hz, 2 H), 7.19-7.35 (m, 9 H), 7.47-7.54 (m, 4 H), 7.70 (d, J=9.2 Hz, 2 H), 8.10 (d, J=8 Hz, 1 H), 8.51 (d, J=4.8 Hz, 1 H), 8.79 (s, 1 H).

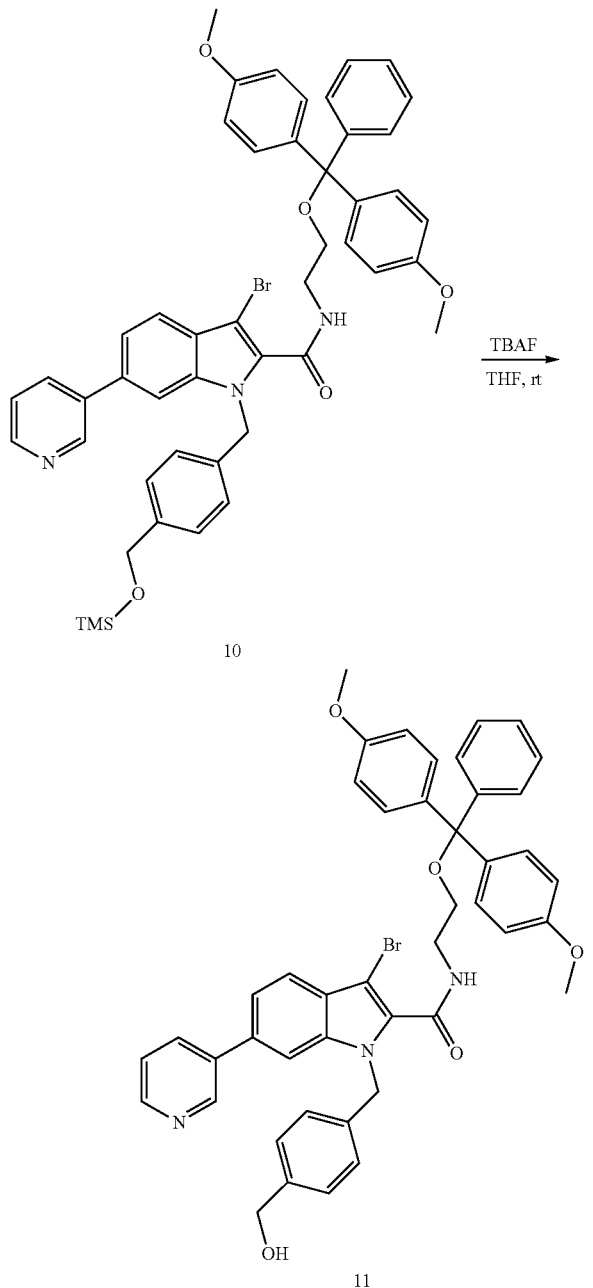

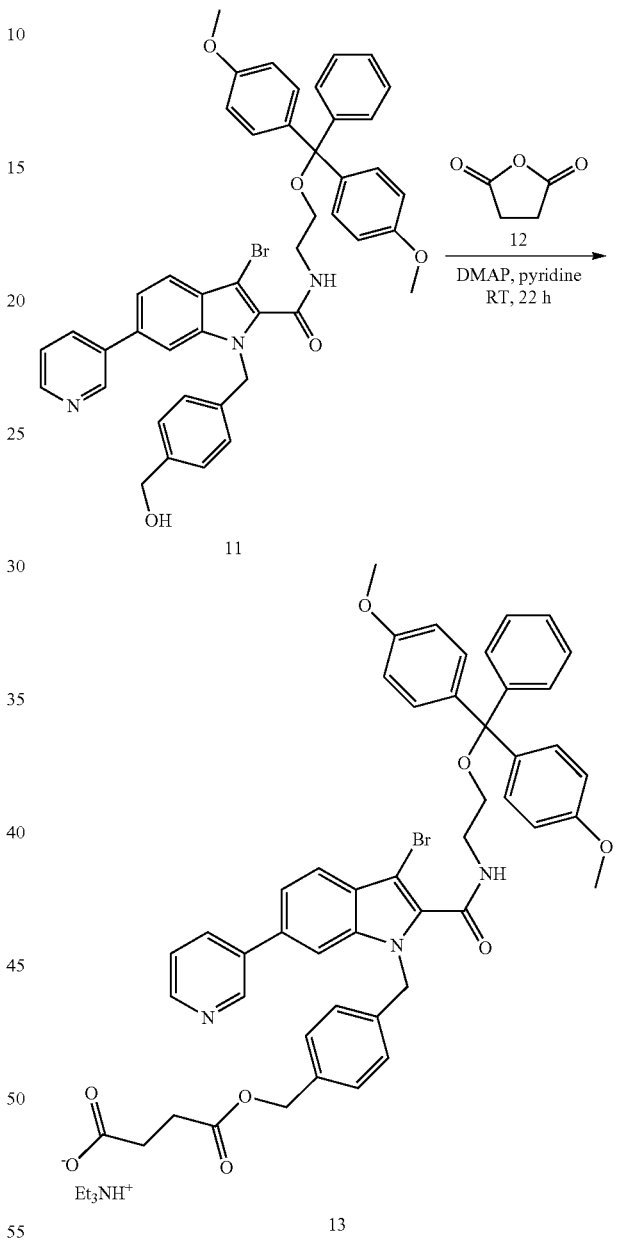

Into a 500-mL round-bottom flask was placed a solution of 10 (15 g, 17.6 mmol) in THF (150 mL) and TBAF (7 g, 26.8 mmol). The resulting solution was stirred for 30 min at rt. The resulting solution was diluted with 300 mL of water and extracted with 500 mL of ethyl acetate. The organic layer was washed with water (2×300 mL) and 300 mL of To a solution of 1.57 g (2.00 mmol) 11 and 244 mg (2.00 mmol) N,N-dimethylaminopyridine (DMAP) in 8 mL dry pyridine under argon was added 400 mg (4.00 mmol) succinic anhydride (12). The reaction mixture was stirred at room temperature for 22 h and then 0.5 mL water was added. Stirring was continued for 30 min. The reaction mixture was taken up in 100 mL dichloromethane and washed with 50 mL ice-cold 10% aqueous citric acid and water (2×50 mL). The aqueous layers were reextracted with 50 mL dichloromethane. The combined organic layers were dried over Na$_2$SO$_4$ and evaporated. The remaining oil was coevaporated twice with toluene and the crude product purified by silica gel chromatography (dichloromethane/methanol/triethylamine 94:5:1) to give 2.05 g (2.00 mmol, quant.) 13 as an off-white foam. $^1$H NMR (400 MHz, CDCl$_3$): 1.05 (t, J=7.2 Hz, 9 H), 2.45 (t, J=6.5 Hz, 2 H), 2.54 (t, J=6.5 Hz, 2 H), 2.66 (q, J=7.2 Hz, 6 H), 3.29 (t, J=4.9 Hz, 2 H), 3.60 (q, J=5.1 Hz, 2 H), 3.70 (s, 6 H), 4.97 (s, 2 H), 5.75 (s, 2 H), 6.72-6.76 (m, 4 H), 7.01 (d, J=8.1 Hz, 2 H), 7.12-7.23 (m, 6 H), 7.26-7.31 (m, 5 H), 7.35-7.41 (m, 4 H), 7.63 (d, J=8.3 Hz, 1 H), 7.79 (dt, J=8.1, 1.9 Hz, 1 H), 8.49 (dd, J=4.8, 1.5 Hz, 1 H), 8.73 (d, J=2.0 Hz, 1 H).

2.C. Synthesis of X052 Succinate Ester

Scheme 1: Overview of the synthesis of succinate 6.

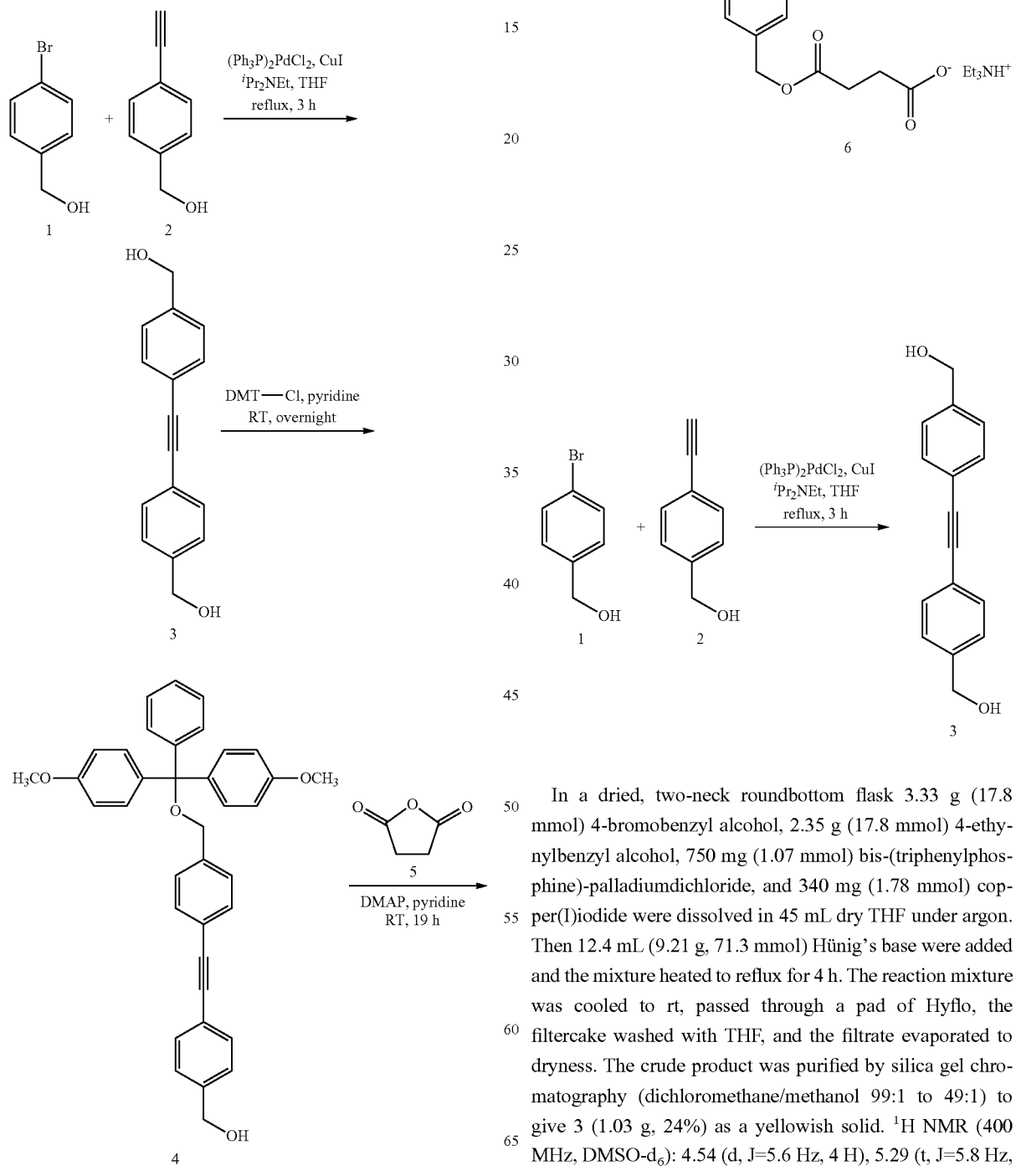

In a dried, two-neck roundbottom flask 3.33 g (17.8 mmol) 4-bromobenzyl alcohol, 2.35 g (17.8 mmol) 4-ethynylbenzyl alcohol, 750 mg (1.07 mmol) bis-(triphenylphosphine)-palladiumdichloride, and 340 mg (1.78 mmol) copper(I)iodide were dissolved in 45 mL dry THF under argon. Then 12.4 mL (9.21 g, 71.3 mmol) Hünig's base were added and the mixture heated to reflux for 4 h. The reaction mixture was cooled to rt, passed through a pad of Hyflo, the filtercake washed with THF, and the filtrate evaporated to dryness. The crude product was purified by silica gel chromatography (dichloromethane/methanol 99:1 to 49:1) to give 3 (1.03 g, 24%) as a yellowish solid. $^1$H NMR (400 MHz, DMSO-d$_6$): 4.54 (d, J=5.6 Hz, 4 H), 5.29 (t, J=5.8 Hz, 2 H), 7.37 (d, J=8.3 Hz, 4 H), 7.51 (d, J=8.1 Hz, 4 H).

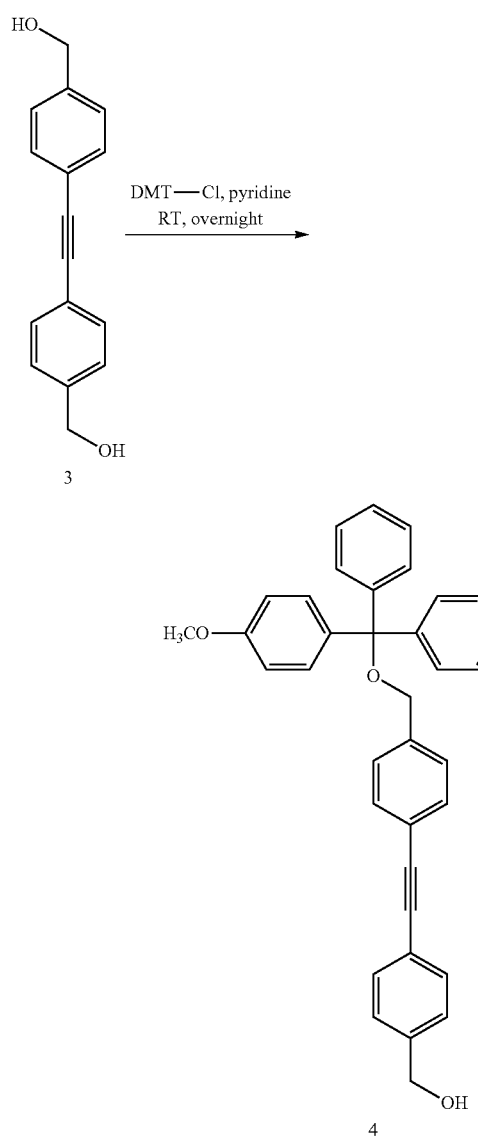

Diol 3 (960 mg, 4.03 mmol) was dissolved in 17 mL pyridine under argon and cooled to 0° C. Then 4,4'-dimethoxytriphenylchloromethane (DMT-Cl, 1.37 mg, 4.03 mmol) was added portionwise over 15 min. The solution was stirred overnight at ambient temperature. The reaction mixture was dissolved in 100 mL dichloromethane and extracted twice with 50 mL sat. aqueous NaHCO$_3$ each. The aqueous layers where reextracted with 100 mL dichloromethane. The combined organic layers were dried over Na$_2$SO$_4$ and evaporated to dryness. The crude product was coevaporated twice with toluene and purified by silica gel chromatography (heptane/ethyl acetate 3:1 to 2:1 with 0.1% Et$_3$N) to give 4 as a foam in 61% yield (1.32 g, 2.44 mmol). $^1$H NMR (400 MHz, CDCl$_3$): 1.67 (t br., 1 H), 3.72 (s, 6 H), 4.11 (s, 2 H), 4.64 (s br., 2 H) 6.76-6.79 (m, 4 H), 7.13-7.17 (m, 1 H), 7.21-7.34 (m, 10 H), 7.41-7.47 (m, 6 H).

To a solution of 1.30 g (2.40 mmol) 4 and 290 mg (2.40 mmol) N,N-dimethylaminopyridine (DMAP) in 12 mL dry pyridine under argon was added 480 mg (4.81 mmol) succinic anhydride (5). The reaction mixture was stirred at room temperature for 19 h and then quenched by addition of 1.5 mL water. Stirring was continued for 60 min before the reaction mixture was diluted with 150 mL dichloromethane and washed with 75 mL ice-cold 10% aqueous citric acid and water (2×75 mL). The aqueous layers were reextracted with 150 mL dichloromethane. The combined organic layers were dried over Na$_2$SO$_4$ and evaporated. The remaining oil was coevaporated twice with toluene and the crude product purified by silica gel chromatography (dichloromethane/methanol/triethylamine 97:2:1) to give 1.36 g (1.83 mmol, 76%) 6 as an off-white, sticky foam. $^1$H NMR (400 MHz, CDCl$_3$): 1.16 (t, J=7.3 Hz, 9H), 2.50 (t, J=6.5 Hz, 2 H), 2.60 (t, J=6.7 Hz, 2 H), 2.87 (q, J=7.3 Hz, 6 H), 3.72 (s, 6 H), 4.11 (s, 2 H), 5.05 (s, 2 H), 5.65 (s br., 1 H), 6.75-6.79 (m, 4 H), 7.13-7.16 (m, 1 H), 7.21-7.34 (m, 10 H), 7.41-7.44 (m, 6 H).

2.D. Synthesis of X058 Succinate Ester
Scheme 1: Overview of the synthesis of succinate 13
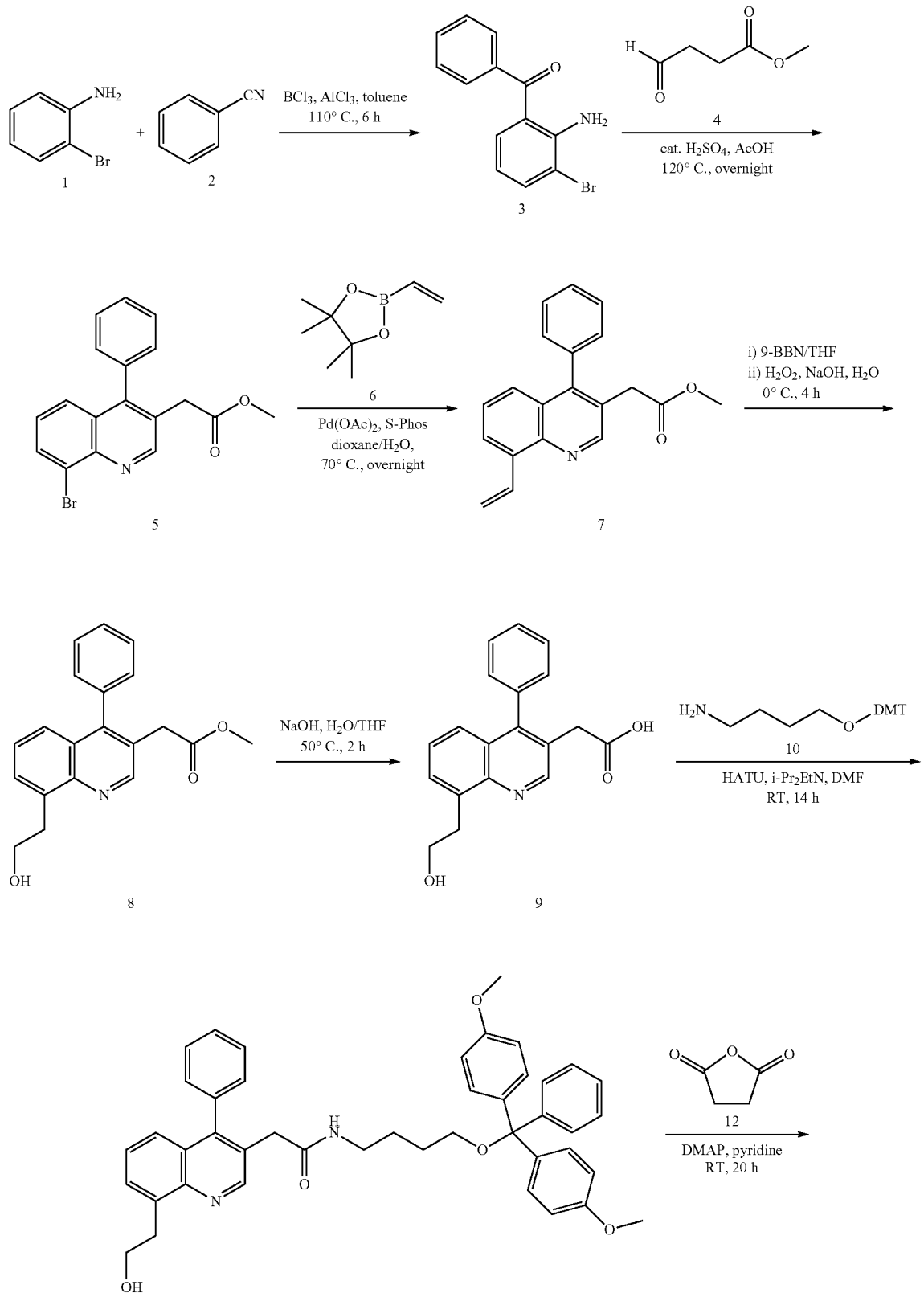

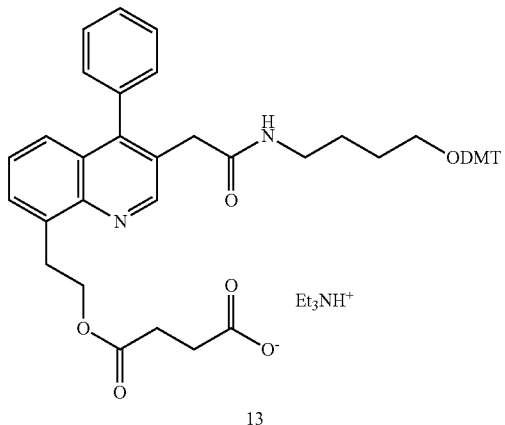

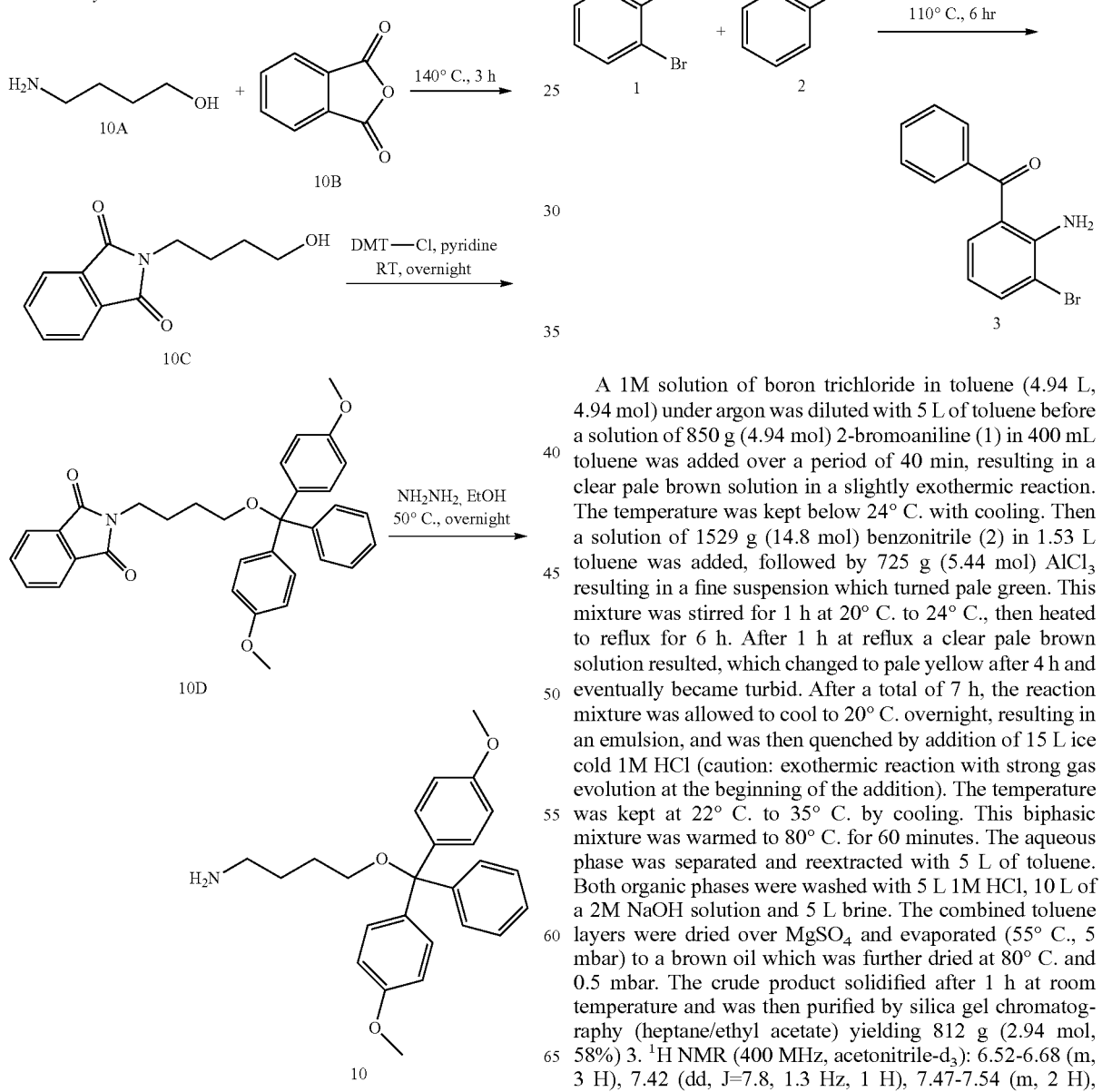

A 1M solution of boron trichloride in toluene (4.94 L, 4.94 mol) under argon was diluted with 5 L of toluene before a solution of 850 g (4.94 mol) 2-bromoaniline (1) in 400 mL toluene was added over a period of 40 min, resulting in a clear pale brown solution in a slightly exothermic reaction. The temperature was kept below 24° C. with cooling. Then a solution of 1529 g (14.8 mol) benzonitrile (2) in 1.53 L toluene was added, followed by 725 g (5.44 mol) AlCl$_3$ resulting in a fine suspension which turned pale green. This mixture was stirred for 1 h at 20° C. to 24° C., then heated to reflux for 6 h. After 1 h at reflux a clear pale brown solution resulted, which changed to pale yellow after 4 h and eventually became turbid. After a total of 7 h, the reaction mixture was allowed to cool to 20° C. overnight, resulting in an emulsion, and was then quenched by addition of 15 L ice cold 1M HCl (caution: exothermic reaction with strong gas evolution at the beginning of the addition). The temperature was kept at 22° C. to 35° C. by cooling. This biphasic mixture was warmed to 80° C. for 60 minutes. The aqueous phase was separated and reextracted with 5 L of toluene. Both organic phases were washed with 5 L 1M HCl, 10 L of a 2M NaOH solution and 5 L brine. The combined toluene layers were dried over MgSO$_4$ and evaporated (55° C., 5 mbar) to a brown oil which was further dried at 80° C. and 0.5 mbar. The crude product solidified after 1 h at room temperature and was then purified by silica gel chromatography (heptane/ethyl acetate) yielding 812 g (2.94 mol, 58%) 3. $^1$H NMR (400 MHz, acetonitrile-d$_3$): 6.52-6.68 (m, 3 H), 7.42 (dd, J=7.8, 1.3 Hz, 1 H), 7.47-7.54 (m, 2 H), 7.57-7.64 (m, 3 H), 7.66 (dd, J=7.8, 1.3 Hz, 1 H).

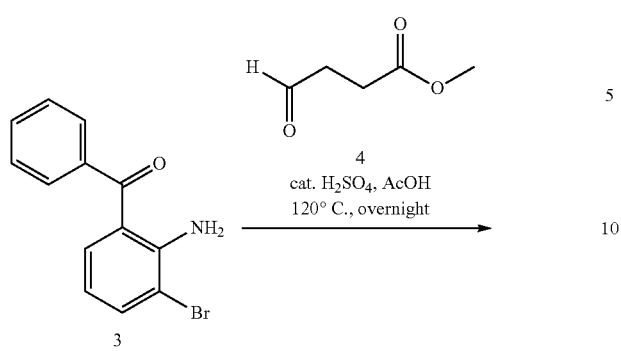
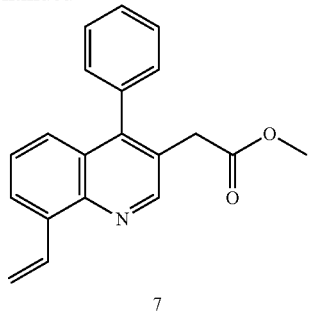

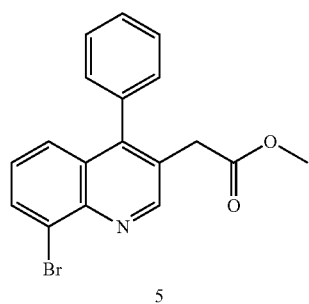

Under argon and with vigorous stirring 120 g (1033 mmol) methyl-4-oxobutanoate (4) was added at once to a solution of benzophenone 3 (233 g, 808 mmol) in 3.5 L glacial acid, resulting in a clear yellow solution. After addition of 2.5 mL (4.60 g, 46.9 mmol) concentrated sulfuric acid the color changed to pale red. The solution was heated to reflux overnight. The yellow solution was then cooled to room temperature and slowly poured in to an ice cold solution of 3 kg ammonium chloride in 10 L of water. The mixture was extracted twice with 5 L of dichloromethane each. The combined organic layers were extracted twice with 6 L saturated, aqueous NaHCO$_3$ solution (caution: gas evolution). The organic layer was dried over MgSO$_4$ and evaporated to dryness to give 338 g of crude product as pale yellow solid. This material was crystallized from 6 L heptane/ethyl acetate 4:1 yielding 136 g (382 mmol, 47%) 5 as colorless crystals. $^1$H NMR (400 MHz, acetonitrile-d$_3$): 3.58 (s, 3 H), 3.65 (s, 2 H), 7.25-7.31 (m, 2 H), 7.32-7.38 (m, 1 H), 7.40-7.45 (m, 1 H), 7.53-7.61 (m, 3 H), 8.07 (dd, J=7.6, 1.5 Hz, 1 H), 8.97 (s, 1 H).

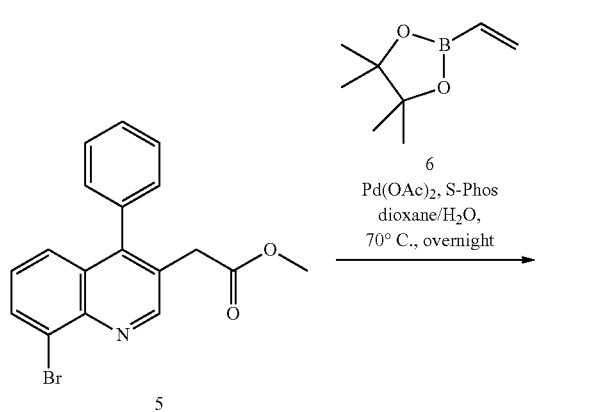

Phenylquinoline 5 (338 g, 949 mmol), vinyl boronate 6 (175 g, 1139 mmol), and potassium carbonate (266 g, 1926 mmol) were dissolved in 4.6 L 1,4-dioxane/water 1:1 under argon. The mixture was stirred for 5 min before adding 31.9 g (78 mmol)S—PHOS and 10.0 g (44.6 mmol) palladium (II)acetate. The mixture was warmed to 70° C. and stirred under argon for 5 h. The yellow mixture was then cooled to room temperature, diluted with 3 L tert.-butylmethylether and extracted twice with 2.5 L water, followed by 2 L brine. The aqueous phases were reextracted with 2 L tert.-butyl-methylether. The combined organic layers were dried with MgSO$_4$ and evaporated to dryness resulting in 348 g of a yellow oil. The crude product was purified by silica gel chromatography (heptane/ethyl acetate 4:1) giving 196 g (645 mmol, 68%) 7. $^1$H NMR (400 MHz, acetonitrile-d$_3$): 3.58 (s, 3 H), 3.63 (s, 2 H), 5.50 (dd, J=11.1, 1.5 Hz, 1 H), 6.04 (dd, J=17.9, 1.8 Hz, 1 H), 7.24-7.30 (m, 2 H), 7.35 (dd, J=8.3, 1.3 Hz, 1 H), 7.43-7.50 (m, 1 H), 7.51-7.59 (m, 3 H), 7.97 (dd, J=7.1, 1.0 Hz, 1 H), 8.06 (dd, J=17.9, 11.4 Hz, 1 H), 8.91 (s, 1 H)

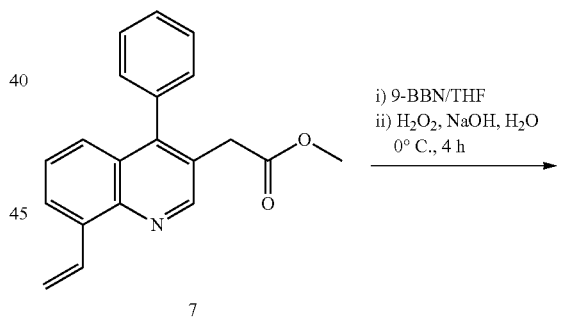

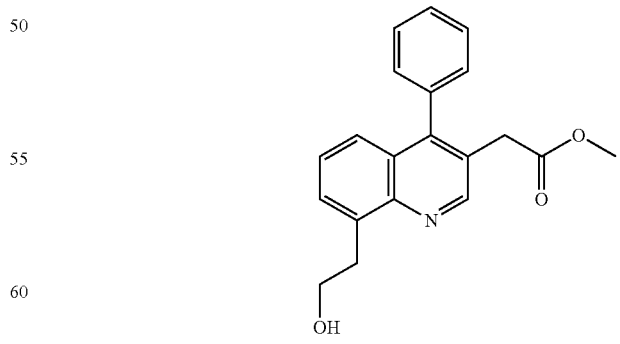

Vinyl-quinoline 7 (194 g, 640 mmol) was dissolved in 3 L THF under argon. The yellow solution was cooled to 15° C. and stirred for 10 min. Then 1.8 L of a 0.5M solution of 9-borabicylo[3.3.1]nonane in THF (900 mmol) was added dropwise during a period of 30 min at 15 to 18° C. Stirring was continued at room temperature overnight. After cooling to −50° C. (dry ice/acetone), 300 mL of a 30% hydrogen peroxide solution in water (2937 mmol) was added dropwise over 5 min (exothermic reaction), followed by the addition of 520 mL of a 3M aqueous NaOH solution (1560 mmol) which resulted in a yellow suspension. The reaction mixture was allowed to warm to 0 to 2° C. and then stirred for 3 h at this temperature. The yellow suspension was diluted with 3 L water and then extracted twice with 3 L ethyl acetate. Both organic layers were washed with 2 L water followed by 2 L brine. The combined organic phases were dried over $MgSO_4$ and evaporated to give a pale brown oil which was purified by silica gel chromatography (2-3% methanol in dichloromethane) yielding 163 g (507 mmol, 79%) 8. $^1$H NMR (400 MHz, DMSO-$d_6$): 3.42 (t, J=6.8 Hz, 2 H), 3.53 (s, 3 H), 3.65 (s, 2 H), 3.76-3.84 (m, 2 H), 4.54 (t, J=5.3 Hz, 1 H), 7.19 (dd, J=8.6, 1.5 Hz, 1 H), 7.21-7.25 (m, 2 H), 7.40 (dd, J=8.1, 7.1 Hz, 1 H), 7.49-7.59 (m, 3 H), 7.62 (d, J=7.1 Hz, 1 H), 8.91 (s, 1 H).

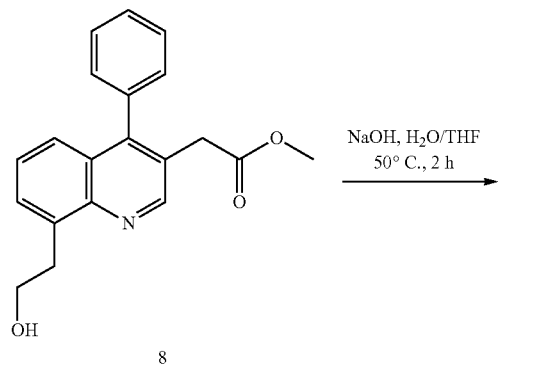

8

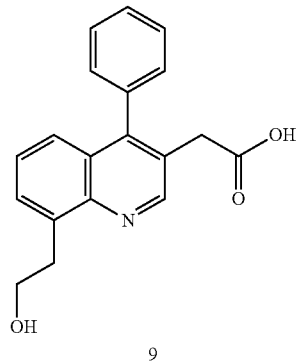

9

Methyl ester 8 (64.5 g, 201 mmol) was dissolved in 600 ml methanol. To this solution was added 450 mL of 0.5M aqueous NaOH (225 mmol). The turbid solution was stirred for 1 h at 50° C. Then the reaction mixture was evaporated to about 600 mL and the residue extracted twice with 800 mL tert.-butylmethylether each. The ether layers were washed with 300 mL water. The combined water phases were evaporated to dryness and the residue coevaporated twice with toluene to give 67 g of a beige solid. This material was dissolved in 1 L water and then 250 mL 1M aqueous citric acid was added carefully. The resulting suspension was stirred for 15 min and then extracted twice with 1 L ethyl acetate each. The organic layers were dried over MgSO4 and evaporated to dryness, yielding 54.1 g (176 mmol, 88%) acid 9 as beige solid. $^1$H NMR (400 MHz, $D_2O$): 3.80 (t, J=6.8 Hz, 2H), 3.82 (s, 2 H), 4.32 (t, J=6.8 Hz, 2 H), 7.58-7.64 (m, 2 H), 7.67-7.73 (m, 1 H), 7.73-7.79 (m, 1 H), 7.87-7.95 (m, 3 H), 7.97 (dd, J=7.1, 1.5 Hz, 1 H), 9.14 (s, 1 H).

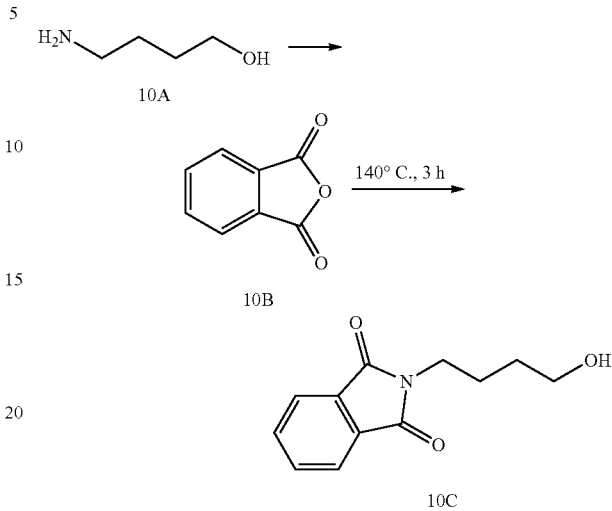

Phthalic anhydride (10B, 140 g, 945 mmol) was mixed with 4-amino-1-butanol (10A) and heated to 140° C. for 3 hours. Over the course of the reaction, the colorless suspension turned into clear, light yellow liquid. The mixture was allowed to cool to 80° C. and poured onto 3 kg of crushed ice. The ice mixture was extracted three times with 2 L of dichloromethane each. The combined organic phases were washed with 2 L saturated aqueous $NaHCO_3$, twice with 2 L water, and then with 2 L brine. The organic layer was dried over $MgSO_4$ and concentrated to give 195 g 10C (889 mmol, 95%) as beige solid This material was used in the next step without further purification. $^1$H NMR (400 MHz, acetonitrile-$d_3$): 1.48-1.58 (m, 2H), 1.67-1.78 (m, 2 H), 2.37 (t, J=5.3 Hz, 1 H), 3.50-3.57 (m, 2 H), 3.66 (t, J=7.3 Hz, 2 H), 7.75-7.85 (m, 4 H).

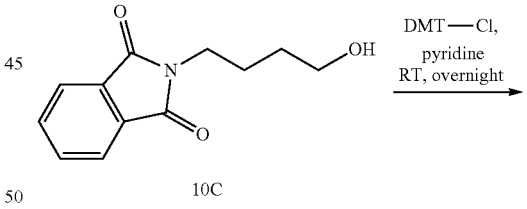

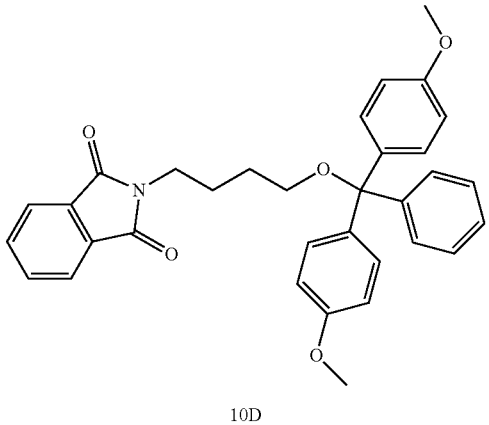

Phthalimide 10C (193 g, 880 mmol) was dissolved in 2.5 L pyridine under argon. Then 4,4'-dimethoxytriphenylchloromethane (DMT-Cl, 328 g, 968 mmol) was added in four portions over 10 min. The temperature of the reaction mixture rose from 23° C. to 26° C. and the yellow solution turned red, then back to yellow again. The solution was stirred overnight at ambient temperature. To quench the reaction 200 mL methanol was added 200 ml and the reaction mixture subsequently evaporated. The residue was dissolved in 5 L ethyl acetate and extracted twice with 5 L 5% aqueous citric acid, once with 5% aqueous NaHCO$_3$ and finally with 5 L brine. The aqueous layers where reextracted with 2 L ethyl acetate. The combined organic layers were dried over MgSO$_4$ and evaporated to dryness. The crude product, 495 g of a brown oil, was purified by silica gel chromatography (heptane/ethyl acetate 4:1 to 3:1). DMT-protected linker 10D was obtained in 81% yield (381 g, 730 mmol). $^1$H NMR (400 MHz, DMSO-d$_6$): 1.48-1.60 (m, 2 H), 1.62-1.74 (m, 2 H), 3.01 (t, J=6.1 Hz, 2 H), 3.56 (t, J=7.1 Hz, 2 H), 3.73 (s, 6 H), 6.82-6.88 (m, 4 H), 7.16-7.25 (m, 5 H), 7.25-7.31 (m, 2 H), 7.32-7.37 (m, 2 H), 7.78-7.87 (m, 4 H).

ther each. The organic phases were washed twice with 4 L 5% aqueous NaHCO$_3$, then with 4 L brine. The combined ether layers were dried over MgSO$_4$ and evaporated to give 226 g (578 mmol) 10 as a pale yellow oil which was used in the next step without additional purification. $^1$H NMR (400 MHz, acetonitrile-d$_3$): 1.42-1.54 (m, 2 H), 1.56-1.66 (m, 2 H), 2.61 (t, J=7.1 Hz, 2 H), 3.06 (t, J=6.6 Hz, 2 H), 3.78 (s, 6 H), 6.84-6.90 (m, 4 H), 7.19-7.26 (m, 1 H), 7.28-7.35 (m, 6 H), 7.41-7.47 (m, 2 H).

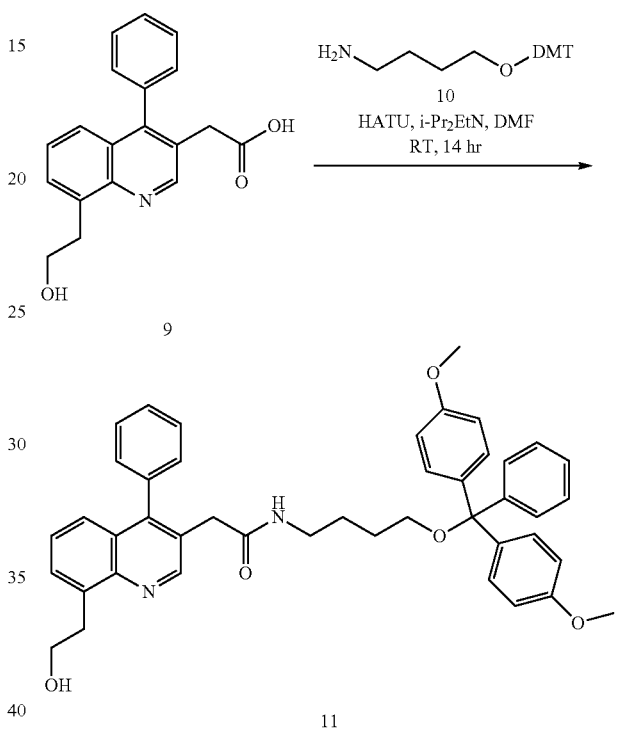

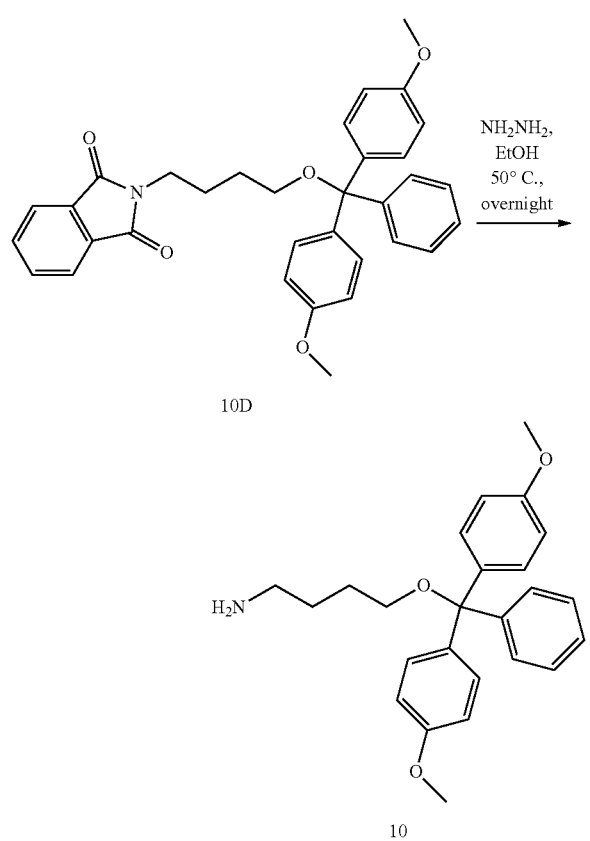

Phthalimide 10D (302 g, 579 mmol) was dissolved in 7 L ethanol at 50° C. and 320 mL (327 g, 3.57 mol) hydrazine hydrate was added. The reaction mixture was heated for 5 h to 50° C. The colorless suspension was cooled to room temperature and diluted with 15 L of water. The resulting emulsion was extracted twice with 6 L tert.-butylmethyle- Quinoline acetic acid 9 (92 g, 279 mmol) was dissolved in 1.5 L DMF under argon and a solution of 128 g (327 mmol) DMT-protected aminobutanol 10 in 1 L DMF followed by 146 mL (108 g, 838 mmol) ethyldiisopropylamine were added. Finally, 138 g (363 mmol) HATU was added to the pale yellow, turbid solution, resulting in an exothermic reaction. The temperature was kept below 25° C. with ice-bath cooling. The reaction mixture was stirred at room temperature for 6 h and then diluted with 3 L aqueous NaHCO$_3$. This mixture was extracted twice with 3 L tert.-butylmethylether each. The organic layers were washed with brine, combined, dried, and evaporated. The crude product (180 g pale brown oil) was purified by silica gel chromatography (dichloromethane/methanol/triethylamine 98:2: 0.25) to give 134 g (197 mmol, 70%) 11 as colorless foam. $^1$H NMR (400 MHz, DMSO-d$_6$): 1.35-1.57 (m, 4 H), 2.97 (t, J=6.3 Hz, 4 H), 3.34-3.48 (m, 4 H), 3.73 (s, 6 H), 3.76-3.83 (m, 2 H), 4.54 (t, J=5.3 Hz, 1 H), 6.84-6.90 (m, 4 H), 7.15-7.32 (m, 10 H), 7.34-7.41 (m, 3 H), 7.42-7.53 (m, 3 H), 7.58 (dd, J=6.8, 1.3 Hz, 1 H), 7.62 (t, J=4.8 Hz, 1 H), 8.83 (s, 1 H).

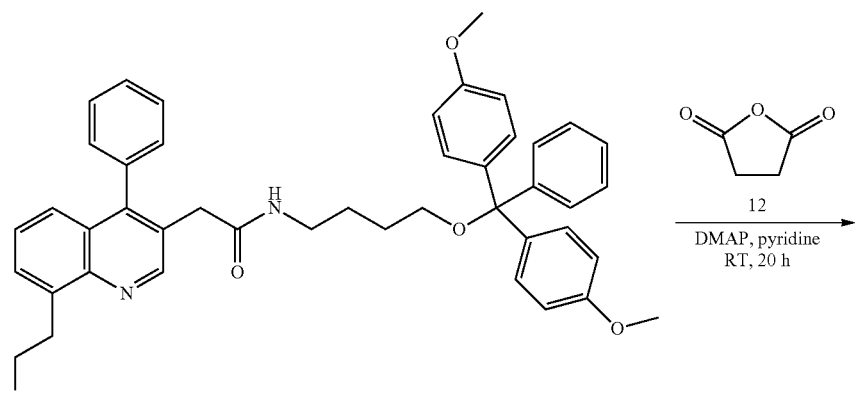

11

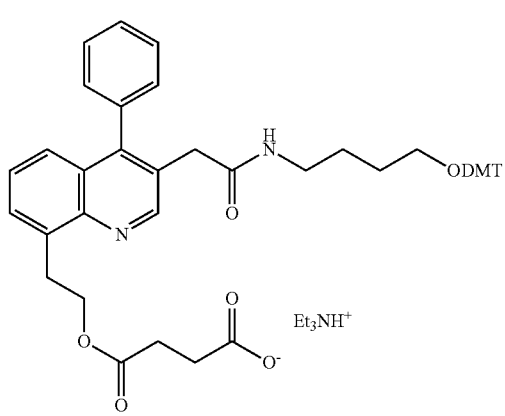

13

Alcohol 11 (43.8 g, 64.4 mmol) and N,N-dimethylaminopyridine (DMAP, 7.87 g, 64.4 mmol) were dissolved in 600 mL pyridine under argon. Then 12.9 g (128 mmol) succinic anhydride (12) was added and the reaction mixture stirred at room temperature for 20 h. The reaction was quenched by addition of 10 mL water and stirring continued for 30 min. The reaction mixture was diluted with 1200 mL dichloromethane and washed with 600 mL ice-cold 10% aqueous citric acid and twice with 600 mL water. The aqueous layers were reextracted with 600 mL dichloromethane. The combined organic layers were dried over $Na_2SO_4$ and evaporated. The crude product was coevaporated twice with 100 mL toluene and then purified by silica gel chromatography (dichloromethane/methanol/triethylamine 97:2:1 to 94:5:1) to give 57.5 g (quantitative) 13 as an off-white foam. $^1$H NMR (400 MHz, $CDCl_3$): 1.17 (t, J=7.3 Hz, 9 H), 1.46-1.60 (m, 4 H), 2.52 (t, J=7.2 Hz, 2 H), 2.61 (t, J=7.0 Hz, 2 H), 2.82 (q, J=7.3 Hz, 6 H), 3.06 (t, J=5.8 Hz, 2 H), 3.16 (q, J=6.3 Hz, 2 H), 3.49 (s, 2 H), 3.64 (t, J=6.8 Hz, 2 H), 3.80 (s, 6 H), 4.53 (t, J=7.5 Hz, 2 H), 5.38 (t br., 1 H), 6.08 (s br., 1 H), 6.80-6.84 (m, 4 H), 7.20 (t, J=7.3 Hz, 1 H), 7.26-7.38 (m, 10 H), 7.41-7.52 (m, 5 H), 7.59 (d, J=6.3 Hz, 1H), 8.92 (s, 1 H).

2.E. Synthesis of X067 Succinate Ester

Scheme 1: Overview of the synthesis of 6.

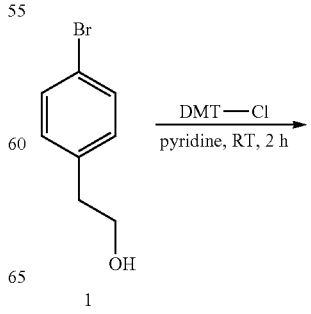

1

-continued

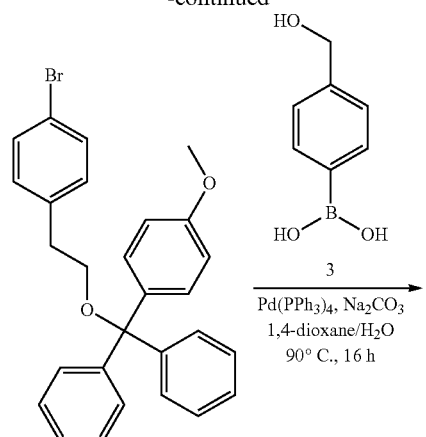

2

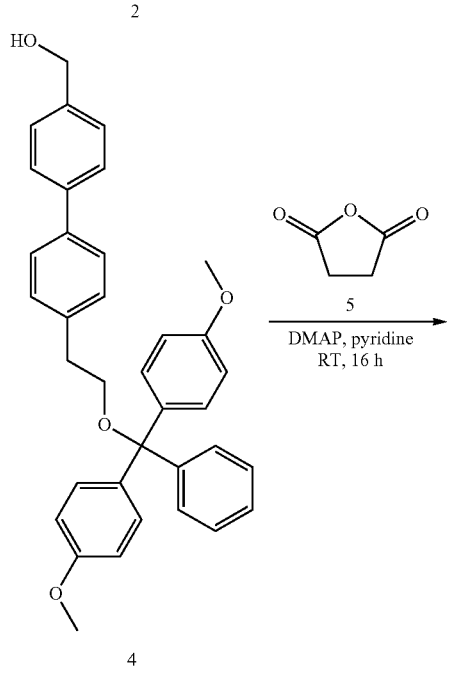

4

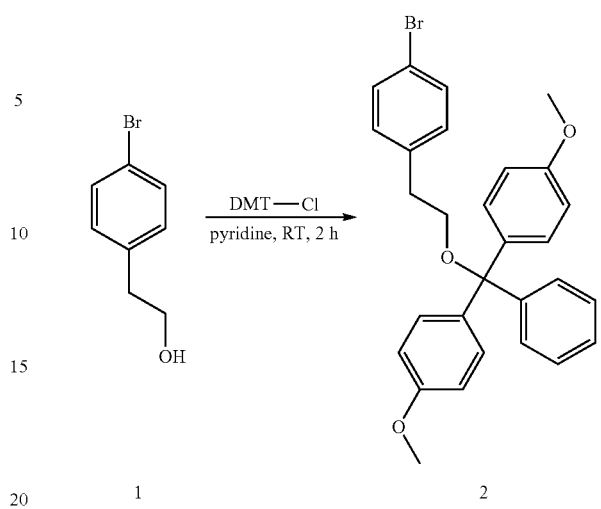

To a 250 mL roundbottom flask was added 2-(4-bromophenyl)ethanol 1 (1.00 g, 4.97 mmol), pyridine (25 mL) and 4,4'-(chloro(phenyl)methylene)bis(methoxybenzene) (DMT-Cl) (1.69 g, 4.97 mmol). The solution was stirred at rt for 2 h. 1 mL of MeOH was added, and the solution was stirred at rt for 10 min. The solution was then concentrated under vacuum, dissolved in 250 mL of EtOAc, and washed with 100 mL sat. aq. NaHCO$_3$, 100 mL of water, and 100 mL of brine. The organic layer was dried with sodium sulfate, concentrated under vacuum, and purified by silica gel chromatography (heptane/ethyl acetate/NEt$_3$) to give 2 (2.35 g, 94%) as a foamy solid. $^1$H NMR (400 MHz, DMSO-d$_6$): 2.80 (t, J=6.6 Hz, 2 H), 3.12 (t, J=6.6 Hz, 2 H), 3.72 (s, 6 H), 6.81-6.87 (m, 4 H), 7.12-7.22 (m, 7 H), 7.26 (d, J=4.0 Hz, 4 H), 7.44-7.50 (m, 2 H).

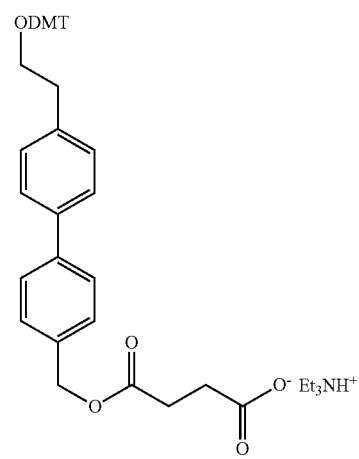

6

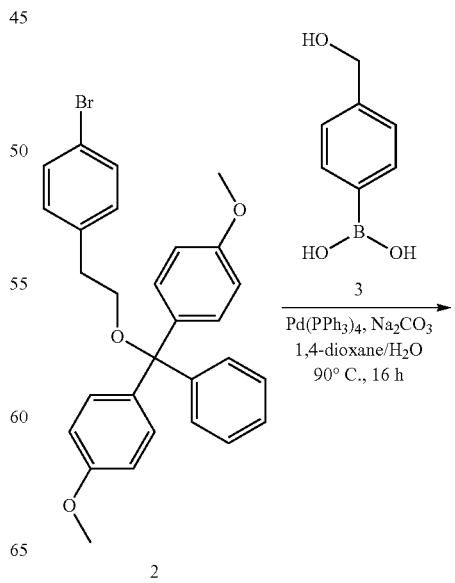

2

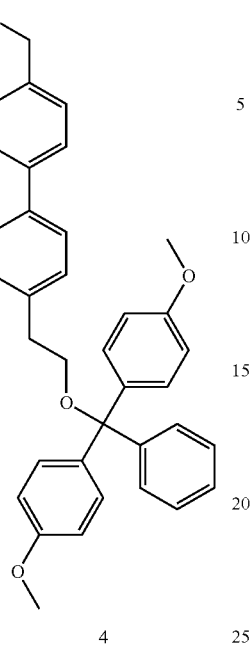

To a 40 mL glass vial with rubber septa was added 2 (0.70 g, 1.39 mmol), 4-(hydroxymethyl)phenylboronic acid 3 (0.25 g, 1.67 mmol), Pd(PPh$_3$)$_4$ (80 mg, 0.070 mmol), 2 M (aq) Na$_2$CO$_3$ (2.1 mL, 4.17 mmol), and 1,4-dioxane (7 mL). The contents were briefly placed under vacuum, and then placed under a nitrogen atmosphere. The vial was sealed and heated at 90° C. for 16 h. After cooling to rt, EtOAc was added and the mixture was washed with sat. aq. NaHCO$_3$ and brine. The organic portion was dried with sodium sulfate, concentrated under vacuum, and purified by silica gel chromatography (heptane/ethyl acetate/NEt$_3$) to give 3 (0.64 g, 87%) as a foamy solid. $^1$H NMR (400 MHz, DMSO-d$_6$): 2.86 (t, J=6.6 Hz, 2 H), 3.16 (t, J=6.6 Hz, 2 H), 3.72 (s, 6 H), 4.52 (d, J=6.1 Hz, 2 H), 5.19 (t, J=5.8 Hz, 1 H), 6.81-6.87 (m, 4 H), 7.18 (d, J=9.1 Hz, 4 H), 7.20-7.22 (m, 1 H), 7.24-7.33 (m, 6 H), 7.38 (d, J=8.6 Hz, 2 H), 7.57 (d, J=8.1 Hz, 2 H), 7.60 (d, J=8.1 Hz, 2 H).

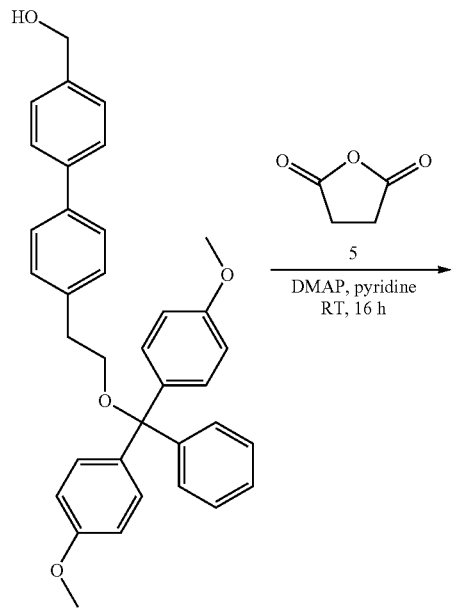

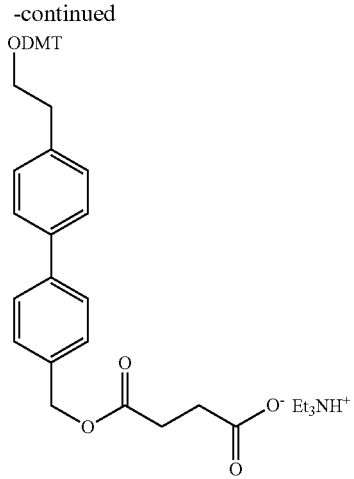

To a solution of 3.68 g (6.93 mmol) 4 and 847 mg (6.93 mmol) N,N-dimethylaminopyridine (DMAP) in 35 mL dry pyridine under argon was added 1.39 g (13.9 mmol) succinic anhydride (5). The reaction mixture was stirred at room temperature for 16 h and then 2.5 mL water was added. Stirring was continued for 30 min. The reaction mixture was taken up in 300 mL dichloromethane and washed with 150 mL ice-cold 10% aqueous citric acid and water (2×150 mL). The aqueous layers were reextracted with 150 mL dichloromethane. The combined organic layers were dried over Na$_2$SO$_4$ and evaporated. The remaining oil was coevaporated twice with toluene and the crude product purified by silica gel chromatography (dichloromethane/methanol/triethylamine 97:2:1) to give 4.68 g (6.39 mmol, 92%) 6 as an off-white foam. $^1$H NMR (400 MHz, CDCl$_3$): 1.14 (t, J=7.4 Hz, 9 H), 2.51 (t, J=6.8 Hz, 2 H), 2.60 (t, J=6.5 Hz, 2 H), 2.82-2.90 (m, 8 H), 3.24 (t, J=6.8 Hz, 2 H), 3.70 (s, 6 H), 5.08 (s, 2 H), 6.69-6.73 (m, 4 H), 7.08-7.21 (m, 9 H), 7.28-7.35 (m, 4 H), 7.42 (d, J=8.1 Hz, 2 H), 7.48 (d, J=8.0 Hz, 2 H), 8.04 (s br., 1 H).

2. F. Synthesis of X069 Succinate Ester

Scheme 1: Overview of the synthesis of succinate 7

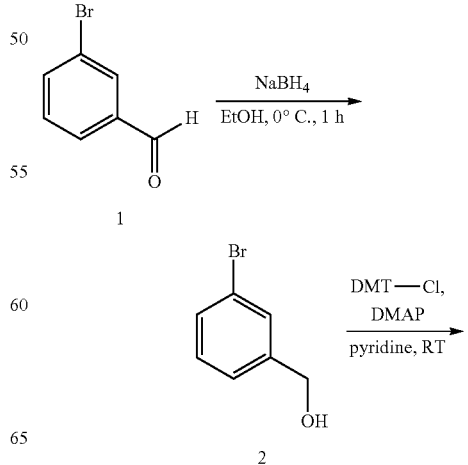

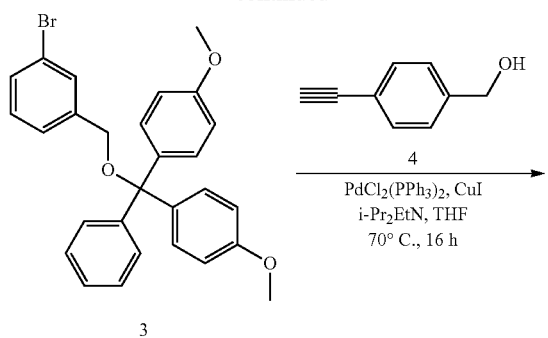

3

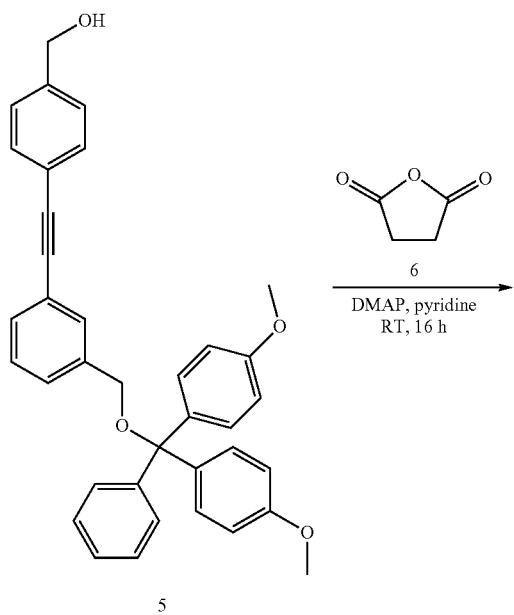

5

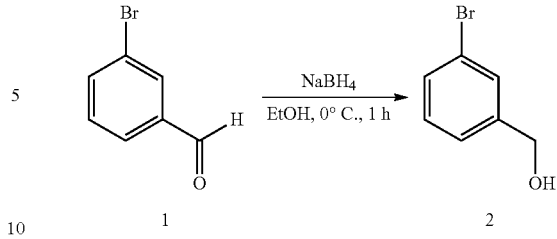

Compound 2 was prepared according to *Eur. J. Org. Chem,* 2002, 19, 3326-3335. In a 250 mL roundbottom was added 3-bromobenzaldehyde 1 (10.0 g, 54.0 mmol) and EtOH (25 mL). The solution was cooled to 0° C. in an ice-water bath, sodium borohydride (1.11 g, 29.5 mmol) was added, and the mixture was stirred at 0° C. for 1 h. Sodium sulfate decahydrate was added, and the reaction was stirred at rt for 1 h to quench the borohydride. Diethyl ether was added, and the mixture was washed with water. The organic layer was dried with sodium sulfate and concentrated under vacuum to give 2 (9.50 g, 94%) as a clear oil. $^1$H NMR (400 MHz, CDCl$_3$): 2.34 (br. s, 1 H), 4.61 (br. s, 2 H), 7.13-7.33 (m, 2 H), 7.40 (d, J=7.6 Hz, 1 H), 7.49 (s, 1 H).

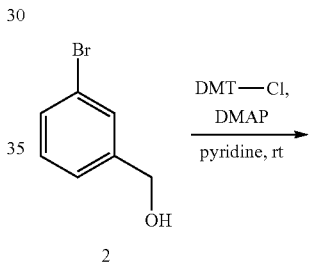

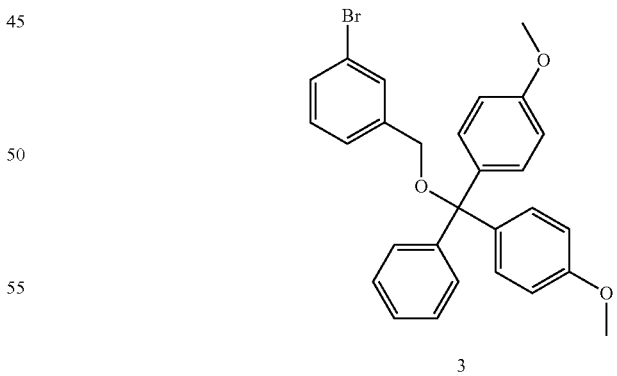

To a 500 mL roundbottom flask was added 2 (9.50 g, 50.8 mmol), 4,4'-(chloro(phenyl)methylene)bis(methoxybenzene) (DMT-Cl) (17.2 g, 50.8 mmol), DMAP (0.310 g, 0.050 mmol), and pyridine (200 mL). The solution was placed under an atmosphere of nitrogen, and stirred overnight at rt. EtOAc was added, and the solution was washed with sat. aq. NaHCO₃. The organic layer was concentrated under vacuum, and purified by silica gel chromatography (heptane/ethyl acetate/NEt₃) to give 3 (23.3 g, 94%) as a foamy solid. ¹H NMR (400 MHz, CDCl₃): 3.74 (s, 6 H), 4.12 (s, 2 H), 6.92 (dd, J=8.0 Hz, 4 H), 7.21-7.48 (m, 13 H).

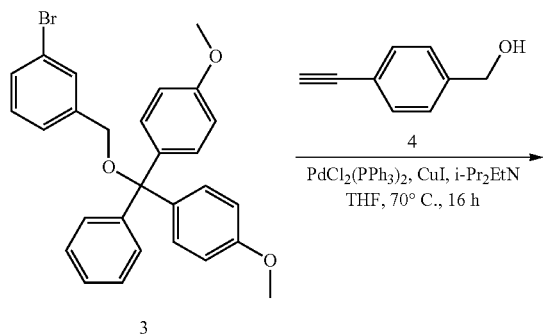

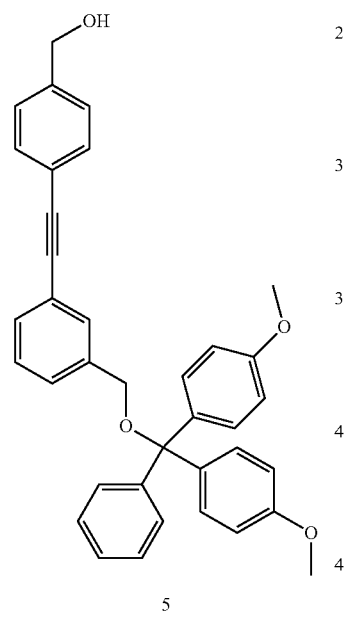

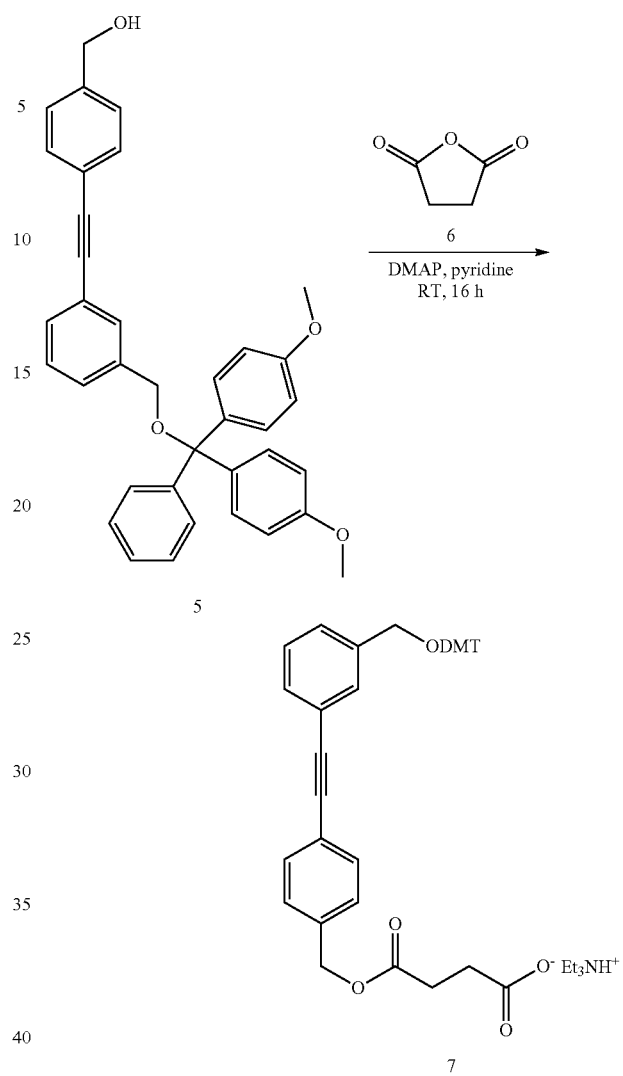

To a 40 mL glass vial with rubber septum was added 3 (1.00 g, 2.04 mmol), 4-ethynylbenzyl alcohol 4 (0.405 g, 3.06 mmol), PdCl₂(PPh₃)₂ (86 mg, 0.123 mmol), CuI (39 mg, 0.204 mmol), iPr₂EtN (1.06 g, 8.17 mmol) and THF (7 mL). The contents were briefly placed under vacuum, and then placed under a nitrogen atmosphere. The vial was sealed and heated at 70° C. for 16 h. After cooling to rt, the mixture was filtered through celite, washing with EtOAc, and the filtrated was concentrated under vacuum. The residue was purified by silica gel chromatography (heptane/ethyl acetate/NEt₃) to give 5 (0.680 g, 62%) as a foamy solid. ¹H NMR (400 MHz, CDCl₃): 3.74 (s, 6 H), 4.12 (s, 2 H), 4.53 (d, J=4.0 Hz, 2 H), 5.29 (t, J=4.0 Hz, 1 H), 6.93 (dd, J=8.0 Hz, 4 H), 7.19-7.58 (m, 17 H).

To a solution of 4.55 g (8.42 mmol) 5 and 1.03 g (8.42 mmol) N,N-dimethylaminopyridine (DMAP) in 42 mL dry pyridine under argon was added 1.68 g (16.8 mmol) succinic anhydride (6). The reaction mixture was stirred at room temperature for 16 h and then 2.5 mL water was added. Stirring was continued for 30 min. The reaction mixture was taken up in 300 mL dichloromethane and washed with 150 mL ice-cold 10% aqueous citric acid and water (2×150 mL). The aqueous layers were reextracted with 150 mL dichloromethane. The combined organic layers were dried over Na₂SO₄ and evaporated. The remaining oil was coevaporated twice with toluene and the crude product purified by silica gel chromatography (dichloromethane/methanol/triethylamine 97:2:1) to give 5.81 g (7.83 mmol, 93%) 7 as an off-white, sticky foam. ¹H NMR (400 MHz, CDCl₃): 1.14 (t, J=7.4 Hz, 9 H), 2.50 (t, J=6.5 Hz, 2 H), 2.60 (t, J=6.6 Hz, 2 H), 2.86 (q, J=7.3 Hz, 6 H), 3.72 (s, 6 H), 4.09 (s, 2 H), 5.05 (s, 2 H), 5.95 (s br., 1 H), 6.75-6.79 (m, 4 H), 7.15 (tt, J=7.3, 1.5 Hz, 1 H), 7.21-7.36 (m, 11 H), 7.42-7.45 (m, 5 H).

2.G. General Procedure for the High Density Loading of Controlled Pore Glass Supports with PAZ Ligand Succinates

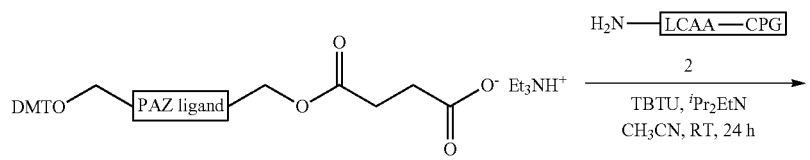

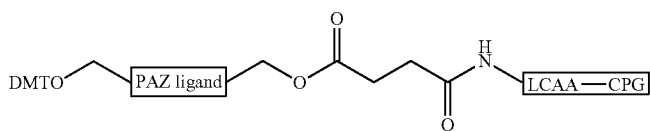

In an Erlenmeyer flask 1.00 mmol PAZ ligand succinate salt 1 was dissolved in 50 mL dry acetonitrile under argon. To this solution 353 mg (1.10 mmol) O-(1H-benzo-1,2,3-triazol-1-yl)-N,N,N',N'-tetramethyl-uronium tetrafluoroborate (TBTU) was added and the solution shaken for 10 min. Then 10 g long chain alkylamine controlled pore glass (LCAA/CNA-600-CPG, PrimeSynthesis, 2) was added and the reaction mixture gently agitated for 5 min. Finally, 0.685 mL (517 mg, 4.00 mmol) Hünig's base was added and the flask gently shaken for 24 h on an orbital shaker. Loading density was assessed by detritylating an aliquote of the CPG (3-5 mg CPG washed with acetonitrile, dried in vacuo, added to 25 mL 3% dichloroacetic acid in dichloromethane (v/v), absorbance at 504 nm determined). If loading density was in the desired range (60-90 micromol/g), the CPG was filtered off and washed extensively with acetonitrile. Underivatized amino groups were capped by treating the CPG with x mL each of a mixture of acetic anhydride/2,6-lutidine/THF 1:1:8 (v/v/v) and a solution of 1-methylimidazole in THF 16:84 (v/v). The mixture was gently shaken for 15 min at room temperature. Then the CPG was filtered off, washed with acetonitrile and dried under vacuum overnight. Loading density was determined again as above. Loading yields for the succinates in examples 1-6 were in the range of 64-75 micromol/g.

2.H. Synthesis of X050, X059, X061, X062, X065, X068 Alcohols and Succinate Esters Prepared in an Analogous Manner to X027

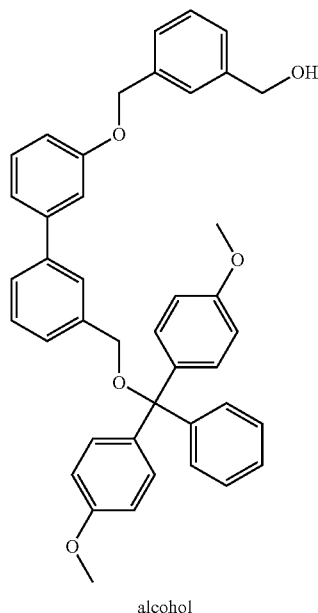

X050 alcohol

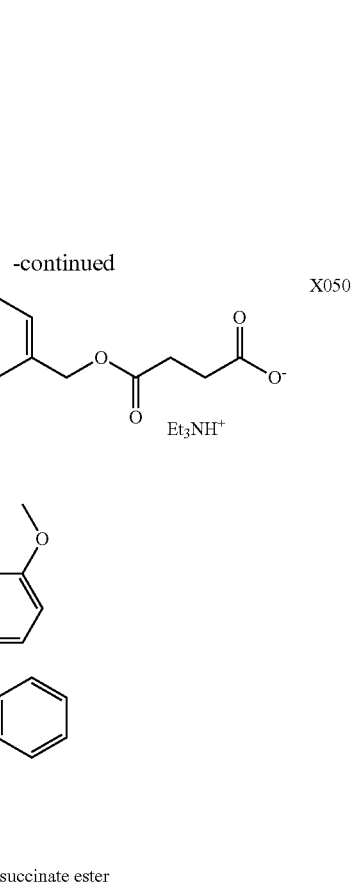

-continued

X050 succinate ester

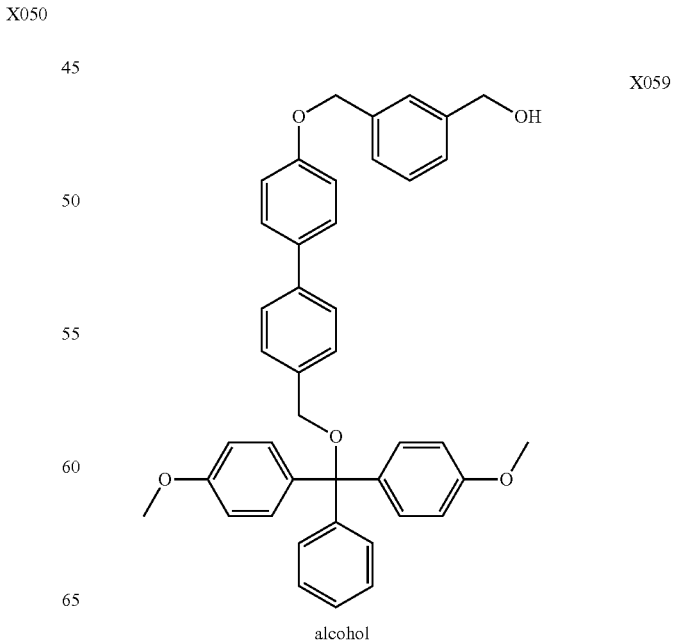

X059 alcohol

X059
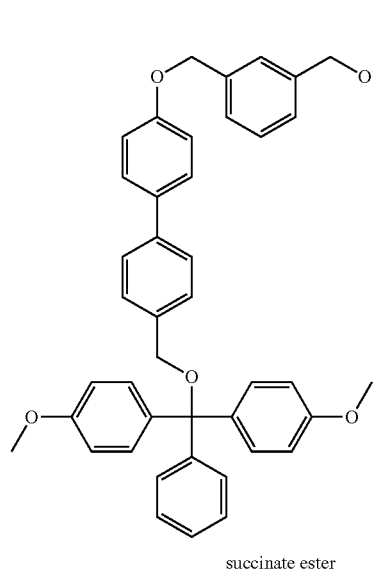
succinate ester
X061
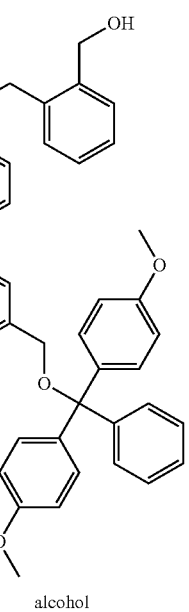
alcohol
X060
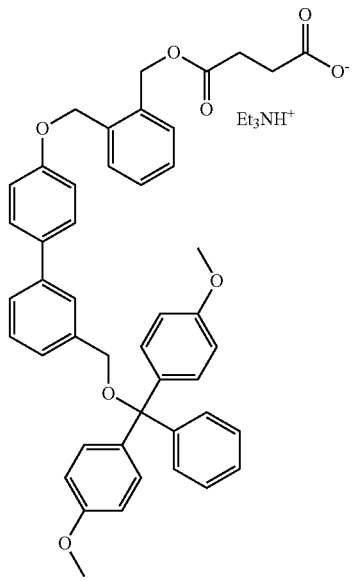
succinate ester
X062
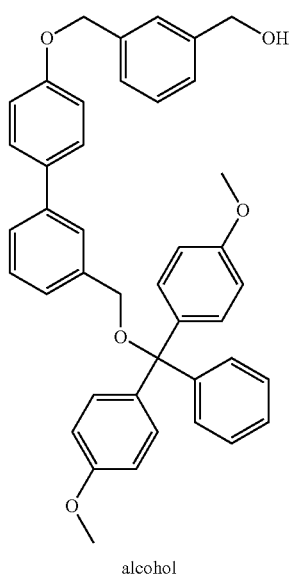
alcohol

217
-continued
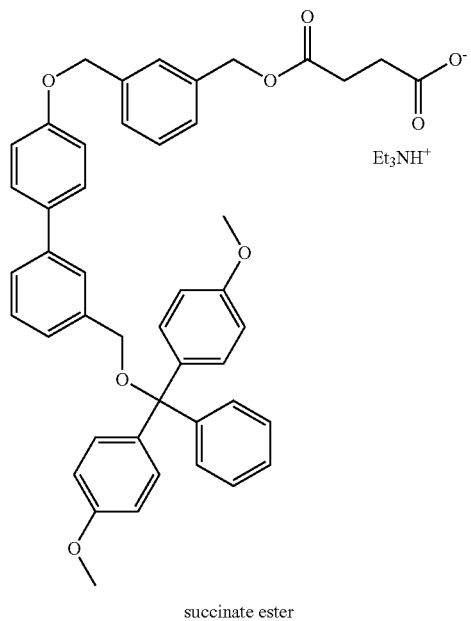
X062
succinate ester
X065
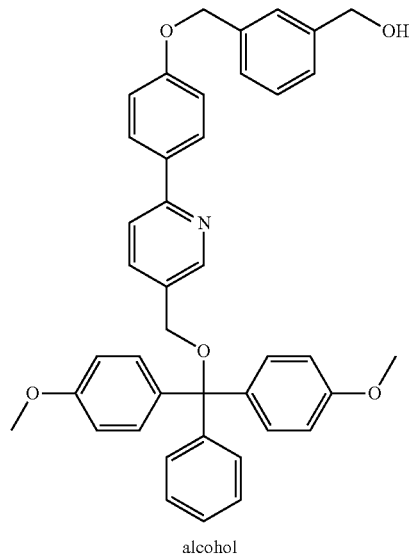
alcohol
218
-continued
X065
succinate ester
X068
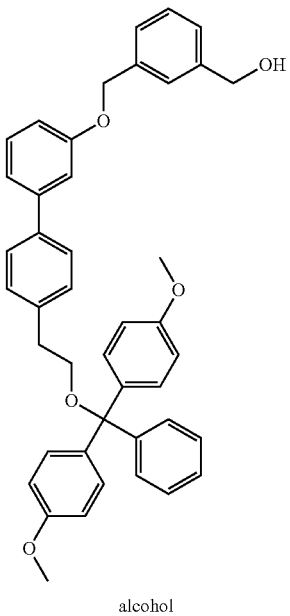
alcohol

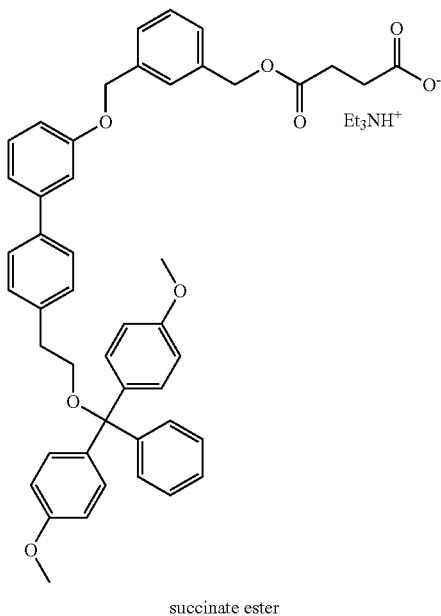

succinate ester

X050 alcohol: $^1$H NMR (400 MHz, DMSO-d$_6$) δ ppm 3.73 (s, 6 H) 4.19 (s, 2 H) 4.51 (d, J=5.56 Hz, 2 H) 5.17 (s, 2 H) 5.21 (t, J=5.81 Hz, 1 H) 6.89-6.95 (m, 4 H) 7.01 (dd, J=8.08, 2.02 Hz, 1 H) 7.19-7.30 (m, 4 H) 7.30-7.40 (m, 9 H) 7.40-7.49 (m, 5 H) 7.53 (s, 1 H) 7.57 (d, J=7.58 Hz, 1 H). MS (ESI–) m/z: calcd for C$_{42}$H$_{38}$O$_5$ 622.3. found 667.9 [MH$^-$+formic acid].

X059 alcohol: $^1$H NMR (400 MHz, DMSO-d$_6$) δ ppm 3.74 (s, 6 H) 4.10 (s, 2 H) 4.52 (s, 2 H) 5.15 (s, 2 H) 5.22 (br. s., 1 H) 6.90-6.96 (m, 4 H) 7.07-7.13 (m, 2 H) 7.22-7.30 (m, 2 H) 7.30-7.38 (m, 8 H) 7.39-7.48 (m, 5 H) 7.60 (d, J=8.08 Hz, 4 H). MS (ESI–) m/z: calcd for C$_{42}$H$_{38}$O$_5$ 622.3. found 621.1 [MH$^-$].

X061 alcohol: $^1$H NMR (400 MHz, DMSO-d$_6$) δ ppm 3.74 (s, 6 H) 4.17 (s, 2 H) 4.63 (d, J=5.05 Hz, 2 H) 5.17-5.22 (m, 3 H) 6.93 (d, J=8.59 Hz, 4 H) 7.11 (d, J=8.59 Hz, 2 H) 7.22-7.37 (m, 10 H) 7.40-7.52 (m, 7 H) 7.58 (d, J=8.59 Hz, 2 H). MS (ESI–) m/z: calcd for C$_{42}$H$_{38}$O$_5$ 622.3. found 667.6 [MH$^-$+formic acid].

X062 alcohol: $^1$H NMR (400 MHz, DMSO-d$_6$) δ ppm 3.74 (s, 6 H) 4.16 (s, 2 H) 4.52 (d, J=6.06 Hz, 2 H) 5.14 (s, 2 H) 5.19-5.23 (m, 1 H) 6.90-6.95 (m, 4 H) 7.07-7.12 (m, 2 H) 7.21-7.29 (m, 2 H) 7.30-7.38 (m, 9 H) 7.39-7.48 (m, 5 H) 7.49-7.53 (m, 1 H) 7.55-7.60 (m, 2 H). MS (ESI–) m/z: calcd for C$_{42}$H$_{38}$O$_5$ 622.3. found 667.7 [MH$^-$+formic acid].

X065 alcohol: $^1$H NMR (400 MHz, DMSO-d$_6$) δ ppm 3.75 (s, 6 H) 4.16 (s, 2 H) 4.52 (d, J=6.06 Hz, 2 H) 5.17 (s, 2 H) 5.21 (t, J=5.81 Hz, 1 H) 6.93 (d, J=8.59 Hz, 4 H) 7.12 (d, J=9.09 Hz, 2 H) 7.22-7.39 (m, 10 H) 7.41-7.47 (m, 3 H) 7.78 (dd, J=8.34, 2.27 Hz, 1 H) 7.85-7.90 (m, 1 H) 8.03 (d, J=9.09 Hz, 2 H) 8.55 (d, J=1.52 Hz, 1 H). MS (ESI+) m/z: calcd for C$_{41}$H$_{37}$NO$_5$ 623.3. found 624.7 [MH$^+$].

X068 alcohol: $^1$H NMR (400 MHz, DMSO-d$_6$) δ ppm 2.87 (t, J=6.57 Hz, 2 H) 3.16 (t, J=6.57 Hz, 2 H) 3.72 (s, 6 H) 4.51 (d, J=5.56 Hz, 2 H) 5.17 (s, 2 H) 5.21 (t, J=5.81 Hz, 1 H) 6.85 (d, J=8.59 Hz, 4 H) 6.99 (dd, J=8.08, 1.52 Hz, 1 H) 7.18 (d, J=9.09 Hz, 2 H) 7.20-7.38 (m, 13 H) 7.43 (s, 1 H) 7.59 (d, J=8.59 Hz, 2 H). MS (ESI+) m/z: calcd for C$_{43}$H$_{40}$O$_5$ 636.3. found 659.7 [M+Na].

2.I. Synthesis of X060 and X064 Alcohols and Succinate Esters

Prepared in an analogous manner to X067

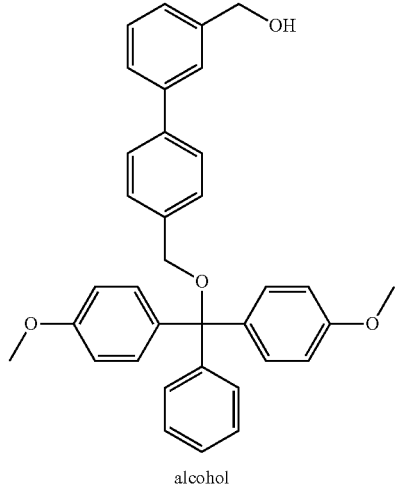

alcohol X060

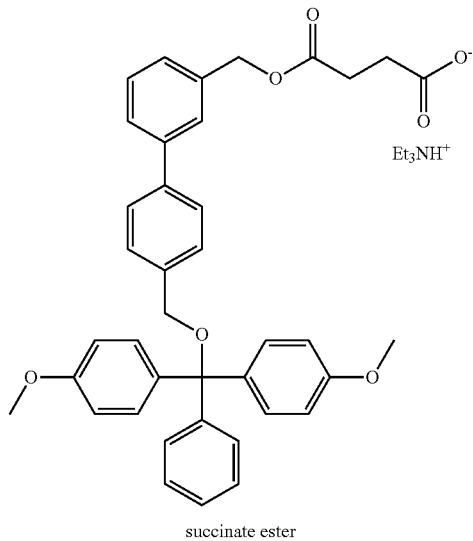

succinate ester X060

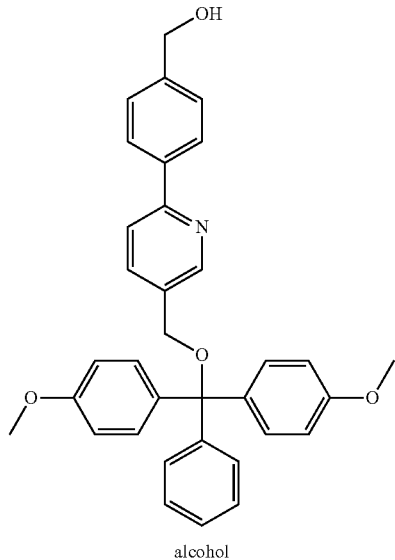

alcohol X064

221

-continued

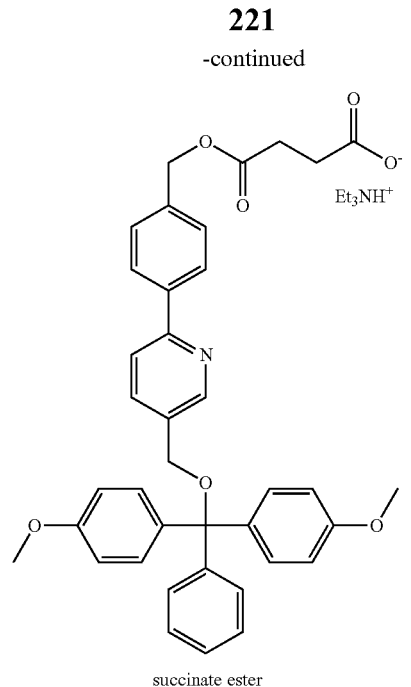

succinate ester

X060 alcohol: $^1$H NMR (400 MHz, DMSO-$d_6$) δ ppm $^1$H NMR (400 MHz, DMSO-$d_6$) δ ppm 3.75 (s, 6 H) 4.12 (s, 2 H) 4.57 (d, J=5.56 Hz, 2 H) 5.20-5.26 (m, 1 H) 6.90-6.96 (m, 4 H) 7.22-7.28 (m, 1 H) 7.29-7.38 (m, 7 H) 7.39-7.48 (m, 5 H) 7.53 (d, J=8.08 Hz, 1 H) 7.60 (s, 1 H) 7.64 (d, J=8.08 Hz, 2 H). MS (ESI+) m/z: calcd for $C_{35}H_{32}O_4$ 516.2. found 303.4 [DMT$^+$].

X064 alcohol: $^1$H NMR (400 MHz, DMSO-$d_6$) δ ppm 3.75 (s, 6 H) 4.18 (s, 2 H) 4.56 (d, J=5.56 Hz, 2 H) 5.24 (t, J=5.81 Hz, 1 H) 6.93 (d, J=9.09 Hz, 4H) 7.25 (t, J=7.33 Hz, 1 H) 7.32 (d, J=9.09 Hz, 4 H) 7.34-7.39 (m, 2 H) 7.44 (t, J=8.08 Hz, 4 H) 7.82 (dd, J=8.34, 2.27 Hz, 1 H) 7.93 (d, J=8.08 Hz, 1 H) 8.04 (d, J=8.08 Hz, 2 H) 8.59 (d, J=2.02 Hz, 1 H). MS (ESI+) m/z: calcd for $C_{34}H_{31}NO_4$ 517.2. found 518.8 [MH$^+$].

2.J. Synthesis of X063 Succinate Ester

222

-continued

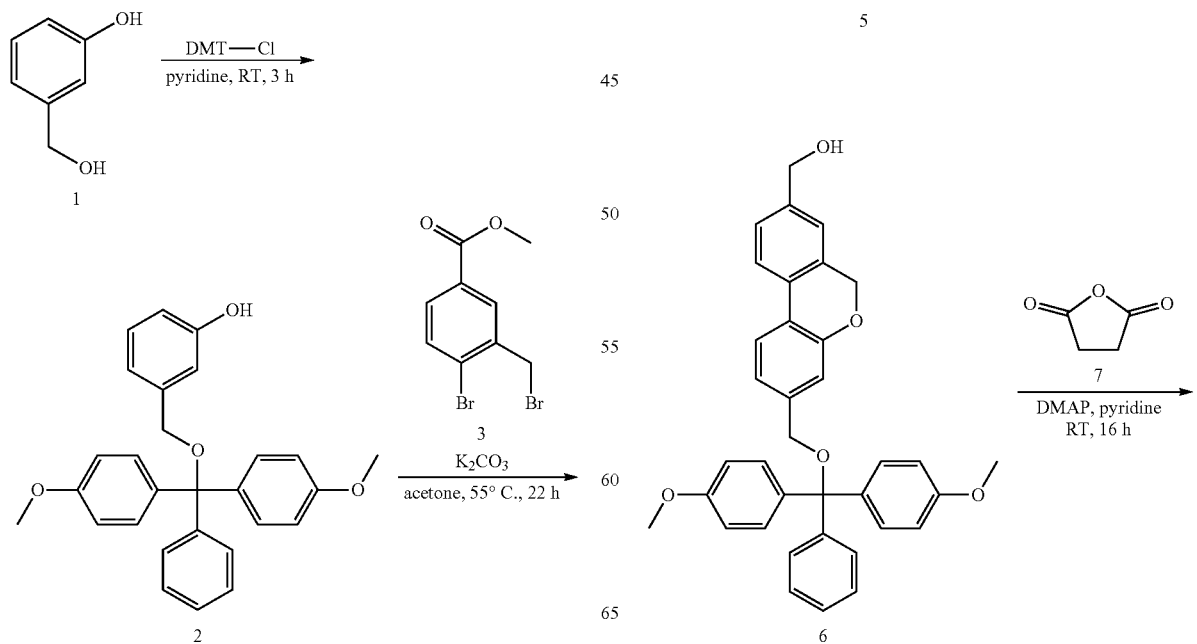

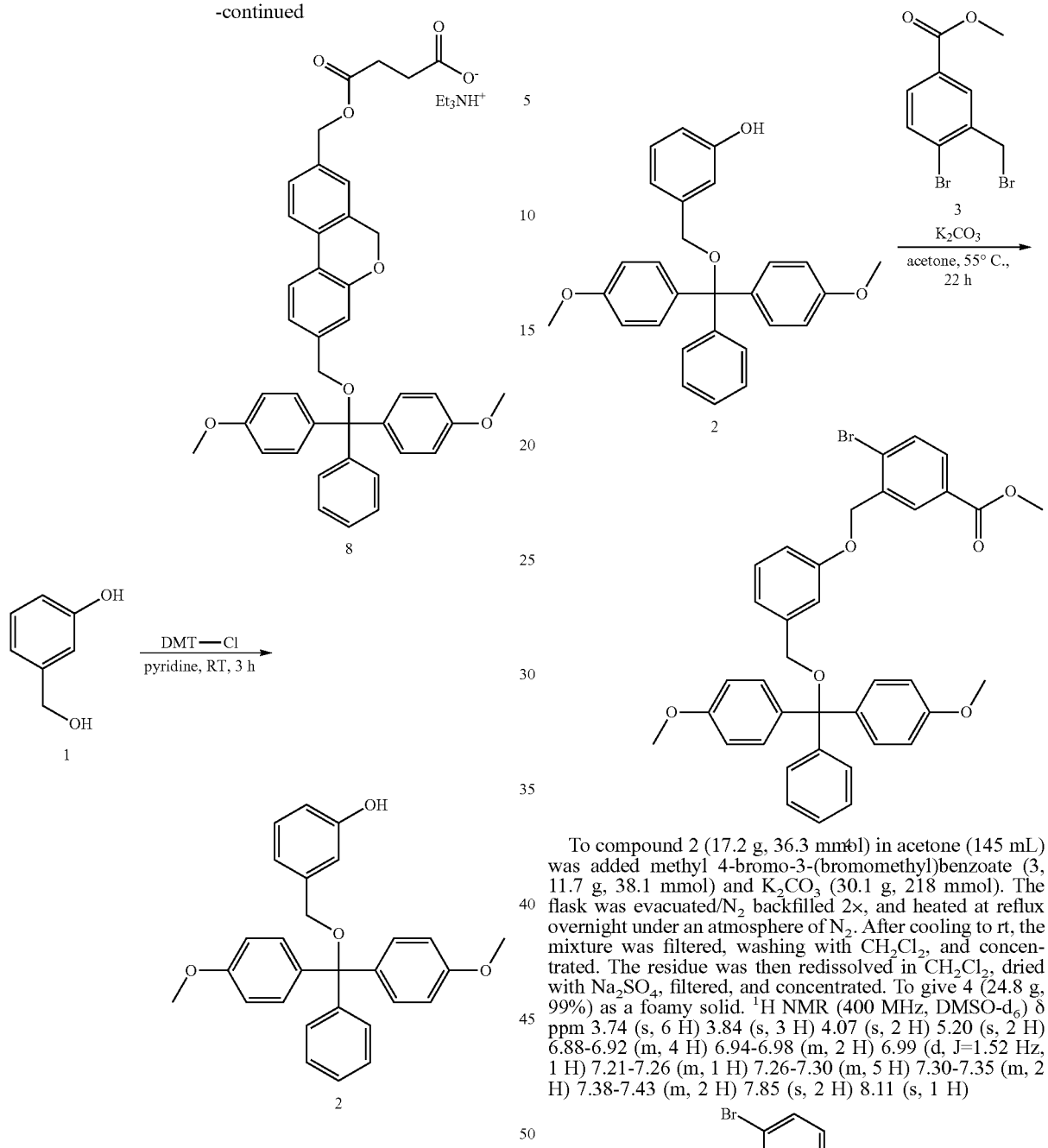
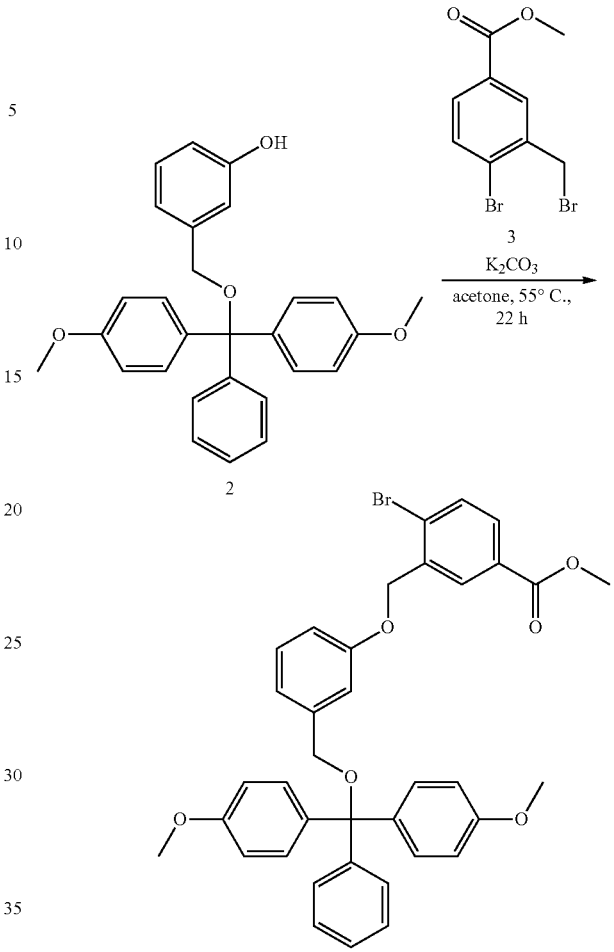
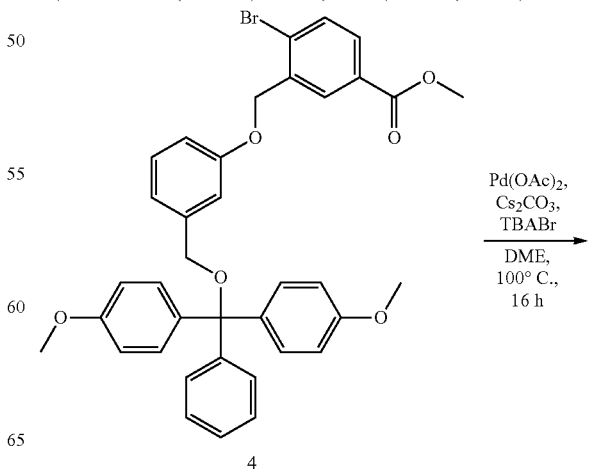

3-(hydroxymethyl)phenol (1, 6.21 g, 50.0 mmol) was dissolved in pyridine (100 mL) and cooled to 0° C. DMT-Cl (16.9 g, 50 mmol) was added and the solution was stirred at rt for 2 h. 500 mL of EtOAc was added, the solution was washed 1× each with 400 mL sat. aq. NaHCO$_3$, water, and brine. The organic portion was dried with Na$_2$SO$_4$, filtered, and concentrated under vacuum. The mixture was re-dissolved in acetone/toluene and concentrated, repeating this process 4-times. The residue was then concentrated under vacuum overnight to give 2 (20.9 g, 98%) as a foamy solid.

$^1$H NMR (400 MHz, DMSO-d$_6$) δ ppm 3.74 (s, 6 H) 3.97 (s, 2 H) 6.66 (dd, J=8.08, 1.52 Hz, 1 H) 6.72 (d, J=7.58 Hz, 1 H) 6.83 (d, J=1.52 Hz, 1 H) 6.89-6.95 (m, 4 H) 7.12 (t, J=7.83 Hz, 1 H) 7.17 (d, J=7.58 Hz, 1 H) 7.27-7.32 (m, 4 H) 7.34 (t, J=7.58 Hz, 2 H) 7.40-7.46 (m, 2 H) 9.37 (s, 1H).

To compound 2 (17.2 g, 36.3 mmol) in acetone (145 mL) was added methyl 4-bromo-3-(bromomethyl)benzoate (3, 11.7 g, 38.1 mmol) and K$_2$CO$_3$ (30.1 g, 218 mmol). The flask was evacuated/N$_2$ backfilled 2×, and heated at reflux overnight under an atmosphere of N$_2$. After cooling to rt, the mixture was filtered, washing with CH$_2$Cl$_2$, and concentrated. The residue was then redissolved in CH$_2$Cl$_2$, dried with Na$_2$SO$_4$, filtered, and concentrated. To give 4 (24.8 g, 99%) as a foamy solid. $^1$H NMR (400 MHz, DMSO-d$_6$) δ ppm 3.74 (s, 6 H) 3.84 (s, 3 H) 4.07 (s, 2 H) 5.20 (s, 2 H) 6.88-6.92 (m, 4 H) 6.94-6.98 (m, 2 H) 6.99 (d, J=1.52 Hz, 1 H) 7.21-7.26 (m, 1 H) 7.26-7.30 (m, 5 H) 7.30-7.35 (m, 2 H) 7.38-7.43 (m, 2 H) 7.85 (s, 2 H) 8.11 (s, 1 H)

-continued

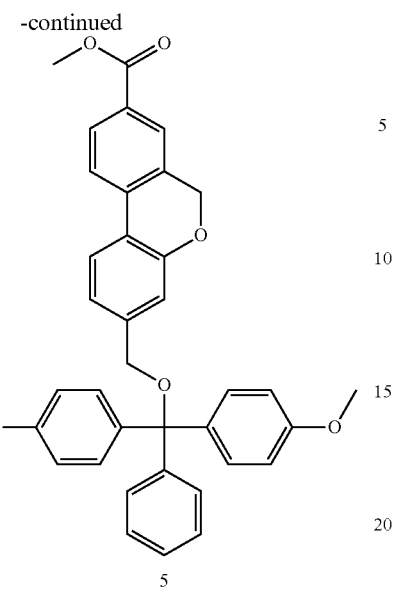

5

-continued

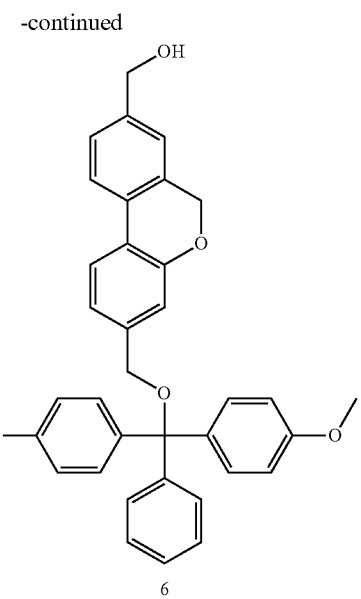

6

To compound 4 (24.8 g, 35.8 mmol) in dimethoxyethane (350 mL) was added Bu₄NBr (17.3 g, 53.7 mmol), Cs₂CO₃ (17.5 g, 53.7 mmol), and Pd(OAc)₂ (2.01 g, 8.96 mmol). The flask was degassed with two cycles of vacuum/N₂ backfill and heated to reflux overnight, under an atmosphere of N₂. After cooling to rt, the mixture was filtered through celite, eluting with THF, and concentrated. The residue was dissolved in 500 mL EtOAc, washed with 400 mL sat. aq. NaHCO₃, 2×400 mL water, and 400 mL of brine. The organic fraction was dried with Na₂SO₄, filtered, and concentrated under vacuum. The residue was purified by silica gel chromatography (CH₂Cl₂/triethylamine), giving 5 (15.1 g, 68%) as a foamy solid. $^1$H NMR (400 MHz, DMSO-d$_6$) δ ppm 3.74 (s, 6 H) 3.87 (s, 3 H) 4.11 (s, 2 H) 5.23 (s, 2 H) 6.89-6.96 (m, 4 H) 7.01 (d, J=1.52 Hz, 1 H) 7.08 (dd, J=8.08, 1.52 Hz, 1 H) 7.22-7.27 (m, 1 H) 7.29-7.33 (m, 4 H) 7.33-7.38 (m, 2 H) 7.41-7.46 (m, 2 H) 7.88-7.93 (m, 2 H) 7.93-7.99 (m, 2 H)

Lithium aluminum hydride (43.4 mL of 1.0 M suspension in THF, 43.4 mmol) was added to a solution of compound 5 (12.0 g, 19.3 mmol) in THF (150 mL) at 0° C. After 2 hours at 0° C., the reaction mixture was quenched by dropwise addition of 20 mL EtOAc, with stirring at 0° C. for 10 min. 1.65 mL H₂O, 1.65 mL 20% aq. NaOH, and 4.95 mL H₂O were added successively. The mixture was then stirred at rt for 1 h, dried with Na₂SO₄, filtered through celite, and concentrated under vacuum. The residue was purified by silica gel chromatography (ethyl acetate/heptane/triethylamine), giving 6 (8.47 g, 81%) as a foamy solid. $^1$H NMR (400 MHz, DMSO-d$_6$) δ ppm 3.75 (s, 6 H) 4.07 (s, 2 H) 4.52 (d, J=5.56 Hz, 2 H) 5.13 (s, 2 H) 5.21-5.25 (m, 1 H) 6.89-6.95 (m, 4 H) 6.96 (d, J=1.52 Hz, 1 H) 7.03 (dd, J=8.08, 1.52 Hz, 1 H) 7.22 (s, 1 H) 7.23-7.28 (m, 1 H) 7.29-7.33 (m, 4 H) 7.33-7.38 (m, 3 H) 7.41-7.46 (m, 2 H) 7.76 (d, J=7.58 Hz, 1 H) 7.81 (d, J=8.08 Hz, 1 H). MS (ESI+) m/z: calcd for C₃₆H₃₂O₅ 544.2. found 545.2 [MH⁺].

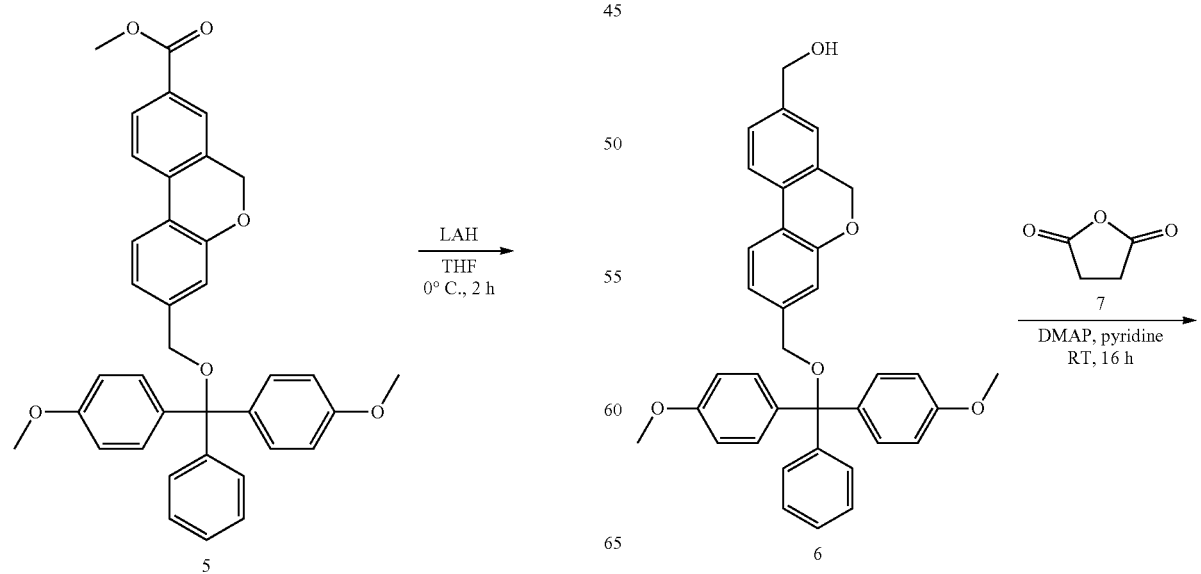

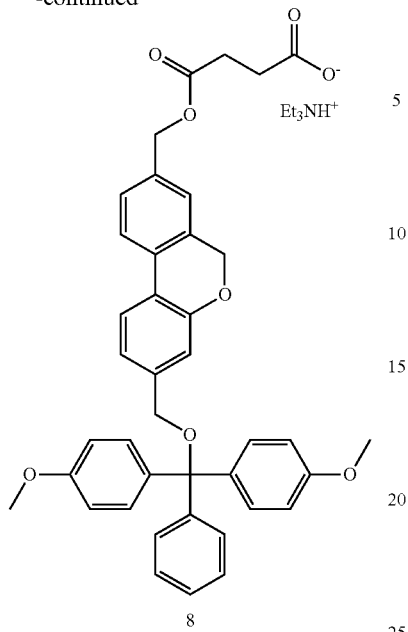

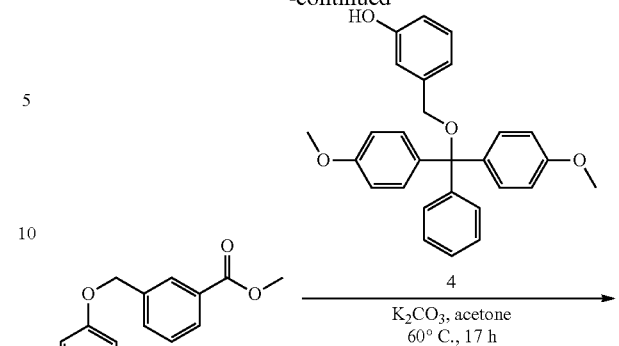

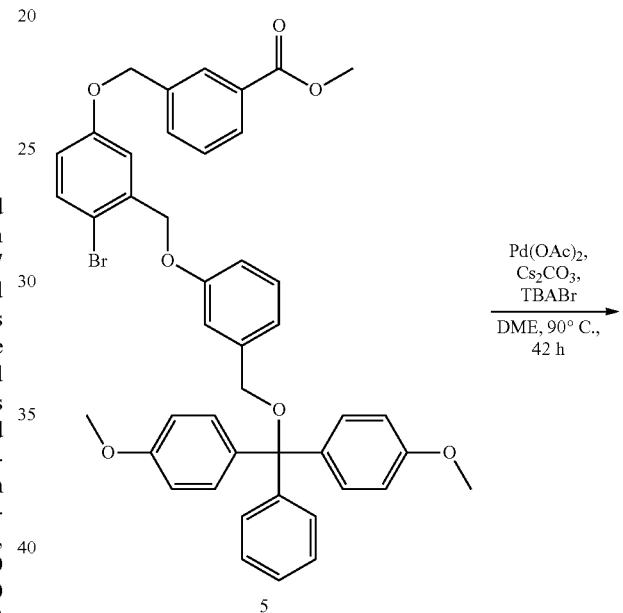

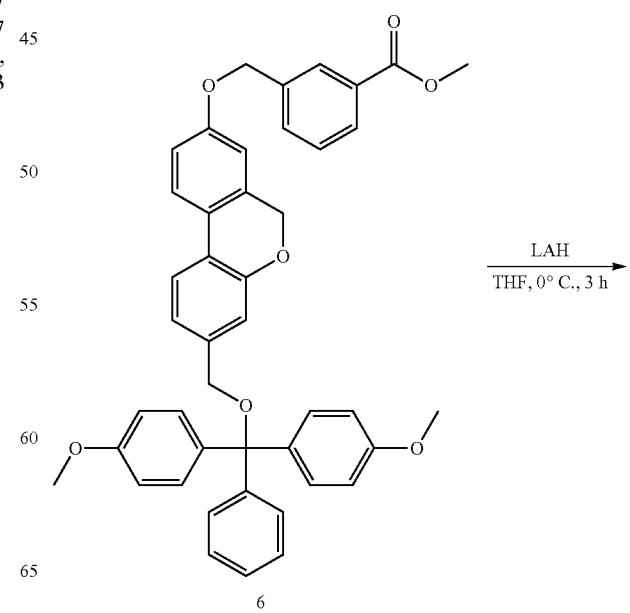

Dimethylaminopyridine (0.124 g, 1.02 mmol) was added to a solution of compound 6 (0.554 g, 1.02 mmol) in pyridine (5 mL) at rt under argon. Succinic anhydride 7 (0.204 g, 2.03 mmol) was added and the solution was stirred at rt for 6 h. 0.5 mL $H_2O$ was added, and the solution was stirred for 30 min. 100 mL of $CH_2Cl_2$ was added, and the solution was washed 1× with 50 mL cold 10% aq. citric acid and 2× each with 50 mL of water. The aqueous fractions were reextracted with 1×50 mL of $CH_2Cl_2$. The combined organic fractions were dried with $Na_2SO_4$, filtered, concentrated under vacuum and then diluted/concentrated 2× with toluene. The residue was purified by silica gel chromatography (dichloromethane/methanol/triethylamine) (49:1/1%), giving 8 (0.78 g, 103%) as a foamy solid. $^1$H NMR (400 MHz, $CDCl_3$) δ ppm 1.45 (t, J=7.20 Hz, 2.5 H) 2.52-2.60 (m, 2 H) 2.65-2.71 (m, 2 H) 3.60 (q, J=7.33 Hz, 1.7 H) 3.79 (s, 6 H) 4.16 (s, 2 H) 5.12 (s, 2 H) 5.13 (s, 2 H) 6.82-6.87 (m, 4 H) 7.03 (dd, J=8.08, 1.26 Hz, 1 H) 7.08 (s, 1 H) 7.17 (s, 1 H) 7.19-7.25 (m, 1 H) 7.28-7.33 (m, 2 H) 7.33-7.37 (m, 1 H) 7.38-7.44 (m, 4 H) 7.49-7.54 (m, 2 H) 7.66 (t, J=7.83 Hz, 2 H)

2.K. Synthesis of X066 Succinate Ester

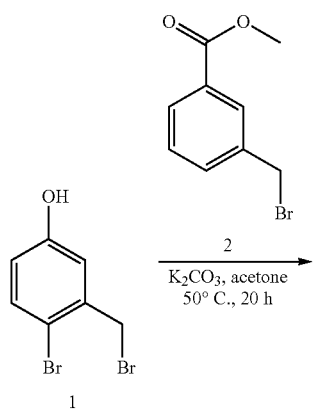

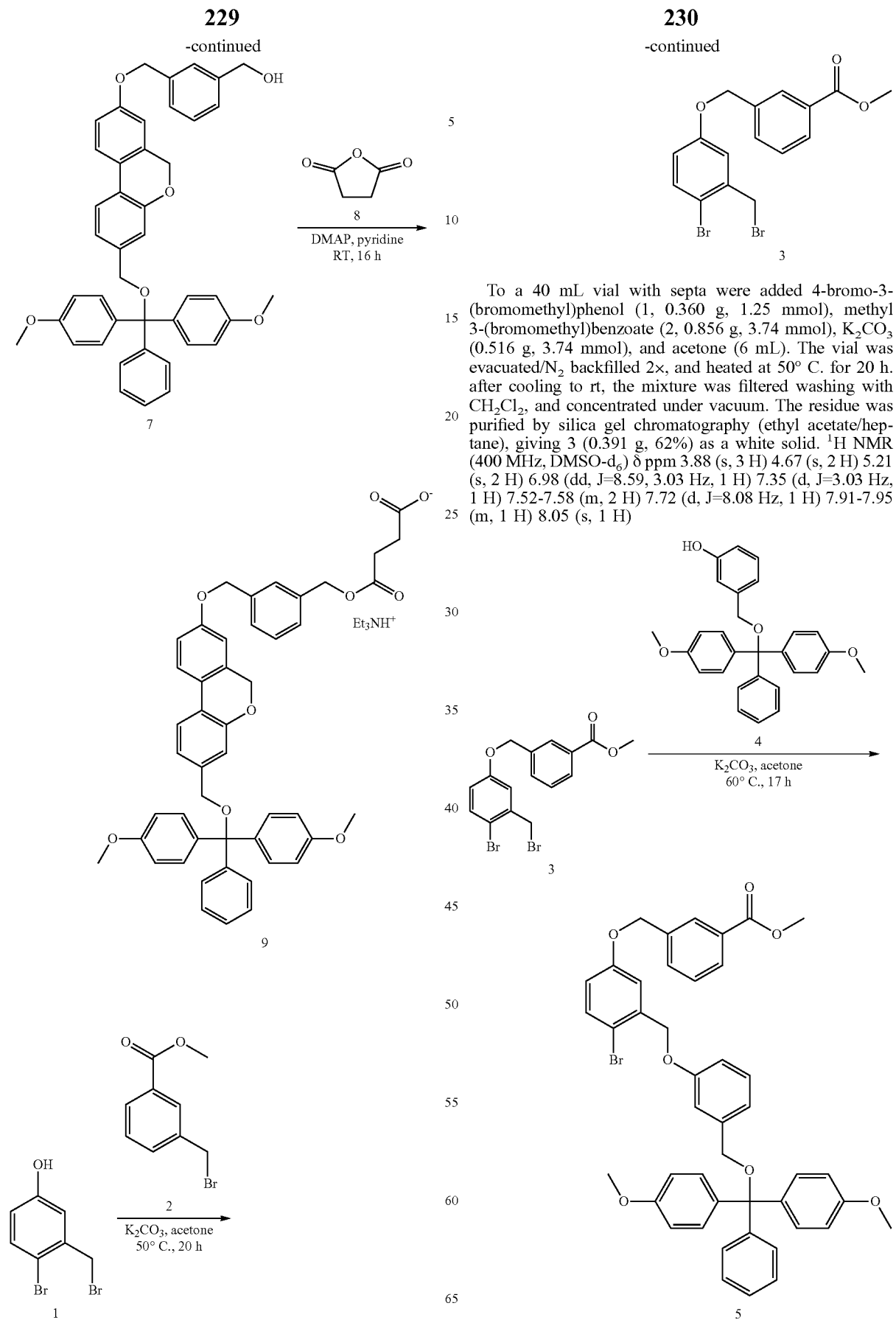

To a 40 mL vial with septa were added 4-bromo-3-(bromomethyl)phenol (1, 0.360 g, 1.25 mmol), methyl 3-(bromomethyl)benzoate (2, 0.856 g, 3.74 mmol), $K_2CO_3$ (0.516 g, 3.74 mmol), and acetone (6 mL). The vial was evacuated/$N_2$ backfilled 2×, and heated at 50° C. for 20 h. after cooling to rt, the mixture was filtered washing with $CH_2Cl_2$, and concentrated under vacuum. The residue was purified by silica gel chromatography (ethyl acetate/heptane), giving 3 (0.391 g, 62%) as a white solid. $^1$H NMR (400 MHz, DMSO-$d_6$) δ ppm 3.88 (s, 3 H) 4.67 (s, 2 H) 5.21 (s, 2 H) 6.98 (dd, J=8.59, 3.03 Hz, 1 H) 7.35 (d, J=3.03 Hz, 1 H) 7.52-7.58 (m, 2 H) 7.72 (d, J=8.08 Hz, 1 H) 7.91-7.95 (m, 1 H) 8.05 (s, 1 H)

Synthesis of compound 4 is described in the synthesis of X063. To a 40 mL vial with a septa was added compounds 3 (0.390 g, 0.763 mmol), 4 (0.390 g, 0.915 mmol), K$_2$CO$_3$ (0.316 g, 2.29 mmol) and acetone (4 mL). The vial was sealed and the contents were evacuated/N$_2$ backfilled 2×. The vial was then heated at 60° C. for 17 h. After cooling to rt, the mixture was filtered washing with CH$_2$Cl$_2$, and concentrated under vacuum. The residue was purified by silica gel chromatography (ethyl acetate/heptane/triethylamine), giving 5 (0.448 g, 77%) as a foamy solid. $^1$H NMR (400 MHz, DMSO-d$_6$) δ ppm 3.74 (s, 6 H) 3.85 (s, 3 H) 4.10 (s, 2 H) 5.08 (s, 2 H) 5.20 (s, 2 H) 6.87-6.92 (m, 4 H) 6.92-7.02 (m, 4 H) 7.19-7.26 (m, 3 H) 7.26-7.35 (m, 7 H) 7.39-7.45 (m, 2 H) 7.50 (t, J=7.83 Hz, 1 H) 7.56 (d, J=8.59 Hz, 1 H) 7.68 (d, J=7.58 Hz, 1 H) 7.90 (d, J=7.58 Hz, 2 H) 8.02 (s, 1 H)

Pd(OAc)$_2$ (0.026 g, 0.11 mmol). The vial was sealed, degassed with two cycles of vacuum/N$_2$ backfill, and heated at 90° C. overnight. ~33% conversion was observed after 17 h by LCMS. An additional 0.100 g of Pd(OAc)$_2$ (0.44 mmol) was added, and the reaction was continued for an additional 24 h. After cooling to rt, the mixture was filtered through celite eluting with EtOAc. The solution was then washed 1× each with aq. sat. NaHCO$_3$, water and brine. The organic portion was dried with Na$_2$SO$_4$, filtered, and concentrated under vacuum. The residue was purified by silica gel chromatography (ethyl acetate/heptane/triethylamine), giving 6 (0.105 g, 27%) as a foamy solid. $^1$H NMR (400 MHz, DMSO-d6) δ ppm 3.75 (s, 6 H) 3.87 (s, 3 H) 4.08 (s, 2 H) 5.09 (s, 2 H) 5.24 (s, 2 H) 6.88-6.95 (m, 5 H) 6.95-7.00 (m, 2 H) 7.05 (dd, J=8.34, 2.78 Hz, 2 H) 7.21-7.26 (m, 2 H) 7.29-7.36 (m, 6 H) 7.39-7.46 (m, 2 H) 7.55 (t, J=7.83 Hz, 1 H) 7.69-7.77 (m, 3 H) 7.92 (d, J=8.08 Hz, 1 H) 8.05 (s, 1 H)

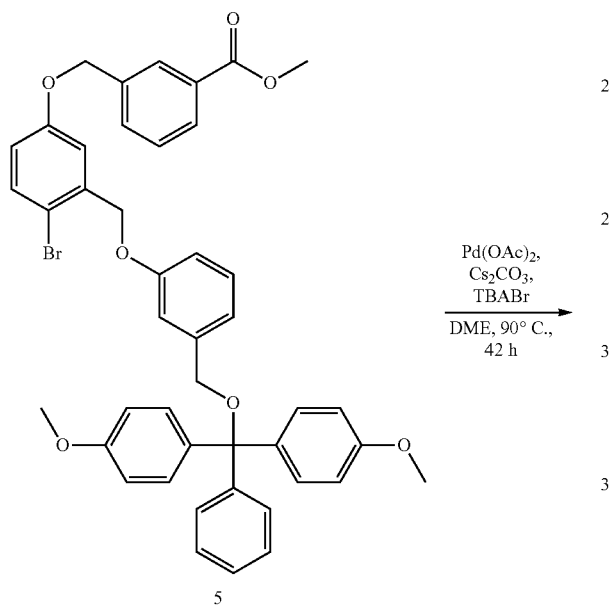

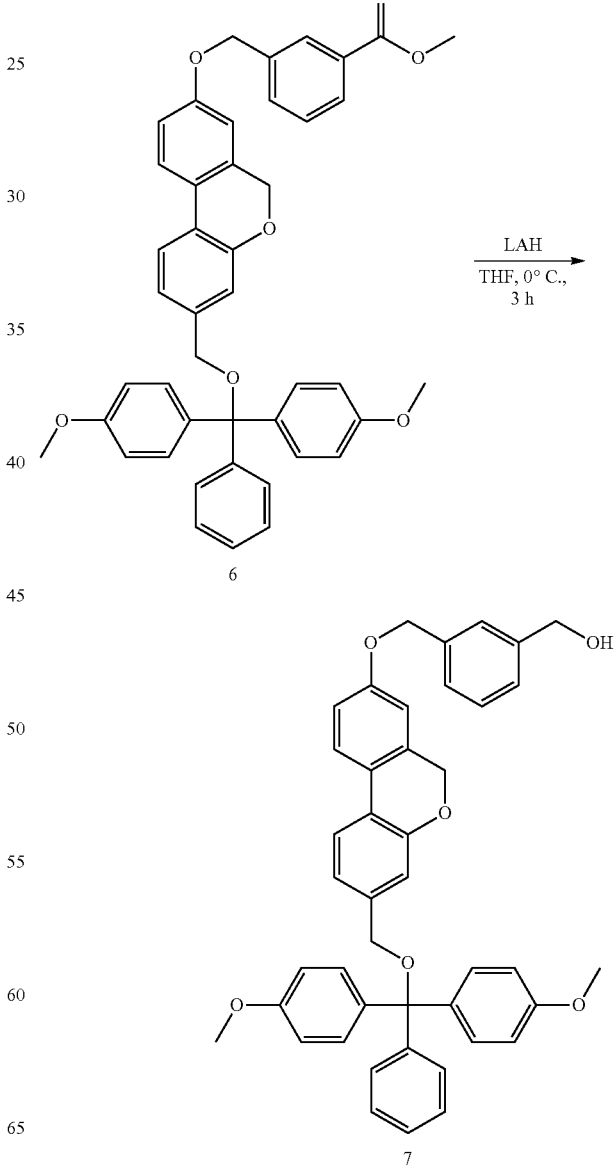

To compound 5 (0.540 g, 0.569 mmol) in a vial with a septa, was added dimethoxyethane (5.7 mL), Bu$_4$NBr (0.275 g, 0.853 mmol), Cs$_2$CO$_3$ (0.278 g, 0.853 mmol), and Compound 6 (0.135 g, 0.199 mmol) in THF (2 mL) was cooled to 0° C., under an atmosphere of N$_2$. A 1M suspension of LAH in THF (0.477 mL, 0.477 mmol) was added dropwise, and the solution was stirred at 0° C. for 3 h. 1 mL EtOAc was added dropwise, and the solution was stirred at 0° C. for 20 min. 0.018 mL H$_2$O, 0.018 mL 20% aq. NaOH, and 0.054 mL H$_2$O were added successively, and the mixture was stirred at rt for 1 h. the mixture was dried with Na$_2$SO$_4$, filtered through celite washing with EtOAc, and concentrated under vacuum. The residue was purified by silica gel chromatography (ethyl acetate/heptane/triethylamine), giving 7 (0.110 g, 85%) as a foamy solid. $^1$H NMR (400 MHz, DMSO-d$_6$) δ ppm 3.75 (s, 6 H) 4.08 (s, 2 H) 4.52 (d, J=5.56 Hz, 2 H) 5.04 (t, J=5.81 Hz, 1 H) 5.08 (s, 2 H) 5.14 (s, 2 H) 6.89-6.94 (m, 5 H) 6.95 (d, J=2.53 Hz, 1 H) 6.98 (dd, J=8.08, 1.52 Hz, 1 H) 7.03 (dd, J=8.59, 2.53 Hz, 1 H) 7.24 (t, J=7.33 Hz, 1 H) 7.26-7.37 (m, 9 H) 7.40-7.46 (m, 3 H) 7.72 (d, J=8.08 Hz, 2 H). MS (ESI+) m/z: calcd for C$_{43}$H$_{38}$O$_6$ 650.3. found 303.4 [DMT$^+$].

Dimethylaminopyridine (0.019 g, 0.157 mmol) was added to a solution of compound 7 (0.102 g, 0.157 mmol) in pyridine (3 mL) at rt under argon. Succinic anhydride 8 (0.031 g, 0.313 mmol) was added, and the solution was stirred at rt for 16 h. 0.5 mL of H$_2$O was added and the solution was stirred for 30 min. 50 mL of CH$_2$Cl$_2$ was added, the solution was washed 1× with 25 mL cold 10% aq. citric acid and 2× each with 25 mL of water. The aqueous fractions were reextracted with 1×25 mL of CH$_2$Cl$_2$. The organic fractions were dried with Na$_2$SO$_4$, filtered, concentrated under vacuum, and diluted/concentrated 2× with toluene. The residue was purified by silica gel chromatography (dichloromethane/methanol/triethylamine) (49:1/1%), giving 9 (0.10 g, 76%) as an oil. $^1$H NMR (400 MHz, CDCl$_3$) δ ppm 1.46 (t, J=7.33 Hz, 2.1H) 2.57 (t, J=6.82 Hz, 2 H) 2.68 (t, J=6.82 Hz, 2 H) 3.61 (q, J=7.16 Hz, 1.4 H) 3.80 (s, 6 H) 4.15 (s, 2 H) 5.09 (s, 2 H) 5.09 (s, 2 H) 5.15 (s, 2 H) 6.78 (d, J=2.53 Hz, 1 H) 6.82-6.88 (m, 4 H) 6.95-7.04 (m, 2 H) 7.06 (s, 1 H) 7.18-7.25 (m, 1 H) 7.28-7.36 (m, 3 H) 7.36-7.46 (m, 7 H) 7.50-7.55 (m, 2 H) 7.61 (dd, J=8.34, 2.27 Hz, 2 H)

2.L. Synthesis of X051 Succinate

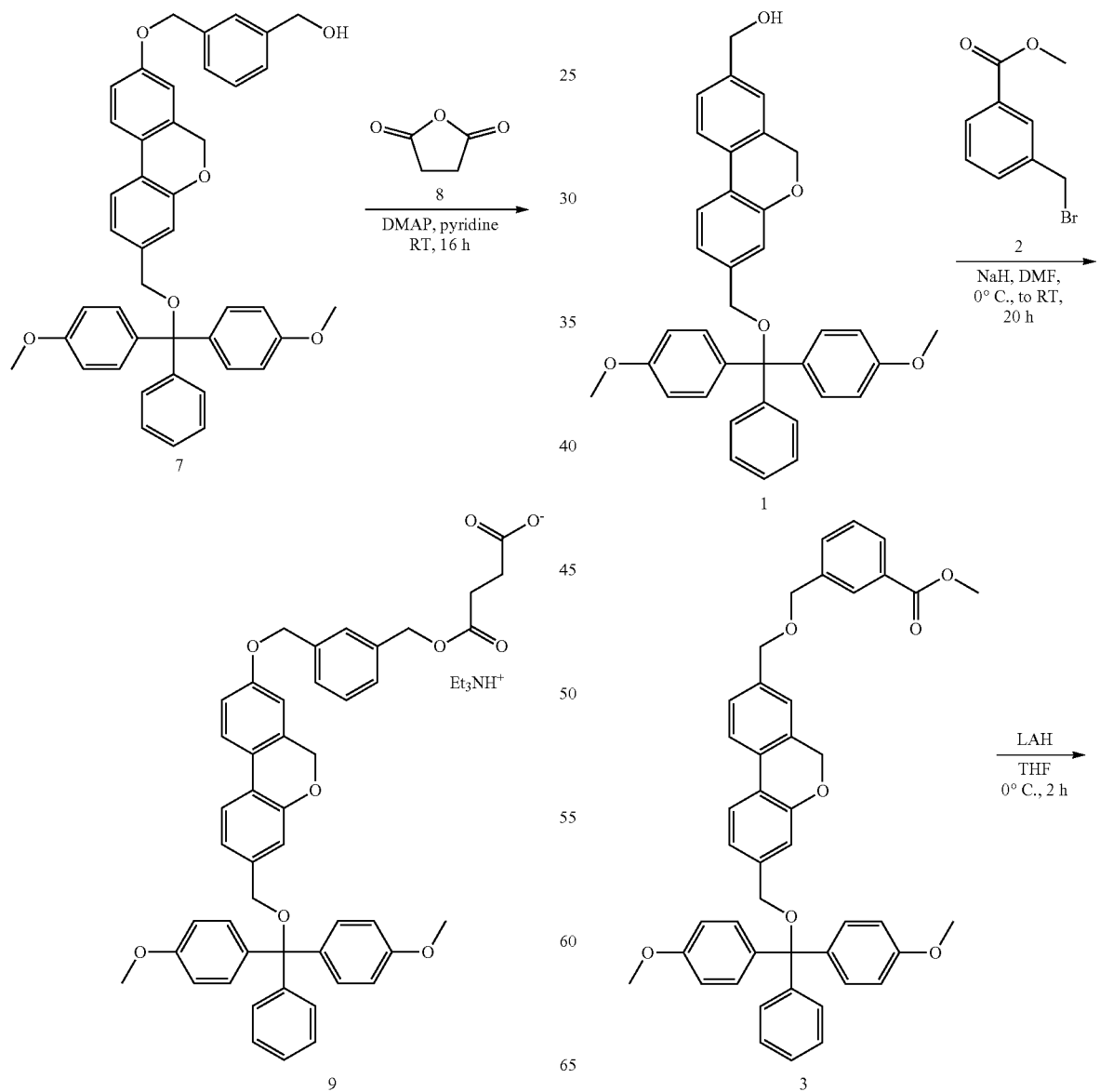

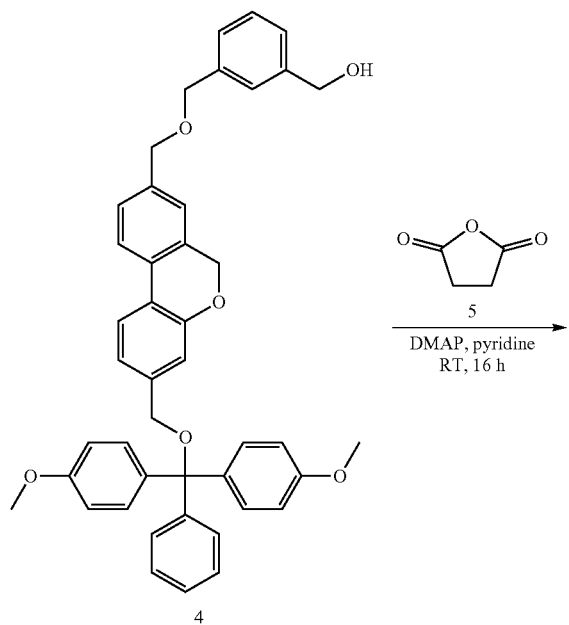

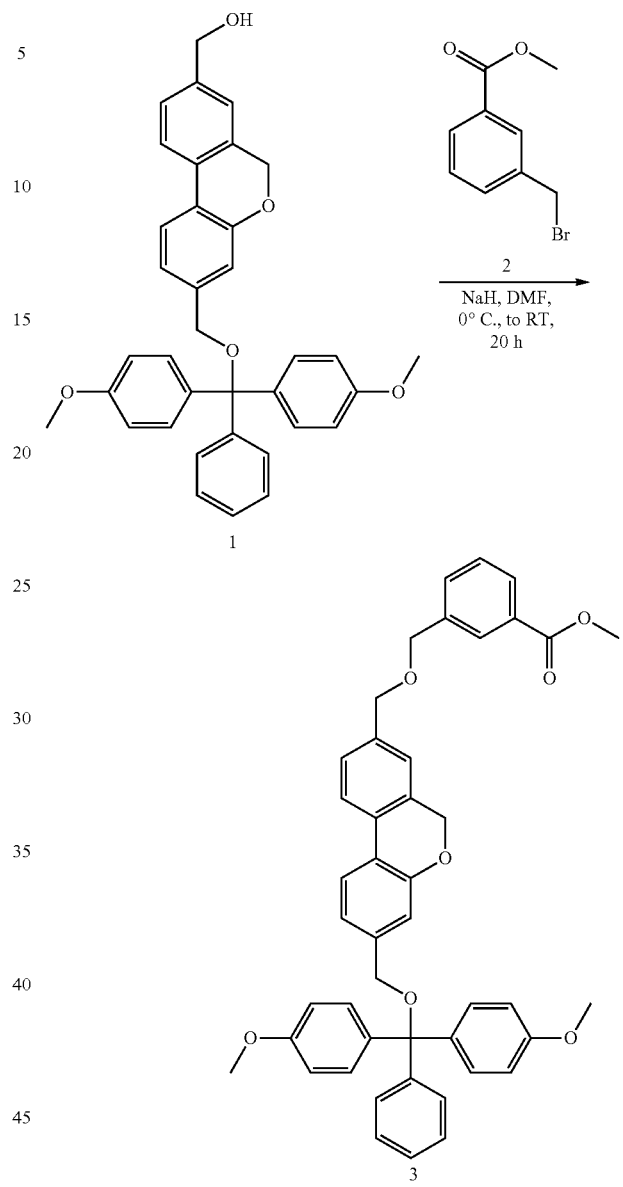

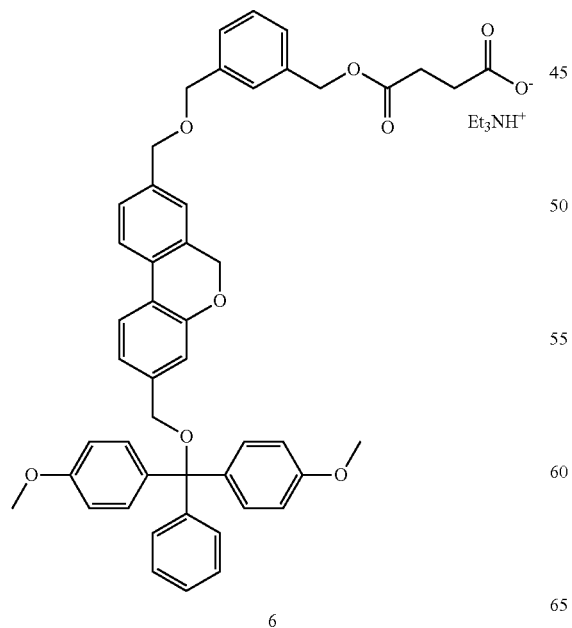

The synthesis of compound 1 is described in the synthesis of X063. Compound 1 (6.70 g, 12.3 mmol) was dissolved in THF (123 mL), evacuated/$N_2$ purged 2×, and cooled to 0° C. A 60% dispersion of NaH in mineral oil was added (0.886 g, 36.9 mmol), and the mixture was stirred at 0° C. for 20 min. Methyl 3-(bromomethyl)benzoate (2, 3.38 g, 14.8 mmol) was then added, and the mixture was stirred at rt for 20 h. The reaction mixture was then diluted with 400 mL of EtOAc and washed 1× with 400 mL sat. aq. $NaHCO_3$. The aqueous layer was back-extracted with 200 mL of EtOAc, and the combined organic layers were washed 1× each with 400 mL water and brine. The organic portion was dried with $Na_2SO_4$, filtered, and concentrated under vacuum. The residue was purified by silica gel chromatography (ethyl acetate/heptane/triethylamine), giving 3 (6.55 g, 77%) as a foamy solid. The product contained ~13% of the corresponding ester ethyl ester that was carried forward to the next step as an equivalent precursor. Methyl ester: $^1$H NMR (400 MHz, DMSO-$d_6$) δ ppm 1.32 (t, J=7.07 Hz, 0.38 H) 3.74 (s, 6 H) 3.86 (s, 2.52 H) 4.08 (s, 2 H) 4.32 (q, J=7.07 Hz, 0.25 H) 4.58 (s, 2 H) 4.64 (s, 2 H) 5.14 (s, 2 H) 6.93 (d, J=8.59 Hz, 4 H) 6.97 (d, J=1.52 Hz, 1H) 7.04 (dd, J=8.08, 1.52 Hz, 1 H) 7.25 (t, J=7.33 Hz, 1 H) 7.28 (s, 1 H) 7.31 (d, J=9.09 Hz, 4 H) 7.33-7.41 (m, 3 H) 7.44 (d, J=7.58 Hz, 2 H) 7.53 (t, J=7.83 Hz, 1 H) 7.66 (d, J=8.08 Hz, 1 H) 7.80 (d, J=8.08 Hz, 1 H) 7.83 (d, J=8.08 Hz, 1 H) 7.90 (d, J=7.58 Hz, 1 H) 7.97 (s, 1 H)

and the solution was stirred at 0° C. for 20 min. Then 0.86 mL H$_2$O, 0.86 mL 20% aq. NaOH, and 2.58 mL H$_2$O were added successively. The mixture was stirred at rt for 1 h, dried with Na$_2$SO$_4$, filtered through celite washing with EtOAc, and concentrated under vacuum. The residue was purified by silica gel chromatography (ethyl acetate/heptane/triethylamine), giving 4 (5.98 g, 96%) as a foamy solid.

$^1$H NMR (400 MHz, DMSO-$d_6$) δ ppm 3.74 (s, 6 H) 4.08 (s, 2 H) 4.50 (d, J=6.06 Hz, 2 H) 4.55 (s, 2 H) 4.55 (s, 2 H) 5.14 (s, 2 H) 5.18 (t, J=5.81 Hz, 1 H) 6.93 (d, J=8.59 Hz, 4 H) 6.97 (d, J=1.01 Hz, 1 H) 7.01-7.06 (m, 1 H) 7.21-7.28 (m, 4 H) 7.28-7.33 (m, 5 H) 7.33-7.40 (m, 4 H) 7.41-7.46 (m, 2 H) 7.80 (d, J=8.08 Hz, 1 H) 7.83 (d, J=8.08 Hz, 1 H). MS (ESI+) m/z: calcd for C$_{44}$H$_{40}$O$_6$ 664.3. found 665.3 [MH$^+$].

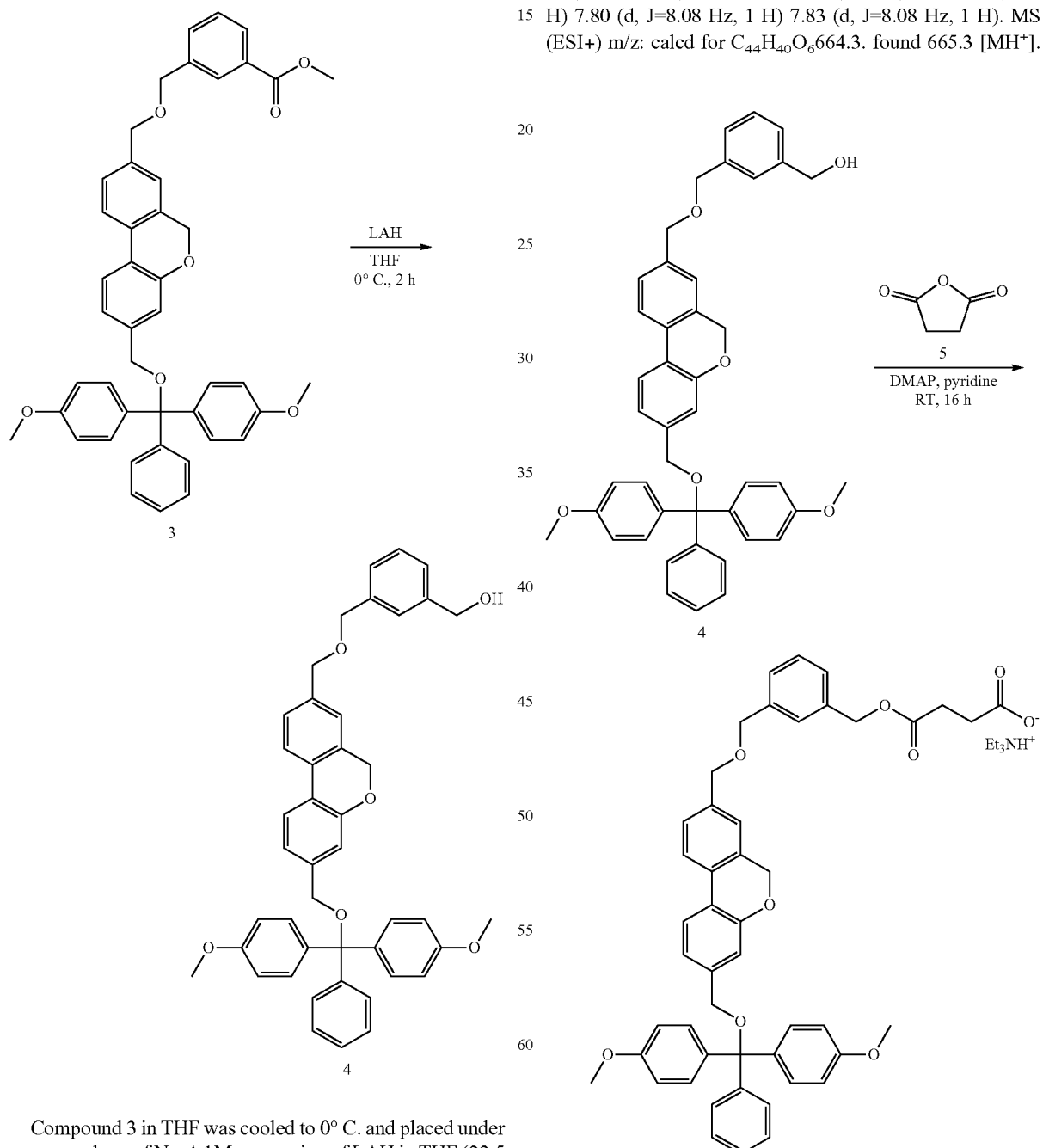

Compound 3 in THF was cooled to 0° C. and placed under an atmosphere of N$_2$. A 1M suspension of LAH in THF (22.5 mL, 22.5 mmol) was added dropwise, and the solution was stirred at 0° C. for 2 h. 1 mL EtOAc was added dropwise, Dimethylaminopyridine (0.37 g, 3.01 mmol) was added to a solution of compound 4 (2.00 g, 3.01 mmol) in pyridine (15 mL) at rt under argon. Succinic anhydride 7 (0.60 g, 6.02 mmol) was added, and the solution was stirred at rt for 17 h. 1 mL of $H_2O$ was added and the solution was stirred for 1 h. 100 mL of $CH_2Cl_2$ was added, and the solution was washed 1× with 50 mL cold 10% aq. citric acid and 2× each with 50 mL of water. The aqueous fractions were reextracted with 1×50 mL of $CH_2Cl_2$. The combined organic fractions were dried with $Na_2SO_4$, filtered, concentrated under vacuum, and diluted/concentrated 2× with toluene. The residue was purified by silica gel chromatography (dichloromethane/methanol/triethylamine) (39:1/1%), giving 6 (2.48 g, 95%) as an oil. $^1$H NMR (400 MHz, $CDCl_3$) δ ppm 1.17 (t, J=7.33 Hz, 14.2 H) 2.56 (t, J=6.69 Hz, 2 H) 2.68 (t, J=7.45 Hz, 2 H) 2.84 (q, J=7.33 Hz, 9.5H) 3.80 (s, 6 H) 4.16 (s, 2 H) 4.57 (s, 2 H) 4.58 (s, 2 H) 5.14 (s, 2 H) 5.14 (s, 2 H) 6.82-6.88 (m, 4 H) 7.01-7.05 (m, 1 H) 7.09 (s, 1 H) 7.18 (s, 1 H) 7.19-7.25 (m, 1 H) 7.28-7.34 (m, 5 H) 7.34-7.38 (m, 2 H) 7.39-7.44 (m, 4 H) 7.49-7.55 (m, 2 H) 7.68 (dd, J=7.96, 4.42 Hz, 2 H)

2.M. Synthesis of X097 Succinate Ester

Scheme 1: Overview of the synthesis of 6.

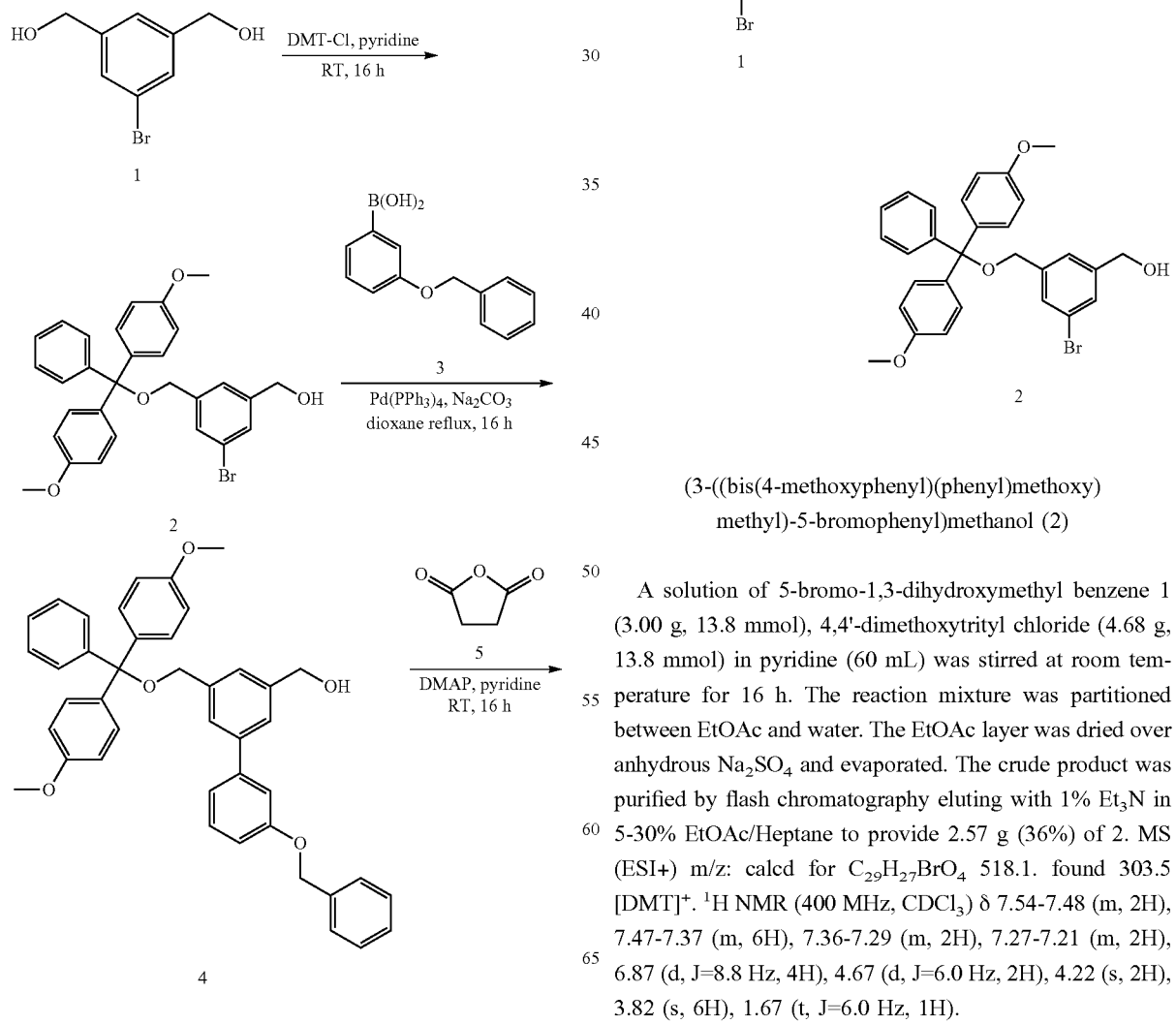

(3-((bis(4-methoxyphenyl)(phenyl)methoxy)methyl)-5-bromophenyl)methanol (2)

A solution of 5-bromo-1,3-dihydroxymethyl benzene 1 (3.00 g, 13.8 mmol), 4,4'-dimethoxytrityl chloride (4.68 g, 13.8 mmol) in pyridine (60 mL) was stirred at room temperature for 16 h. The reaction mixture was partitioned between EtOAc and water. The EtOAc layer was dried over anhydrous $Na_2SO_4$ and evaporated. The crude product was purified by flash chromatography eluting with 1% $Et_3N$ in 5-30% EtOAc/Heptane to provide 2.57 g (36%) of 2. MS (ESI+) m/z: calcd for $C_{29}H_{27}BrO_4$ 518.1. found 303.5 [DMT]$^+$. $^1$H NMR (400 MHz, $CDCl_3$) δ 7.54-7.48 (m, 2H), 7.47-7.37 (m, 6H), 7.36-7.29 (m, 2H), 7.27-7.21 (m, 2H), 6.87 (d, J=8.8 Hz, 4H), 4.67 (d, J=6.0 Hz, 2H), 4.22 (s, 2H), 3.82 (s, 6H), 1.67 (t, J=6.0 Hz, 1H).

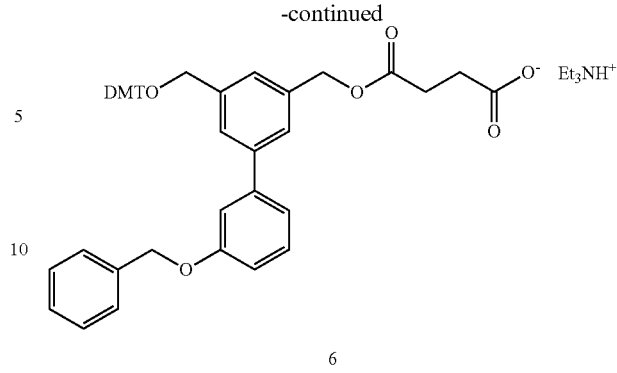

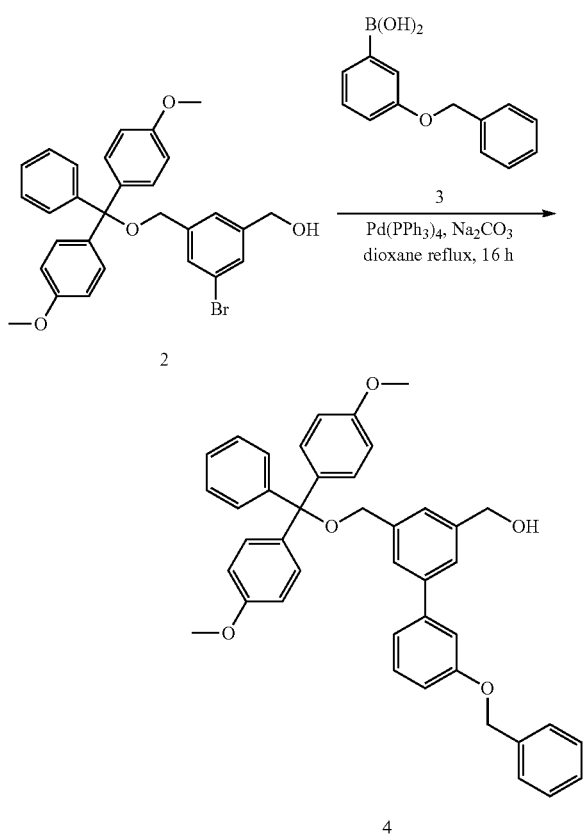

(3'-(benzyloxy)-5-((bis(4-methoxyphenyl)(phenyl)methoxy)methyl)-[1,1'-biphenyl]-3-yl)methanol (4)

To a mixture of bromide 2 (0.50 g, 0.963 mmol), 3-benzyloxybenzene boronic acid 3 (0.263 g, 1.155 mmol) and Pd(PPh$_3$)$_4$ (0.111 g, 0.096 mmol) in 1,4-dioxane (6 mL) under nitrogen atmosphere was added 2M aq. Na$_2$CO$_3$ (1.44 mL). The mixture was heated at reflux overnight. The reaction is then cooled to room temperature and partitioned between EtOAc and sat. aq. NaHCO$_3$. The organic layer was evaporated and the crude product was purified by flash chromatography eluting with 1% Et$_3$N in 5-30% EtOAc/Heptane to provide 0.454 g (70%) of 4. MS (ESI+) m/z: calcd for C$_{42}$H$_{38}$O$_5$ 622.3; found 303.5 [DMT]$^+$. $^1$H NMR (400 MHz, DMSO) δ 7.52-7.43 (m, 5H), 7.41-7.29 (m, 12H), 7.27-7.16 (m, 3H), 7.01 (m, 1H), 6.95-6.86 (m, 4H), 5.18 (s, 2H), 5.07 (t, J=5.8 Hz, 1H), 4.57 (d, J=5.8 Hz, 2H), 4.18 (s, 2H), 3.74 (s, 6H).

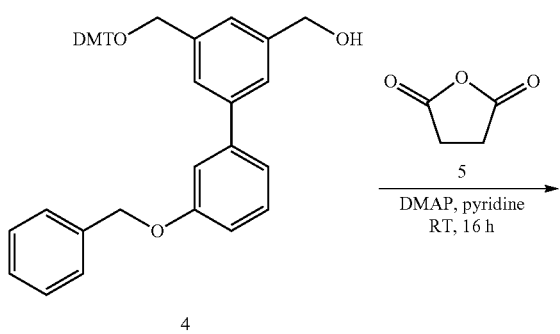

To a solution of 452 mg (0.726 mmol) 4 and 89 mg (0.726 mmol) N,N-dimethylaminopyridine (DMAP) in 5 mL dry pyridine under argon was added 145 mg (1.45 mmol) succinic anhydride (5). The reaction mixture was stirred at room temperature for 18 h and then 0.5 mL water was added. Stirring was continued for 30 min. The reaction mixture was diluted with 100 mL dichloromethane and washed with 50 mL ice-cold 10% aqueous citric acid and water (2×50 mL). The aqueous layers were reextracted with 50 mL dichloromethane. The combined organic layers were dried over Na$_2$SO$_4$ and evaporated. The remaining oil was coevaporated twice with toluene and the crude product purified by silica gel chromatography (dichloromethane/methanol/triethylamine 94:5:1) to give 510 mg (0.619 mmol, 85%) 6 as a colorless foam. $^1$H NMR (400 MHz, CDCl$_3$): 1.22 (t, J=7.3 Hz, 9 H), 2.57-2.59 (m, 2 H), 2.67-2.69 (m, 2 H), 2.97 (q, J=7.3 Hz, 6 H), 3.79 (s, 6 H), 4.24 (s, 2 H), 5.14 (s, 2 H), 5.18 (s, 2 H), 5.72 (s br., 1 H), 6.84-6.88 (m, 4 H), 6.98 (ddd, J=0.7, 2.2, 8.2 Hz, 1 H), 7.19-7.54 (m, 20 H).

2.N. Synthesis of X098 Succinate Ester

Scheme 1: Overview of the synthesis of 6.

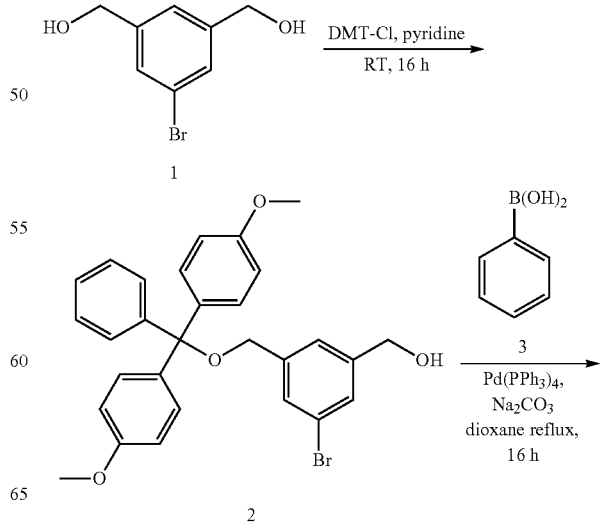

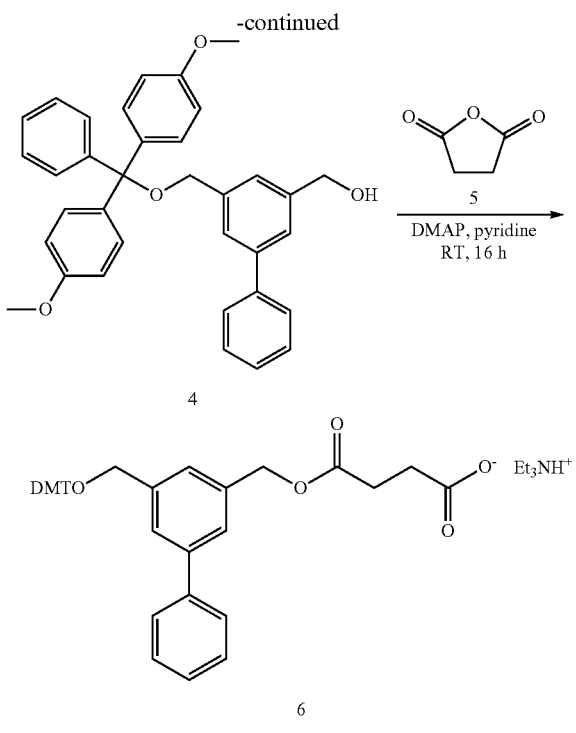

4

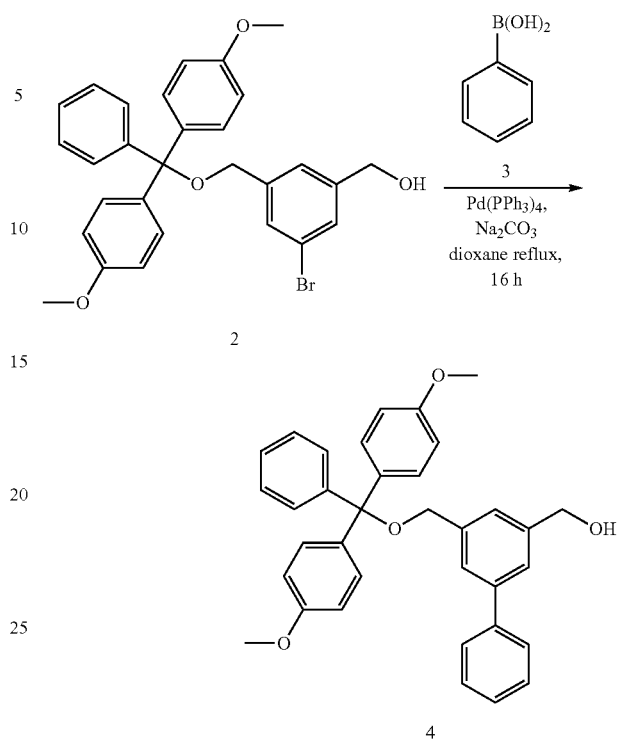

2

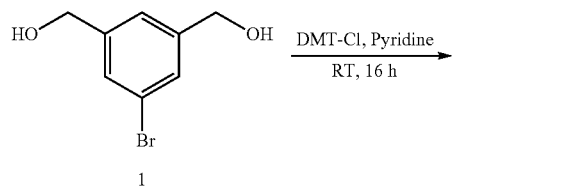

6

1

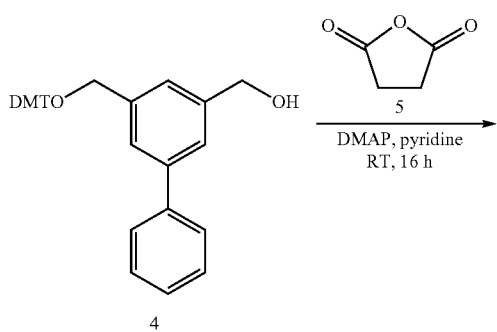

2

(3-((bis(4-methoxyphenyl)(phenyl)methoxy)
methyl)-5-bromophenyl)methanol (2)

Same as Above

A solution of 5-bromo-1,3-dihydroxymethyl benzene 1 (3.00 g, 13.8 mmol), 4,4'-dimethoxytrityl chloride (4.68 g, 13.8 mmol) in pyridine (60 mL) was stirred at room temperature for 16 h. The reaction mixture was partitioned between EtOAc and water. The EtOAc layer was dried over anhydrous $Na_2SO_4$ and evaporated. The crude product was purified by flash chromatography eluting with 1% $Et_3N$ in 5-30% EtOAc/Heptane to provide 2.57 g (36%) of 2. MS (ESI+) m/z: calcd for $C_{29}H_{27}BrO_4$ 518.1; found 303.5 $[DMT]^+$. $^1H$ NMR (400 MHz, $CDCl_3$) δ 7.54-7.48 (m, 2H), 7.47-7.37 (m, 6H), 7.36-7.29 (m, 2H), 7.27-7.21 (m, 2H), 6.87 (d, J=8.8 Hz, 4H), 4.67 (d, J=6.0 Hz, 2H), 4.22 (s, 2H), 3.82 (s, 6H), 1.67 (t, J=6.0 Hz, 1H).

(5-((bis(4-methoxyphenyl)(phenyl)methoxy)
methyl)-[1,1'-biphenyl]-3-yl)methanol (4)

To a mixture of the bromide 2 (0.500 g, 0.960 mmol), benzene boronic acid 3 (0.141 g, 1.16 mmol), and $Pd(PPh_3)_4$ (0.111 g, 0.096 mmol) in 1,4-dioxane (6 mL) under nitrogen atmosphere was added 2M aq. $Na_2CO_3$ (1.44 mL). The mixture was heated at reflux overnight. The reaction was then cooled to room temperature and partitioned between EtOAc and sat. aq. $NaHCO_3$. The organic layer was evaporated and the crude product was purified by flash chromatography eluting with 1% $Et_3N$ in 5-30% EtOAc/Heptane to provide 0.380 g (76%) of 4. MS (ESI+) m/z: calcd for $C_{35}H_{32}O_4$ 516.2; found 303.5 $[DMT]^+$. $^1H$ NMR (400 MHz, DMSO) δ 7.61 (dd, J=8.3, 1.3 Hz, 2H), 7.51-7.42 (m, 5H), 7.39-7.28 (m, 9H), 7.27-7.20 (m, 1H), 6.95-6.86 (m, 4H), 5.08 (t, J=5.8 Hz, 1H), 4.57 (d, J=5.8 Hz, 2H), 4.19 (s, 2H), 3.74 (s, 6H).

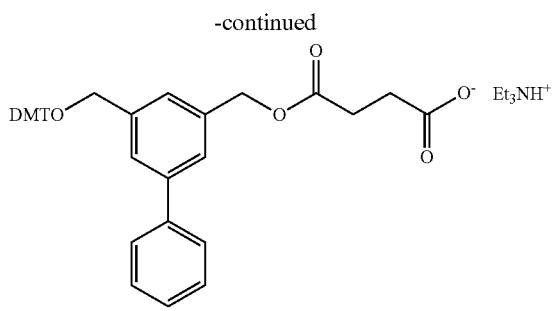

6

To a solution of 380 mg (0.736 mmol) 4 and 90 mg (0.736 mmol) N,N-dimethylaminopyridine (DMAP) in 5 mL dry pyridine under argon was added 147 mg (1.47 mmol) succinic anhydride (5). The reaction mixture was stirred at room temperature for 18 h and then 0.5 mL water was added. Stirring was continued for 30 min. The reaction mixture was diluted with 100 mL dichloromethane and washed with 50 mL ice-cold 10% aqueous citric acid and water (2×50 mL). The aqueous layers were reextracted with 50 mL dichloromethane. The combined organic layers were dried over $Na_2SO_4$ and evaporated. The remaining oil was coevaporated twice with toluene and the crude product purified by silica gel chromatography (dichloromethane/methanol/triethylamine 94:5:1) to give 460 mg (0.641 mmol, 87%) 6 as an off-white foam. $^1$H NMR (400 MHz, $CDCl_3$): 1.22 (t, J=7.2 Hz, 9 H), 2.59 (t, J=7.1 Hz, 2 H), 2.71 (t, J=7.1 Hz, 2 H), 2.94 (q, J=7.2 Hz, 6 H), 3.81 (s, 6 H), 4.26 (s, 2 H), 5.20 (s, 2 H), 6.04 (s br., 1 H), 6.85-6.89 (m, 4 H), 7.22-7.55 (m, 15 H), 7.62 (d, J=7.9 Hz, 2 H).

2.O. Synthesis of siRNA Conjugated with X109 ss-siRNA=antisense single strand sequence used in conjugation=U002pUpApApU004pU004pApU004pCpU-004pApU004pU004pCpCpGpU005 pA005pC027 (SEQ ID NO: 138)

Where C027 is ribitol

Scheme 1: Overview of the synthesis of 3.

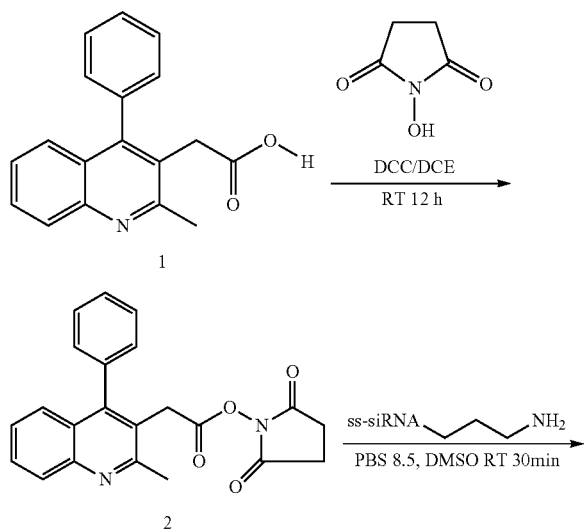

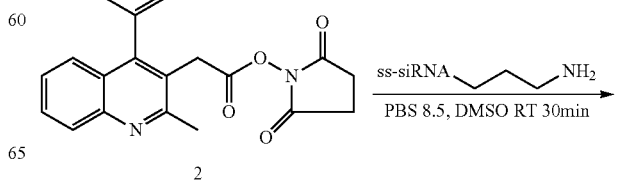

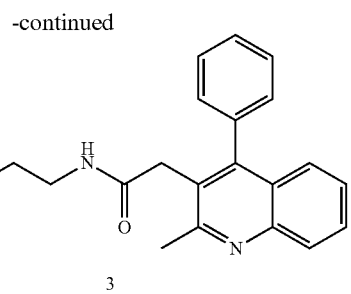

3

A mixture of 1 (100 mg, 0.361 mmol), N-hydroxysuccinimide (83 mg, 0.721 mmol) and DCC (149 mg, 0.721 mmol) in DCE (4 mL) was stirred at RT for 12 h. The reaction mixture was quenched with sat. aq. $NaHCO_3$ (4 mL). The organic layer was separated from the water layer, and was washed with water (1 mL) and brine (1 mL). The organic solvent was removed under vacuum. The crude product was purified by recrystallization from methanol to give 2 (27.7 mg, 0.074 mmol) in 21% yield. ESI MS (m/z, MH$^+$): 375.4; $^1$H NMR (400 MHz, CHLOROFORM-d) δ ppm 2.85 (d, J=5.52 Hz, 4 H) 2.89 (s, 3 H) 3.94 (s, 2 H) 7.31-7.48 (m, 4 H) 7.49-7.64 (m, 3 H) 7.71 (t, J=6.78 Hz, 1 H) 8.12 (br. s., 1 H).

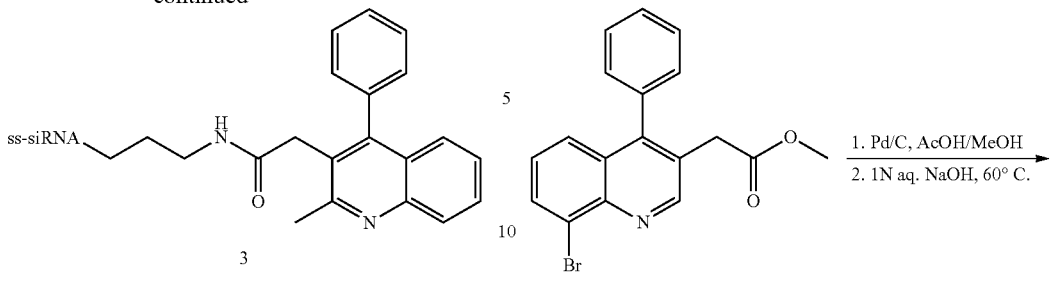

To 2 (2.23 mg, 5.96 umol) in DMSO (73.2 uL) was added a freshly prepared ss-siRNA-(CH$_2$)$_3$—NH$_2$ solution (3.66 mg, 0.596 umol in 73.2 uL PBS 8.5 buffer). The reaction mixture was vortexed and sat at RT for 30 min. The crude product was purified by HPLC with 5-60% 100 mM triethylammonium acetate in acetonitrile/water to afford 3 (1.09 mg, 0.164 umol) in 27.5% yield. TOF MS (ES$^-$): 6403.

2.P. Synthesis of siRNA Conjugated with X110

Scheme 2: Overview of the synthesis of 4.

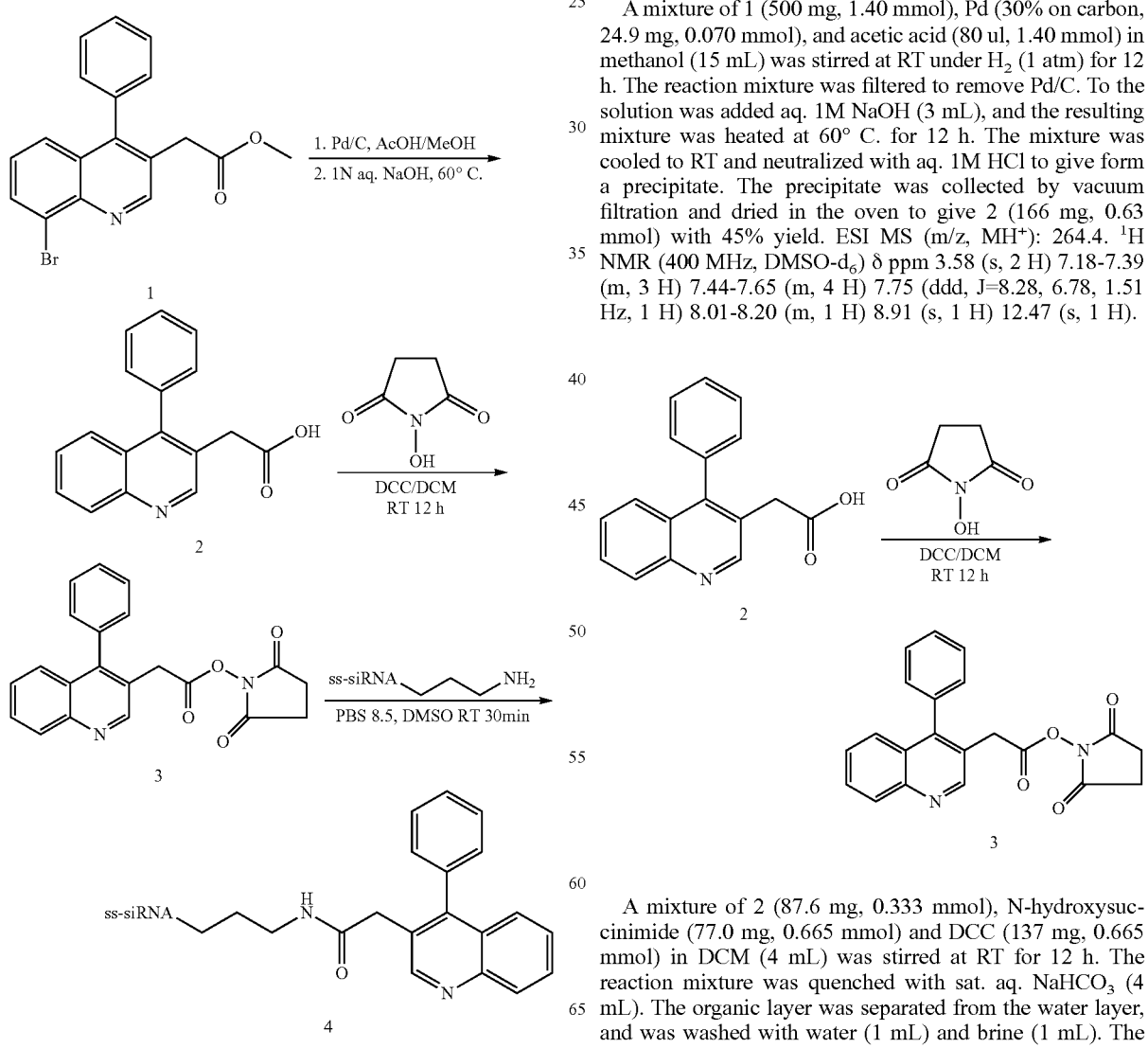

A mixture of 1 (500 mg, 1.40 mmol), Pd (30% on carbon, 24.9 mg, 0.070 mmol), and acetic acid (80 ul, 1.40 mmol) in methanol (15 mL) was stirred at RT under H$_2$ (1 atm) for 12 h. The reaction mixture was filtered to remove Pd/C. To the solution was added aq. 1M NaOH (3 mL), and the resulting mixture was heated at 60° C. for 12 h. The mixture was cooled to RT and neutralized with aq. 1M HCl to give form a precipitate. The precipitate was collected by vacuum filtration and dried in the oven to give 2 (166 mg, 0.63 mmol) with 45% yield. ESI MS (m/z, MH$^+$): 264.4. $^1$H NMR (400 MHz, DMSO-d$_6$) δ ppm 3.58 (s, 2 H) 7.18-7.39 (m, 3 H) 7.44-7.65 (m, 4 H) 7.75 (ddd, J=8.28, 6.78, 1.51 Hz, 1 H) 8.01-8.20 (m, 1 H) 8.91 (s, 1 H) 12.47 (s, 1 H).

A mixture of 2 (87.6 mg, 0.333 mmol), N-hydroxysuccinimide (77.0 mg, 0.665 mmol) and DCC (137 mg, 0.665 mmol) in DCM (4 mL) was stirred at RT for 12 h. The reaction mixture was quenched with sat. aq. NaHCO$_3$ (4 mL). The organic layer was separated from the water layer, and was washed with water (1 mL) and brine (1 mL). The organic solvent was removed under vacuum. The crude product was purified by recrystallization from methanol to give 3 (27.7 mg, 0.074 mmol) in 49% yield. ESI MS (m/z, MH+): 361.2. $^1$H NMR (400 MHz, DMSO-$d_6$) δ ppm 2.79 (br. s., 4 H) 4.05 (s, 2 H) 7.29-7.37 (m, 2 H) 7.40 (s, 1 H) 7.50-7.64 (m, 4 H) 7.80 (s, 1 H) 8.10 (s, 1 H) 9.02 (s, 1 H).

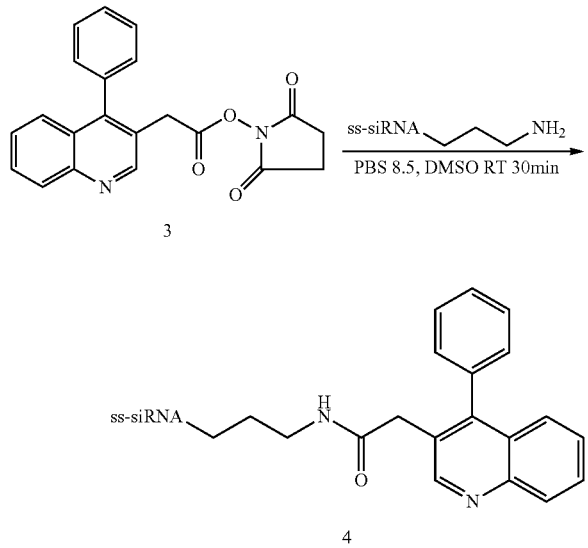

To 3 (1.76 mg, 4.88 umol) in DMSO (240 uL) was added a freshly ss-siRNA-(CH$_2$)$_3$—NH$_2$ solution (2 mg, 0.325 umol in 40 uL PBS 8.5 buffer). The reaction mixture was vortexed and sat at RT for 30 min. The crude product was purified by HPLC with 5-60% 100 mM triethylammonium acetate in acetonitrile/water to afford 4 (0.526 mg, 0.082 umol) in 25% yield. TOF MS (ES$^-$): 6388.

2. Q. Synthesis of siRNA Conjugated with X111

1 is commercial, but synthesis is not known in the literature

Scheme 3: Overview of the synthesis of 3.

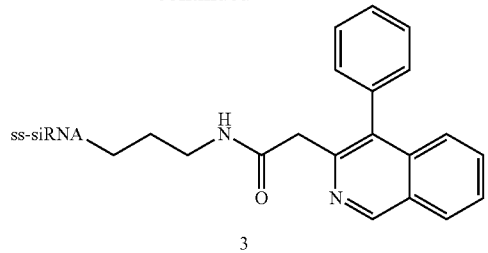

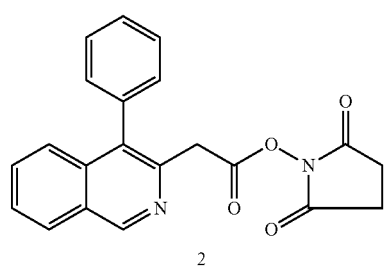

A mixture of 1 (81 mg, 0.308 mmol), N-hydroxysuccinimide (70.8 mg, 0.615 mmol) and DCC (127 mg, 0.615 mmol) in DCM (4 mL) was stirred at RT for 12 h. The reaction mixture was quenched with sat. aq. NaHCO$_3$ (4 mL). The organic layer was separated from the water layer, and was washed with water (1 mL) and brine (1 mL). The organic solvent was removed under vacuum. The crude product was purified by recrystallization from methanol to give 2 (43.7 mg, 0.121 mmol) in 39% yield. ESI MS (m/z, MH+): 361.4. $^1$H NMR (400 MHz, METHANOL-$d_4$) δ ppm 2.82 (s, 4 H) 4.07 (s, 2 H) 7.36-7.42 (m, 2 H) 7.46-7.51 (m, 1 H) 7.55-7.64 (m, 3 H) 7.70-7.77 (m, 2 H) 8.20 (dt, J=4.52, 2.26 Hz, 1 H) 9.29 (s, 1 H).

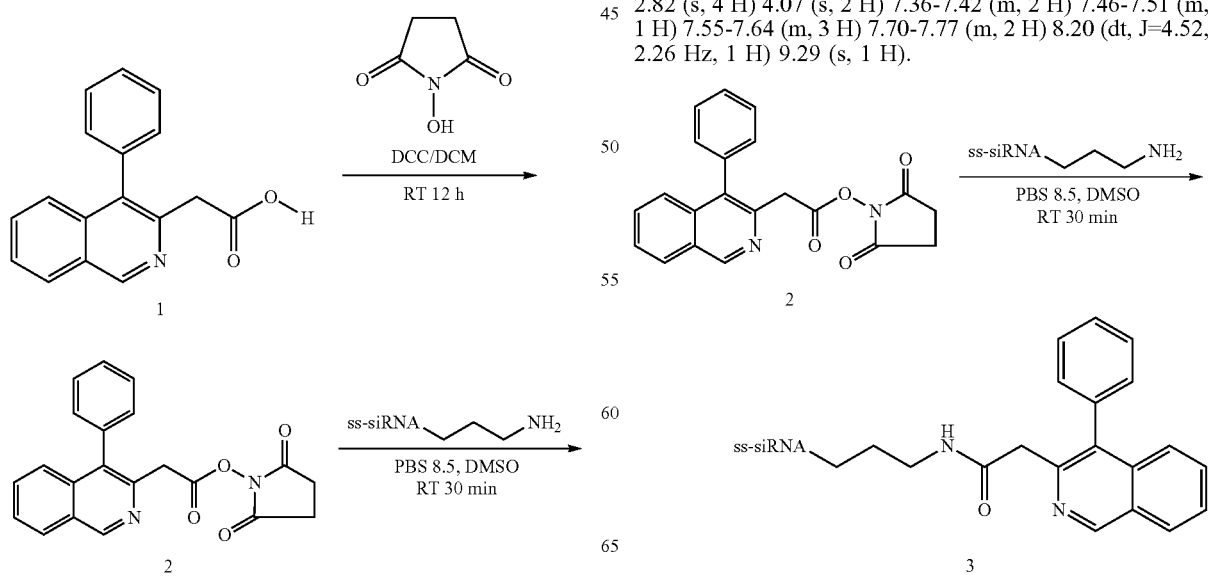

To 2 (2.35 mg, 6.51 umol) in DMSO (240 uL) was added a freshly ss-siRNA-(CH$_2$)$_3$—NH$_2$ solution (2 mg, 0.325 umol in 80 uL PBS 8.5 buffer). The reaction mixture was vortexed and sat at RT for 30 min. The crude product was purified by HPLC with 5-60% 100 mM triethylammonium acetate in acetonitrile/water to afford 3 (0.68 mg, 0.082 umol) in 33% yield. TOF MS (ES$^-$): 6390.

2.R. Synthesis of siRNA Conjugated with X112

Scheme 4: Overview of the synthesis of 3.

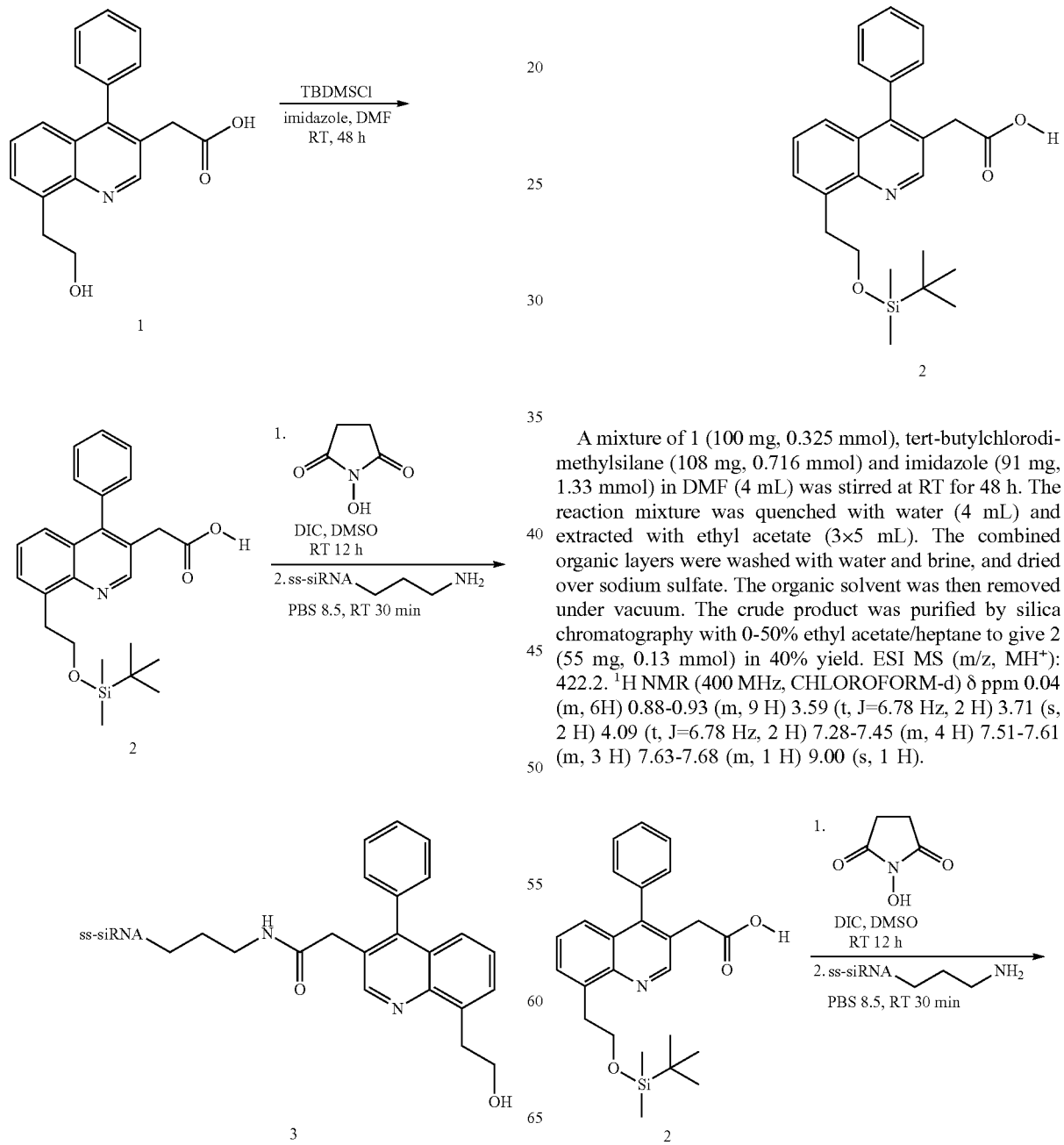

A mixture of 1 (100 mg, 0.325 mmol), tert-butylchlorodimethylsilane (108 mg, 0.716 mmol) and imidazole (91 mg, 1.33 mmol) in DMF (4 mL) was stirred at RT for 48 h. The reaction mixture was quenched with water (4 mL) and extracted with ethyl acetate (3×5 mL). The combined organic layers were washed with water and brine, and dried over sodium sulfate. The organic solvent was then removed under vacuum. The crude product was purified by silica chromatography with 0-50% ethyl acetate/heptane to give 2 (55 mg, 0.13 mmol) in 40% yield. ESI MS (m/z, MH$^+$): 422.2. $^1$H NMR (400 MHz, CHLOROFORM-d) δ ppm 0.04 (m, 6H) 0.88-0.93 (m, 9 H) 3.59 (t, J=6.78 Hz, 2 H) 3.71 (s, 2 H) 4.09 (t, J=6.78 Hz, 2 H) 7.28-7.45 (m, 4 H) 7.51-7.61 (m, 3 H) 7.63-7.68 (m, 1 H) 9.00 (s, 1 H).

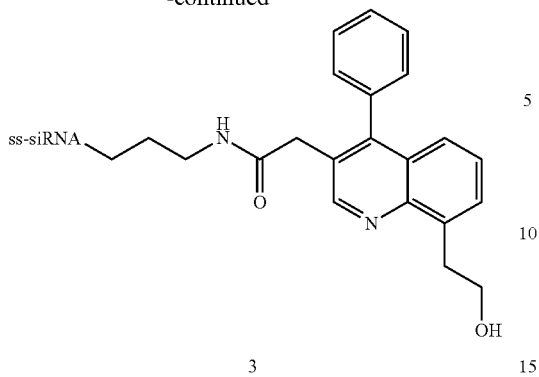

A mixture of N-hydroxysuccinimide (2.73 mg, 0.024 mmol), 2 (5.0 mg, 0.012 mmol), and DIC (2 mg, 0.325 umol) in DMSO (200 uL) was stirred at RT for 12 h. 10 uL reaction mixture was diluted with 190 uL DMSO. To the resulting solution was added a freshly ss-siRNA-(CH$_2$)$_3$—NH$_2$ solution (2.19 mg, 0.356 umol in 80 ul PBS 8.5 buffer). The reaction mixture was vortexed and sat at RT for 2 h. The crude product was purified by HPLC with 10-40% 100 mM triethylammonium acetate in acetonitrile/water to afford 3 (0.79 mg, 0.123 umol) in 35% yield. TOF MS (ES$^-$): 6435.

2.S. Synthesis of siRNA Conjugated with X113

1 is commercial and synthesis is known in the literature. Zhang, Yan et al. From PCT Int. Appl., 2010083384, 22 Jul. 2010.

Scheme 5: Overview of the synthesis of 2.

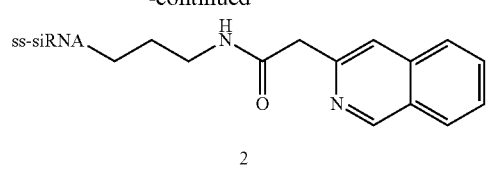

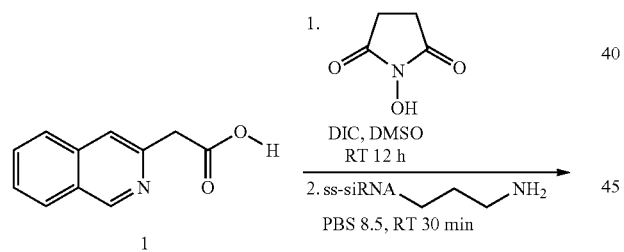

A mixture of N-hydroxysuccinimide (6.18 mg, 0.054 mmol), 1 (5.0 mg, 0.027 mmol), and DIC (6.77 mg, 0.054 mmol) in DMSO (200 uL) was stirred at RT for 12 h. 10 uL of reaction mixture was diluted with 190 uL DMSO. To the resulting solution was added a freshly ss-siRNA-(CH$_2$)$_3$—NH$_2$ solution (2.46 mg, 0.401 umol in 80 uL PBS 8.5 buffer). The reaction mixture was vortexed and sat at RT for 2 h. The crude product was purified by HPLC with 10-40% 100 mM triethylammonium acetate in acetonitrile/water to afford 2 (0.24 mg, 0.038 umol) in 10% yield. TOF MS (ES$^-$): 6315.

2. S. 1. General Procedure for the High Density Loading of Controlled Pore Glass Supports with PAZ Ligand Succinates

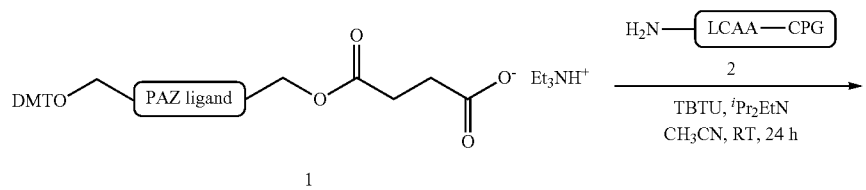

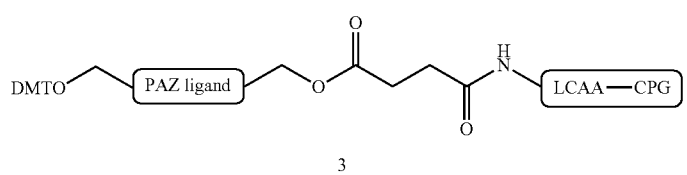

In an Erlenmeyer flask 1.00 mmol PAZ ligand succinate salt 1 was dissolved in 50 mL dry acetonitrile under argon. To this solution 353 mg (1.10 mmol) O-(1H-benzo-1,2,3-triazol-1-yl)-N,N,N',N'-tetramethyl-uronium tetrafluoroborate (TBTU) was added and the solution shaken for 10 min. Then 10 g long chain alkylamine controlled pore glass (LCAA/CNA-600-CPG, PrimeSynthesis, 2) was added and the reaction mixture gently agitated for 5 min. Finally, 0.685 mL (517 mg, 4.00 mmol) Hünig's base was added and the flask gently shaken for 24 h on an orbital shaker. Loading density was assessed by detritylating an aliquote of the CPG (3-5 mg CPG washed with acetonitrile, dried in vacuo, added to 25 mL 3% dichloroacetic acid in dichloromethane (v/v), absorbance at 504 nm determined). If loading density was in the desired range (60-90 micromol/g), the CPG was filtered off and washed extensively with acetonitrile. Underivatized amino groups were capped by treating the CPG with x mL each of a mixture of acetic anhydride/2,6-lutidine/THF 1:1:8 (v/v/v) and a solution of 1-methylimidazole in THF 16:84 (v/v). The mixture was gently shaken for 15 min at room temperature. Then the CPG was filtered off, washed with acetonitrile and dried under vacuum overnight. Loading density was determined again as above. Loading yields for the succinates in examples 1-6 were in the range of 64-75 micromol/g.

2. T. Synthesis of siRNA Conjugated with X1011

Scheme 1: Overview of the synthesis of 2.

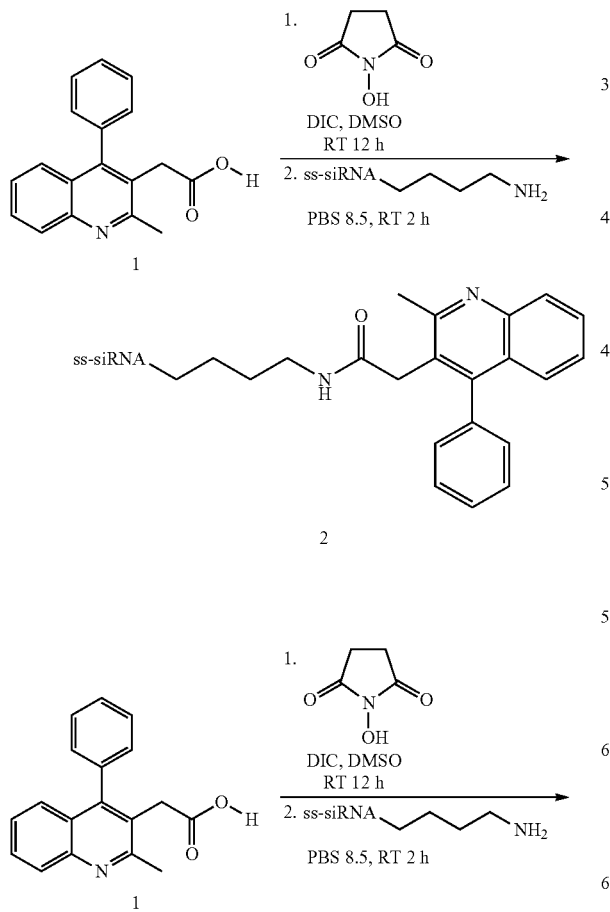

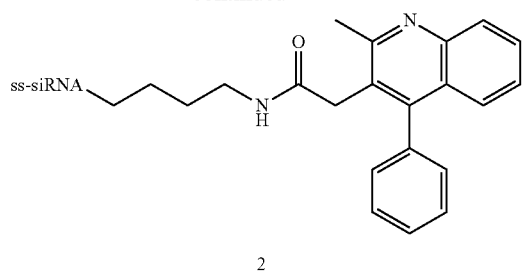

A mixture of N-hydroxysuccinimide (2.489 mg, 0.022 mmol), 1 (3.0 mg, 0.011 mmol), and DIC (2.73 mg, 0.022 mmol) in DMSO (200 uL) was stirred at RT for 12 h. 10 uL of reaction mixture was diluted with 190 uL DMSO. To the resulting solution was added a freshly ss-siRNA-(CH$_2$)$_4$—NH$_2$ solution (2.00 mg, 0.325 umol in 80 uL PBS 8.5 buffer). The reaction mixture was vortexed and sat at RT for 2 h. The crude product was purified by HPLC with 10-40% 100 mM triethylammonium acetate in acetonitrile/water to afford 2. TOF MS (ES$^-$): 6418.

2. U. Synthesis of siRNA Conjugated with X1012 and X1018

Scheme 2: Overview of the synthesis of 3.

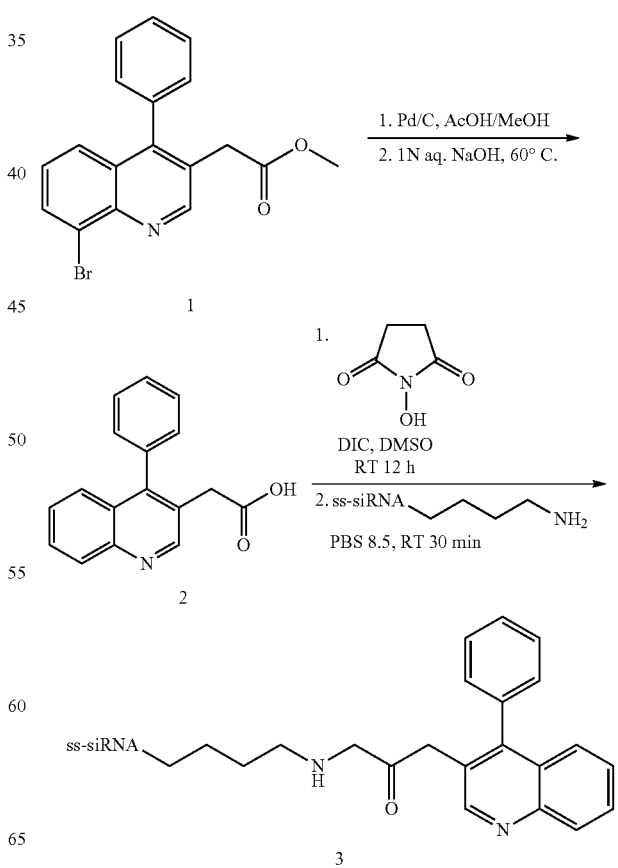

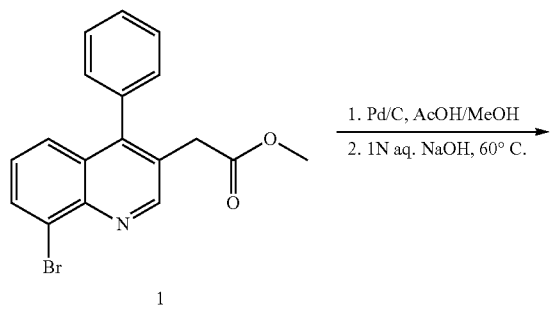

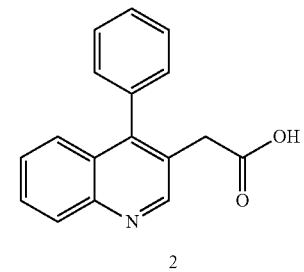

A mixture of 1 (500 mg, 1.40 mmol), Pd (30% on carbon, 24.9 mg, 0.070 mmol), and acetic acid (80 ul, 1.40 mmol) in methanol (15 mL) was stirred at RT under $H_2$ (1 atm) for 12 h. The reaction mixture was filtered to remove Pd/C. To the solution was added aq. 1M NaOH (3 mL), and the resulting mixture was heated at 60° C. for 12 h. The mixture was cooled to RT and neutralized with aq. 1M HCl to give form a precipitate. The precipitate was collected by vacuum filtration and dried in the oven to give 2 (166 mg, 0.63 mmol) with 45% yield. ESI MS (m/z, MH$^+$): 264.4. $^1$H NMR (400 MHz, DMSO-$d_6$) δ ppm 3.58 (s, 2 H) 7.18-7.39 (m, 3 H) 7.44-7.65 (m, 4 H) 7.75 (ddd, J=8.28, 6.78, 1.51 Hz, 1 H) 8.01-8.20 (m, 1 H) 8.91 (s, 1 H) 12.47 (s, 1 H).

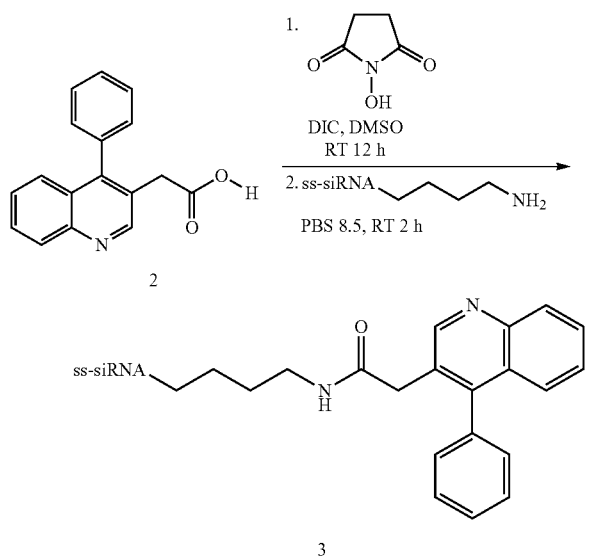

A mixture of N-hydroxysuccinimide (2.489 mg, 0.022 mmol), 2 (2.85 mg, 0.011 mmol), and DIC (2.73 mg, 0.022 mmol) in DMSO (200 uL) was stirred at RT for 12 h. 10 uL of reaction mixture was diluted with 190 uL DMSO. To the resulting solution was added a freshly ss-siRNA-$(CH_2)_4$—$NH_2$ solution (2.00 mg, 0.325 umol in 80 uL PBS 8.5 buffer). The reaction mixture was vortexed and sat at RT for 2 h. The crude product was purified by HPLC with 10-40% 100 mM triethylammonium acetate in acetonitrile/water to afford 3. ESI MS (ES$^+$): 6405.

2. U. Synthesis of siRNA Conjugated with X1018

Scheme 3: Overview of the synthesis of 4

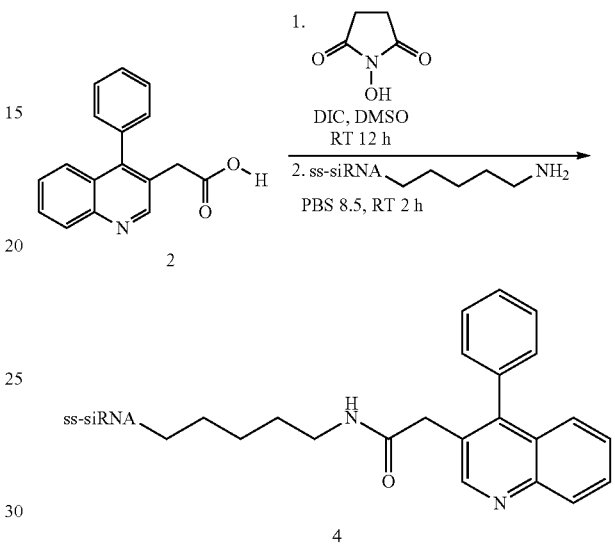

A mixture of N-hydroxysuccinimide (2.483 mg, 0.022 mmol), 2 (2.84 mg, 0.011 mmol), and DIC (2.72 mg, 0.022 mmol) in DMSO (200 uL) was stirred at RT for 12 h. 10 uL of reaction mixture was diluted with 190 uL DMSO. To the resulting solution was added a freshly ss-siRNA-$(CH_2)_5$—$NH_2$ solution (2.00 mg, 0.325 umol in 80 uL PBS 8.5 buffer). The reaction mixture was vortexed and sat at RT for 2 h. The crude product was purified by HPLC with 10-40% 100 mM triethylammonium acetate in acetonitrile/water to afford 4.

2. V. Synthesis of siRNA Conjugated with X1013

Scheme 4: Overview of the synthesis of 2.

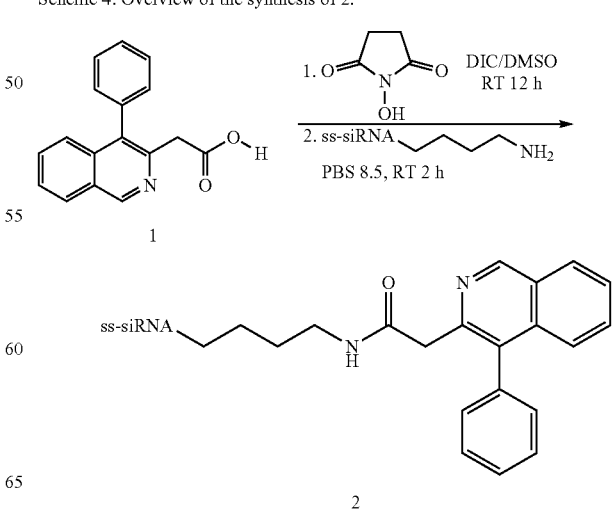

259

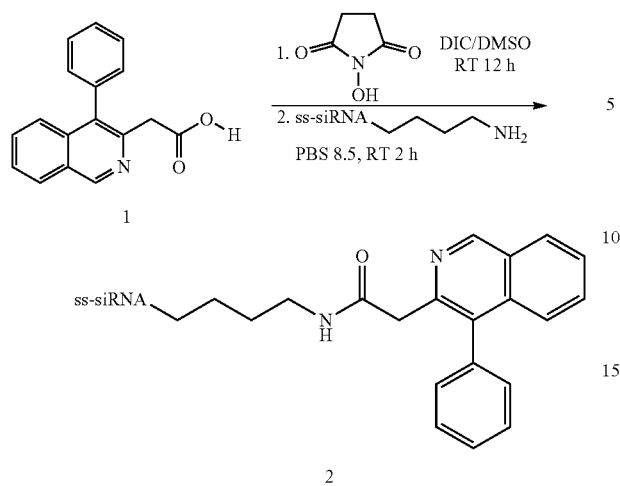

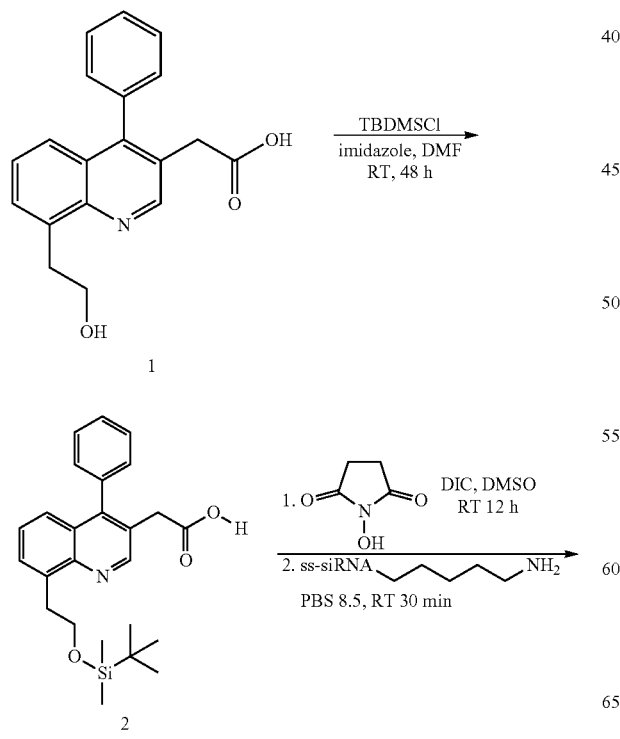

A mixture of N-hydroxysuccinimide (2.489 mg, 0.022 mmol), 2 (2.85 mg, 0.011 mmol), and DIC (2.73 mg, 0.022 mmol) in DMSO (200 uL) was stirred at RT for 12 h. 10 uL of reaction mixture was diluted with 190 uL DMSO. To the resulting solution was added a freshly ss-siRNA-$(CH_2)_4$—$NH_2$ solution (2.00 mg, 0.325 umol in 80 uL PBS 8.5 buffer). The reaction mixture was vortexed and sat at RT for 2 h. The crude product was purified by HPLC with 10-40% 100 mM triethylammonium acetate in acetonitrile/water to afford 2. TOF MS (ES$^-$): 6404.

2.W. Synthesis of siRNA Conjugated with X1019

Scheme 5: Overview of the synthesis of 3.

260

-continued

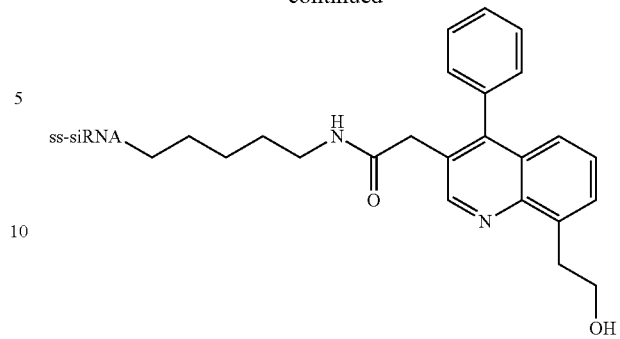

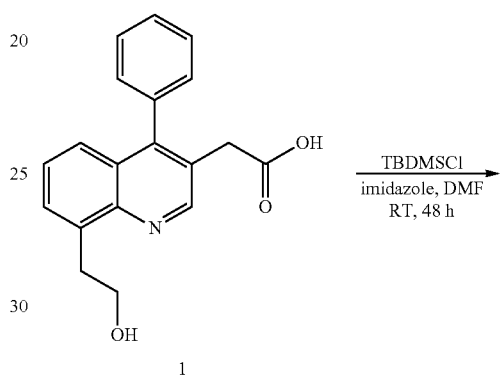

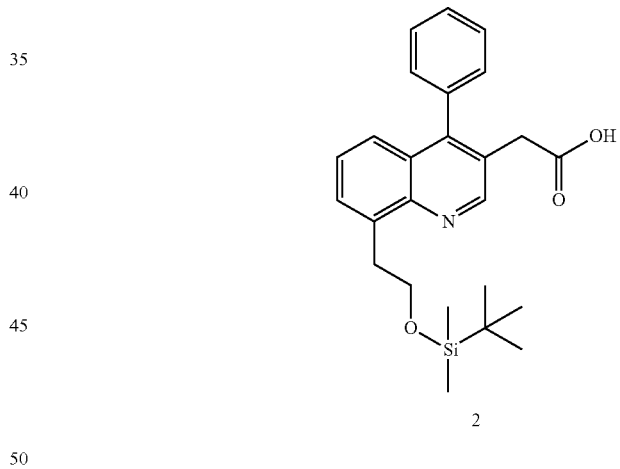

A mixture of 1 (100 mg, 0.325 mmol), tert-butylchlorodimethylsilane (108 mg, 0.716 mmol) and imidazole (91 mg, 1.33 mmol) in DMF (4 mL) was stirred at RT for 48 h. The reaction mixture was quenched with water (4 mL) and extracted with ethyl acetate (3×5 mL). The combined organic layers were washed with water and brine, and dried over sodium sulfate. The organic solvent was then removed under vacuum. The crude product was purified by silica chromatography with 0-50% ethyl acetate/heptane to give 2 (55 mg, 0.13 mmol) in 40% yield. ESI MS (m/z, MH$^+$): 422.2. $^1$H NMR (400 MHz, CHLOROFORM-d) δ ppm 0.04 (m, 6 H) 0.88-0.93 (m, 9 H) 3.59 (t, J=6.78 Hz, 2 H) 3.71 (s, 2 H) 4.09 (t, J=6.78 Hz, 2 H) 7.28-7.45 (m, 4 H) 7.51-7.61 (m, 3 H) 7.63-7.68 (m, 1 H) 9.00 (s, 1 H).

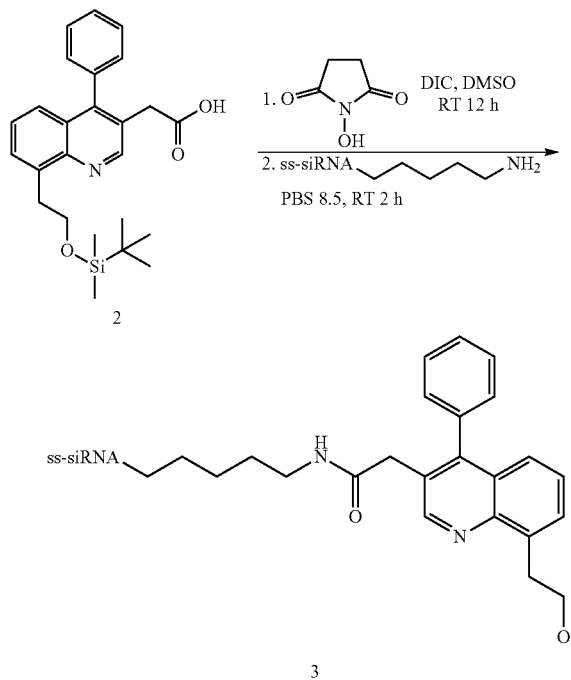

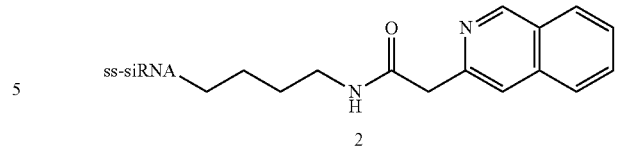

A mixture of N-hydroxysuccinimide (2.48 mg, 0.022 mmol), 2 (4.55 mg, 0.011 mmol), and DIC (2.72 mg, 0.022 mmol) in DMSO (200 uL) was stirred at RT for 12 h. 10 uL reaction mixture was diluted with 190 uL DMSO. To the resulting solution was added a freshly ss-siRNA-(CH$_2$)$_3$—NH$_2$ solution (2 mg, 0.324 umol in 80 ul PBS 8.5 buffer). The reaction mixture was vortexed and sat at RT for 2 h. The crude product was purified by HPLC with 10-40% 100 mM triethylammonium acetate in acetonitrile/water to afford 3. TOF MS (ES$^-$): 6462.

2. X. Synthesis of siRNA Conjugated with X1015

Scheme 6: Overview of the synthesis of 2.

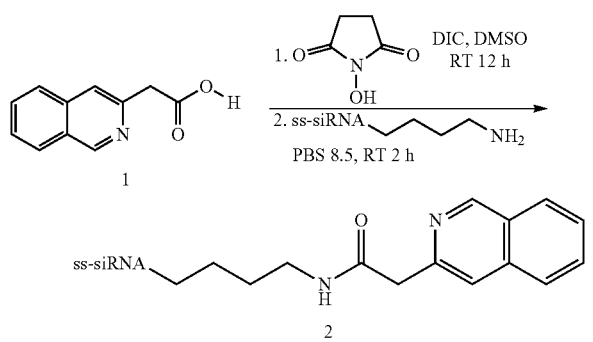

A mixture of N-hydroxysuccinimide (2.49 mg, 0.022 mmol), 1 (2.02 mg, 0.011 mmol), and DIC (2.73 mg, 0.022 mmol) in DMSO (200 uL) was stirred at RT for 12 h. 10 uL of reaction mixture was diluted with 190 uL DMSO. To the resulting solution was added a freshly ss-siRNA-(CH$_2$)$_4$—NH$_2$ solution (2 mg, 0.325 umol in 80 uL PBS 8.5 buffer). The reaction mixture was vortexed and sat at RT for 2 h. The crude product was purified by HPLC with 10-40% 100 mM triethylammonium acetate in acetonitrile/water to afford 2. TOF MS (ES$^-$): 6327.

2.Y. Synthesis of siRNA Conjugated with X1020

Scheme 7: Overview of the synthesis of 2.

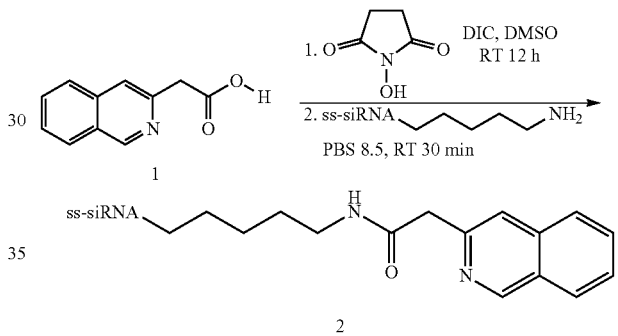

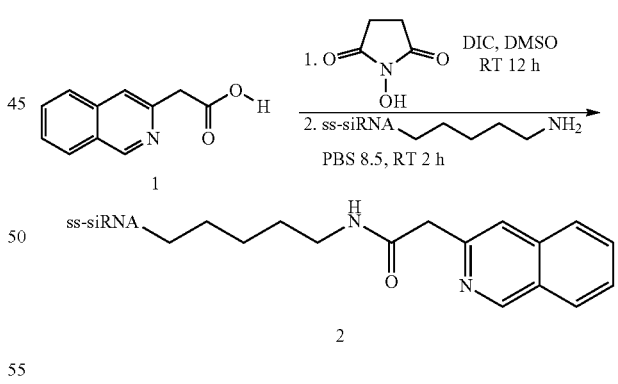

A mixture of N-hydroxysuccinimide (2.48 mg, 0.022 mmol), 1 (2.02 mg, 0.011 mmol), and DIC (2.72 mg, 0.022 mmol) in DMSO (200 uL) was stirred at RT for 12 h. 10 uL of reaction mixture was diluted with 190 uL DMSO. To the resulting solution was added a freshly ss-siRNA-(CH$_2$)$_5$—NH$_2$ solution (2 mg, 0.324 umol in 80 uL PBS 8.5 buffer). The reaction mixture was vortexed and sat at RT for 2 h. The crude product was purified by HPLC with 10-40% 100 mM triethylammonium acetate in acetonitrile/water to afford 2. TOF MS (ES$^-$): 6341.

2. Z. Synthesis of siRNA Conjugated with X1009

Scheme 7: Overview of the synthesis of 8.

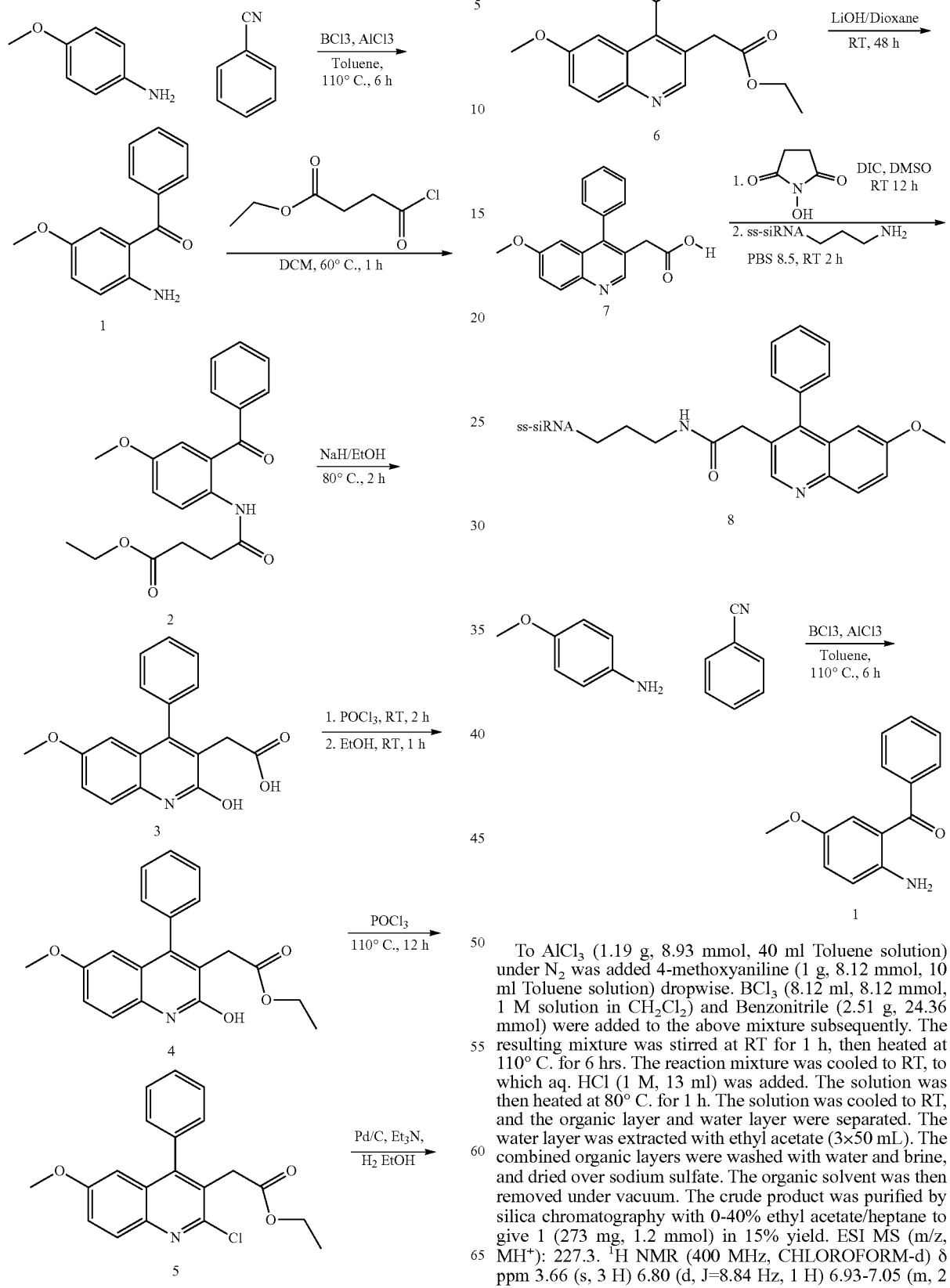

To AlCl$_3$ (1.19 g, 8.93 mmol, 40 ml Toluene solution) under N$_2$ was added 4-methoxyaniline (1 g, 8.12 mmol, 10 ml Toluene solution) dropwise. BCl$_3$ (8.12 ml, 8.12 mmol, 1 M solution in CH$_2$Cl$_2$) and Benzonitrile (2.51 g, 24.36 mmol) were added to the above mixture subsequently. The resulting mixture was stirred at RT for 1 h, then heated at 110° C. for 6 hrs. The reaction mixture was cooled to RT, to which aq. HCl (1 M, 13 ml) was added. The solution was then heated at 80° C. for 1 h. The solution was cooled to RT, and the organic layer and water layer were separated. The water layer was extracted with ethyl acetate (3×50 mL). The combined organic layers were washed with water and brine, and dried over sodium sulfate. The organic solvent was then removed under vacuum. The crude product was purified by silica chromatography with 0-40% ethyl acetate/heptane to give 1 (273 mg, 1.2 mmol) in 15% yield. ESI MS (m/z, MH$^+$): 227.3. $^1$H NMR (400 MHz, CHLOROFORM-d) δ ppm 3.66 (s, 3 H) 6.80 (d, J=8.84 Hz, 1 H) 6.93-7.05 (m, 2 H) 7.40-7.49 (m, 2 H) 7.49-7.58 (m, 1 H) 7.63-7.72 (m, 2 H).

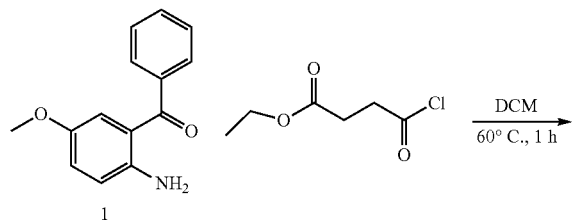

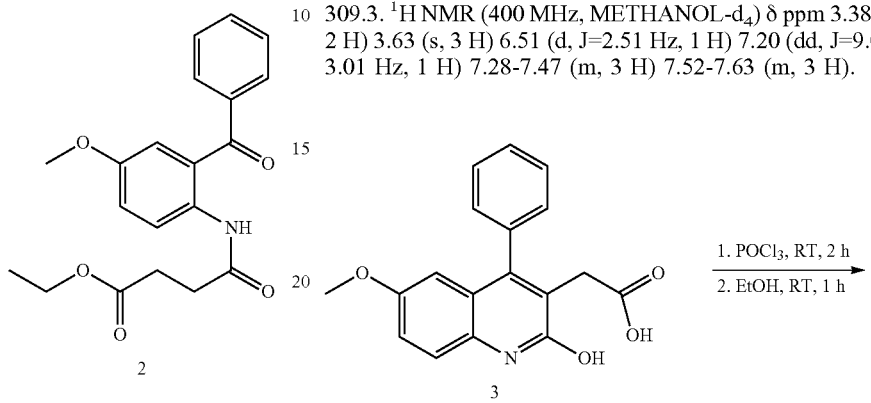

A mixture of 1 (269 mg, 1.18 mmol) and ethyl 4-chloro-4-oxobutanoate (214 mg, 1.3 mmol) in DCM (10 ml) was heated at 60° C. for 1 h. The reaction mixture was cooled and quenched with aq. 1 M NaOH (5 ml). Organic layer and water layer were separated. The water layer was extracted with dichloromethane (3×5 ml). The combined organic layers were washed with water and brine, and dried over sodium sulfate. The organic solvent was then removed under vacuum. The crude product was purified by silica chromatography with 0-60% ethyl acetate/heptane to give 2 (305 mg, 0.86 mmol) in 73% yield. ESI MS (m/z, MH+): 355.5. ¹H NMR (400 MHz, CHLOROFORM-d) δ ppm 1.26 (t, J=7.28 Hz, 3 H) 2.74 (s, 4 H) 3.77 (s, 3 H) 4.16 (q, J=7.03 Hz, 2 H) 7.06 (d, J=3.01 Hz, 1 H) 7.14 (dd, J=9.03, 3.01 Hz, 1 H) 7.48-7.55 (m, 2 H) 7.60-7.66 (m, 1 H) 7.73-7.79 (m, 2 H) 8.50 (d, J=9.03 Hz, 1 H) 10.45 (br. s., 1 H).

A mixture of 2 (305 mg, 0.86 mmol) and sodium hydride (343 mg, 8.58 mmol) in ethanol (10 ml) was heated at 80° C. for 2 h. The reaction mixture was cooled to RT and quenched with water (5 ml) then neutralized with aq. 1 M HCl (2 ml). The resulting solution was extracted with ethyl acetate (3×10 mL). The combined organic layers were washed with water and brine, and dried over sodium sulfate. The organic solvent was then removed under vacuum to give 3 (250 mg, 0.81 mmol) in 94% yield. ESI MS (m/z, MH+): 309.3. ¹H NMR (400 MHz, METHANOL-d₄) δ ppm 3.38 (s, 2 H) 3.63 (s, 3 H) 6.51 (d, J=2.51 Hz, 1 H) 7.20 (dd, J=9.03, 3.01 Hz, 1 H) 7.28-7.47 (m, 3 H) 7.52-7.63 (m, 3 H).

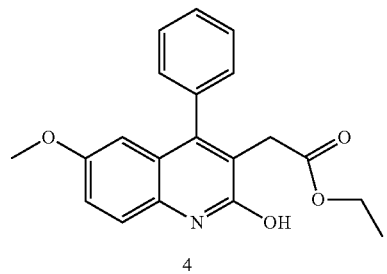

A solution of 3 (250 mg, 0.81 mmol) in POCl₃ (10 ml) was stirred at RT for 2 h. POCl₃ was removed under vacuum, the resulting residue was quenched with ethanol (20 ml). The solution was stirred at RT for 1 h, then ethanol was removed under vacuum. To the residue was added dichloromethane (30 ml) and aq. 1 M NaOH (20 ml). Organic layer and water layer were separated. The water layer was extracted with dichloromethane (2×20 ml). The combined organic layers were washed with water, brine and dried over sodium sulfate. The organic solvent was removed under vacuum to give 4 (270 mg, 0.8 mmol) in 99% yield. ESI MS (m/z, MH+): 338.2. ¹H NMR (400 MHz, CHLOROFORM-d) δ ppm 1.23-1.27 (m, 3 H) 3.48 (s, 2 H) 3.66 (s, 3 H) 4.04-4.22 (m, 2 H) 6.55 (d, J=2.51 Hz, 1 H) 7.09-7.15 (m, 1 H) 7.24 (d, J=9.03 Hz, 1 H) 7.29-7.34 (m, 2 H) 7.44-7.64 (m, 3 H) 10.49 (br. s., 1 H).

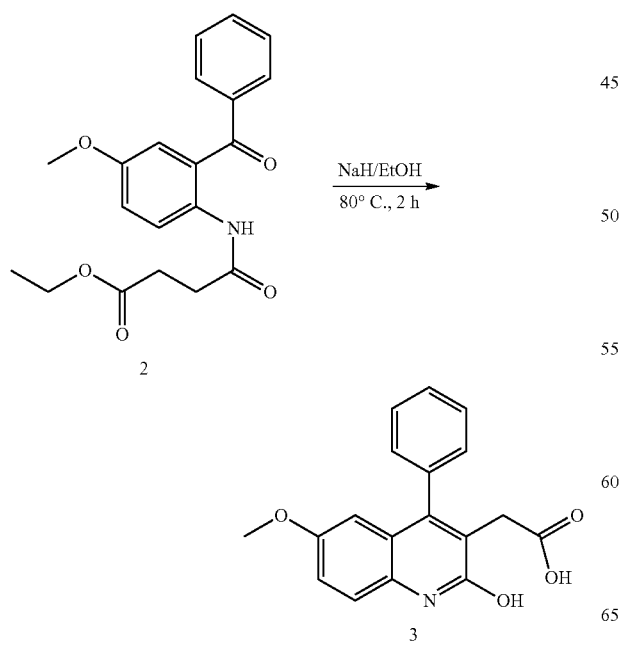

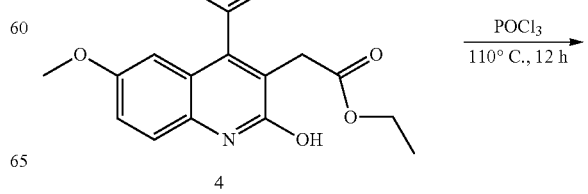

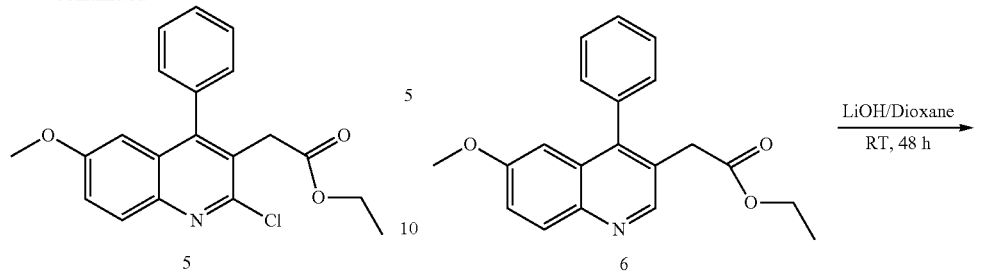

A solution of 4 (270 mg, 0.8 mmol) in POCl$_3$ (10 ml) was heated at 110° C. for 12 h. POCl$_3$ was removed under vacuum. To the residue was added dichloromethane (20 ml) and aq. 1 M NaOH (20 ml). The organic layer and water layer were separated. The water layer was extracted with dichloromethane (2×20 ml). The combined organic layers were washed with water, brine and dried over sodium sulfate. The organic solvent was removed under vacuum to give 5 (265 mg, 0.75 mmol) in 92% yield. ESI MS (m/z, MH$^+$): 356.1. $^1$H NMR (400 MHz, CHLOROFORM-d) δ ppm 1.22-1.27 (m, 3 H) 3.70 (s, 5 H) 4.17 (q, J=7.03 Hz, 2 H) 6.62 (d, J=3.01 Hz, 1 H) 7.20-7.34 (m, 2 H) 7.38 (dd, J=9.03, 2.51 Hz, 1 H) 7.46-7.63 (m, 3 H) 8.01 (d, J=9.03 Hz, 1 H).

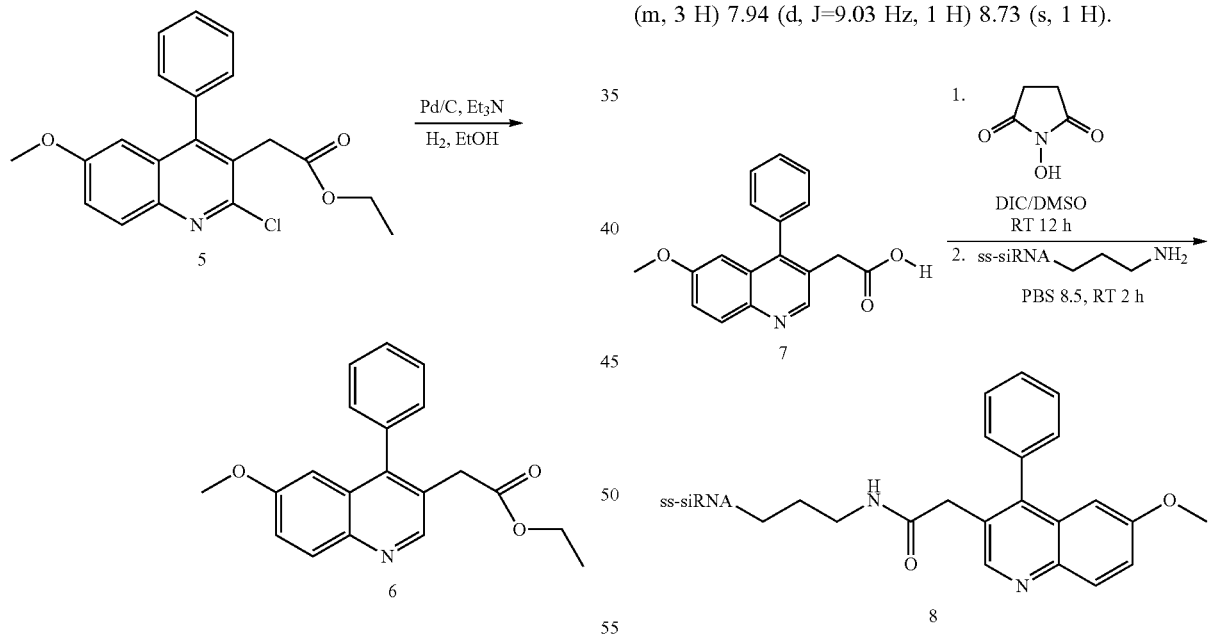

A mixture of 5 (265 mg, 0.745 mmol), triethylamine (1.28 g, 12.66 mmol), and Pd/C (10%, 79 mg, 0.745 mmol) in ethanol (20 ml) was stirred under H$_2$ (1 atm) at RT for 12 h. The reaction mixture was filtered to remove Pd/C. The organic solvent was removed under vacuum to give 6 (182 mg, 0.57 mmol) in 76% yield. ESI MS (m/z, MH$^+$): 322.1. $^1$H NMR (400 MHz, CHLOROFORM-d) δ ppm 1.12 (t, J=7.15 Hz, 3 H) 3.51 (s, 2 H) 3.62 (s, 3 H) 4.01 (q, J=7.19 Hz, 2 H) 6.61 (d, J=2.76 Hz, 1 H) 7.18-7.31 (m, 3 H) 7.39-7.50 (m, 3 H) 7.97 (d, J=9.29 Hz, 1 H) 8.68 (s, 1 H).

A mixture of 6 (50 mg, 0.16 mmol), aq. 1 M LiOH (0.17 ml, 0.17 mmol) in Dioxane (1 ml) was stirred at RT for 48 hrs. A precipitation from the reaction mixture was filtered and dried to give 7 (32 mg, 0.107 mmol) in 69% yield as lithium salt. ESI MS (m/z, MH$^+$): 294.2. $^1$H NMR (400 MHz, METHANOL-d$_4$) δ ppm 3.48 (s, 2 H) 3.63-3.73 (m, 3 H) 6.75 (d, J=2.51 Hz, 1 H) 7.28-7.43 (m, 3 H) 7.48-7.64 (m, 3 H) 7.94 (d, J=9.03 Hz, 1 H) 8.73 (s, 1 H).

A mixture of N-hydroxysuccinimide (2.49 mg, 0.022 mmol), 7 (3.18 mg, 0.011 mmol), and DIC (2.74 mg, 0.022 mmol) in DMSO (200 uL) was stirred at RT for 12 h. 10 uL of reaction mixture was diluted with 190 uL DMSO. To the resulting solution was added a freshly ss-siRNA-(CH$_2$)$_3$—NH$_2$ solution (2 mg, 0.325 umol in 80 uL PBS 8.5 buffer). The reaction mixture was vortexed and sat at RT for 2 h. The crude product was purified by HPLC with 10-40% 100 mM triethylammonium acetate in acetonitrile/water to afford 8. TOF MS (ES$^-$): 6422.

2. AA. Synthesis of siRNA Conjugated with X1016

Scheme 8: Overview of the synthesis of 9.

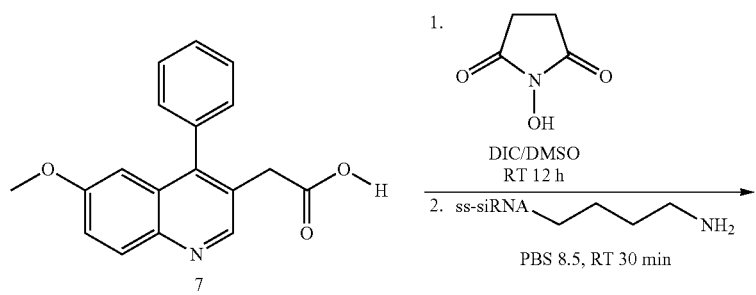

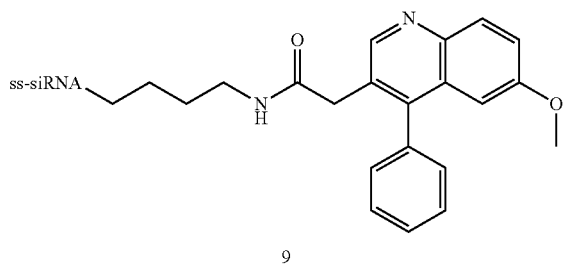

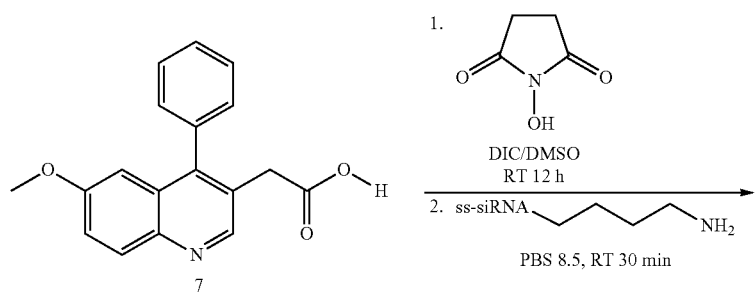

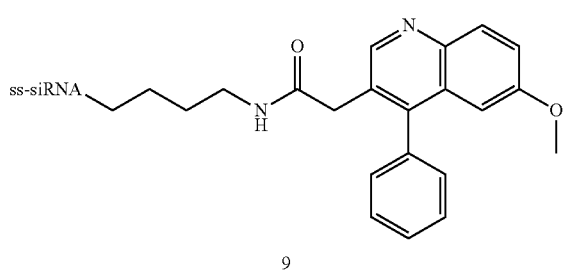

A mixture of N-hydroxysuccinimide (2.49 mg, 0.022 mmol), 7 (3.18 mg, 0.011 mmol), and DIC (2.74 mg, 0.022 mmol) in DMSO (200 uL) was stirred at RT for 12 h. 10 uL of reaction mixture was diluted with 190 uL DMSO. To the resulting solution was added a freshly ss-siRNA-(CH$_2$)$_4$—NH$_2$ solution (2 mg, 0.325 umol in 80 uL PBS 8.5 buffer). The reaction mixture was vortexed and sat at RT for 2 h. The crude product was purified by HPLC with 10-40% 100 mM triethylammonium acetate in acetonitrile/water to afford 9. TOF MS (ES$^-$): 6434.

2. BB. Synthesis of siRNA Conjugated with X1021

Scheme 9: Overview of the synthesis of 10.

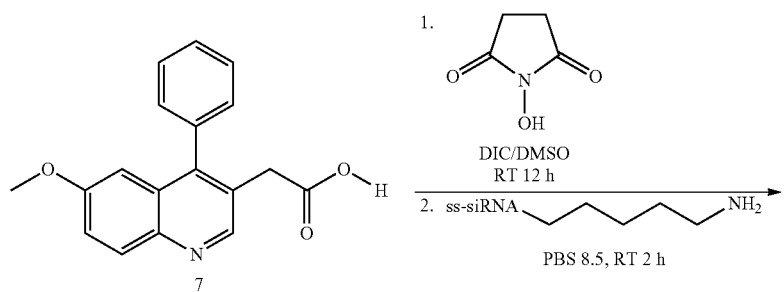

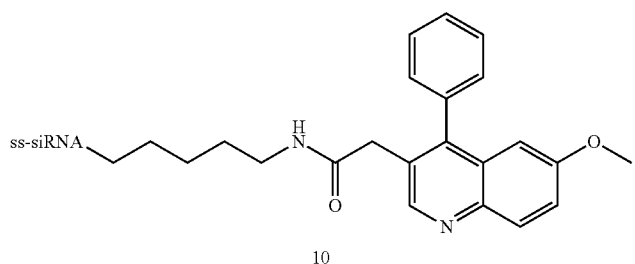

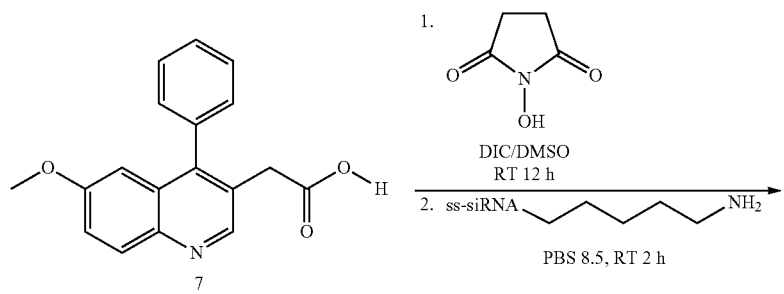

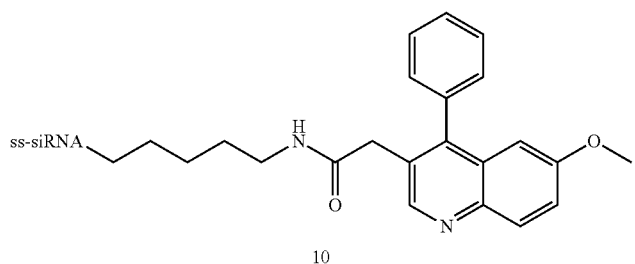

A mixture of N-hydroxysuccinimide (2.48 mg, 0.022 mmol), 7 (3.16 mg, 0.011 mmol), and DIC (2.72 mg, 0.022 mmol) in DMSO (200 uL) was stirred at RT for 12 h. 10 uL of reaction mixture was diluted with 190 uL DMSO. To the resulting solution was added a freshly ss-siRNA-$(CH_2)_5$—$NH_2$ solution (2 mg, 0.325 umol in 80 uL PBS 8.5 buffer). The reaction mixture was vortexed and sat at RT for 2 h. The crude product was purified by HPLC with 10-40% 100 mM triethylammonium acetate in acetonitrile/water to afford 10. TOF MS (ES$^-$): 6448.

2. CC. Synthesis of siRNA Conjugated with X1010
Scheme 10: Overview of the synthesis of 10.
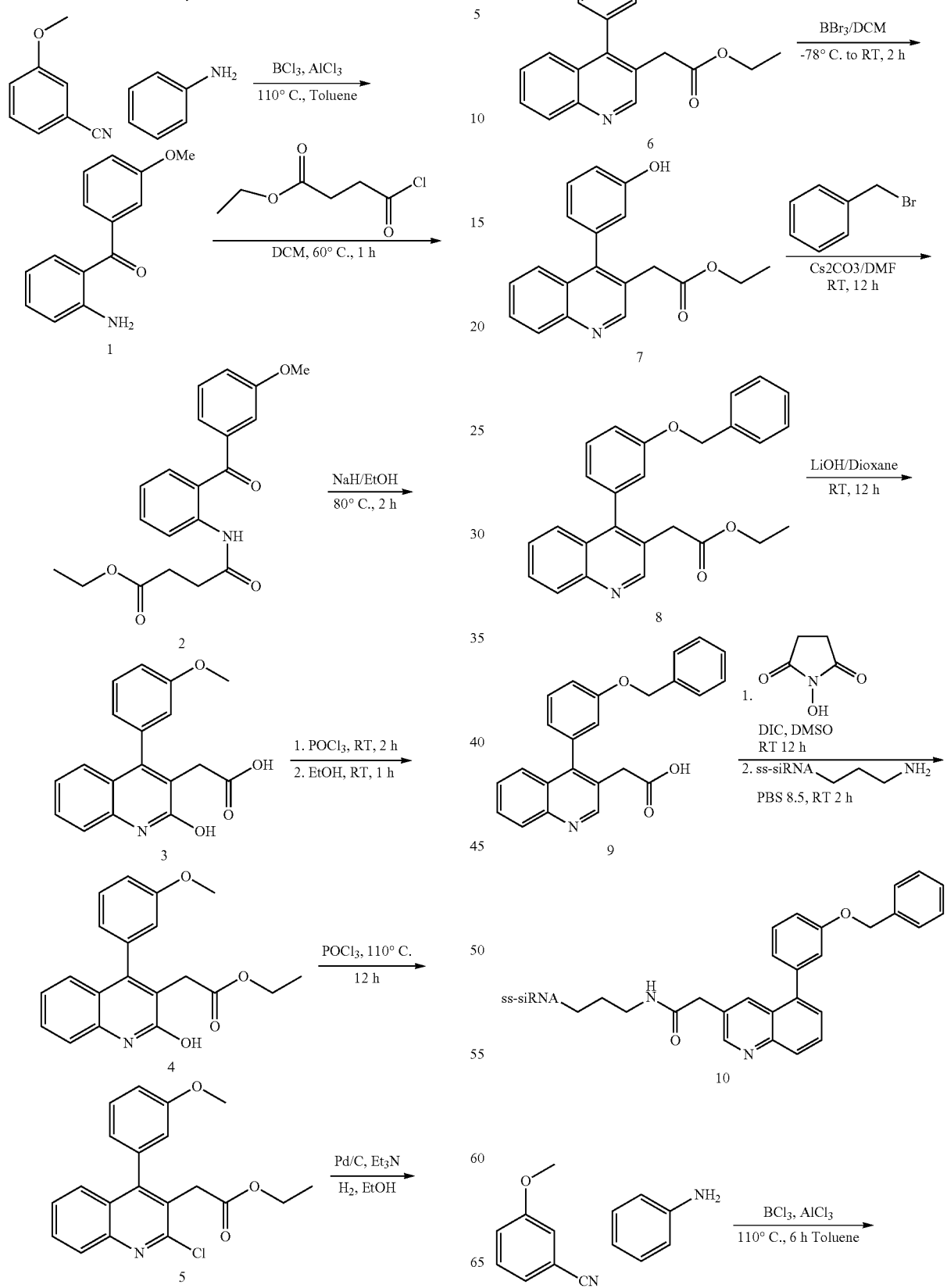

-continued

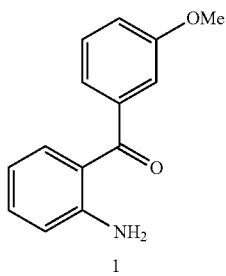

To BCl₃ (10.74 ml, 10.74 mmol, 1 M solution in CH₂Cl₂) under N₂ was added aniline (1 g, 10.74 mmol, 10 ml Toluene solution) dropwise. 3-methoxybenzonitrile (4.29 g, 32.2 mmol) and AlCl₃ (1.575 g, 11.81 mmol, 40 ml Toluene solution) were added to the above mixture subsequently. The resulting mixture was stirred at RT for 1 h, then heated at 110° C. for 6 hrs. The reaction mixture was cooled to RT, to which aq. HCl (1 M, 13 ml) was added. The solution was then heated at 80° C. for 1 h. The solution was cooled to RT, and the organic layer and water layer were separated. The water layer was extracted with ethyl acetate (3×50 mL). The combined organic layers were washed with water and brine, and dried over sodium sulfate. The organic solvent was then removed under vacuum. The crude product was purified by silica chromatography with 0-40% ethyl acetate/heptane to give 1 (875 mg, 3.85 mmol) in 36% yield. ESI MS (m/z, MH⁺): 227.9. ¹H NMR (400 MHz, CHLOROFORM-d) δ ppm 3.74 (s, 3 H) 6.00 (br. s., 2 H) 6.44-6.56 (m, 1 H) 6.63 (dd, J=8.53, 1.00 Hz, 1 H) 6.93-7.00 (m, 1 H) 7.04-7.11 (m, 2 H) 7.14-7.31 (m, 2 H) 7.37 (dd, J=8.03, 1.51 Hz, 1 H).

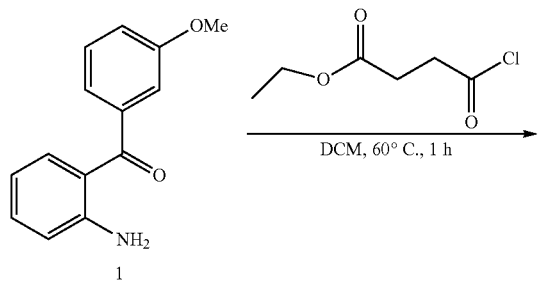

A mixture of 1 (570 mg, 2.51 mmol) and ethyl 4-chloro-4-oxobutanoate (454 mg, 2.76 mmol) in DCM (20 ml) was heated at 60° C. for 1 h. The reaction mixture was cooled and quenched with aq. 1 M NaOH (5 ml). The organic layer and water layer were separated. The water layer was extracted with dichloromethane (3×15 ml). The combined organic layers were washed with water and brine, and dried over sodium sulfate. The organic solvent was then removed under vacuum to give 2 (824 mg, 2.32 mmol) in 92% yield. ESI MS (m/z, MH⁺): 355.4. ¹H NMR (400 MHz, CHLOROFORM-d) δ ppm 1.25-1.48 (m, 3 H) 2.73-3.01 (m, 4 H) 3.88 (s, 3 H) 4.18 (q, J=7.07 Hz, 2 H) 7.05-7.20 (m, 2 H) 7.22-7.30 (m, 2 H) 7.37-7.45 (m, 1 H) 7.53-7.64 (m, 2 H) 8.64 (d, J=8.59 Hz, 1 H) 10.90 (br. s., 1 H).

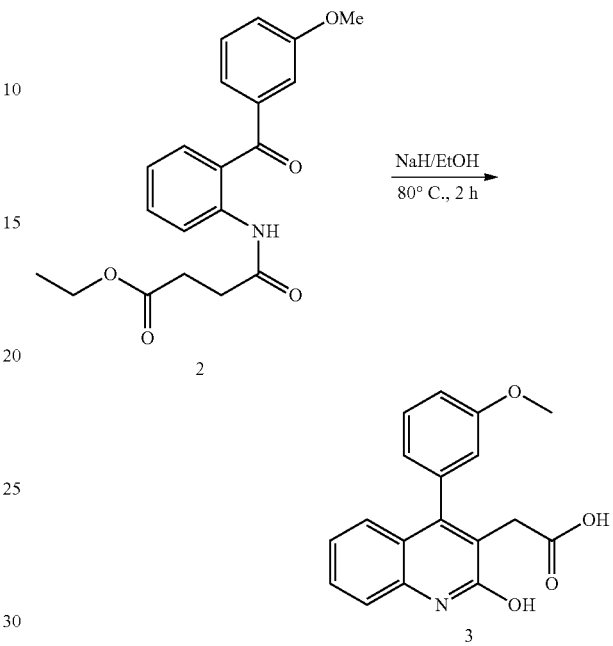

A mixture of 2 (824 mg, 2.32 mmol) and sodium hydride (927 mg, 23.19 mmol) in ethanol (20 ml) was heated at 80° C. for 2 h. The reaction mixture was cooled to RT and quenched with water (5 ml) then neutralized with aq. 1 M HCl (2 ml). The resulting solution was extracted with ethyl acetate (3×10 mL). The combined organic layers were washed with water and brine, and dried over sodium sulfate. The organic solvent was then removed under vacuum to give 3 (583 mg, 0.81 mmol) in 81% yield. ESI MS (m/z, MH⁺): 310.1. ¹H NMR (400 MHz, CHLOROFORM-d) δ ppm 3.49-3.64 (m, 2 H) 3.83-3.89 (m, 3 H) 6.83-6.96 (m, 2 H) 7.00-7.28 (m, 4 H) 7.37-7.56 (m, 4 H) 12.02-12.32 (m, 2 H).

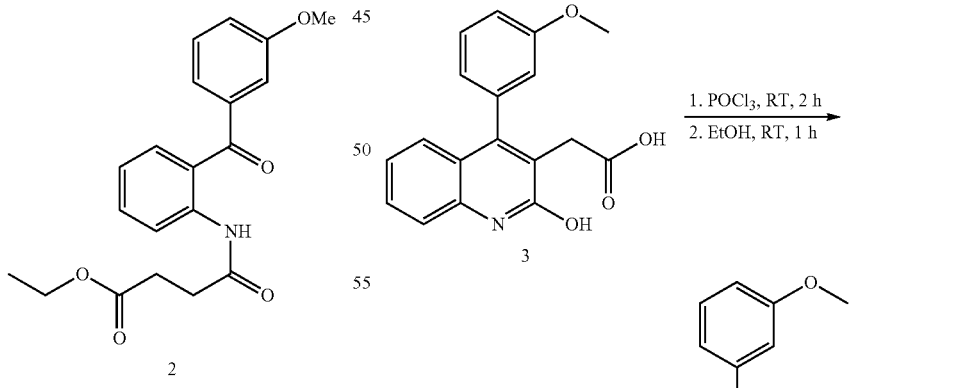

A solution of 3 (583 mg, 1.89 mmol) in POCl₃ (10 ml) was stirred at RT for 2 h. POCl₃ was removed under vacuum, the resulting residue was quenched with ethanol (20 ml). The solution was stirred at RT for 1 h, then ethanol was removed under vacuum. To the residue was added dichloromethane (30 ml) and aq. 1 M NaOH (20 ml). Organic layer and water layer were separated. The water layer was extracted with dichloromethane (2×20 ml). The combined organic layers were washed with water, brine and dried over sodium sulfate. The organic solvent was removed under vacuum to give 4 (760 mg, 2.25 mmol) in 120% yield. ESI MS (m/z, MH+): 338.1. $^1$H NMR (400 MHz, CHLOROFORM-d) δ ppm 1.26 (t, J=7.07 Hz, 3 H) 3.44-3.64 (m, 2 H) 3.85 (s, 3 H) 4.17 (q, J=7.16 Hz, 2 H) 6.85-6.93 (m, 2 H) 7.03 (ddd, J=8.46, 2.65, 1.01 Hz, 1 H) 7.11 (ddd, J=8.21, 6.95, 1.01 Hz, 1 H) 7.17 (dd, J=8.21, 1.39 Hz, 1 H) 7.32-7.39 (m, 1H) 7.40-7.52 (m, 2 H) 11.43 (br. s., 1 H)

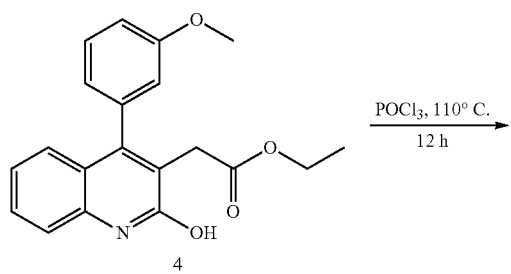

A solution of 4 (760 mg, 2.25 mmol) in POCl$_3$ (10 ml) was heated at 110° C. for 12 h. POCl$_3$ was removed under vacuum. To the residue was added dichloromethane (20 ml) and aq. 1 M NaOH (20 ml). The organic layer and water layer were separated. The water layer was extracted with dichloromethane (2×20 ml). The combined organic layers were washed with water, brine and dried over sodium sulfate. The organic solvent was removed under vacuum to give 5 (650 mg, 1.83 mmol) in 97% yield. ESI MS (m/z, MH+): 355.4. $^1$H NMR (400 MHz, CHLOROFORM-d) δ ppm 1.25 (t, J=7.28 Hz, 3 H) 3.75 (d, J=1.00 Hz, 2 H) 3.85 (s, 3 H) 4.18 (q, J=7.03 Hz, 2 H) 6.78-6.92 (m, 2 H) 6.97-7.13 (m, 1 H) 7.39-7.60 (m, 3 H) 7.76 (d, J=2.01 Hz, 1 H) 8.15 (d, J=8.53 Hz, 1 H).

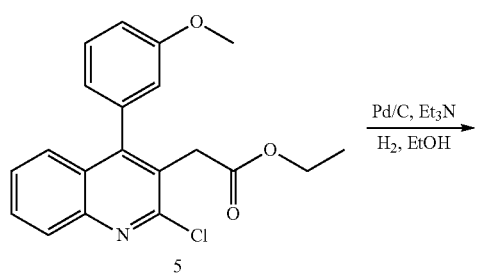

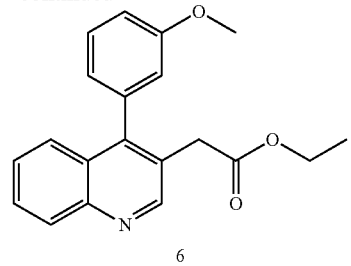

A mixture of 5 (650 mg, 1.83 mmol), triethylamine (3.14 g, 31.1 mmol), and Pd/C (10%, 194 mg, 1.827 mmol) in ethanol (20 ml) was stirred under H$_2$ (1 atm) at RT for 12 h. The reaction mixture was filtered to remove Pd/C. The organic solvent was removed under vacuum to give 6 (460 mg, 1.43 mmol) in 78% yield. ESI MS (m/z, MH+): 321.5. $^1$H NMR (400 MHz, CHLOROFORM-d) δ ppm 1.20-1.26 (m, 3 H) 1.44 (t, J=7.53 Hz, 9 H) 3.12 (qd, J=7.28, 4.77 Hz, 6 H) 3.65 (s, 2 H) 3.79-3.93 (m, 3 H) 4.12 (q, J=7.19 Hz, 2 H) 6.82-6.92 (m, 2 H) 7.06 (ddd, J=8.53, 2.51, 1.00 Hz, 1 H) 7.39-7.58 (m, 3 H) 7.72 (ddd, J=8.41, 6.65, 1.51 Hz, 1 H) 8.19 (d, J=8.53 Hz, 1 H) 8.93 (s, 1 H) 12.20 (br. s., 3 H).

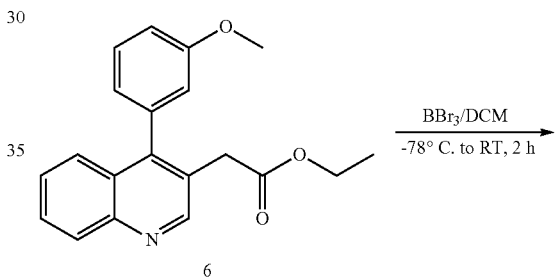

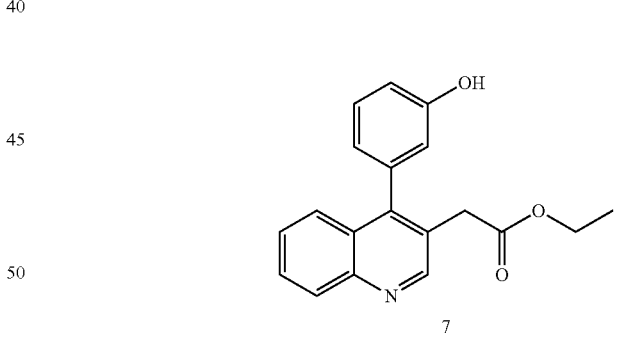

To a solution of 6 (400 mg, 1.245 mmol) in DCM (15 ml) was added BBr$_3$ (1 M in DCM, 3.73 ml, 3.73 mmol) at −78° C. The reaction mixture was warmed to RT in 2 h. The mixture was cooled down to −78° C., and quenched with ethanol. The organic solvent was removed under vacuum. To the resulting residue was added ethyl acetate (15 ml) and water (15 ml). The organic and water layer were separated. The water layer was extracted with ethyl acetate (3×15 ml). The combined organic layers were washed with water, brine and dried over sodium sulfate. The organic solvent was removed under vacuum. The crude was purified by recrystallization from dichloromethane to give 7 (282 mg, 0.92 mmol) in 74% yield. ESI MS (m/z, MH$^+$): 308.2. $^1$H NMR (400 MHz, DMSO-d$_6$) δ ppm 1.11 (t, J=7.03 Hz, 3 H) 3.68 (s, 2 H) 3.91-4.11 (m, 2 H) 6.50-6.70 (m, 2 H) 6.81-6.97 (m, 1 H) 7.30-7.48 (m, 2 H) 7.51-7.63 (m, 1 H) 7.78 (ddd, J=8.53, 7.03, 1.51 Hz, 1 H) 8.08 (d, J=8.03 Hz, 1 H) 8.93 (s, 1H) 9.75 (br. s., 1 H).

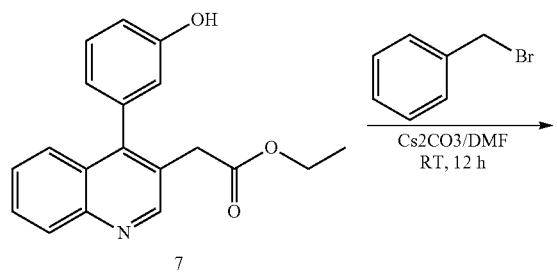

A mixture of 7 (20 mg, 0.065 mmol), benzyl bromide (16.69 mg, 0.098 mmol) and cesium carbonate (42.4 mg, 0.13 mmol) in DMF (500 ul) was stirred at RT for 12 hrs. The reaction mixture was filtered to remove insoluble material. The crude product was purified by HPLC with 5% NH$_4$OH in 5-95% acetonitrile/water to give 8 (6.9 mg, 0.017 mmol) in 26.7% yield. ESI MS (m/z, MH$^+$): 398.3. $^1$H NMR (400 MHz, CHLOROFORM-d) δ ppm 1.22 (t, J=7.03 Hz, 3 H) 3.64 (s, 2 H) 4.12 (q, J=7.03 Hz, 2 H) 5.11 (s, 2 H) 6.76-7.02 (m, 2 H) 7.13 (ddd, J=8.53, 2.51, 1.00 Hz, 1 H) 7.31-7.56 (m, 8 H) 7.71 (ddd, J=8.28, 6.78, 2.01 Hz, 1 H) 8.17 (d, J=8.53 Hz, 1 H) 8.92 (s, 1 H).

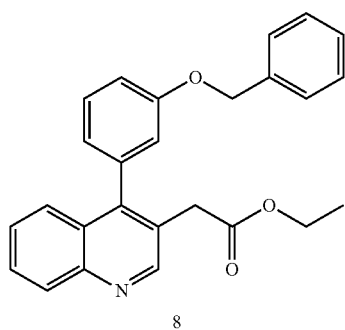

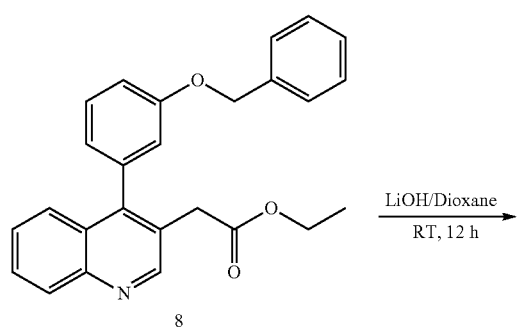

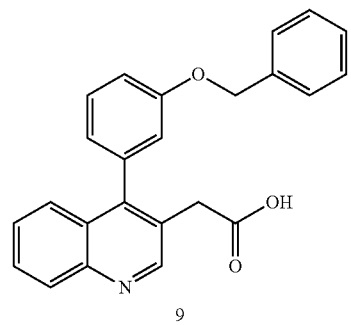

A mixture of 8 (6.9 mg, 0.017 mmol), aq. 1 M LiOH (0.019 ml, 0.019 mmol) in Dioxane (0.5 ml) was stirred at RT for 12 hrs. The organic solvent was removed under vacuum to give 9 (6 mg, 0.016 mmol) in 92% yield as lithium salt. ESI MS (m/z, MH$^+$): 370.2. $^1$H NMR (400 MHz, METHANOL-d$_4$) δ ppm 3.42-3.60 (m, 2 H) 5.07-5.19 (m, 2 H) 6.94 (dt, J=7.53, 1.25 Hz, 1 H) 7.06 (dd, J=2.51, 1.51 Hz, 1 H) 7.14 (ddd, J=8.53, 2.51, 1.00 Hz, 1 H) 7.25-7.42 (m, 3 H) 7.42-7.53 (m, 2 H) 7.70 (ddd, J=8.41, 4.64, 3.51 Hz, 2 H) 8.04 (d, J=8.03 Hz, 1 H) 8.56 (s, 2 H) 8.88 (s, 1 H).

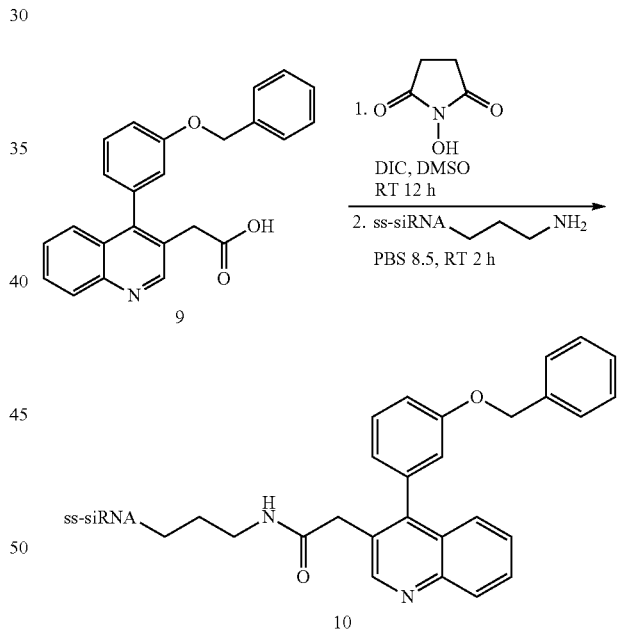

A mixture of N-hydroxysuccinimide (2.49 mg, 0.022 mmol), 9 (4.08 mg, 0.011 mmol), and DIC (2.74 mg, 0.022 mmol) in DMSO (200 uL) was stirred at RT for 12 h. 10 uL of reaction mixture was diluted with 190 uL DMSO. To the resulting solution was added a freshly ss-siRNA-(CH$_2$)$_3$—NH$_2$ solution (2 mg, 0.325 umol in 80 uL PBS 8.5 buffer). The reaction mixture was vortexed and sat at RT for 2 h. The crude product was purified by HPLC with 10-40% 100 mM triethylammonium acetate in acetonitrile/water to afford 10. TOF MS (ES$^-$): 6495.

2. DD. Synthesis of siRNA Conjugated with X1017

Scheme 11: Overview of the synthesis of 11.

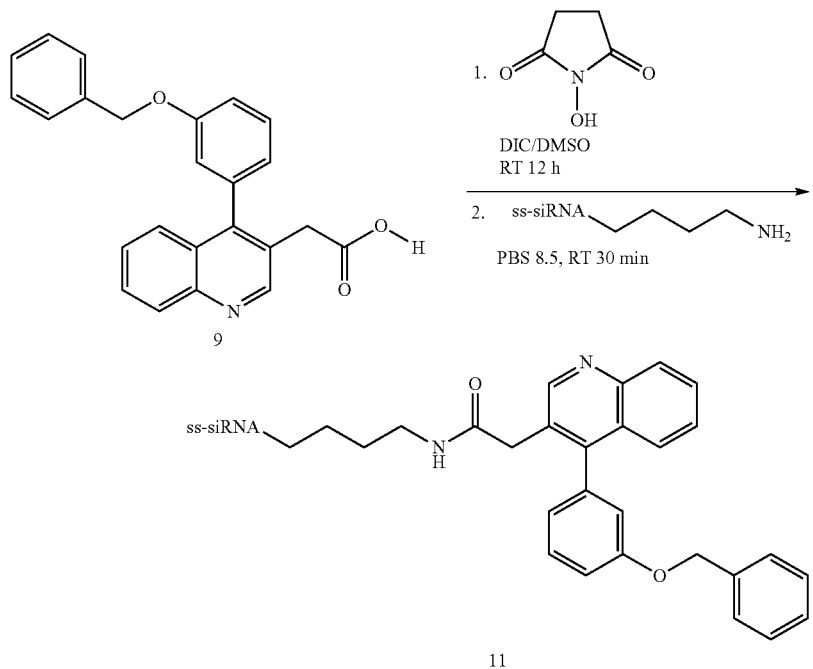

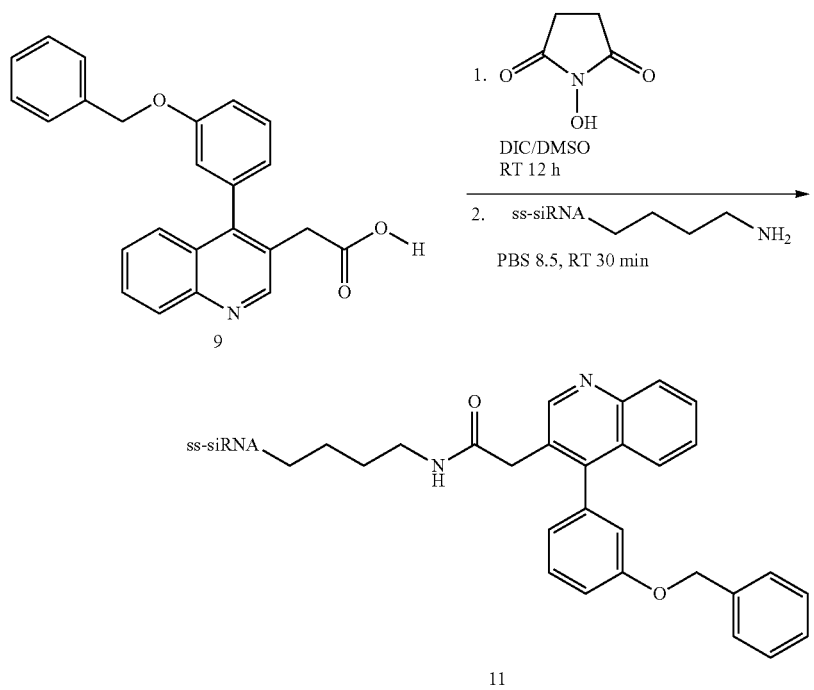

A mixture of N-hydroxysuccinimide (2.49 mg, 0.022 mmol), 9 (4.07 mg, 0.011 mmol), and DIC (2.73 mg, 0.022 mmol) in DMSO (200 uL) was stirred at RT for 12 h. 10 uL of reaction mixture was diluted with 190 uL DMSO. To the resulting solution was added a freshly ss-siRNA-(CH$_2$)$_4$—NH$_2$ solution (2 mg, 0.325 umol in 80 uL PBS 8.5 buffer). The reaction mixture was vortexed and sat at RT for 2 h. The crude product was purified by HPLC with 10-40% 100 mM triethylammonium acetate in acetonitrile/water to afford 11. TOF MS (ES$^-$): 6510.

2. EE. Synthesis of siRNA Conjugated with X1022

Scheme 12: Overview of the synthesis of 12.

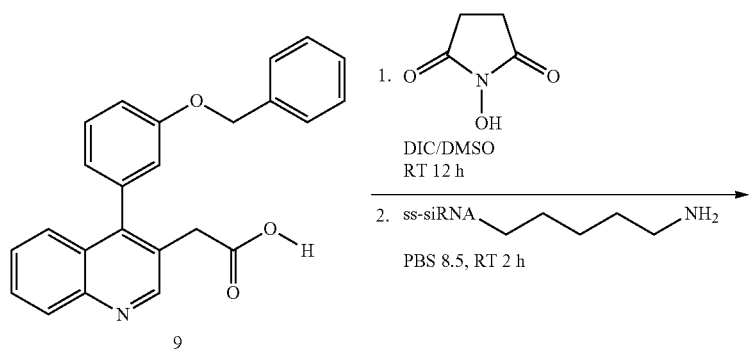

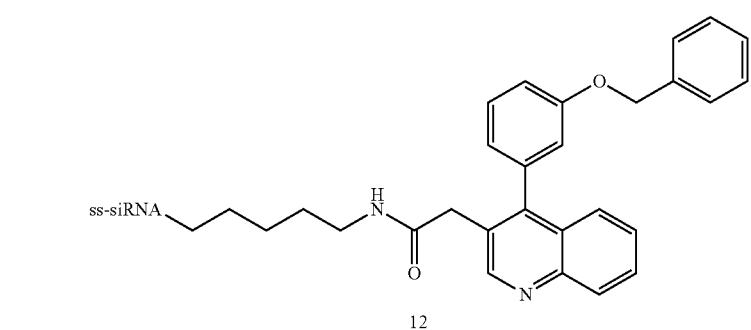

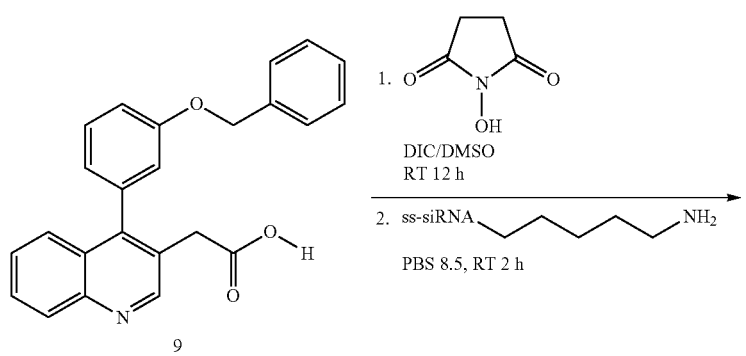

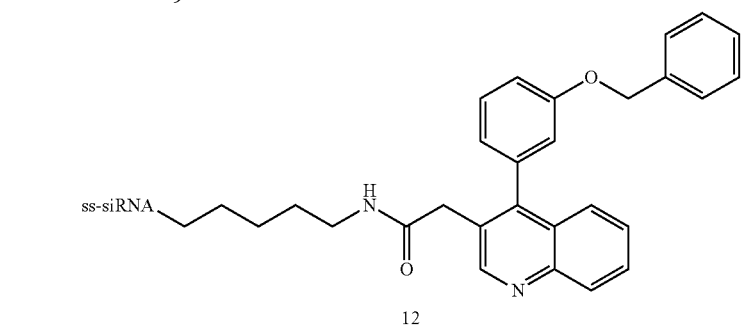

A mixture of N-hydroxysuccinimide (2.48 mg, 0.022 mmol), 9 (4.06 mg, 0.011 mmol), and DIC (2.72 mg, 0.022 mmol) in DMSO (200 uL) was stirred at RT for 12 h. 10 uL of reaction mixture was diluted with 190 uL DMSO. To the resulting solution was added a freshly ss-siRNA-(CH$_2$)$_5$—NH$_2$ solution (2 mg, 0.325 umol in 80 uL PBS 8.5 buffer). The reaction mixture was vortexed and sat at RT for 2 h. The crude product was purified by HPLC with 10-40% 100 mM triethylammonium acetate in acetonitrile/water to afford 12. TOF MS (ES$^-$): 6524.

2. FF. Synthesis of siRNA Conjugated with X1024

Scheme 13: Overview of the synthesis of 2.

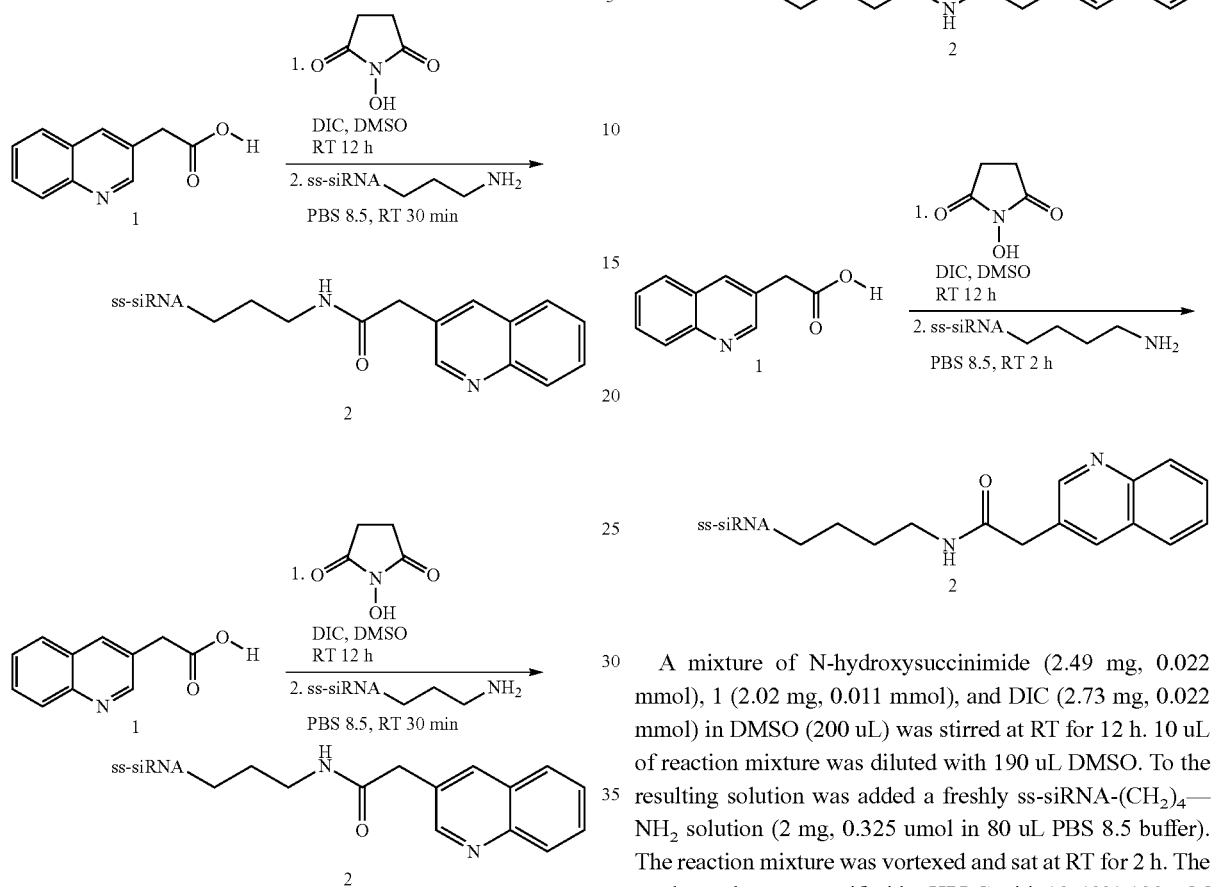

A mixture of N-hydroxysuccinimide (2.5 mg, 0.0522 mmol), 1 (2.5 mg, 0.013 mmol), and DIC (2.74 mg, 0.022 mmol) in DMSO (200 uL) was stirred at RT for 12 h. 10 uL of reaction mixture was diluted with 190 uL DMSO. To the resulting solution was added a freshly ss-siRNA-(CH$_2$)$_3$—NH$_2$ solution (2.0 mg, 0.325 umol in 80 uL PBS 8.5 buffer). The reaction mixture was vortexed and sat at RT for 2 h. The crude product was purified by HPLC with 10-40% 100 mM triethylammonium acetate in acetonitrile/water to afford 2. TOF MS (ES$^-$): 6315.

2. GG. Synthesis of siRNA Conjugated with X1026

Scheme 14: Overview of the synthesis of 2.

A mixture of N-hydroxysuccinimide (2.49 mg, 0.022 mmol), 1 (2.02 mg, 0.011 mmol), and DIC (2.73 mg, 0.022 mmol) in DMSO (200 uL) was stirred at RT for 12 h. 10 uL of reaction mixture was diluted with 190 uL DMSO. To the resulting solution was added a freshly ss-siRNA-(CH$_2$)$_4$—NH$_2$ solution (2 mg, 0.325 umol in 80 uL PBS 8.5 buffer). The reaction mixture was vortexed and sat at RT for 2 h. The crude product was purified by HPLC with 10-40% 100 mM triethylammonium acetate in acetonitrile/water to afford 2. TOF MS (ES$^-$): 6327.

2. HH. Synthesis of siRNA Conjugated with X1025

Scheme 15: Overview of the synthesis of 2.

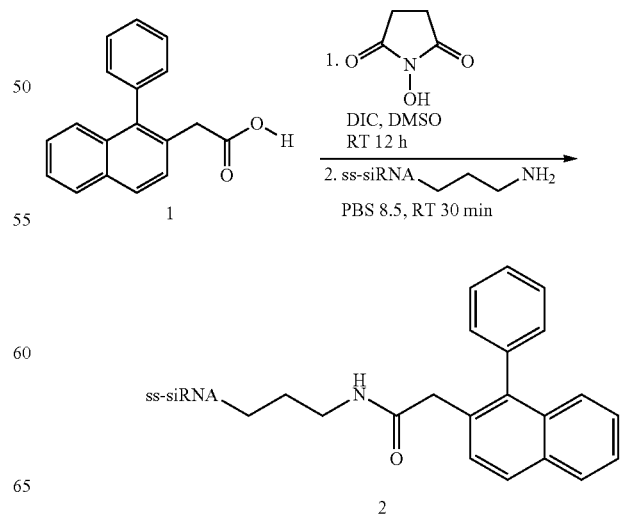

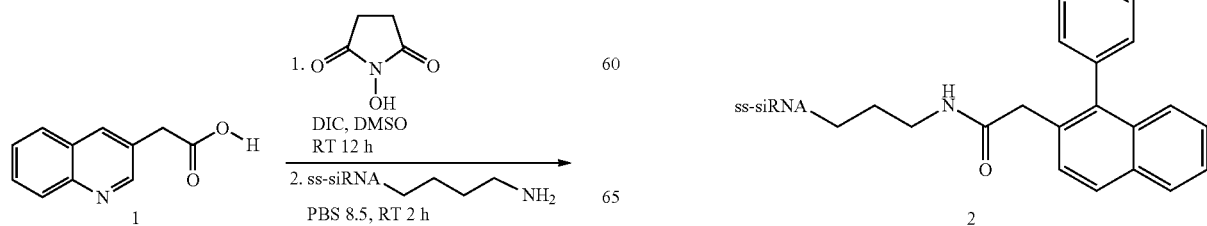

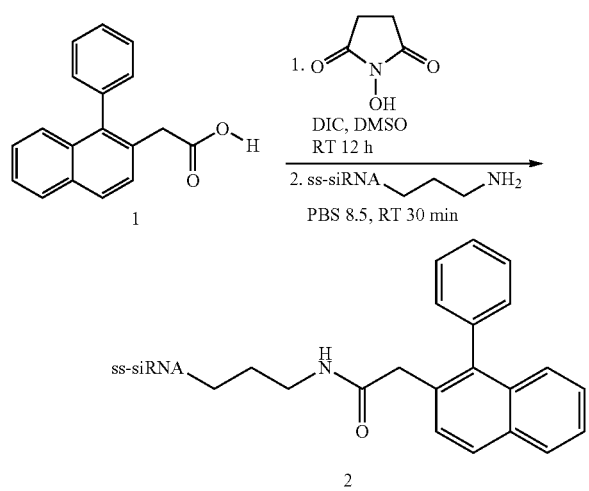

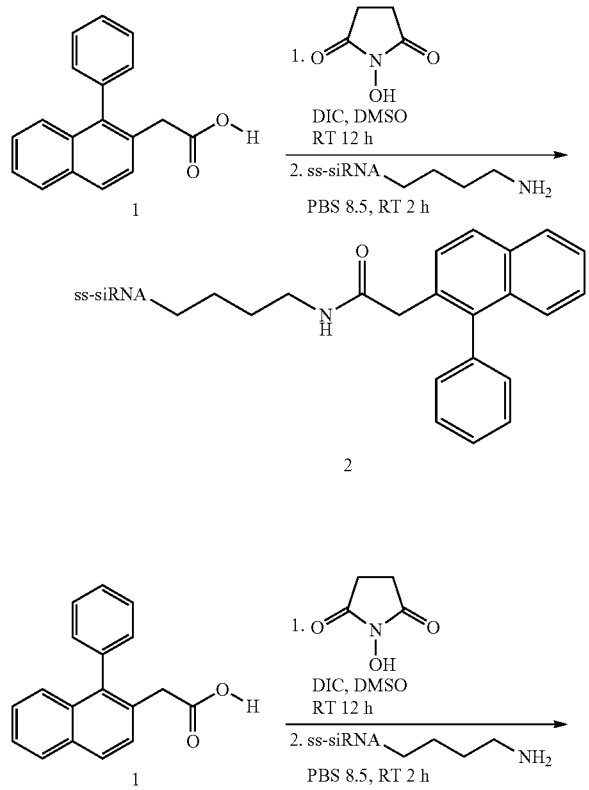

A mixture of N-hydroxysuccinimide (2.49 mg, 0.022 mmol), 1 (2.84 mg, 0.01 mmol), and DIC (2.74 mg, 0.022 mmol) in DMSO (200 uL) was stirred at RT for 12 h. 10 uL of reaction mixture was diluted with 190 uL DMSO. To the resulting solution was added a freshly ss-siRNA-(CH$_2$)$_3$—NH$_2$ solution (2.0 mg, 0.325 umol in 80 uL PBS 8.5 buffer). The reaction mixture was vortexed and sat at RT for 2 h. The crude product was purified by HPLC with 10-40% 100 mM triethylammonium acetate in acetonitrile/water to afford 2. TOF MS (ES$^-$): 6390.

2. II. Synthesis of siRNA Conjugated with X1027

Scheme 16: Overview of the synthesis of 2.

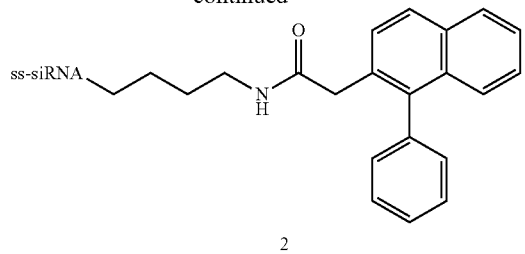

A mixture of N-hydroxysuccinimide (2.49 mg, 0.022 mmol), 1 (2.84 mg, 0.011 mmol), and DIC (2.73 mg, 0.022 mmol) in DMSO (200 uL) was stirred at RT for 12 h. 10 uL of reaction mixture was diluted with 190 uL DMSO. To the resulting solution was added a freshly ss-siRNA-(CH$_2$)$_4$—NH$_2$ solution (2 mg, 0.325 umol in 80 uL PBS 8.5 buffer). The reaction mixture was vortexed and sat at RT for 2 h. The crude product was purified by HPLC with 10-40% 100 mM triethylammonium acetate in acetonitrile/water to afford 2. TOF MS (ES$^-$): 6404.

2. JJ. Synthesis of siRNA Conjugated with X1028

Scheme 17: Overview of the synthesis of 2.

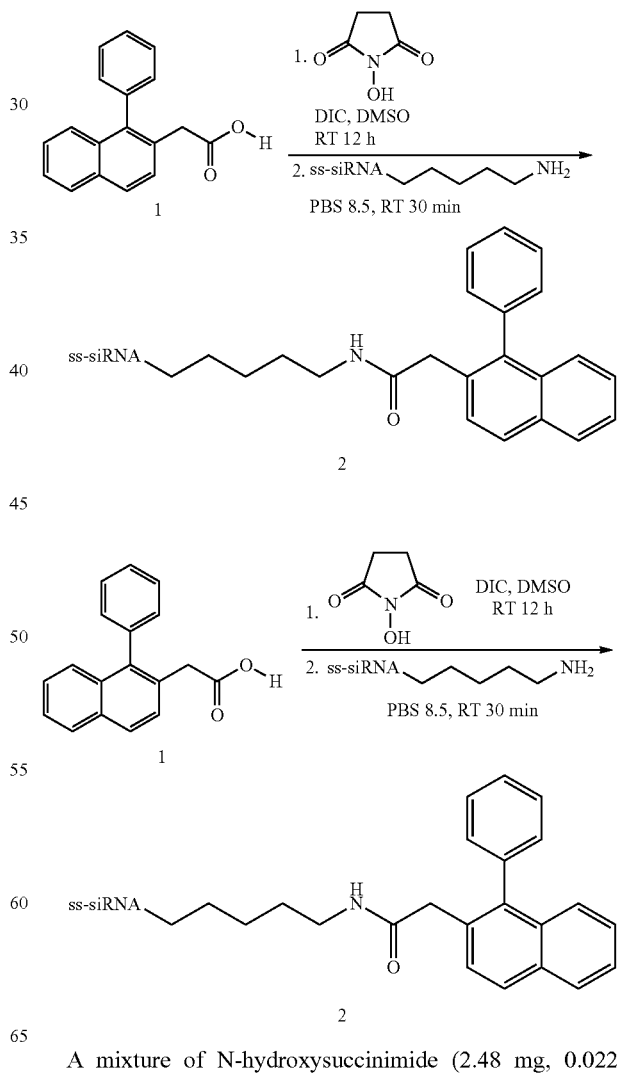

A mixture of N-hydroxysuccinimide (2.48 mg, 0.022 mmol), 1 (2.90 mg, 0.011 mmol), and DIC (2.72 mg, 0.022 mmol) in DMSO (200 uL) was stirred at RT for 12 h. 10 uL of reaction mixture was diluted with 190 uL DMSO. To the resulting solution was added a freshly ss-siRNA-(CH$_2$)$_5$—NH$_2$ solution (2 mg, 0.324 umol in 80 uL PBS 8.5 buffer). The reaction mixture was vortexed and sat at RT for 2 h. The crude product was purified by HPLC with 10-40% 100 mM triethylammonium acetate in acetonitrile/water to afford 2. TOF MS (ES$^-$): 6417.

2.KK. Synthesis of siRNA Conjugated with X1062

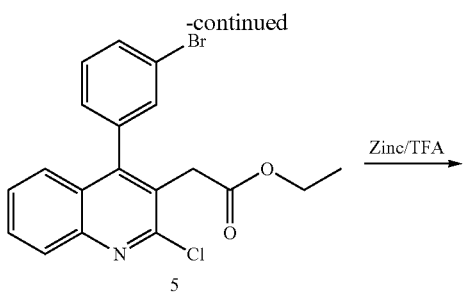

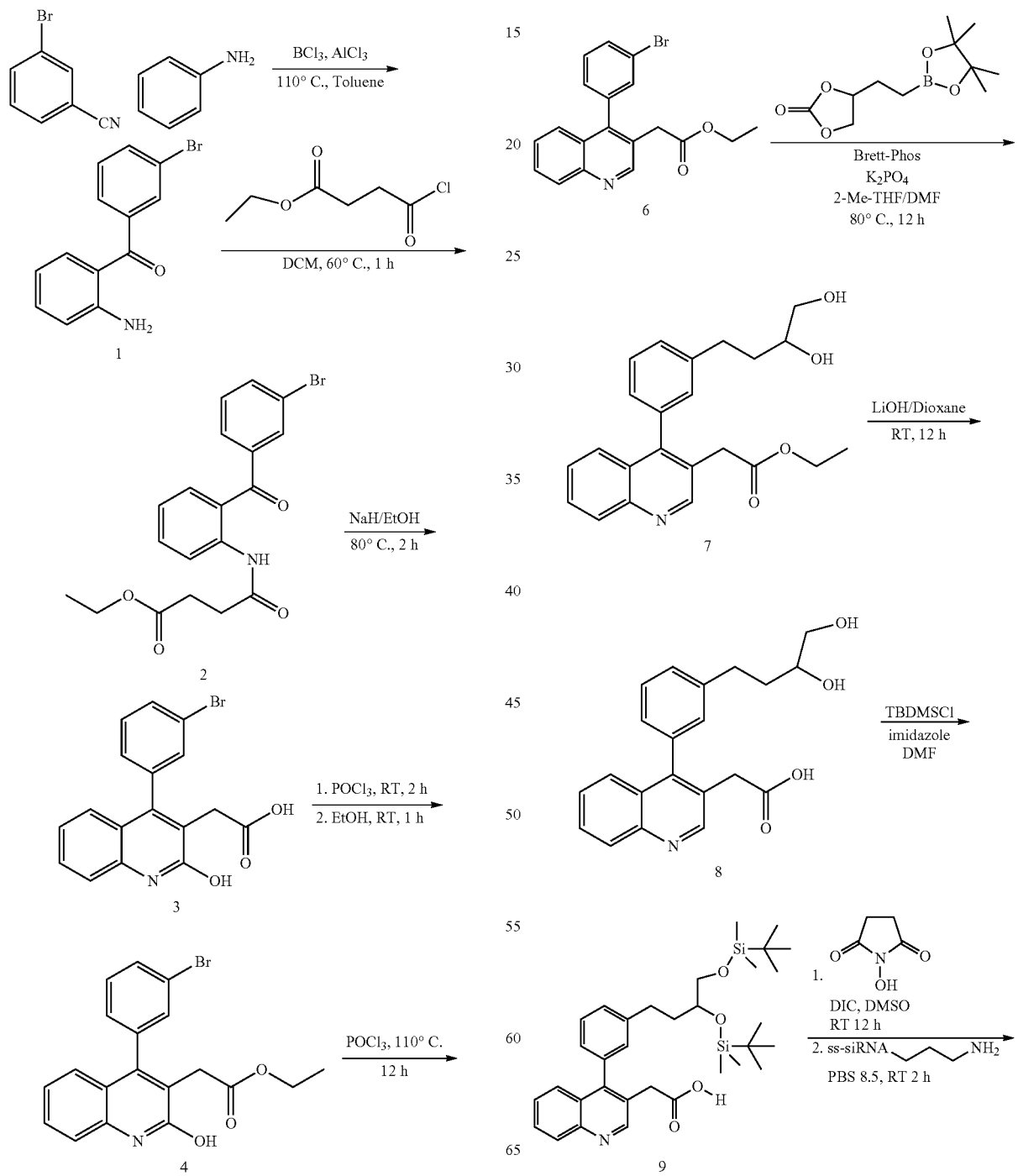

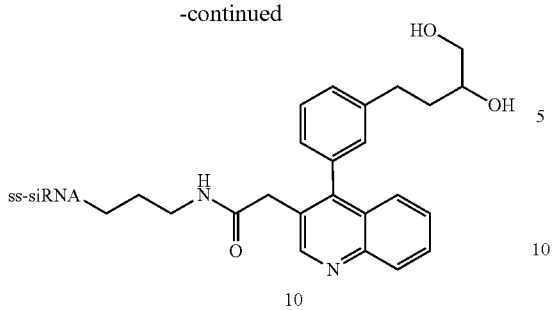

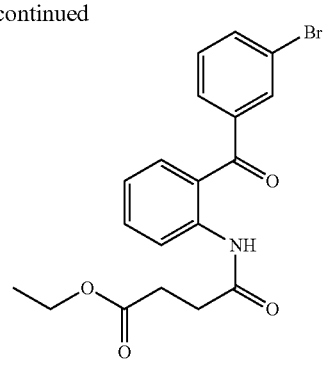

A mixture of 1 (1.02 g, 3.69 mmol) and ethyl 4-chloro-4-oxobutanoate (0.669 g, 4.06 mmol) in DCM (60 ml) was heated at 60° C. for 1 h. The reaction mixture was cooled and quenched with aq. 1 M NaOH (15 ml). The organic layer and water layer were separated. The water layer was extracted with dichloromethane (3×50 ml). The combined organic layers were washed with water and brine, and dried over sodium sulfate. The organic solvent was then removed under vacuum to give 2 (1.44 g, 3.56 mmol) in 96% yield. ESI MS (m/z, MH$^+$): 406.2. $^1$H NMR (400 MHz, Chloroform-d) δ 10.88 (s, 1H), 8.65 (d, J=8.4 Hz, 1H), 7.86 (d, J=1.8 Hz, 1H), 7.74 (d, J=8.0 Hz, 1H), 7.65-7.51 (m, 3H), 7.39 (t, J=7.8 Hz, 1H), 7.12 (t, J=7.7 Hz, 1H), 4.17 (q, J=7.1 Hz, 2H), 2.77 (dt, J=10.3, 5.2 Hz, 4H), 1.27 (t, J=7.1 Hz, 4H).

To AlCl$_3$ (7.88 g, 59.1 mmol) in Toluene (200 ml) was added aniline (5 g, 53.7 mmol, 4.59 ml, in 50 ml Toluene) dropwise under N$_2$. 3-bromobenzonitrile (29.3 g, 161 mmol) was added to the above mixture subsequently. The resulting mixture was stirred at RT for 1 h, then heated at 110° C. for 6 hrs. The reaction mixture was cooled to RT, to which aq. HCl (1 M, 3 ml) was added. The solution was then heated at 80° C. for 1 h. The solution was cooled to RT, and the organic layer and water layer were separated. The water layer was extracted with ethyl acetate (3×100 mL). The combined organic layers were washed with water and brine, and dried over sodium sulfate. The organic solvent was then removed under vacuum. The crude product was purified by silica chromatography with 0-40% ethyl acetate/heptane to give 1 (4.31 g, 15.6 mmol) in 29% yield. ESI MS (m/z, MH$^+$): 278.1 $^1$H NMR (400 MHz, CHLOROFORM-d) δ ppm 6.16 (br. s., 2 H) 6.64 (t, J=7.53 Hz, 1 H) 6.76 (d, J=8.53 Hz, 1 H) 7.29-7.49 (m, 3 H) 7.56 (d, J=7.53 Hz, 1 H) 7.67 (d, J=8.03 Hz, 1 H) 7.74-7.84 (m, 1 H)

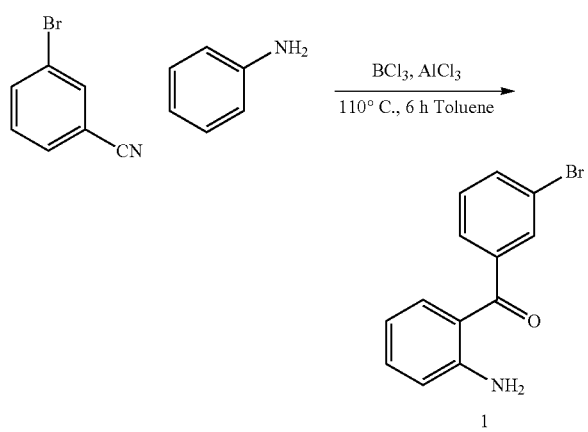

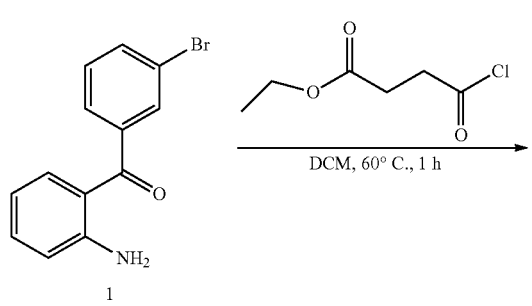

A mixture of 2 (1.44 g, 3.56 mmol) and sodium hydride (1.425 g, 35.6 mmol) in ethanol (20 ml) was heated at 80° C. for 2 h. The reaction mixture was cooled to RT and quenched with water (5 ml) then neutralized with aq. 1 M HCl (2 ml). The resulting solution was extracted with ethyl acetate (3×50 mL). The combined organic layers were washed with water and brine, and dried over sodium sulfate. The organic solvent was then removed under vacuum to give 3 (1.2 g, 3.63 mmol) in 94% yield. ESI MS (m/z, MH+): 360.2. ¹H NMR (400 MHz, Chloroform-d) δ 11.71-11.63 (m, 1H), 11.55-11.42 (m, 3H), 11.37 (d, J=8.3 Hz, 1H), 11.30-11.22 (m, 1H), 11.12 (td, J=7.6, 7.0, 1.2 Hz, 1H), 11.00 (dd, J=8.2, 1.4 Hz, 1H), 7.33 (d, J=3.5 Hz, 2H), 4.87-4.82 (m, 2H).

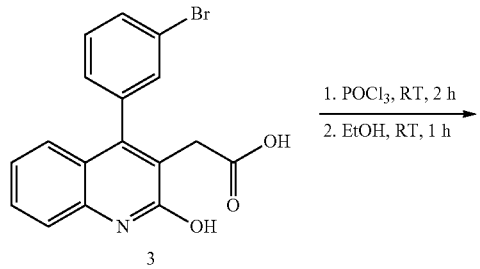

A solution of 3 (1.2 g, 1.89 mmol) in POCl₃ (15 ml) was stirred at RT for 2 h. POCl₃ was removed under vacuum, the resulting residue was quenched with ethanol (50 ml). The solution was stirred at RT for 2 h, then ethanol was removed under vacuum. To the residue was added dichloromethane (50 ml) and aq. 1 M NaOH (20 ml). Organic layer and water layer were separated. The water layer was extracted with dichloromethane (2×50 ml). The combined organic layers were washed with water, brine and dried over sodium sulfate. The organic solvent was removed under vacuum to give 4 (1.76 mg, 4.56 mmol) in 136% yield. ESI MS (m/z, MH+): 388.2. ¹H NMR (400 MHz, Chloroform-d) δ 7.65 (dt, J=8.2, 1.4 Hz, 1H), 7.54-7.46 (m, 2H), 7.45-7.37 (m, 2H), 7.27 (dt, J=7.8, 1.5 Hz, 1H), 7.17-7.04 (m, 2H), 4.18-4.16 (m, 2H), 3.50 (d, J=1.5 Hz, 2H), 1.27 (h, J=3.7 Hz, 3H).

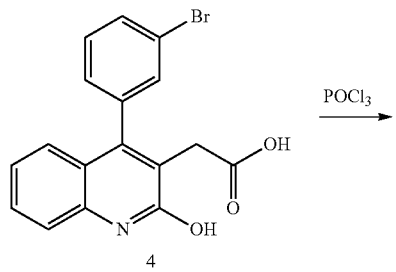

A solution of 4 (1.76 g, 4.56 mmol) in POCl₃ (10 ml) was heated at 110° C. for 12 h. POCl₃ was removed under vacuum. To the residue was added dichloromethane (50 ml) and aq. 1 M NaOH (20 ml). The organic layer and water layer were separated. The water layer was extracted with dichloromethane (2×50 ml). The combined organic layers were washed with water, brine and dried over sodium sulfate. The organic solvent was removed under vacuum to give 5 (440 mg, 1.09 mmol) in 32.5% yield. ESI MS (m/z, MH+): 406.0. ¹H NMR (400 MHz, Chloroform-d) δ 8.14-8.05 (m, 1H), 7.76 (ddd, J=8.4, 6.9, 1.4 Hz, 1H), 7.69 (ddd, J=8.0, 1.9, 1.0 Hz, 1H), 7.53-7.41 (m, 3H), 7.36 (dd, J=8.3, 1.3 Hz, 1H), 7.26 (dt, J=7.7, 1.3 Hz, 1H), 4.19 (q, J=7.1 Hz, 2H), 3.72 (s, 2H), 1.27 (t, J=7.1 Hz, 3H).

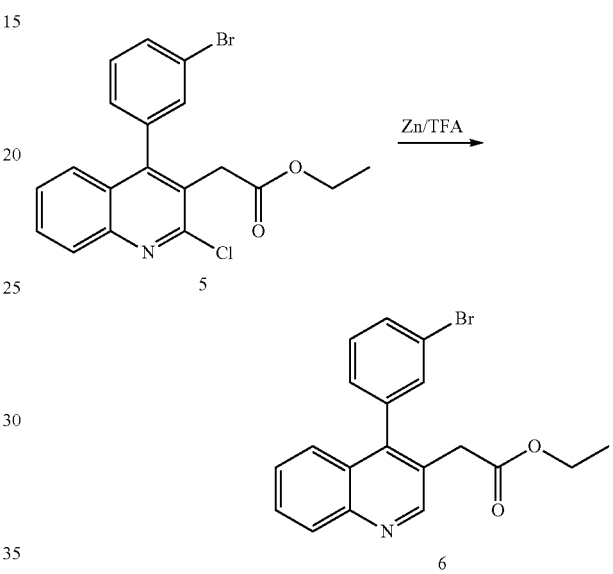

A mixture of 5 (50 mg, 0.124 mmol), Zinc power (40.4 mg, 0.618 mmol) in TFA (1 ml) was heated at 40° C. for 12 h. The reaction mixture was quenched with NaOH (1M, 1 ml). The organic layer was extracted with dichloromethane (2×10 ml). The combined organic layers were washed with water, brine and dried over sodium sulfate. The organic solvent was removed under vacuum. The crude product was purified by silica flash chromotograph with elute 0-50% EtOAc/Heptane to give 6 (39 mg, 0.105 mmol) in 85% yield. ESI MS (m/z, MH+): 372.1. ¹H NMR (400 MHz, CHLOROFORM-d) ppm 1.24 (t, J=7.15 Hz, 3 H) 3.63 (s, 2 H) 4.02-4.27 (m, 2 H) 7.12-7.33 (m, 1 H) 7.37-7.61 (m, 4 H) 7.61-7.71 (m, 1 H) 7.75 (t, J=1.51 Hz, 1 H) 8.21 (d, J=8.53 Hz, 1 H) 8.94 (s, 1 H).

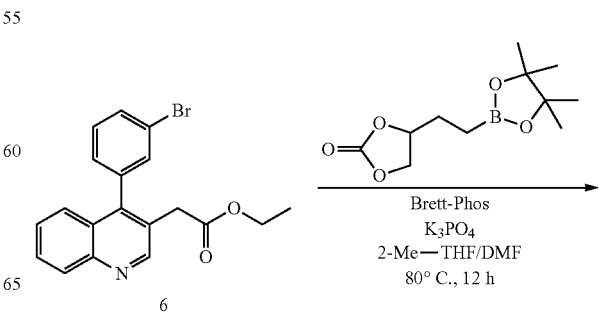

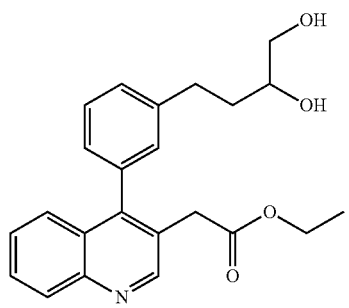

7

A mixture of 4-(2-(4,4,5,5-tetramethyl-1,3,2-dioxaborolan-2-yl)ethyl)-1,3-dioxolan-2-one) (255 mg, 1.05 mmol), 6 (39 mg, 0.105 mmol), (Brettphos)paddadium(II) phenethylamine chloride (4.21 mg, 5.27 umol) and 1M aqueous $K_3PO_4$ (421 uL, 0.421 mmol) in 2-Me THF (500 uL) and DMF (500 uL) was heated at 80° C. for 12 h. The reaction mixture was filtered to remove insoluble material. The organic solvent was removed under vacuum. The crude was purified by HPLC with 5% TFA in 5-95% acetonitrile/water to give 7 (15 mg, 0.04 mmol) in 37.5% yield. ESI MS (m/z, MH⁺): 380.4. ¹H NMR (400 MHz, CHLOROFORM-d) ppm 1.22 (td, J=7.15, 2.26 Hz, 3 H) 1.73-1.92 (m, 2 H) 2.72-2.98 (m, 2 H) 3.49 (dd, J=11.04, 7.53 Hz, 1 H) 3.56-3.84 (m, 4 H) 4.04-4.20 (m, 2 H) 7.15 (d, J=7.53 Hz, 1 H) 7.13 (d, J=8.78 Hz, 1 H) 7.37 (d, J=7.53 Hz, 1 H) 7.43-7.56 (m, 3 H) 7.74 (br. s., 1 H) 8.22 (br. s., 1 H) 8.94 (br. s., 1 H).

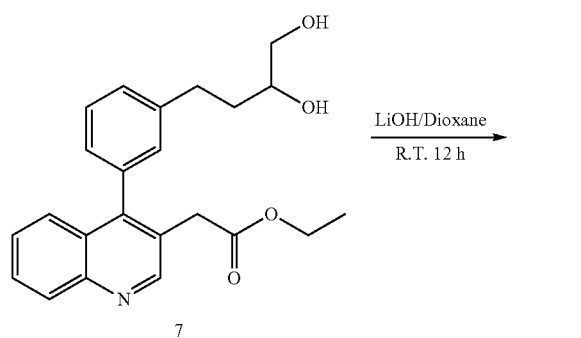

A mixture of 7 (15 mg, 0.04 mmol) and aq. 1 M LiOH (87 uL ml, 0.087 mmol) in dioxane (200 ul) was stirred at RT for 12 hrs. The organic solvent was removed under vacuum to give 8 (14.17 mg, 0.04 mmol) in 100% yield as lithium salt. ESI MS (m/z, MH⁺): 352.4. ¹H NMR (400 MHz, METHANOL-d₄) δ ppm 1.62-1.80 (m, 1 H) 1.80-1.98 (m, 1 H) 2.78 (ddd, J=13.33, 6.76, 3.16 Hz, 1 H) 2.84-2.99 (m, 1 H) 3.46-3.55 (m, 3 H) 3.55-3.68 (m, 3 H) 6.98-7.25 (m, 2 H) 7.31-7.59 (m, 4 H) 7.74 (ddd, J=8.40, 6.38, 1.89 Hz, 1 H) 8.06 (d, J=8.34 Hz, 1 H) 8.86 (s, 1 H).

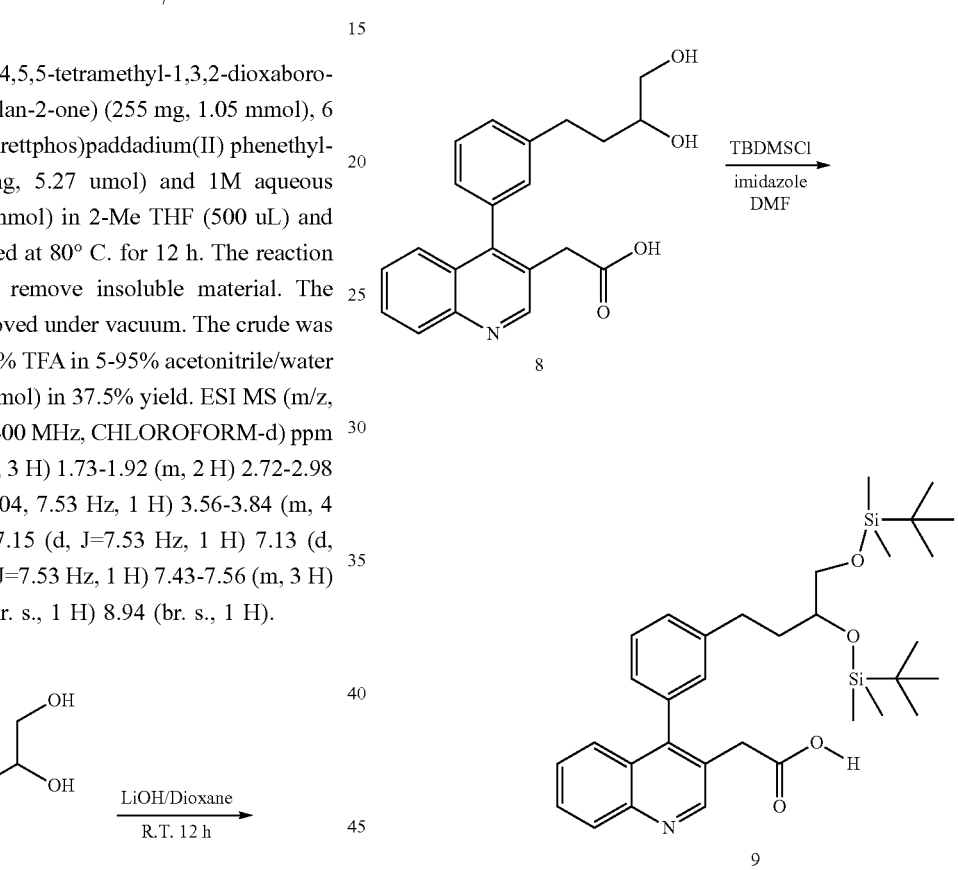

A mixture of 8 (14 mg, 0.039 mmol), TBDMSCl and imidazole (43.6 mg, 0.641 mmol) in DMF (4 ml) was stirred at RT for 24 hrs. The reaction mixture was quenched with water (1 ml). The organic layer was extracted with ethylestate (3×5 ml). The combined organic layers were washed with water, brine and dried over sodium sulfate. The organic solvent was removed under vacuum. The crude product was purified by silica flash chromotograph with elute 0-50% EtOAc/Heptane to give 9 (15.9 mg, 0.025 mmol) in 63.2% yield. ESI MS (m/z, MH⁺): 580.6. ¹H NMR (400 MHz, METHANOL-d₄) δ ppm-0.12-0.13 (m, 8 H) 0.69-0.98 (m, 12 H) 1.17-1.36 (m, 5 H) 2.60-2.90 (m, 2 H) 3.38-3.62 (m, 6 H) 3.73 (d, J=4.55 Hz, 1 H) 7.02-7.15 (m, 2 H) 7.24-7.38 (m, 1 H) 7.39-7.47 (m, 3 H) 7.64-7.74 (m, 1 H) 7.98-8.06 (m, 1 H) 8.68-8.89 (m, 1 H).

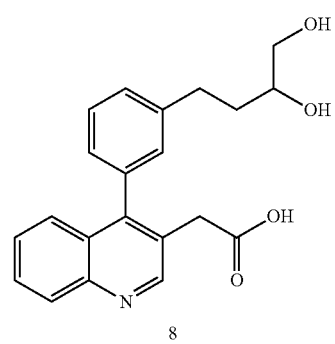

8

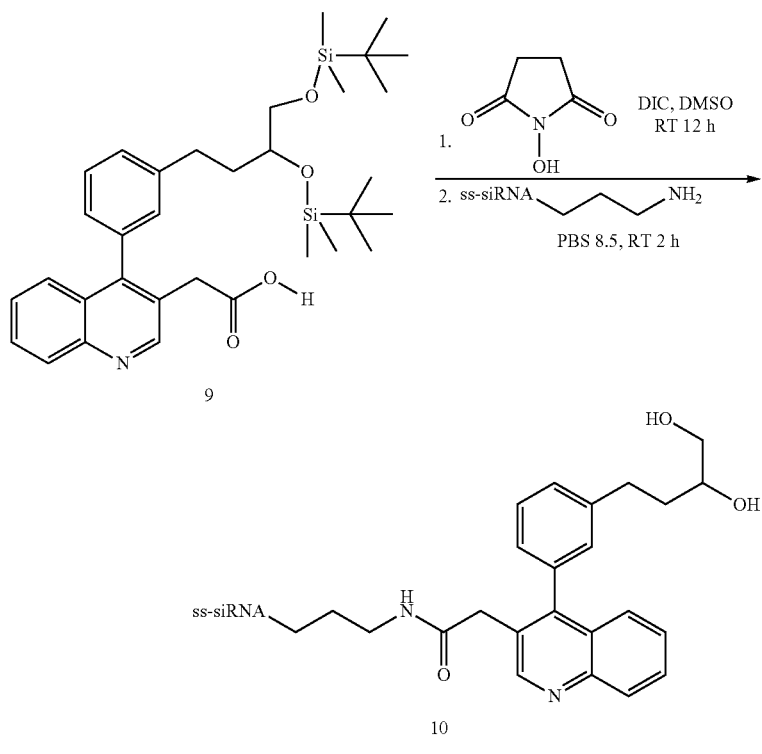

A mixture of N-hydroxysuccinimide (2.49 mg, 0.022 mmol), 9 (6.26 mg, 0.011 mmol), and DIC (2.74 mg, 0.022 mmol) in DMSO (200 uL) was stirred at RT for 12 hrs. 10 uL of reaction mixture was diluted with 190 uL DMSO. To the resulting solution was added a freshly ss-siRNA-(CH$_2$)$_3$—NH$_2$ solution (2 mg, 0.325 umol in 80 uL PBS 8.5 buffer). The reaction mixture was vortexed and sat at RT for 2 h. The crude product was purified by HPLC with 10-40% 100 mM triethylammonium acetate in acetonitrile/water to afford 10. TOF MS (ES$^-$): 6478.

2.LL. Synthesis of siRNA Conjugated with X1063

Scheme 2: Overview of the synthesis of 11.

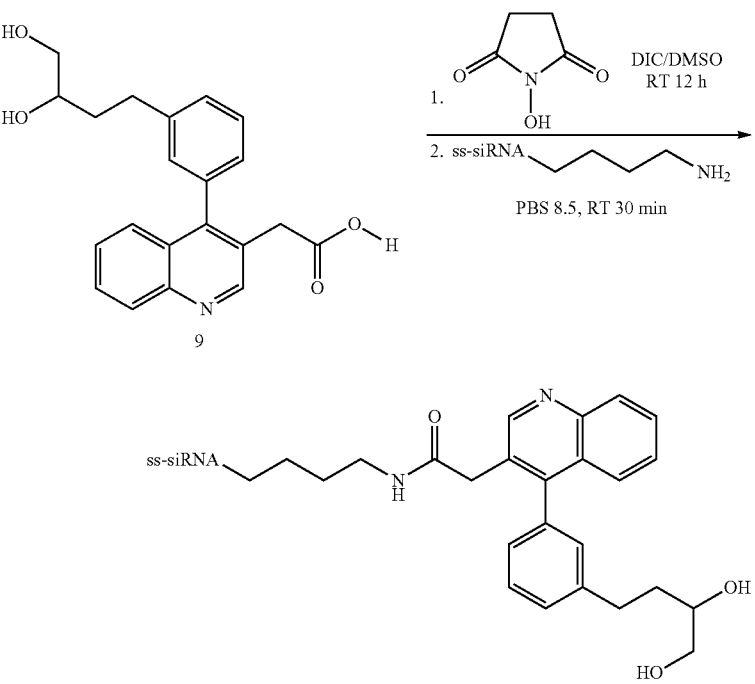

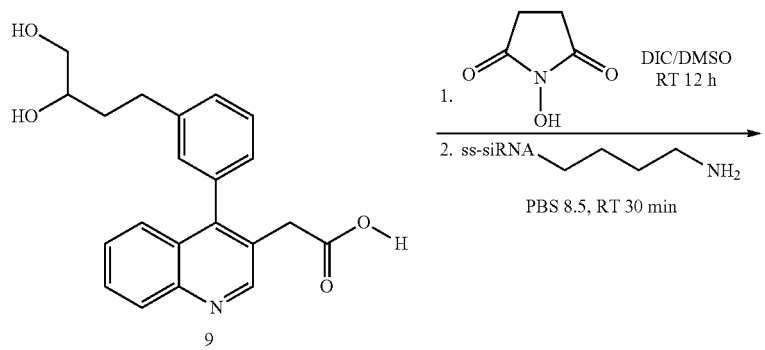

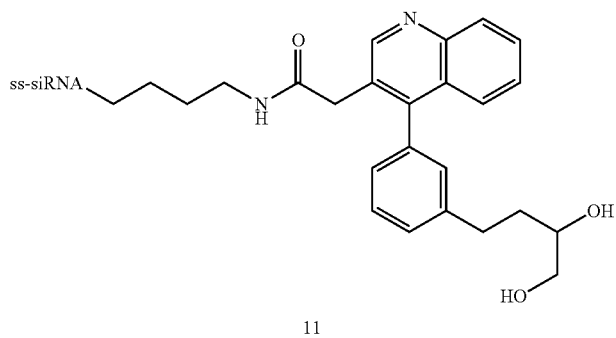

A mixture of N-hydroxysuccinimide (2.49 mg, 0.022 mmol), 9 (6.26 mg, 0.011 mmol), and DIC (2.73 mg, 0.022 mmol) in DMSO (200 uL) was stirred at RT for 12 h. 10 uL of reaction mixture was diluted with 190 uL DMSO. To the resulting solution was added a freshly ss-siRNA-(CH$_2$)$_4$—NH$_2$ solution (2 mg, 0.325 umol in 80 uL PBS 8.5 buffer). The reaction mixture was vortexed and sat at RT for 2 h. The crude product was purified by HPLC with 10-40% 100 mM triethylammonium acetate in acetonitrile/water to afford 11. TOF MS (ES$^-$): 6492.

2.MM. Synthesis of siRNA Conjugated with X1064

Scheme 3: Overview of the synthesis of 12.

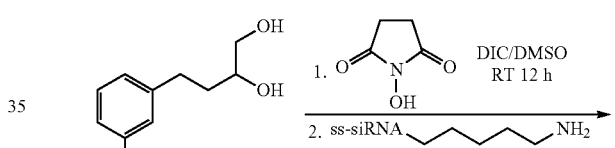

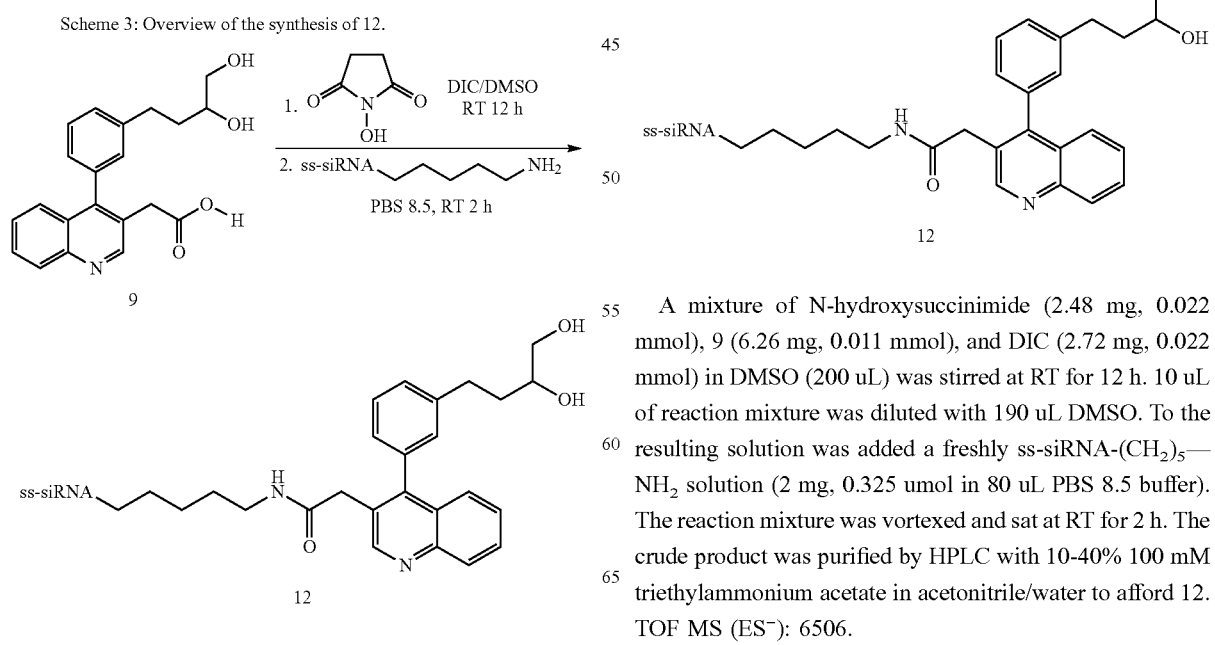

A mixture of N-hydroxysuccinimide (2.48 mg, 0.022 mmol), 9 (6.26 mg, 0.011 mmol), and DIC (2.72 mg, 0.022 mmol) in DMSO (200 uL) was stirred at RT for 12 h. 10 uL of reaction mixture was diluted with 190 uL DMSO. To the resulting solution was added a freshly ss-siRNA-(CH$_2$)$_5$—NH$_2$ solution (2 mg, 0.325 umol in 80 uL PBS 8.5 buffer). The reaction mixture was vortexed and sat at RT for 2 h. The crude product was purified by HPLC with 10-40% 100 mM triethylammonium acetate in acetonitrile/water to afford 12. TOF MS (ES$^-$): 6506.

Example 3

PAZ Ligand Conjugate 3' End Cap Activity In Vitro and In Vivo and Structure

PAZ ligand conjugates were studied as a part of a 7-mer RNA conjugate structure in X-ray crystal and NMR structural studies (data not shown).

RNA interference activity of duplexes comprising various 3' end caps was also analyzed; in vitro and in vivo potency was studied, as shown in Example 3A (in vitro data) and 3B (in vivo data).

Example 3A

In Vitro Potency of RNAi Agents Comprising a 3' End Cap (PAZ Ligand)

Potency of HAMP siRNA—PAZ Ligand Conjugates is studied.

Hepcidin mRNA down regulation in HuH-7 cells is studied at 3 doses.

Two test sequences: hs_HAMP_400 and 402
Parent stem format: A106S42 (2'-OMe chemistry
19 PAZ ligands on guide (antisense) strand+/− ribitol spacer, +/−MOE clamp (wherein the MOE clamp is a 2'-MOE modification on each of the two last base-pairing nucleotides on each strand counting from 5' to 3').

Figure 7:
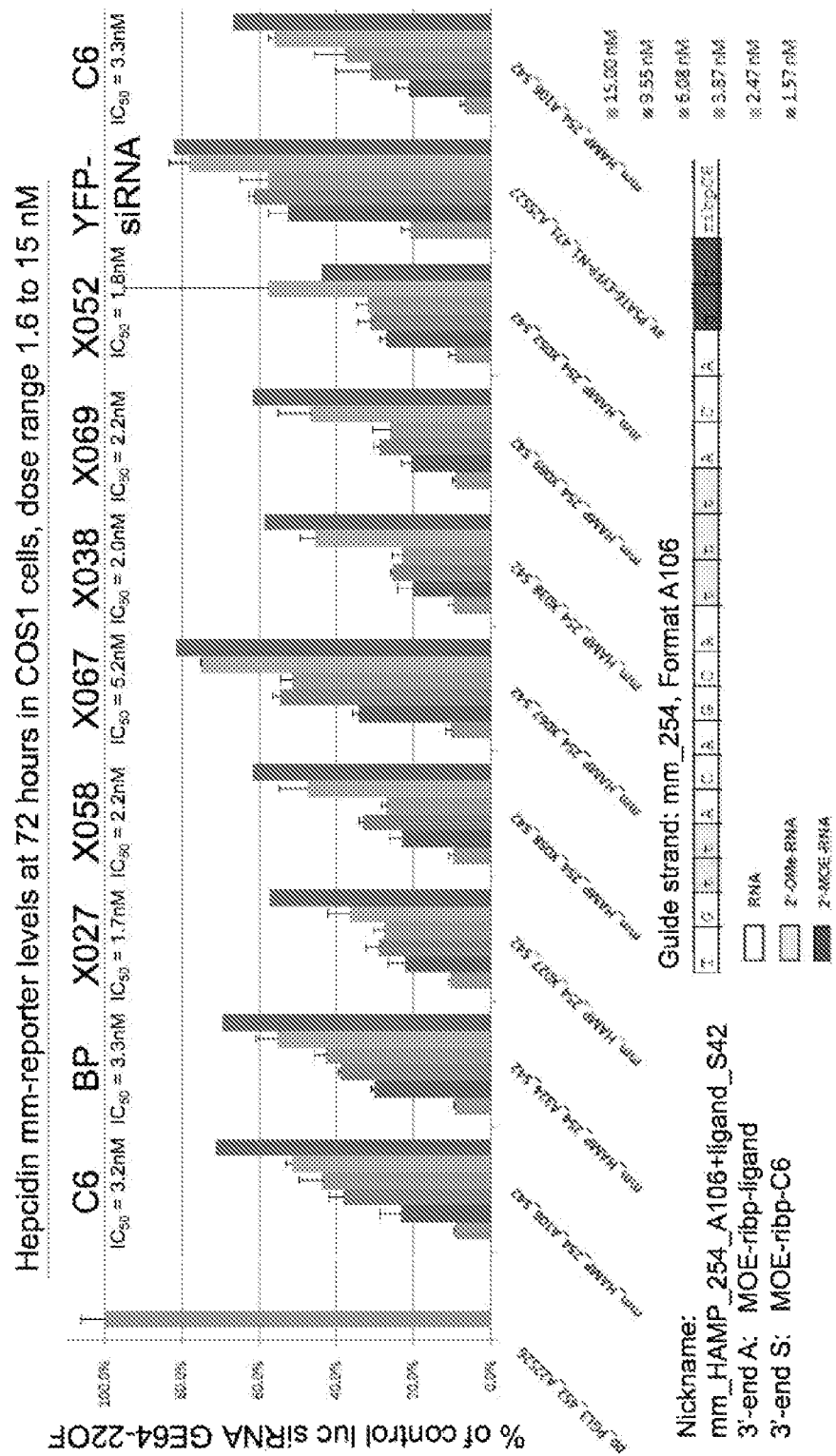
FIG. 7 shows the residual gene activity [wherein residual gene activity=100%-knock down (KD)] of RNAi agents comprising a 3' end cap (C6, BP, X027, X058, X067, X038, X069, or X052), at a range from 1.57 nM to 15 nM. The format of the strands is indicated, as described in Example 3A. These are RNAi agents to mouse Hepcidin.

In vitro dose-response in Huh-7 cells is determined.
Results are shown in FIGS. 5A and 5B and 7 and in Table 5, below.

FIGS. 5A and 5B show the in vitro RNA interference or KD (knockdown) mediated by various RNAi agents comprising a 3' end cap: BP (biphenyl), C6, X027, X038, X050, X051, X052, X058, X059, X060, X061, X062, X063, X064, X065, X066, X067, X068, and X069 on the guide (antisense) strand. Two sequences were tested (hs_HAMP_400 and _402), where 400 is a sequence beginning at position 400 of the human HAMP (Hepcidin) gene and 402 is an overlapping sequence beginning at position 402

These were tested with (Rib) and without (−) a ribitol spacer; and with (MOE) and without (−) a 2'-MOE clamp (as diagrammed in FIGS. 6A and 6B). Various hs_HAMP 400 and 402 are depicted in FIG. 6A (Guide or antisense strand) and 6B (corresponding Sense strand).

Figure 4:
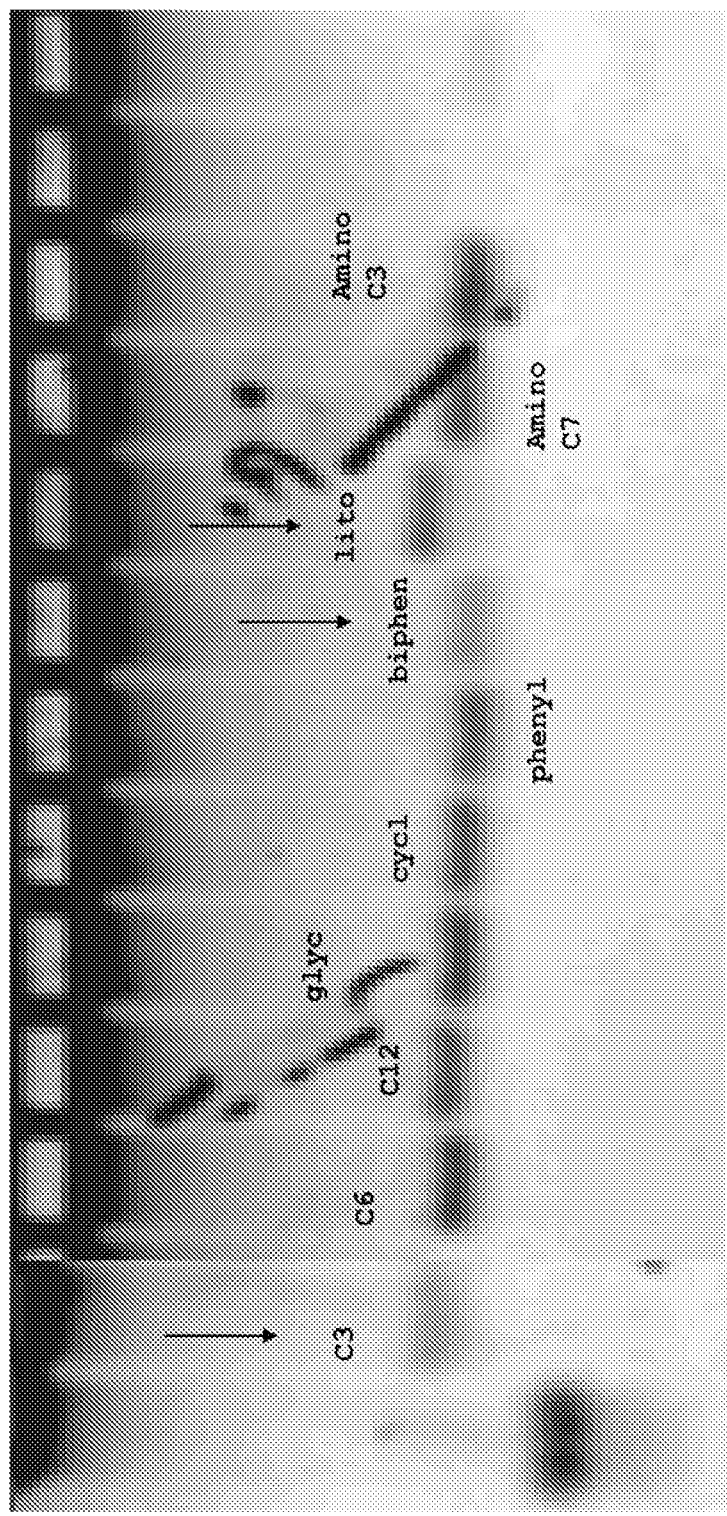
FIG. 4 shows the quality control of various RNAi agents used in Example 1.

The data are provided in FIGS. 5A and 5B. The circled data points in FIGS. 4A and 4B represent the most potent format for hs_HAMP_400 and the most potent format for the hs_HAMP_402.

Additional data is provided in Table 5, below. This Table indicates the Nickname ("Oligo Identifier") for the 3' end cap, and the DMT, Succinate and Carboxylate variants thereof; the Carboxylate Kd; the KD (knockdown) mediated by a Hepcidin RNAi agent comprising the 3' end cap (format: S402+ribitol+MOE clamp) at 5 nM in vitro; and the approximate (approx.) IC50

TABLE 6

| Oligo Identifier (Nickname) | Hepcidin KD at 5 nM in vitro (%) | Hepcidin (approx.) IC50 μM |
|---|---|---|
| BP (biphenyl) | 68 | 2.3 |
| X027 | 57 | 3.3 |
| X038 | 62 | 2.6 |
| X050 | 61 | 4.0 |

TABLE 6-continued

| Oligo Identifier (Nickname) | Hepcidin KD at 5 nM in vitro (%) | Hepcidin (approx.) IC50 μM |
|---|---|---|
| X051 | 61 | 3.4 |
| X052 | 64 | 3.0 |
| X058 | 68 | 2.7 |
| X059 | 55 | 4.1 |
| X060 | 65 | 3.5 |
| X061 | 61 | 3.0 |
| X062 | 63 | 3.5 |
| X063 | 56 | 3.7 |
| X064 | 60 | 3.1 |
| X065 | 66 | 3.0 |
| X066 | 49 | 4.9 |
| X067 | 66 | 2.5 |
| X068 | 63 | 3.0 |
| X069 | 81 | 1.5 |
| C6 | 66 | 2.6 |

FIG. 7 shows the residual gene activity (wherein residual gene activity=100%−KD) of Hepcidin mm-reporter levels at 72 hours in COS1 cells after various doses of RNAi agents comprising a 3' end cap, at a range from 1.57 nM to 15 nM. The format of the strands is indicated. The 3' end of the sense strand terminates in a 2' MOE-clamp—ribp (ribitol spacer)—C6. The 3' end of the antisense strand terminates in a 2' MOE-clamp—ribp (ribitol spacer)—ligand, wherein the ligands used were 3' end caps (X027, X058, X067, etc.).

These data show the efficacy of RNAi agent comprising a 3' end cap which is BP (biphenyl), C6, X027, X038, X050, X051, X052, X058, X059, X060, X061, X062, X063, X064, X065, X066, X067, X068, or X069.

Example 3B

In Vivo Potency of RNAi Agents Comprising a 3' End Cap (PAZ Ligand)

Example 3A showed the in vitro potency of various RNAi agents comprising a 3' end cap.

Example 3B shows the in vivo potency of various RNAi agents comprising a 3' end cap.

These in vivo experiments used these parameters:
Mice (n=5/group) injected via IV bolus (tail vein):
LNP569
  PBS
  LNP569-Hamp254-X052 (SL52-49CE)-3 mg/kg
  LNP569-Hamp254-X058 (IL54-43-XE)-3 mg/kg
  LNP569-Hamp254-X067 (YL55-48RE)-3 mg/kg
  LNP569-Hamp254-X038 (CL51-55IE)-3 mg/kg
  LNP569-Hamp254-X069 (GA35-24OF)-3 mg/kg
  LNP569-Hamp254-X027 (ML59-39NE)-3 mg/kg
  LNP569-Hamp254-C6 control-3 mg/kg
LNP569 is a lipid nanoparticle preparation of the RNAi agent.

Figure 8A:
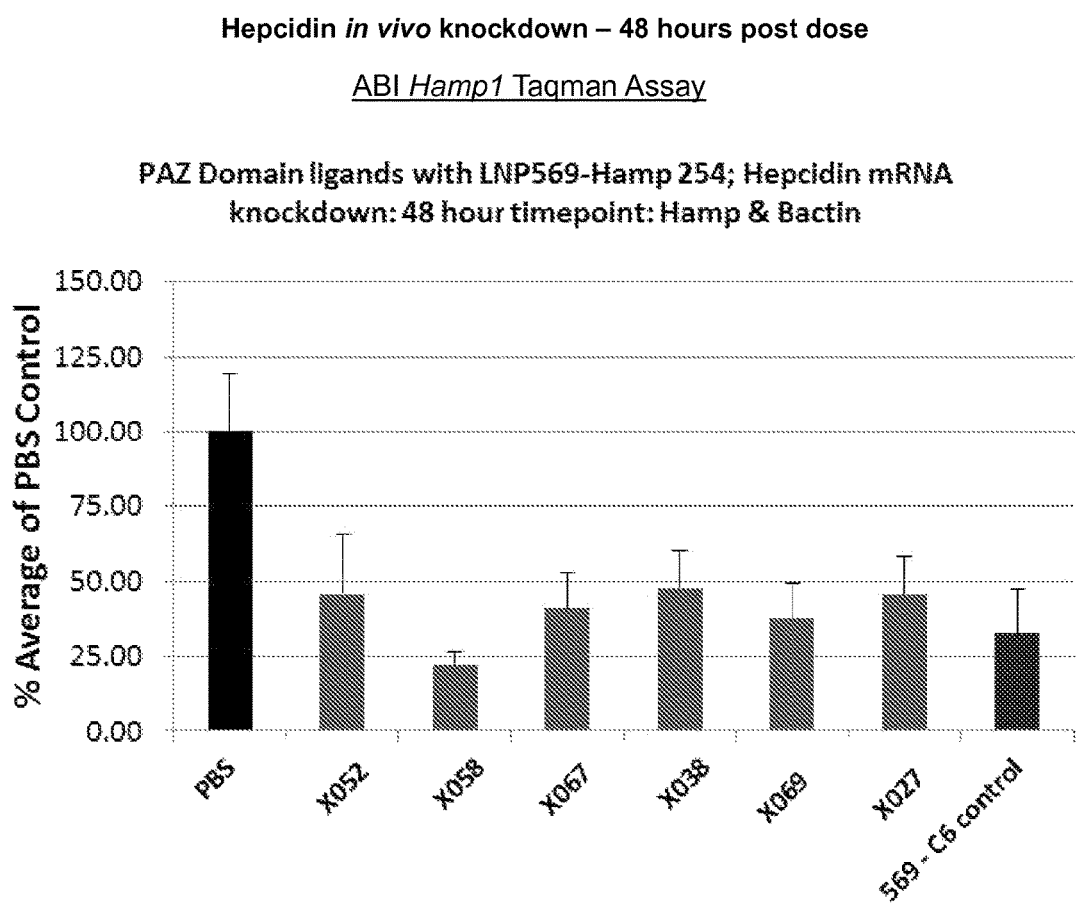
FIGS. 8A and 8B show that in both the ABI Hamp1 Taqman assay (FIG. 8A) and the Hamp1 specific Taqman Assay (FIG. 8B) all of the RNAi agents with a 3' end cap were able to mediate knockdown in vivo at 48 hours post-dose, with a 1×3 mg/kg dose. 3' end caps used were: X052, X058, X067, X038, X069, and X027, with C6 as a control, as described in Example 3B. These are RNAi agents to mouse Hepcidin tested in vivo.
Figure 8B:
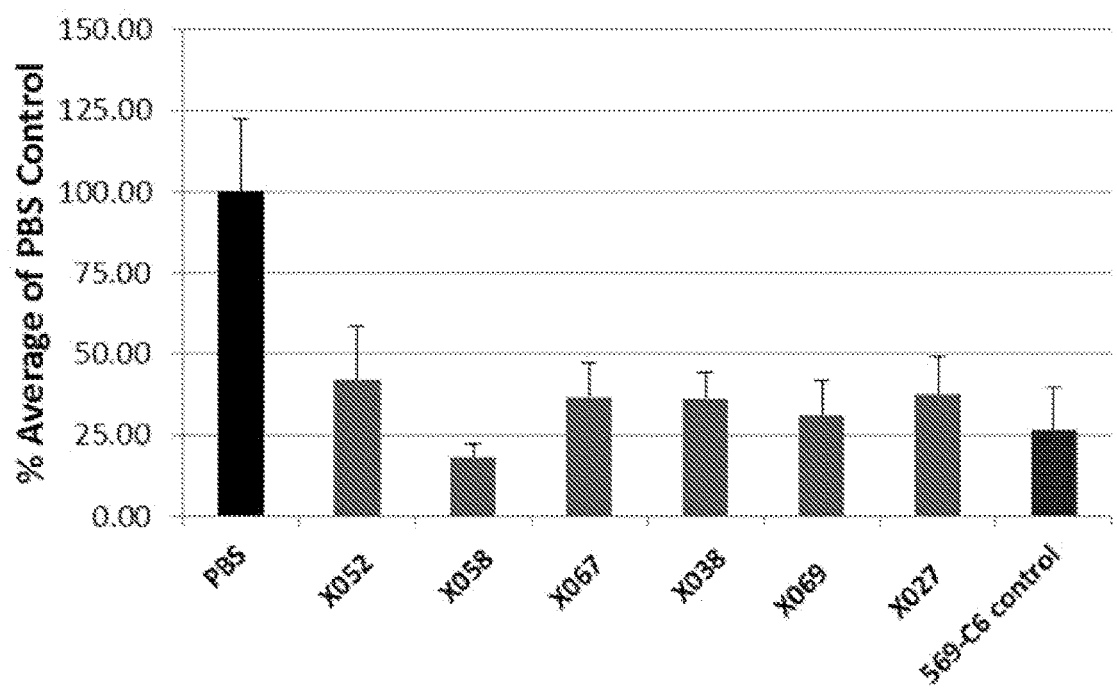

Two timepoints-48 and 168 hrs post-injection (both 3 mg/kg).
Assess hepcidin knockdown in liver (mRNA-qPCR)
Key Questions are Asked:
Are PAZ domain ligands active in vivo? (48 hour timepoint).
Do PAZ domain ligands provide benefit for duration of knockdown? (168 hour timepoint).
The results are shown in FIGS. 8A and 8B.
FIGS. 8A and 8B show that in both the ABI Hamp1 Taqman assay (FIG. 8A) and the Hamp1 specific Taqman Assay (FIG. 8B) all of the RNAi agents were able to mediate Hepcidin knockdown in vivo at 48 hours post-dose, with a 1×3 mg/kg dose. 3' end caps used were: X052, X058, X067, X038, X069, and X027, with C6 as a control.

The finding that RNAi agents with 3' end caps of X052, X058, X067, X038, X069, X027, or C6 were still able to mediate RNA interference at 48 hours indicates that the 3' end caps protect the RNAi agents against degradation or digestion (e.g., by nucleases in the serum).

Figure 9A:
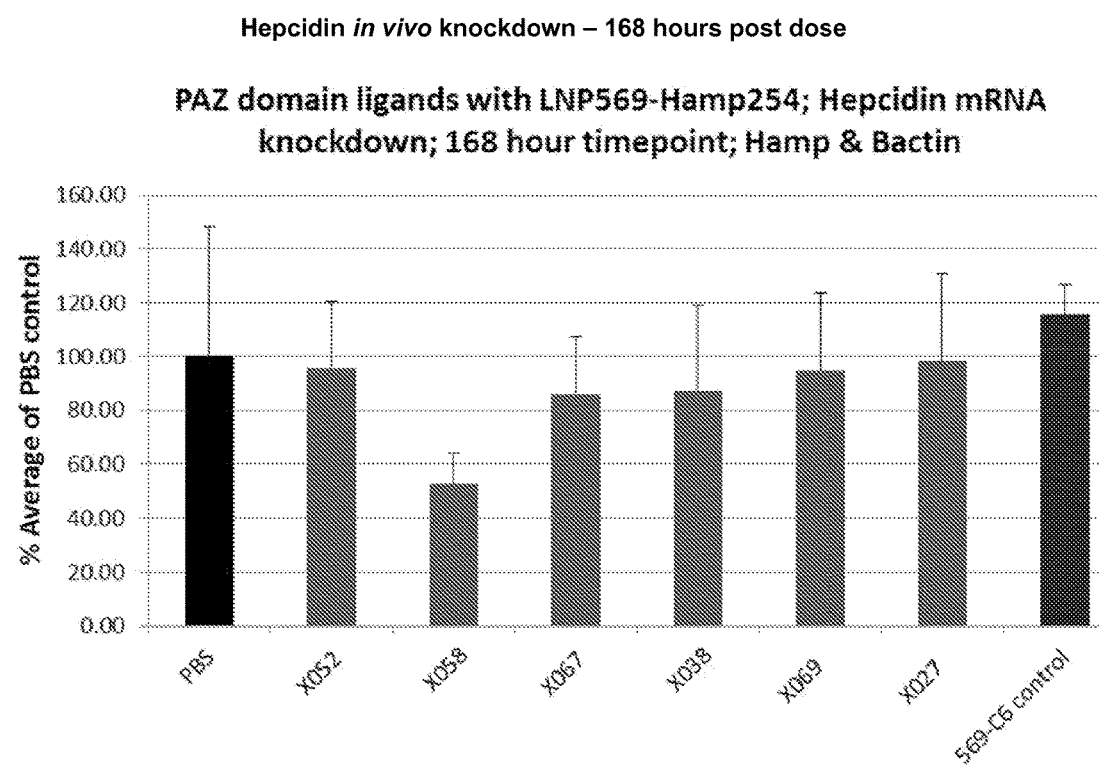
FIG. 9A shows that the duplex comprising the X058 3' end cap was still able to mediate RNA interference (measured by Hepcidin knockdown) at 168 hours (7 days) post-dose in vivo, with a 1×3 mg/kg dose, as described in Example 3B.

FIG. 9A shows that in the Hamp1 specific Taqman assay, the duplex comprising the X058 3' end cap was still able to mediate RNA interference (measured by Hepcidin knockdown) at 168 hours post-dose in vivo. Thus, >50% knockdown was observed in mice after 7 days with a single dose.

Figure 9B:
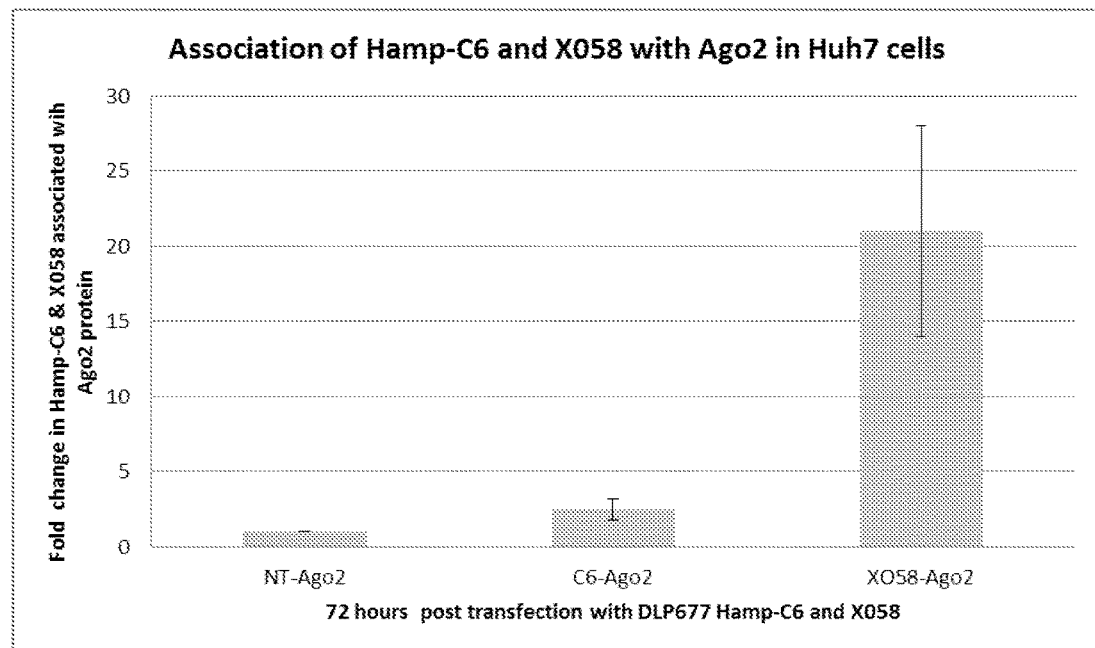
FIG. 9B shows the increased association of the duplex comprising the X058 3' end cap with Ago2, compared to the association of the duplex comprising the C6 3' end cap. These are RNAi agents to mouse Hepcidin tested in vivo.

Without being bound by any particular theory, this disclosure notes that the increased potency and duration of knockdown mediated by RNAi agents with a X058 3' end cap may be due to the increased association of X058 with Ago2. FIG. 9B shows the X058 and C6 Ago2 Pulldown experiment using Hepcidin 18-mer oligonucleotides.

Briefly, antibodies to Ago2 were used to pull down Ago2 from cells 72 after dosage with RNAi agents comprising either a X058 or C6 3' end cap, or a non-targeting (NT) control RNAi agent. Analysis was then performed to determine levels of RNAi agents, as shown. FIG. 9B shows that, after 72 hrs, much more RNAi agent with X058 was associated with Ago2 than the RNAi agent with C6.

Thus, these data show that:

HAMP 18-mer (254) siRNAs with X038, X052, X058, X067, or X069 PAZ ligands on guide strand are active in vivo.

X058 shows convincing increased potency and duration of knockdown.

Additional In Vivo Testing.

An additional in vivo testing was done with different chemical formats: (A160_S38, S42, S45 & A161_S38, S42, S45).

In the Antisense Strand:
A160_→F in position 2 and ribC6 overhang
A161_→F in position 2, 5, 6, 7 and ribC6 overhang
  In the sense strand:
_S38→C6 overhang
_S42→ribC6 overhang
_S45→BP overhang Parameters used in this experiment were:
Mice (n=5/group) injected via IV bolus (tail vein):
LNP569
PBS
LNP569-Hamp254 A160_S38-3 mg/kg
LNP569-Hamp254 A160_S42-3 mg/kg
LNP569-Hamp254 A160_S45-3 mg/kg
LNP569-Hamp254 A161_S38-3 mg/kg
LNP569-Hamp254 A161_S42-3 mg/kg
LNP569-Hamp254 A161_S45-3 mg/kg
48 Hour Timepoint.
Assess Hepcidin Knockdown in Liver (mRNA-qPCR)

Figure 10:
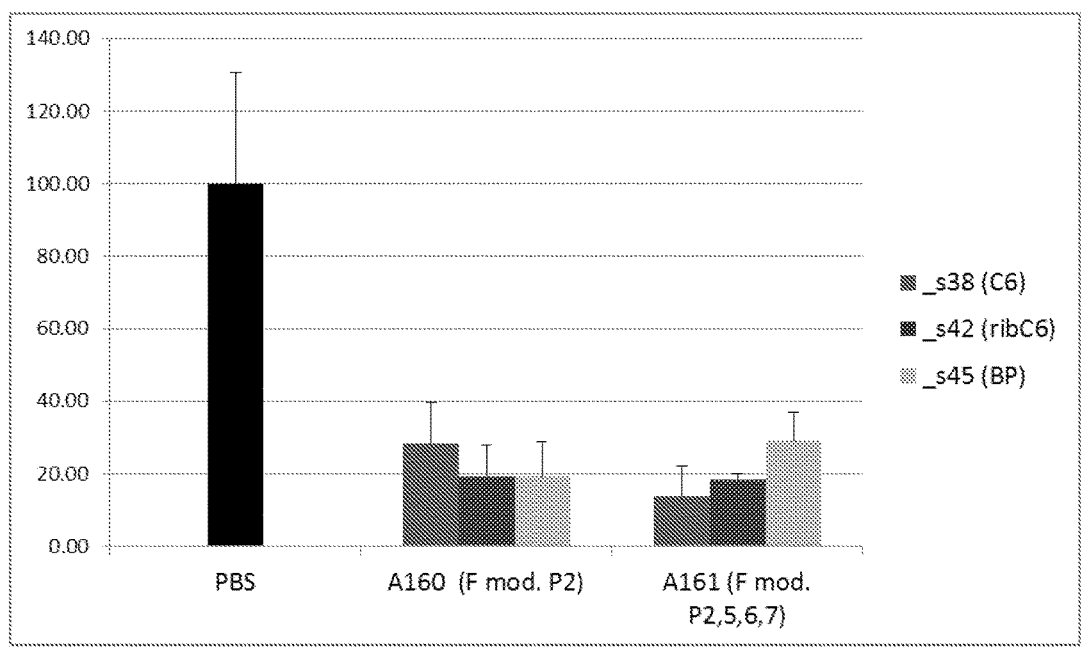
FIG. 10 shows the in vivo comparison of RNAi agents of A160 & A161 formats and various 3' end caps (C6 or BP) or a ribitol spacer and a 3' end cap (ribC6), as described in Example 3B. These are human Hepcidin RNAi agents.

The results are shown in FIG. 10. FIG. 10 shows the In vivo comparison of A160 & A161 format [various passenger (sense) strand overhangs]. This experiment was done 48 hours post-dose, with a 1×3 mg/kg dose.

These data show the in vivo efficacy of RNAi agents comprising any of several 3' end caps: BP, C6, X052, X058, X067, X038, X069, X027, Example 4

Additional Studies Showing Efficacy of 3' End Caps

Additional studies are performed using RNAi agents comprising a 3' end cap.

Figure 16A:
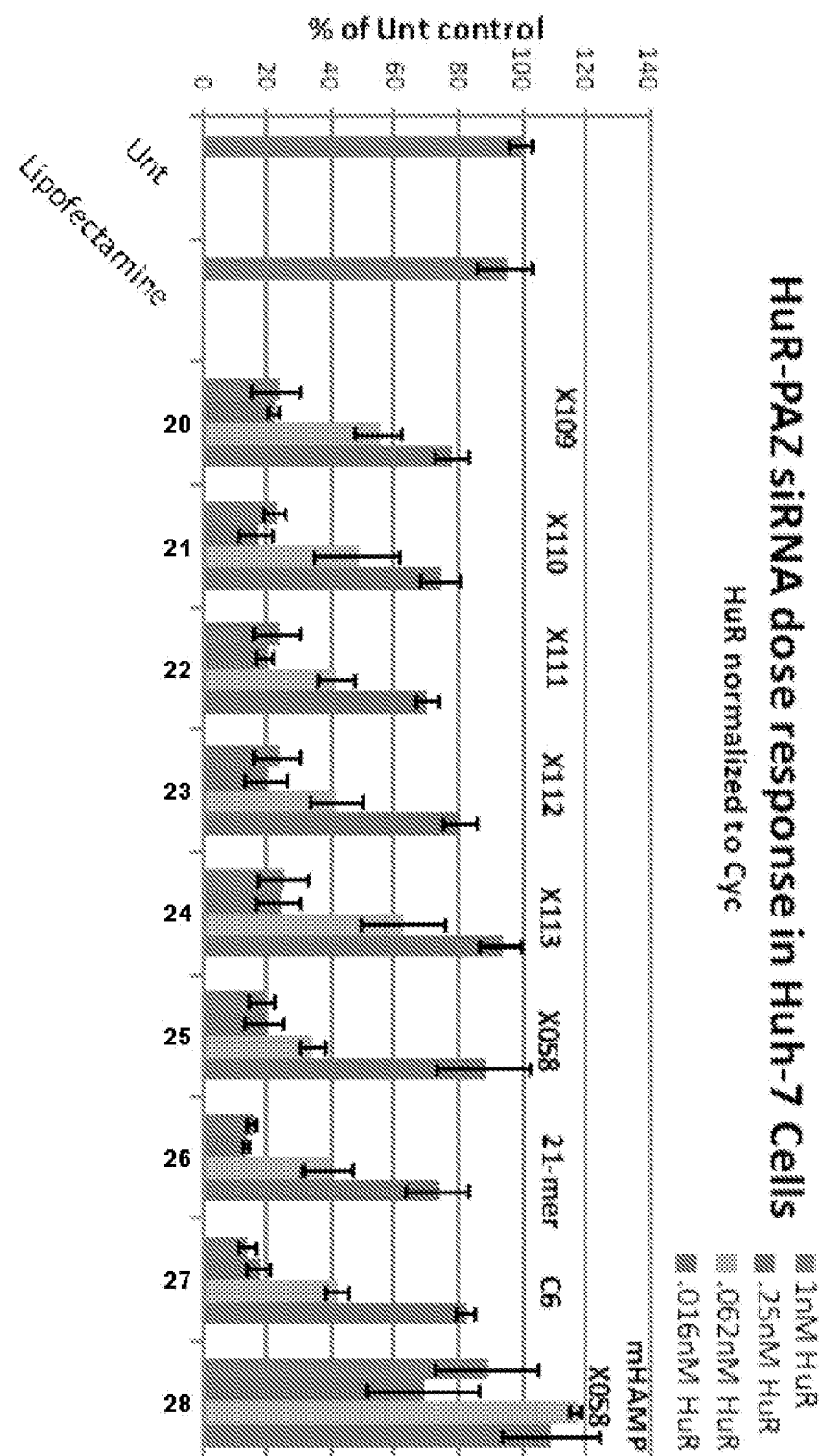
FIG. 16A shows the in vitro efficacy of RNAi agents comprising any of various 3' end caps: X058, X109, X110, X111, X112, X113, or C6 (positive control).

FIG. 16A shows the efficacy of RNAi agents wherein the 3' end cap is X109, X110, X111, X112, X113, X058 or C6. HuR is the target. Doses used are: 1 nM, 0.25 nM, 0.62 nM, and 0.16 nM. RNAi agents comprising any of the 3' end caps were able to mediate RNA interference, particularly at the highest doses used.

In particular, HuR-PAZ ligands X110, X111 and X112 appear to be similar in potency as X058.

Table 6, below, provides additional data showing the efficacy of 18-mer format RNAi agents with various 3' end caps: X059, X050, X061, X051, X027, X062, X060, C6 (X003), X068, X065, X069, X097, X066, X098, X052, X063, BP (X014), X038, X067, X058, X064, and ribprib (X025).

TABLE 7

Efficacy of RNAi agents with a 3' end cap to ELAVL1/HuR in cells in vitro

| Nickname siTrack | siRNA | AV 5.04 | 9.95 | 19.85 | SD 5.04 | 9.95 | 19.85 |
|---|---|---|---|---|---|---|---|
| | | % residual mRNA (qRT-PCR) | | | | | |
| untreated-HB | untreated | 100.54 | | | 10.76 | | |
| av_PSAT6-EYFP-N1_471_A25S27 | eYFP neg. control 1 | 110.06 | 104.72 | 101.98 | 6.52 | 13.38 | 11.84 |
| av_PNAS-280_1_A25S27 | eYFP neg. control 2 | 102.15 | 96.16 | 98.87 | 15.02 | 6.60 | 9.41 |
| hs_ELAVL1_1186_MAN_S42 | 18-mer siRNA with X059 | 45.17 | 20.58 | 10.24 | 2.84 | 0.63 | 0.79 |
| hs_ELAVL1_1186_MAN_S42 | 18-mer siRNA with X050 | 26.69 | 11.48 | 6.92 | 0.99 | 2.40 | 1.41 |
| hs_ELAVL1_1186_MAN_S42 | 18-mer siRNA with X061 | 26.11 | 11.49 | 6.25 | 5.81 | 0.99 | 0.74 |
| hs_ELAVL1_1186_MAN_S42 | 18-mer siRNA with X051 | 25.35 | 10.80 | 6.88 | 3.28 | 0.61 | 0.86 |
| hs_ELAVL1_1186_MAN_S42 | 18-mer siRNA with X027 | 24.54 | 11.67 | 6.17 | 2.90 | 1.38 | 1.03 |
| hs_ELAVL1_1186_MAN_S42 | 18-mer siRNA with X062 | 24.35 | 11.68 | 5.66 | 2.88 | 1.46 | 1.17 |
| hs_ELAVL1_1186_MAN_S42 | 18-mer siRNA with X060 | 23.86 | 9.27 | 5.62 | 1.10 | 0.86 | 0.76 |
| hs_ELAVL1_1186_A106_S42 | 18-mer siRNA with C6 (X003) | 22.42 | 9.77 | 5.65 | 1.90 | 1.60 | 1.31 |
| hs_ELAVL1_1186_MAN_S42 | 18-mer siRNA with X068 | 22.40 | 10.77 | 5.89 | 2.25 | 1.92 | 1.31 |
| hs_ELAVL1_1186_MAN_S42 | 18-mer siRNA with X065 | 22.24 | 10.50 | 5.20 | 3.44 | 1.26 | 0.96 |
| hs_ELAVL1_1186_MAN_S42 | 18-mer siRNA with X069 | 21.93 | 9.57 | 6.13 | 6.25 | 1.11 | 1.57 |
| hs_ELAVL1_1186_MAN_S42 | 18-mer siRNA with X097 | 21.26 | 9.83 | 6.29 | 3.45 | 1.98 | 1.27 |
| hs_ELAVL1_1186_MAN_S42 | 18-mer siRNA with X066 | 21.12 | 10.25 | 5.77 | 2.04 | 1.14 | 0.43 |
| hs_ELAVL1_1186_MAN_S42 | 18-mer siRNA with X098 | 21.06 | 9.94 | 6.15 | 4.39 | 2.16 | 1.29 |
| hs_ELAVL1_1186_MAN_S42 | 18-mer siRNA with X052 | 21.02 | 8.32 | 6.75 | 1.41 | 1.29 | 0.93 |
| hs_ELAVL1_1186_MAN_S42 | 18-mer siRNA with X063 | 20.53 | 10.91 | 5.61 | 3.01 | 0.86 | 0.18 |

TABLE 7-continued

Efficacy of RNAi agents with a 3' end cap to ELAVL1/HuR in cells in vitro

| Nickname siTrack | siRNA | AV 5.04 | 9.95 | 19.85 | SD 5.04 | 9.95 | 19.85 |
|---|---|---|---|---|---|---|---|
| | | % residual mRNA (qRT-PCR) | | | | | |
| hs_ELAVL1_1186_A324_S42 | 18-mer siRNA with BP (X014) | 20.38 | 9.37 | 6.19 | 2.56 | 1.37 | 0.67 |
| hs_ELAVL1_1186_A27_S30 | 19-mer pos. control | 19.90 | 8.03 | 5.40 | 1.40 | 0.98 | 0.37 |
| hs_ELAVL1_1186_MAN_S42 | 18-mer siRNA with X038 | 19.80 | 10.60 | 5.26 | 2.52 | 0.75 | 0.75 |
| hs_ELAVL1_1186_MAN_S42 | 18-mer siRNA with X067 | 19.07 | 11.38 | 5.82 | 2.02 | 3.00 | 0.94 |
| hs_ELAVL1_1186_MAN_S42 | 18-mer siRNA with X058 | 18.40 | 10.36 | 6.23 | 2.70 | 2.78 | 0.42 |
| hs_ELAVL1_1186_MAN_S42 | 18-mer siRNA with X064 | 18.33 | 9.84 | 6.49 | 3.03 | 0.45 | 1.67 |
| hs_ELAVL1_1186_MAN_S42 | 18-mer siRNA with ribprib (X025) | 17.10 | 9.78 | 5.75 | 3.69 | 1.38 | 0.75 |
| hs_ELAVL1_1186_A22_S26 | 21-mer pos. control | 16.68 | 8.61 | 5.15 | 2.39 | 1.17 | 0.86 |

This table provides: the nickname of the RNAi agent (column 1); the length and the 3' end cap used and identification of controls (column 2); % residual mRNA level, as determined by qRT-PCR, at doses of 5.04, 9.95, and 19.85 nM (columns 3-5); standard deviation (SD) (columns 6-8). HuR is normalized to Cyc. 5.04, 9.95, 19.85, 5.04, 9.95, 19.85 represent dosing (nM).

The knockdown (RNA interference activity) can be readily calculated by subtracting the % residual mRNA from 100%. Thus, the final line shows that the 21-mer pos. (positive) control exhibits 16.68% residual mRNA, indicating 83.32% knockdown.

These data show the efficacy of RNAi agent comprising a first and a second strand, wherein the 3' end of the first and/or second strand terminates in a phosphate and further comprises in 5' to 3' order: a spacer (e.g., ritbitol), a phosphate, and a 3' end cap.

These data show that efficacious RNAi agents can be constructed wherein the 3' end is BP (X014), C6 (X003), ribprib (X025), X027, X038, X050, X051, X052, X058, X059, X060, X061, X062, X063, X064, X065, X066, X067, X068, X069, X097, or X098.

Example 5

Efficacy of RNAi Agents Comprising a C8 or C10 3' End Cap

RNAi agents comprising a C8 or C10 3' end cap are tested.

19-mer SSB siRNA with C8 or C10 overhang are tested.

Figure 17C:
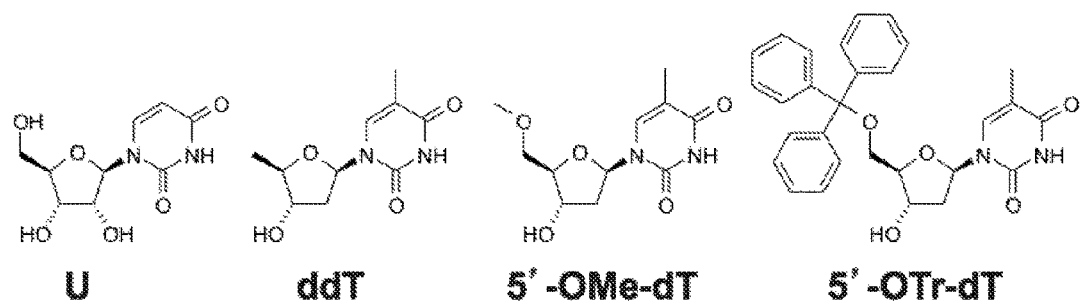
Figure 17D:
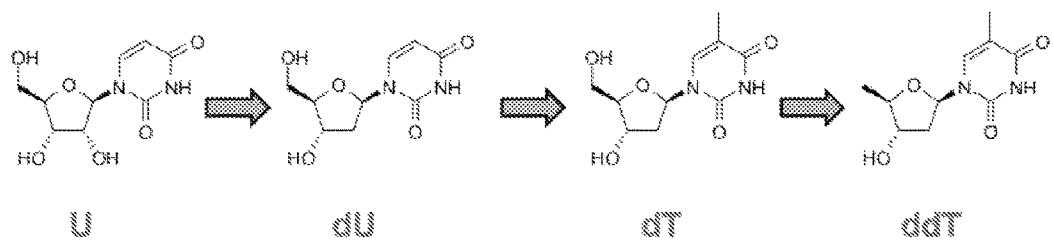
Figure 17E:
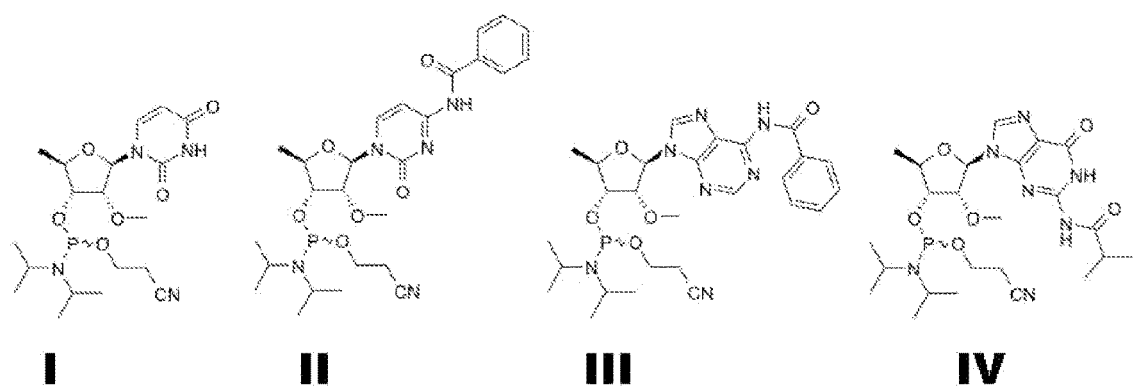
Figure 17F:
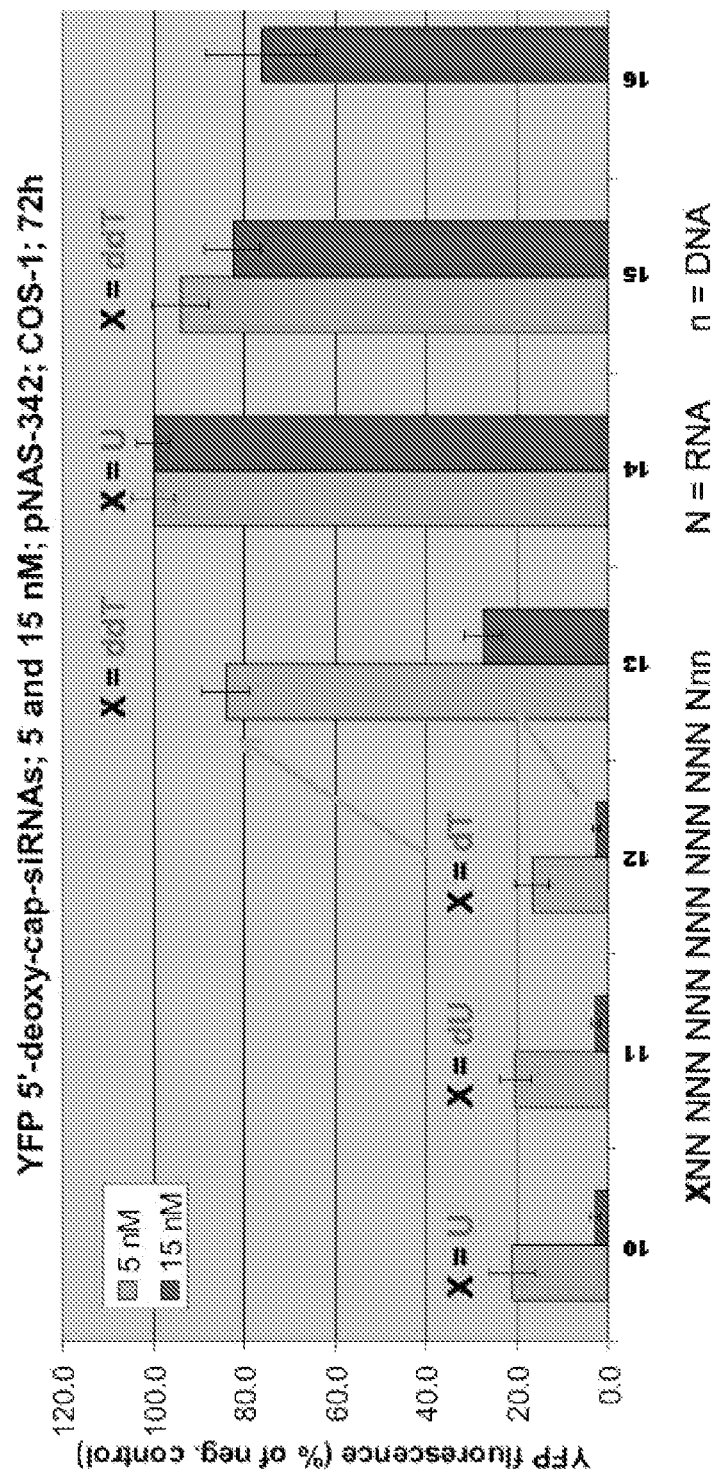
Figure 17G:
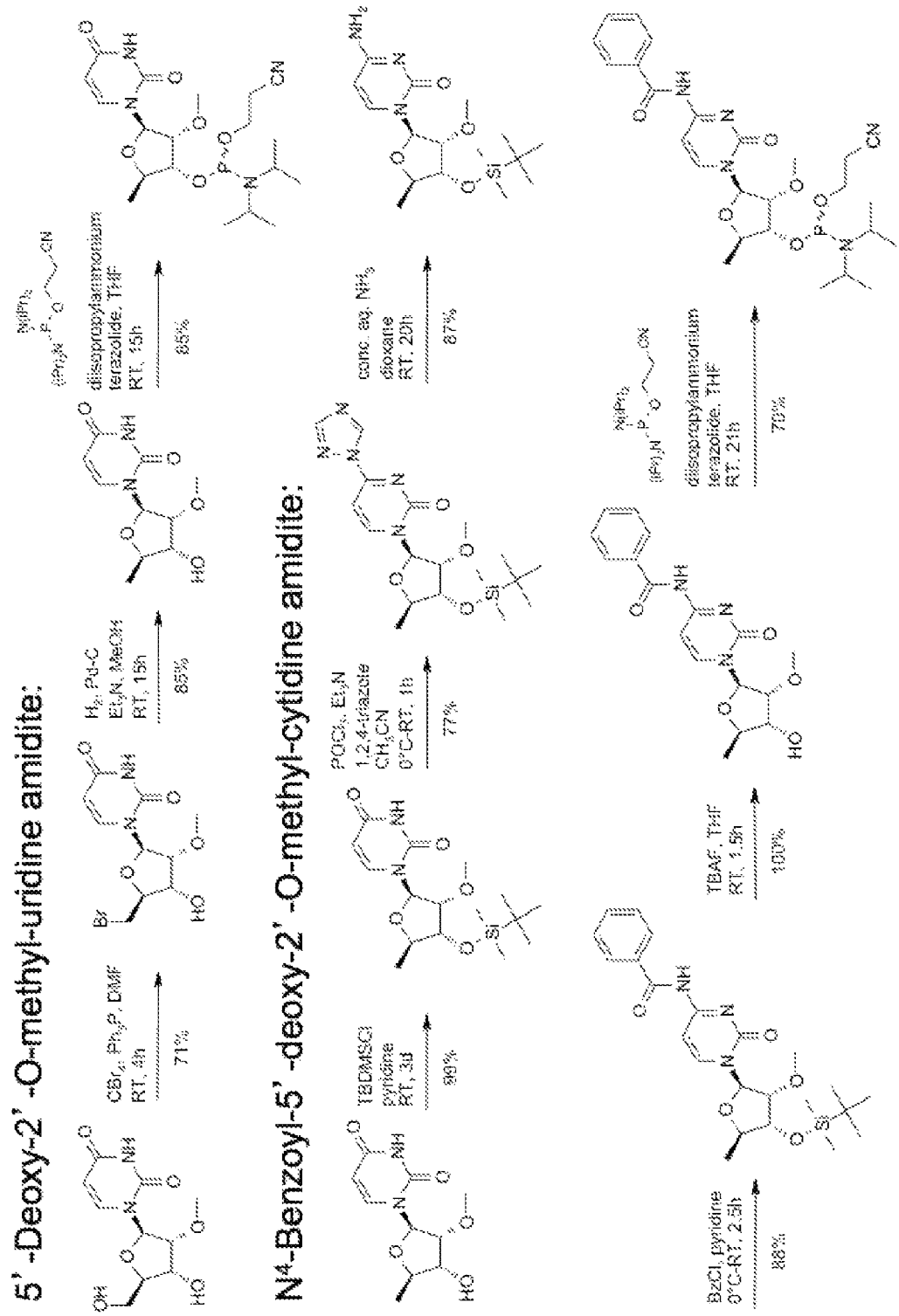
Figure 17H:
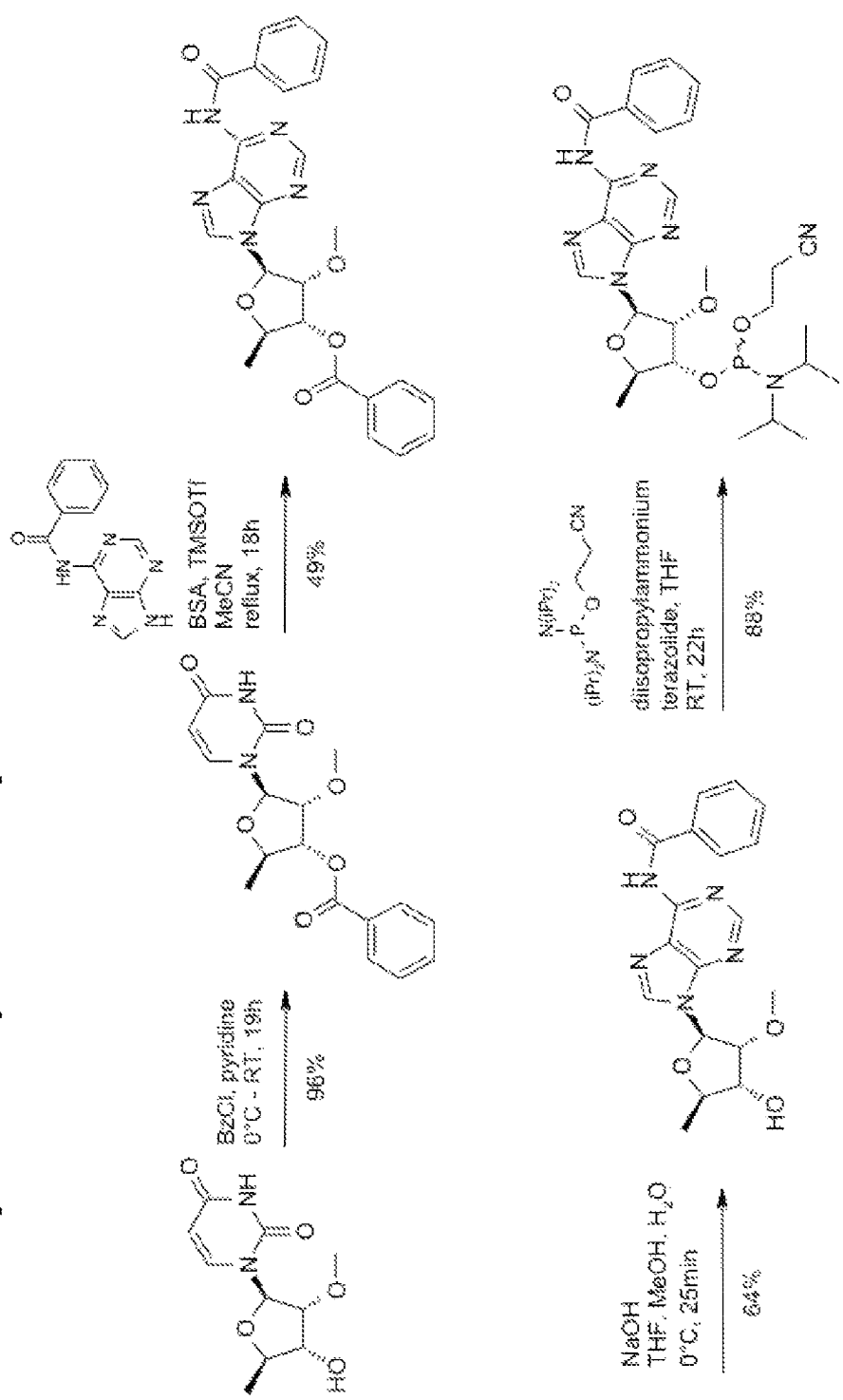
Figure 17I:
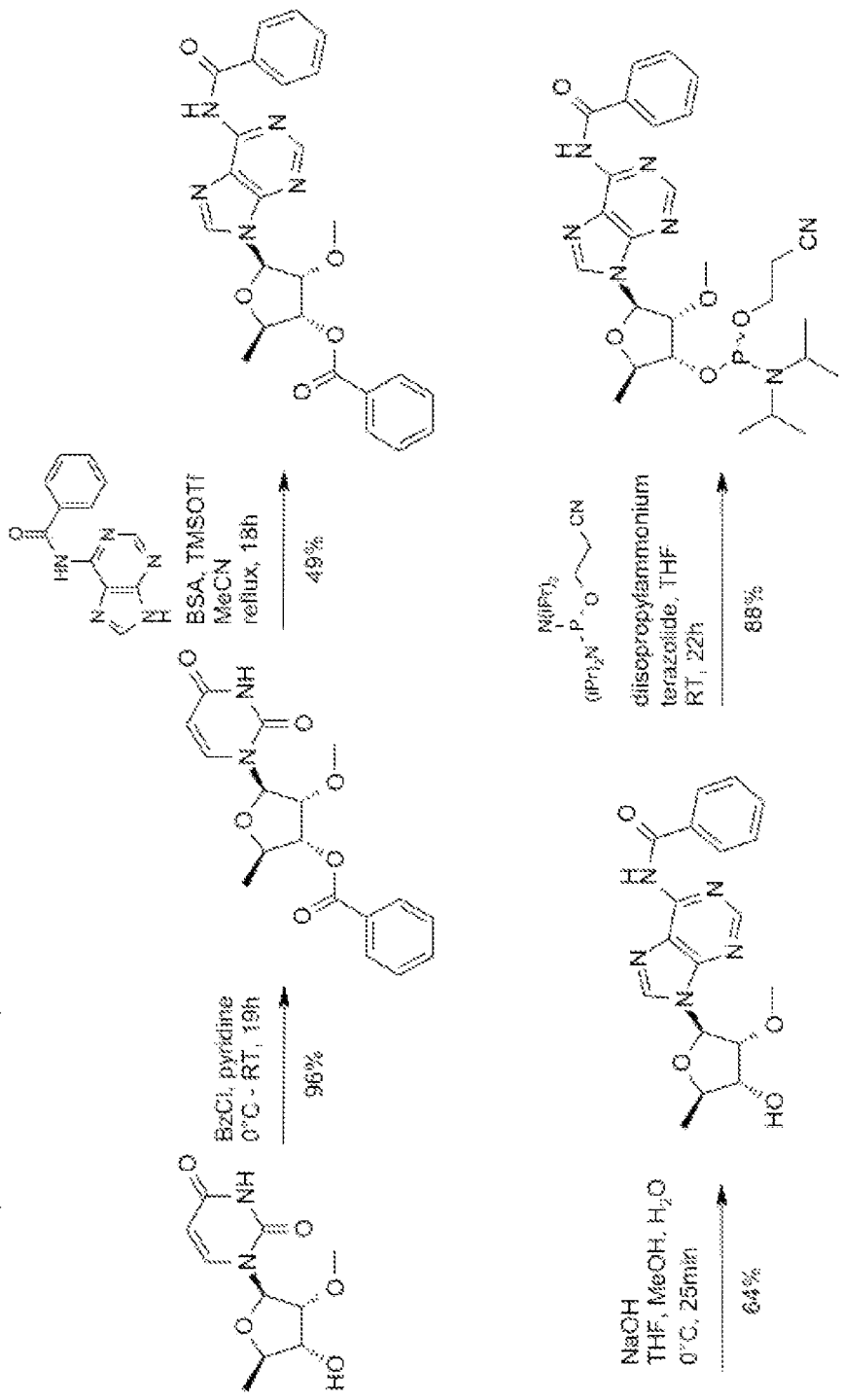

FIGS. 18A and 18B show the results, while FIG. 17C diagrams the various 3' end caps used.

RNAi agents comprising a C8 or C10 3' end cap were able to mediate RNA interference.

19-mer SSB siRNA with C10 overhang gives less potent mRNA downregulation at 3d than 21-mer positive control, but better duration of effect.

Thus, the C10 modified 19mer siRNA is not giving the same maximum target knock-down at an early timepoint (day 3), but holds up longer (more potent knockdown at day 10). The C10 3' end cap thus provides a superior duration of action.

Experimental data shows that efficacious RNAi agents can be constructed comprising a 3' end cap which is C6, C8 or C10. In addition, the C10 3' end cap has the advantage of increased duration of activity in vivo.

Example 6

RNAi Agents Comprising Phosphorothioate and/or RNA, DNA, 2'-MOE, 2'-F, or LNA CLAMP Variants a RNAi agent to F7 (Factor VII) are prepared.

These variants comprise, as examples, a 3' end cap which is phosphorothioate-C3 (PS-C3), and/or a clamp. In the clamp, the last two base-pairing nt counting from 5' to 3' are modified.

Results are shown in FIG. 20A-E.

FIG. 20 shows the efficacy of 3' end caps and clamps comprising various modifications. FIGS. 20A and B show the efficacy of RNAi agents comprising a 3' end cap of phosphorothioate-C3 (PS-C3). FIGS. 20 C, D and E show the efficacy of RNAi agents comprising a 2' clamp, wherein the last two base-pairing nt counting from 5' to 3' are RNA, DNA, 2'-MOE, 2'-F, or LNA.

Figure 20E:
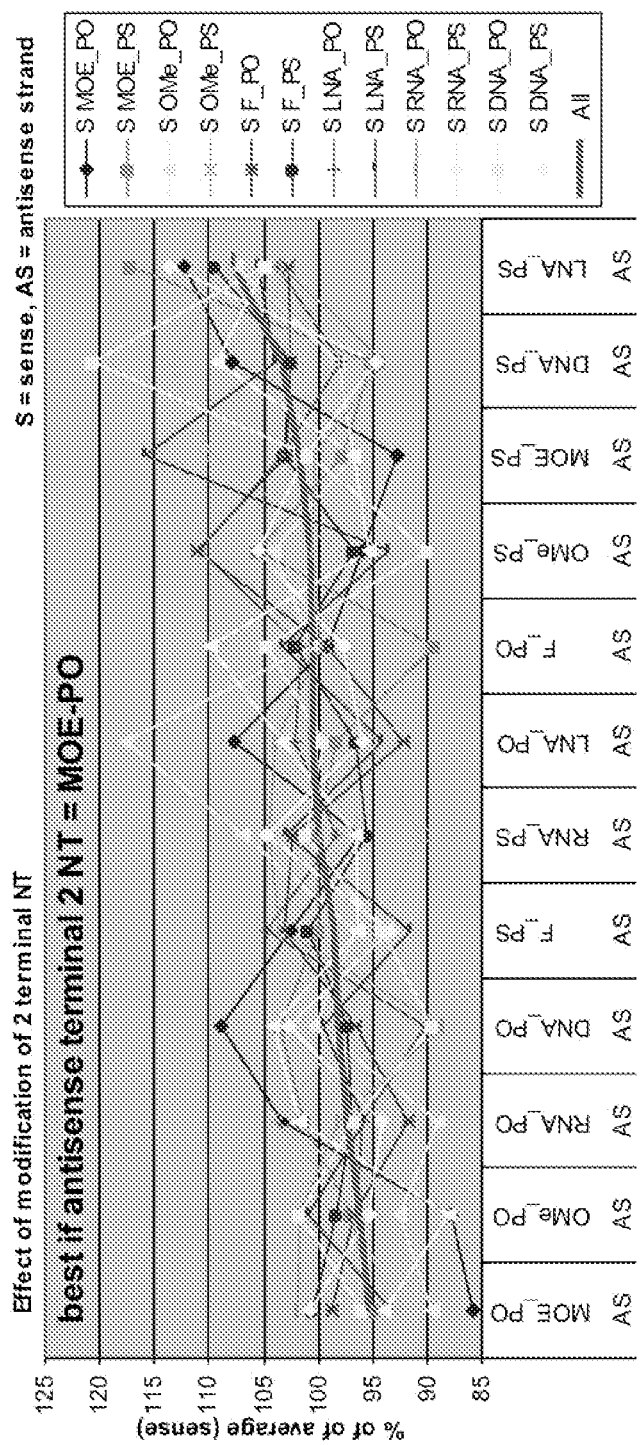

For the RNAi agents in FIGS. 20D and 20E, all the tested RNAi agents were efficacious. It is noted that the percentages do not represent knockdown, but knockdown relative to other RNAi agents. 100%, for example, represents the average knockdown of all antisense strands of these efficacious RNAi agents.

These data thus show that efficacious RNAi agents can be constructed which comprise a RNA, DNA, 2'-MOE, 2'-F, or LNA, and in which the modified internucleoside linker is a phosphorothioate.

Example 7

RNAi Agents Comprising a C3, C4, or C5 Linker in the 3' End Cap

Figure 23A:
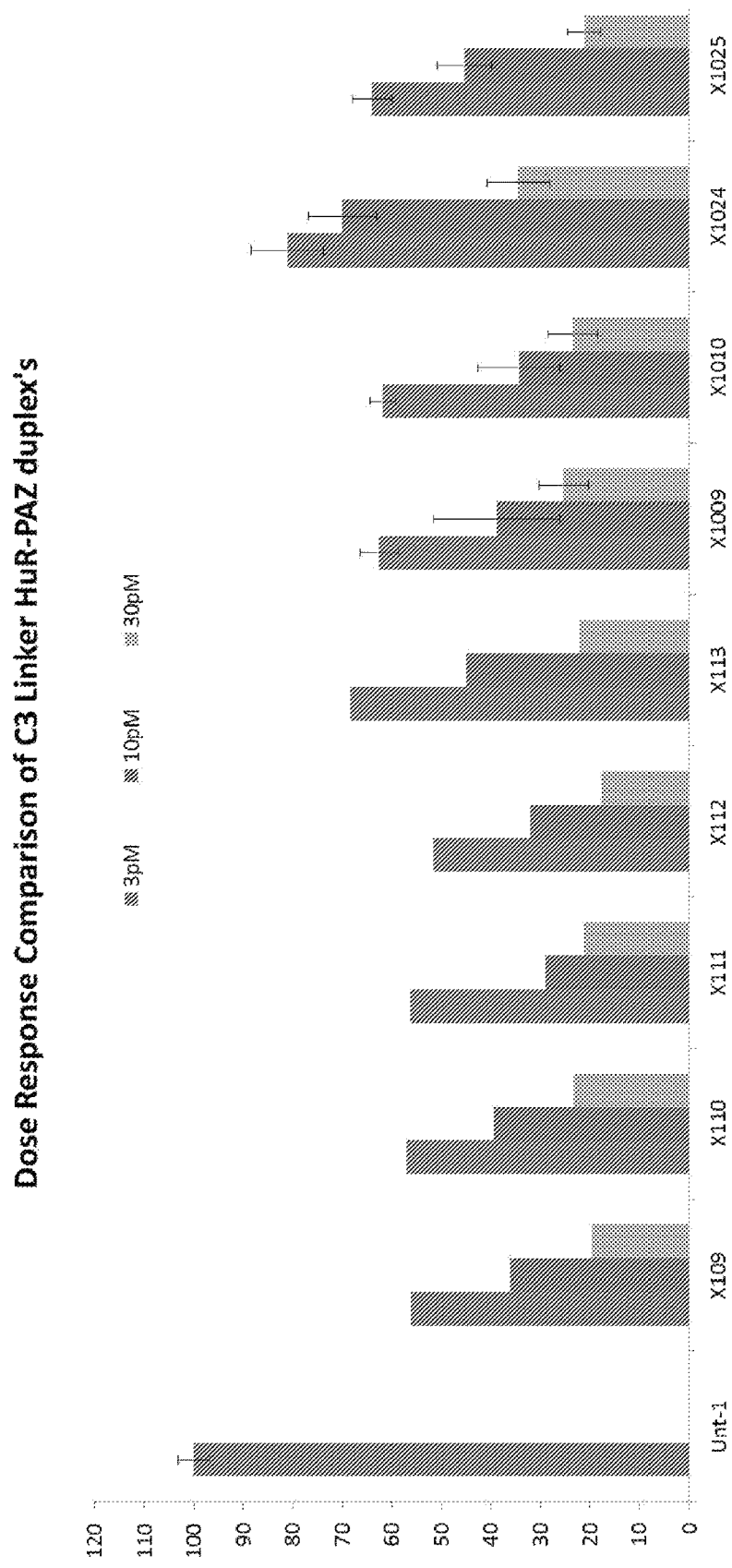
Figure 23C:
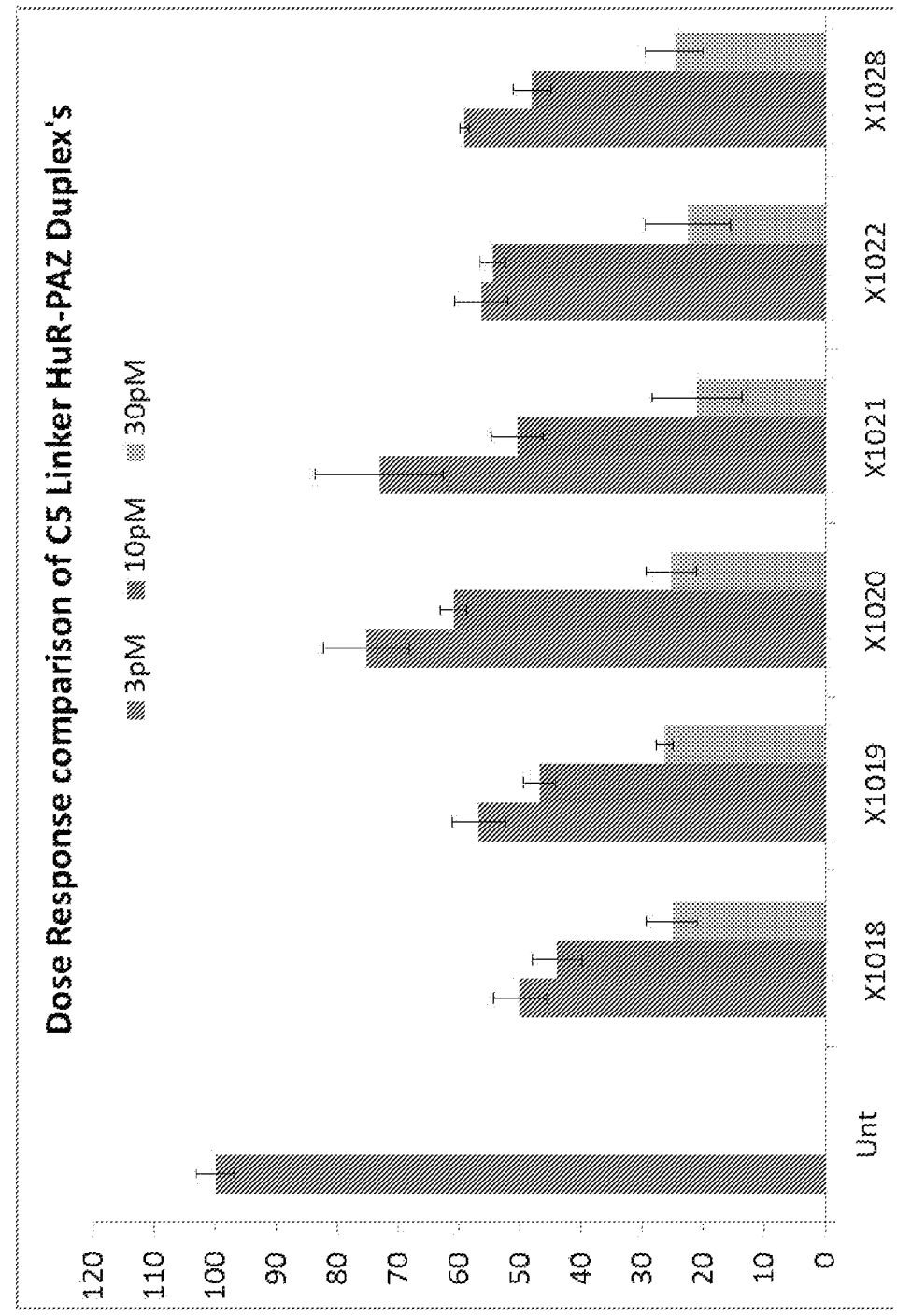

This Example shows efficacy of RNAi agents comprising a 3' end cap which is: X109, X110, X111, X112, X113, X1009, X1010, X1024 or X1025 (FIG. 23A); X1011, X1012, X1013, X058, X1015, X1016, X1017, X1026, X1027 (FIG. 23B): or X1018; X1019, X1020, X1021, X1022 or X1028 (FIG. 23C).

The 3' end caps shown in FIG. 20A comprise a C3; the 3' end caps in FIG. 20B comprise a C4; and the 3' end caps in FIG. 20C comprise a C5. These data show that RNAi agents comprising any of these 3' end caps is effacious.

A HuR RNAi agent is used.

In these experiments, Huh-7 cells are transfected using RNAiMax in a 96-well plate format. RNA is isolated 48 hours post-transfection. HuR mRNA is normalized to PPIA endogenous control. RNAi agent concentrations of 3, 10 and 30 pM are chosen based on IC50 data of the PAZ ligands (3' end caps) previously analyzed. For the X109 to X113 data, an average of two previous data sets is provided.

In general, length of the linker within the 3' end cap does not significantly affect potency of any of the 3' end caps.

In separate but related experiments, IC50 data was determined for several 3' end caps using HuR RNAi agents in Huh-7 cells. Data points for two separate studies are shown below:

| siRNA 3' end cap | pM IC50 study#1 | pM IC50 study#2 |
|---|---|---|
| X058 | 5.85 | 12.78 |
| X109 | 3.47 | 3.85 |
| X110 | 1.50 | 6.42 |
| X111 | 1.21 | 3.63 |
| X112 | 0.72 | 2.38 |
| X113 | 2.71 | 4.55 |

These data show that RNAi agents comprising a 3' end cap which is X058, X109, X110, X111, X112 or X113 are each efficacious.

Example 8

Additional RNAi Agents Comprising a C3, C4, or C5 Linker in the 3' End Cap

This example shows the efficacy of various RNAi agents comprising a 3' end cap which is: X110, X1012, X1018, X111, X1013, X112, X058, X1019, X1025, X1027, or X1028.

This various 3' end caps (illustrated in Table 1) vary in the length of the linker (C3, C4 or C5) between $R_2$ and the head group.

As a note of clarification, this disclosure notes that the terms "C3" [—$(CH_2)_3$—], "C4" [—$(CH_2)_4$—], and "C5" [—$(CH_2)_5$-] are generally used herein to designate spacers, similar terms (C3, C4, C5 "linkers") are also used to designate a portion of a 3' end cap. In FIG. 13, the different linkers are used to differentiate portions of various 3' end caps. It is also noted that the term "C3" is used to designate a C3 3' end cap (e.g., FIG. 15A), a C3 spacer (FIG. 21), and a C3 linker (FIG. 13).

The target gene for this example is HuR. Huh-7 cells are transfected using RNAiMax transfection reagent. 24 well plates are seeded with 40,000 cells per well. "Reverse transfection" with 1 nM RNAi agent/well is done, followed by incubation for approximately 18 hours. Duplicate plates are set up using one for RNA extraction and the other for duration. Transfection media is replaced with fresh growth media (no RNAi agent) and cells are incubated for an additional 2 days before RNA isolation or split for duration experiments.

Cells are split on days 3 and 7 post-transfection. RNA is isolated at days 3, 7 and 10 post-transfection for HuR mRNA analysis.

Figure 24A:
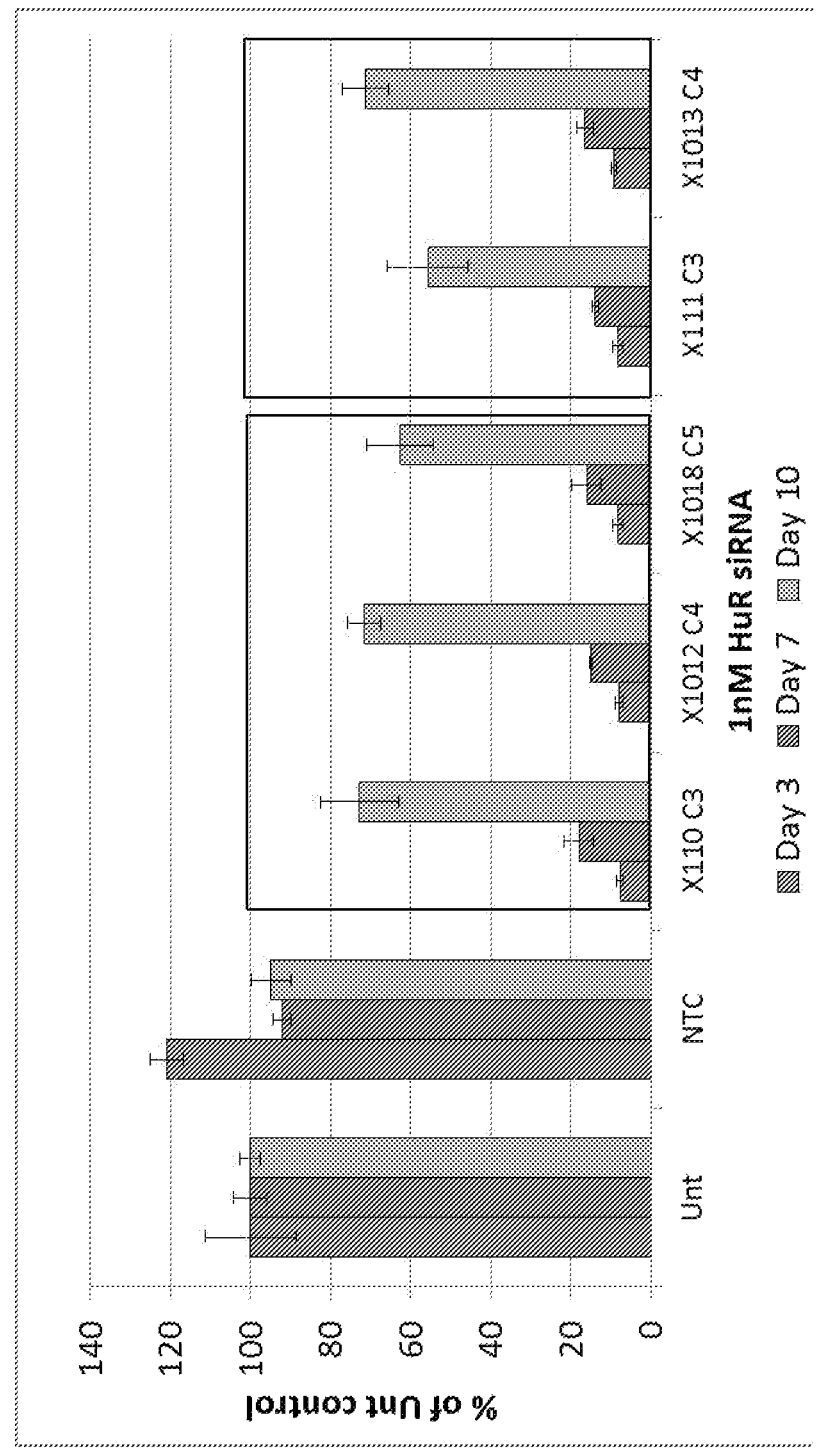
FIGS. 24A and B show efficacy and duration of RNAi agents comprising a 3' end cap which is: X110, X1012, X1018, X111, X1013, X112, X058, X1019, X1025, X1027, or X1028.
Figure 24B:
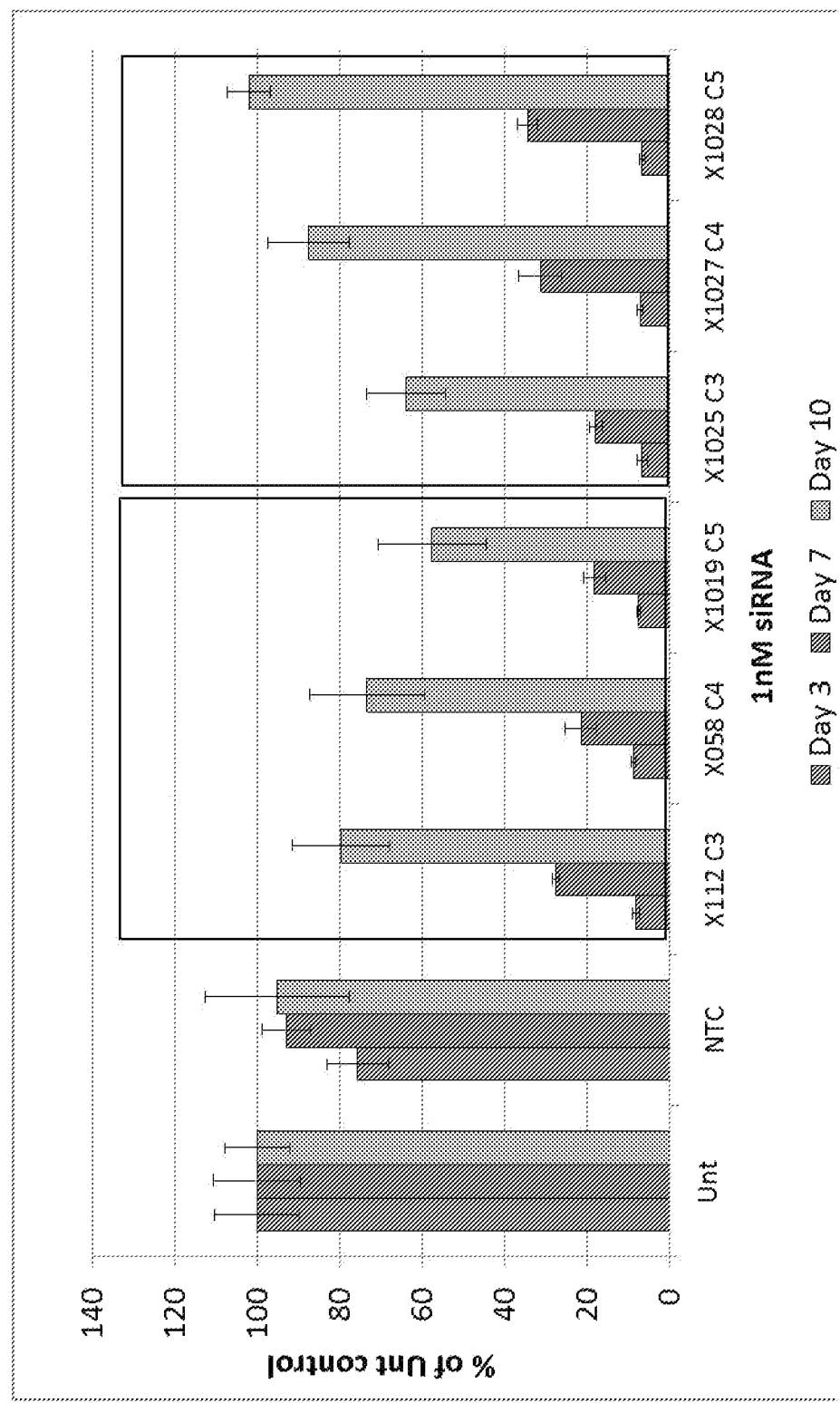

Results are shown in FIGS. 24A and 24B. The control (NTC) is a mFVII 21-mer RNAi agent. In FIG. 24A, ligand LME844 (X110, X1012 and X1018), the linker length does not appear to alter the duration of activity. For ligand PKF027-895 (X111 and X1013), the shorter linker (C3) and the C4 linker are not significantly different.

In FIG. 24B, for ligand LP1230 (X1025, X1027 and X1028), the duration of the C3 linker is better than the longer linkers. There is evidence of this as early as Day 7 post-transfection.

For ligand LKS871 (X112, X058 and X1019), the longer linker appears to have slightly better activity at the later time point and the "trend" is there at Day 7, as well, although the error bars overlaps and it is probably not significant. The X058 activity at Day 10 is about 15% less than demonstrated in a previous duration study, but there will be study to study variability for these types of analyses.

These data show that RNAi agents comprising a 3' end cap which is X112, X058, X1019, X1025, X1027, or X1028 are each efficacious.

Example 9

Efficacy of Additional 3' End Caps

The 3' end caps X1062, X1063 and X1064 were each found to be efficacious when used on RNAi agents. For example, these were effective on HuR siRNAs, wherein the HuR siRNAs were 18-mers as described herein, wherein the 3' end of each strand terminates in a phosphate and further comprises, in 5' to 3' direction, a spacer which is ribitol, a second phosphate, and a 3' end cap which is X1062, X1063 or X1064. Huh7 cells were transfected with siRNAs using RNAi Max transfection reagent; 24-well plates were seeded with 40,000 cells per well; reverse transfection was performed with 1 nM siRNA per well, and cells were incubated for about 18 hours. Transfection medium was replaced (without siRNA), and cells were incubated for an additional 2 days before RNA isolation or split for seeding. Cells were split on days 3 and 7 post transfection for duration time points. RNA was isolated at days 3, 7 and 10 post-transfection for HuR mRNA analysis. HuR siRNAs with 3' end caps which were X1062 demonstrated efficacy (knockdown) of 89.0, 77.9 and 32.7% after 3, 7 or 10 days. HuR siRNAs with 3' end caps which were X1063 and X1064 showed 89.6, 81.5, and 43.7%; and 67.0, 30.9 and 0.0%, respectively, after 3, 7 and 10 days.

Embodiments

1. A compound of formula Ia:

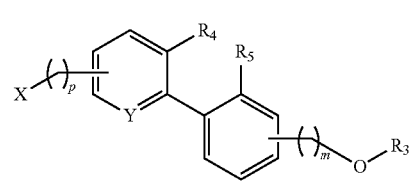

in which:

X is H; OH, wherein the hydroxyl group can optionally be functionalized as succinate or attached to a solid support; ODMT; carboxylic acid; the 3' end of a strand of a RNAi agent; or the 3' end of a molecule comprising a strand of a RNAi agent, wherein the 3' end of the strand terminates in a phosphate or modified internucleoside linker and further comprises in 5' to 3' order: a spacer, and a second phosphate or modified internucleoside linker;

Y is CH or N;

m is 0 or 1;

p is 1, 2 or 3;

$R_3$ is hydrogen, 2-(hydroxy-methyl)-benzyl, 3-(hydroxymethyl)-benzyl, succinate, or a solid support;

wherein the $(CH_2)_m$—O—$R_3$ moiety is attached to the phenyl ring at position 3 or 4;

R4 is hydrogen;
R5 is hydrogen; or
R4 and R5, together with the phenyl rings to which R4 and R5 are attached, form 6H-benzo[c]chromene.
2. The compound of embodiment 1 selected from:
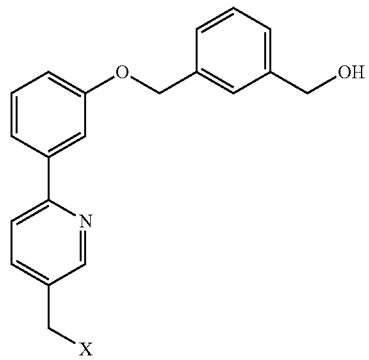
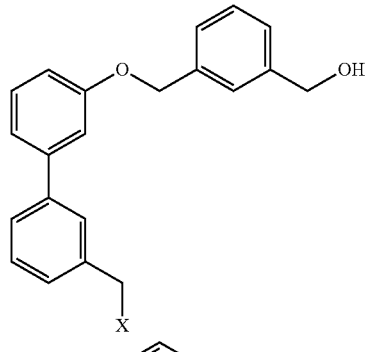
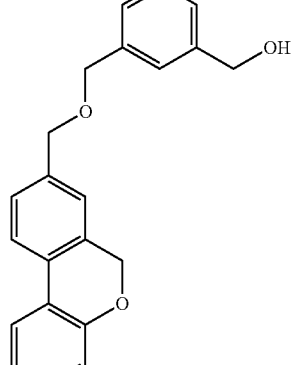
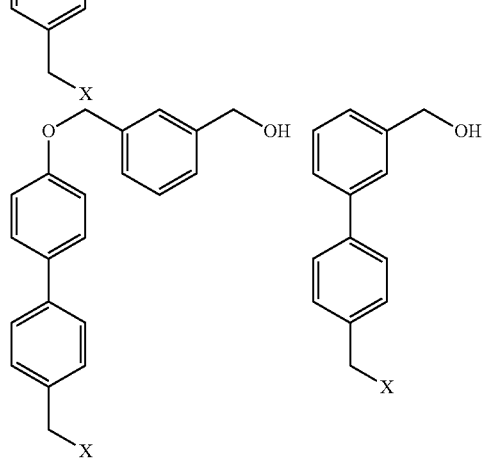
-continued
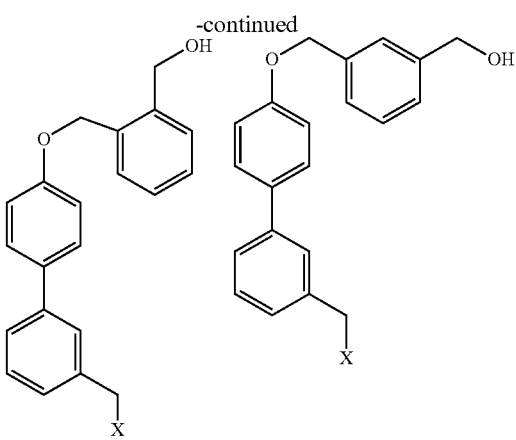
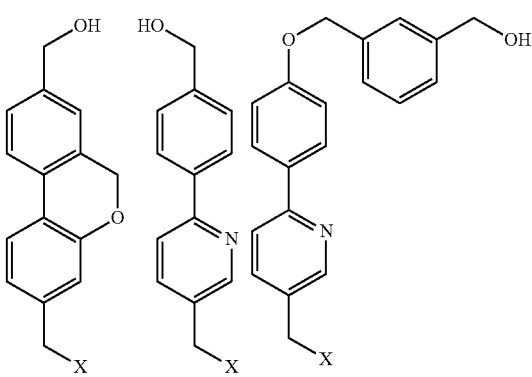
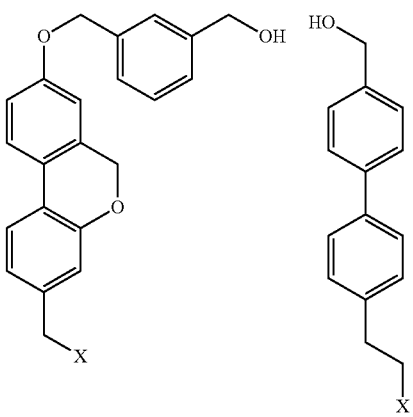
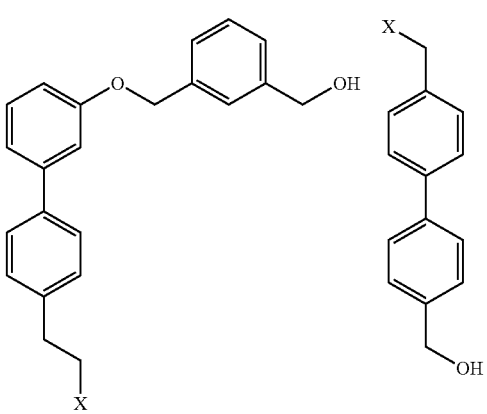

3. A compound of formula Ib:

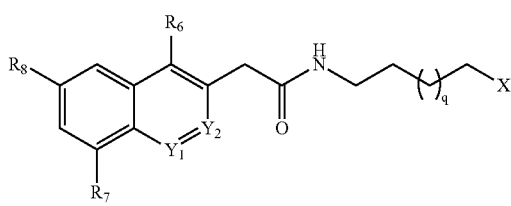

in which:
X is H; OH, wherein the hydroxyl group can optionally be functionalized as succinate or attached to a solid support; ODMT; carboxylic acid; the 3' end of a strand of a RNAi agent; or the 3' end of a molecule comprising a strand of a RNAi agent, wherein the 3' end of the strand terminates in a phosphate or modified internucleoside linker and further comprises in 5' to 3' order: a spacer, and a second phosphate or modified internucleoside linker;

q is 0, 1 or 2;

$R_6$ is phenyl which is unsubstituted or substituted with a group selected from benzoxy and 3,4-dihydroxybutyl;

$R_7$ is hydrogen or hydroxy-ethyl, wherein if $R_7$ is hydroxy-ethyl, the hydroxyl can be optionally functionalized as succinate or attached to a solid support;

$R_8$ is hydrogen or methoxy; $Y_1$ is CH or N; and $Y_2$ is N or $CR_9$; wherein $R_9$ is selected from hydrogen and methyl.

4. The compound of embodiment 3 selected from:

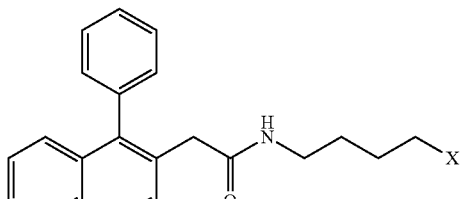

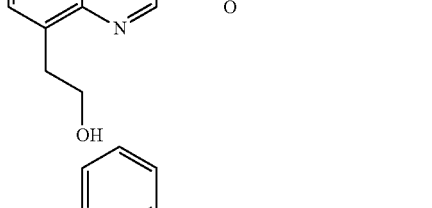

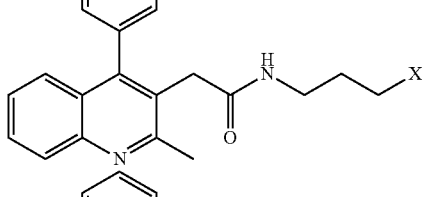

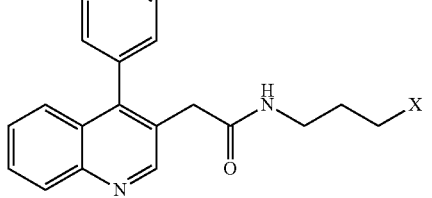

-continued

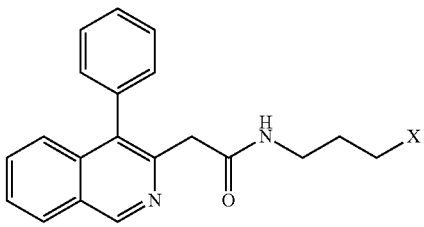

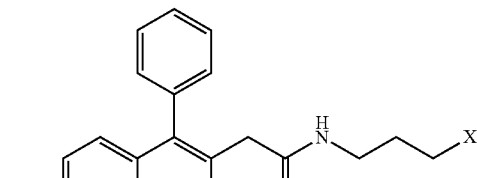

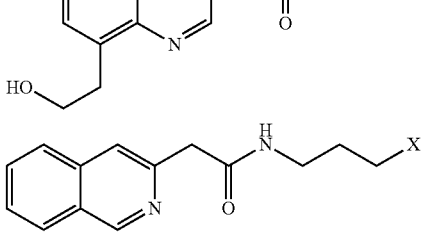

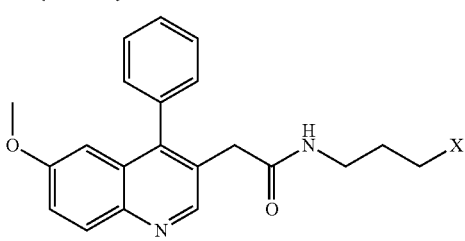

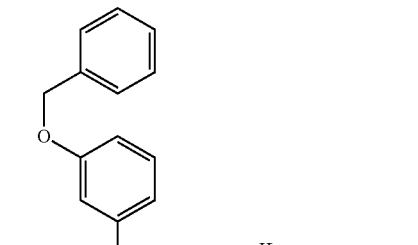

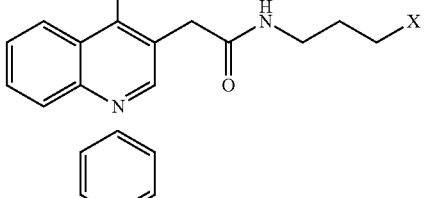

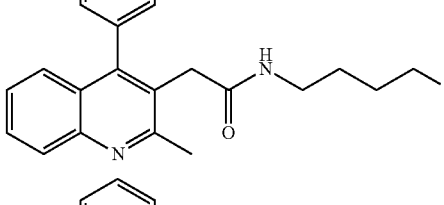

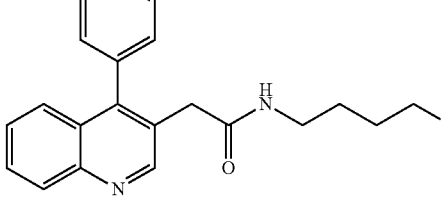

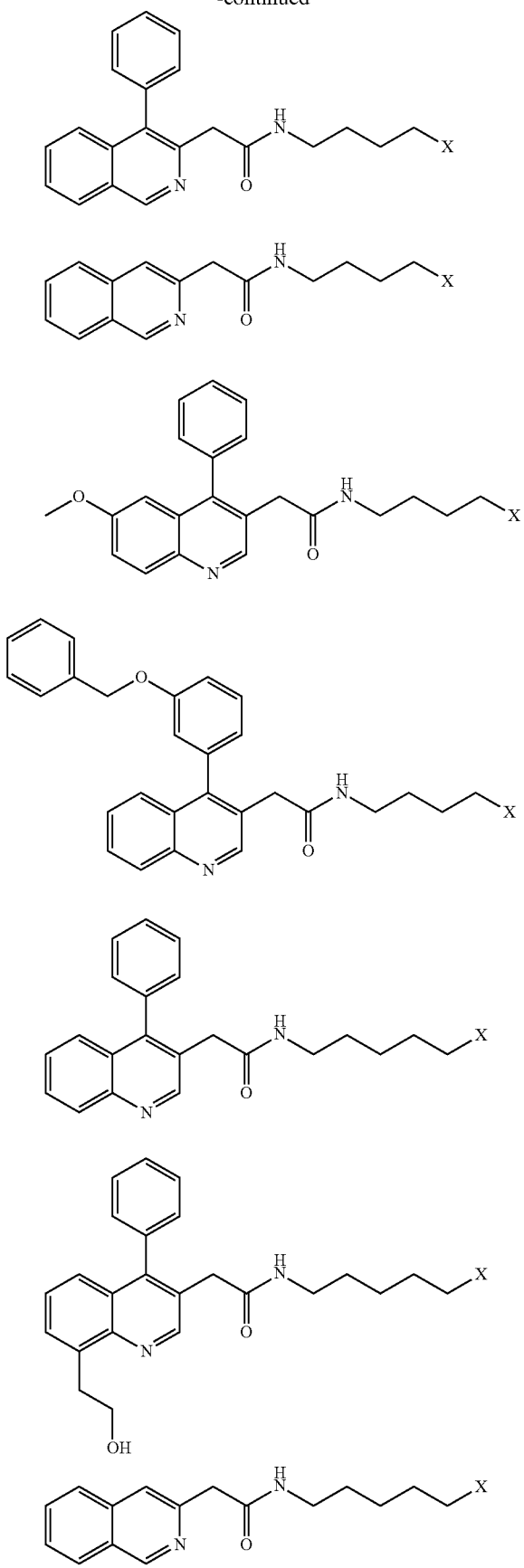
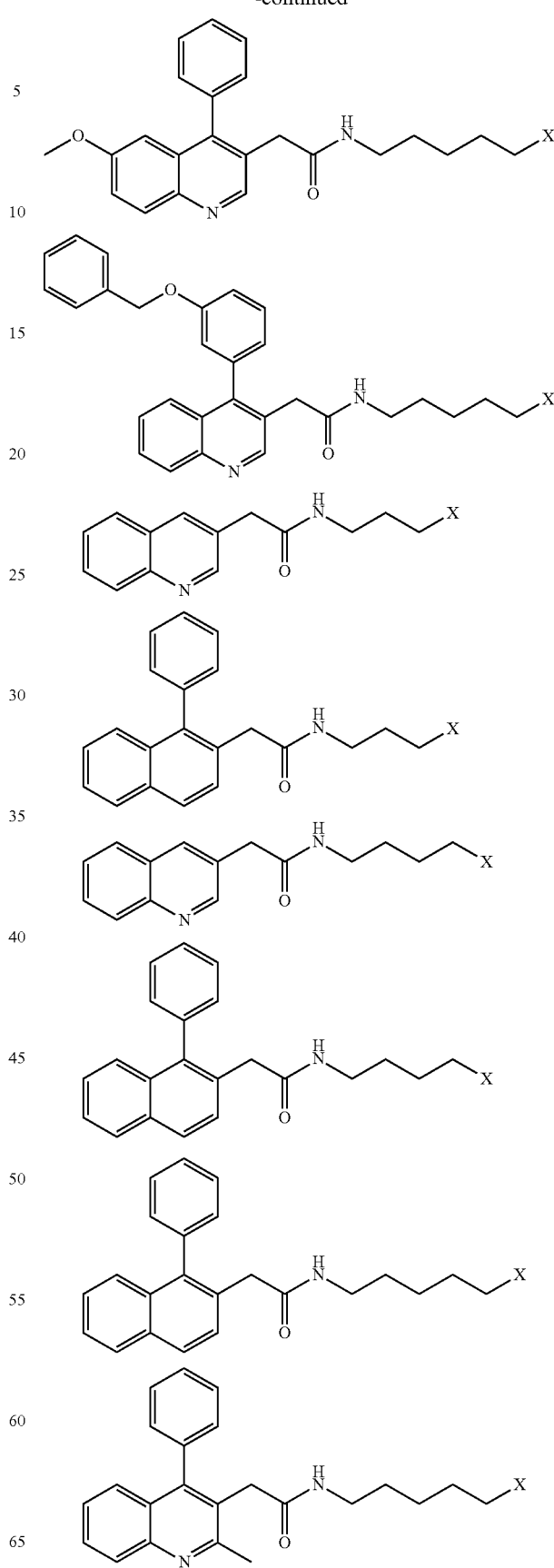

315
-continued

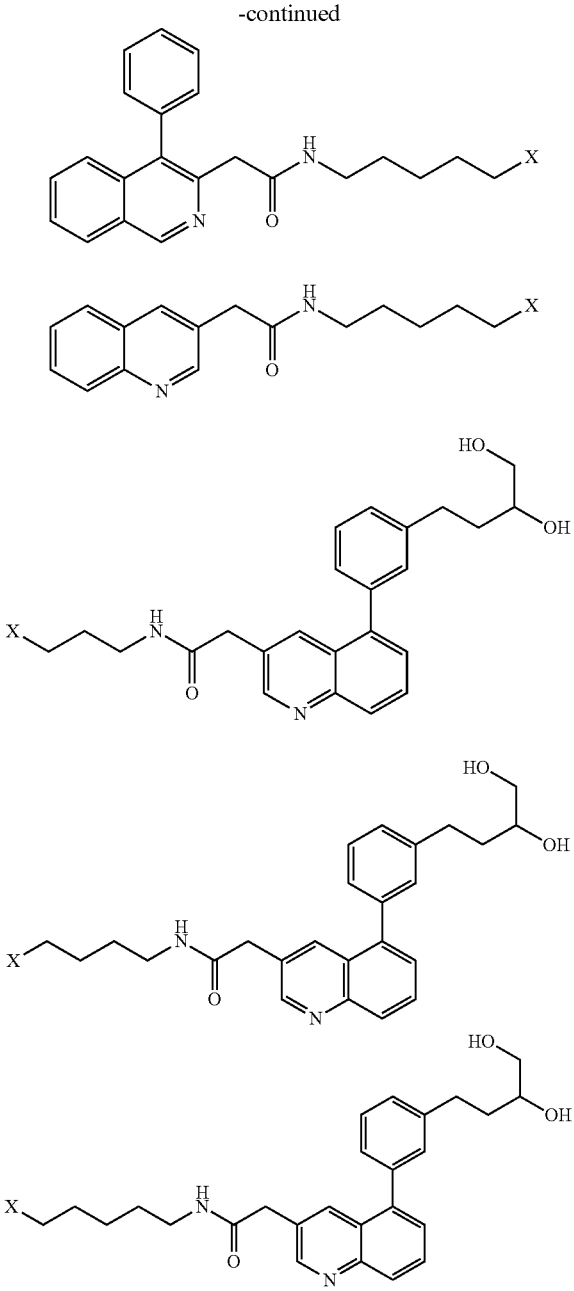

5. A compound selected from:

316
-continued

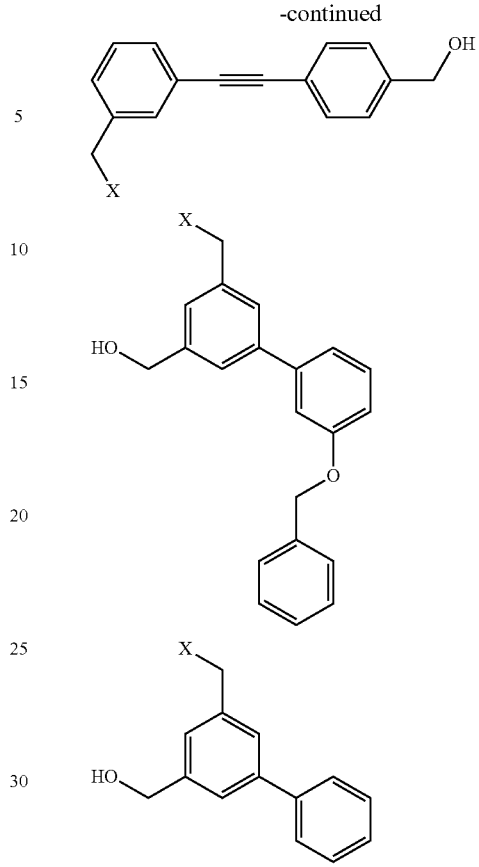

In which:

X is H; OH, wherein the hydroxyl group can optionally be functionalized as succinate or attached to a solid support; ODMT; carboxylic acid; the 3' end of a strand of a RNAi agent; or the 3' end of a molecule comprising a strand of a RNAi agent, wherein the 3' end of the strand terminates in a phosphate or modified internucleoside linker and further comprises in 5' to 3' order: a spacer, and a second phosphate or modified internucleoside linker, and q is selected from 1 and 2.

6. A method for capping the 3' end of a strand of an RNAi agent comprising a method of the steps of:

reacting the RNAi agent with a compound selected from:

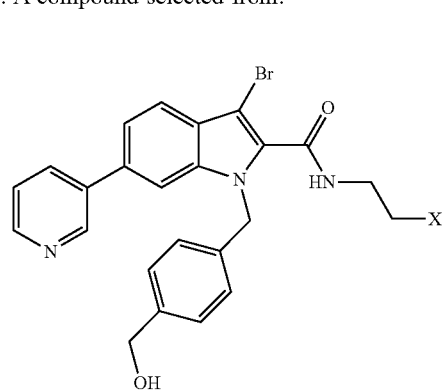

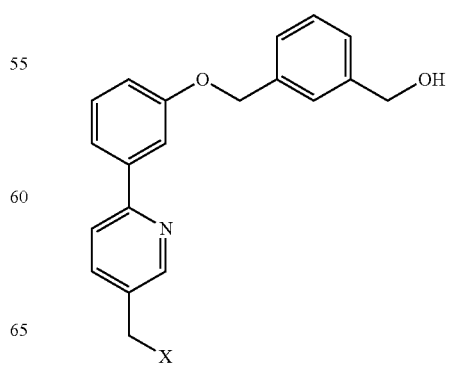

317
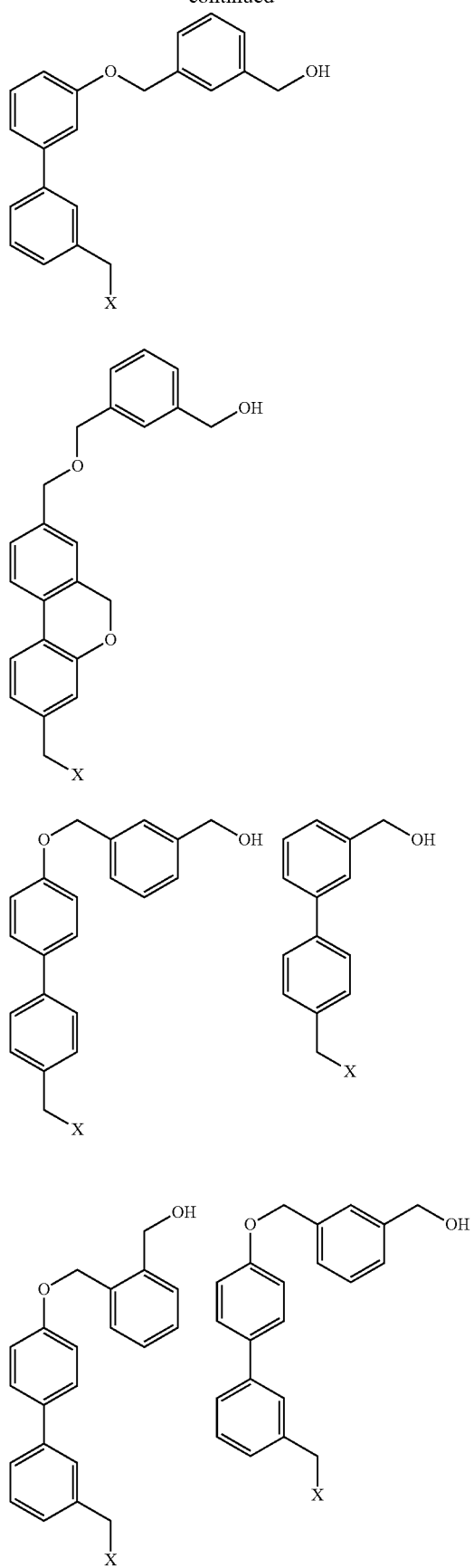
318
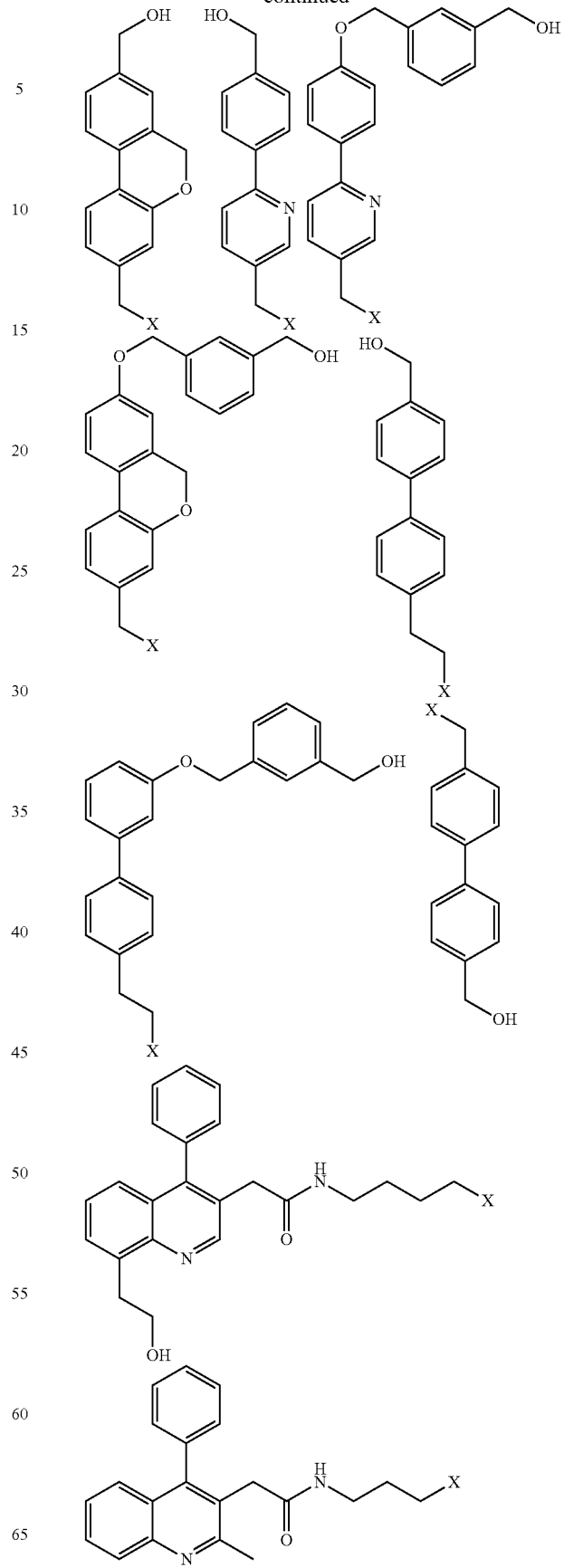

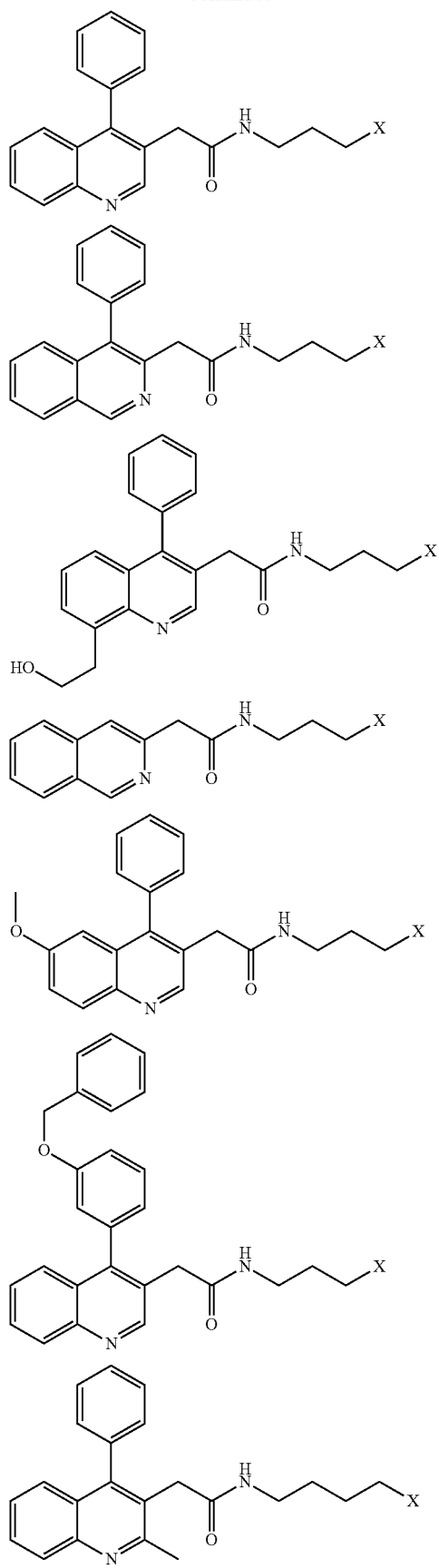
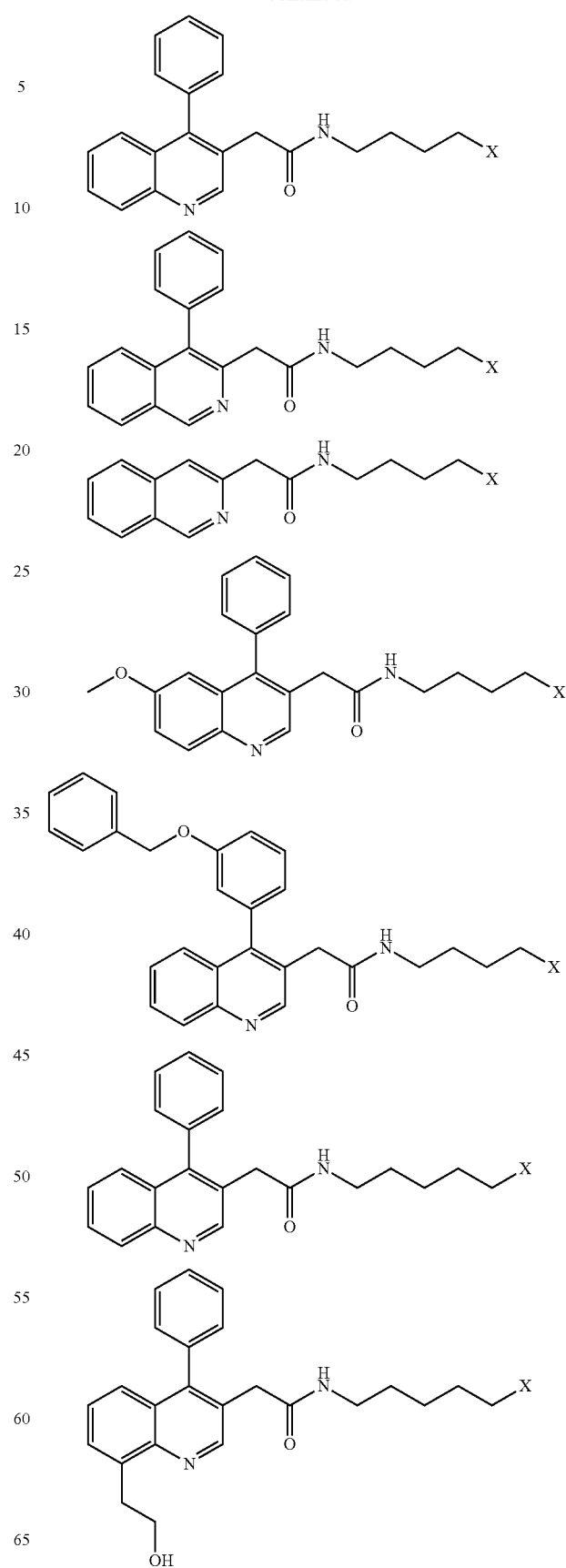

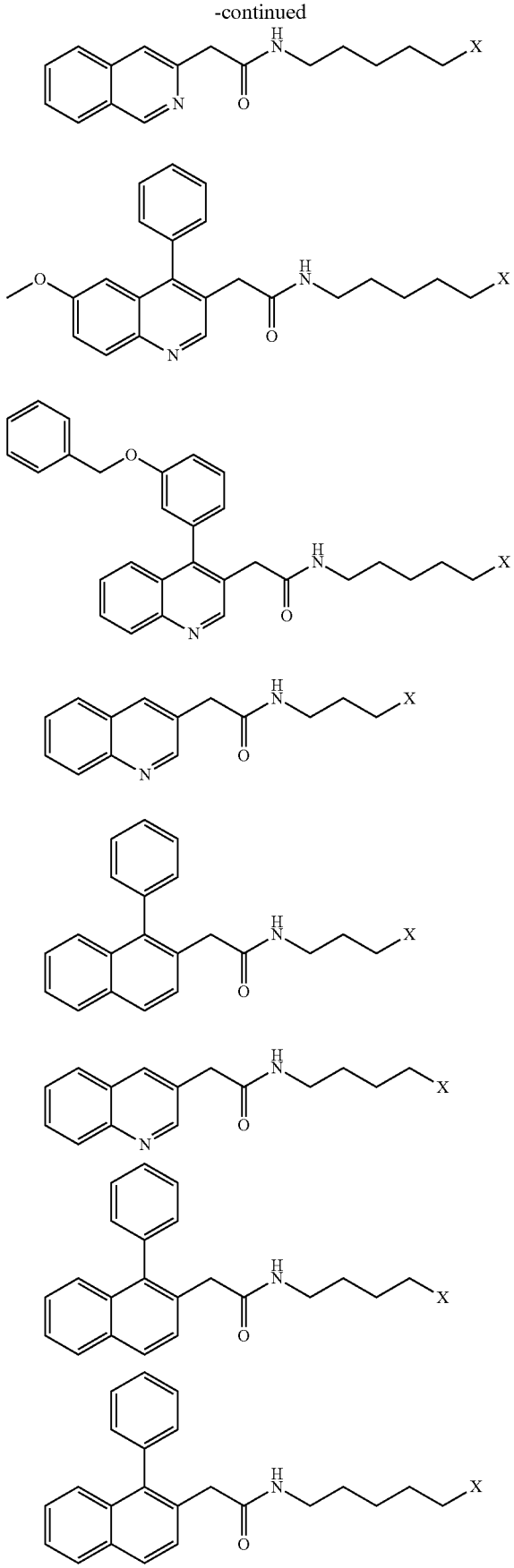
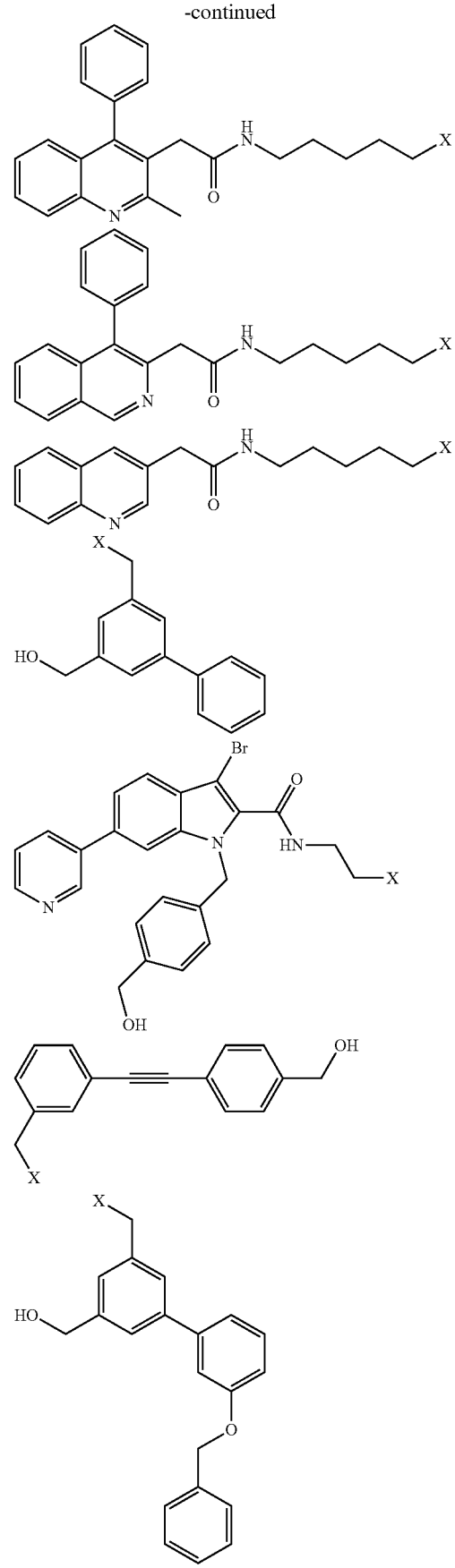

In which:
X is selected from H, OH, ODMT and carboxylate, wherein the hydroxyl group can be optionally functionalized as succinate or attached to a solid support;
Using solid-phase synthesis methods to replace X with a strand of a RNAi agent; or
Constructing a RNAi agent strand on a solid support;
Reacting the strand with the compound, and
Cleaving the RNAi agent strand from the solid support.

7. A compound of formula Ia, wherein X is H, OH, ODMT or carboxylate, wherein the hydroxyl group can be optionally functionalized as succinate or attached to a solid support; and $R_3$ is hydrogen, 2-(hydroxy-methyl)-benzyl, 3-(hydroxy-methyl)-benzyl, succinate, or a solid support.

8. A composition comprising a RNAi agent comprising a first strand and a second strand, wherein the 3'-terminus of at least one strand comprises a 3' end cap, wherein the 3' end cap is a compound of any of embodiments 1 to 6, wherein X is the first or second strand.

9. The composition of embodiment 8, wherein the first and/or second strands of the RNAi agent are no more than about 49 nucleotides long.

10. The composition of embodiment 8, wherein the first and/or second strands of the RNAi agent are no more than about 30 nucleotides long.

11. The composition of embodiment 8, wherein the first and/or second strand are 18 or 19 nucleotides long.

12. The composition of embodiment 8, wherein the first strand is the anti-sense strand and is 18 or 19 nucleotides long.

13. The composition of embodiment 8, wherein the RNAi agent has 1 or 2 blunt-ends.

14. The composition of embodiment 8, wherein the RNAi agent comprises an overhang on at least one 5' end or 3' end.

15. The composition of embodiment 8, wherein the RNAi agent comprises a 1 to 6 nucleotide overhang on at least one 5' end or 3' end.

16. The composition of embodiment 8, wherein the RNAi agent comprises a spacer.

17. The composition of embodiment 16, wherein the spacer is a ribitol.

18. The composition of embodiment 16, wherein the spacer is a ribitol, 2'-deoxy-ribitol, diribitol, 2'-methoxyethoxy-ribitol (ribitol with 2'-MOE), C3, C4, C5, C6, or 4-methoxybutane-1,3-diol.

19. The composition of embodiment 8, wherein at least one nucleotide of the RNAi agent is modified.

20. The composition of embodiment 19, wherein said at least one modified nucleotide is selected from among 2' alkoxyribonucleotide, 2' alkoxyalkoxy ribonucleotide, or 2'-fluoro ribonucleotide.

21. The composition of embodiment 19, wherein said at least one modified nucleotide is selected from 2'-OMe, 2'-MOE and 2'-H.

22. The composition of embodiment 8, wherein one or more nucleotides is modified or is DNA or is replaced by a peptide nucleic acid (PNA), locked nucleic acid (LNA), morpholino nucleotide, threose nucleic acid (TNA), glycol nucleic acid (GNA), arabinose nucleic acid (ANA), 2'-fluoroarabinose nucleic acid (FANA), cyclohexene nucleic acid (CeNA), anhydrohexitol nucleic acid (HNA), and/or unlocked nucleic acid (UNA); and/or at least one nucleotide comprises a modified internucleoside linker (e.g., wherein at least one phosphate of a nucleotide is replaced by a modified internucleoside linker), wherein the modified internucleoside linker is selected from phosphorothioate, phosphorodithioate, phosphoramidate, boranophosphonoate, an amide linker, and a compound of formula (I)

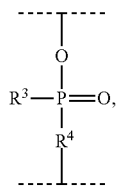

where $R^3$ is selected from $O^-$, $S^-$, $NH_2$, $BH_3$, $CH_3$, $C_{1-6}$ alkyl, $C_{6-10}$ aryl, $C_{1-6}$ alkoxy and $C_{6-10}$ aryl-oxy, wherein $C_{1-6}$ alkyl and $C_{6-10}$ aryl are unsubstituted or optionally independently substituted with 1 to 3 groups independently selected from halo, hydroxyl and $NH_2$; and $R^4$ is selected from O, S, NH, or $CH_2$.

23. The composition of embodiment 8, wherein the first two base-pairing nucleotides on the 3' end of the first and/or second strand are modified.

24. The composition of embodiment 8, wherein the first two base-pairing nucleotides on the 3' end of the first and/or second strand are 2'-MOE.

25. The composition of embodiment 8, wherein the 3' terminal phosphate of the first and/or second strands is replaced by a modified internucleoside linker.

26. The composition of embodiment 8, wherein first and/or the second strand is a sense strand comprising an 5' end cap which reduces the amount of the RNA interference mediated by the sense strand.

27. In various embodiments, the sense strand comprises a 5' end cap selected: a nucleotide lacking a 5' phosphate or 5'-OH; a nucleotide lacking a 5' phosphate or a 5'-OH and also comprising a 2-OMe or 2'-MOE modification; 5'-deoxy-2'-O-methyl modification; 5'-OME-dT; ddT; and 5'-OTr-dT.

28. A composition comprising a RNAi agent comprising a first strand and a second strand, wherein the 3'-end of at least one strand terminates in a phosphate or modified internucleoside linker and further comprises a 3' end cap, wherein the 3' end cap is selected from a compound of formula Ia or Ib or a compound from any Table herein, wherein X is the first or second strand, or any 3' end cap disclosed herein; and wherein: (a) the first and/or second strand is a 49-mer or shorter, is about 30 nucleotides long or shorter, is 19 nucleotides long, or between 15 and 49 nucleotides long; (b) optionally the RNAi agent has 1 or 2 blunt-ends or the RNAi agent comprises an overhang, optionally a 1 to 6 nucleotide overhang on at least one 5' end or 3' end; (c) optionally one or both strands are RNA or optionally at least one nucleotide of the RNAi agent is modified, wherein optionally said at least one modified nucleotide is selected from among 2' alkoxyribonucleotide, 2' alkoxyalkoxy ribonucleotide, or 2'-fluoro ribonucleotide, and optionally said at least one modified nucleotide is selected from 2'-OMe, 2'-MOE and 2'-H; and wherein optionally the first two base-pairing nucleotides on the 3' end of the first and/or second strand are modified, and optionally the first two base-pairing nucleotides on the 3' end of the first and/or second strand are 2'-MOE; and wherein optionally one or more nucleotides is modified or is DNA or is replaced by a peptide nucleic acid (PNA), locked nucleic acid (LNA), morpholino nucleotide, threose nucleic acid (TNA), glycol nucleic acid (GNA), arabinose nucleic acid (ANA), 2'-fluoroarabinose nucleic acid (FANA), cyclohexene nucleic acid (CeNA), anhydrohexitol nucleic acid (HNA), and/or unlocked nucleic acid (UNA); (d) at least one nucleotide comprises a modified internucleoside linker, wherein the modified internucleoside linker is selected from phosphorothioate, phosphorodithioate, phosphoramidate, boranophosphonoate, an amide linker, and a compound of formula (I); and wherein optionally the 3' terminal phosphate of the first and/or second strands is replaced by a modified internucleoside linker; and/or (e) optionally the first or the second strand is a sense strand comprising an 5' end cap which reduces the amount of the RNA interference mediated by the sense strand, wherein optionally the 5' end cap selected a nucleotide lacking a 5' phosphate or 5'-OH; a nucleotide lacking a 5' phosphate or a 5'-OH and also comprising a 2-OMe or 2'-MOE modification; 5'-deoxy-2'-O-methyl modification; 5'-OME-dT; ddT; and 5'-OTr-dT.

29. A composition comprising a RNAi agent comprising a first strand and a second strand, wherein the 3'-end of at least one strand terminates in a phosphate or modified internucleoside linker and further comprises, in 5' to 3' order: a spacer, a second phosphate or modified internucleoside linker, and a 3' end cap, wherein the 3' end cap is any 3' end cap disclosed herein or is selected from a compound of formula Ia or Ib or a compound from any Table herein, wherein X is the first or second strand which terminates in a phosphate or modified internucleoside linker and further comprises, in 5' to 3' order: a spacer, a second phosphate or modified internucleoside linker; and wherein: (a) the first and/or second strand is a 49-mer or shorter, is about 30 nucleotides long or shorter, is 19 nucleotides long, or between 15 and 49 nucleotides long; (b) optionally the RNAi agent has 1 or 2 blunt-ends or the RNAi agent comprises an overhang, optionally a 1 to 6 nucleotide overhang on at least one 5' end or 3' end; (c) optionally one or both strands are RNA or optionally at least one nucleotide of the RNAi agent is modified, wherein optionally said at least one modified nucleotide is selected from among 2' alkoxyribonucleotide, 2' alkoxyalkoxy ribonucleotide, or 2'-fluoro ribonucleotide, and optionally said at least one modified nucleotide is selected from 2'-OMe, 2'-MOE and 2'-H; and wherein optionally the first two base-pairing nucleotides on the 3' end of the first and/or second strand are modified, and optionally the first two base-pairing nucleotides on the 3' end of the first and/or second strand are 2'-MOE; and wherein optionally one or more nucleotides is modified or is DNA or is replaced by a peptide nucleic acid (PNA), locked nucleic acid (LNA), morpholino nucleotide, threose nucleic acid (TNA), glycol nucleic acid (GNA), arabinose nucleic acid (ANA), 2'-fl uoroarabinose nucleic acid (FANA), cyclohexene nucleic acid (CeNA), anhydrohexitol nucleic acid (HNA), and/or unlocked nucleic acid (UNA); (d) the spacer is a ribitol, 2'-deoxy-ribitol, diribitol, 2'-methoxyethoxy-ribitol (ribitol with 2'-MOE), C3, C4, C5, C6, or 4-methoxybutane-1,3-diol; (e) at least one nucleotide comprises a modified internucleoside linker, wherein the modified internucleoside linker is selected from phosphorothioate, phosphorodithioate, phosphoramidate, boranophosphonoate, an amide linker, and a compound of formula (I); and wherein optionally the 3' terminal phosphate of the first and/or second strands is replaced by a modified internucleoside linker; and/or (f) optionally the first or the second strand is a sense strand comprising an 5' end cap which reduces the amount of the RNA interference mediated by the sense strand, wherein optionally the 5' end cap selected a nucleotide lacking a 5' phosphate or 5'-OH; a nucleotide lacking a 5' phosphate or a 5'-OH and also comprising a 2-OMe or 2'-MOE modification; 5'-deoxy-2'-O-methyl modification; 5'-OME-dT; ddT; and 5'-OTr-dT.

30. A composition comprising an RNAi agent of embodiment 25 and a pharmaceutically acceptable carrier.

31. A composition comprising an RNAi agent of embodiment 25 and a pharmaceutically acceptable carrier, for use as a medicament.

32. A method for inhibiting or reducing the level and/or activity of a target gene in a cell comprising the step of introducing into the cell one or more RNAi agent of embodiment 25.

Unless defined otherwise, the technical and scientific terms used herein have the same meaning as that usually understood by a specialist familiar with the field to which the disclosure belongs.

Unless indicated otherwise, all methods, steps, techniques and manipulations that are not specifically described in detail can be performed and have been performed in a manner known per se, as will be clear to the skilled person. Reference is for example again made to the standard handbooks and the general background art mentioned herein and to the further references cited therein. Unless indicated otherwise, each of the references cited herein is incorporated in its entirety by reference.

Claims are non-limiting and are provided below.

Although particular embodiments and claims have been disclosed herein in detail, this has been done by way of example for purposes of illustration only, or is not intended to be limiting with respect to the scope of the appended claims, or the scope of subject matter of claims of any corresponding future application. In particular, it is contemplated by the inventors that various substitutions, alterations, and modifications may be made to the disclosure without departing from the spirit and scope of the disclosure as defined by the claims. The choice of nucleic acid starting material, clone of interest, or library type is believed to be a matter of routine for a person of ordinary skill in the art with knowledge of the embodiments described herein. Other embodiments, advantages, and modifications considered to be within the scope of the following claims. Those skilled in the art will recognize or be able to ascertain, using no more than routine experimentation, many equivalents of the specific embodiments of the disclosure described herein. Such equivalents are intended to be encompassed by the following claims. Redrafting of claim scope in later filed corresponding applications may be due to limitations by the patent laws of various countries and should not be interpreted as giving up subject matter of the claims.

We claim:

1. An RNAi agent of formula Ib:

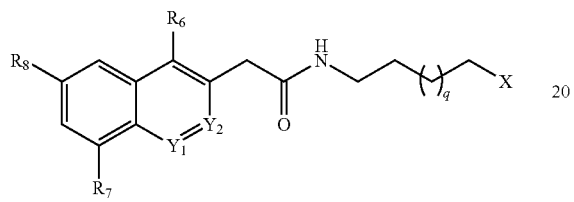

Ib wherein:

X comprises a strand of the RNAi agent;

q is 0, 1 or 2;

$R_6$ is phenyl which is unsubstituted or substituted with a group selected from benzoxy and 3,4-dihydroxybutyl;

$R_7$ is hydrogen or hydroxy-ethyl, wherein if $R_7$ is hydroxy-ethyl, the hydroxyl is optionally functionalized as succinate or attached to a solid support;

$R_8$ is hydrogen or methoxy;

$Y_1$ is CH or N; and $Y_2$ is N or $CR_9$; wherein $R_9$ is selected from hydrogen and methyl.

2. The RNAi agent of claim 1, wherein X is attached at the 3' end of a strand of the RNAi agent.

3. The RNAi agent of claim 2, wherein the strand of the RNAi agent terminates at its 3' end in a phosphate or modified internucleoside linker, and X is attached at the phosphate or modified internucleoside linker.

4. The RNAi agent of claim 2, wherein the strand of the RNAi agent terminates at its 3' end in a phosphate or modified internucleoside linker, the phosphate or modified internucleoside linker is substituted by a spacer, which is substituted by a second phosphate or modified internucleoside linker, in 5' to 3' order, and X is attached at the second phosphate or modified internucleoside linker.

5. The RNAi agent of claim 1 selected from:

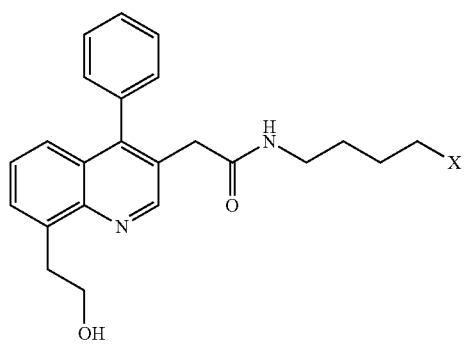

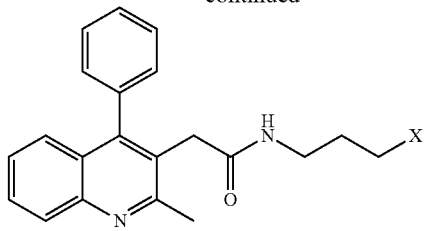

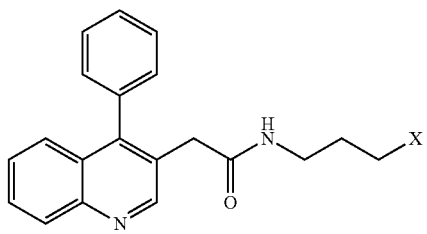

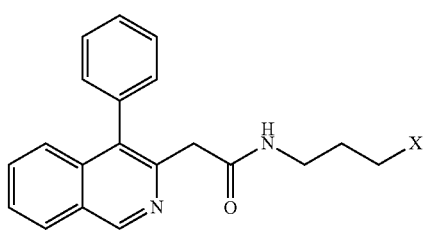

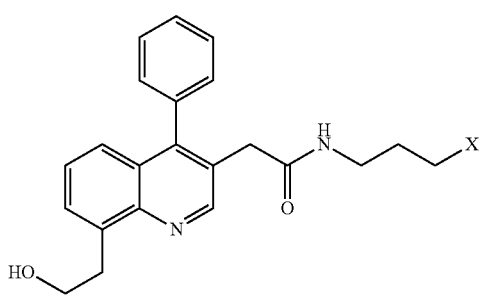

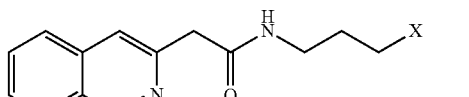

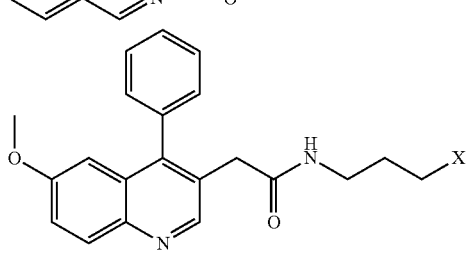

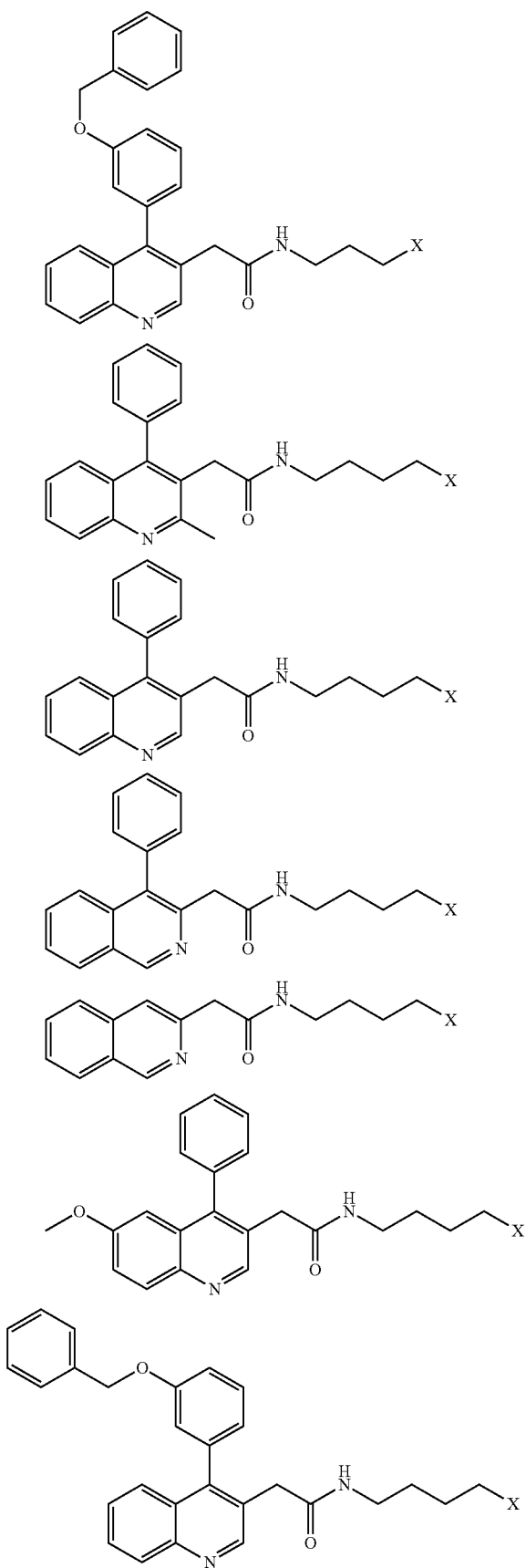
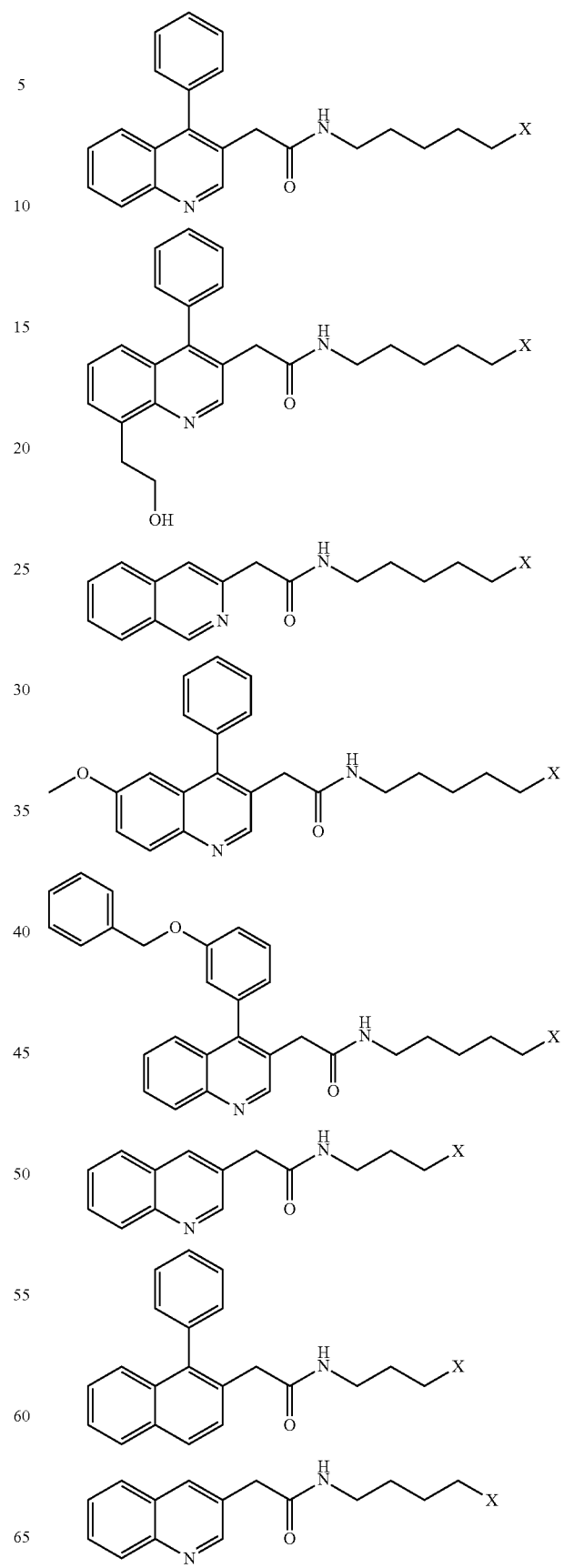

389
-continued

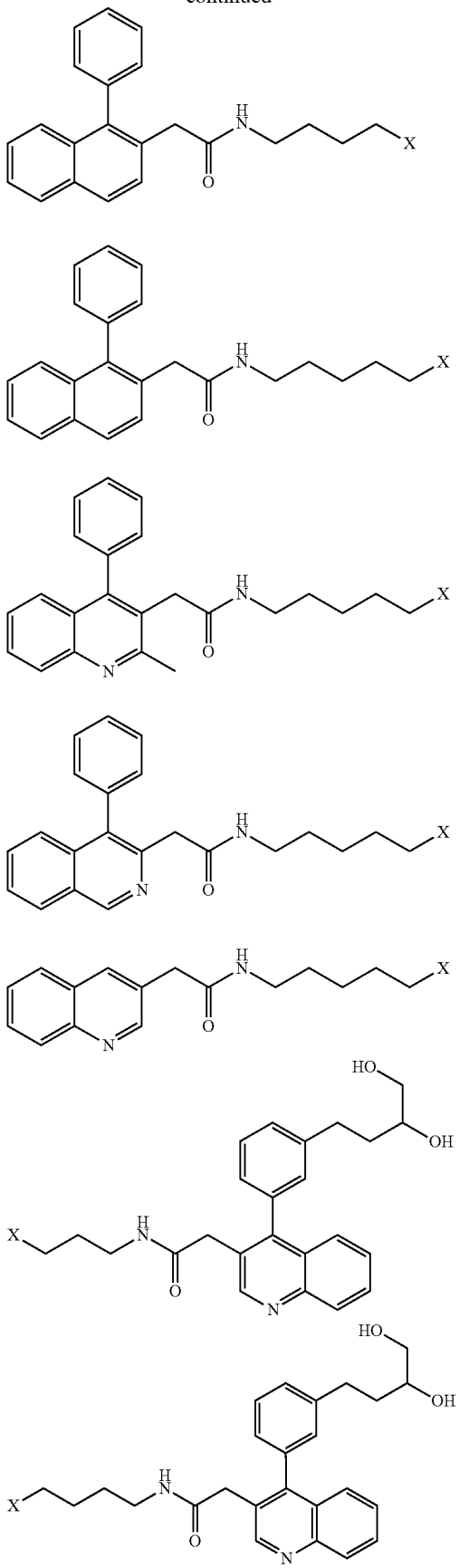

390
-continued

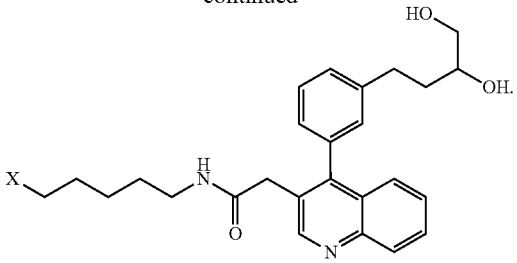

6. The RNAi agent of claim 1, wherein the strand of the RNAi agent is a first strand and X further comprises a second strand.

7. The RNAi agent of claim 6, wherein the first strand is an antisense strand.

8. The RNAi agent of claim 6, wherein the first and/or second strands are no more than about 30 nucleotides long.

9. The RNAi agent of claim 6 having 1 or 2 blunt ends.

10. The RNAi agent of claim 6 having an overhang on at least one 5' end or 3' end.

11. The RNAi agent of claim 6, wherein X further comprises a spacer.

12. The RNAi agent of claim 11, wherein the spacer is an abasic nucleotide.

13. The RNAi agent of claim 11, wherein the spacer is a ribitol, 2'-deoxy-ribitol, diribitol, 2'-methoxyethoxy-ribitol (ribitol with 2'-MOE), C3, C4, C5, C6, or 4-methoxybutane-1,3-diol.

14. The RNAi agent of claim 6, wherein at least one nucleotide of the RNAi agent is modified.

15. The RNAi agent of claim 14, wherein the at least one modified nucleotide is selected from 2' alkoxyribonucleotide, 2' alkoxyalkoxy ribonucleotide, 2'-fluoro ribonucleotide, 2'-OMe, 2'-MOE and 2'-H.

16. The RNAi agent of claim 6, wherein one or more nucleotides is modified, is DNA, or is replaced by a peptide nucleic acid (PNA), locked nucleic acid (LNA), morpholino nucleotide, threose nucleic acid (TNA), glycol nucleic acid (GNA), arabinose nucleic acid (ANA), 2'-fluoroarabinose nucleic acid (FANA), cyclohexene nucleic acid (CeNA), anhydrohexitol nucleic acid (HNA), and/or unlocked nucleic acid (UNA); and/or at least one nucleotide comprises a modified internucleoside linker, wherein the modified internucleoside linker is selected from phosphorothioate, phosphorodithioate, phosphoramidate, boranophosphonate, an amide linker, and a compound of formula (I)

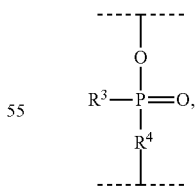

where $R^3$ is selected from $O^-$, $S^-$, $NH_2$, $BH_3$, $CH_3$, $C_{1-6}$ alkyl, $C_{6-10}$ aryl, $C_{1-6}$ alkoxy and $C_{6-10}$ aryl-oxy, wherein $C_{1-6}$ alkyl and $C_{6-10}$ aryl are unsubstituted or optionally independently substituted with 1 to 3 groups independently selected from halo, hydroxyl and $NH_2$; and $R^4$ is selected from O, S, NH, or $CH_2$.

17. The RNAi agent of claim 6 comprising a sense strand, the sense strand comprising a 5' end cap selected from a nucleotide lacking a 5' phosphate or 5'-OH; a nucleotide lacking a 5' phosphate or a 5'-OH and also comprising a 2-OMe or 2'-MOE modification; 5'-deoxy-2'-O-methyl modification; 5'-OME-dT; ddT; and 5'-OTr-dT.

18. A composition comprising the RNAi agent of claim 1 and a pharmaceutically acceptable carrier.

* * * * *